US012466821B2

(12) United States Patent
Becker et al.

(10) Patent No.: US 12,466,821 B2
(45) Date of Patent: Nov. 11, 2025

(54) ANTIVIRAL PYRIDOPYRAZINEDIONE COMPOUNDS

(71) Applicant: Novartis AG, Basel (CH)

(72) Inventors: Christopher Becker, Pleasant Hill, CA (US); Xiaolin Li, Alameda, CA (US); Peichao Lu, Pleasant Hill, CA (US); Naomi Samadara Rajapaksa, Fremont, CA (US); David Charles Tully, Danville, CA (US); Xiaojing Michael Wang, Livermore, CA (US); Qian Zhao, Louisville, CO (US)

(73) Assignee: Novartis AG, Basel (CH)

( * ) Notice: Subject to any disclaimer, the term of this patent is extended or adjusted under 35 U.S.C. 154(b) by 955 days.

(21) Appl. No.: 17/352,734

(22) Filed: Jun. 21, 2021

(65) Prior Publication Data

US 2023/0052629 A1 Feb. 16, 2023

Related U.S. Application Data

(62) Division of application No. 16/569,107, filed on Sep. 12, 2019, now Pat. No. 11,072,610.

(60) Provisional application No. 62/730,361, filed on Sep. 12, 2018.

(51) Int. Cl.

| | |
|---|---|
| ***C07D 471/04*** | (2006.01) |
| ***A61P 31/22*** | (2006.01) |
| *A61K 31/4985* | (2006.01) |
| *A61P 31/12* | (2006.01) |

(52) U.S. Cl.
CPC ............ *C07D 471/04* (2013.01); *A61P 31/22* (2018.01)

(58) Field of Classification Search
CPC ........ C07D 471/04; A61P 31/22; A61P 31/12; A61K 31/4985
See application file for complete search history.

(56) References Cited

U.S. PATENT DOCUMENTS

| | | | |
|---|---|---|---|
| 4,661,493 | A | 4/1987 | Gibbs |
| 5,149,778 | A | 9/1992 | Adams et al. |
| 5,484,771 | A | 1/1996 | Beaulieu et al. |
| 5,502,036 | A | 3/1996 | Adams et al. |
| 5,552,384 | A | 9/1996 | D eziel et al. |
| 5,830,864 | A | 11/1998 | Deziel et al. |
| 6,111,090 | A | 8/2000 | Gorman et al. |
| 6,284,798 | B1 | 9/2001 | Amtmann et al. |
| 7,025,962 | B1 | 4/2006 | Gorman et al. |
| 7,618,632 | B2 | 11/2009 | Collins et al. |
| 7,812,135 | B2 | 10/2010 | Smith et al. |
| 7,943,743 | B2 | 5/2011 | Korman et al. |
| 8,008,449 | B2 | 8/2011 | Korman et al. |
| 8,354,509 | B2 | 1/2013 | Carven et al. |
| 8,388,967 | B2 | 3/2013 | Smith et al. |
| 8,586,023 | B2 | 11/2013 | Shiku et al. |
| 8,591,886 | B2 | 11/2013 | Ponath et al. |
| 8,609,089 | B2 | 12/2013 | Langermann et al. |
| 2007/0191387 | A1 | 8/2007 | Wunberg et al. |
| 2010/0028330 | A1 | 2/2010 | Collins et al. |
| 2011/0150892 | A1 | 6/2011 | Thudium et al. |
| 2012/0039906 | A1 | 2/2012 | Olive |
| 2012/0114649 | A1 | 5/2012 | Langermann et al. |
| 2020/0079772 | A1 | 3/2020 | Becker et al. |

FOREIGN PATENT DOCUMENTS

| | | | |
|---|---|---|---|
| CN | 108178757 | A | 6/2018 |
| EP | 090505 | B1 | 8/1990 |
| EP | 0408973 | B1 | 10/1996 |
| EP | 1947183 | B1 | 7/2013 |
| EP | 2161336 | B2 | 3/2017 |
| EP | 1866339 | B2 | 9/2021 |
| WO | 9318056 | A1 | 9/1993 |
| WO | 9724343 | A1 | 7/1997 |
| WO | 9745401 | A1 | 12/1997 |
| WO | 9811073 | A1 | 3/1998 |
| WO | 9835685 | A1 | 8/1998 |
| WO | 9845259 | A2 | 10/1998 |
| WO | 9852948 | A1 | 11/1998 |
| WO | 9918071 | A1 | 4/1999 |
| WO | 9918072 | A1 | 4/1999 |

(Continued)

OTHER PUBLICATIONS (2017) "Letermovir Assessment Report" European Medicines Agency, Committee for Medicinal Products for Human Use (CHMP), 1-124.

(Continued)

*Primary Examiner* — Bruck Kifle
*Assistant Examiner* — Kevin S Martin
(74) *Attorney, Agent, or Firm* — Barnes & Thornburg LLP

(57) ABSTRACT

The invention provides compounds of Formula (I)

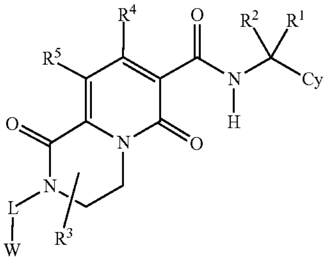

as described herein, along with pharmaceutically acceptable salts, pharmaceutical compositions containing such compounds, and methods to use these compounds, salts and compositions for treating viral infections, particularly infections caused by herpesviruses.

10 Claims, 1 Drawing Sheet

Specification includes a Sequence Listing.

(56) References Cited

FOREIGN PATENT DOCUMENTS

| | | | |
|---|---|---|---|
| WO | 9918073 | A1 | 4/1999 |
| WO | 9920758 | A1 | 4/1999 |
| WO | 9932450 | A1 | 7/1999 |
| WO | 9932477 | A1 | 7/1999 |
| WO | 9940196 | A1 | 8/1999 |
| WO | 9947507 | A2 | 9/1999 |
| WO | 0039131 | A1 | 7/2000 |
| WO | 00040561 | A1 | 7/2000 |
| WO | 00040563 | A1 | 7/2000 |
| WO | 0053610 | A2 | 9/2000 |
| WO | 0058270 | A2 | 10/2000 |
| WO | 0103720 | A2 | 1/2001 |
| WO | 0125239 | A2 | 4/2001 |
| WO | 0170706 | A2 | 9/2001 |
| WO | 0170742 | A1 | 9/2001 |
| WO | 0172728 | A2 | 10/2001 |
| WO | 0174816 | A1 | 10/2001 |
| WO | 0181318 | A1 | 11/2001 |
| WO | 0198275 | A2 | 12/2001 |
| WO | 0202558 | A1 | 1/2002 |
| WO | 0204422 | A2 | 1/2002 |
| WO | 0204444 | A2 | 1/2002 |
| WO | 0204445 | A1 | 1/2002 |
| WO | 0204462 | A1 | 1/2002 |
| WO | 0206513 | A2 | 1/2002 |
| WO | 02053543 | A1 | 7/2002 |
| WO | 02064145 | A1 | 8/2002 |
| WO | 02070487 | A1 | 9/2002 |
| WO | 03020728 | A1 | 3/2003 |
| WO | 03020729 | A1 | 3/2003 |
| WO | 03026652 | A1 | 4/2003 |
| WO | 03053971 | A1 | 7/2003 |
| WO | 03053972 | A1 | 7/2003 |
| WO | 03059878 | A2 | 7/2003 |
| WO | 03059911 | A2 | 7/2003 |
| WO | 03059912 | A1 | 7/2003 |
| WO | 03099276 | A1 | 12/2003 |
| WO | 04022566 | A1 | 3/2004 |
| WO | 04022567 | A1 | 3/2004 |
| WO | 04022568 | A1 | 3/2004 |
| WO | 04065367 | A1 | 8/2004 |
| WO | 04078163 | A2 | 9/2004 |
| WO | 04083177 | A2 | 9/2004 |
| WO | 2004082577 | A2 | 9/2004 |
| WO | 04087140 | A1 | 10/2004 |
| WO | 04087169 | A1 | 10/2004 |
| WO | 04106345 | A2 | 12/2004 |
| WO | 04111037 | A1 | 12/2004 |
| WO | 05007190 | A1 | 1/2005 |
| WO | 05012545 | A2 | 2/2005 |
| WO | 05016927 | A1 | 2/2005 |
| WO | 05018557 | A2 | 3/2005 |
| WO | 05055808 | A2 | 6/2005 |
| WO | 05072361 | A2 | 8/2005 |
| WO | 05115451 | A2 | 12/2005 |
| WO | 06083289 | A2 | 8/2006 |
| WO | 06121168 | A1 | 11/2006 |
| WO | 07005874 | A2 | 1/2007 |
| WO | 07024922 | A1 | 3/2007 |
| WO | 07092435 | A2 | 8/2007 |
| WO | 07133822 | A1 | 11/2007 |
| WO | 08137779 | A2 | 11/2008 |
| WO | 09019553 | A2 | 2/2009 |
| WO | 09101611 | A1 | 8/2009 |
| WO | 09114335 | A2 | 9/2009 |
| WO | 09137493 | A1 | 11/2009 |
| WO | 10003118 | A1 | 1/2010 |
| WO | 10019570 | A2 | 2/2010 |
| WO | 10026029 | A1 | 3/2010 |
| WO | 10027827 | A2 | 3/2010 |
| WO | 10077634 | A1 | 7/2010 |
| WO | 11028683 | A1 | 3/2011 |
| WO | 11051726 | A2 | 5/2011 |
| WO | 11066342 | A2 | 6/2011 |
| WO | 11090754 | A1 | 7/2011 |
| WO | 12115256 | A1 | 8/2012 |
| WO | 12151195 | A1 | 11/2012 |
| WO | 13039954 | A1 | 3/2013 |
| WO | 13079174 | A1 | 6/2013 |
| WO | 13085890 | A1 | 6/2013 |
| WO | 13152063 | A1 | 10/2013 |
| WO | 13152065 | A2 | 10/2013 |
| WO | 2013171712 | A1 | 11/2013 |
| WO | 14008218 | A1 | 1/2014 |
| WO | 14070976 | A1 | 5/2014 |
| WO | 14070978 | A1 | 5/2014 |
| WO | 14070979 | A1 | 5/2014 |
| WO | 15069844 | A1 | 5/2015 |
| WO | 15153683 | A1 | 10/2015 |
| WO | 15154820 | A1 | 10/2015 |
| WO | 2015150957 | A1 | 10/2015 |
| WO | 17193030 | A1 | 11/2017 |
| WO | 20053654 | A1 | 3/2020 |

OTHER PUBLICATIONS

Abad, C. L. et al. (2016) "Treatment of alpha and beta herpesvirus infections in solid organ transplant recipients" Expert Review of Anti-infective Therapy, 15(2):93-110.

Bennett et al. (2003) J. Immunol. 170:711-8.

Blank et al. (2005) Cancer Immunol. Immunother. 54:307-314.

Blank, C. et al. (Epub Dec. 29, 2006) Immunol. Immunother. 56(5):7 39-745.

Boeckh, M. et al. (2006) "Long-term acyclovir for prevention of varicella zoster virus disease after allogeneic hematopoietic cell transplantation—a randomized double-blind placebo-controlled study" Blood, 107(5):1800-1805.

Brown et al. (2003) J. Immunol. 170:1257-66.

Chen, S. et al. (2019) "Antiviral Agents as Therapeutic Strategies Against Cytomegalovirus Infections" Viruses, 12 (21):1-11.

Danve-Szatanek, C. et al. (2004) "Surveillance Network for Herpes Simplex Virus Resistance to Antiviral Drugs: 3-Year Follow-Up" Journal of Clinical Microbiology, 42(1):242-249.

Deleenheer, B. et al. (2018) "Pharmacokinetic drug evaluation of letermovir prophylaxis for cytomegalovirus in hematopoietic stem cell transplantation" Expert Opinion on Drug Metabolism & Toxicology, 14(12):1197-1207.

Dong et al. (2003) J. Mol. Med. 81:281-7.

Grantham, J. et al. (2019) "Development of a Sequencing Based Assay for Dectection of Resistance Mutations To Letermovir in UL56" Viracor, Eurofins Clinical Diagnostics, Poster.

Gugliesi, F. et al. (2020) "Where do we Stand after Decades of Studying Human Cytomegalovirus?" Microorganisms 8(685):1-30.

Hakki, M. et al. (2020) "Moving Past Ganciclovir and Foscarnet: Advances in CMV Therapy" Current Hematologic Malignancy Reports, 1-13.

Hamid, O. et al. (2013) New England Journal of Medicine 369 (2): 134-44.

Hill, J. et al. (2019) "Human Herpesvirus 6B and Lower Respiratory Tract Disease After Hematopoietic Cell Transplantation" Journal of Clinical Oncology 37: 1-13.

Hill, J. et al. (2019) Supplement to "Human Herpesvirus 6B and Lower Respiratory Tract Disease After Hematopoietic Cell Transplantation".

Hussein, I. et al. (2020) "The discovery and development of filociclovir for the prevention and treatment of human cytomegalovirus-related disease" Antiviral Research, 1-5.

International Search Report, issued in PCT/IB2019/001008, dated Feb. 24, 2020.

International Search Report, issued in PCT/US2020/052375, dated Feb. 1, 2021.

Ishida, Y. et al. (1992) EMBO J. 11:3887-3895.

Itell, H., et al. (2017) "Rhesus Monkeys for a Nonhuman Primate Model of Cytomegalovirus Infections" Curr Opin Virol. 25:126-133.

Iwai et al. (2002) Proc. Natl. Acad. Sci. USA 99:12293-7.

Konishi et al. (2004) Clin. Cancer Res. 10:5094-100.

(56) References Cited

OTHER PUBLICATIONS

Lau, C. et al. (2020) "LBA16—Letermovir Cytomegalovirus (CMV) Prophylaxis in Adult Seropositive Cord Blood Transplant (CBT) Recipients Is Highly Efficacious and Likely Cost-Effective" [ downloaded from https://tct.confex.com/tct/2020/meetingapp.cgi/Paper/15827] Poster No. LBA16, Transplantation & Cellular Therapy Meetings, World Center Marriott, Orlando, Florida, Feb. 22, 2020.
Letermovir Clinical Pharmacology and Biopharmaceutics Review(s) for 209939 and 209940, Aug. 8, 2017.
Lin, A. et al. (2019) "Letermovir for primary and secondary cytomegalovirus prevention in allogeneic hematopoietic cell transplant recipients: Real-world experience" Transpl Infect Dis. 21:1-6.
Lischka, P. et al. (2010) "In Vitro and In Vivo Activities of the Novel Anticytomegalovirus Compound AIC246" Anitmicrobial Agents and Chemotherapy 54(3):1290-1297.
Ljungman, P. et al. (2019) "A Mortality Analysis of Letermovir Prophylaxis for Cytomegalovirus (CMV) in CMV-seropositive Recipients of Allogeneic Hematopoietic Cell Transplantation" Clinical Infectious Diseases, 1-9.
Ma et.al. (2006). Real-time monitoring of DNA polymerase activity using molecular beacon. Analytical Biochemistry, 353 (1): 141-143.
Marschall, M. et al. (2011) "In Vitro Evaluation of the Activities of the Novel Anticytomegalovirus Compound AIC246 (Letermovir) against Herpesviruses and Other Human Pathogenic Viruses" Antimicrobial Agents and Chemotherapy, 1135-1137.
Marty, F. et al. (2017) "Letermovir Prophylaxis for Cytomegalovirus in Hematopoietic-Cell Transplantation" N Engl J Med 377:2433-2444.
Marty, F. et al. (2018) "A Randomized, Double-Blind, Placebo-Controlled Phase 3 Trial of Oral Brincidofovir for Cytomegalovirus Prophylaxis in Allogeneic Hematopoietic Cell Transplantation" Biol Blood Marrow Transplant 25:369-381.
Marty, F. et al. (2019) "Outcomes of patients with detectable CMV DNA at randomization in the phase III trial of letermovir for the prevention of CMV infection in allogeneic hematopoietic cell transplantation" The American Society of Transplantation and the American Society of Transplant Surgeons [https://doi.org/10.1111/ajt.15764].
Morfin, F., et al. (2004) "HSV excretion after bone marrow transplantation: a 4-year survey" Journal of Clinical Virology, 30:341-345.
Northup, A. et al J. Med. Chem. 2013, 56, 2294.
Oien, N. et al. (2002) "Broad-Spectrum Antiherpes Activities of 4-Hydroxyquinoline Carboxamides, a Novel Class of Herpesvirus Polymerase Inhibitors" Anitmicrobial Agents Chemotherapy 46(3):724-730.
Okazaki et al. (2002) Curr Opin Immunol 14: 391779-82.
PNAS 2003, 100(24), 14223-14228.
Powers, C. et al. (2008) "Rhesus CMV: an emerging animal model for human CMV" Med Microbiol Immunol 197:109-115.
Qiao, J. et al. (2009) "Highly efficacious factor Xa inhibitors containing a-substituted phenylcycloalkyl P4 moieties" Bioorganic & Medicinal Chemistry Letters 19:462-468.
Schnute, M. et al. (2005) "4-Oxo-4,7-dihydrothieno[2,3-b]pyridines as Non-Nucleoside Inhibitors of Human Cytomegalovirus and Related Herpesvirus Polymerases" J. Med. Chem. 48:5794-5804.
Seo, S. et al. (2015) "Idiopathic pneumonia syndrome after hematopoietic cell transplantation: evidence of occult infectious etiologies" Blood, 125(24):3789-3797.
Stoelben, S. et al. (2013) "Preemptive treatment of Cytomegalovirus infection in kidney transplant recipients with etermovir: results of a Phase 2a study" Transplant International, 27:77-86.
Stranska, R. et al. (2005) "Survey of acyclovir-resistant herpes simplex virus in the Netherlands: prevalence and characterization" Journal of Clinical Virology 32:7-18.
Trapani et al., "Synthesis and Benzodiazepine Receptor Binding of 5H-Pyrido[2,1-C][1,4]Benzothiazines," II Farmaco, vol. 45, No. 6, (1990), pp. 589-602.
Van Delden, C. et al. (2020) "Burden and Timeline of Infectious Diseases in the First Year After Solid Organ Transplantation in the Swiss Transplant Cohort Study" Clinical Infectious Diseases, 1-11.
Van Delden, C. et al. (2020) Supplement for "Burden and timeline of infectious diseases in the first year after solid organ transplantation in the Swiss Transplant Cohort study".
Woo et al. (2012) Cancer Res. 72(4):917-27.
Yahav, D. et al. (2009) "Antiviral prophylaxis in haematological patients: Systematic review and meta-analysis" European Journal of Cancer, 45:3131-3148.
CAS Registry Record for 2167128-03-0 (2H-Pyrido [1, 2-a] pyrazine-7-carboxylic acid, 1, 3, 4, 6-tetrahydro-1, 6-dioxo-, methyl eater), entered STN Dec. 31, 2017, 1 page.
CAS Registry Record for 2167411-05-2 (2H-Pyrido [1, 2-a] pyrazine-7-carboxylic acid, 1, 3, 4, 6-tetrahydro-1, 6-dioxo-), entered STN Jan. 1, 2018, 1 page.
Zhou, X. et al. (2019) "First-Onset Herpesviral Infection and Lung Injury in Allogeneic Hematopoietic Cell Transplantation" American Journal of Respiratory and Critical Care Medicine 200(1):63-74.
Zhou, X. et al. (2019) Supplement to "First onset herpesviral infection and lung injury in allogeneic hematopoietic cell transplantation".
CAS Registry No. 2167411-03-0; Date Entered STN: Dec. 31, 2017; Methyl 1,3,4,6-Tetrahydro-1,6-dioxo-2H-pyrido[1,2-a]pyrazine-7-carboxylate.

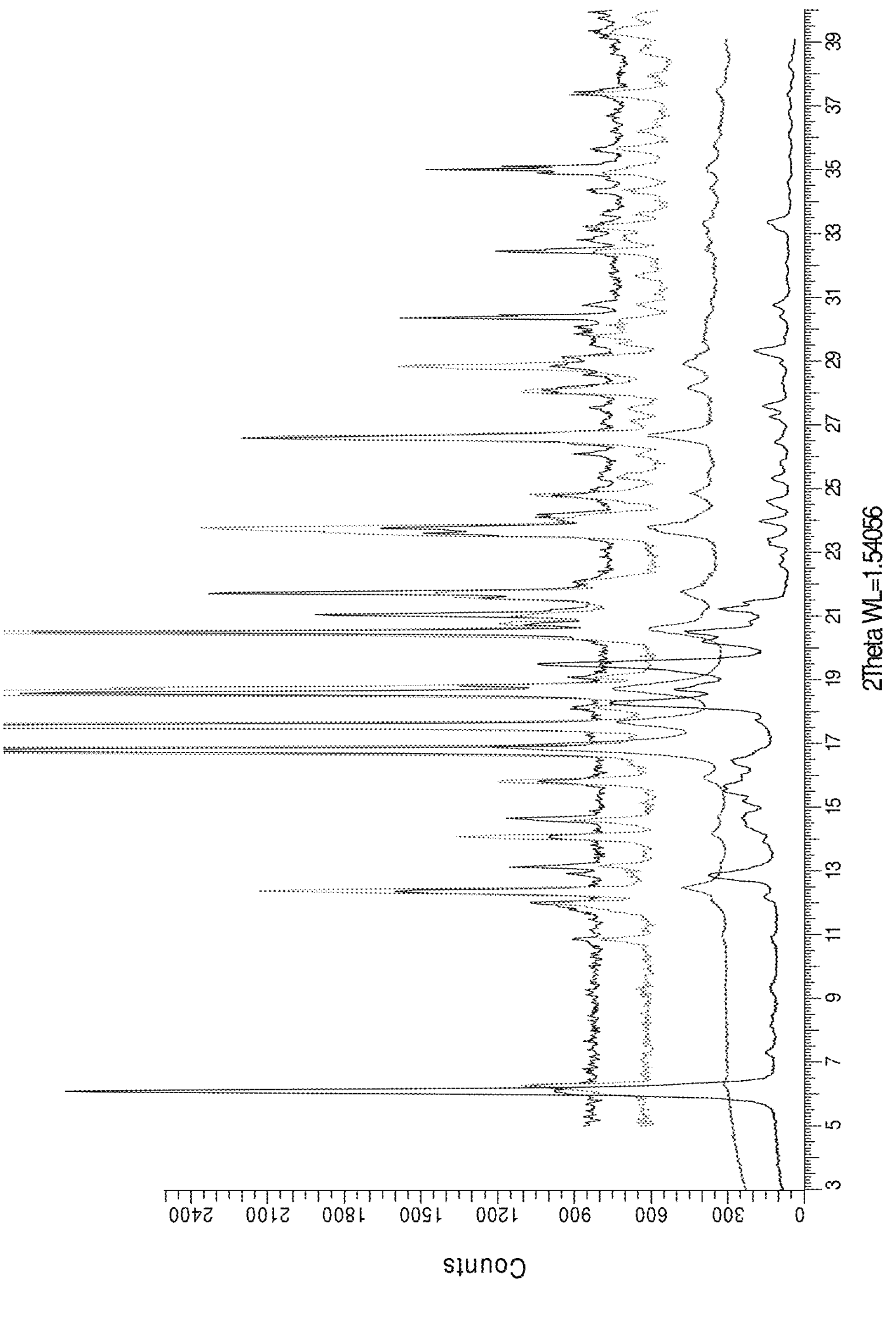
XRPD spectra for polymorphs of the compound of Example 1.

SEQUENCE LISTING

```
<160> NUMBER OF SEQ ID NOS: 17

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1

tagtcggtgg gctgtgt                                                   17


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

aactgggtcc atgtagggat                                                20


<210> SEQ ID NO 3
<211> LENGTH: 22
<212> TYPE: DNA
<213> ORGANISM: Artificial Sequence
<220> FEATURE:
<223> OTHER INFORMATION: Probe

<400> SEQUENCE: 3

tgcttgagct cctgcgtcgt ac                                             22


<210> SEQ ID NO 4
<211> LENGTH: 20
<212> TYPE: DNA
<213> ORGANISM: Artificial Sequence
<220> FEATURE:
<223> OTHER INFORMATION: Primer or Probe

<400> SEQUENCE: 4

cctccgtatc gggacttcaa                                                20
```

<210> SEQ ID NO 5
<211> LENGTH: 20
<212> TYPE: DNA
<213> ORGANISM: Artificial Sequence
<220> FEATURE:
<223> OTHER INFORMATION: Primer or probe

<400> SEQUENCE: 5
tgaccgtcct cgcatacgta 20

<210> SEQ ID NO 6
<211> LENGTH: 16
<212> TYPE: DNA
<213> ORGANISM: Artificial Sequence
<220> FEATURE:
<223> OTHER INFORMATION: Primer or probe

<400> SEQUENCE: 6
ttggcgaaga gctaac 16

<210> SEQ ID NO 7
<211> LENGTH: 22
<212> TYPE: DNA
<213> ORGANISM: Artificial Sequence
<220> FEATURE:
<223> OTHER INFORMATION: Primer or probe

<400> SEQUENCE: 7
acacccctta tccccatact ag 22

<210> SEQ ID NO 8
<211> LENGTH: 22
<212> TYPE: DNA
<213> ORGANISM: Artificial sequence
<220> FEATURE:
<223> OTHER INFORMATION: Primer or probe

<400> SEQUENCE: 8
atggttgata ttgctagggt gg 22

<210> SEQ ID NO 9
<211> LENGTH: 23
<212> TYPE: DNA
<213> ORGANISM: Artificial Sequence
<220> FEATURE:
<223> OTHER INFORMATION: Primer or probe

<400> SEQUENCE: 9
accgctaaca ttactgcagg cca 23

<210> SEQ ID NO 10
<211> LENGTH: 20
<212> TYPE: DNA
<213> ORGANISM: Artificial Sequence
<220> FEATURE:
<223> OTHER INFORMATION: Primer or probe

<400> SEQUENCE: 10
cggccgtgat ggaggctatg 20

<210> SEQ ID NO 11
<211> LENGTH: 18
<212> TYPE: DNA
<213> ORGANISM: Artificial Sequence
<220> FEATURE:

<223> OTHER INFORMATION: Primer or probe

<400> SEQUENCE: 11
agacagaggc caccacgg 18

<210> SEQ ID NO 12
<211> LENGTH: 23
<212> TYPE: DNA
<213> ORGANISM: Artificial Sequence
<220> FEATURE:
<223> OTHER INFORMATION: Primer or probe

<400> SEQUENCE: 12
tgacctttgg ctcggcctcc tgc 23

<210> SEQ ID NO 13
<211> LENGTH: 22
<212> TYPE: DNA
<213> ORGANISM: Artificial Sequence
<220> FEATURE:
<223> OTHER INFORMATION: HuALB reverse

<400> SEQUENCE: 13
gctgtcatct cttgtgggct gt 22

<210> SEQ ID NO 14
<211> LENGTH: 22
<212> TYPE: DNA
<213> ORGANISM: Artificial sequence
<220> FEATURE:
<223> OTHER INFORMATION: Primer or probe

<400> SEQUENCE: 14
aaactcatgg gagctgctgg tt 22

<210> SEQ ID NO 15
<211> LENGTH: 26
<212> TYPE: DNA
<213> ORGANISM: Artificial Sequence
<220> FEATURE:
<223> OTHER INFORMATION: Primer or probe

<400> SEQUENCE: 15
cctgtcatgc ccacacaaat ctctcc 26

<210> SEQ ID NO 16
<211> LENGTH: 18
<212> TYPE: DNA
<213> ORGANISM: Artificial Sequence
<220> FEATURE:
<223> OTHER INFORMATION: Primer B

<400> SEQUENCE: 16
gacgggaagg acgggaag 18

<210> SEQ ID NO 17
<211> LENGTH: 33
<212> TYPE: DNA
<213> ORGANISM: Artificial Sequence
<220> FEATURE:
<223> OTHER INFORMATION: Molecular beacon

<400> SEQUENCE: 17
cctctccgtg tcttgtactt cccgtcagag agg 33

ANTIVIRAL PYRIDOPYRAZINEDIONE COMPOUNDS

RELATED APPLICATIONS

This application is a divisional of U.S. patent application Ser. No. 16/569,107, filed Sep. 12, 2019, which claims the benefit of U.S. Provisional Application No. 62/730,361, filed Sep. 12, 2018, both of which are hereby incorporated herein by reference in their entirety.

SEQUENCE LISTING

The instant application contains a Sequence Listing which has been submitted electronically in ASCII format and is hereby incorporated by reference in its entirety. The ASCII copy, created on Jun. 17, 2021, is named 81971_332527_ST25.txt and is 3.3 KB in size.

FIELD OF THE INVENTION

The present invention relates to novel bicyclic pyridone compounds that are inhibitors of herpesvirus replication, and are thus useful to treat herpesvirus infections. The compounds inhibit viral DNA polymerases of various herpesviruses, including cytomegalovirus (CMV), herpes simplex viruses, and others. The invention provides novel bicyclic pyridone compounds as disclosed herein, pharmaceutical compositions containing such compounds, and methods of using these compounds and compositions in the treatment and prevention of herpesvirus disease.

BACKGROUND

Human CMV, also known as human herpesvirus 5 (HHV-5), is a β-herpesvirus that affects all populations, worldwide, including adults and children with normal or compromised immune systems. While often asymptomatic in healthy individuals, CMV can become life-threatening in immunocompromised individuals. CMV is also cause for concern during pregnancy, as it can be transmitted from mother to fetus and cause severe birth defects. No treatment is approved to prevent or treat congenital CMV infection. In the transplant setting, the current anti-CMV therapies include the nucleoside analogs Valganciclovir (valGCV), Ganciclovir (GCV) and Cidofovir (CDV), and a pyrophosphate analog, Foscarnet (FOS). Each of these therapeutic agents inhibits the CMV DNA polymerase, a protein encoded by the UL54 gene, which is an enzyme essential for viral replication (PNAS 2003, 100(24), 14223-14228; WO2013/152063; WO 2005/012545). In solid organ transplant recipients, the first line therapy consists of either prophylaxis or preemptive treatment with GCV, or the orally bioavailable prodrug valGCV. GCV significantly decreases the risk of disease, and can effectively treat active CMV infection. However, the drug is poorly tolerated. GCV and valGCV can cause severe bone marrow suppression which, in stem cell transplant recipients, puts the patient at risk for engraftment failure. Second line therapies such as CDV and FOS, are associated with severe nephrotoxicity. Moreover, resistance to current anti-CMV nucleoside analogs is a significant cause of treatment failure. Novel classes of CMV therapeutic agents are therefore needed, particularly non-nucleoside compounds, to provide safer CMV treatments and to combat herpesviruses that are resistant to known classes of antivirals.

In addition to CMV, herpesviruses that cause widespread human viral infections include Epstein-Barr virus (EBV), Varicella zoster virus (VZV), and herpes simplex viruses HSV-1 and HSV-2. Other herpesviruses that cause disease in humans include human herpesvirus 6, human herpesvirus 7, and Kaposi's sarcoma-associated herpesvirus Herpesvirus infections are not only widespread, they also persist lifelong in their host in latent stage. By one estimate, over 90% of adult humans are latently infected with at least one herpesvirus that may be reactivated years later. Zoster (Shingles), for example, results when the varicella zoster virus (VZV) is reactivated from latency, typically many years after the original infection (chicken pox) has been controlled. Zoster is a painful condition that affects primarily older adults and individuals with immune dysfunction. Complications include post-herpetic neuralgia, a potentially debilitating and chronic pain syndrome, against which anti-VZV inhibitors (nucleosides) only have a marginal impact.

Immunocompromised individuals such as transplant patients are at high risk for herpesvirus reactivation such as CMV, HSV or VZV. Thus a safe and potent viral inhibitor with broad herpesvirus activity would be extremely valuable. The current invention provides novel compounds that are active against several herpesviruses, including CMV, HSV, VZV and EBV.

SUMMARY

The present invention provides novel non-nucleoside compounds that inhibit herpesvirus DNA polymerases, with potent antiviral activity in vitro. Compounds are active against several herpesviruses, including, CMV, HSV, VZV and EBV. A potent non-nucleoside polymerase inhibitor has significant advantages over the current anti-CMV agents. First, unlike nucleoside analogs, the compounds are not incorporated by human polymerases and are thus expected to have a better safety profile than the current anti-CMV drugs. Second, the compounds described herein are active on GCV-resistant virus, thus having a potential for rescue therapy in patients with cross-resistance to nucleoside analogs. Finally, the compounds are active against several human herpesviruses providing opportunity for a broad clinical use. The invention also provides pharmaceutical compositions containing the novel compounds as well as methods to use the compounds and compositions to inhibit herpesvirus replication or reactivation, and to treat disease conditions associated with or caused by herpesviruses. Further objects of this invention are described in the following description and the examples.

In one aspect, the invention provides compounds of Formula (I):

(I)

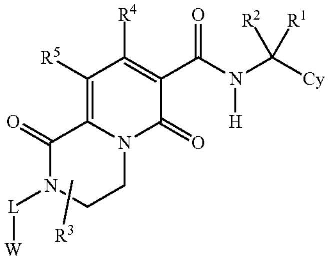

or a pharmaceutically acceptable salt thereof, wherein:

Cy is phenyl, pyridinyl, pyrimidinyl, or a 5-8 membered cycloalkyl, and Cy is optionally substituted with up to three groups selected from halo, CN, hydroxy, —N(R')$_2$, $C_{3-6}$ cycloalkyl, $C_{1-3}$ alkoxy, $C_{1-3}$haloalkyl, and $C_{1-3}$ alkyl substituted up to three (0-3) times with Z, wherein two of said $C_{1-3}$ alkyl substituted up to three times with Z, when directly attached to the same carbon atom, can be taken together with the carbon to which both are attached to form a 3-5 membered cycloalkyl ring substituted up to three times with Z; R' is selected from H and $C_{1-3}$ alkyl;

$R^2$ is selected from H and $C_{1-3}$ alkyl;

or R' and $R^2$ taken together with the carbon to which they are attached can form a 3-6 membered cycloalkyl ring;

$R^3$ represents up to two (0-2) optional substituents on the ring to which -L-W is directly attached, each of which is independently selected from halo, CN, $C_{1-3}$ alkoxy, $C_{1-3}$ alkyl, COOR', and C(O)NR'R';

$R^4$ is H, halo, or $C_{1-3}$ alkyl;

$R^5$ is selected from H, halo, CN, $C_{1-3}$ alkoxy, —NR'R', $C_{1-3}$ alkyl substituted up to three times with $Z^5$, $C_{2-4}$ alkenyl substituted up to three times with $Z^5$, $C_{2-4}$ alkynyl substituted up to three times with $Z^5$, and a ring selected from a 3-6 membered cycloalkyl ring, a 4-6 membered heterocyclic ring containing one or two heteroatoms selected from N, O and S as ring members, and a 5-6 membered heteroaryl ring containing up to four heteroatoms selected from N, O and S as ring members, where the 3-6 membered cycloalkyl ring, 4-6 membered heterocyclic ring, or 5-6 membered heteroaryl ring is optionally substituted with 1-2 $Z^5$;

L is a C1-C4 straight chain or branched alkylene linker, or L can be a C1-C4 straight chain or branched alkylene linker or a bond when W is an optionally substituted ring;

W is H, —OH, —OR, —C(O)NR'R', —COOR', —NR'COOR, —NR'C(O)R, —SO2R, —SO2NR'R', —NR'SO2R, —P(O)(OR')2, or an optionally substituted ring selected from 3-6 membered cycloalkyl, phenyl, 5-6-membered heterocyclyl containing one or two N, O or S heteroatoms as ring members, and 5-membered heteroaryl containing up to 4 heteroatoms selected from N, O and S as ring members that is optionally fused to phenyl, wherein the optional substituents for said optionally substituted ring are 1-3 groups selected from $C_{1-3}$ alkyl, oxo, halo, $C_{1-3}$ haloalkyl, -L2-OH, -L2-OR, -L2-OC(O)—NR'R', -L2-SO2R, -L2-SO2NR'R', -L2-SO2NR'—C(O)R, -L2-C(O)—NR'—SO2R, -L2-SOR, -L2-S(═O)(═NR')R, -L2-NR'SO2NR'R', -L2-NR'SO2R, -L2-NR'R', -L2-NR'C(O)R', -L2-NR-'COOR, -L2-C(O)NR'R', and -L2-COOR';

R at each occurrence is selected from C1-4 alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-4}$ alkyl, $C_{1-2}$ haloalkyl, oxo, -L3-CN, -L3-halo, -L3-C1-3 alkoxy, -L3-OH, -L3OC(O)—NR'R', -L3-SO2R', -L3-SO2NR'R', L3-SO2NR', —C(O)R", -L3-C(O)—NR', —SOR2', -L3-S(O)R', -L3-S(═O)(═NR')R', -L3-NR'SO2NR'R', -L3NR'SO2R', -L3-NR'R', -L3-NR'C(O)R', -L3-NR-'COOR', -L3-C(O)NR'R', and -L3-COOR', -L3-(5-6-membered heterocyclyl containing one or two N, O or S heteroatoms as ring members), -L3-C3-5 cycloalkyl, and -L3-(5-6 membered heteroaryl ring having up to four heteroatoms comprising 1-4 nitrogen atoms, 0-1 oxygen atoms, and 0-1 sulfur atoms as ring members), where the $C_{1-4}$ alkyl, 5-6-membered heterocyclyl, C3-5 cycloalkyl and 5-6 membered heteroaryl ring are each optionally further substituted with up to three groups independently selected from halo, $C_{1-3}$ alkyl, C1-3 haloalkyl, -L4-OR', -L4-CN, and -L4-N(R')2;

R' at each occurrence is independently selected from H, C1-4 alkyl optionally substituted with halo, —OH, amino, or $C_{1-2}$ alkoxy, and C3-6 cycloalkyl optionally substituted with halo, —OH, amino, or $C_{1-2}$ alkoxy;

or two R' taken together with a nitrogen atom to which both are directly attached can form a 4-6 membered ring optionally containing an additional N, O or S as a ring member and optionally substituted with one to three groups selected from $C_{1-2}$ alkyl, $C_{1-2}$ alkoxy, oxo, and hydroxy;

each L2 and L3 and L4 is independently a bond or a straight chain or branched $C_{1-3}$ alkylene;

Z and Z5 are independently selected at each occurrence from halo, hydroxy, CN, $C_{1-3}$ alkoxy, $C_{1-3}$ alkyl, and C3-5 cycloalkyl, and two Z groups, or two Z5 groups, taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl.

BRIEF DESCRIPTION OF DRAWINGS

FIG. 1 XRPD spectra showing two polymorphs (NX-7 and NX-12) of the compound of Example 1, and their behavior when slurried together in ethanol.

DETAILED DESCRIPTION

For purposes of interpreting this specification, the following definitions will apply, and whenever appropriate, terms used in the singular will also include the plural.

Terms used in the specification have the following meanings unless the context clearly indicates otherwise:

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

"Optionally substituted" means the group referred to can be substituted at one or more positions by any one or any combination of the radicals listed thereafter. The number, placement and selection of substituents is understood to encompass only those substitutions that a skilled chemist would expect to be reasonably stable; thus 'oxo' would not be a substituent on an aryl or heteroaryl ring, for example, and a single carbon atom would not have three hydroxy or amino substituents. Unless otherwise specified, optional substituents are typically up to four groups selected from halo, oxo, CN, amino, hydroxy, —$C_{1-3}$ alkyl, —OR*, —NR*$_2$, —SR*, —$SO_2$R*, —COOR*, and —CONR*$_2$, where each R* is independently H or $C_{1-3}$ alkyl, "Aryl" as used herein refers to a phenyl or naphthyl group unless otherwise specified. Aryl groups unless otherwise specified may be optionally substituted with up to four groups selected from halo, CN, amino, hydroxy, $C_{1-3}$ alkyl, —OR*, —NR*$_2$, —SR*, —$SO_2$R*, —COOR*, and —CONR*$_2$, where each R* is independently H or $C_{1-3}$ alkyl.

"Halo" or "halogen" as used herein, may be fluorine, chlorine, bromine or iodine.

"$C_{1-6}$ alkyl" or "$C_1$-$C_6$ alkyl.", as used herein, denotes straight chain or branched alkyl having 1-6 carbon atoms. If a different number of carbon atoms is specified, such as $C_4$ or $C_3$, then the definition is to be amended accordingly, such as "$C_{1-4}$ alkyl" will represent methyl, ethyl, propyl, isopropyl, butyl, isobutyl, sec-butyl and tort-butyl.

"$C_{1-6}$alkylene" or "$C_1$-$C_6$ alkylene", as used herein, denotes straight chain or branched alkyl having 1-6 carbon atoms and two open valences for connection to two other groups. If a different number of carbon atoms is specified, such as $C_4$ or $C_3$, then the definition is to be amended accordingly, such as "$C_{1-4}$ alkylene" will represent methylene (—$CH_2$—), ethylene (—$CH_2CH_2$—), straight chain or branched propylene (—$CH_2CH_2CH_2$— or —$C_2$—CHMe-$CH_2$—), and the like.

"$C_{1-6}$ alkoxy", as used herein, denotes straight chain or branched alkoxy (—O-Alkyl) having 1-6 carbon atoms. If a different number of carbon atoms is specified, such as $C_4$ or $C_3$, then the definition is to be amended accordingly, such as "alkoxy" will represent methoxy, ethoxy, propoxy, isopropoxy, butoxy, isohutoxy, sec-butoxy and tert-butoxy.

"$C_{1-4}$ Haloalkyl" or "$C_1$-$C_1$ haloalkyl" as used herein, denotes straight chain or branched alkyl having 1-4 carbon atoms wherein at least one hydrogen has been replaced with a halogen. The number of halogen replacements can be from one up to the number of hydrogen atoms on the unsubstituted alkyl group. If a different number of carbon atoms is specified, such as $C_6$ or $C_3$, then the definition is to be amended accordingly, Thus "$C_{1-4}$ haloalkyl" will represent methyl, ethyl, propyl, isopropyl, butyl, isobutyl, sec-butyl and tort-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CH(CF_3)$— or $CF_3CF_2CF_2CF_2$—.

"$C_{3-8}$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be amended accordingly.

"4- to 8-Membered heterocyclyl", "5- to 6-membered heterocyclyl". "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings; unless otherwise specified, such rings contain 1 to 7, 1 to 5, or 1 to 3 heteroatoms selected from the group consisting of nitrogen, oxygen and sulfur as ring members, and the rings may be saturated, or partially saturated but not aromatic. The heterocyclic group can be attached to another group at a nitrogen or a carbon atom. The term "heterocyclyl" includes single ring groups, fused ring groups and bridged groups. Examples of such heterocyclyl include, but are not limited to pyrrolidine, piperidine, piperazine, pyrrolidinone, morpholine, tetrahydrofuran, tetrahydrothiophene, tetrahydrothiopyran, tetrahydropyran, 1,4-dioxane, 1,4-oxathiane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diaza-bicyclo[2.2.1]heptane, azetidine, ethylenedioxo, oxetane or thiazole. In certain embodiments, if not otherwise specified, heterocyclic groups have 1-2 heteroatoms selected from N, O and S as ring members, and 4-7 ring atoms, and are optionally substituted with up to four groups selected from halo, oxo, CN, amino, hydroxy, $C_{1-3}$ alkyl, —OR*, —NR*$_2$, —SR*, —$SO_2$R*, —COOR*, and —CONR*$_2$, where each R* is independently H or $C_{1-3}$ alkyl. In particular, heterocyclic groups containing a sulfur atom are optionally substituted with one or two oxo groups on the sulfur.

"Heteroaryl" is a completely unsaturated (aromatic) ring. The term "heteroaryl." refers to a 5-14 membered monocyclic- or bicyclic- or tricyclic-aromatic ring system, having 1 to 8 heteroatoms selected from N, O or S. Typically, the heteroaryl is a 5-10 membered ring or ring system (e.g., 5-7 membered monocyclic group or an 8-lit membered bicyclic group), often a 5-6 membered ring containing up to four heteroatoms selected from N, O and S, though often a heteroaryl ring contains no more than one divalent O or S in the ring. Typical heteroaryl groups include furan, isothiazole, thiadiazole, oxadiazole, indazole, indole, quinoline, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-1,2,3-triazolyl), tetrazolyl, triazine, pyrimidine, 2-, 3-, or 4-pyridyl, 3- or 4-pyridazinyl, 3-, 4-, or 5-pyrazinyl, 2-pyridinyl, and 2-, 4-, or 5-pyrimidinyl. Heteroaryl groups are and are optionally substituted with up to four groups selected from halo, CN, amino, hydroxy, $C_{1-3}$ alkyl, —OR*, —NR*$_2$, —SR*, —$SO_2$R*, —COOK*, and —CONR*$_2$, where each R* is independently H or $C_{1-3}$ alkyl.

The term "hydroxy" or "hydroxyl" refers to the group

Various embodiments of the invention are described herein. It will be recognized that features specified in each embodiment may be combined with other specified features to provide further embodiments. The following enumerated embodiments are representative of the invention:

1. A compound of formula (I):

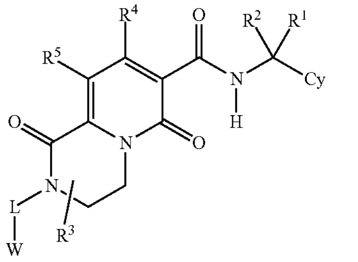

(I)

or a pharmaceutically acceptable salt thereof, wherein:

Cy is phenyl, pyridinyl, pyrimidinyl, or a 5-8 membered cycloalkyl, and Cy is optionally substituted with up to three groups selected from halo, CN, hydroxy, —N(R')$_2$, $C_{3-6}$ cycloalkyl, $C_{1-3}$ alkoxy, $C_{1-3}$ haloalkyl, and $C_{1-3}$ alkyl substituted up to three (0-3) times with Z, wherein two of said $C_{1-3}$ alkyl substituted up to three times with Z, when directly attached to the same carbon atom, can be taken together with the carbon to which both are attached to form a 3-5 membered cycloalkyl ring substituted up to three times with Z;

$R^1$ is selected from H and $C_{1-3}$ alkyl;

$R^2$ is selected from H and $C_{1-3}$ alkyl;

or $R^1$ and $R^2$ taken together with the carbon to which they are attached can form a 3-6 membered cycloalkyl ring;

$R^3$ represents up to two (0-2) optional substituents on the ring to which -L-W is directly attached, each of which is independently selected from halo, CN, $C_{1-3}$ alkoxy, $C_{1-3}$ alkyl, COOR', and C(O)NR'R';

$R^4$ is H, halo, or $C_{1-3}$ alkyl;

$R^5$ is selected from H, halo, CN, $C_{1-3}$ alkoxy, —NR'R', $C_{1-3}$ alkyl substituted up to three times with $Z^5$, $C_{2-4}$ alkenyl substituted up to three times with $Z^5$, $C_{2-4}$ alkynyl substituted up to three times with $Z^5$, and a ring selected from a 3-6 membered cycloalkyl ring, a 4-6 membered heterocyclic ring containing one or two heteroatoms selected from N, O and S as ring members, and a 5-6 membered heteroaryl ring containing up to four heteroatoms selected from N, O and S as ring members, where the 3-6 membered cycloalkyl ring, 4-6 membered heterocyclic ring, or 5-6 membered heteroaryl ring is optionally substituted with 1-2 $Z^5$;

L is a $C_1$-$C_4$ straight chain or branched alkylene linker, or L can be a $C_1$-$C_4$ straight chain or branched alkylene linker or a bond when W is an optionally substituted ring;

W is H, —OH, —OR, —C(O)NR'R', —COOR', —NR'R', —NR'COOR, —NR'C(O)R, —$SO_2$R, —$SO_2$NR'R', —NR'$SO_2$R, —P(O)(OR')$_2$, or an optionally substituted ring selected from 3-6 membered cycloalkyl, phenyl, 5-6-membered heterocyclyl containing one or two N, O or S heteroatoms as ring members, and 5-membered heteroaryl containing up to 4 heteroatoms selected from N, O and S as ring members that is optionally fused to phenyl, wherein the optional substituents for said optionally substituted ring are 1-3 groups selected from $C_{1-3}$ alkyl, oxo, halo, $C_{1-3}$ haloalkyl, -$L^2$-OH, -$L^2$-OR, -$L^2$-OC(O)—NR'R', -$L^2$-$SO_2$R, -$L^2$-SO2NR'R', -$L^2$-$SO_2$NR'—C(O)R, -$L^2$-C(O)—NR'—SO2R, -$L^2$-SOR, -$L^2$-S(═O)(═NR')R, -$L^2$-NR'$SO_2$NR'R', -$L^2$-NR'$SO_2$R, -$L^2$-NR' R', -$L^2$-NR' C(O)R', -$L^2$-NR' COOR, -$L^2$-C(O)NR'R', and -$L^2$-COOR';

R at each occurrence is selected from $C_1$-4 alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-4}$ alkyl, $C_{1-2}$ haloalkyl, oxo, -$L^3$-CN, -$L^3$-halo, -$L^3$-$C_{1-3}$ alkoxy, -$L^3$-OH, -$L^3$-OC(O)—NR'R', -$L^3$-SO2R', -$L^3$-$SO_2$NR'R', -$L^3$-$SO_2$NR'—C(O)R', -$L^3$-C(O)—NR'—$SO_2$R', -$L^3$-SOR', -$L^3$-S(═O)(═NR')R', -$L^3$-NR'$SO_2$NR'R', -$L^3$-NR'$SO_2$R', -$L^3$-NR'R', -$L^3$-NR'C(O)R', -$L^3$-NR' COOR', -$L^3$-C(O)NR'R', and -$L^3$-COOR', -$L^3$-(5-6-membered heterocyclyl containing one or two N, O or S heteroatoms as ring members), -$L^3$-$C_{3-5}$ cycloalkyl, and -$L^3$-(5-6 membered heteroaryl ring having up to four heteroatoms comprising 1-4 nitrogen atoms, 0-1 oxygen atoms, and 0-1 sulfur atoms as ring members), where the $C_{1-4}$ alkyl, 5-6-membered heterocyclyl, $C_{3-5}$ cycloalkyl and 5-6 membered heteroaryl ring are each optionally further substituted with up to three groups independently selected from halo, $C_{1-3}$ alkyl, $C_{1-3}$ haloalkyl, -$L^4$-OR', -$L^4$-CN, and -$L^4$-N(R')$_2$;

R' at each occurrence is independently selected from H, $C_{1-4}$ alkyl optionally substituted with halo, —OH, amino, or $C_{1-2}$ alkoxy, and $C_{3-6}$ cycloalkyl optionally substituted with halo, —OH, amino, or $C_{1-2}$ alkoxy;

or two R' taken together with a nitrogen atom to which both are directly attached can form a 4-6 membered ring optionally containing an additional N, O or S as a ring member and optionally substituted with one to three groups selected from $C_{1-2}$ alkyl, $C_{1-2}$ alkoxy, oxo, and hydroxy;

each $L^2$ and $L^3$ and $L^4$ is independently a bond or a straight chain or branched $C_{1-3}$ alkylene;

Z and $Z^5$ are independently selected at each occurrence from halo, hydroxy, CN, $C_{1-3}$ alkoxy, $C_{1-3}$ alkyl, and $C_{3-5}$ cycloalkyl, and two Z groups, or two $Z^5$ groups, taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl.

2. The compound according to embodiment 1 or a pharmaceutically acceptable salt thereof, wherein $R^1$ is H.

3. The compound according to embodiment 1 or embodiment 2 or a pharmaceutically acceptable salt thereof, wherein $R^2$ is H. In an alternative embodiment, $R^2$ is methyl.

4. The compound according to any one of embodiments 1 to 3 or a pharmaceutically acceptable salt thereof, wherein Cy is selected from phenyl, pyridin-3-yl, and cyclohexyl, each of which is optionally substituted with 1 to 3 groups selected from halo, $CF_3$, and CN. In some of these embodiments, Cy is phenyl with 1 or 2 substituents selected from Cl, F, Br and CN. In some of these embodiments, the substituents on the phenyl ring Cy are at the meta and/or para positions of the phenyl ring.

5. The compound according to any of the preceding embodiments or a pharmaceutically acceptable salt thereof, wherein $R^4$ is H.

6. The compound according to any of the preceding embodiments or a pharmaceutically acceptable salt thereof, wherein $R^5$ is H, halo, methyl, or halomethyl. In some of these embodiments, $R^5$ is H.

7. The compound according to any of the preceding embodiments or a pharmaceutically acceptable salt thereof, wherein $R^3$ is absent or $R^3$ represents one or two methyl groups. In some of these embodiments, $R^3$ is absent, i.e., it represents 0 substituents.

8. The compound according to any of the preceding embodiments or a pharmaceutically acceptable salt thereof, wherein L is $—CH_2$- or $—(CH_2)_2—$. In some of these embodiments, L is $—CH_2—$.

9. The compound according to any of the preceding embodiments or a pharmaceutically acceptable salt thereof, wherein W is cyclopropyl substituted with a group selected from $C_{1-3}$ alkyl, oxo, halo, $C_{1-3}$ alkoxy, OH, $—SO_2R$, $—SO_2NR'R'$, —SOR, —S(═O)(═NR')R, $—NR'SO_2NR'R'$, $—NR'SO_2R$, —NR'R', —OR, —NR-'COOR, —C(O)NR'R', and COOR'.

10. The compound according to any of embodiments 1-8 or a pharmaceutically acceptable salt thereof, wherein the moiety W-L- is selected from the group consisting of

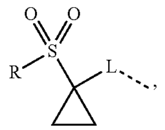
,
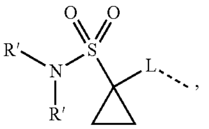
,
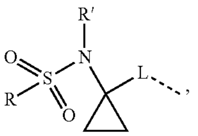
,
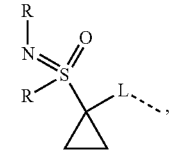
,
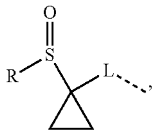
,
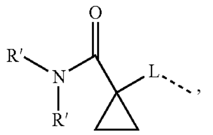
,
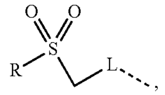
,
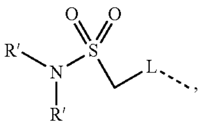
,
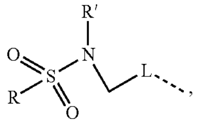
,
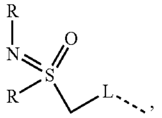
,
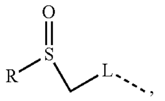
, and
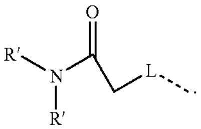
.

In some of these embodiments, L is $CH_2$. R in these embodiments is sometimes selected from methyl, ethyl, isopropyl and cyclopropyl at each occurrence. R' in these embodiments is sometimes selected from H and methyl at each occurrence.

11. The compound according to any of the preceding embodiments or a pharmaceutically acceptable salt thereof, wherein Cy is phenyl, and is optionally substituted with 1 or 2 groups selected from halo, CN, OH, $C_{1-3}$ alkyl, and $C_{1-3}$ alkoxy.

12. The compound according to embodiment 11, or a pharmaceutically acceptable salt thereof, wherein Cy is selected from

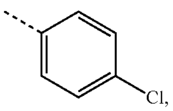
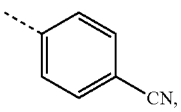
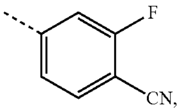
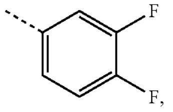
and
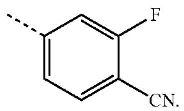

13. The compound according to any of the preceding embodiments, or a pharmaceutically acceptable salt thereof, wherein the compound of Formula (I) is of the Formula (II):

(II)

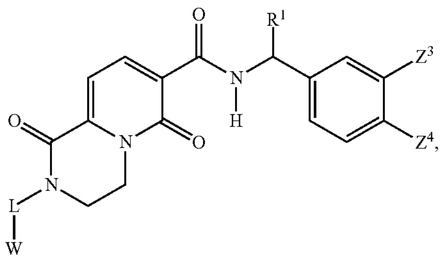

wherein:

$R^1$ is H or methyl;

$Z^3$ and $Z^4$ are independently selected from H, halo, CN, Me, and OMe;

L is a $C_1$-$C_4$ straight chain or branched alkylene linker;

W is $—SO_2R$, $—SO_2NR'R'$, $—NR'SO_2R$, or an optionally substituted $C_1$-$C_3$ alkyl, or an optionally substituted 3-6 membered cycloalkyl;

wherein the optional substituents for said optionally substituted $C_1$-$C_3$ alkyl and optionally substituted cycloalkyl are 1-3 groups independently selected from $C_{1-3}$ alkyl, oxo, halo, $C_{1-3}$ alkoxy, OH, $—SO_2R$, $—SO_2NR'R'$, $—NR'SO_2NR'R'$, $—NR'SO_2R$, —NR'R', —OR, —NR'COOR, —C(O)NR'R', and COOR', R at each occurrence is independently selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups independently selected from $C_{1-3}$ alkyl, oxo, CN, halo, $C_{1-3}$ alkoxy, OH, and C3-5 cycloalkyl;

R' at each occurrence is independently selected from H and $C_{1-4}$ alkyl optionally substituted with halo, —OH or $C_{1-2}$ alkoxy;

or two R' taken together with a nitrogen atom to which both are directly attached can form a 4-6 membered ring optionally containing an additional N, O or S as a ring member and optionally substituted with one or two groups selected from $C_{1-2}$ alkyl, $C_{1-2}$ alkoxy, oxo, and hydroxy;

or a pharmaceutically acceptable salt thereof.

14. The compound of any of the preceding embodiments, or a pharmaceutically acceptable salt thereof, wherein the compound of Formula (I) is of Formula (III):

(III)

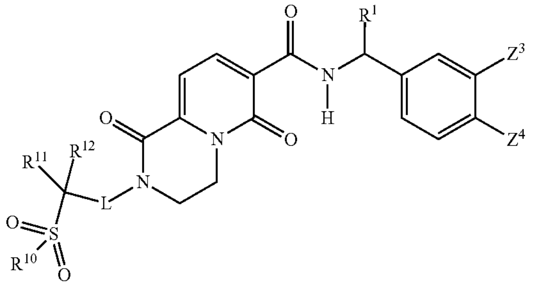

wherein $R^{11}$ and $R^{12}$ are each independently H or $C_1$, —$C_3$ alkyl, or $R^{11}$ and $R^{12}$ taken together with the carbon atom to which they are attached form a $C_{3-5}$ cycloalkyl ring;

$R^{10}$ is selected from $C_1$-$C_3$ alkyl, $C_3$-$C_5$ cycloalkyl, and —$NR^{13}R^{14}$, where $R^{13}$ and $R^{14}$ are independently selected from H and $C_{1-3}$ alkyl, or $R^{13}$ and $R^{14}$ taken together with the N to which both are attached form a ring selected from azetidine, pyrrolidine, piperidine, piperazine and morpholine, wherein the azetidine, pyrrolidine, piperidine, piperazine or morpholine is optionally substituted by one to three groups independently selected from oxo, $C_1$ alkyl, $C_{1-3}$ alkoxy, CN, and halo;

L is a bond, $CH_2$, or $CH_2CH_2$;

$R^1$ is H or Me; and $Z^3$ and $Z^4$ are independently selected from H, CN, and halo.

15. The compound of embodiment 14, wherein $Z^3$ and $Z^4$ are not both H.

16. The compound of embodiment 14, wherein $R^1$ is H.

17. The compound of embodiment 14, wherein $R^{10}$ is cyclopropyl.

18. The compound of any of Examples 1-212 or a pharmaceutically acceptable salt thereof. This embodiment includes each of the Examples represented in the Table of Bioactivity Data herein.

19. A pharmaceutical composition, comprising a compound of any of the preceding embodiments admixed with at least one pharmaceutically acceptable carrier.

20. A method to treat a herpesvirus infection, which comprises administering to a patient having a herpesvirus infection a compound of any of embodiments 1-17 or a pharmaceutical composition comprising a compound of any of embodiments 1-17.

21. The method of embodiment 20, wherein the herpesvirus is selected from cytomegalovirus (CMV), Epstein-Barr virus (EBV), Varicella zoster virus (VZV), herpes simplex virus including HSV-1 and HSV-2, herpesvirus 6, human herpesvirus 7, and Kaposi's sarcoma-associated herpesvirus.

22. A compound of Formula (IV):

(IV)

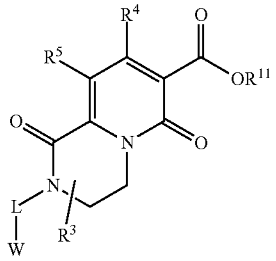

wherein:

$R^{11}$ is H or $C_1$-$C_6$ alkyl optionally substituted up to three times with Z;

$R^3$ represents up to two (0-2) optional substituents on the ring to which -L-W is directly attached, each of which is independently selected from halo, CN, $C_{1-3}$ alkoxy, $C_{1-3}$ alkyl, COOR', and C(O)NR'R';

$R^4$ is H, halo, or $C_{1-3}$ alkyl;

$R^5$ is selected from H, halo, CN, $C_{1-3}$ alkoxy, —NR'R', $C_{1-3}$ alkyl substituted up to three times with $Z^5$, $C_{2-4}$ alkenyl substituted up to three times with $Z^5$, $C_{2-4}$ alkynyl substituted up to three times with $Z^5$, and a ring selected from a 3-6 membered cycloalkyl ring, a 4-6 membered heterocyclic ring containing one or two heteroatoms selected from N, O and S as ring members, and a 5-6 membered heteroaryl ring containing up to four heteroatoms selected from N, O and S as ring members, where the 3-6 membered cycloalkyl ring, 4-6 membered heterocyclic ring, or 5-6 membered heteroaryl ring is optionally substituted with 1-2 $Z^5$;

L is a $C_1$-$C_4$ straight chain or branched alkylene linker or a bond;

W is H, —OH, —OR, —C(O)NR'R', —COOR', —NR'R', —NR'COOR, —NR'C(O)R, —$SO_2$R, —$SO_2$NR'R', —NR'$SO_2$R, —P(O)$(OR')_2$, or an optionally substituted ring selected from 3-6 membered cycloalkyl, phenyl, 5-6-membered heterocyclyl containing one or two N, O or S heteroatoms as ring members, and 5-membered heteroaryl containing up to 4 heteroatoms selected from N, O and S as ring members that is optionally fused to phenyl, wherein the optional substituents for said optionally substituted ring are 1-3 groups selected independently from $C_{1-3}$ alkyl, oxo, halo, $C_{1-3}$ haloalkyl, -$L^2$-OC(O)—NR'R', -$L^2$-$SO_2$R, -$L^2$-$SO_2$NR'R', -$L^2$-$SO_2$NR'—C(O)R, -$L^2$C(O)—NR'—$SO_2$R, -$L^2$-SOR, -$L^2$-S(═O)(═NR') R, -$L^2$-NR'$SO_2$NR'R', -$L^2$-NR'$SO_2$R, -$L^2$-NR'R', -$L^2$-NR'C(O)R', -$L^2$-NR'COOR, -$L^2$-C(O)NR'R', and -$L^2$-COOR';

R at each occurrence is selected independently from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups independently selected from $C_{1-4}$ alkyl, $C_{1-2}$ haloalkyl, oxo, -$L^3$-CN, -$L_{1-3}$ halo, -$L^3$C1-3alkoxy, -$L^3$OH, -$L^3$-OC(O)—NR'R', -$L^3$-$SO_2$R'; -$L^3$-SO2NR'R', -$L^3$-$SO_2$NR'—C(O)R', -$L^3$-C(O)—NR'—$SO_2$R', -$L^3$-SOR', -$L^3$-S(═O)(═NR')R', -$L^3$-NR'$SO_2$NR'R', -$L^3$-NR'$SO_2$R', -$L^3$-NR'R', -$L^3$-NR'C (O)R', $-L^3$-NR'COOR', $-L^3$-C(O)NR'R', and $-L^3$-COOR', $-L^3$-(5-6-membered heterocyclyl containing one or two N, O or S heteroatoms as ring members), $-L^3-C_{3-5}$ cycloalkyl, and $-L^3$-(5-6 membered heteroaryl ring having up to four heteroatoms comprising 1-4 nitrogen atoms, 0-1 oxygen atoms, and 0-1 sulfur atoms as ring members), where the $C_{1-4}$ alkyl, 5-6-membered heterocyclyl, $C_{3-5}$ cycloalkyl and 5-6 membered heteroaryl ring are each optionally further substituted with up to three groups independently selected from halo, $C_{1-3}$ alkyl, $C_{1-3}$ haloalkyl, $-L^4$-OR', $-L^4$-CN, and $-L^4$-N(R')2;

R' at each occurrence is independently selected from H, $C_{1-4}$ alkyl optionally substituted with halo, —OH, amino, or $C_{1-2}$ alkoxy, and $C_{3-6}$ alkyl optionally substituted with halo, —OH, amino, or $C_{1-2}$ alkoxy;

or two R' taken together with a nitrogen atom to which both are directly attached can form a 4-6 membered ring optionally containing an additional N, O or S as a ring member and optionally substituted with one to three groups selected from C1-2 alkyl, C1-2 alkoxy, oxo, and hydroxy;

each $L^2$ and $L^3$ and $L^4$ is independently a bond or a straight chain or branched C1-3 alkylene;

Z and $Z^5$ are independently selected at each occurrence from halo, hydroxy, CN, $C_{1-3}$ alkoxy, $C_{1-3}$ alkyl, and C3-5 cycloalkyl, and two Z groups, or two $Z^5$ groups, taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl; or a salt thereof.

23. The compound of embodiment 22, wherein $R^{11}$ is H or $C_1$-$C_6$ alkyl.

24. The compound of embodiment 22 or embodiment 23, wherein $R^3$ is absent.

25. The compound of any of embodiments 22-24, wherein $R^4$ and $R^5$ each represent H.

26. The compound according to embodiment 22, wherein:

L is a $C_1$-$C_4$ straight chain or branched alkylene linker;

W is —$SO_2$R, —$SO_2$NR'R', —NR'$SO_2$R, or an optionally substituted $C_1$-$C_3$ alkyl, or an optionally substituted 3-6 membered cycloalkyl;

wherein the optional substituents for said optionally substituted $C_1$-$C_3$ alkyl and optionally substituted cycloalkyl are 1-3 groups independently selected from $C_{1-3}$ alkyl, oxo, halo, $C_{1-3}$ alkoxy, OH, —$SO_2$R, —$SO_2$NR'R', —NR'$SO_2$NR'R', —NR'$SO_2$R, —NR'R', —OR, —NR'COOR, —C(O)NR'R', and COOR', R at each occurrence is independently selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-3}$ alkyl, oxo, CN, halo, $C_{1-3}$ alkoxy, OH, and $C_{3-5}$ cycloalkyl; R' at each occurrence is independently selected from H and $C_{1-4}$ alkyl optionally substituted with halo, —OH or $C_{1-2}$ alkoxy;

or two R' taken together with a nitrogen atom to which both are directly attached can form a 4-6 membered ring optionally containing an additional N, O or S as a ring member and optionally substituted with one or two groups selected from $C_{1-2}$ alkyl, $C_{1-2}$ alkoxy, oxo, and hydroxy.

27. The compound according to any of embodiments 22-26, wherein the grotto W-L- is selected from the grotto consisting of:

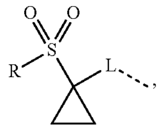,
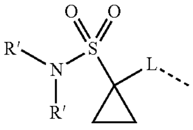,
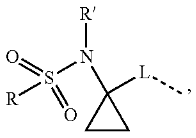,
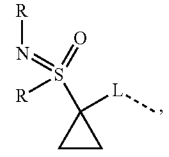,
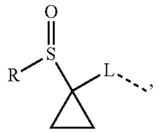,
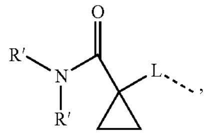,
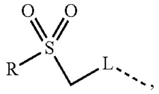,
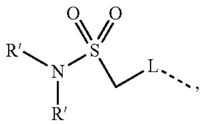,
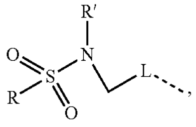,
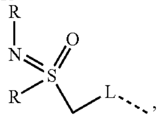,
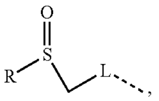, and
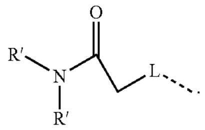.

28. The compound according to any of embodiments 22-27, wherein L is $CH_2$.

29. The compound according to any of embodiments 22-28, wherein R at each occurrence is selected independently from methyl, ethyl, isopropyl and cyclopropyl.

30. The compound according to any of embodiments 22-29, wherein R' at each occurrence is selected from H and methyl.

31. A method of making a compound according to embodiment 1, comprising:

contacting a compound of Formula (V)

(V)

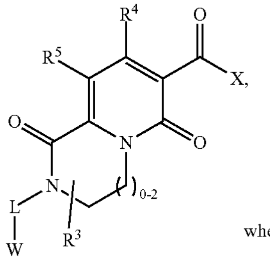

wherein

X represents —OH or a leaving group; $R^3$ represents up to two (0-2) optional substituents on the ring containing two nitrogen atoms, where each $R^3$ is independently selected from halo, CN, $C_{1-3}$ alkoxy, $C_{1-3}$ alkyl, COOR', C(O)$NH_2$, and C(O)NRR';

$R^4$ is H, halo, or $C_{1-3}$ alkyl;

$R^5$ is selected from H, halo, CN, $C_{1-3}$ alkoxy, —$NH_2$, —NRR', $C_{1-3}$ alkyl substituted up to three times with $Z^5$, $C_{2-4}$ alkenyl substituted up to three times with Z5, $C_{2-4}$ alkynyl substituted up to three times with $Z^5$, and a ring selected from a 3-6 membered cycloalkyl ring, a 4-6 membered heterocyclic ring containing one or two heteroatoms selected from N, O and S as ring members, and a 5-6 membered heteroaryl ring containing up to four heteroatoms selected from N, O and S as ring members, where the 3-6 membered cycloalkyl ring, 4-6 membered heterocyclic ring, or 5-6 membered heteroaryl ring is optionally substituted with 1-2 $Z^5$;

L is a $C_1$-$C_4$ straight chain or branched alkylene linker;

W is —OR', —NH2, —NRR', —NR'COOR, —NR'C(O)R', —SO2R, —SO2NH2, —SO2NRR', —NR'$SO_2$R, or an optionally substituted $C_1$-$C_3$ alkyl, or an optionally substituted ring selected from 3-6 membered cycloalkyl, 5-6-membered heterocyclyl containing one or two N, O or S heteroatoms as ring members, and 5-membered heteroaryl containing up to 4 heteroatoms selected from N, O and S as ring members, wherein the optional substituents for said optionally substituted $C_1$-$C_3$ alkyl and optionally substituted ring are 1-3 groups independently selected from $C_{1-3}$ alkyl, oxo, halo, $C_{1-3}$ alkoxy, OH, —$SO_2$R, —$SO_2$NR'R', —SOR, —S(═O)(═NR')R, —NR'$SO_2$NR'R', —NR'$SO_2$R, —$NH_2$, —NR'R', —OR, —NR'COOR, —C(O)$NH_2$, —C(O)NRR', and COOR'.

R at each occurrence is independently selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected independently from $C_{1-3}$ alkyl, oxo, CN, halo, $C_{1-3}$ alkoxy, OH, and $C_{1-5}$ cycloalkyl;

R' at each occurrence is independently selected from H and $C_{1-4}$ alkyl optionally substituted with halo, —OH or $C_{1-2}$ alkoxy;

or R and R' taken together with a nitrogen atom to which both are directly attached can form a 4-6 membered ring optionally containing an additional N, O or S as a ring member and optionally substituted with one or two groups selected from $C_{1-2}$ alkyl, $C_{1-2}$ alkoxy, oxo, and hydroxy;

Y at each occurrence is independently selected from halo, $C_{1-2}$ alkyl, $C_{1-2}$ haloalkyl, and $C_{1-2}$ alkoxy;

each $Z^5$ is selected independently at each occurrence from halo, hydroxy, CN, $C_{1-3}$ alkoxy, $C_{1-3}$ alkyl, and two $Z^5$ groups, taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl;

with a compound of Formula (VI):

(VI)

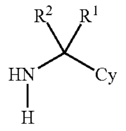

wherein Cy is phenyl, pyridinyl, pyrimidinyl, or a 5-8 membered cycloalkyl, and Cy is optionally substituted with up to three groups selected from halo, CN, hydroxy, —N(R')$_2$, $C_{3-6}$ cycloalkyl, $C_{1-3}$ alkoxy, $C_{1-3}$ haloalkyl, and $C_{1-3}$ alkyl substituted up to three (0-3) times with Z, wherein two of said $C_{1-3}$ alkyl substituted up to three times with Z, when directly attached to the same carbon atom, can be taken together with the carbon to which both are attached to form a 3-5 membered cycloalkyl ring substituted up to three times with Z;

$R^1$ is selected from H and $C_{1-3}$ alkyl;

$R^2$ is selected from H and $C_{1-3}$ alkyl;

or $R^1$ and $R^2$ taken together with the carbon to which they are attached can form a 3-6 membered cycloalkyl ring;

Z is independently selected at each occurrence from halo, hydroxy, CN, $C_{1-3}$ alkoxy, $C_{1-3}$ alkyl, and $C_{3-5}$ cycloalkyl, and two Z groups taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl.

32. The method according to embodiment 31, wherein the leaving group is selected from the group consisting of halo and an acyl group.

33. The method according to embodiment 31 or embodiment 32, wherein the acyl group is —OC(O)—O—R*, where R* represents a $C_1$-$C_6$ alkyl, optionally substituted with up to three halo or C1-3 alkoxy groups.

34. The method according to any of embodiments 31-33, wherein the compound of Formula (V) is a compound of the formula (VB):

(VB)

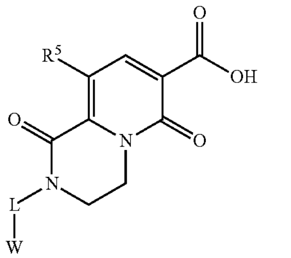

where $R^5$ is H or halo; L is —$CH_2$—; and W is cyclopropyl substituted with —$SO_2$R, where R is as defined for Formula (V).

In certain embodiments, the compound of Formula (I) is of the formula (II):

(II)

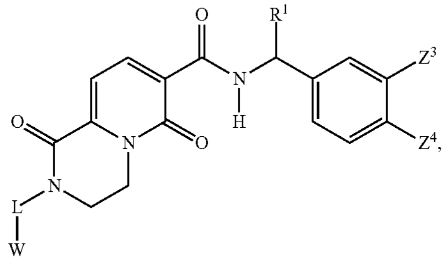

wherein:

R1 is H or Methyl;

Z3 and Z4 are independently selected from H, halo, CN, Me, and OMe;

L is a C1-C4 straight chain or branched alkylene linker;

W is —SO2R, —SO2NR'R', —NR'SO2R, or an optionally substituted C1-C3 alkyl, or an optionally substituted 3-6 membered cycloalkyl;

wherein the optional substituents for said optionally substituted C1-C3 alkyl and optionally substituted cycloalkyl are 1-3 groups independently selected from $C_{1-3}$ alkyl, oxo, halo, $C_{1-3}$ alkoxy, OH, —SO2R, —SO2NR'R', —NR'SO2NR'R', —NR'SO2R, —NR'R', —OR, —NR'COOR, —C(O)NR'R', and COOR', R at each occurrence is independently selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-3}$ alkyl, oxo, CN, halo, $C_{1-3}$ alkoxy, OH, and C3-5 cycloalkyl;

R' at each occurrence is selected from H and $C_{1-4}$ alkyl optionally substituted with halo, —OH or $C_{1-2}$ alkoxy;

or two R' taken together with a nitrogen atom to which both are directly attached can form a 4-6 membered ring optionally containing an additional N, O or S as a ring member and optionally substituted with one or two groups selected from $C_{1-2}$ alkyl, $C_{1-2}$ alkoxy, oxo, and hydroxy;

or a pharmaceutically acceptable salt thereof.

Preferred compounds of Formula (I) include compounds of Formula (III):

(III)

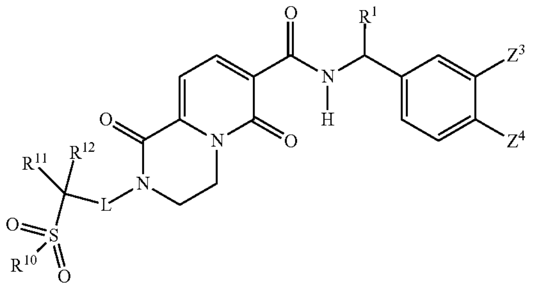

wherein R11 and R12 each represent H or C1-C3 alkyl, or R11 and R12 taken together with the carbon atom to which they are attached form a C3-5 cycloalkyl ring;

R10 is selected from C1-C3 alkyl, C3-05 cycloalkyl, and —NR13R14, where R13 and R14 are independently selected from H and $C_{1-3}$ alkyl, or R13 and R14 taken together with the N to which both are attached form a ring selected from azetidine, pyrrolidine, piperidine, piperazine and morpholine that is optionally substituted by one to three groups selected from oxo, $C_{1-3}$ alkyl, $C_{1-3}$ alkoxy, CN, and halo; L is a bond or CH2 or CH2CH2; R1 can be H or Me; and Z3 and Z4 are selected from H, CN, and halo. Preferably, Z3 and Z4 are not both H. Frequently, R1 is H. In certain embodiments of the compounds of formula (III), $R^{10}$ is cyclopropyl.

Another aspect of the invention provides compounds of Formula (IV):

(IV)

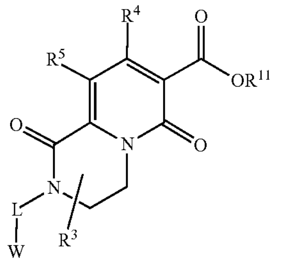

wherein:

$R^{11}$ is H or $C_1$-$C_6$ alkyl optionally substituted up to three times with Z;

$R^3$ represents up to two (0-2) optional substituents on the ring to which -L-W is directly attached, each of which is independently selected from halo, CN, $C_{1-3}$ alkoxy, $C_{1-3}$ alkyl, COOR', and C(O)NR'R';

$R^4$ is H, halo, or $C_{1-3}$ alkyl;

$R^5$ is selected from H, halo, CN, $C_{1-3}$ alkoxy, —NR'R', $C_{1-3}$ alkyl substituted up to three times with $Z^5$, $C_{2-4}$ alkenyl substituted up to three times with $Z^5$, $C_{2-4}$alkynyl substituted up to three times with $Z^5$, and a ring selected from a 3-6 membered cycloalkyl ring, a 4-6 membered heterocyclic ring containing one or two heteroatoms selected from N, O and S as ring members, and a 5-6 membered heteroaryl ring containing up to four heteroatoms selected from N, O and S as ring members, where the 3-6 membered cycloalkyl ring, 4-6 membered heterocyclic ring, or 5-6 membered heteroaryl ring is optionally substituted with 1-2 $Z^5$;

L is a $C_1$-$C_4$ straight chain or branched alkylene linker or a bond;

W is H, —OH, —OR, —C(O)NR'R', —COOR', —NR'R', —NR'COOR, —NR'C(O)R, —$SO_2$R, —$SO_2$NR'R', —NR'$SO_2$R, —P(O)(OR')$_2$, or an optionally substituted ring selected from 3-6 membered cycloalkyl, phenyl, 5-6-membered heterocyclyl containing one or two N, O or S heteroatoms as ring members, and 5-membered heteroaryl containing up to 4 heteroatoms selected from N, O and S as ring members that is optionally fused to phenyl, wherein the optional substituents for said optionally substituted ring are 1-3 groups selected from $C_{1-3}$ alkyl, oxo, halo, $C_{1-3}$ haloalkyl, -$L^2$-OH, -$L^2$-OR, -$L^2$-OC(O)—NR'R', -$L^2$-$SO_2$R, -$L^2$-$SO_2$NR'R', -$L^2$-$SO_2$NR'—C(O)R, -$L^2$-C(O)—NR'—$SO_2$R, -$L^2$-SOR, -$L^2$-S(═O)(═NR')R, -$L^2$-NR'$SO_2$NR'R', -$L^2$-NR'$SO_2$R, -$L^2$-NR'R', -$L^2$-NR'C(O)R', -$L^2$-NR'COOR, -$L^2$-C(O)NR'R', and -$L^2$-COOR';

R at each occurrence is selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-4}$ alkyl, $C_{1-2}$ haloalkyl, oxo, -$L^3$-CN, -$L^3$-halo, -$L^3$-$C_{1-3}$ alkoxy, -$L^3$-OH, -$L^3$-OC(O)—NR'R', -$L^3$-$SO_2$R', -$L^3$-$SO_2$NR'R', -$L^3$-$SO_2$NR'—C(O)R', -$L^3$-C(O)—NR'—$SO_2$R', -$L^3$-SOR', -$L^3$-S(═O)(═NR')R', -$L^3$-NR'$SO_2$NR'R', -$L^3$-NR'$SO_2$R', $-L^3$-NR'R', $-L^3$-NR'C(O)R', $-L^3$-NR'COOR', $-L^3$-C(O)NR'R', and $-L^3$-COOR', $-L^3$-(5-6-membered heterocyclyl containing one or two N, O or S heteroatoms as ring members), $-L^3-C_{3-5}$ cycloalkyl, and $-L^3$-(5-6 membered heteroaryl ring having up to four heteroatoms comprising 1-4 nitrogen atoms, 0-1 oxygen atoms, and 0-1 sulfur atoms as ring members), where the $C_{1-4}$ alkyl, 5-6-membered heterocyclyl, $C_{3-5}$ cycloalkyl and 5-6 membered heteroaryl ring are each optionally further substituted with up to three groups independently selected from halo, $C_{1-3}$ alkyl, $C_{1-3}$ haloalkyl, $-L^4$-OR', $-L^4$-CN, and $-L^4-N(R')_2$;

R' at each occurrence is independently selected from H, $C_{1-4}$ alkyl optionally substituted with halo, —OH, amino, or $C_{1-2}$ alkoxy, and $C_{3-6}$ alkyl optionally substituted with halo, —OH, amino, or $C_{1-2}$ alkoxy;

or two R' taken together with a nitrogen atom to which both are directly attached can form a 4-6 membered ring optionally containing an additional N, O or S as a ring member and optionally substituted with one to three groups selected from $C_{1-2}$ alkyl, $C_{1-2}$ alkoxy, oxo, and hydroxy;

each $L^2$ and $L^3$ and $L^4$ is independently a bond or a straight chain or branched $C_{1-3}$ alkylene;

Z and $Z^5$ are independently selected at each occurrence from halo, hydroxy, CN, $C_{1-3}$ alkoxy, $C_{1-3}$ alkyl, and $C_{3-5}$ cycloalkyl, and two Z groups, or two $Z^5$ groups, taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl; or a salt thereof.

In some embodiments of the compounds of Formula (IV), R11 is H or C1-C6 alkyl. In some of these embodiments, R3 is absent. In some of these embodiments, R4 and R5 each represent H.

In some embodiments of the compounds of Formula (IV), L is a $C_1$-$C_4$ straight chain or branched alkylene linker;

W is $—SO_2R$, $—SO_2NR'R'$, $—NR'SO_2R$, or an optionally substituted $C_1$-$C_3$ alkyl, or an optionally substituted 3-6 membered cycloalkyl;

wherein the optional substituents for said optionally substituted $C_1$-$C_3$ alkyl and optionally substituted cycloalkyl are 1-3 groups independently selected from $C_{1-3}$ alkyl, oxo, halo, $C_{1-3}$ alkoxy, OH, $—SO_2R$, $—SO_2NR'R'$, $—NR'SO_2NR'R'$, $—NR'SO_2R$, —NR'R', —OR, —NR'COOR, —C(O)NR'R', and COOR', R at each occurrence is independently selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-3}$ alkyl, oxo, CN, halo, $C_{1-3}$ alkoxy, OH, and C3-5 cycloalkyl;

R' at each occurrence is selected from H and $C_{1-4}$ alkyl optionally substituted with halo, —OH or $C_{1-2}$ alkoxy;

or two R' taken together with a nitrogen atom to which both are directly attached can form a 4-6 membered ring optionally containing an additional N, O or S as a ring member and optionally substituted with one or two groups selected from $C_{1-2}$ alkyl, $C_{1-2}$ alkoxy, oxo, and hydroxy.

In some such embodiments, the group W-L- is selected from the group consisting of

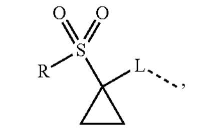
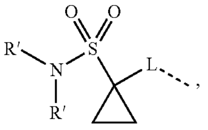
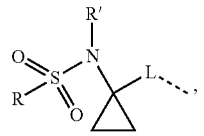
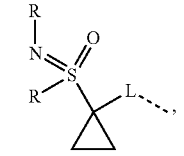
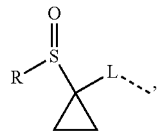
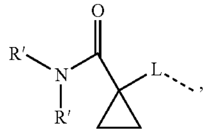
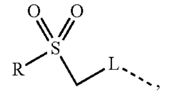
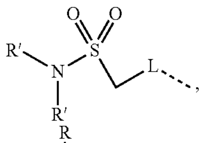
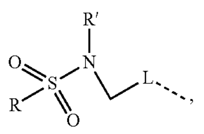
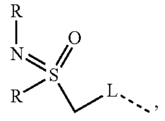
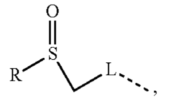
and
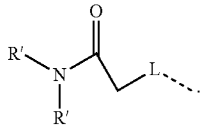

In some of these embodiments, L is $CH_2$. R in these embodiments is sometimes selected from methyl, ethyl, isopropyl and cyclopropyl at each occurrence. R' in these embodiments is sometimes selected from H and methyl at each occurrence.

These compounds are novel and useful as intermediates for preparation of the compounds of Formula (I)-(III) described herein.

Another embodiment of the invention provides a compound as described above, or a pharmaceutically acceptable salt thereof, as a medicament.

Also within the scope of this invention is the use of a compound of formula (I), or a pharmaceutically acceptable salt thereof, for the manufacture of a medicament for the treatment or prevention of a herpesvirus disease and/or infection in a human being, including CMV.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a CMV infection or other herpesvirus in a human being having or at risk of having the infection. The herpesvirus may be selected from cytomegalovirus (CMV), Epstein-Barr virus (EBV), Varicella zoster virus (VZV), herpes simplex virus including HSV-1 and HSV-2, herpesvirus 6, human herpesvirus 7, and Kaposi' s sarcoma-associated herpesvirus.

The invention also provides the use of a pharmaceutical composition as described hereinabove for the treatment of CMV disease or other herpesvirus infection in a human being having or at risk of having the disease. The CMV disease or other herpesvirus infection may include, for example, CMV infection in an immunocompromised patient, such as a transplant recipient; congenital CMV; genital herpes; oral herpes or cold sores; herpetic keratitis; neonatal herpes; herpes encephalitis; varicella (chickenpox); herpes zoster (shingles); infectious mononucleosis; post-transplant lymphoproliferative disease (PTLD); Castelman's disease; and hemophagocytic lymphohistiocytosis.

Another aspect of the invention provides a method of treating a disease or disorder in a patient which may be induced, exacerbated, and/or accelerated by a CMV disease or other herpesvirus infection. These diseases and disorders include Alzheimer's disease, chronic fatigue syndrome (CFS), systemic lupus erythematosus (SLE), multiple sclerosis (MS), rheumatoid arthritis (RA), juvenile idiopathic arthritis (JIA), inflammatory bowel disease (IBD), celiac disease, and Type 1 diabetes.

Another aspect of the invention involves a method of treating or preventing a herpesvirus disease and/or infection in a human being by administering to the human being an antivirally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat a herpesvirus disease and/or infection; and packaging material comprising a label which indicates that the composition can be used to treat disease and/or infection by a herpesvirus such as CMV; wherein the composition comprises a compound of formula (I) according to this invention or a pharmaceutically acceptable salt thereof.

Still another aspect of this invention relates to a method of inhibiting the replication of CMV or another herpesvirus, comprising exposing the virus to an effective amount of the compound of formula (I), or a salt thereof, under conditions where replication of the virus is inhibited. This method can be practiced in vitro or in vivo.

Further included in the scope of the invention is the use of a compound of formula (I), or a salt thereof, to inhibit the replication of CMV.

In some embodiments, the compound of Formula (I) is co-administered with at least one additional agent selected from: a herpesvirus entry inhibitor, a herpesvirus early transcription event inhibitor, a herpesvirus helicase-primase inhibitor, another herpesvirus DNA polymerase inhibitor, an inhibitor of UL97 kinase, a herpesvirus protease inhibitor, a herpesvirus terminase inhibitor, a herpesvirus maturation inhibitor, an inhibitor of another target in the herpesvirus life cycle, a herpesvirus vaccine and a herpesvirus biological agent. In preferred embodiments, the herpesvirus is CMV.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being. Such agents can be selected from: a herpesvirus entry inhibitor; a herpesvirus early transcription event inhibitor; a herpesvirus helicase-primase inhibitor; a herpesvirus DNA polymerase inhibitor such as Ganciclovir (Cytovene®), Valganciclovir (Valcyte®; Cymeval®), Cidofovir (Vistide®), Foscarnet (Foscavir®), CMX001, cyclopropavir (MBX-400) and Valaciclovir (Valtrex®; Zelitrex®); an inhibitor of UL97 kinase such as Maribavir; a herpesvirus protease inhibitor; a herpesvirus terminase inhibitor such as AIC246 (Letermovir); a herpesvirus maturation inhibitor; other inhibitors such as Artesunate; a CMV vaccine such as TransVax and a herpesvirus biological agent such as Cytogam (Cytotect®).

Many compounds of the invention contain one or more chiral centers. These compounds may be made and used as single isomers or as mixtures of isomers. Methods for separating the isomers, including diastereomers and enantiomers, are known in the art, and examples of suitable methods are described herein. In certain embodiments, the compounds of the invention are used as a single substantially pure isomer, meaning at least 90% of a sample of the compound is the specified isomer and less than 10% of the sample is any other isomer or mixture of isomers. Preferably, at least 95% of the sample is a single isomer. Selection of a suitable isomer is within the ordinary level of skill, as one isomer will typically be more active in the herpesvirus DNA polymerase in vitro assay described herein and will be the preferred isomer. Where in vitro activity differences between isomers are relatively small, e.g. less than about a factor of 4, a preferred isomer may be selected based on activity level against viral replication in cell culture, using methods such as those described herein: the isomer having a lower IC-50 or EC-50 is preferred.

The compounds of the invention may be synthesized by the general synthetic routes below, specific examples of which are described in more detail in the Examples.

The invention also provides methods of making compounds of Formula I as described herein and intermediates useful for preparation of compounds of Formula (I). The invention thus also includes a method to make a compound of Formula (I), which comprises contacting a compound of Formula (V)

(V)

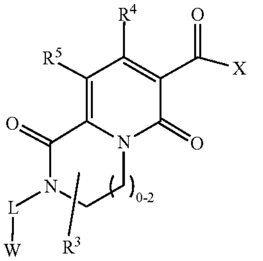

X represents —OH or a leaving group;

$R^3$ represents up to two (0-2) optional substituents on the ring containing two nitrogen atoms, where each $R^3$ is independently selected from halo, CN, $C_{1-3}$ alkoxy, $C_{1-3}$ alkyl, COOR', $C(O)NH_2$, and C(O)NRR';

$R^4$ is H, halo, or $C_{1-3}$ alkyl;

$R^5$ is selected from H, halo, CN, $C_{1-3}$ alkoxy, $—NH_2$, —NRR', $C_{1-3}$ alkyl substituted up to three times with $Z^5$, $C_{2-4}$ alkenyl substituted up to three times with $Z^5$, $C_{2-4}$ alkynyl substituted up to three times with $Z^5$, and a ring selected from a 3-6 membered cycloalkyl ring, a 4-6 membered heterocyclic ring containing one or two heteroatoms selected from N, O and S as ring members, and a 5-6 membered heteroaryl ring containing up to four heteroatoms selected from N, O and S as ring members, where the 3-6 membered cycloalkyl ring, 4-6 membered heterocyclic ring, or 5-6 membered heteroaryl ring is optionally substituted with 1-2 $Z^5$;

L is a $C_1$-$C_4$ straight chain or branched alkylene linker;

W is —OR', $—NH_2$, —NRR', —NR'COOR, —NR'C(O)R', $—SO_2R$, $—SO_2NH_2$, $—SO_2NRR'$, $—NR'SO_2R$, or an optionally substituted $C_1$-$C_3$ alkyl, or an optionally substituted ring selected from 3-6 membered cycloalkyl, 5-6-membered heterocyclyl containing one or two N, O or S heteroatoms as ring members, and 5-membered heteroaryl containing up to 4 heteroatoms selected from N, O and S as ring members, wherein the optional substituents for said optionally substituted $C_1$-$C_3$ alkyl and optionally substituted ring are 1-3 groups selected from $C_{1-3}$ alkyl, oxo, halo, $C_{1-3}$ alkoxy, OH, —SO2R, $—SO_2NR'R'$, —SOR, —S(=O)(=NR')R, $—NR'SO_2NR'R'$, $—NR'SO_2R$, $—NH_2$, —NR'R', —OR, —NR'COOR, $—C(O)NH_2$, —C(O)NRR', and COOR'.

R at each occurrence is selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-3}$ alkyl, oxo, CN, halo, $C_{1-3}$ alkoxy, OH, and $C_{3-5}$ cycloalkyl;

R' at each occurrence is selected from H and $C_{1-4}$ alkyl optionally substituted with halo, —OH or $C_{1-2}$ alkoxy;

or R and R' taken together with a nitrogen atom to which both are directly attached can form a 4-6 membered ring optionally containing an additional N, O or S as a ring member and optionally substituted with one or two groups selected from $C_{1-2}$ alkyl, $C_{1-2}$ alkoxy, oxo, and hydroxy;

Y at each occurrence is independently selected from halo, $C_{1-2}$ alkyl, $C_{1-2}$ haloalkyl, and $C_{1-2}$ alkoxy;

each $Z^5$ is selected independently at each occurrence from halo, hydroxy, CN, $C_{1-3}$ alkoxy, $C_{1-3}$ alkyl, and two $Z^5$ groups, taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl;

with a compound of Formula (VI):

(VI)

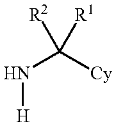

wherein Cy is phenyl, pyridinyl, pyrimidinyl, or a 5-8 membered cycloalkyl, and Cy is optionally substituted with up to three groups selected from halo, CN, hydroxy, $—N(R')_2$, $C_{3-6}$ cycloalkyl, $C_{1-3}$ alkoxy, $C_{1-3}$ haloalkyl, and $C_{1-3}$ alkyl substituted up to three (0-3) times with Z, wherein two of said $C_{1-3}$ alkyl substituted up to three times with Z, when directly attached to the same carbon atom, can be taken together with the carbon to which both are attached to form a 3-5 membered cycloalkyl ring substituted up to three times with Z; $R^1$ is selected from H and $C_{1-3}$ alkyl;

$R^2$ is selected from H and $C_{1-3}$ alkyl;

or $R^1$ and $R^2$ taken together with the carbon to which they are attached can form a 3-6 membered cycloalkyl ring;

Z is independently selected at each occurrence from halo, hydroxy, CN, $C_{1-3}$ alkoxy, $C_{1-3}$ alkyl, and $C_{3-5}$ cycloalkyl, and two Z groups taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl.

Typically, for these methods, the compounds of Formula (V) and Formula (VI) are brought together or mixed in the presence of an inert solvent under conditions suitable for formation of an amide bond, including known methods used for peptide synthesis. For example, where X represents —OH, any of wide range of known dehydrating agents suitable for formation of an amide bond from an amine and a carboxylic acid can be used. Some of these are illustrated by the Examples herein, and include carbodiimides (e.g., dicyclohexyl carbodiimide; diisopropyl carbodiimide; EDC; and the like). Optionally, reaction with a carbodiimide can be facilitated by the presence of an activating agent such as HOBt, HOAt, N-hydroxysuccinimide, or the like. Alternatively, the acid of Formula (V) or a salt thereof can be activated by reaction with an activating agent such as HATU, HBTU, BOP, PyBOP, PyBrOP, TBTU, COMU, or TFFH, optionally in the presence of a base such as triethylamine, DIPEA, DMAP, pyridine, and the like, prior to being contacted with the amine compound of Formula (VI). Where X represents a leaving group, it can be halo (preferably C1), or an acyl group such as —OC(O)—O—R* where R* represents a C1-C6 alkyl, optionally substituted with up to three halo or $C_{1-3}$ alkoxy groups.

In certain embodiments, the compound of Formula (V) is a compound of the formula (VB):

(VB)

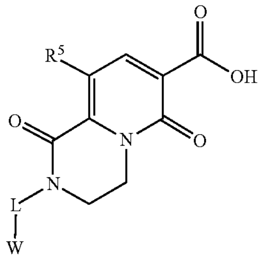

where $R^5$ is H or halo; L is $-CH_2-$; and W is cyclopropyl substituted with $-SO_2R$, where R is as defined for Formula (V).

The compounds of Formula (V) and (VB) as described above and methods of using them to make compounds of the invention are also aspects of the invention.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn- Ingold- Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)– or (S)–.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)– and (S)– isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers or diastereomers, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is intended to represent unlabeled forms as well as isotopically labeled forms of the compounds of the present invention having up to three atoms with non-natural isotope distributions, e.g., sites that are enriched in deuterium or 13C or 15N. Isotopically labeled compounds have structures depicted by the formulas given herein except that one or more atoms are replaced by an atom having a selected atomic mass or mass number other than the natural-abundance mass distribution. Examples of isotopes that can be usefully over-incorporated into compounds of the invention include isotopes of hydrogen, carbon, nitrogen, oxygen, phosphorous, fluorine, and chlorine, such as 2H, 3H, 11C, 13C, 14C, 15N, 18F 31P, 32P, 35S, 36Cl, 125I respectively. The invention includes various isotopically labeled compounds of the present invention, for example those into which radioactive isotopes, such as 3H and 14C, or those in which non-radioactive isotopes, such as 2H and 13C are present at levels substantially above normal isotope distribution. Such isotopically labelled compounds are useful in metabolic studies (with 14C, for example), reaction kinetic studies (with, for example 2H or 3H), detection or imaging techniques, such as positron emission tomography (PET) or single-photon emission computed tomography (SPECT) including drug or substrate tissue distribution assays, or in radioactive treatment of patients. In particular, an 18F labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent typically employed. Labeled samples may be useful with quite low isotope incorporation, such as where a radiolabel is used to detect trace amounts of the compound.

Further, more extensive substitution with heavier isotopes, particularly deuterium (i.e., 2H or D), may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention, and typically a sample of a compound having deuterium as a substituent has at least 50% deuterium incorporation at the labeled position(s). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. D2O, d6-acetone, d6-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the invention can be administered by known methods, including oral, parenteral, inhalation, and the like. In certain embodiments, the compound of the invention is administered orally, as a pill, lozenge, troche, capsule, solution, or suspension. In other embodiments, a compound of the invention is administered by injection or infusion. Infusion is typically performed intravenously, often over a period of time between about 15 minutes and 4 hours. In other embodiments, a compound of the invention is administered intranasally or by inhalation; inhalation methods are particularly useful for treatment of respiratory infections. Compounds of the present invention exhibit oral bioavailability, so oral administration is sometimes preferred.

A compound of the present invention may also be used in combination with other agents (combination partners), e.g., an additional antiviral agent that is or is not of the formula I, for treatment of a viral infection in a subject.

By the term "combination", is meant either a fixed combination in one dosage unit form, as separate dosage forms suitable for use together either simultaneously or sequentially, or as a kit of parts for the combined administration where a compound of the present invention and a combination partner may be administered independently at the same time or separately within time intervals that especially allow that the combination partners show a cooperative, e.g., synergistic, effect, or any combination thereof.

In certain embodiments of the present invention, a compound of the present invention is used in combination with a second antiviral agent, such as those named herein.

The second antiviral agent may be administered in combination with the compounds of the present inventions wherein the second antiviral agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

In some embodiments, a combination of a compound of the invention and a second antiviral agent may provide synergistic activity. The compound of the invention and second antiviral agent may be administered together, separate but simultaneously, or sequentially.

An "effective amount" of a compound is that amount necessary or sufficient to treat or prevent a viral infection and/or a disease or condition described herein. In an example, an effective amount of a herpesvirus or CMV DNA polymerase inhibitor of Formula I is an amount sufficient to treat viral infection in a subject. In another example, an effective amount of the DNA polymerase inhibitor is an amount sufficient to treat a viral infection, such as, but not limited to CMV, VZV or EBV, in a subject in need of such treatment. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a viral infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of at least one compound of Formula (I) or any subgenus thereof as active ingredient in combination with a pharmaceutically acceptable carrier, or optionally two or more pharmaceutically acceptable carriers.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable carriers are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration may comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Intravenous infusion is sometimes a preferred method of delivery for compounds of the invention. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, more preferably from about 0.01 to about 50 mg per kg per day, and still more preferably from about 0.1 to about 20 mg per kg per day. An effective amount is that amount which prevents or treats a viral infection, such as CMV or another herpesvirus.

If desired, the effective daily dose of the active compound may be administered as a single dose per day, or as two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered by infusion are typically administered in one to three doses per day. When multiple doses are administered within a day, the doses may be administered at intervals of about 4 hours, about 6 hours, about 8 hours or about 12 hours.

While it is possible for a compound of the present invention to be administered alone, it is preferable to administer the compound as a pharmaceutical composition such as those described herein. Thus methods of using the compounds of the invention include administering the compound as a pharmaceutical composition, wherein at least one compound of the invention is admixed with a pharmaceutically acceptable carrier prior to administration.

Use of Compounds of the Invention in combination with immunomodulators

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) Curr Opin Immunol 14: 391779-82; Bennett et al. (2003) J. Immunol. 170:711-8). PD-1 is expressed on activated B cells, T cells, and monocytes. PD-1 is an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antiviral compounds, these immunomodulators can enhance the antiviral response, and thus enhance efficacy relative to treatment with the antiviral compound alone.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

By "in combination with," it is not intended to imply that the therapy or the therapeutic agents must be administered at the same time and/or formulated for delivery together, although these methods of delivery are within the scope described herein. The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antiviral compounds described herein are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-L1 or PD-L2 fused to a constant region (e.g., an Fc region of an immunoglobulin sequence).

In some embodiments, the immunomodulator is a PD-1 inhibitor such as AMP-224.

In some embodiments, the immunomodulator is a PD-L1 inhibitor such as anti-PD-L1 antibody.

In some embodiments, the immunomodulator is an anti-PD-L1 binding antagonist chosen from YW243.55. S70, MPDL3280A, MEDI-4736, MSB-0010718C, or MDX-1105. MDX-1105, also known as BMS-936559, is an anti-PD-L1 antibody described in WO2007/005874. Antibody YW243.55. S70 is an anti-PD-L1 described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509, WO2009/114335, and WO2013/079174.

In some embodiments, the immunomodulator is Pidilizumab (CT-011; Cure Tech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S. Publication No. 20120039906. Other anti-PD-L1 binding agents useful as immunomodulators for methods of the invention include YW243.55. S70 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No. 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) Cancer Res. 72(4):917-27).

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antiviral compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antiviral compounds of the invention in combination with an immunomodulator include these, which may be used along with a compound of Formula I or any subgenus or species thereof that is disclosed herein:

i. A method to treat a viral infection in a subject, comprising administering to the subject a compound of Formula (I) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specificity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.570, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016.

xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg., e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

General Synthetic Procedures

The compounds as described herein may be synthesized by the general synthetic routes below, specific examples of which are described in more detail in the Examples.

All starting materials, building blocks, reagents, acids, bases, dehydrating agents, solvents, and catalysts utilized to synthesize the compounds of the invention are either commercially available or can be produced by organic synthesis methods known to one of ordinary skill in the art (Houben-Weyl 4th Ed. 1952, Methods of Organic Synthesis, Thieme, Volume 21).

LIST OF ABBREVIATIONS

Ac acetyl
ACN or MeCN Acetonitrile
AcOEt/EtOAc Ethyl acetate
AcOH acetic acid
aq aqueous
Bn benzyl
Bu butyl (nBu=n-butyl, tBu=tert-butyl)
CDI Carbonyldiimidazole
CH3CN Acetonitrile
DBU 1,8-Diazabicyclo[5.4.0]-undec-7-ene
$Boc_2O$ di-tert-butyl dicarbonate
DCE 1,2-Dichloroethane
DCM Dichloromethane
DIAD Diisopropyl azodicarboxylate
DiBAl-H Diisobutylaluminum Hydride
DIPEA or DIEA N-Ethyldiisopropylamine
DMA N,N-dimethylacetamide
DMAP Dimethylaminopyridine
DMF N,N-Dimethylformamide
DMSO Dimethylsulfoxide
EDC 1-Ethyl-3-(3-dimethylaminopropyl)carbodiimide
EI Electrospray ionisation
$Et_2O$ Diethylether
$Et_3N$ Triethylamine
Ether Diethylether EtOAc Ethyl acetate
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HMPA Hexamethylphosphoramide
HOBt 1-Hydroxybenzotriazole
HPLC High Performance Liquid Chromatography
$H_2O$ Water
IPA isopropanol
L liter(s)
LC-MS Liquid Chromatography Mass Spectrometry
LiHMDS Lithium bis(trimethylsilyl)amide
$MgSO_4$ Magnesium Sulfate
Me methyl
MeI Iodomethane
MeOH Methanol
mg milligram
min minute(s)
mL milliliter
MS Mass Spectrometry
MsCl methanesulfonyl chloride
$NaHCO_3$ Sodium Bicarbonate
$Na_2SO_4$ Sodium Sulfate
$NH_2OH$ hydroxylaminc
Pd/C palladium on charcoal
$Pd(OH)_2$ palladium hydroxide
PC protecting group
Ph phenyl
$Ph_3P$ triphenyl phosphine
Prep Preparative
Rf ratio of fronts
RP reverse phase Compounds of the present invention are prepared from commonly available compounds using procedures known to those skilled in the art in view of the examples and schemes provided herein.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der Organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g., using chromatographic methods, distribution methods, (re-) crystallization, and the like.

EXAMPLES

The invention is further illustrated by the following examples, which should not be construed as limiting. The assays used throughout the Examples are well established in the art: demonstration of efficacy in these assays is generally regarded as predictive of efficacy in subjects.

The compounds of the invention can be produced by organic synthesis methods known to one of ordinary skill in the art with reference to the following reaction schemes and examples. General methods for synthesis of compounds of Formula (I) are provided in Schemes I to III below.

Scheme I. General method for synthesis of compounds of Formula (I).

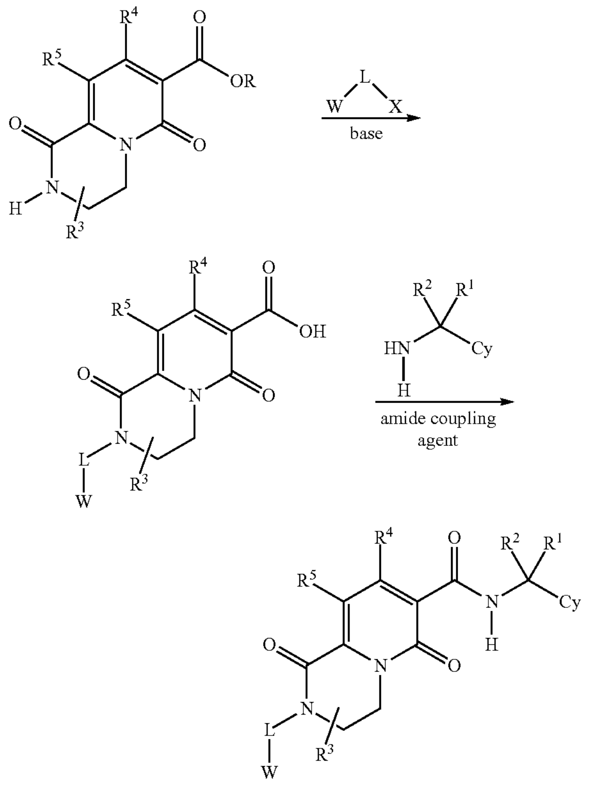

Scheme I shows a general method for synthesizing many compounds of Formula (I) from intermediates described herein. The bicyclic intermediate (e.g., Intermediate I-1) can be N-alkylated to attach the W-L- moiety of interest, especially where L is attached through —CH2-. W-L-X represents a suitable alkylating agent for such reactions, where X is a leaving group such as halo (preferably Br or I) or a sulfonate leaving group such as mesylate, tosylate, or triflate. The W-L- moiety can of course contain functional groups that can be further modified in the product of Formula (I), such as hydroxyl groups or amine groups, preferably in protected form, which can be deprotected and further derivatized using methods well known in the art.

R can be a simple alkyl ester such as methyl, ethyl, propyl, isopropyl, t-butyl or n-butyl; and if W-L- contains an ester, R can be a different ester such as benzyl that can be readily differentiated from the one in W-L-, so R can be selectively hydrolyzed for the coupling reaction in Scheme I. In some of the examples, the R is an ester that hydrolyzes under the alkylation reaction conditions, presumably due to the presence of adventitious moisture or hydroxide; in other examples, a separate hydrolysis step is used such as addition of lithium, sodium or potassium hydroxide and water. The resulting free carboxylate compound is then readily coupled to a suitable amine containing a desired Cy group using standard amide bond formation conditions and reagents that are well known in the art. This can be a direct amidation of the carboxylate, or it can be accomplished by converting the carboxylic acid into an activated intermediate (acyl chloride, acyl anhydride, etc.) as known in the art and illustrated by the accompanying examples.

Scheme II. Alternative preparation of compounds of Formula (I).

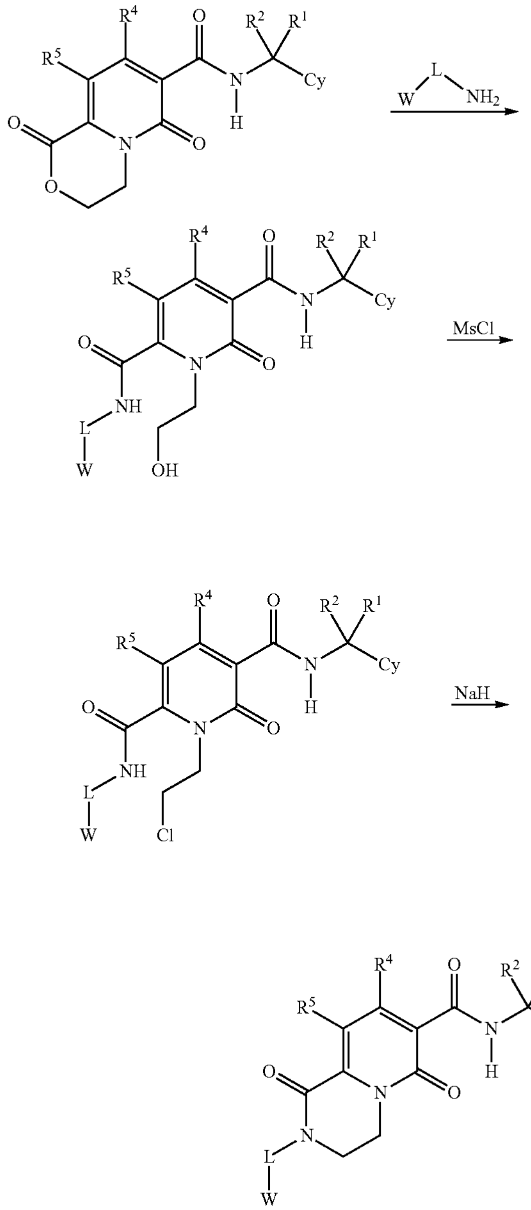

Scheme II depicts an alternate synthesis of compounds of Formula I, illustrated by Example 51 below. This synthesis scheme begins with an intermediate made as described herein (see, e.g., I-17 below), and uses an amine to introduce the W-L- moiety of interest by opening a lactone. The first intermediate shown contains a free primary hydroxyl group, which is readily converted into a leaving group (Cl in the example, but an alkylsulfonate or arylsulfonate could be used instead). Under base conditions (e.g., NaH), the leaving group is readily displaced to form a new six-membered ring having the desired W-L- group attached. As for Scheme I, the W-L- moiety that is introduced can contain functional groups, optionally in protected form, that can be subsequently modified as desired. Example 51, for example, has a thioether in the W-L- group, and the sulfur atom is oxidized to provide a desired sulfone.

Scheme III. Additional synthesis route for compounds of Formula I.

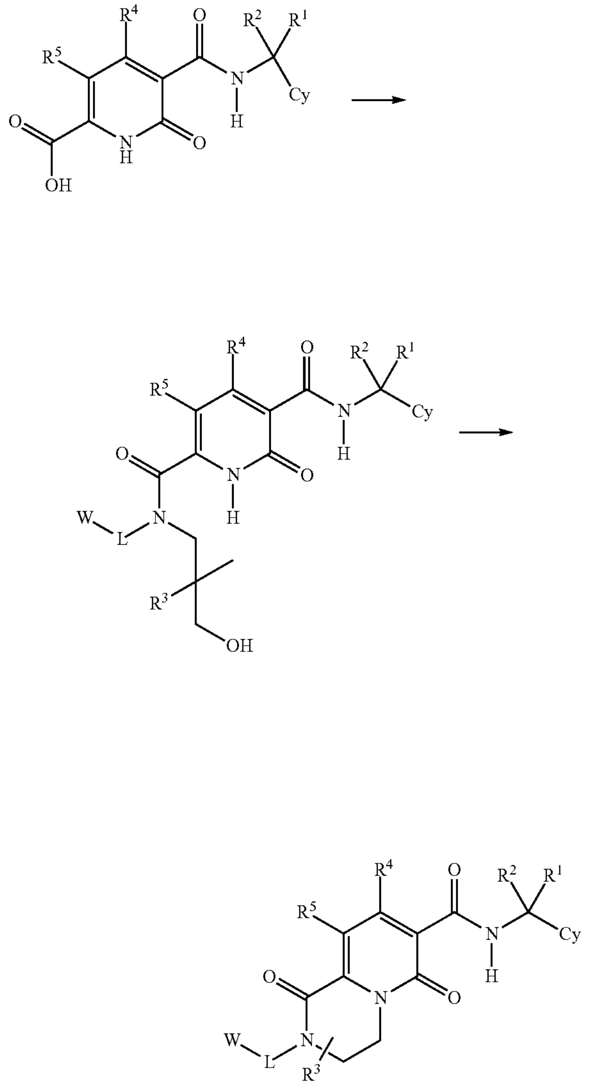

Scheme III provides yet another method to make compounds of Formula (I), beginning with a carboxy-pyridone derivative whose synthesis is described herein (e.g., Ex. 91). The starting material is made as described herein (e.g., I-17C), and is coupled by conventional methods to a hydroxyethyl-substituted amine derivative wherein the amine nitrogen is attached to a desired W-L-moiety. After the coupling is done, the free hydroxyl is converted to a leaving group such as Cl or mesylate, etc., and is then cyclized onto the pyridone ring nitrogen under basic conditions; alternatively, the coupling can be accomplished under typical Mitsunobu conditions (e.g., treatment with triphenylphosphine and DIAD). Here again, the W-L- moiety can contain functional groups, optionally in protected form, that can subsequently be used to further modify or derivatize the W-L- portion to provide a desired target compound.

Using these methods along with additional extensions, modifications and variations illustrated by the following Examples, a skilled person can readily prepare various compounds of Formula I.

Preparation of Key Intermediates

Intermediate 1 butyl 1,6-dioxo-2,3,4,6-tetrahydro-1H-pyrido[1,2-a]pyrazine-7-carboxylate

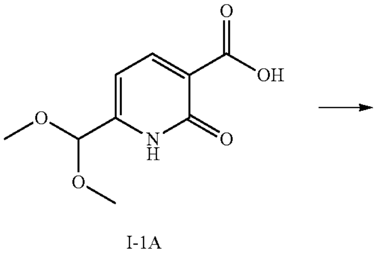

I-1A

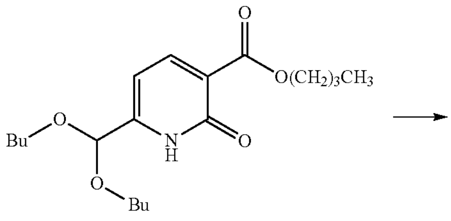

I-1B

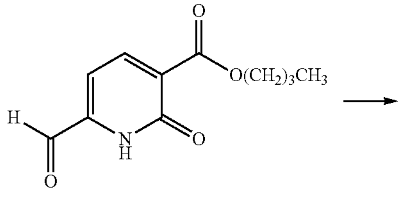

I-1C

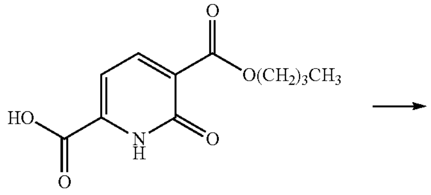

I-1D

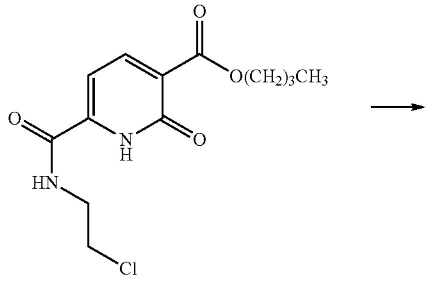

I-1E

-continued

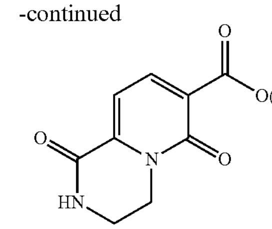

I-1

Butyl 6-(dibutoxymethyl)-2-oxo-1,2-dihydropyridine-3-carboxylate (I-1B). To a slurry of 6-(dimethoxymethyl)-2-oxo-1,2-dihydropyridine-3-carboxylic acid (I-1A) (5 g, 23.45 mmol) in n-BuOH (100 mL) was added TsOH·$H_2O$ (0.446 g, 2.345 mmol). The resulting mixture was stirred at 110° C. overnight, after which it was cooled to RT and concentrated under reduced pressure. I-1B was isolated as a dark red oil and as a mixture of Bu/Bu and Me/Bu acetals. LCMS m/z: 312 (M+1) OBu/OMe, 354 (M+1) OBu/OBu.

Butyl 6-formyl-2-oxo-1,2-dihydropyridine-3-carboxylate (I-1C). I-1B (8.29 g, 23.45 mmol) was dissolved in TFA (200 mL). To the acidic solution was added $H_2O$ (10 mL). The resulting solution was stirred at RT for 5 h, after which it was concentrated under reduced pressure. The dark residue was taken up in DCM and washed with $H_2O$ and saturated sodium bicarbonate. The organic layer was dried over sodium sulfate and concentrated under reduced pressure to afford I-1C as a dark brown foam. LCMS m/z: 224 (M+1). $^1H$ NMR (400 MHz, $CDCl_3$) δ ppm 0.95-1.03 (m, 3H) 1.48 (dq, J=15.01, 7.43 Hz, 2H) 1.73-1.84 (m, 2H) 4.42 (t, J=6.65 Hz, 2H) 7.44 (br. s., 1H) 8.35 (d, J=7.53 Hz, 1H) 9.90 (br. s., 1H).

5-(butoxycarbonyl)-6-oxo-1,6-dihydropyridine-2-carboxylic acid (I-1D). To a chilled (0° C.) solution of I-1C (3.53 g, 15.81 mmol) in t-BuOH (85 mL)/$H_2O$ (85 mL) was added 2-methyl-2-butene (50.3 mL, 474 mmol) followed by $NaH_2PO_4H_2O$ (3.27 g, 23.72 mmol) and $NaClO_2$ (2.145 g, 23.72 mmol). After 2.5 h, the reaction mixture was diluted with $CHCl_3$ and 2 M HCl. The phases were separated and the aqueous layer extracted with $CHCl_3$. The organic extracts were dried over sodium sulfate and concentrated under reduced pressure. The tan solid was triturated with $Et_2O$ and heptane. The resulting precipitate was collected via vacuum filtration and dried on the frit. I-1D was isolated as a tan solid. LCMS m/z: 240 (M+1). $^1H$ NMR (400 MHz, DMSO-d6) δ ppm 0.91 (t, J=7.38 Hz, 3H) 1.40 (dq, J=14.91, 7.40 Hz, 2H) 1.59-1.68 (m, 2H) 4.20 (t, J=6.50 Hz, 2H) 7.00 (br. s., 1H) 8.06 (d, J=7.24 Hz, 1H).

Butyl 6-((2-chloroethyl)carbamoyl)-2-oxo-1,2-dihydropyridine-3-carboxylate (I-1E). To a solution of I-1D (1.47 g, 6.14 mmol) in DCM (75 mL) was added DIEA (2.146 mL, 12.29 mmol) followed by TMSCl (1.571 mL, 12.29 mmol). The resulting solution was stirred at RT for 1.5 h. The reaction mixture was cooled to 0° C. and $SOCl_2$ (0.942 mL, 12.90 mmol) was added slowly. The resulting mixture was allowed to warm to RT over the course of 2.5 h. The reaction was cooled to 0° C. and 2-chloroethanamine HCl (2.85 g, 24.58 mmol) was added, followed by slow addition of DIEA (5.37 mL, 30.7 mmol). Upon addition of the base the yellow mixture became extremely dark. After stirring overnight, the reaction mixture was diluted with DCM, washed with 2 M HCl and brine, and dried over magnesium sulfate. The dried organic layer was concentrated under reduced pressure. I-1E was isolated as a dark oil. LCMS m/z: 301 (M+1).

Butyl 1,6-dioxo-2,3,4,6-tetrahydro-1H-pyrido[1,2-a]pyrazine-7-carboxylate (I-1). To a solution of I-1E (0.767 g, 2.55 mmol) in ACN (51.0 mL) was added DIEA (2.227 mL, 12.75 mmol). The resulting mixture was stirred at 90° C. After consumption of the starting material, the reaction mixture was cooled to RT and concentrated under reduced pressure. The residue was taken up in DCM, washed sequentially with 2 M HCl and saturated sodium bicarbonate, and dried over sodium sulfate. The dried organic layer was concentrated under reduced pressure. The title compound (I-1) was isolated as a dark solid. LCMS m/z: 265 (M+1). $^1H$ NMR (400 MHz, $CDCl_3$) δ ppm 0.96 (t, J=7.38 Hz, 3H) 1.46 (dq, J=15.03, 7.43 Hz, 2H) 1.69-1.79 (m, 2H) 3.63-3.73 (m, 2H) 4.29-4.37 (m, 4H) 6.46 (br. s., 1H) 7.17 (d, J=7.39 Hz, 1H) 8.15 (d, J=7.39 Hz, 1H).

Intermediate 2

(1-(cyclopropylsulfonyl)cyclopropyl)methyl methanesulfonate

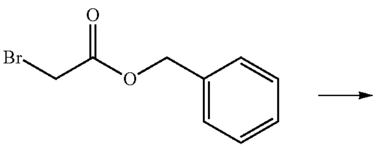

I-2A

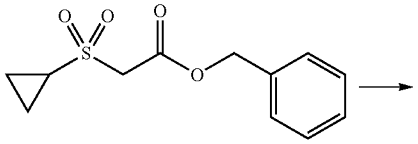

I-2B

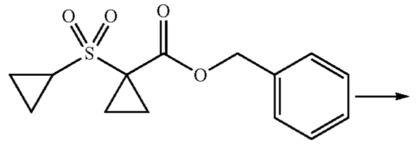

I-2C

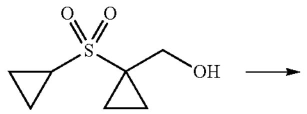

I-2D

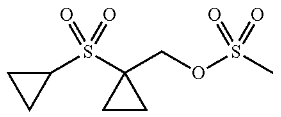

I-2

Benzyl 2-(cyclopropylsulfonyl)acetate (I-2B). To a slurry of sodium cyclopropanesulfinate (5.79 g, 45.2 mmol) in DMF (30 mL) was added benzyl 2-bromoacetate (5.97 mL, 37.7 mmol). The resulting mixture was stirred overnight at RT, after which it was diluted with $H_2O$ and $Et_2O$. The aqueous layer was extracted with $Et_2O$. The combined $Et_2O$ layers were washed with brine, dried over sodium sulfate, and concentrated under reduced pressure to afford I-2B (9.37 g, 36.8 mmol, 98% yield) as a light yellow oil. $^1H$ NMR (400

MHz, $CDCl_3$) δ ppm 1.02-1.09 (m, 2H) 1.24-1.31 (m, 2H) 2.67-2.76 (m, 1H) 4.03-4.09 (m, 2H) 5.26 (s, 2H) 7.34-7.44 (m, 5H).

Benzyl 1-(cyclopropylsulfonyl)cyclopropanecarboxylate (I-2C). To a solution of I-2B (9.37 g, 36.8 mmol) in DMF (350 mL) were added $K_2CO_3$ (10.18 g, 73.7 mmol) followed by 1,2-dibromoethane (3.81 mL, 44.2 mmol). The resulting mixture was stirred at 60° C. for 12 h, after which it was cooled to RT and diluted with $Et_2O$. The resulting insolubles were filtered off. The filtrate was washed with water. The aqueous layer was extracted with $Et_2O$. The combined ether extracts were washed with brine and concentrated under reduced pressure. The oil was purified by column chromatography ($SiO_2$, 0-100% DCM/heptane) to afford I-2C as a colorless oil. $^1$H NMR (400 MHz, $CDCl_3$) δ ppm 0.95-1.01 (m, 2H) 1.20-1.25 (m, 2H) 1.63-1.68 (m, 2H) 1.72-1.78 (m, 2H) 3.00 (tt, J=8.09, 4.90 Hz, 1H) 5.22-5.26 (m, 2H) 7.32-7.41 (m, 5H).

(1-(cyclopropylsulfonyl)cyclopropyl)methanol (I-2D). To a solution of I-2C (6.53 g, 23.29 mmol) in THF (50 mL) was added $LiBH_4$ (2 M in THF, 11.65 mL, 23.29 mmol). The resulting yellow solution was stirred at RT overnight. The reaction was quenched by addition of the reaction mixture to a 2 M HCl/ice mixture. The biphasic mixture was extracted with DCM. The combined organic extracts were dried over sodium sulfate and concentrated under reduced pressure. The colorless oil was purified by column chromatography ($SiO_2$, 0-100% EtOAc/heptane) to afford I-2D as a colorless oil. LCMS m/z: 177 (M+1). $^1$H NMR (400 MHz, $CDCl_3$) δ ppm 1.01-1.10 (m, 4H) 1.23-1.29 (m, 2H) 1.47-1.52 (m, 2H) 2.50-2.59 (m, 2H) 3.92 (d, J=6.11 Hz, 2H).

(1-(cyclopropylsulfonyl)cyclopropyl)methyl methanesulfonate (I-2). To a solution of I-2D (3.7 g, 20.99 mmol) in DCM (40 mL) were added DIEA (7.33 mL, 42.0 mmol) and MsCl (1.800 mL, 23.09 mmol). The reaction went from colorless to yellow in color. After 45 min, the reaction mixture was diluted with DCM, washed with 2M HCl, and dried over sodium sulfate. The dried organic layer was concentrated to afford the title compound (I-2) as an amber-colored oil. $^1$H NMR (400 MHz, $CDCl_3$) δ ppm 1.06-1.13 (m, 2H) 1.18-1.23 (m, 2H) 1.23-1.29 (m, 2H) 1.61-1.67 (m, 2H) 2.50-2.59 (m, 1H) 3.09 (s, 3H) 4.54 (s, 2H).

Intermediate 3

(1-((4-((tert-butyldimethylsilyl)oxy)butan-2-yl)sulfonyl)cyclopropyl)methyl methanesulfonate

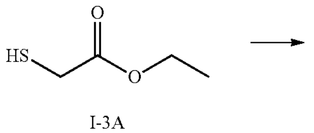

I-3A

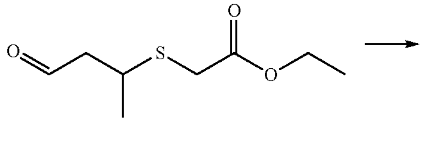

I-3B

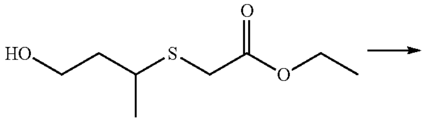

I-3C

-continued

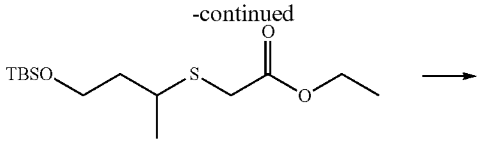

I-3D

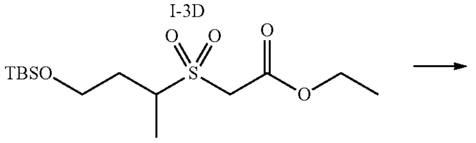

I-3E

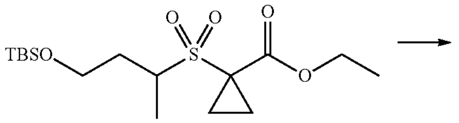

I-3F

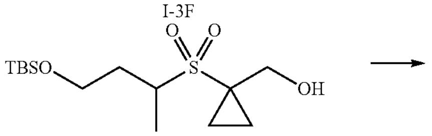

I-3G

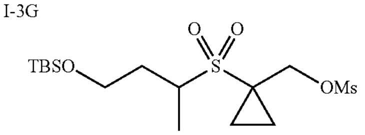

I-3

Ethyl 2-((4-oxobutan-2-yl)thio)acetate (I-3B). To a solution of I-3A (0.909 mL, 8.32 mmol) in DCM (20 mL) were added $NEt_3$ (1.160 mL, 8.32 mmol) followed by crotonaldehyde cis & trans (0.689 mL, 8.32 mmol). The resulting mixture was stirred at RT for about 1 h. The reaction was diluted with DCM and washed with 2 M HCl. The organic layer was dried over sodium sulfate and concentrated under reduced pressure. I-3B was isolated as a colorless oil. LCMS m/z: 191 (M+1). $^1$H NMR (500 MHz, $CDCl_3$) δ ppm 1.29 (t, J=7.25 Hz, 3H) 1.38 (d, J=6.94 Hz, 3H) 2.63 (dt, J=7.25, 1.58 Hz, 1H) 2.76 (dquin, J=6.46, 1.73, 1.73, 1.73, 1.73 Hz, 1H) 3.27-3.30 (m, 2H) 3.47 (d, J=6.94 Hz, 1H) 4.15-4.25 (m, 3H) 9.75-9.78 (m, 1H).

Ethyl 2-((4-hydroxybutan-2-yl)thio)acetate (I-3C). To a chilled (0° C.) solution of I-3B (1.47 g, 7.73 mmol) in THF (25 mL) was added $NaBH_4$ (0.146 g, 3.86 mmol). The resulting mixture was stirred at RT for about 1.5 h, after which it was cooled to 0° C. and quenched with 2 M HCl. The aqueous mixture was extracted with DCM. The combined organic extracts were dried over sodium sulfate and concentrated under reduced pressure. I-3C was isolated as a colorless oil. LCMS m/z: 193 (M+1).

Ethyl 2-((4-((tert-butyldimethylsilyl)oxy)butan-2-yl)thio)acetate (I-3D). To a solution of I-3C (1.35 g, 7.02 mmol) in DCM (25 mL) were added imidazole (0.956 g, 14.04 mmol) followed by TBSCl (1.164 g, 7.72 mmol). The resulting mixture was stirred at RT. Upon completion of the reaction, it was diluted with DCM and washed with 2 M HCl and brine. The organic layer was dried over sodium sulfate and concentrated under reduced pressure. I-3D was isolated as a colorless oil. LCMS m/z: 307 (M+1).

Ethyl 2-((4-((tert-butyldimethylsilyl)oxy)butan-2-yl)sulfonyl)acetate (I-3E). To a solution of I-3D (2 g, 6.52 mmol) in DCM (50 mL) was added mCPBA (2.92 g, 13.05 mmol). After stirring overnight at RT, the reaction mixture was diluted with DCM and filtered through a plug of Celite. The filtrate was washed with saturated sodium bicarbonate and brine. The organic layer was concentrated under reduced pressure. The residue was purified by column chromatography ($SiO_2$, 0-50% EtOAc/heptane) to afford I-3E as a colorless oil. LCMS m/z: 339 (M+1). $^1H$ NMR (400 MHz, $CDCl_3$) δ ppm 0.07 (s, 6H) 0.90 (s, 9H) 1.33 (t, J=7.14 Hz, 3H) 1.45 (d, J=6.90 Hz, 3H) 1.70 (ddt, J=14.02, 9.38, 4.76, 4.76 Hz, 1H) 2.25-2.36 (m, 1H) 3.59-3.69 (m, 1H) 3.73 (ddd, J=10.42, 8.66, 4.55 Hz, 1H) 3.83 (dt, J=10.48, 5.30 Hz, 1H) 3.98 (td, J=14.04, 5.92 Hz, 2H) 4.28 (q, J=7.14 Hz, 2H).

Ethyl 1-((4-((tert-butyldimethylsilyl)oxy)butan-2-yl) sulfonyl)cyclopropanecarboxylate (I-3F) was prepared from I-3E following a procedure analogous to that described for I-2C. I-3F was isolated as a dark orange oil. LCMS m/z: 365 (M+1).

(1-((4-((tert-butyldimethylsilyl)oxy)butan-2-yl)sulfonyl) cyclopropyl)methanol (I-3G) was prepared from I-3F following a procedure analogous to that described for I-2D. I-3G was isolated as a colorless oil. LCMS m/z: 323 (M+1). $^1H$ NMR (400 MHz, $CDCl_3$) δ ppm 0.08 (s, 6H) 0.90 (s, 9H) 1.05 (td, J=5.09, 1.47 Hz, 2H) 1.42 (d, J=6.85 Hz, 3H) 1.50 (td, J=5.28, 1.96 Hz, 2H) 1.58-1.64 (m, 1H) 2.37 (dd, J=8.80, 5.04 Hz, 1H) 2.63 (t, J=5.72 Hz, 1H) 3.62-3.73 (m, 2H) 3.83 (dt, J=10.27, 5.09 Hz, 1H) 3.88 (d, J=5.48 Hz, 2H).

(1-((4-((tert-butyldimethylsilyl)oxy)butan-2-yl)sulfonyl) cyclopropyl)methyl methanesulfonate (I-3) was prepared from I-3G following an analogous procedure to that described for I-2. I-3 was isolated as an orange oil. LCMS m/z: 401 (M+1).

Intermediate 4

(1-((1-((benzyloxy)methyl)cyclopropyl)sulfonyl) cyclopropyl)methyl methanesulfonate

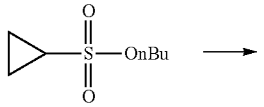

I-4A

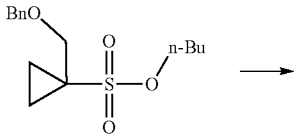

I-4B

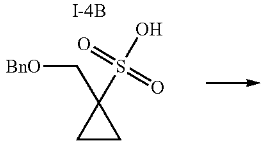

I-4C

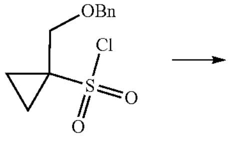

I-4D

-continued

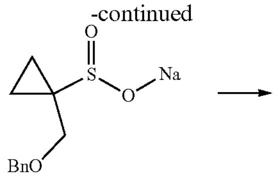

I-4E

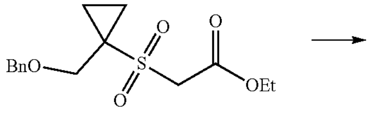

I-4F

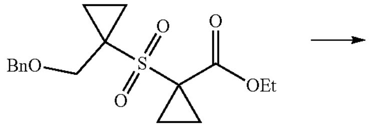

I-4G

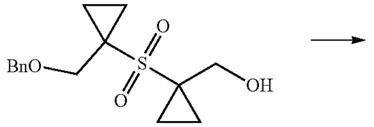

I-4H

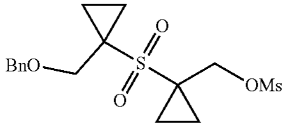

I-4

Butyl 1-((benzyloxy)methyl)cyclopropane-1-sulfonate (I-4B). A solution of I-4A (4.28 mL, 28.1 mmol) in THF (200 mL) was cooled to −78° C. nBuLi (13.46 mL, 33.7 mmol) was added while keeping the temperature below −75° C. After addition was complete, the yellow solution was stirred for about 15 min Benzyloxymethyl chloride (4.68 mL, 33.7 mmol) was added, and the reaction mixture was warmed to RT overnight. The reaction mixture was cooled to 0° C. and quenched with $H_2O$. The aqueous mixture was diluted with EtOAc and the phases were separated. The organic layer was washed with brine, dried over sodium sulfate, and concentrated under reduced pressure. The oily residue was purified by column chromatography ($SiO_2$-50% EtOAc/heptane) to afford the title compound (I-4B) as a colorless oil. LCMS m/z: 299 (M+1). $^1H$ NMR (400 MHz, $CDCl_3$) δ ppm 0.86-0.92 (m, 3H) 1.08-1.13 (m, 2H) 1.37 (dq, J=15.00, 7.44 Hz, 2H) 1.46-1.51 (m, 2H) 1.61-1.71 (m, 2H) 3.79 (s, 2H) 4.23 (t, J=6.60 Hz, 2H) 4.55 (s, 2H) 7.26-7.38 (m, 5H).

1-((benzyloxy)methyl)cyclopropane-1-sulfonic acid (I-4C). To a solution of I-4B (6.14 g, 20.58 mmol) in DME (100 mL)/$H_2O$ (100 mL) was added potassium thiocyanate (2.1 g, 21.61 mmol). The resulting mixture was stirred at reflux overnight, after which it was cooled to RT and diluted with $H_2O$ and EtOAc. The phases were separated, and the aqueous layer was concentrated under reduced pressure to afford I-4C as a yellow solid. LCMS m/z: 243 (M+1). $^1H$ NMR (400 MHz, DMSO-d6) δ ppm 0.57-0.61 (m, 2H) 0.78-0.83 (m, 2H) 3.73 (s, 2H) 4.45 (s, 2H) 7.21-7.36 (m, 5H).

1-((benzyloxy)methyl)cyclopropane-1-sulfonyl chloride (I-4D). To a mixture of I-4C (5.7 g, 20.26 mmol) in DMF (5.5 mL) was added $SOCl_2$ (55 mL, 754 mmol). The resulting mixture was stirred at reflux. After about 45 min the reaction mixture became homogenous, and it was concentrated under reduced pressure. The yellow residue was taken up in EtOAc and washed with brine. The organic layer was dried over sodium sulfate and concentrated under reduced pressure. I-4D was isolated as an orange oil. $^1H$ NMR (400 MHz, $CDCl_3$) δ ppm 1.37-1.43 (m, 2H) 1.76-1.82 (m, 2H) 4.00 (s, 2H) 4.61 (s, 2H) 7.27-7.40 (m, 5H).

(((1-hydrosulfonylcyclopropyl)methoxy)methyl)benzene sodium salt (I-4E). To a solution of sodium sulfite (3.48 g, 27.6 mmol) in $H_2O$ (15 mL) was added $NaHCO_3$ (4.64 g, 55.2 mmol). The resulting mixture was stirred at 50° C. for about 45 min, after which I-4D (7.2 g, 27.6 mmol) was added. The resulting mixture was stirred at 50° C. overnight and then concentrated under reduced pressure. The tan residue was triturated with MeOH. The insolubles were filtered off and the filter cake washed with MeOH. The filtrate was concentrated under reduced pressure. I-4E was isolated as a tan solid. LCMS m/z: 277 (M+1). $^1H$ NMR (400 MHz, DMSO-d6) δ ppm 0.22 (d, J=2.54 Hz, 2H) 0.62 (d, J=2.49 Hz, 2H) 3.62 (s, 2H) 4.44 (s, 2H) 7.29 (d, J=1.91 Hz, 5H).

ethyl 2-((1-((benzyloxy)methyl)cyclopropyl)sulfonyl)acetate (I-4F). To a slurry of I-4E (6.6 g, 26.6 mmol) in DMF (25 mL) was added ethyl bromoacetate (2.96 mL, 26.6 mmol). The resulting mixture was stirred at RT overnight and was then diluted with $Et_2O$. The insolubles were filtered off and the filtrate was washed with brine. The organic layer was dried over sodium sulfate and concentrated under reduced pressure. I-4F was isolated as an orange oil. LCMS m/z: 313 (M+1). $^1H$ NMR (400 MHz, $CDCl_3$) δ ppm 0.98-1.03 (m, 2H) 1.30 (t, J=1.00 Hz, 3H) 1.57-1.63 (m, 2H) 3.78 (s, 2H) 4.20-4.27 (m, 2H) 4.28 (s, 2H) 4.57 (s, 2H) 7.27-7.40 (m, 5H).

Ethyl 1-((1-((benzyloxy)methyl)cyclopropyl)sulfonyl)cyclopropanecarboxylate (I-4G) was prepared from I-4F following a procedure analogous to that described for I-2C. I-4G was isolated as a light yellow oil. LCMS m/z: 339 (M+1). $^1H$ NMR (400 MHz, $CDCl_3$) δ ppm 1.05-1.10 (m, 2H) 1.23 (t, J=7.19 Hz, 3H) 1.57-1.63 (m, 2H) 1.71-1.77 (m, 2H) 1.78-1.84 (m, 2H) 3.71 (s, 2H) 4.13 (q, J=7.11 Hz, 2H) 4.48 (s, 2H) 7.26-7.38 (m, 5H).

(1-((1-((benzyloxy)methyl)cyclopropyl)sulfonyl)cyclopropyl)methanol (I-4H) was prepared from I-4G following a procedure analogous to that described for I-2D. I-4H was isolated as a colorless oil that solidified on vacuum overnight. LCMS m/z: 297 (M+1). $^1H$ NMR (400 MHz, $CDCl_3$) δ ppm 0.95-1.01 (m, 2H) 1.05-1.11 (m, 2H) 1.48-1.55 (m, 2H) 1.62-1.70 (m, 2H) 3.47 (t, J=5.65 Hz, 1H) 3.75 (s, 2H) 3.83 (d, J=5.67 Hz, 2H) 4.56 (s, 2H) 7.29-7.43 (m, 5H).

(1-((1-((benzyloxy)methyl)cyclopropyl)sulfonyl)cyclopropyl)methyl methanesulfonate (I-4) was prepared from I-4G following a procedure analogous to that described for I-2. I-4 was isolated as an orange oil. $^1H$ NMR (400 MHz, $CDCl_3$) δ ppm 1.06-1.13 (m, 4H) 1.57-1.66 (m, 4H) 3.00 (s, 3H) 3.75 (s, 2H) 4.51 (s, 2H) 4.53 (s, 2H) 7.27-7.40 (m, 5H).

Intermediate 5

(1-((1-(fluoromethyl)cyclopropyl)sulfonyl)cyclopropyl)methyl methanesulfonate

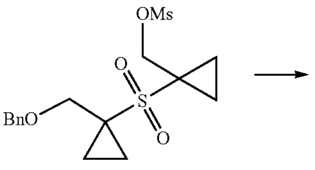

I-4

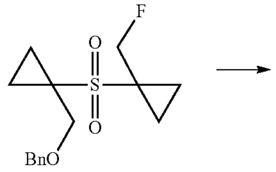

I-5B

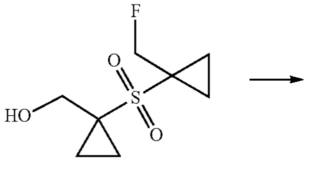

I-5C

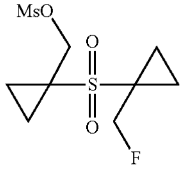

I-5

(((1-((1-(fluoromethyl)cyclopropyl)dulfonyl)cyclopropyl)methoxy)methyl)benzene (I-5B). To a solution of 1-4 (0.315 g, 0.841 mmol) in THF (0.5 mL)/iPrOH (1 mL) was added CsF (0.192 g, 1.262 mmol). The resulting mixture was heated to 100° C. After 72 h, the reaction mixture was cooled to RT and diluted with $Et_2O$. The insolubles were filtered off through a pad of Celite, and the filtrate was concentrated under reduced pressure. The residue purified by column chromatography ($SiO_2$, 0-50% EtOAc/heptane) to afford I-5B as a colorless oil. LCMS m/z: 299 (M+1). $^1H$ NMR (400 MHz, $CDCl_3$) δ ppm 1.01-1.07 (m, 2H) 1.07-1.12 (m, 2H) 1.54-1.63 (m, 4H) 3.79 (s, 2H) 4.53 (s, 2H) 4.58 (d, J=48.86 Hz, 1H) 7.27-7.39 (m, 5H).

(1-((1-(fluoromethyl)cyclopropyl)sulfonyl)cyclopropyl)methanol (I-5C). To a solution of I-5B (0.166 g, 0.556 mmol) in AcOH was added Pd/C (5.92 mg, 5.56 μmol). The atmosphere was exchanged for $H_2$. After completion of the reaction, the mixture was filtered through an Acros filter disc. The filtrate was concentrated under reduced pressure to afford I-5C as an off-white semi-solid. LCMS m/z: 209 (M+1).

(1-((1-(fluoromethyl)cyclopropyl)sulfonyl)cyclopropyl)methyl methanesulfonate (I-5) was prepared from I-5C following an analogous procedure to that described for I-2. I-5 was isolated as a yellow oil. LCMS m/z: 287 (M+1).

Intermediate 6

(1-((1-(methoxymethyl)cyclopropyl)sulfonyl)cyclopropyl)methyl methanesulfonate

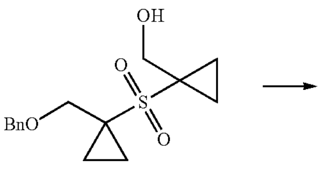

I-4H

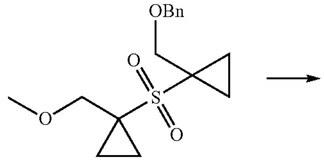

I-6A

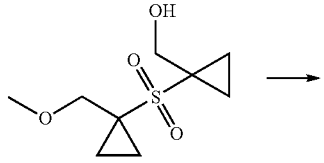

I-6B

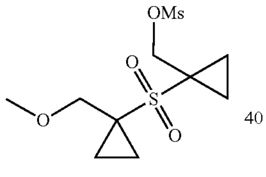

I-6

(((1-((1-(methoxymethyl)cyclopropyl)sulfonyl)cyclopropyl)methoxy)methyl)benzene (I-6A). To a solution of I-4H (0.25 g, 0.844 mmol) in THF (3 mL) were added NaH (60% suspension in mineral oil, 0.037 g, 0.928 mmol) followed by MeI (0.053 mL, 0.852 mmol). The resulting mixture was stirred at RT overnight. The reaction mixture was diluted with EtOAc and washed with 2 M HCl and brine. The organic layer was dried over sodium sulfate and concentrated under reduced pressure. I-6A was isolated as a yellow oil. LCMS m/z: 311 (M+1). $^1$H NMR (500 MHz, $CDCl_3$) δ ppm 0.98-1.02 (m, 2H) 1.06-1.11 (m, 2H) 1.48-1.52 (m, 2H) 1.53-1.57 (m, 2H) 3.32 (s, 3H) 3.72 (s, 2H) 3.83 (s, 2H) 4.55 (s, 2H) 7.30-7.40 (m, 5H).

(1-((1-(methoxymethyl)cyclopropyl)sulfonyl)cyclopropyl)methanol (I-6B) was prepared from I-6A following an analogous procedure to that described for I-5C. I-6B was isolated as a yellow oil. LCMS m/z: 211 (M+1).

(1-((1-(methoxymethyl)cyclopropyl)sulfonyl)cyclopropyl)methyl methanesulfonate (I-6) was prepared from I-6B following an analogous procedure to that described for I-2. I-6 was isolated as a brown oil. LCMS m/z: 299, (M+1).

Intermediate 7 tert-butyl 3-((1-(((methylsulfonyl)oxy)methyl)cyclopropyl)sulfonyl)azetidine-1-carboxylate

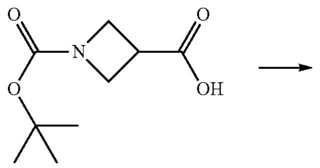

I-7A

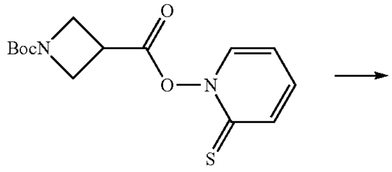

I-7B

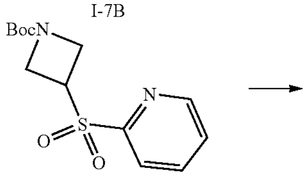

I-7C

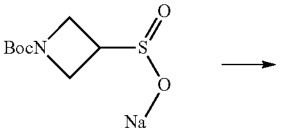

I-7D

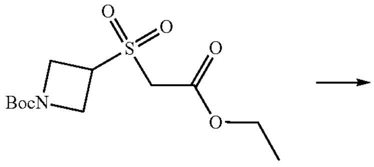

I-7E

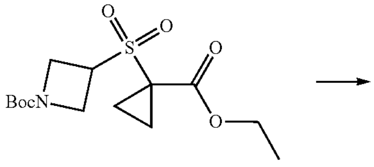

I-7F

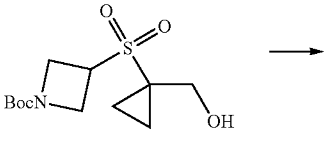

I-7G

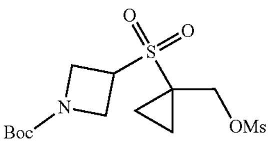

I-7

1-tert-butyl 3-(2-thioxopyridin-1(2H)-yl) azetidine-1,3-dicarboxylate (I-7B). A solution of I-7A (5 g, 24.85 mmol)

in DCM (50 mL) was cooled to 0° C. To the chilled solution were added oxalyl chloride (3.26 mL, 37.3 mmol) and a drop of DMF which immediately caused vigorous bubbling. The reaction mixture was allowed to slowly warm to RT. Upon completion of the reaction, the mixture was cooled to 0° C. and covered in aluminum foil. DMAP (0.304 g, 2.485 mmol) followed by sodium 2-thioxopyridin-1(2H)-olate (5 g, 33.5 mmol) were added. After 1 h and 45 min, the reaction was cooled to 0° C. and quenched with $H_2O$. The phases were separated and the organic layer was filtered through a plug of Celite and rinsed with DCM. The filtrate was concentrated under reduced pressure to afford the title compound (I-7B) as a dark viscous oil. LCMS m/z: 311 (M+1).

tert-butyl 3-(pyridin-2-ylsulfonyl)azetidine-1-carboxylate (I-7C). I-7B (7.71 g, 24.84 mmol) was dissolved in EtOAc (50 mL), and the solution was stirred under irradiation from a 150 W lamp. After 1 h, the reaction mixture was cooled to RT and diluted with water (50.0 mL). The flask was cooled to 0° C., and ruthenium trichloride (0.026 g, 0.124 mmol) was added followed by sodium periodate (31.9 g, 149 mmol). The resulting mixture was stirred at RT overnight and was then diluted with EtOAc and $H_2O$. The insolubles were filtered off and the filter cake was rinsed with EtOAc. The biphasic filtrate was separated, and the organic layer was dried over sodium sulfate and concentrated under reduced pressure. The residue was dry loaded onto Celite and purified by column chromatography ($SiO_2$, 0-100% EtOAc/heptane) to afford the title compound (I-7C) as a light yellow oil. LCMS m/z: 299 (M+1), 243 (M-55). $^1H$ NMR (400 MHz, $CDCl_3$) δ ppm 1.45 (s, 9H) 4.16-4.23 (m, 2H) 4.39 (br. s., 2H) 4.41-4.53 (m, 1H) 7.58 (ddd, J=7.65, 4.72, 1.12 Hz, 1H) 7.96-8.03 (m, 1H) 8.09-8.14 (m, 1H) 8.69-8.76 (m, 1H).

sodium 1-(tert-butoxycarbonyl)azetidine-3-sulfinate (I-7D). To a solution of I-7C (2.84 g, 9.52 mmol) in THF (45 mL) was added sodium ethanethiolate (2.402 g, 28.6 mmol). After stirring 24 h, additional sodium ethanethiolate (2.402 g, 28.6 mmol) was added at RT. Upon completion of the reaction, the mixture was diluted with heptane and the resulting mixture was filtered. The gooey filter cake was washed with $Et_2O$. The semi-solid was taken up in EtOH and concentrated in vacuo. The title compound (I-7D) was isolated as an off-white solid and was used without further purification. LCMS m/z: 166 (M-55). $^1H$ NMR (400 MHz, $D_2O$) δ ppm 1.40-1.49 (m, 9H) 3.12-3.23 (m, 1H) 4.03 (d, J=4.55 Hz, 2H) 4.05-4.14 (m, 2H).

tert-butyl 3-((2-ethoxy-2-oxoethyl)sulfonyl)azetidine-1-carboxylate (I-7E). To a mixture of I-7D (4.54 g, 18.68 mmol) in DMF (100 mL) was added ethyl 2-bromoacetate (1.723 mL, 15.57 mmol). The reaction mixture was stirred at RT for 10 min, after which it was diluted with $H_2O$ and $Et_2O$. The phases were separated and the aqueous layer extracted with $Et_2O$. The combined ether extracts were washed with brine, dried over sodium sulfate, and concentrated under reduced pressure. The residue was purified by column chromatography ($SiO_2$, elution from heptane to DCM to acetone) to afford the title compound (I-7E) as a yellow oil. LCMS m/z: 252 (M-55). $^1H$ NMR (400 MHz, $CDCl_3$) δ ppm 1.34 (t, J=1.00 Hz, 3H) 1.45 (s, 9H) 3.95 (s, 2H) 4.13 (q, J=7.16 Hz, 1H) 4.25-4.35 (m, 6H).

tert-butyl 3-((1-(ethoxycarbonyl)cyclopropyl)sulfonyl)azetidine-1-carboxylate (I-7F) was prepared from I-7E following a procedure analogous to that described for I-2C. The title compound was isolated as a yellow oil. $^1H$ NMR (400 MHz, $CDCl_3$) δ ppm 1.29 (t, J=7.14 Hz, 3H) 1.44 (s, 9H) 1.63-1.69 (m, 2H) 1.78-1.84 (m, 2H) 4.14-4.20 (m, 2H) 4.20-4.26 (m, 2H) 4.38 (dd, J=9.44, 6.16 Hz, 2H) 4.46-4.55 (m, 1H).

tert-butyl 3-((1-(hydroxymethyl)cyclopropyl)sulfonyl)azetidine-1-carboxylate (I-7G) was prepared from I-7F following a procedure analogous to that described for I-2D. I-7G was isolated as a colorless oil. LCMS m/z: 236 (M-55). $^1H$ NMR (400 MHz, $CDCl_3$) δ ppm 0.98-1.03 (m, 2H) 1.44 (s, 9H) 1.48-1.54 (m, 2H) 2.43 (t, J=4.94 Hz, 1H) 3.86 (d, J=4.94 Hz, 2H) 4.08-4.15 (m, 1H) 4.17 (d, J=8.46 Hz, 1H) 4.22-4.30 (m, 1H) 4.30-4.36 (m, 2H).

tert-butyl 3-((1-(((methylsulfonyl)oxy)methyl)cyclopropyl)sulfonyl)azetidine-1-carboxylate (I-7) was prepared from I-7G following a procedure analogous to that described for I-2. I-7 was isolated as a yellow oil. LCMS m/z: 392 (M+23), 314 (M-55).

Intermediate 8

(1-(cyclopentylsulfonyl)cyclopropyl)methyl methanesulfonate

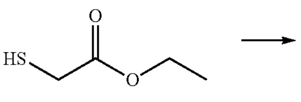

I-8A

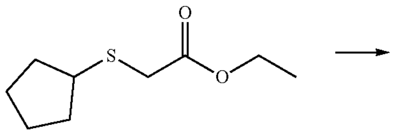

I-8B

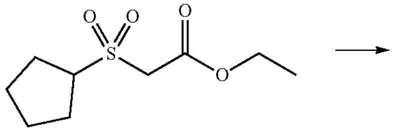

I-8C

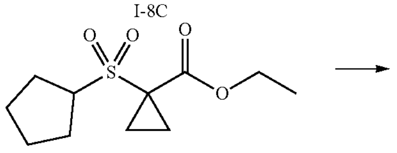

I-8D

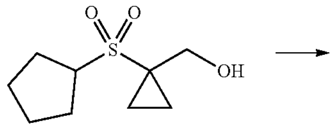

I-8E

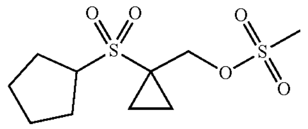

I-8

Ethyl 2-(cyclopentylthio)acetate (I-8B). To a solution of I-8A (3.08 mL, 28.1 mmol) in acetone (80 mL) were added $K_2CO_3$ (5.29 g, 38.3 mmol) and cyclopentyl iodide (2.95 mL, 25.5 mmol). The resulting mixture was stirred at 60° C. overnight. The reaction was cooled to RT and filtered to remove excess base. The filtrate was concentrated under reduced pressure, and the residue was taken up in EtOAc and $H_2O$. The phases were separated and the organic layer was washed with saturated sodium thiosulfate (3×). The organic layer was dried over sodium sulfate and concentrated under reduced pressure. The title compound (I-8B) was isolated as a colorless oil. $^1H$ NMR (400 MHz, $CDCl_3$) δ ppm 1.25-1.31 (m, 3H) 1.46-1.63 (m, 4H) 1.67-1.89 (m, 2H) 1.96-2.09 (m, 2H) 3.19-3.28 (m, 3H) 4.15-4.22 (m, 2H).

Ethyl 2-(cyclopentylsulfonyl)acetate (I-8C). To a solution of I-8B (3.97 g, 21.08 mmol) in EtOH (100 mL) was added Oxone (25.9 g, 42.2 mmol) and a catalytic amount of $H_2O$. The resulting slurry was stirred overnight at RT, after which it was concentrated under reduced pressure. The residue was taken up in $CHCl_3$ and $H_2O$. The phases were separated and the organic layer was washed with saturated sodium thiosulfate, dried over sodium sulfate, and concentrated under reduced pressure. The resulting yellow residue was purified by column chromatography ($SiO_2$, 0-100% DCM/heptane) to afford I-8C as a light yellow oil. $^1H$ NMR (400 MHz, $CDCl_3$) δ ppm 1.30-1.36 (m, 3H) 1.64-1.75 (m, 2H) 1.79-1.91 (m, 2H) 2.02-2.17 (m, 4H) 3.78-3.88 (m, 1H) 3.94 (s, 2H) 4.24-4.32 (m, 2H).

ethyl 1-(cyclopentylsulfonyl)cyclopropanecarboxylate (I-8D) was prepared from I-8B following a procedure analogous to that described for I-2C. LCMS m/z: 247 (M+1).

(1-(cyclopentylsulfonyl)cyclopropyl)methanol (I-8E) was prepared from I-8D following a procedure analogous to that described for I-2D. $^1H$ NMR (400 MHz, $CDCl_3$) δ ppm 0.98-1.04 (m, 2H) 1.48-1.53 (m, 2H) 1.63-1.70 (m, 2H) 1.77-1.87 (m, 2H) 2.05-2.12 (m, 4H) 2.55 (t, J=5.38 Hz, 1H) 3.77 (quin, J=8.30 Hz, 1H) 3.88 (d, J=4.84 Hz, 2H).

(1-(cyclopentylsulfonyl)cyclopropyl)methyl methanesulfonate (I-8) was prepared from I-8E following a procedure analogous to that described for 1-2. $^1H$ NMR (400 MHz, $CDCl_3$) δ ppm 1.15-1.21 (m, 2H) 1.61-1.68 (m, 4H) 1.77-1.84 (m, 2H) 2.05-2.11 (m, 4H) 3.07 (s, 3H) 3.68 quin, J=8.20 Hz, 1H) 4.53 (s, 2H).

Intermediate 9

(1-((3-((tert-butyldimethyl silyl)oxy)propyl)sulfonyl)cyclopropyl)methyl methanesulfonate

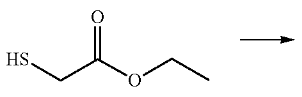

I-9A

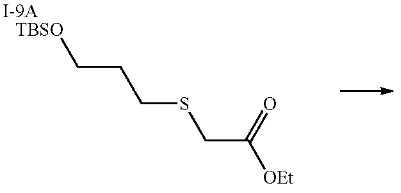

I-9B

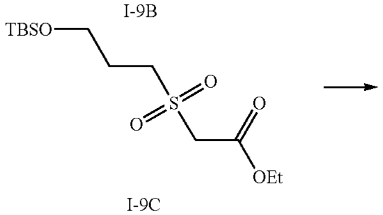

I-9C

-continued

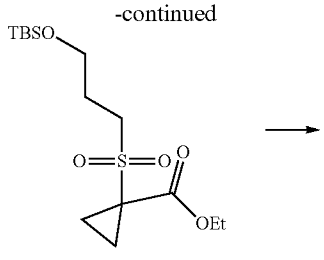

I-9D

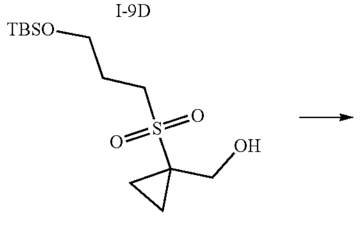

I-9E

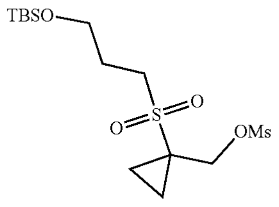

I-9

Ethyl 2-((3-((tert-butyldimethylsilyl)oxy)propyl)thio)acetate (I-9B). To a solution of I-9A (1.429 mL, 13.03 mmol) in acetone (50 mL) were added $K_2CO_3$ (2.456 g, 17.77 mmol), (3-bromopropoxy)(tert-butyl)dimethylsilane (2.74 mL, 11.85 mmol), and NaI (0.355 g, 2.369 mmol). The resulting mixture was stirred at 60° C. Upon completion of the reaction, the mixture was cooled to RT and filtered to remove insolubles. The filtrate was concentrated under reduced pressure. The residue was taken up in EtOAc and $H_2O$. The phases were separated, and the organic layer was washed with aqueous sodium thiosulfate, dried over sodium sulfate, and concentrated under reduced pressure. I-9B was isolated as a colorless oil. $^1H$ NMR (400 MHz, $CDCl_3$) δ ppm 0.06 (s, 6H) 0.90 (s, 9H) 1.29 (t, J=7.14 Hz, 3H) 1.82 (quin, J=1.00 Hz, 2H) 2.72 (t, J=7.24 Hz, 2H) 3.22 (s, 2H) 3.70 (t, J=6.04 Hz, 2H) 4.20 (t, J=7.10 Hz, 2H).

Ethyl 2-((3-((tert-butyldimethylsilyl)oxy)propyl)sulfonyl)acetate (I-9C). To a solution of I-9B (3.68 g, 12.58 mmol) in DCM (100 mL) was added mCPBA (5.64 g, 25.2 mmol). After stirring overnight, the reaction mixture was diluted with DCM, washed with saturated sodium bicarbonate, and dried over sodium sulfate. The dried organic layer was concentrated under reduced pressure to afford the title compound as a colorless oil. $^1H$ NMR (400 MHz, $CDCl_3$) δ ppm 0.07 (s, 1H) 0.91 (s, 9H) 1.34 (t, J=7.14 Hz, 3H) 2.08 (dd, J=10.10, 5.75 Hz, 2H) 3.34-3.41 (m, 2H) 3.76 (t, J=5.80 Hz, 2H) 3.97 (s, 2H) 4.29 (q, J=7.14 Hz, 2H).

Ethyl 1-((3-((tert-butyldimethylsilyl)oxy)propyl)sulfonyl)cyclopropanecarboxylate (I-9D) was prepared from I-9C following a procedure analogous to that described for I-2C. The title compound was isolated as a colorless oil. $^1H$ NMR (400 MHz, $CDCl_3$) δ ppm 0.06 (s, 6H) 0.89 (s, 9H) 1.31 (t, J=6.87 Hz, 3H) 1.60-1.66 (m, 2H) 1.73-1.80 (m, 2H) 1.99-2.11 (m, 2H) 3.47-3.56 (m, 2H) 3.73 (t, J=5.80 Hz, 2H) 4.20-4.31 (m, 2H).

(1-((3-((tert-butyldimethylsilyl)oxy)propyl)sulfonyl)cyclopropyl)methanol (I-9E) was prepared from I-9D following a procedure analogous to that described for I-2D. The title compound was isolated as a colorless oil. $^1H$ NMR (400 MHz, $CDCl_3$) δ ppm 0.06 (s, 6H) 0.89 (s, 9H) 0.99-1.05 (m, 2H) 1.46-1.52 (m, 2H) 2.01-2.12 (m, 2H) 2.48 (t, J=5.77 Hz, 1H) 3.23-3.31 (m, 2H) 3.73 (t, J=5.84 Hz, 2H) 3.89 (d, J=5.77 Hz, 2H).

(1-((3-((tert-butyldimethylsilyl)oxy)propyl)sulfonyl)cyclopropyl)methyl methanesulfonate (I-9) was prepared from I-9E following a procedure analogous to that described for 1-2. The title compound was isolated as an orange oil. $^1H$ NMR (400 MHz, $CDCl_3$) δ ppm 0.04-0.10 (m, 6H) 0.88-0.92 (m, 9H) 1.18-1.24 (m, 2H) 1.62-1.68 (m, 2H) 2.04-2.13 (m, 2H) 3.08 (s, 3H) 3.22-3.29 (m, 2H) 3.75 (t, J=5.82 Hz, 2H) 4.54 (s, 2H).

Intermediate 10

(1-(tert-butylsulfonyl)cyclopropyl)methyl methanesulfonate

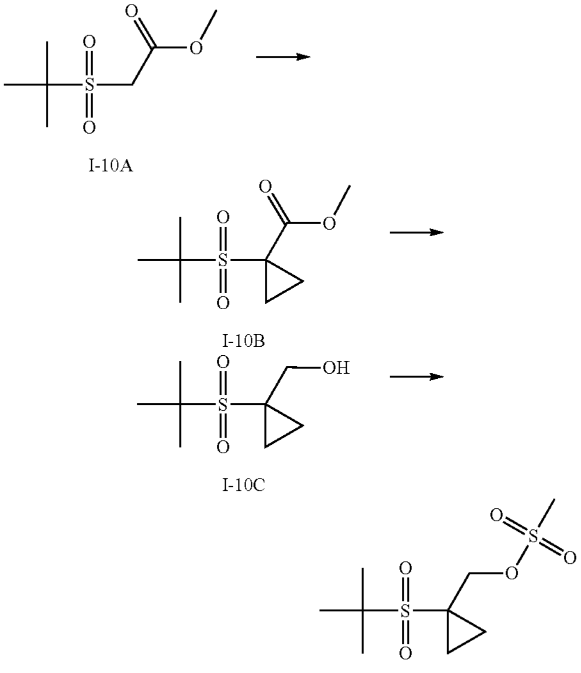

I-10A

I-10B

I-10C

I-10 methyl 1-(tert-butylsulfonyl)cyclopropanecarboxylate (I-10B) was prepared from I-10A following a procedure analogous to that described for I-2C. The title compound was isolated as a waxy solid. $^1H$ NMR (400 MHz, $CDCl_3$) δ ppm 1.47 (s, 9H) 1.60-1.65 (m, 2H) 1.78-1.83 (m, 2H) 3.79 (s, 3H).

(1-(tert-butylsulfonyl)cyclopropyl)methanol (I-10C) was prepared from I-10B following a procedure analogous to that described for I-2D. I-10C was isolated as a white solid. $^1H$ NMR (400 MHz, $CDCl_3$) δ ppm 1.03-1.07 (m, 2H) 1.49-1.51 (m, 9H) 1.55-1.60 (m, 2H) 2.82-2.87 (m, 1H) 3.88 (d, J=5.97 Hz, 2H).

(1-(tert-butylsulfonyl)cyclopropyl)methyl methanesulfonate (I-10) was prepared from I-10C following a procedure analogous to that described for 1-2. The title compound was isolated as an amber waxy solid. $^1H$ NMR (400 MHz, $CDCl_3$) δ ppm 1.23-1.28 (m, 2H) 1.50 (s, 9H) 1.71-1.77 (m, 2H) 3.08 (s, 3H) 4.59 (s, 2H).

Intermediate 11

(1-(oxetan-3-ylsulfonyl)cyclopropyl)methyl methanesulfonate

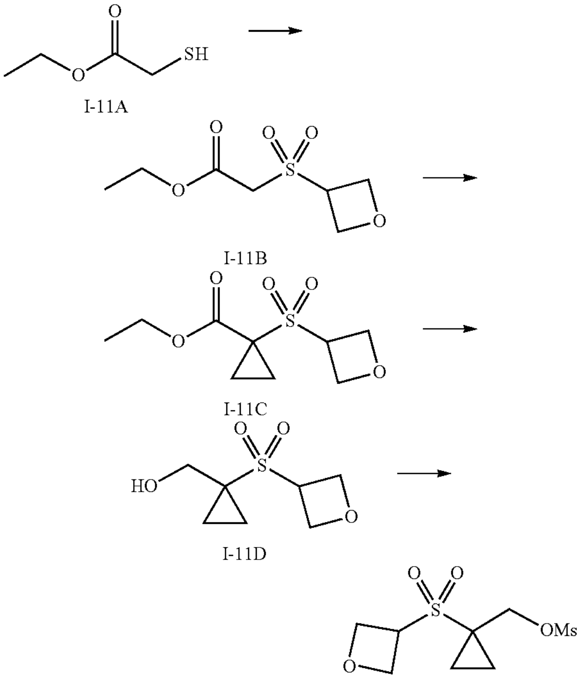

I-11A

I-11B

I-11C

I-11D

I-11E

Ethyl 2-(oxetan-3-ylsulfonyl)acetate (I-11B). To a solution of 3-iodooxetane (0.957 mL, 10.87 mmol) in acetone (50 mL) were added $K_2CO_3$ (2.254 g, 16.31 mmol) and ethyl 2-mercaptoacetate (1.311 mL, 11.96 mmol). The resulting slurry was stirred at 60° C. overnight, after which it was cooled to RT and filtered to remove insolubles. The filter cake was rinsed with acetone. The filtrate was concentrated under reduced pressure, and the resulting residue was taken up in EtOH and treated with Oxone (13.37 g, 21.74 mmol) and approximately 0.3 mL of water. After 5 h, the mixture was filtered to remove insolubles and the filtrate was concentrated under reduced pressure. The oily residue was taken up in DCM and washed with aqueous sodium thiosulfate. The organic layer was dried over sodium sulfate and concentrated under reduced pressure. The title compound was isolated as a colorless oil. LCMS m/z: 209 (M+1). $^1H$ NMR (400 MHz, $CDCl_3$) δ ppm 1.33 (t, J=7.14 Hz, 3H) 3.95 (s, 2H) 4.26 (q, J=7.16 Hz, 2H) 4.73-4.83 (m, 1H) 4.91 (t, J=7.68 Hz, 2H) 4.98-5.06 (m, 2H).

Ethyl 1-(oxetan-3-ylsulfonyl)cyclopropanecarboxylate (I-11C) was prepared from I-11B following a procedure analogous to that described for I-2C. I-11C was isolated as a light yellow oil. LCMS m/z: 235, (M+1). $^1H$ NMR (400 MHz, $CDCl_3$) δ ppm 1.28 (t, J=7.16 Hz, 3H) 1.62-1.69 (m, 2H) 1.77-1.84 (m, 2H) 4.22 (q, =7.14 Hz, 2H) 4.83-4.91 (m, 3H) 5.07-5.15 (m, 2H).

(1-(oxetan-3-ylsulfonyl)cyclopropyl)methanol (I-11D) was prepared from I-11C following a procedure analogous to that described for I-2D. I-11D was isolated as a colorless oil. LCMS m/z: 193 (M+1). $^1$H NMR (400 MHz, $CDCl_3$) δ ppm 0.98-1.04 (m, 2H) 1.48-1.55 (m, 2H) 2.02 (t, J=4.92 Hz, 1H) 3.86 (d, J=4.89 Hz, 2H) 4.68-4.80 (m, 1H) 4.86 (t, J=7.60 Hz, 2H) 5.01-5.10 (m, 2H).

(1-(oxetan-3-ylsulfonyl)cyclopropyl)methyl methanesulfonate (I-11) was prepared from I-11D following a procedure analogous to that described for 1-2. The title compound was isolated as a light yellow oil. LCMS m/z: 271 (M+1). $^1$H NMR (400 MHz, $CDCl_3$) δ ppm 1.20-1.26 (m, 2H) 1.63-1.69 (m, 2H) 3.07 (s, 3H) 4.48 (s, 2H) 4.63-4.71 (m, 1H) 4.89 (t, J=7.73 Hz, 2H) 5.00-5.06 (m, 2H).

Intermediate 12

(1-(isopropylsulfonyl)cyclopropyl)methyl methanesulfonate

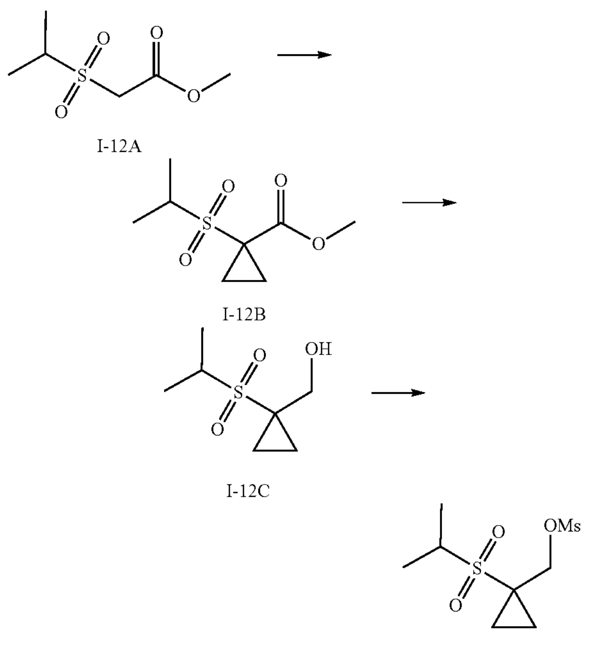

I-12A

I-12B

I-12C

I-12

Methyl 1-(isopropylsulfonyl)cyclopropanecarboxylate (I-12B) was prepared from I-12A following a procedure analogous to that described for I-2C. LCMS m/z: 207 (M+1).

(1-(isopropylsulfonyl)cyclopropyl)methanol (I-12C) was prepared from I-12B following a procedure analogous to that described for I-2D. I-12C was isolated as an off-white solid. LCMS m/z: 179 (M+1). $^1$H NMR (400 MHz, $CDCl_3$) δ ppm 0.99-1.04 (m, 2H) 1.40 (d, J=6.90 Hz, 6H) 1.47-1.52 (m, 2H) 2.47 (t, J=5.62 Hz, 1H) 3.56 (dt, J=13.73, 6.85 Hz, 1H) 3.87 (d, J=5.62 Hz, 2H).

(1-(isopropylsulfonyl)cyclopropyl)methyl methanesulfonate (I-12) was prepared from I-12C following a procedure analogous to that described for 1-2. The title compound was isolated as a dark viscous oil. LCMS m/z: 257 (M+1). $^1$H NMR (400 MHz, $CDCl_3$) δ ppm 1.17-1.23 (m, 2H) 1.42 (d, J=6.80 Hz, 6H) 1.63-1.68 (m, 2H) 3.08 (s, 3H) 3.46 (dt, J=13.63, 6.80 Hz, 1H) 4.53 (s, 2H).

Intermediate 13

(1-(ethylsulfonyl)cyclopropyl)methyl methanesulfonate

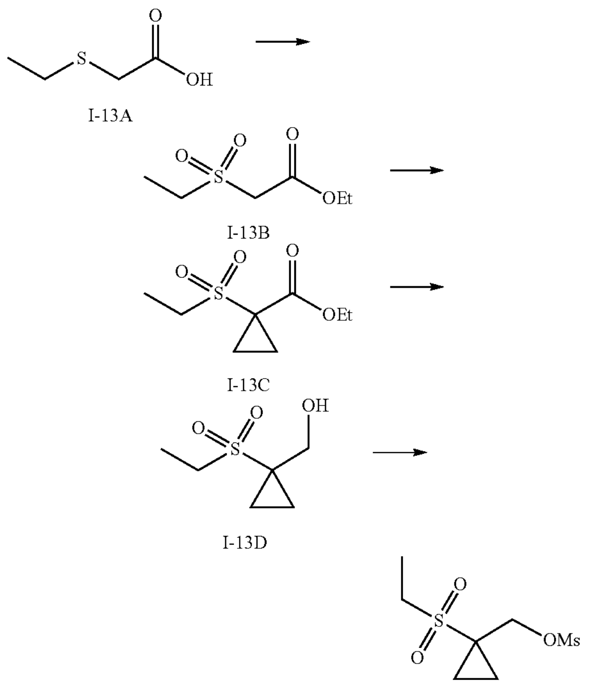

I-13A

I-13B

I-13C

I-13D

I-13

Ethyl 2-(ethylsulfonyl)acetate (I-13B). To a solution of I-13A (3.00 mL, 29.1 mmol) in EtOH (50 mL) was added $H_2SO_4$ conc (1 drop). The resulting solution was refluxed overnight. The reaction mixture was then cooled to 0° C., and Oxone (35.7 g, 58.1 mmol) was added. Upon completion of the reaction, the mixture was filtered. The filter cake was rinsed with EtOH, and the filtrate was concentrated under reduced pressure. The residue was taken up in DCM and washed with brine. The organic layer was dried over sodium sulfate and concentrated under reduced pressure. I-13B was isolated as a colorless oil. LCMS m/z: 181 (M+1). $^1$H NMR (400 MHz, $CDCl_3$) δ ppm 1.33 (t, J=7.14 Hz, 3H) 1.45 (t, J=7.48 Hz, 3H) 3.29 (q, J=7.45 Hz, 2H) 3.95 (s, 2H) 4.28 (q, J=7.14 Hz, 2H).

Ethyl 1-(ethylsulfonyl)cyclopropanecarboxylate (I-13C) was prepared from I-13B following a procedure analogous to that described for I-2C. I-13C was isolated as a colorless oil. LCMS m/z: 207 (M+1). $^1$H NMR (400 MHz, $CDCl_3$) δ ppm 1.29-1.34 (m, 3H) 1.41 (t, J=7.53 Hz, 3H) 1.63-1.68 (m, 2H) 1.76-1.81 (m, 2H) 3.47 (q, J=7.53 Hz, 2H) 4.22-4.30 (m, 2H).

(1-(ethylsulfonyl)cyclopropyl)methanol (I-13D) was prepared from I-13C following a procedure analogous to that described for I-2D. I-13D was isolated as a colorless oil. LCMS m/z: 165 (M+1). $^1$H NMR (400 MHz, $CDCl_3$) δ ppm 1.00-1.05 (m, 2H) 1.42 (t, J=7.51 Hz, 3H) 1.48-1.53 (m, 2H) 2.45 (t, J=5.65 Hz, 1H) 3.22 (q, J=7.50 Hz, 2H) 3.90 (d, J=5.67 Hz, 2H).

(1-(ethylsulfonyl)cyclopropyl)methyl methanesulfonate (I-13) was prepared from I-13D following a procedure analogous to that described for 1-2. The title compound was isolated as a dark oil. LCMS m/z: 243 (M+1). $^1$H NMR (400 MHz, $CDCl_3$) δ ppm 1.18-1.23 (m, 2H) 1.43 (t, J=7.48 Hz, 3H) 1.63-1.67 (m, 2H) 3.09 (s, 3H) 3.19 (q, J=7.48 Hz, 2H) 4.53 (s, 2H).

Intermediate 14

(1-(methylsulfonyl)cyclopropyl)methyl methanesulfonate

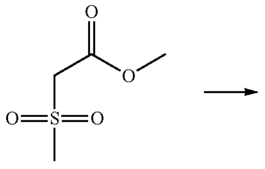

I-14A

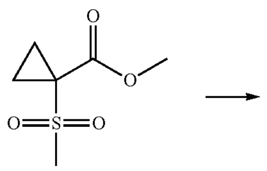

I-14B

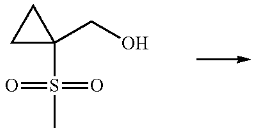

I-14C

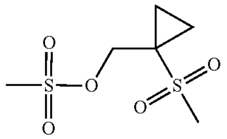

I-14

Methyl 1-(methylsulfonyl)cyclopropanecarboxylate (I-14B) was prepared from I-14A following a procedure analogous to that described for I-2C. I-14B was isolated as a light yellow oil. $^1$H NMR (400 MHz, $CDCl_3$) δ ppm 1.65-1.70 (m, 2H) 1.79-1.84 (m, 2H) 3.20 (s, 3H) 3.81 (s, 3H).

(1-(methylsulfonyl)cyclopropyl)methanol (I-14C) was prepared from I-14B following a procedure analogous to that described for I-2D. I-14C was isolated as a colorless oil. LCMS m/z: 151 (M+1). $^1$H NMR (400 MHz, $CDCl_3$) δ ppm 1.01-1.08 (m, 2H) 1.48-1.54 (m, 2H) 2.48 (t, J=5.45 Hz, 1H) 3.04 (s, 3H) 3.92 (d, J=5.53 Hz, 2H).

(1-(methylsulfonyl)cyclopropyl)methyl methanesulfonate (I-14) was prepared from I-14C following a procedure analogous to that described for 1-2. The title compound was isolated as tan solid. LCMS m/z: 229 (M+1). $^1$H NMR (400 MHz, $CDCl_3$) δ ppm 1.22 (td, J=5.97, 1.52 Hz, 2H) 1.65 (ddd, J=5.92, 5.28, 1.47 Hz, 2H) 3.03 (s, 3H) 3.06-3.11 (m, 3H) 4.54 (s, 2H).

Intermediate 15

(1-(methylsulfonyl)cyclobutyl)methyl methanesulfonate

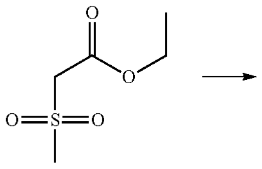

I-15A

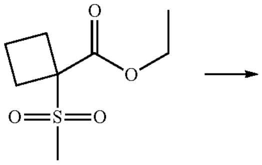

I-15B

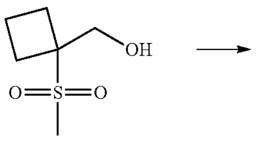

I-15C

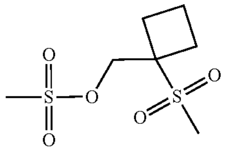

I-15

Ethyl 1-(methylsulfonyl)cyclobutanecarboxylate (I-15B). To a slurry of I-15A (0.794 mL, 6.02 mmol) and $K_2CO_3$ (1.663 g, 12.03 mmol) in DMF (20 mL) was added 1,3-dibromopropane (0.736 mL, 7.22 mmol). The resulting mixture was stirred at 60° C. Upon completion of the reaction, the mixture was diluted with $Et_2O$ and filtered through a plug of Celite. The filtrate was diluted with $Et_2O$ and washed with brine. The aqueous layer was extracted with $Et_2O$. The combined ethereal extracts were dried over sodium sulfate and concentrated under reduced pressure. The residue was purified by column chromatography ($SiO_2$, 0-50% DCM/heptane) to afford I-15B as a colorless oil. LCMS: m/z: 207 (M+1). $^1$H NMR (400 MHz, $CDCl_3$) δ ppm 1.35 (t, J=7.14 Hz, 3H) 1.98-2.21 (m, 2H) 2.60-2.72 (m, 2H) 2.77-2.90 (m, 2H) 2.96 (s, 3H) 4.32 (q, J=7.14 Hz, 2H).

(1-(methylsulfonyl)cyclobutyl)methanol (I-15C) was prepared from I-15B following a procedure analogous to that described for I-2D. I-15C was isolated as a colorless oil. $^1$H NMR (400 MHz, $CDCl_3$) δ ppm 2.01-2.18 (m, 4H) 2.51 (br. s., 1H) 2.63-2.74 (m, 2H) 2.86 (s, 3H) 4.10 (s, 2H).

(1-(methylsulfonyl)cyclobutyl)methyl methanesulfonate (I-15) was prepared from I-15C following an analogous procedure to that described for I-2. I-15 was isolated as a tan solid. $^1$H NMR (400 MHz, $CDCl_3$) δ ppm 2.05-2.24 (m, 4H) 2.72-2.84 (m, 2H) 2.87 (s, 3H) 3.11 (s, 3H) 4.66 (s, 2H).

Intermediate 16

2-(1,1-dioxidotetrahydrothiophen-2-yl)ethyl methanesulfonate

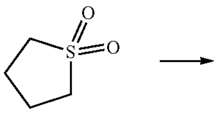

I-16A

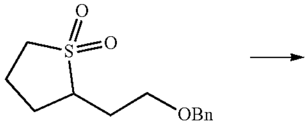

I-16B

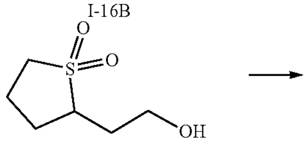

I-16C

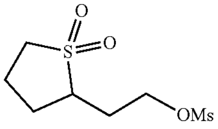

I-16

2-(2-(benzyloxy)ethyl)tetrahydrothiophene 1,1-dioxide (I-16B). A solution of I-16A (2.362 mL, 24.96 mmol) in THF (50 mL) was cooled to−78° C. To the chilled solution was added nBuLi (10.98 mL, 27.5 mmol) dropwise, followed by dropwise addition of benzyl-2-bromoethyl ether (3.99 mL, 25.2 mmol). The resulting solution was allowed to slowly warm to RT. Upon completion of the reaction, the mixture was cooled to 0° C. and quenched with $H_2O$. The aqueous mixture was diluted with EtOAc. The phases were separated and the organic layer was washed with 2 M HCl and brine, dried over sodium sulfate, and concentrated under reduced pressure. The oily residue was purified by column chromatography ($SiO_2$, 0-50% EtOAc/heptane) to afford I-16B as a colorless oil. LCMS m/z: 255 (M+1). $^1$H NMR (400 MHz, $CDCl_3$) δ ppm 1.73-1.90 (m, 2H) 2.02-2.13 (m, 1H) 2.14-2.39 (m, 3H) 2.94-3.03 (m, 1H) 3.11-3.24 (m, 2H) 3.59-3.71 (m, 2H) 4.46-4.59 (m, 2H) 7.27-7.41 (m, 5H).

2-(2-hydroxyethyl)tetrahydrothiophene 1,1-dioxide (I-16C). To a solution of I-16B (2.1 g, 8.26 mmol) in EtOH (10 mL) was added Pd/C (0.05 g, 0.047 mmol). The resulting mixture was vigorously stirred under an atmosphere of $H_2$ overnight. The reaction mixture was filtered through a pad of Celite with MeOH. The filtrate was concentrated under reduced pressure to afford I-16C as a colorless oil. LCMS m/z: 165 (M+1). $^1$H NMR (400 MHz, $CDCl_3$) δ ppm 1.74-1.92 (m, 3H) 1.97-2.27 (m, 3H) 2.32-2.44 (m, 1H) 2.93-3.05 (m, 1H) 3.11-3.25 (m, 2H) 3.72-3.91 (m, 2H).

2-(1,1-dioxidotetrahydrothiophen-2-yl)ethyl methanesulfonate (I-16) was prepared from I-16C following a procedure analogous to that described for 1-2. The title compound was isolated as a golden oil. LCMS m/z: 243 (M+1). $^1$H NMR (400 MHz, $CDCl_3$) δ ppm 1.80 (dd, J=13.30, 6.26 Hz, 1H) 2.01-2.16 (m, 2H) 2.22 (d, J=6.26 Hz, 1H) 2.27-2.47 (m, 2H) 2.96-3.03 (m, 1H) 3.05 (s, 3H) 3.10-3.23 (m, 2H) 4.36-4.41 (m, 2H).

Intermediate 17

N-(4-chlorobenzyl)-1,6-dioxo-1,3,4,6-tetrahydro-pyrido[2,1-c][1,4]oxazine-7-carboxamide

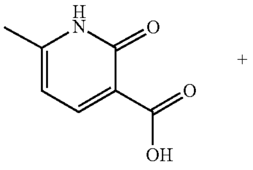

+

I-17A

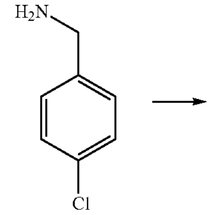

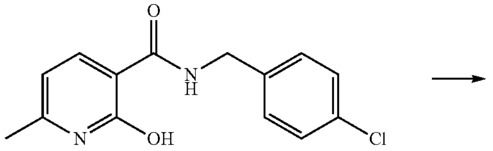

I-17B

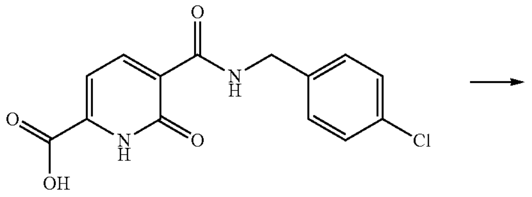

I-17C

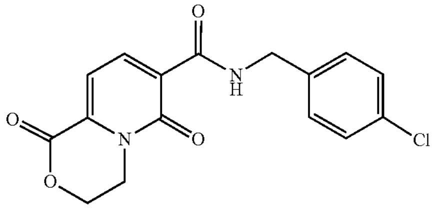

I-17

N-(4-chlorobenzyl)-6-methyl-2-oxo-1,2-dihydropyridine-3-carboxamide (I-17B). To a solution of 6-methyl-2-oxo-1,2-dihydropyridine-3-carboxylic acid (5 g, 32.7 mmol), HOBt (6.00 g, 39.2 mmol) and EDC·HCl (7.51 g, 39.2 mmol) in DMF (100 mL) was added a solution of 4-chlorobenzylamine (5.96 mL, 49.0 mmol) in DMF (50 mL). The resulting solution was stirred at RT. After 72 h, additional 4-chlorobenzylamine (3 mL) was added, resulting in further conversion. The reaction mixture was cooled to 0° C. and ice was added directly to the mixture. The cloudy mixture was adjusted to pH 1 with 2 M HCl. The resulting white precipitate was collected via vacuum filtration. The filter cake was washed with $H_2O$ and heptane and was dried on the frit overnight. I-17B isolated as a white solid. LCMS m/z: 277 (M+1). $^{1}$H NMR (400 MHz, DMSO-d6) δ ppm 2.29 (s, 3H) 4.50 (d, J=6.26 Hz, 2H) 6.31 (dd, J=7.43, 0.78 Hz, 1H) 7.29-7.35 (m, 2H) 7.35-7.43 (m, 2H) 8.23 (d, J=7.43 Hz, 1H) 10.11 (t, J=5.87 Hz, 1H) 12.48 (br. s., 1H).

5-((4-chlorobenzyl)carbamoyl)-6-oxo-1,6-dihydropyridine-2-carboxylic acid (I-17C). To a sealed tube charged with $SeO_2$ (20 g, 180 mmol) were added I-17B (3 g, 10.84 mmol) and dioxane (120 mL). The resulting mixture was stirred at 120° C. for 72 h, after which it was cooled to RT and filtered through a plug of Celite and $Na_2SO_4$. The filtrate was concentrated to a yellow solid. The solid was taken up in 150 mL of DMF and treated with Oxone (13.33 g, 21.68 mmol). The resulting mixture was stirred at RT overnight, after which it was cooled to 0° C. and ice was directly added to the mixture. The contents were diluted with $H_2O$ and adjusted to pH 1 with 2 M HCl. The resulting precipitate was collected via vacuum filtration. I-17C was isolated as a yellow solid. LCMS m/z: 307 (M+1). $^{1}$H NMR (500 MHz, DMSO-d6) δ ppm 4.49-4.57 (m, 2H) 7.09 (d, J=7.25 Hz, 1H) 7.35 (d, J=8.51 Hz, 2H) 7.41 (d, J=8.20 Hz, 2H) 8.43 (d, J=7.25 Hz, 1H) 10.18 (br. s., 1H) 12.40 (br. s., 1H).

N-(4-chlorobenzyl)-1,6-dioxo-1,3,4,6-tetrahydropyrido[2,1-c][1,4]oxazine-7-carboxamide (I-17). To a solution of I-17C (1 g, 3.26 mmol) and $Cs_2CO_3$ (1.594 g, 4.89 mmol) in DMF (50 mL) was added 1,2-dibromoethane (0.309 mL, 3.59 mmol). The resulting mixture was stirred at 60° C. overnight. The reaction mixture was diluted with EtOAc and filtered through a plug of Celite. The filtrate was washed with brine (4×). The organic layer was dried over sodium sulfate and concentrated under reduced pressure. 1-17 was isolated as a tan solid. LCMS m/z: 333 (M+1). $^{1}$H NMR (500 MHz, $CD_3OD$) δ ppm 4.37 (t, J=4.73 Hz, 2H) 4.62 (d, J=5.99 Hz, 3H) 4.69-4.74 (m, 2H) 7.36 (s, 4H) 7.43 (dd, J=7.57, 0.95 Hz, 1H) 8.55-8.58 (m, 1H) 10.40 (br. s., 1H).

Intermediate 18

2-(2-aminoethyl)isothiazolidine 1,1-dioxide

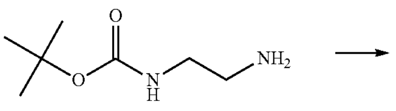

I-18A

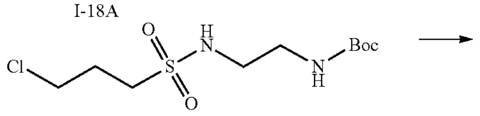

I-18B

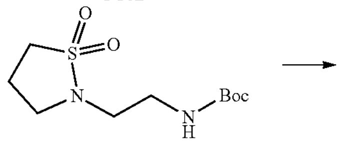

I-18C

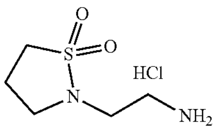

I-18 tert-butyl (2-(3-chloropropylsulfonamido)ethyl)carbamate (I-18B). To a solution of I-18A (1.815 mL, 12.48 mmol) and DIEA (2.398 mL, 13.73 mmol) in THF (100 mL) cooled to 0° C. was added 3-chloropropane-1-sulfonyl chloride (1.670 mL, 13.73 mmol). The reaction was allowed to warm to RT. Upon completion of the reaction, the mixture was diluted with EtOAc and $H_2O$. The phases were separated and the organic layer was washed with $H_2O$ and brine. The organic layer was dried over sodium sulfate and concentrated under reduced pressure. I-18B was isolated as an orange solid. LCMS m/z: 245 (M-55). $^{1}$H NMR (400 MHz, DMSO-d6) δ ppm 1.32-1.40 (m, 9H) 2.02-2.11 (m, 2H) 2.94 (t, J=5.67 Hz, 2H) 2.96-3.03 (m, 2H) 3.05-3.13 (m, 2H) 3.70-3.75 (m, 2H) 6.78-6.87 (m, 1H) 7.20 (t, J=5.28 Hz, 1H).

tert-butyl (2-(1,1-dioxidoisothiazolidin-2-yl)ethyl)carbamate (I-18C). To a solution of I-18B (2 g, 6.65 mmol) in DMF (50 mL) chilled to 0° C. was added NaH (60% suspension in mineral oil, 0.293 g, 7.31 mmol). The resulting mixture was allowed to warm to RT. After 4 d, the reaction mixture was cooled to 0° C. and diluted with $H_2O$ and EtOAc. The phases were separated, and the aqueous layer was extracted with EtOAc (4×). The combined organics were washed with brine, dried over sodium sulfate, and concentrated. I-18C was isolated as a light orange oil and was used without further purification. LCMS m/z: 265 (M+1). $^{1}$H NMR (500 MHz, DMSO-d6) δ ppm 1.37 (s, 9H) 2.20 (quin, J=7.09 Hz, 2H) 3.08 (q, J=6.52 Hz, 2H) 3.12-3.18 (m, 2H) 3.20 (t, J=6.62 Hz, 2H) 6.84 (br. s., 1H).

2-(2-aminoethyl)isothiazolidine 1,1-dioxide (I-18). To a solution of I-18C (1.4 g, 5.30 mmol) in dioxane (5.30 mL) was added 4 M HCl in dioxane (3 mL, 12.00 mmol). The resulting mixture was stirred at RT overnight. The reaction mixture was concentrated under reduced pressure and triturated with $Et_2O$ and heptane affording 1-18. LCMS m/z: 165 (M+1).

Intermediate 19

(1-(methylsulfonyl)azetidin-3-yl)methanamine

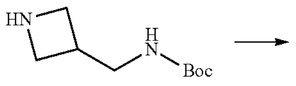

I-19A

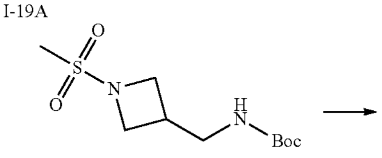

I-19B

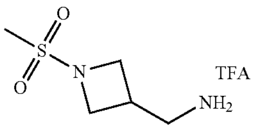

I-19 tert-butyl ((1-(methylsulfonyl)azetidin-3-yl)methyl)carbamate (I-19B). To a solution of I-19A (0.3 g, 1.611 mmol) and DIEA (0.844 mL, 4.83 mmol) in DCM (10 mL) was added MsCl (0.138 mL, 1.772 mmol). The resulting mixture was stirred at RT for 2 h. The reaction mixture was diluted with DCM and 2 M HCl. The phases were separated, and the organic layer was washed with 2 M HCl (2×). The aqueous extracts were extracted with $CHCl_3$ (2×). The combined organic layers were dried over sodium sulfate and concentrated under reduced pressure to afford I-19B as a maroon solid. $^1$H NMR (400 MHz, $CDCl_3$) δ ppm 1.42-1.48 (m, 9H) 2.78 (dt, J=13.11, 6.75 Hz, 1H) 2.86 (s, 3H) 3.36 (t, J=6.46 Hz, 2H) 3.67 (dd, J=8.02, 5.67 Hz, 2H) 3.99 (t, J=8.22 Hz, 2H).

(1-(methylsulfonyl)azetidin-3-yl)methanamine (I-19). To a solution of I-19B (0.417 g, 1.578 mmol) in DCM (5 mL) was added TFA (2 mL, 26.0 mmol). The resulting mixture was stirred at RT for 3 h. The reaction mixture was concentrated under reduced pressure to afford 1-19 as a maroon oil. LCMS m/z: 165 (M+1).

Intermediate 20

(1-(methylsulfonyl)azetidin-2-yl)methanamine

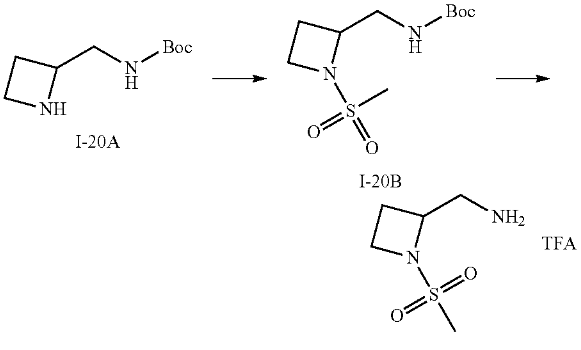

I-20A I-20B I-20 tert-butyl ((1-(methylsulfonyl)azetidin-2-yl)methyl)carbamate (I-20B) was prepared from I-20A following a procedure analogous to that described for I-19B. $^1$H NMR (400 MHz, $CDCl_3$) δ ppm 1.46 (s, 8H) 1.54-1.60 (m, 1H) 1.83-1.98 (m, 1H) 2.17-2.30 (m, 1H) 2.82-2.91 (m, 3H) 3.24-3.41 (m, 2H) 3.46-3.59 (m, 2H) 4.26 (br. s., 1H) 4.69 (br. s., 1H).

(1-(methylsulfonyl)azetidin-2-yl)methanamine (I-20) was prepared from I-20B following a procedure analogous to that described for I-19C. LCMS m/z: 165 (M+1).

Intermediate 21

(1-((1-fluorocyclopropyl)sulfonyl)cyclopropyl) methyl methanesulfonate

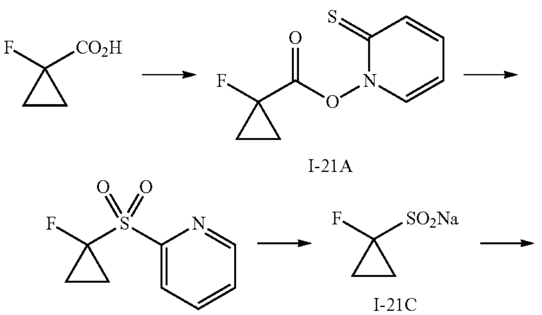

I-21A I-21B I-21C

-continued

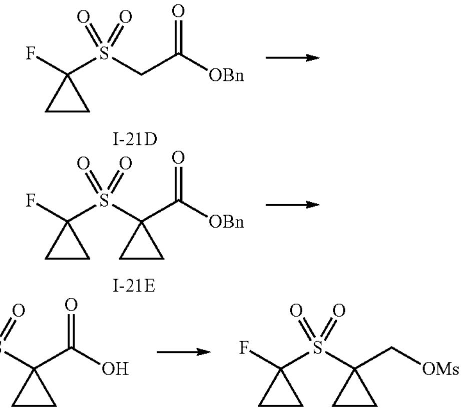

I-21D I-21E I-21F I-21

2-thioxopyridin-1(2H)-yl 1-fluorocyclopropanecarboxylate (I-21A) was prepared from 1-fluorocyclopropanecarboxylic acid following a procedure analogous to that described for I-7B. I-21A was obtained as a dark residue. MS m/z 214.2 (M+1).

2-((1-fluorocyclopropyl)sulfonyl)pyridine (I-21B) was prepared from I-21A following a procedure analogous to that described for I-7C. I-21B was isolated as a white solid. MS m/z 202.2 (M+1).

Sodium 1-fluorocyclopropane-1-sulfinate (I-21C). Ethanethiol (3.97 ml, 53.7 mmol) was added slowly to a stirred suspension of sodium hydride (60% suspension in mineral oil, 1.073 g, 26.8 mmol) in THF (29.8 mL) at 0° C. under argon. After 5 min, a solution of I-21B (1.8 g, 8.95 mmol) in THF (14.9 mL) was added. The mixture was warmed to RT and then to 50° C. After 2 h, the reaction mixture was diluted with DI water and brought to pH 6 with 2 N HCl and saturated aqueous $NaHCO_3$. The biphasic mixture was concentrated in vacuo. The crude product was suspended in MeOH and filtered through a pad of celite. The filtrate was concentrated and dried under vacuum to afford I-21C as an off-white solid. 41 NMR (400 MHz, D20) δ ppm 0.85-1.17 (m, 4H).

Benzyl 2-((1-fluorocyclopropyl)sulfonyl)acetate (I-21D). Benzyl 2-bromoacetate (1.084 mL, 6.84 mmol) was added to a stirred mixture of I-21C (1.0 g, 6.84 mmol) in DMF (6.84 mL) at RT. After 3 h, the reaction contents were diluted with DI water and DCM, and the layers were separated. The aqueous phase was extracted with DCM (2×), and the combined organic phase was dried over $Na_2SO_4$, filtered, and concentrated. The crude residue was purified on $SiO_2$ (0-50% EtOAc/heptane) to afford I-21D as a clear oil. $^1$H NMR (400 MHz, $CDCl_3$) δ ppm 1.33-1.48 (m, 2H) 1.48-1.66 (m, 3H) 4.24 (d, J=0.64 Hz, 2H) 5.25 (s, 2H) 7.27-7.50 (m, 5H). MS m/z 295.1 (M+1).

Benzyl 1-((1-fluorocyclopropyl)sulfonyl)cyclopropanecarboxylate (I-21E) was prepared from I-21D following a procedure analogous to that described for I-2C. The title compound was isolated as a clear oil. $^1$H NMR (400 MHz, $CDCl_3$) δ ppm 1.19-1.45 (m, 2H) 1.59-1.71 (m, 2H) 1.71-1.85 (m, 2H) 1.88-2.04 (m, 2H) 5.21 (s, 2H) 7.31-7.55 (m, 5H). MS m/z 299.1 (M+1).

(1-((1-fluorocyclopropyl)sulfonyl)cyclopropyl)methanol (I-21F) was prepared from I-21E following a procedure analogous to that described for I-2D. I-21F was obtained as a clear oil. MS m/z 195.1 (M+1).

(1-((1-fluorocyclopropyl)sulfonyl)cyclopropyl)methyl methanesulfonate (I-21) was prepared from I-21F following a procedure analogous to that described for I-2. I-21 was obtained as a clear oil. MS m/z 273.1 (M+1).

Intermediate 22

(1-(cyclobutylsulfonyl)cyclopropyl)methyl methanesulfonate

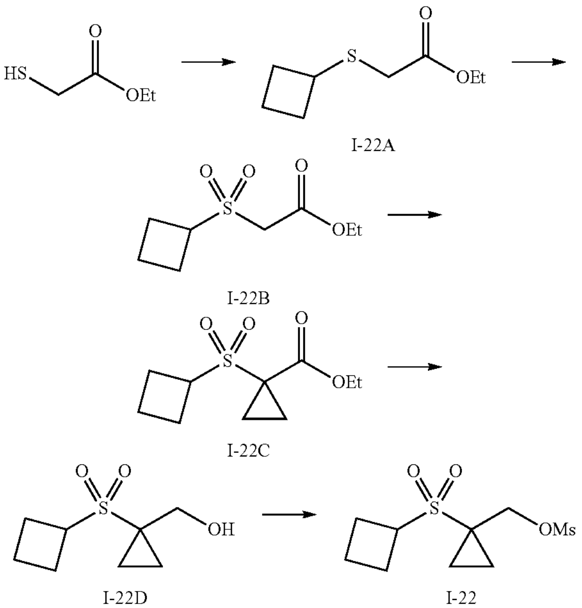

I-22A, I-22B, I-22C, I-22D, I-22

Ethyl 2-(cyclobutylthio)acetate (I-22A). A microwave vial was charged with DMF (14.8 mL), ethyl 2-mercaptoacetate (890 mg, 7.41 mmol), $K_2CO_3$ (1075 mg, 7.78 mmol), 18-crown-6 (196 mg, 0.741 mmol), and bromocyclobutane (500 mg, 3.70 mmol). The vial was sealed and the mixture was stirred at 90° C. over 3 d and then under microwave irradiation for 1 h at 100° C. The reaction mixture was poured into water and extracted with DCM (3×). The organic layer was dried with $Na_2SO_4$, filtered, and concentrated to yield I-22A as an orange oil. 41 NMR (400 MHz, $CDCl_3$) δ ppm 1.26 (td, J=7.13, 2.62 Hz, 2H) 1.84-2.10 (m, 4H) 2.25-2.42 (m, 3H) 3.16 (d, J=2.59 Hz, 2H) 3.50-3.63 (m, 1H) 4.15 (qd, J=7.13, 2.57 Hz, 1H). MS m/z 175.1 (M+1).

Ethyl 2-(cyclobutylsulfonyl)acetate (I-22B). Oxone (3.41 g, 5.55 mmol) was added to a stirred solution of I-22A (0.645 g, 3.7 mmol) in DMF (14.8 mL) at RT. The mixture was stirred overnight, during which it changed from an orange suspension to a pale yellow one. The reaction mixture was diluted with water and extracted with DCM (3×). The combined organic layer was dried over $Na_2SO_4$, filtered, and concentrated to afford the title compound (I-22B), which contained residual DMF and was used without further purification. MS m/z 207.1 (M+1).

Ethyl 1-(cyclobutylsulfonyl)cyclopropanecarboxylate (I-22C) was prepared from I-22B following a procedure analogous to that described for I-2C. $^1H$ NMR (400 MHz, $CDCl_3$) δ ppm 1.24-1.36 (m, 3H) 1.49-1.63 (m, 2H) 1.70-1.80 (m, 2H) 1.87-2.15 (m, 2H) 2.18-2.37 (m, 2H) 2.48-2.71 (m, 2H) 4.23 (q, J=7.14 Hz, 2H) 4.39-4.59 (m, 1H). MS m/z 233.2 (M+1).

(1-(cyclobutylsulfonyl)cyclopropyl)methanol (I-22D) was prepared from I-22C following a procedure analogous to that described for I-2D. MS m/z 191.1 (M+1).

(1-(cyclobutylsulfonyl)cyclopropyl)methyl methanesulfonate (1-22) was prepared from I-22D following a procedure analogous to that described for 1-2. MS m/z 269.2 (M+1).

Intermediate 23

Tert-butyl 3-((1-(((methylsulfonyl)oxy)methyl)cyclopropyl)sulfonyl)pyrrolidine-1-carboxylate

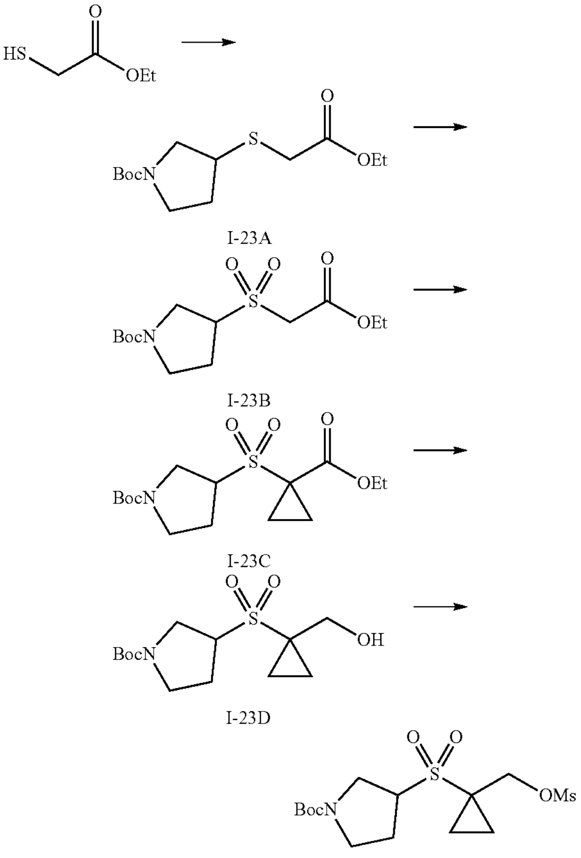

I-23A, I-23B, I-23C, I-23D, I-23 tert-butyl 3-((2-ethoxy-2-oxoethyl)thio)pyrrolidine-1-carboxylate (I-23A). Two microwave vials were each charged with DMF (14.8 mL), ethyl 2-mercaptoacetate (1.763 mL, 15.99 mmol), $K_2CO_3$ (0.553 g, 4.00 mmol), and 18-crown-6 (1.057 g, 4.00 mmol). To one vial was added (S)-tert-butyl 3-bromopyrrolidine-1-carboxylate (1.0 g, 4.00 mmol), and to the other was added (R)-tert-butyl 3-bromopyrrolidine-1-carboxylate (1.0 g, 4.00 mmol). The vials were sealed and stirred in the microwave for 60 min at 100° C. The reaction mixtures were combined, poured into water, and extracted with DCM (3×). The organic layer was dried with $Na_2SO_4$, filtered, and concentrated to yield I-23A, which was used without further purification. MS m/z 290.3 (M+1).

Tert-butyl 3-((2-ethoxy-2-oxoethyl)sulfonyl)pyrrolidine-1-carboxylate (I-23B) was prepared from I-23A following a procedure analogous to that described for I-22B. MS m/z 323.3 (M+1).

Tert-butyl 3-((1-(ethoxycarbonyl)cyclopropyl)sulfonyl)pyrrolidine-1-carboxylate (I-23C) was prepared from I-23B following a procedure analogous to that described for I-2C. MS m/z 292.1 (M-tBu+1).

Tert-butyl 3-((1-(hydroxymethyl)cyclopropyl)sulfonyl)pyrrolidine-1-carboxylate carboxylate (I-23D) was prepared from I-23C following a procedure analogous to that described for I-2D. MS m/z 250.1 (M-tBu+1).

Tert-butyl 3-((1-(((methylsulfonyl)oxy)methyl)cyclopropyl)sulfonyl)pyrrolidine-1-carboxylate (I-23) was prepared from I-23D following a procedure analogous to that described for 1-2. MS m/z 384.2 (M+1), 328.1 (M-tBu+1).

Intermediate 24

(1-((3,3-difluorocyclobutyl)sulfonyl)cyclopropyl)methyl methanesulfonate

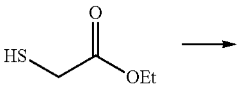

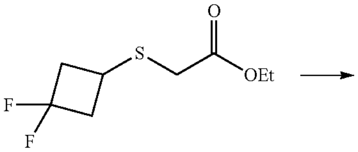

I-24A

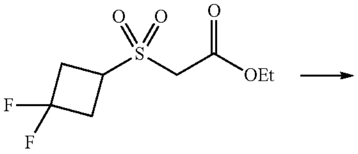

I-24B

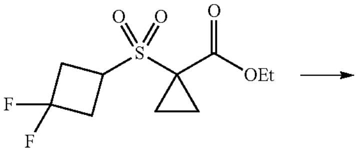

I-24C

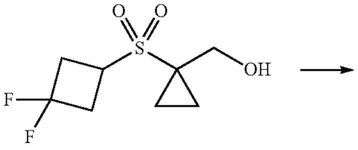

I-24D

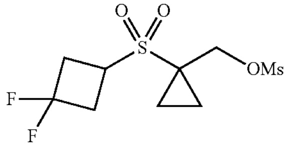

I-24

Ethyl 2-((3,3-difluorocyclobutyl)thio)acetate (I-24A). A microwave vial was charged with DMF (14.8 mL), ethyl 2-mercaptoacetate (0.645 mL, 5.85 mmol), $K_2CO_3$ (849 mg, 6.14 mmol), 18-crown-6 (155 mg, 0.585 mmol), and 3-bromo-1,1-difluorocyclobutane (500 mg, 2.92 mmol). The vial was sealed and stirred in the microwave for 1 h at 100° C. The reaction mixture was poured into water and extracted with DCM (3×). The organic layer was dried with $Na_2SO_4$, filtered, and concentrated to yield I-24A, which was used without further purification.

Ethyl 2-((3,3-difluorocyclobutyl)sulfonyl)acetate (I-24B) was prepared from I-24A following a procedure analogous to that described for I-22B. $^1H$ NMR (400 MHz, $CDCl_3$) δ ppm 1.24-1.42 (m, 3H) 2.83-3.04 (m, 2H) 3.04-3.22 (m, 2H) 3.93 (s, 2H) 3.95-4.09 (m, 1H) 4.17-4.39 (m, 3H). No ionization by LCMS.

Ethyl 1-((3,3-difluorocyclobutyl)sulfonyl)cyclopropanecarboxylate (I-24C) was prepared from I-24B following a procedure analogous to that described for I-2C. $^1H$ NMR (400 MHz, $CDCl_3$) δ ppm 1.14-1.39 (m, 5H) 1.54-1.70 (m, 2H) 1.70-1.87 (m, 2H) 2.78-2.99 (m, 2H) 3.01-3.27 (m, 2H) 4.11-4.32 (m, 3H). MS m/z 269.1 (M+1).

(1-((3,3-difluorocyclobutyl)sulfonyl)cyclopropyl)methanol (I-24D) was prepared from I-24C following a procedure analogous to that described for I-2D. MS m/z 227.1 (M+1).

(1-((3,3-difluorocyclobutyl)sulfonyl)cyclopropyl)methyl methanesulfonate (I-24) was prepared from I-24D following a procedure analogous to that described for 1-2. MS m/z 305.1 (M+1).

Intermediate 25

(1-((3,3-difluoroazetidin-1-yl)sulfonyl)cyclopropyl)methyl methanesulfonate

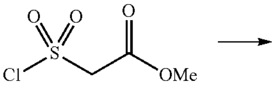

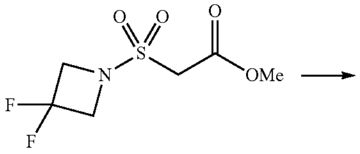

I-25A

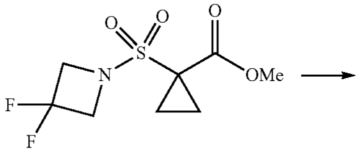

I-25B

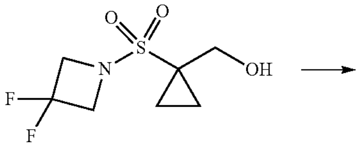

I-25C

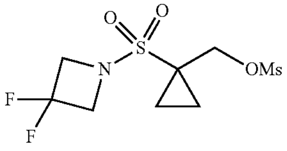

I-25

Methyl 2-((3,3-difluoroazetidin-1-yl)sulfonyl)acetate (I-25A) was prepared according to the general procedure in Northup, A. et al J. Med. Chem. 2013, 56, 2294. Huenig's Base (4.25 mL, 24.32 mmol) was added to a suspension of 3,3-difluoroazetidin-1-ium chloride (900 mg, 6.95 mmol) in DCM (34.7 mL) at 0° C. and under $N_2$. After 5 min, methyl 2-(chlorosulfonyl)acetate (1799 mg, 10.42 mmol) was added dropwise to the reaction flask. The reaction mixture was allowed to warm to RT gradually and was stirred over 4 d. The reaction mixture was partitioned between DCM and water. The aqueous phase was extracted with DCM (2×), and the combined organic layer was washed with 1 N HCl and brine, dried over $Na_2SO_4$, filtered, and concentrated to afford I-25A. No ionization by LCMS.

Methyl 1-((3,3-difluoroazetidin-1-yl)sulfonyl)cyclopropanecarboxylate (I-25B) was prepared from I-25A following a procedure analogous to that described for I-2C. $^1H$ NMR (400 MHz, $CDCl_3$) δ ppm 1.25 (t, J=7.14 Hz, 2H) 1.61-1.68 (m, 2H) 1.70-1.84 (m, 2H) 3.78 (s, 3H) 4.42 (t, J=12.23 Hz, 4H). MS m/z 256.1 (M+1).

(1-((3,3-difluoroazetidin-1-yl)sulfonyl)cyclopropyl)methanol (I-25C) was prepared from I-25B following a procedure analogous to that described for I-2D. MS m/z 228.2 (M+1).

(1-((3,3-difluoroazetidin-1-yl)sulfonyl)cyclopropyl)methyl methanesulfonate (I-25) was prepared from I-25C following a procedure analogous to that described for 1-2. MS m/z 306.1 (M+1).

Intermediate 26

(1-(azetidin-1-ylsulfonyl)cyclopropyl)methyl methanesulfonate

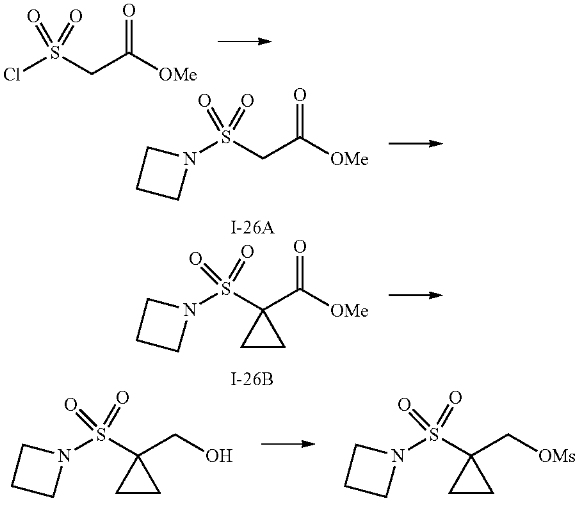

I-26A

I-26B

I-26

Methyl 2-(azetidin-1-ylsulfonyl)acetate (I-26A). To a solution of azetidine (2.343 mL, 34.8 mmol) in DCM (26.1 mL) at 0° C. was added dropwise a solution of methyl 2-(chlorosulfonyl)acetate (3 g, 17.38 mmol) in DCM (8.7 mL). The reaction mixture was allowed to come to RT gradually. Brine was added, and the contents were extracted with DCM (3×). The combined organic layer was dried over $Na_2SO_4$, filtered, and concentrated in vacuo to afford I-26A as a yellow oil. This material was used without further purification. MS m/z 194.0 (M+1).

Methyl 1-(azetidin-1-ylsulfonyl)cyclopropanecarboxylate (I-26B) was prepared from I-26A following a procedure analogous to that described for I-2C. $^1H$ NMR (400 MHz, $CDCl_3$) δ ppm 1.49-1.64 (m, 2H) 1.64-1.77 (m, 2H) 2.12-2.35 (m, 2H) 3.76 (s, 3H) 4.03-4.22 (m, 4H). MS m/z 220.1 (M+1).

(1-(azetidin-1-ylsulfonyl)cyclopropyl)methanol (I-26C) was prepared from I-26B following a procedure analogous to that described for I-2D. MS m/z 192.1 (M+1).

(1-(azetidin-1-ylsulfonyl)cyclopropyl)methyl methanesulfonate (1-26) was prepared from I-26C following a procedure analogous to that described for 1-2. MS m/z 269.3 (M+1).

Intermediate 27

(1-(2-oxooxazolidin-3-yl)cyclopropyl)methyl methanesulfonate

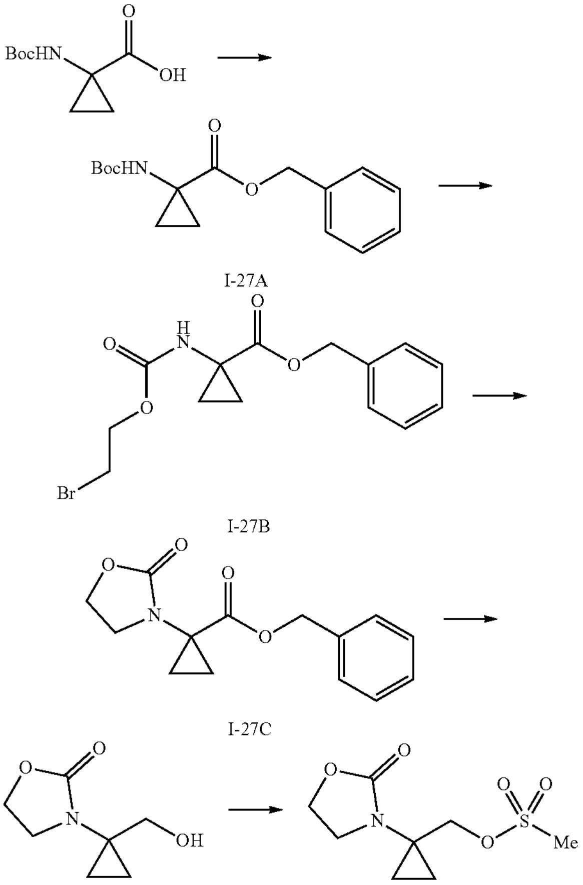

I-27A

I-27B

I-27C

I-27D

I-27

Benzyl 1-((tert-butoxycarbonyl)amino)cyclopropanecarboxylate (I-27A). Benzyl bromide (1.688 mL, 14.19 mmol) was added dropwise at RT to a stirred mixture of 1-((text-butoxycarbonyl)amino)cyclopropanecarboxylic acid (1.19 g, 5.91 mmol), and $NEt_3$ (2.0 mL, 14.19 mmol) in DMF (23.6 mL). The reaction mixture was stirred at RT for 5 d, after which DI water (80 mL) was added. The resulting suspension was stirred at RT for 10 min and the title compound (I-27A), a white solid, was collected by vacuum filtration. MS m/z 292.3 (M+1).

Benzyl 1-(((2-bromoethoxy)carbonyl)amino)cyclopropanecarboxylate (I-27B). To a solution of I-27A (800 mg, 2.75 mmol) in DCM (10.3 mL) at 0° C. and under $N_2$ was added TFA (10.3 mL) over 2 min. The reaction was allowed to warm to RT and was stirred for 16 h. TFA and DCM were removed by rotary evaporation, and the resulting clear oil was concentrated twice from heptane.

The residue was dissolved in DCM (15 mL) and cooled to 0° C. under $N_2$. DMAP (67.1 mg, 0.549 mmol) and $NEt_3$ (1.148 mL, 8.24 mmol) were added followed by dropwise addition of a solution of 2-bromoethyl carbonochloridate (0.295 mL, 2.75 mmol) in DCM (5 mL). After 3 h, the mixture was diluted with DCM and washed with 1 N $Na_2CO_3$. The aqueous layer was extracted with DCM (2×). The combined organic layer was dried over $Na_2SO_4$, filtered, and concentrated to yield the I-27B as an off-white solid. MS m/z 344.2 (M+1).

Benzyl 1-(2-oxooxazolidin-3-yl)cyclopropanecarboxylate (I-27C). Sodium hydride (60% suspension in mineral oil, 165 mg, 4.13 mmol) was added to a solution of I-27B (941 mg, 2.75 mmol) in THF (27.5 mL) at 0° C. and under $N_2$. The reaction mixture was allowed to warm to RT and was stirred for 16 h, after which it was partitioned between EtOAc and DI water. The aqueous layer was extracted with DCM (2×), and the combined organic layer was dried over $Na_2SO_4$, filtered, and concentrated to afford I-27C as a cloudy pale yellow oil. MS m/z 262.2 (M+1).

3-(1-(hydroxymethyl)cyclopropyl)oxazolidin-2-one (I-27D) was prepared from I-27C following a procedure analogous to that described for I-2D. MS m/z 158.0 (M+1).

(1-(2-oxooxazolidin-3-yl)cyclopropyl)methyl methanesulfonate (1-27) was prepared from I-27D following a procedure analogous to that described for 1-2. MS m/z 236.1 (M+1).

Intermediate 28

(1-(N,N-dimethylsulfamoyl)cyclopropyl)methyl methanesulfonate

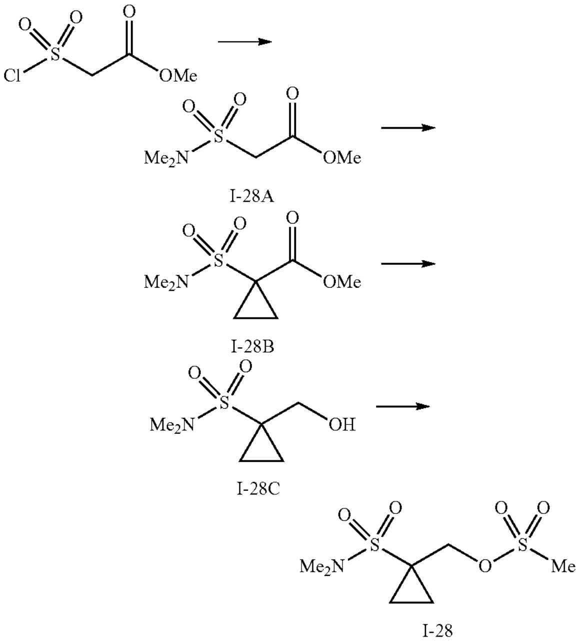

I-28A

I-28B

I-28C

I-28

Methyl 2-(N,N-dimethylsulfamoyl)acetate (I-28A) was prepared according to Northup, A. et al *J. Med. Chem.* 2013, 56, 2294. To a solution of dimethylamine, 2 M in THF (19.47 mL, 38.9 mmol) in DCM (10 mL) at 0° C. was added dropwise a solution of methyl 2-(chlorosulfonyl)acetate (3.36 g, 19.47 mmol) in DCM (10 mL). The reaction mixture was allowed to come to RT gradually. Brine was added, and the contents were extracted with DCM (3×). The organic layer was dried over $Na_2SO_4$, filtered, and concentrated in vacuo to afford I-28A as a yellow-orange oil. $^1H$ NMR (500 MHz, $CDCl_3$) δ ppm 2.89-3.00 (m, 6H) 3.83 (s, 3H) 3.95-4.02 (m, 2H). MS m/z 182.2 (M+1).

Methyl 1-(N,N-dimethylsulfamoyl)cyclopropanecarboxylate (I-28B) was prepared from I-28A following a procedure analogous to that described for I-2C. $^1H$ NMR (500 MHz, $CDCl_3$) δ ppm 1.61-1.67 (m, 2H) 1.72-1.83 (m, 2H) 3.00 (s, 6H) 3.80 (s, 3H). MS m/z 208.1 (M+1).

1-(hydroxymethyl)-N,N-dimethylcyclopropane-1-sulfonamide (I-28C) was prepared from I-28B following a procedure analogous to that described for I-2D. MS m/z 180.2 (M+1).

(1-(N,N-dimethylsulfamoyl)cyclopropyl)methyl methanesulfonate (1-28) was prepared from I-28C following a procedure analogous to that described for 1-2. $^1H$ NMR (500 MHz, $CDCl_3$) δ ppm 1.09-1.24 (m, 2H) 1.50-1.68 (m, 2H) 2.97 (s, 6H) 3.10 (s, 3H) 4.46 (s, 2H). MS m/z 258.2 (M+1).

Intermediate 29

(1,1-dioxidotetrahydrothiophen-2-yl)methyl methanesulfonate

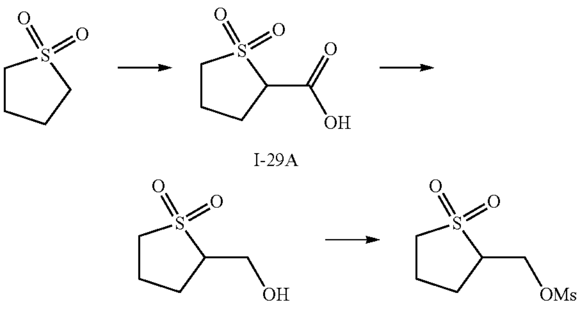

I-29A

I-29B

I-29

Tetrahydrothiophene-2-carboxylic acid 1,1-dioxide (I-29A). A solution of LDA, 2 M in THF (66.6 mL, 133 mmol) was added dropwise to a stirred solution of tetrahydrothiophene 1,1-dioxide (6.30 mL, 66.6 mmol) in THF (333 mL) at −78° C. and under $N_2$. After 30 min, the yellow suspension was brought to RT for 10 min, and then cooled to −50° C. The nitrogen inlet was removed, and $CO_2$ was bubbled through the suspension for 1 h. The reaction mixture became a white suspension, and this was allowed to warm gradually to RT and stir 3 d. The reaction was quenched with DI water, and the mixture was partitioned between water and EtOAc. The aqueous layer was washed with EtOAc (2×). The aqueous layer was acidified with 1 N and 6 N HCl and then extracted with chloroform (3×). NaCl (s) was added to the aqueous phase and it was again extracted with chloroform. The combined organic phase was dried over $Na_2SO_4$, filtered, and concentrated in vacuo to afford I-29A as a yellow oil. The crude product also contained unreacted starting material and residual solvent and was used without further purification. MS m/z 165.0 (M+1).

2-(hydroxymethyl)tetrahydrothiophene 1,1-dioxide (I-29B). Borane tetrahydrofuran complex, 1 M in THF (10.4 mL, 10.40 mmol) was added to a stirred solution of I-29A (680 mg, 4.14 mmol) in THF (41.4 mL) at 0° C. and under $N_2$. The reaction was allowed to warm gradually to RT and was stirred overnight. The reaction was quenched by addition of DI water and partitioned between DCM and water. The aqueous layer was extracted with chloroform (2×) and 3:1 chloroform: isopropanol (3×). The combined organic layer was washed with 1 N HCl, dried over $Na_2SO_4$, filtered, and concentrated to yield I-29B as a clear oil. This material was used without further purification. MS m/z 150.9 (M+1).

(1,1-dioxidotetrahydrothiophen-2-yl)methyl methanesulfonate (1-29) was prepared from I-28C following a procedure analogous to that described for 1-2. The crude product was purified on $SiO_2$ (0-100% EtOAc/heptane) to afford 1-29 as a clear oil. MS m/z 229.1 (M+1).

Intermediate 30

1-(aminomethyl)-N-(tert-butyl)cyclopropane-1-sulfonamide

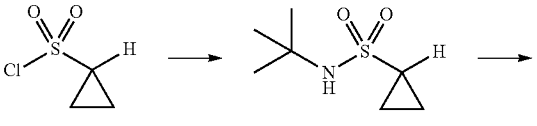

I-30A

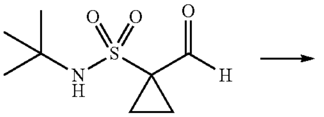

I-30B

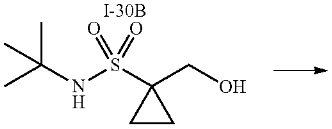

I-30C

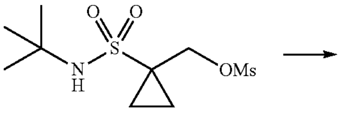

I-30D

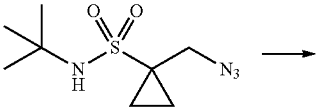

I-30E

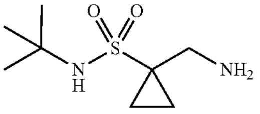

I-30

N-(tert-butyl)cyclopropanesulfonamide (I-30A) was prepared according to WO 2008137779. Neat cyclopropanesulfonyl chloride (11.55 g, 82 mmol) was added dropwise over 5 min to a stirred solution of tertbutylamine (17.34 mL, 164 mmol) in THF (100 mL) at −20° C. (dry ice/acetone) and under $N_2$. The resulting orange solution was allowed to warm gradually to RT and was stirred for 16 h. The resulting suspension was filtered through celite, and the filtrate was concentrated in vacuo. The residue was dissolved in DCM and washed with 1 N HCl, water, and brine. The organic phase was dried over $Na_2SO_4$, filtered, and concentrated. The orange solid was recrystallized from 5:1 heptane:EtOAc to afford I-30A as white crystals.

N-(tert-butyl)-1-formylcyclopropane-1-sulfonamide (I-30B) was prepared according to WO 2012151195. n-butyllithium, 1.6 M in hexane (28.9 mL, 46.3 mmol) was added dropwise over 10 min to a stirred solution of I-30A (4.0 g, 22.57 mmol) in THF (90 mL) at −78° C. under $N_2$. The reaction mixture was stirred 30 min at −78° C. and then 30 min at RT. The flask was cooled to −78° C. and DMF (5.24 mL, 67.7 mmol) was added dropwise. The reaction mixture was allowed to warm gradually to RT and was stirred overnight. The reaction was quenched with DI water and extracted with EtOAc (2×). The aqueous layer was acidified to pH 2 with 1 N HCl, which resulted in gas generation, and was extracted with EtOAc (2×). The organic layers were combined and washed with 1 N HCl and brine. The organic phase was dried over $Na_2SO_4$, filtered, and concentrated in vacuo to afford I-30B as a white solid. $^1$H NMR (400 MHz, $CDCl_3$) δ ppm 1.35 (s, 9H) 1.56-1.69 (m, 2H) 1.79-1.93 (m, 2H) 9.53 (s, 1H). MS m/z 206.3 (M+1).

N-(tert-butyl)-1-(hydroxymethyl)cyclopropane-1-sulfonamide (I-30C) was prepared according to WO 2012151195. Sodium borohydride (0.854 g, 22.57 mmol) was added in 3 portions to a stirred solution of I-30B (4.63 g, 22.57 mmol) in THF (56 mL) at 0° C. After 1.5 h, MeOH (5.60 mL) was added dropwise at 0° C. resulting in rapid gas generation. After 10 min, brine was added to the flask and the contents were extracted with EtOAc (2×) and 3:1 chloroform:isopropanol (1×). The combined organic layer was dried over $Na_2SO_4$, filtered, and concentrated to afford I-30C as a white solid. 41 NMR (400 MHz, $CDCl_3$) δ ppm 0.94-1.07 (m, 2H) 1.31-1.42 (m, 9H) 1.42-1.54 (m, 2H) 2.62-2.84 (m, 1H) 3.85 (s, 2H) 4.27-4.49 (m, 1H). MS m/z 208.3 (M+1).

(1-(N-(tert-butyl)sulfamoyl)cyclopropyl)methyl methanesulfonate (I-30D) was prepared from I-30C following a procedure analogous to that described for 1-2. $^1$H NMR (400 MHz, $CDCl_3$) δ ppm 1.07-1.18 (m, 2H) 1.31-1.42 (m, 10H) 1.54-1.63 (m, 2H) 3.08 (s, 3H) 4.52 (s, 2H). MS m/z 286.1 (M+1).

1-(azidomethyl)-N-(tert-butyl)cyclopropane-1-sulfonamide (I-30E). Sodium azide (1.025 g, 15.77 mmol) was added to a solution of I-30D (1.5 g, 5.26 mmol) in DMF (15.0 mL) at RT. The flask was immersed in a 60° C. oil bath and stirred under $N_2$. After 1 h, the temperature was increased to 90° C. After 5 h, the reaction mixture was cooled to RT, poured onto crushed ice, and extracted with EtOAc (3×). The combined organic layer was dried over $Na_2SO_4$, filtered, and concentrated to afford I-30E. MS m/z 233.3 (M+1).

1-(aminomethyl)-N-(tert-butyl)cyclopropane-1-sulfonamide (I-30). To a slurry of 10% Pd-C (0.280 g, 0.263 mmol) in THF (3.37 mL) under $N_2$ was added a solution of I-30E (1.222 g, 5.26 mmol) in MeOH (84 mL). The atmosphere was exchanged through 3 cycles of vacuum/$H_2$. The reaction mixture was stirred under 1 atm of $H_2$ for 16 h and was then filtered through a pad of celite. The filtrate was concentrated, and the residue was azeotropic ally dried twice with toluene to afford 1-30 as a white solid. $^1$H NMR (400 MHz, $CDCl_3$) δ ppm 0.80-0.90 (m, 2H) 1.37 (s, 9H) 1.40-1.47 (m, 3H) 3.08 (s, 2H) 4.86-5.05 (m, 1H). MS m/z 207.1 (M+1).

Intermediate 31

1-(aminomethyl)-N-(cert-butyl)-N-methylcyclopropane-1-sulfonamide

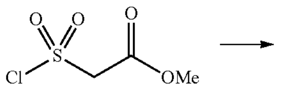

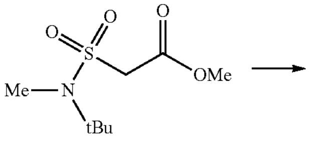

I-31A

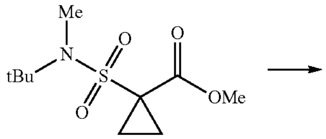

I-31B

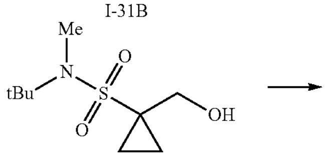

I-31C

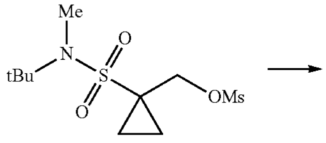

I-31D

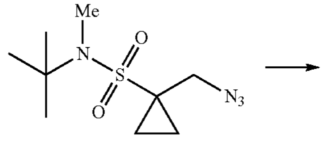

I-31E

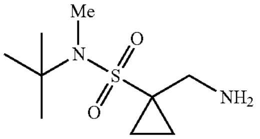

I-31

Methyl 2-(N-(tert-butyl)-N-methylsulfamoyl)acetate (I-31A) was prepared from methyl 2-(chlorosulfonyl)acetate and N,2-dimethylpropan-2-amine following a procedure analogous to that described for I-26A. 1H NMR (400 MHz, $CDCl_3$) δ ppm 1.45 (s, 9H) 2.92 (s, 3H) 3.79 (s, 3H) 4.00 (s, 2H). MS m/z 224.3 (M+1).

Methyl 1-(N-(tert-butyl)-N-methylsulfamoyl)cyclopropanecarboxylate (I-31B) was prepared from I-31A following a procedure analogous to that described for I-2C. $^1$H NMR (400 MHz, $CDCl_3$) δ ppm 1.40 (s, 9H) 1.60-1.68 (m, 2H) 1.73-1.88 (m, 2H) 3.04 (s, 3H) 3.76 (s, 3H). MS m/z 250.3 (M+1), 194.2 (M-tBu+1).

N-(tert-butyl)-1-(hydroxymethyl)-N-methylcyclopropane-1-sulfonamide (I-31C) was prepared from I-31B following a procedure analogous to that described for I-2D. MS m/z 222.3 (M+1), 194.2 (M-tBu+1).

(1-(N-(tert-butyl)-N-methylsulfamoyl)cyclopropyl)methyl methanesulfonate (I-31D) was prepared from I-31C following a procedure analogous to that described for 1-2. MS m/z 244.1 (M-tBu+1).

1-(azidomethyl)-N-(tert-butyl)-N-methylcyclopropane-1-sulfonamide (I-31E) was prepared from I-31D following a procedure analogous to that described for I-30E. MS m/z 191.1 (M-tBu+1).

1-(aminomethyl)-N-(tert-butyl)-N-methylcyclopropane-1-sulfonamide (I-31) was prepared from I-31E following a procedure analogous to that described for 1-30. MS m/z 221.3 (M+1).

Intermediate 32

2-amino-N,N-dimethylethanesulfonamide

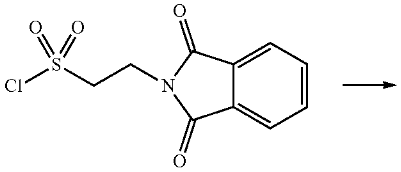

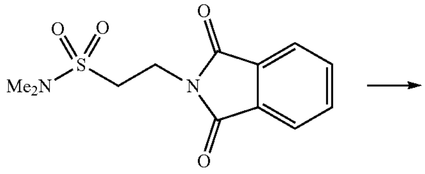

I-32A

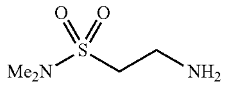

I-32

2-(1,3-dioxoisoindolin-2-yl)-N,N-dimethylethanesulfonamide (I-32A) was prepared according to WO2012115256. To a solution of 2-phthalimidoethanesulfonyl chloride (3.04 g, 11.11 mmol) in THF (40 mL) was added dimethylamine (40%, aqueous) (3.09 mL, 24.44 mmol) dropwise. The flask was capped and the reaction was stirred at RT for 30 min. The mixture was concentrated in vacuo, and the resulting white paste was partitioned between saturated aqueous $NaHCO_3$ and 10:1 EtOAc:DCM. The aqueous layer was extracted twice more with DCM. The combined organic layer was dried over $Na_2SO_4$, filtered, and concentrated to afford I-32A as a white solid. MS m/z 283.7 (M+1).

2-amino-N,N-dimethylethanesulfonamide (1-32) was prepared according to WO2012115256. To a stirred suspension of I-32A (1.3 g, 4.60 mmol) in EtOH (46.0 mL) was added hydrazine hydrate, 65% (0.704 mL, 9.44 mmol) at RT. The mixture was stirred for 1 h at RT, during which a white precipitate formed, and then at reflux (80° C.) for 2 h. Upon stirring at reflux, the solution initially became homogeneous and a white precipitate crashed out. The flask was cooled to RT and the solid was removed through vacuum filtration, rinsing the flask and filter cake with additional EtOH. The filtrate was concentrated in vacuo, and the resulting residue was taken up in DCM. Residual precipitate was again removed through vacuum filtration, and the filtrate was concentrated to yield 2-amino-N,N-dimethylethanesulfonamide 1-32 as a pale yellow oil. $^1$H NMR (500 MHz, $CDCl_3$)

δ ppm 1.56-1.97 (m, 2H) 2.86-2.96 (m, 6H) 3.02-3.13 (m, 2H) 3.24 (t, J=6.15 Hz, 2H). MS m/z 153.1 (M+1).

Intermediate 33

Tert-butyl (2-((2-hydroxypropyl)amino)ethyl)(methyl)carbamate

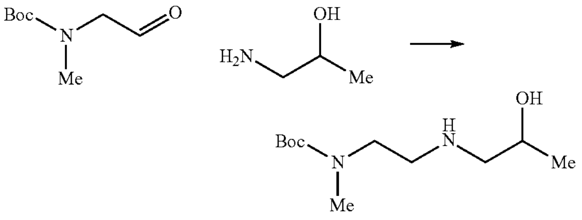

I-33

Tert-butyl (2-((2-hydroxypropyl)amino)ethyl)(methyl) carbamate (1-33) was prepared according to the general procedure in PCT Int. Appl., 2007092435. To a suspension of 10% Pd-C (0.614 g, 0.577 mmol) in EtOAc (2 mL) under nitrogen was added MeOH (80 mL). To the stirred suspension was added tert-butyl methyl(2-oxoethyl)carbamate (2 g, 11.55 mmol) and 1-aminopropan-2-ol (1.337 mL, 17.32 mmol). The atmosphere was exchanged to $H_2$ by 3 cycles of vacuum/$H_2$. The reaction mixture was stirred at RT under $H_2$ for 3 d, after which it was filtered through celite, rinsing with additional methanol. The crude residue was partitioned between EtOAc and saturated aqueous $NaHCO_3$. The organic layer was washed twice more with saturated aqueous $NaHCO_3$, diluted with DCM, dried over $Na_2SO_4$, filtered, and concentrated to afford 1-33 as a clear oil. MS m/z 233.2 (M+1).

Intermediate 34 Tert-butyl (2-((1-hydroxypropan-2-yl)amino)ethyl)(methyl)carbamate

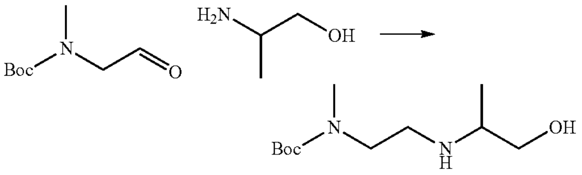

I-34

Tert-butyl (2-((1-hydroxypropan-2-yl)amino)ethyl)(methyl)carbamate (1-34) was prepared from tert-butyl methyl(2-oxoethyl)carbamate and 2-aminopropan-1-ol following a procedure analogous to that described for 1-33. MS m/z 233.3 (M+1).

Intermediate 35

Butyl 9-methyl-1,6-dioxo-2,3,4,6-tetrahydro-1H-pyrido[1,2-a]pyrazine-7-carboxylate

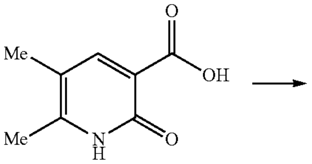

-continued

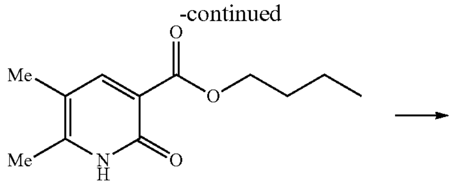

I-35A

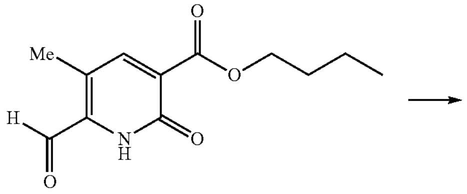

I-35B

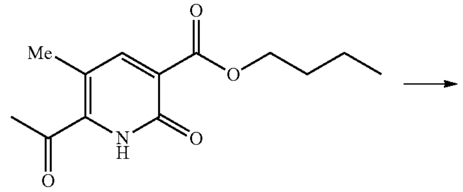

I-35C

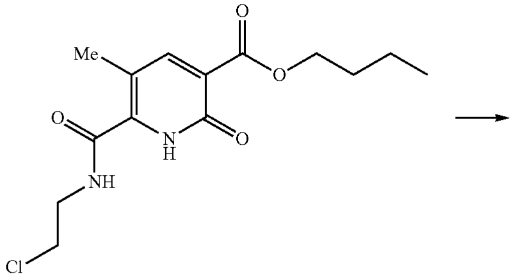

I-35D

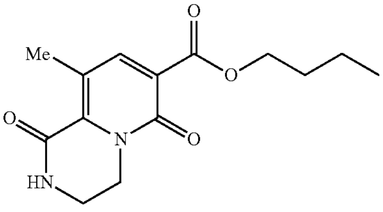

I-35

Butyl 5,6-dimethyl-2-oxo-1,2-dihydropyridine-3-carboxylate (I-35A). To a suspension of 5,6-dimethyl-2-oxo-1,2-dihydropyridine-3-carboxylic acid (5 g, 29.9 mmol) in butan-1-ol (120 mL) was added hydrochloric acid, 37% (3 mL). The resulting suspension was stirred at 115° C. over 6 d. After the reaction was cooled to RT, unreacted acid was separated from the product by vacuum filtration. The filtrate was concentrated in vacuo, using heptane to azeotropically remove butan-1-ol. The resulting residue was suspended in DCM, and the contents were filtered again. The orange filtrate was diluted with DCM and washed once with saturated aqueous $NaHCO_3$. The organic layer was dried over $Na_2SO_4$, filtered, and concentrated to yield an orange oil. Heptane was added, and the contents were re-concentrated to yield the title compound (I-35A) as a yellow-orange powder. MS m/z 224.2 (M+1).

Butyl 6-formyl-5-methyl-2-oxo-1,2-dihydropyridine-3-carboxylate (I-35B). Selenium dioxide (1.908 g, 17.20 mmol) was added to a stirred solution of I-35A (1.92 g, 8.60 mmol) in dioxane (86 mL). The reaction mixture was stirred at reflux for 5 h, after which it was cooled to RT and filtered through a pad of celite and $Na_2SO_4$. The filtrate was concentrated in vacuo. The red-orange solid was suspended in DCM, and the contents were vacuum-filtered through a pad of celite. The filtrate was washed once with DI water, dried over $Na_2SO_4$, filtered, and concentrated in vacuo to afford the I-35B as a yellow-orange solid. MS m/z 238.2 (M+1).

5-(butoxycarbonyl)-3-methyl-6-oxo-1,6-dihydropyridine-2-carboxylic acid (I-35C). To a suspension of I-35B (1.91 g, 8.05 mmol) in tBuOH (33.3 mL), water (33.3 mL), 2-methyl-2-butene (17.06 mL), and acetone (13.88 mL) at 0° C. were sequentially added sodium dihydrogen phosphate (1.449 g, 12.08 mmol) and sodium chlorite (1.365 g, 12.08 mmol). The reaction mixture was gradually warmed to RT and was stirred overnight. The mixture was acidified to pH 2 with 1 N HCl and extracted with DCM (3×). The combined organic layer was dried over $Na_2SO_4$, filtered, and concentrated to yield I-35C. MS m/z 254.2 (M+1).

Butyl 6-((2-chloroethyl)carbamoyl)-5-methyl-2-oxo-1,2-dihydropyridine-3-carboxylate (I-35D) was prepared from I-35C following an analogous procedure to that described for I-1E. The title compound was obtained as a dark brown solid. MS m/z 315.3 (M+1).

Butyl 9-methyl-1,6-dioxo-2,3,4,6-tetrahydro-1H-pyrido[1,2-a]pyrazine-7-carboxylate (1-35). A mixture of I-35D (433 mg, 1.376 mmol) and $K_2CO_3$ (951 mg, 6.88 mmol) in DMF (6.9 mL) was stirred in the microwave at 100° C. for 10 min. The reaction mixture was diluted with DI water and extracted with DCM (3×). The organic layer was dried over $Na_2SO_4$, filtered, and concentrated. The crude product was purified on $SiO_2$ to yield 1-35 as a brown solid. $^1H$ NMR (500 MHz, $CDCl_3$) δ ppm 0.99 (t, J=7.41 Hz, 3H) 1.41-1.53 (m, 2H) 1.53-1.65 (m, 9H) 1.71-1.85 (m, 2H) 2.52 (s, 3H) 3.52-3.70 (m, 2H) 4.24-4.45 (m, 4H). MS m/z 279.2 (M+1).

Intermediate 36

(1-((1-methylcyclopropyl)sulfonyl)cyclopropyl)methyl methanesulfonate

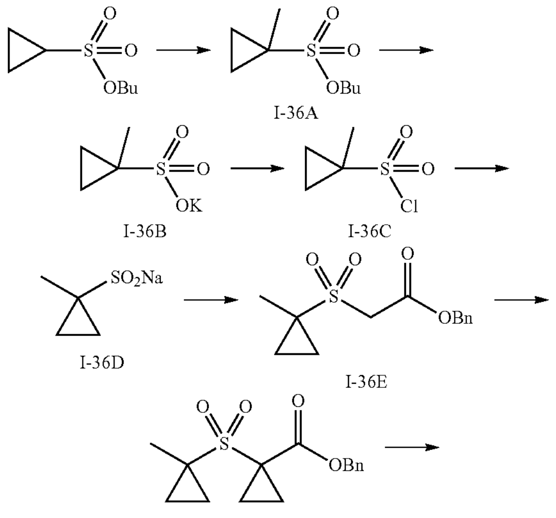

I-36A I-36B I-36C I-36D I-36E I-36F

-continued

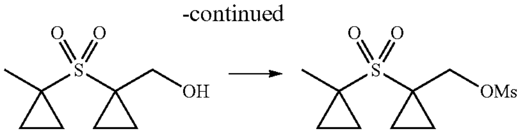

I-36G I-36

Butyl 1-methylcyclopropane-1-sulfonate (I-36A). To butyl cyclopropanesulfonate (11.2 g, 62.8 mmol) in THF (200 mL) at −78° C. was added dropwise butyllithium (47.1 mL, 75 mmol). The reaction was stirred at −78° C. for 1 h and iodomethane (7.82 mL, 126 mmol) was then added. The reaction was stirred at −78° C. for 1 h and allowed to warm to RT. The reaction was quenched with water (5 mL), and the resulting mixture was concentrated. EtOAc (200 mL) and water (50 mL) were added to the residue. The organic phase was washed with brine (50 mL), dried ($Na_2SO_4$), and concentrated. Purification on $SiO_2$ (0-50% EtOAc/heptane) afforded I-36A as a white solid. MS m/z 193.2 (M+1).

Potassium 1-methylcyclopropane-1-sulfonate (I-36B). To I-36A (10.4 g, 54.1 mmol) in water/DME (150 mL/150 mL) was added potassium thiocyanate (5.52 g, 56.8 mmol). The reaction was heated to reflux and stirred for 18 h. Solvents were removed under reduced pressure and the resulting solid was dried at 50° C. under high vacuum for 5 h. The crude product (I-36B) was used without further purification.

Methylcyclopropane-1-sulfonyl chloride (I-36C). To I-36B (9.43 g, 54.1 mmol) in sulfurous dichloride (150 mL, 54.1 mmol) was added DMF (1 mL). The reaction was heated to reflux for 16 h. Volatiles were removed under reduced pressure, and the residue was diluted with DCM (200 mL). The organic phase was washed with water (50 mL), dried ($MgSO_4$), and concentrated to give the crude product (I-36C), which was used without further purification.

Sodium 1-methylcyclopropane-1-sulfinate (I-36D) was prepared from I-36C following a procedure analogous to that described for I-4E. No ionization observed by LCMS.

Benzyl 2-((1-methylcyclopropyl)sulfonyl)acetate (I-36E) was prepared from I-36D following a procedure analogous to that described for I-21D. MS m/z 269.2 (M+1).

Benzyl 1-((1-methylcyclopropyl)sulfonyl)cyclopropanecarboxylate (I-36F) was prepared from I-36E following a procedure analogous to that described for I-2C. MS m/z 295.3 (M+1).

(1-((1-methylcyclopropyl)sulfonyl)cyclopropyl)methanol (I-36G). To a solution of I-36F (5.7 g, 19.36 mmol) in $Et_2O$ (100 mL) was added lithium borohydride (0.633 g, 29.0 mmol), followed by dropwise addition of methanol (1.178 ml, 29.0 mmol). The reaction turned milky and was refluxed at 40° C. for 1 h. The reaction mixture was then cooled to 0° C. and quenched with MeOH (10 mL), followed by HCl (4 M, 15 mL) to reach pH 2. The mixture was concentrated under reduced pressure. The crude product was purified by on $SiO_2$ (0-100% EtOAc/heptane) to afford I-36G as a clear oil. MS m/z 191.2 (M+1).

(1-((1-methylcyclopropyl)sulfonyl)cyclopropyl)methyl methanesulfonate (I-36) was prepared from I-36G following a procedure analogous to that described for I-2. I-36 was obtained as a white solid. MS m/z 269.2.

Intermediate 37

(1-((1-(difluoromethyl)cyclopropyl)sulfonyl)cyclopropyl)methyl methanesulfonate

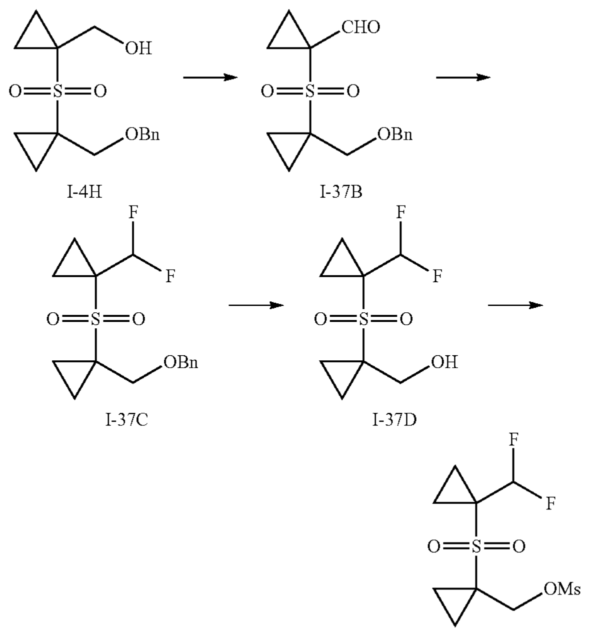

I-4H, I-37B, I-37C, I-37D, I-37

Potassium 1-methylcyclopropane-1-sulfonate (I-37B). A solution of oxalyl dichloride (1.305 mL, 14.91 mmol) in DCM (100 mL) was cooled to −78° C. To the chilled solution was added a solution of DMSO (1.630 mL, 22.94 mmol) in DCM (10 mL). The resulting mixture was stirred at −78° C. for 20 min, after which a solution of I-4H (3.40 g, 11.47 mmol) in DCM (10 mL) was added. The resulting mixture was stirred at −78° C. for 1 h. To the reaction was added $NEt_3$ (7.99 ml, 57.4 mmol). The reaction was allowed to warm to 0° C. and was stirred for 2 h before it was quenched with saturated ammonium chloride. The biphasic mixture was extracted with DCM. The organic extracts were washed with ammonium chloride and brine, dried over $Na_2SO_4$, and concentrated to afford the title product (I-37B) as a yellow oil. MS m/z 295.2 (M+1).

(((1-((1-(difluoromethyl)cyclopropyl)sulfonyl)cyclopropyl)methoxy)methyl)benzene (I-37C). To I-37B (3.38 g, 11.48 mmol) in chloroform (20 mL) was added DAST (4.55 mL, 34.4 mmol). The reaction was stirred at 60° C. for 3 h, after which it was cooled to RT and water (10 mL) was added. The phases were separated and the aqueous layer was extracted with DCM (2×20 mL). The combined organics were dried ($Na_2SO_4$) and concentrated. The residue was purified on $SiO_2$ (0-100% EtOAc/heptane) to afford I-37C. MS m/z 317.3 (M+1).

(1-((1-(difluoromethyl)cyclopropyl)sulfonyl)cyclopropyl)methanol (I-37D). A flask containing I-37C (700 mg, 2.21 mmol) and 10% Pd/C (706 mg, 0.66 mmol) in HOAc (10 mL) was purged with $N_2$ and filled with $H_2$ (balloon). The reaction was stirred for 3 h, after which water (15 mL) was added and the mixture was extracted with DCM (2×30 mL). The combined organics were dried ($Na_2SO_4$) and concentrated to give I-37D. MS m/z 227.1 (M+1).

Ethyl 1-(cyclobutylsulfonyl)cyclopropanecarboxylate (I-37) To I-37D (480 mg, 2.122 mmol) and triethylamine (325 μL, 2.334 mmol) in DCM (10 mL) at 0° C. was added methanesulfonyl chloride (174 μL, 2.228 mmol) drop wise. The reaction was stirred at 0° C. for 1 h and allowed to warm to RT for 30 min. The mixture was quenched by addition of cold water. The phases were separated and the organic layer was dried ($MgSO_4$) and concentrated to give 1-37 as a white solid. MS m/z 305.1 (M+1).

Intermediate 38

(1-(((3-methyloxetan-3-yl)methyl)sulfonyl)cyclopropyl)methyl methanesulfonate

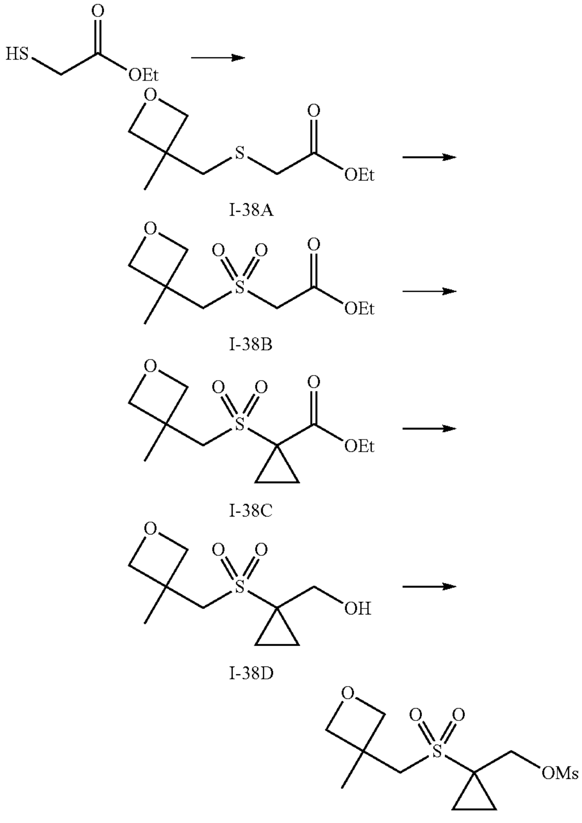

I-38A, I-38B, I-38C, I-38D, I-38

Ethyl 2-(((3-methyloxetan-3-yl)methyl)thio)acetate (I-38A). To a solution of ethyl 2-mercaptoacetate (1.827 ml, 16.66 mmol) in acetone (100 mL) were added $K_2CO_3$ (4.19 g, 30.3 mmol) and 3-(bromomethyl)-3-methyloxetane (2.5 g, 15.15 mmol). To the reaction was added NaI (0.454 g, 3.03 mmol). The resulting mixture was stirred at 60° C. for 3 d. The reaction was cooled to RT and filtered to remove insolubles. The filtrate was concentrated to afford I-38A, which was used without further purification. MS m/z 205.2 (M+1).

Ethyl 2-(((3-methyloxetan-3-yl)methyl)sulfonyl)acetate (I-38B) was prepared from I-38A following a procedure analogous to that described for I-9C. I-38B was isolated as a colorless oil that solidified to waxy solid. MS m/z 237.1 (M+1).

Ethyl 1-(((3-methyloxetan-3-yl)methyl)sulfonyl)cyclopropane-1-carboxylate (I-38C) was prepared from I-38B following a procedure analogous to that described for I-2C. MS m/z 263.2 (M+1).

(1-(((3-methyloxetan-3-yl)methyl)sulfonyl)cyclopropyl) methanol (I-38D) was prepared from I-38C following a procedure analogous to that described for I-2D. MS m/z 221.2 (M+1).

(1-(((3-methyloxetan-3-yl)methyl)sulfonyl)cyclopropyl) methyl methanesulfonate (1-38) was prepared from I-38D following a procedure analogous to that described for 1-2. MS m/z 299.2 (M+1). $^1$H NMR (400 MHz, $CDCl_3$) δ ppm 4.66 (d, J=6.36 Hz, 2H) 4.55 (s, 2H) 4.44 (d, J=6.36 Hz, 2H) 3.55 (s, 2H) 3.10 (s, 3H) 1.68 (s, 3H) 1.62-1.66 (m, 2H) 1.21-1.26 (m, 2H).

Intermediate 39

(1-(((1-(trifluoromethyl)cyclopropyl)methyl)sulfonyl)cyclopropyl)methyl methanesulfonate

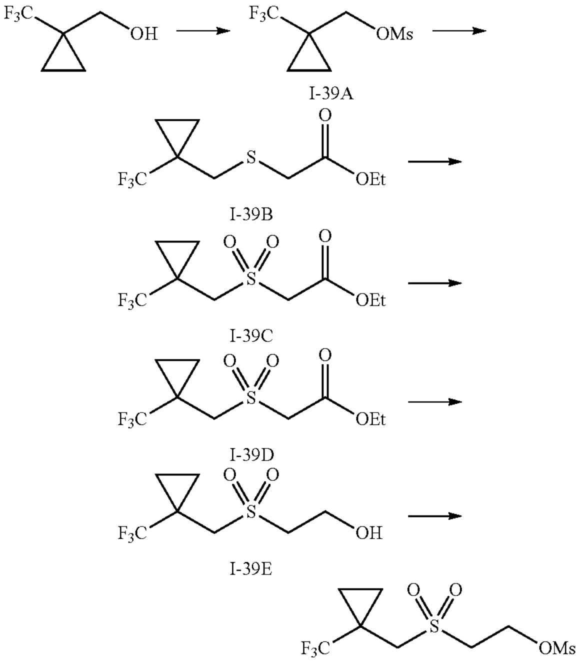

I-39A, I-39B, I-39C, I-39D, I-39E, I-39

(1-(trifluoromethyl)cyclopropyl)methyl methanesulfonate (I-39A) was prepared (1-(trifluoromethyl)cyclopropyl)methanol following a procedure analogous to that described for 1-2. The title compound (I-39A) was isolated as a red oil. $^1$H NMR (400 MHz, $CDCl_3$) δ ppm 4.31 (s, 2H) 3.06 (s, 3H) 1.18-1.24 (m, 2H) 0.93-0.99 (m, 2H).

Ethyl 2-(((1-(trifluoromethyl)cyclopropyl)methyl)thio) acetate (I-39B). To a solution of ethyl 2-mercaptoacetate (681 μl, 6.21 mmol) in acetone (10 mL) were sequentially added $K_2CO_3$ (945 mg, 6.84 mmol), NaI (93 mg, 0.621 mmol), 18-crown-6 (164 mg, 0.621 mmol) and I-39A (678 mg, 3.11 mmol). The resulting mixture was stirred at 60° C. in an oil bath for 16 h. The reaction mixture was diluted with ethyl acetate and water. The organic phase was separated and was washed with brine. The organic phase was dried over sodium sulfate, filtered and concentrated. The resulting residue was dried under high vacuum to give I-39B as brown oil. MS m/z 265.3 (M+23). $^1$H NMR (400 MHz, $CDCl_3$) δ ppm 4.19-4.22 (m, 2H) 3.23 (s, 2H) 3.00 (s, 2H) 1.28-1.31 (m, 3H) 1.04-1.11 (m, 2H) 0.80-0.86 (m, 2H).

Ethyl 2-(((1-(trifluoromethyl)cyclopropyl)methyl)sulfonyl)acetate (I-39C) was prepared from I-39B following a procedure analogous to that described for I-9C. MS m/z 275.2 (M+1). $^1$H NMR (400 MHz, $CDCl_3$) δ ppm 4.25-4.31 (m, 2H) 4.02 (s, 2H) 3.66 (s, 2H) 1.31-1.34 (m, 3H) 1.24-1.28 (m, 2H) 1.18-1.23 (m, 2H).

Ethyl 1-(((1-(trifluoromethyl)cyclopropyl)methyl)sulfonyl)cyclopropane-1-carboxylate (I-39D) was prepared from I-39C following a procedure analogous that described for I-2C. $^1$H NMR (400 MHz, $CDCl_3$) δ ppm 4.16-4.31 (m, 2H) 3.77 (s, 2H) 1.79-1.85 (m, 2H) 1.64-1.70 (m, 2H) 1.27-1.34 (m, 4H) 1.24 (s, 4H).

(1-(41-(trifluoromethyl)cyclopropyl)methyl)sulfonyl)cyclopropyl)methanol (I-39E) was prepared from I-39D following a procedure analogous to that described for I-2D. MS m/z 259.2 (M+1).

(1-(((01-(trifluoromethyl)cyclopropyl)methyl)sulfonyl) cyclopropyl)methyl methanesulfonate (I-39) was prepared from I-39E following a procedure analogous to that described for 1-2. MS m/z 337.2 (M+1).

Intermediate 40

(1-((tetrahydro-2H-pyran-4-yl)sulfonyl)cyclopropyl) methyl methanesulfonate

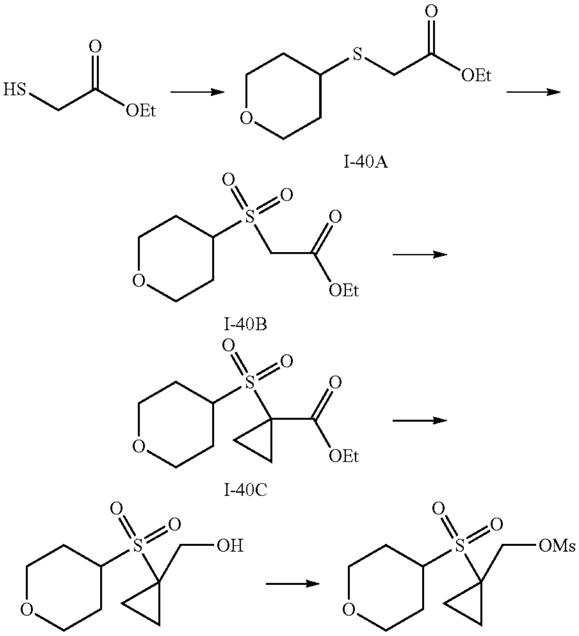

I-40A, I-40B, I-40C, I-40D, I-40

Ethyl 2-((tetrahydro-2H-pyran-4-yl)thio)acetate (I-40A) was prepared from ethyl 2-mercaptoacetate and 4-bromotetrahydro-2H-pyran following a procedure analogous to that described for I-24A. The title product (I-40A) was isolated as an orange oil. MS m/z 205.2 (M+1).

Ethyl 2-((tetrahydro-2H-pyran-4-yl)sulfonyl)acetate (I-40B) was prepared from I-40A following a procedure analogous to that described for I-9C. I-40B was isolated as a colorless oil residue. MS m/z 237 (M+1).

Ethyl 1-((tetrahydro-2H-pyran-4-yl)sulfonyl)cyclopropanecarboxylate (I-40C) was prepared from I-40B following an analogous procedure to that described for I-2C. Compound I-40C was isolated as a light yellow solid. MS m/z 263 (M+1).

(1-((tetrahydro-2H-Pyran-4-yl)sulfonyl)cyclopropyl) methanol (I-40D) was prepared from I-40C following a procedure analogous to that described for I-2D. I-40D was isolated as a white solid. MS m/z 221 (M+1).

(1-((tetrahydro-2H-Pyran-4-yl)sulfonyl)cyclopropyl) methyl methanesulfonate (I-40) was prepared from I-40D following a procedure analogous to that described for 1-2. I-40 was isolated as a brown oil. MS m/z 299 (M+1).

Intermediate 41

(1-(tert-butylsulfinyl)cyclopropyl)methyl methanesulfonate

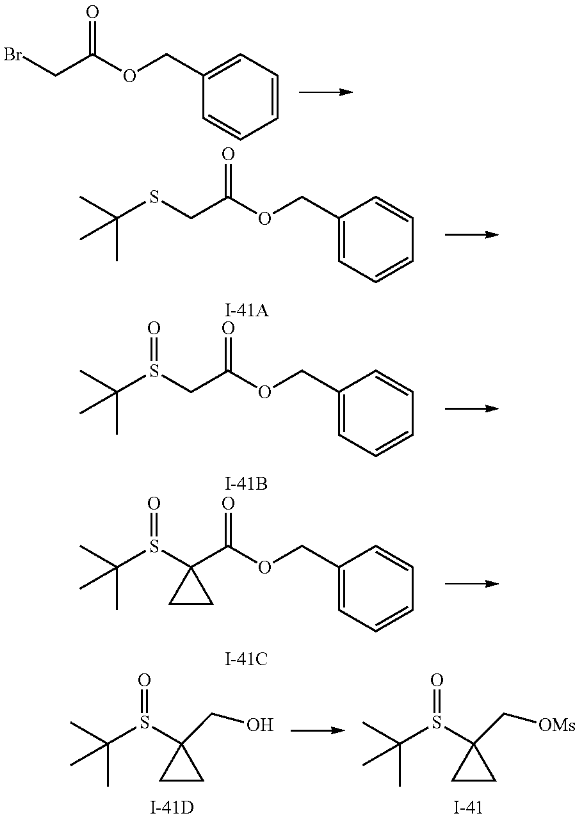

I-41A

I-41B

I-41C

I-41D

I-41

Benzyl 2-(tert-butylthio)acetate (I-41A). To a solution of 2-methylpropane-2-thiol (5.9 mL, 52.4 mmol) in acetone (50 mL) were sequentially added $K_2CO_3$ (11.7 g, 85 mmol), NaI (0.39 g, 2.6 mmol), and benzyl 2-bromoacetate (15 g, 65.5 mmol). The resulting mixture was stirred at 25° C. for 2 h, after which it was diluted with ethyl acetate and water. The organic phase was separated and washed with brine. The organic phase was dried over sodium sulfate, filtered and concentrated. The resulting residue was dried under high vacuum to give I-41A as a yellow oil. MS m/z 239 (M+1).

Benzyl 2-(tert-butylsulfinyl)acetate (I-41B). To solution of I-41A (12.5 g, 52.4 mmol) in methanol (150 mL) and water (15 mL) at 25° C. was added Oxone (17.7 g, 28.8 mmol). The resulting mixture was stirred at 25° C. for 20 min. The suspension was filtered through celite and the filtrate was concentrated. The resulting residue was partitioned between DI water and DCM. The aqueous phase was extracted with DCM (2×), and the combined organic phase was dried over sodium sulfate, filtered, and concentrated. The residue was purified on $SiO_2$ (0-50% EtOAc/heptane) to afford I-41B as a colorless oil. MS m/z 255 (M+1).

Benzyl 1-(tert-butylsulfinyl)cyclopropanecarboxylate (I-41C). To an ice cold solution of I-41B (1.6 g, 6.3 mmol) in DMA (20 mL) was added sodium hydride (60% suspension in mineral oil, 0.45 g, 11.3 mmol). The resulting mixture was stirred at 25° C. for 30 min. To this suspension was added 1,2-dibromoethane (1.4 g, 7.5 mmol), and this was stirred at 25° C. for 3 h. The reaction mixture was partitioned between ethyl acetate (100 mL) and water (50 mL). The organic phase was washed with brine, dried over sodium sulfate, filtered, and concentrated. The residue was purified on $SiO_2$ (0-50% EtOAc/heptane) to give I-41C. MS m/z 281 (M+1).

(1-(tert-Butylsulfinyl)cyclopropyl)methanol (I-41D) was prepared from I-41C following a procedure analogous to that described for I-2D. I-41D was obtained as a colorless oil. MS m/z 177 (M+1).

(1-(tert-Butylsulfinyl)cyclopropyl)methyl methanesulfonate (I-41) was prepared from I-41D following a procedure analogous to that described for 1-2. Title compound 1-41 was obtained as a brown solid. MS m/z 255 (M+1).

Intermediate 42

(1-((cyclopropylmethyl)sulfonyl)cyclopropyl)methyl methanesulfonate

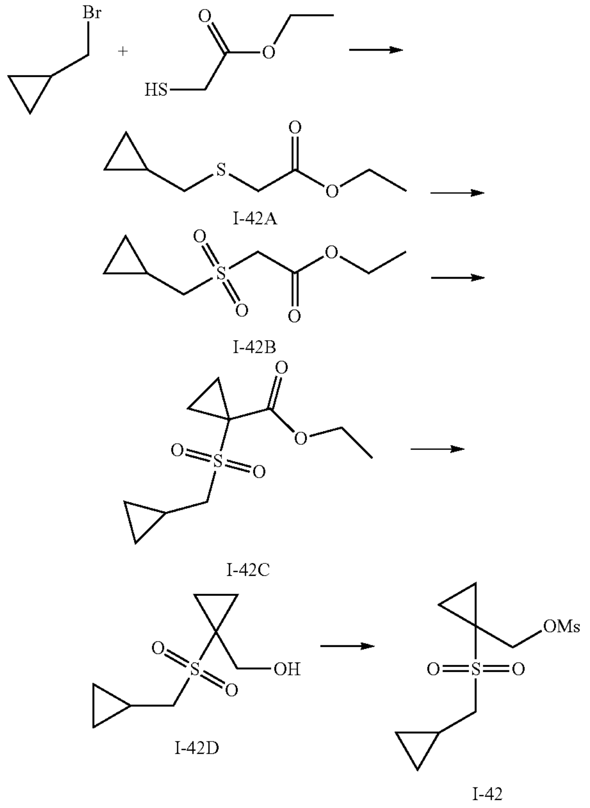

I-42A

I-42B

I-42C

I-42D

I-42

Ethyl 2-((cyclopropylmethyl)thio)acetate (I-42A) was prepared from ethyl 2-mercaptoacetate and (bromomethyl) cyclopropane following a procedure analogous to that described in I-38A. MS m/z 175 (M+1).

Ethyl 2-((cyclopropylmethyl)sulfonyl)acetate (I-42B) was prepared from I-42A following a procedure analogous to that described for I-9C. MS m/z 207 (M+1).

Ethyl 1-((cyclopropylmethyl)sulfonyl)cyclopropanecarboxylate (I-42C) was prepared from I-42B following a procedure analogous to that described for I-2C. Title compound I-42C was isolated as a yellow solid. $^1$H NMR (400 MHz, $CDCl_3$) δ 4.24 (q, J=7.14 Hz, 2H), 3.37 (d, J=7.29 Hz, 2H), 1.79-1.88 (m, 2H), 1.62-1.69 (m, 2H), 1.24-1.33 (m, 3H), 1.05-1.20 (m, 1H), 0.64-0.74 (m, 2H), 0.32-0.45 (m, 2H). MS m/z 233 (M+1).

(1-((Cyclopropylmethyl)sulfonyl)cyclopropyl)methanol (I-42D) was prepared from I-42C following a procedure analogous to that described for I-2D. Title compound I-42D was isolated as a colorless oil. MS m/z 191 (M+1).

(1-((Cyclopropylmethyl)sulfonyl)cyclopropyl)methyl methanesulfonate (1-42) was prepared from I-42D following a procedure analogous to that described for 1-2. Title compound 1-42 was isolated as a yellow solid. MS m/z 269 (M+1).

Intermediate 43

(1-(((1-(cyanomethyl)cyclopropyl)methyl)sulfonyl) cyclopropyl)methyl methanesulfonate

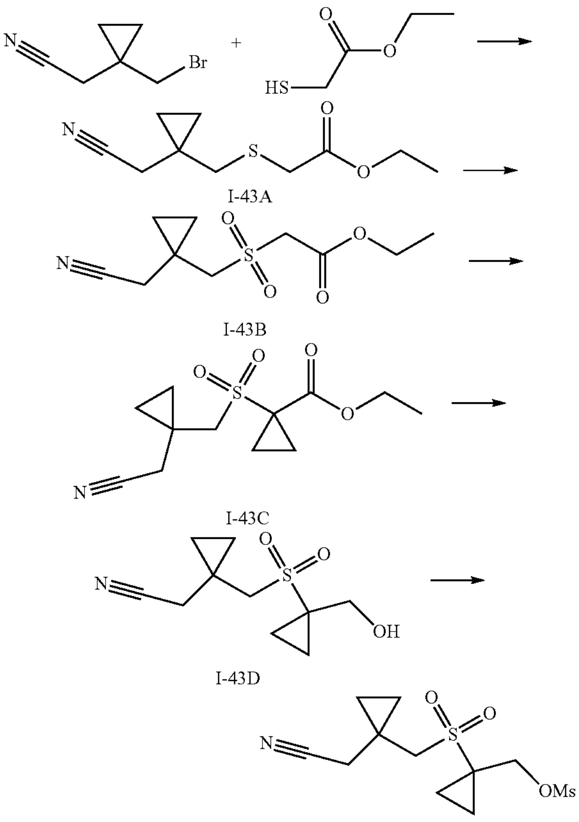

I-43A, I-43B, I-43C, I-43D, I-43

Ethyl 2-(((1-(cyanomethyl)cyclopropyl)methyl)thio)acetate (I-43A) was prepared from ethyl 2-mercaptoacetate and 2-(1-(bromomethyl)cyclopropyl)acetonitrile following a procedure analogous to that described in I-38A. MS m/z 214 (M+1).

Ethyl 2-(((1-(cyanomethyl)cyclopropyl)methyl)sulfonyl) acetate (I-43B) was prepared from I-43A following a procedure analogous to that described for I-9C. Title compound I-43B was isolated as a waxy solid. MS m/z 246 (M+1).

Ethyl 1401-(cyanomethyl)cyclopropyl)methyl)sulfonyl) cyclopropanecarboxylate (I-43C) was prepared from I-43B following a procedure analogous to that described for I-2C. MS m/z 272 (M+1).

2-(1-(((1-(Hydroxymethyl)cyclopropyl)sulfonyl)methyl) cyclopropyl)acetonitrile (I-43D) was prepared from I-43C following a procedure analogous to that described for I-2D. Title compound I-43D was isolated as a colorless oil. MS m/z 230 (M+1).

(1-(((1-(cyanomethyl)cyclopropyl)methyl)sulfonyl)cyclopropyl)methyl methanesulfonate (I-43) was prepared from I-42A following a procedure analogous to that described for I-9C. Title compound 1-43 was isolated as a brown solid. $^1$H NMR (500 MHz, $CDCl_3$) δ 4.55 (s, 2H), 3.29 (s, 2H), 3.15 (s, 3H), 2.77 (s, 2H), 1.63-1.72 (m, 2H), 1.22-1.32 (m, 2H), 0.92-1.02 (m, 2H), 0.78-0.88 (m, 2H). MS m/z 308 (M+1).

Intermediate 44

(1-(((1-methylcyclopropyl)methyl)sulfonyl)cyclopropyl)methyl methanesulfonate

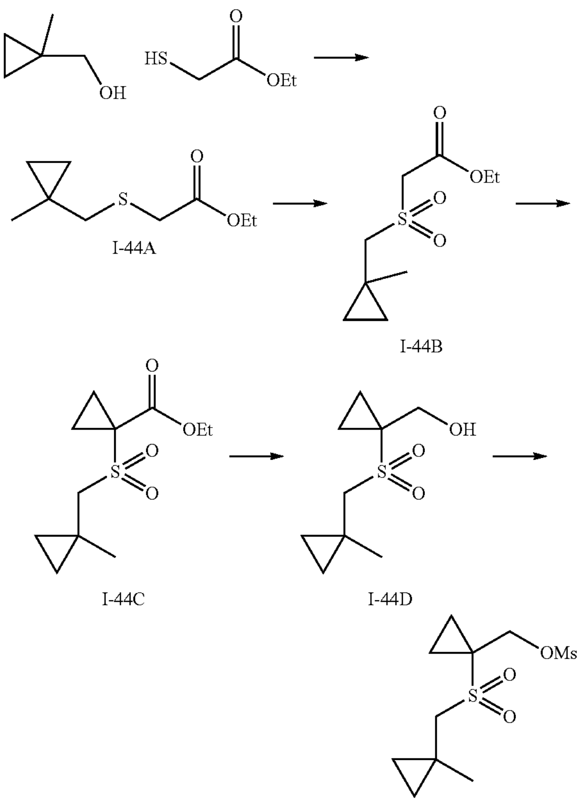

I-44A, I-44B, I-44C, I-44D, I-44

Ethyl 2-(((1-methylcyclopropyl)methyl)thio)acetate (I-44A). To a solution of ethyl 2-mercaptoacetate (3.39 mL, 30.9 mmol) in DCM (50 mL) were added $ZnI_2$ (3.29 g, 10.3 mmol) and (1-methylcyclopropyl)methanol (1.0 mL, 10.3 mmol). The resulting mixture was stirred at 20° C. for 8 d. Saturated aqueous $NaHCO_3$ was added slowly to the reaction, which was stirred vigorously at RT until gas generation ceased. The organic phase was separated and dried over $MgSO_4$. After concentration, the crude I-44A was used in the next step without further purification. MS m/z 189.3 (M+1).

Ethyl 2-(((1-methylcyclopropyl)methyl)sulfonyl)acetate (I-44B) was prepared from I-44A following a procedure analogous to that described for I-9C. Title compound I-44B was obtained as a white solid. MS m/z 221.1 (M+1).

Ethyl 1-(((1-methylcyclopropyl)methyl)sulfonyl)cyclopropane-1-carboxylate (I-44C) was prepared from I-44B following a procedure analogous to that described for I-2C. MS m/z 247.2 (M+1).

(1-(((1-methylcyclopropyl)methyl)sulfonyl)cyclopropyl) methanol (I-44D) was prepared from I-44C following a procedure analogous to that described for I-2D. MS m/z 205.1 (M+1).

(1-(((1-methylcyclopropyl)methyl)sulfonyl)cyclopropyl) methyl methanesulfonate (I-44) was prepared from I-44D following a procedure analogous to that described for 1-2. MS m/z 283.2 (M+1).

Intermediate 45

(1-(((1-cyanocyclopropyl)methyl)sulfonyl)cyclopropyl)methyl methanesulfonate

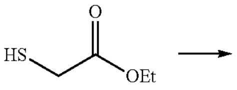

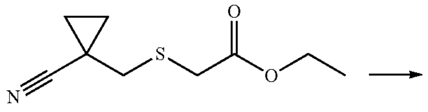

I-45A

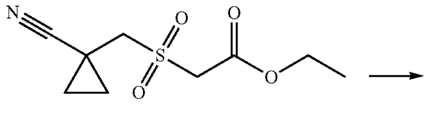

I-45B

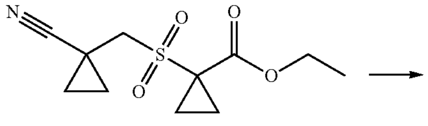

I-45C

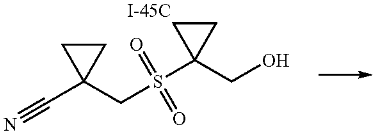

I-45D

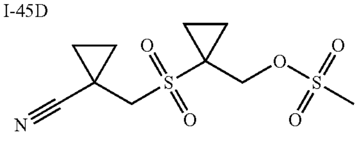

I-45

Ethyl 2-(((1-cyanocyclopropyl)methyl)thio)acetate (I-45A) was prepared from ethyl 2-mercaptoacetate and 1-(bromomethyl)cyclopropane-1-carbonitrile following a procedure analogous to that described in I-38A. Title compound I-45A was isolated as a brown oil. MS m/z 200.1 (M+1).

Ethyl 2-(((1-cyanocyclopropyl)methyl)sulfonyl)acetate (I-45B) was prepared from I-45A following a procedure analogous to that described for I-9C. MS m/z 232.1 (M+1).

Ethyl 1-(((1-cyanocyclopropyl)methyl)sulfonyl)cyclopropane-1-carboxylate (I-45C) was prepared from I-45B following a procedure analogous to that described for I-2C. MS m/z 258.1 (M+1).

1-(((1-(hydroxymethyl)cyclopropyl)sulfonyl)methyl)cyclopropane-1-carbonitrile (I-45D) was prepared from I-45C following a procedure analogous to that described for I-2D. MS m/z 216.1 (M+1).

(1-(((1-cyanocyclopropyl)methyl)sulfonyl)cyclopropyl) methyl methanesulfonate (I-45) was prepared from I-45D following a procedure analogous to that described for 1-2. MS m/z 294.2 (M+1).

Intermediate 46

(1-((1-(((tert-butyldimethyl silyl)oxy)methyl)cyclopropyl)sulfonyl)cyclopropyl)methyl methanesulfonate

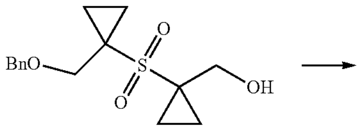

I-4H

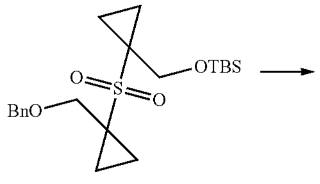

I-46A

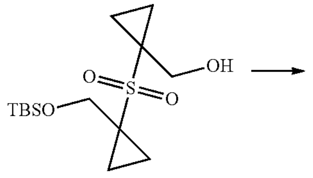

I-46B

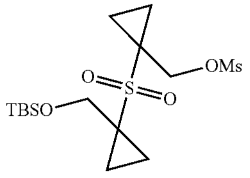

I-46

((1-((1-((benzyloxy)methyl)cyclopropyl)sulfonyl)cyclopropyl)methoxy)(tert-butyl)dimethylsilane (I-46A). To a solution of I-4H (3 g, 10.12 mmol) and imidazole (2.067 g, 30.4 mmol) in DMF (20 mL) was added TBSCl (2.288 g, 15.18 mmol). The resulting mixture was stirred at RT overnight. The reaction mixture was diluted with $Et_2O$ and washed with saturated citric acid, sodium bicarbonate and brine. The organic layer was dried over sodium sulfate and concentrated under reduced pressure. I-46A was isolated as a white solid. LCMS m/z: 411 (M+1). $^1H$ NMR (500 MHz, DMSO-d6) δ ppm 0.00-0.02 (m, 6H) 0.84 (s, 9H) 0.98 (td, J=4.73, 2.21 Hz, 2H) 1.10 (td, J=4.73, 2.52 Hz, 2H) 1.23 (td, J=4.41, 2.21 Hz, 2H) 1.30 (td, J=4.73, 2.21 Hz, 2H) 3.79 (s, 2H) 3.94 (s, 2H) 4.49 (s, 2H) 7.27-7.39 (m, 5H).

(1-((1-(((tert-butyldimethylsilyl)oxy)methyl)cyclopropyl)sulfonyl)cyclopropyl)methanol (I-46B). To a solution of I-46A 1 (1.24 g, 3.02 mmol) in EtOH (10 mL)/AcOH (10 mL) was added Pd/C (0.16 g, 0.150 mmol). The atmosphere was exchanged for $H_2$. The resulting mixture was stirred at RT. Upon completion of the reaction, the mixture was filtered through a plug of Celite. The filtrate was concentrated under reduced pressure. The residue was taken up in DCM and washed with saturated sodium bicarbonate. The organic layer was dried over sodium sulfate and concentrated under reduced pressure. I-46B was isolated as a colorless oil. LCMS m/z: 321 (M+1). $^1$H NMR (500 MHz, DMSO-d6) δ ppm 0.04-0.07 (m, 6H) 0.87 (s, 9H) 1.03 (ttt, J=5.36, 5.36, 3.78, 3.78, 2.52, 2.52 Hz, 4H) 1.17 (td, J=4.73, 2.52 Hz, 2H) 1.24 (td, J=4.41, 2.52 Hz, 2H) 3.79 (s, 2H) 3.95 (s, 2H).

(1-((1-(((tert-butyldimethylsilyl)oxy)methyl)cyclopropyl)sulfonyl)cyclopropyl)methyl methanesulfonate (I-46C) was prepared from I-46B following a procedure analogous to that described for 1-2. LCMS m/z: 399 (M+1).

Intermediate 47

9-bromo-N-(4-chlorobenzyl)-1,6-dioxo-1,3,4,6-tetrahydropyrido[2,1-c][1, 4] oxazine-7-carboxamide

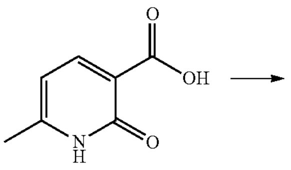

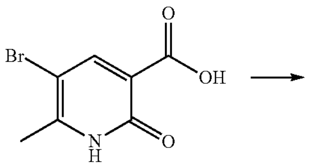

I-47A

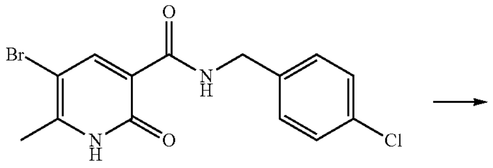

I-47B

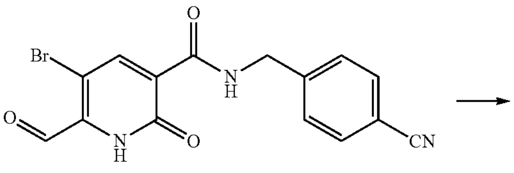

I-47C

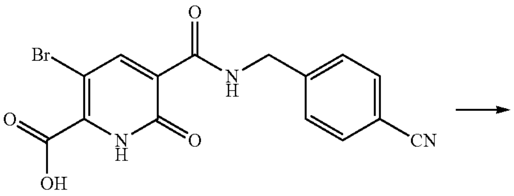

I-47D

-continued

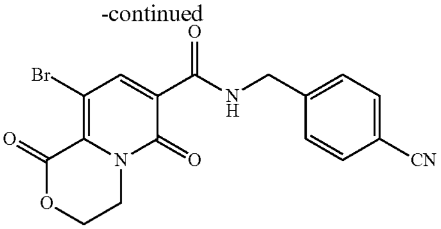

I-47

5-bromo-6-methyl-2-oxo-1,2-dihydropyridine-3-carboxylic acid (I-47A). NaOH (11.8 g, 295.0 mmol, 3.0 equiv) was dissolved in water (150 mL) and cooled to 0° C. Bromine (18.7 g, 118.0 mmol, 1.2 equiv) was added. 6-Methyl-2-oxo-1,2-dihydropyridine-3-carboxylic acid (15 g, 98.0 mmol, 1.0 equiv) was dissolved in NaOH (11.7 g, 292.5 mmol, 2.98 equiv) [in water (45 mL)] at 0° C. NaOBr (prepared above) was added and the reaction mixture was allowed to stir at 0° C. for 1 h. The reaction mixture was acidified by 1 N HCl to pH 4-5. The precipitated solid was filtered, washed with water and hexane, and co-distilled with toluene to afford I-47A. LCMS (m/z): 233.9 [M+I-1]. $^1$H NMR (400 MHz, DMSO-d6) δ 14.45 (s, 1H), 13.72 (s, 1H), 8.58-8.13 (m, 1H), 2.48-2.42 (m, 3H).

5-bromo-N-(4-chlorobenzyl)-6-methyl-2-oxo-1,2-dihydropyridine-3-carboxamide (I-47B) was prepared from I-47A following a procedure analogous to that described for I-17B. LCMS (m/z): 356.0 [M+I-1]. $^1$H NMR (400 MHz, DMSO-d6) δ 12.95 (s, 1H), 9.98 (s, 1H), 8.28 (s, 1H), 7.39 (d, J=8.5 Hz, 2H), 7.33 (d, J=8.5 Hz, 2H), 4.51 (d, J=6.1 Hz, 2H), 2.38 (s, 3H).

5-bromo-N-(4-chlorobenzyl)-6-formyl-2-oxo-1,2-dihydropyridine-3-carboxamide (I-47C). Selenium dioxide (70.7 g, 637.0 mmol, 15.0 equiv) was added to a mixture of I-47B (15 g, 42.0 mmol, 1.0 equiv) in 1,4-dioxane (525 mL). The reaction mixture was stirred at 130° C. for 24 h, after which it was filtered through celite. The filter cake was washed with dichloromethane, and the filtrate was concentrated. The crude residue was purified on $SiO_2$ (100% dichloromethane) to afford I-47C. LCMS (m/z): 369.3 [M+I-1]. $^1$H NMR (400 MHz, DMSO-d6) δ 10.00 (d, J=5.0 Hz, 1H), 9.82 (s, 1H), 8.43 (d, J=23.7 Hz, 1H), 7.39 (dd, J=8.5, 2.3 Hz, 2H), 7.34 (d, J=6.6 Hz, 2H), 4.51 (t, J=5.9 Hz, 2H).

3-bromo-5-((4-chlorobenzyl) carbamoyl)-6-oxo-1,6-dihydropyridine-2-carboxylic acid (I-47D). I-47C (6 g, 16.2 mmol, 1.0 equiv) was dissolved in DMF (50 mL). Oxone (10 g, 32.5 mmol, 2.0 equiv) was added, and the reaction mixture was stirred at RT for 6 h. The reaction mixture was quenched with water. The precipitated solid was filtered, washed with water and hexane, and triturated with 20% dichloromethane in hexane. The solvent was decanted to afford I-47D. LCMS (m/z): 387.0 [M+I-1]. $^1$H NMR (400 MHz, DMSO-d6) δ 13.14 (s, 1H), 9.85 (s, 1H), 8.32 (d, J=28.5 Hz, 1H), 8.37-6.31 (m, 4H), 4.52 (d, J=5.9 Hz, 2H).

9-bromo-N-(4-chlorobenzyl)-1,6-dioxo-1,3,4,6-tetrahydropyrido[2,1-c][1,4]oxazine-7-carboxamide (1-47) was prepared from I-47D following a procedure analogous to that described for 1-17. LCMS (m/z): 411.0 [M+I-1]. $^1$H NMR (400 MHz, DMSO-d6) δ 9.95 (t, J=6.1 Hz, 1H), 8.43 (s, 1H), 7.40 (d, J=8.5 Hz, 2H), 7.35 (d, J=8.5 Hz, 2H), 4.77-4.63 (m, 2H), 4.55 (t, J=5.7 Hz, 2H), 4.42-4.27 (m, 2H).

Intermediate 48 tert-butyl 2-methyl-2-((1-(((methylsulfonyl)oxy) methyl)cyclopropyl)sulfonyl) propanoate

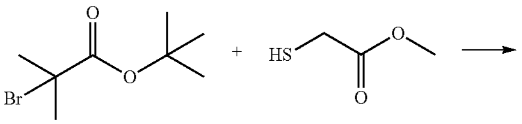

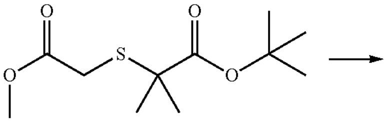

I-48A

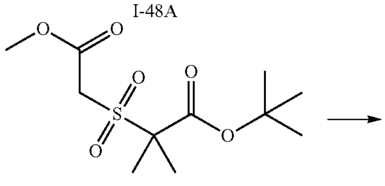

I-48B

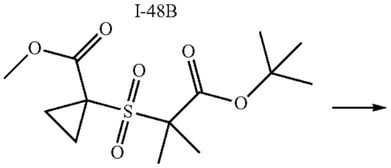

I-48C

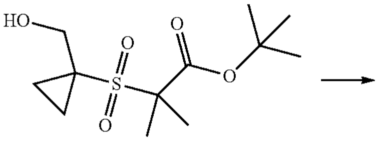

I-48D

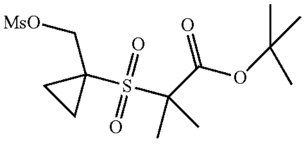

I-48 tert-butyl 2-((2-methoxy-2-oxoethyl)thio)-2-methyl propanoate (I-48A). Methyl 2-mercaptoacetate (4.6 g, 22.0 mmol, 1.0 equiv) was dissolved in methanol (50 mL), and NaOMe (1.2 g, 22.0 mmol, 1.0 equiv) was added. The reaction mixture was stirred at RT for 2 min, after which tert-butyl 2-bromo-2-methylpropanoate (5 g, 22.0 mmol, 1.0 equiv) was added. The reaction mixture was stirred at RT for 18 h, and was then quenched with cold water and extracted with diethyl ether. The organic layer was washed with brine, dried over sodium sulfate, and concentrated to afford a crude residue. The crude residue was purified by silica gel column chromatography (0-10% EtOAc/Hexane) to afford the title compound. $^1$H NMR (400 MHz, DMSO-d6) δ 3.63 (s, 2H), 1.41 (s, 9H), 1.38 (s, 6H). tert-butyl 2-((2-methoxy-2-oxoethyl)sulfonyl)-2-methylpropanoate (I-48B) was prepared from I-48A following a procedure analogous to that described for I-8C, replacing EtOH with EtOAc. $^1$H NMR (400 MHz, DMSO-d6) δ 4.54-4.47 (m, 2H), 3.73 (s, 3H), 1.57-1.50 (m, 6H), 1.45 (d, J=6.0 Hz, 9H).

methyl 1-((1-(tert-butoxy)-2-methyl-1-oxopropan-2-yl) sulfonyl)cyclopropane-1-carboxylate (I-48C). A solution of I-48B (2.5 g, 8.0 mmol, 1.0 equiv) in DMF (5 mL) was degassed for 10 min 1,2-Dibromoethane (2.5 g, 13.3 mmol, 1.5 equiv), $K_2CO_3$ (3.7 g, 26.0 mmol, 3.0 equiv), and TBAB (0.03 g, 0.08 mmol, 0.01 equiv) were added, and the reaction mixture was stirred at 90° C. for 12 h. The reaction mixture was quenched with cold water and extracted with EtOAc. The organic layer was washed with brine, dried over sodium sulfate and concentrated to afford a crude residue. The crude residue was purified by silica gel column chromatography (0-10% EtOAc/Hexane) to afford I-48C. $^1$H NMR (400 MHz, $CDCl_3$) δ 3.85-3.74 (m, 3H), 1.88-1.81 (m, 2H), 1.72-1.67 (m, 8H), 1.52 (d, J=6.5 Hz, 9H).

tert-butyl 2-((1-(hydroxyl methyl)cyclopropyl)sulfonyl)-2-methylpropanoate (I-48D). I-48C (0.98 g, 3.2 mmol, 1.0 equiv) was dissolved in THF (16 mL) and $LiAlH[OC(CH_3)_3]_3$ (1 M in THF) (16 mL) was added dropwise. The reaction mixture was stirred at 60° C. for 24 h. The reaction mixture was quenched with an aqueous slurry of sodium sulfate. The mixture was filtered through a bed of celite, and this was rinsed with excess EtOAc. The filtrate was concentrated to afford the title compound. 41 NMR (400 MHz, DMSO-d6) δ 4.05-3.98 (m, 1H), 3.81 (s, 2H), 1.58 (d, J=14.1 Hz, 6H), 1.45 (d, J=21.7 Hz, 9H), 1.21 (d, J=11.5 Hz, 4H).

tert-butyl 2-methyl-2-((1-(((methylsulfonyl)oxy)methyl) cyclopropyl) sulfonyl) propanoate (1-48). I-48D (0.2 g, 0.72 mmol, 1.0 equiv) was added in THF (4 mL), TEA (0.22 g, 2.2 mmol, 3.0 equiv) was added and the reaction mixture was cooled to 0° C. $MeSO_2Cl$ (0.098 g, 0.86 mmol, 1.2 equiv) was added and the reaction mixture was stirred at 60° C. for 2 h. The reaction mixture was quenched with water and extracted with EtOAc. The organic layer was washed with water, dried over sodium sulfate and concentrated to afford the title compound.

Intermediate 49

(1-((1-methoxy-2-methylpropan-2-yl)sulfonyl)cyclopropyl)methanamine hydrochloride

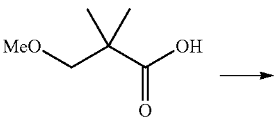

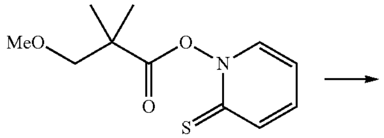

I-49A

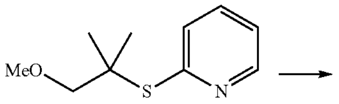

I-49B

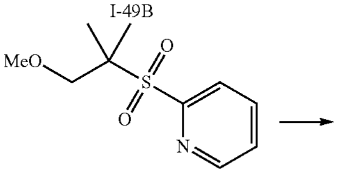

I-49C

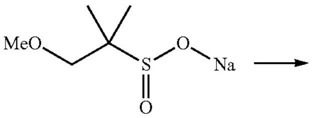

I-49D

-continued

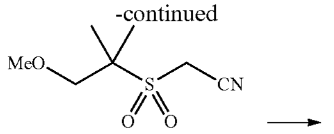

I-49E

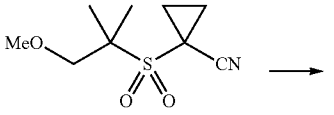

I-49F

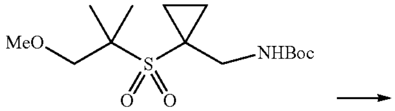

I-49G

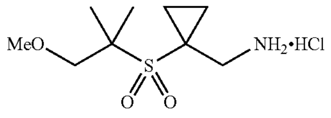

I-49

2-thioxopyridin-1(2H)-yl 3-methoxy-2,2-dimethyl propanoate (I-49A) was prepared from 3-methoxy-2,2-dimethylpropanoic acid following a procedure analogous to that described for I-7B. I-49A was used without purification.

2-((1-methoxy-2-methyl propan-2-yl)thio)pyridine (I-49B). I-49A (4 g, crude) was dissolved in EtOAc (40 mL), and the solution was irradiated with tungsten lamp (375 W) for 2 h to generate I-49B. The product was used in the next step without further purification.

2-((1-methoxy-2-methyl propan-2-yl)sulfonyl)pyridine (I-49C). I-49B (4 g, 20.3 mmol, 1.0 equiv) was added in water (40 mL) and cooled to 10° C. Oxone (28.7 g, 46.7 mmol, 2.3 equiv) was added and the reaction mixture was stirred at RT for 24 h. The reaction mixture was diluted with water and extracted with EtOAc. The organic layer was washed with brine, dried over sodium sulfate, and concentrated to afford a crude residue. The crude residue was purified by silica gel column chromatography (30% EtOAc/Hexane) to afford I-49C. LCMS (m/z): 229.8 [M+1-1]. $^1$H NMR (400 MHz, DMSO-d6) δ 8.80 (ddd, J=4.7, 1.7, 0.8 Hz, 1H), 8.15 (td, J=7.8, 1.7 Hz, 1H), 8.03 (dt, J=7.9, 1.0 Hz, 1H), 7.76 (ddd, J=7.6, 4.7, 1.1 Hz, 1H), 3.48 (s, 2H), 3.09 (s, 3H), 1.31 (s, 6H).

sodium 1-methoxy-2-methylpropane-2-sulfinate (I-49D). I-49C (1.1 g, 4.9 mmol, 1.0 equiv) was dissolved in THF (12 mL) and cooled to 0° C. MeSNa (0.85 g, 12.2 mmol, 2.5 equiv) was added and the reaction mixture was stirred at 0° C. for 2 h and at RT for 24 h. The reaction mixture was concentrated and the residue was triturated with diethyl ether to remove methyl thiopyridine. The crude product was further purified by silica gel column chromatography (20% MeOH/DCM) to afford I-49D. $^1$H NMR (400 MHz, $D_2O$) δ 3.47 (s, 2H), 3.27 (s, 3H), 1.19 (s, 6H).

2-((1-methoxy-2-methylpropan-2-yl)sulfonyl) acetonitrile (I-49E). To a solution of I-49D (0.5 g, 2.9 mmol, 1.0 equiv) in DMF (5 mL), was added 2-bromoacetonitrile (0.37 g, 3.2 mmol, 1.1 equiv). The reaction mixture was stirred at RT for 24 h, after which it was quenched with cold water and extracted with EtOAc. The organic layer was washed with cold water, dried over sodium sulfate and concentrated to afford a crude residue. The crude residue was purified by silica gel column chromatography (20% EtOAc/Hexane) to afford I-49E.

1-((1-methoxy-2-methyl propan-2-yl)sulfonyl)cyclopropane-1-carbonitrile (I-49F). To a solution of I-49E (0.21 g, 1.1 mmol, 1.0 equiv) in DMF (4 mL) were added $K_2CO_3$ (0.75 g, 5.5 mmol, 5.0 equiv) and 1,2-dibromoethane (0.62 g, 3.3 mmol, 3.0 equiv). The reaction mixture was stirred at 80° C. for 2 h, after which the reaction was quenched with cold water and extracted with EtOAc. The organic layer was washed with cold water, dried over sodium sulfate, and concentrated to afford a crude residue. The crude residue was purified by silica gel column chromatography (15% EtOAc/Hexane) to afford I-49F. $^1$H NMR (400 MHz, $CDCl_3$) δ 4.23 (s, 2H), 3.60 (s, 2H), 3.45 (s, 3H), 1.51 (s, 6H). $^1$H NMR (400 MHz, $CDCl_3$) δ 3.62 (s, 2H), 3.43 (d, J=10.7 Hz, 3H), 1.91 (q, J=5.2 Hz, 2H), 1.71 (dd, J=8.7, 5.3 Hz, 2H), 1.56 (s, 6H).

tert-butyl ((1-((1-methoxy-2-methylpropan-2-yl)sulfonyl)cyclopropyl)methyl) carbamate (I-49G). I-49F (0.15 g, 0.7 mmol, 1.0 equiv) was dissolved in methanol (3 mL) and cooled to 0° C. $NiCl_2·6H_2O$ (0.016 g, 0.07 mmol, 0.1 equiv), $(Boc)_2O$ (0.3 g, 1.4 mmol, 2.0 equiv), $NaBH_4$ (0.18 g, 4.83 mmol, 7.0 equiv) were added, and the reaction mixture was stirred at RT for 24 h. The reaction mixture was concentrated, diluted with water and extracted with EtOAc. The organic layer was washed with brine, dried over sodium sulfate, and concentrated to afford a crude residue. The crude residue was purified by silica gel column chromatography (0-20% EtOAc/Hexane) to afford I-49G. $^1$H NMR (400 MHz, DMSO-d6) δ 6.87 (s, 1H), 3.56 (s, 2H), 3.33 (s, 2H), 3.31 (s, 3H), 1.44 (s, 9H), 1.34 (s, 6H), 1.19-1.15 (m, 2H), 0.93 (d, J=2.1 Hz, 2H).

(1-((1-methoxy-2-methylpropan-2-yl)sulfonyl)cyclopropyl) methanamine hydrochloride (I-49). To a solution of I-49G (0.08 g, 0.25 mmol, 1.0 equiv) in dichloromethane (2 mL), was added HCl (4 M in 1,4-dioxane) (1 mL). The reaction mixture was stirred at RT for 2 h. The reaction mixture was concentrated and co-distilled with dichloromethane to afford 1-49. LCMS (m/z): 222.2 [M+H, free amine] $^1$H NMR (400 MHz, DMSO-d6) δ 7.95 (s, 3H), 3.56 (s, 2H), 3.33 (d, J=3.6 Hz, 5H), 1.91 (dd, J=8.9, 5.4 Hz, 1H), 1.75 (dd, J=8.7, 5.2 Hz, 1H), 1.43 (s, 3H), 1.35 (s, 3H), 1.31-1.22 (m, 2H).

Intermediate 50

(1-((1-methoxy-2-methylpropan-2-yl)sulfonyl)cyclopropyl)methyl methanesulfonate

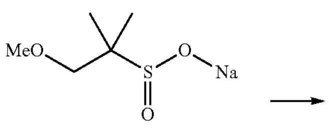

I-49D

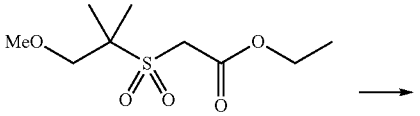

I-50A

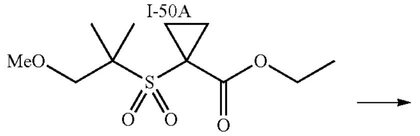

I-50B

-continued

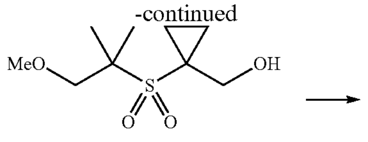

I-50C

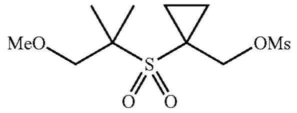

I-50 ethyl 2-((1-methoxy-2-methylpropan-2-yl)sulfonyl)acetate (I-50A) was prepared from I-49D following a procedure analogous to that described for I-7E. $^{1}$H NMR (400 MHz, DMSO-d6) δ 4.15 (s, 2H), 3.30 (d, J=4.4 Hz, 2H), 2.89 (d, J=8.6 Hz, 3H), 2.75-2.71 (m, 3H), 1.30-1.15 (m, 9H).

ethyl 1-((1-methoxy-2-methylpropan-2-yl)sulfonyl)cyclopropane-1-carboxylate (I-50B) was prepared from I-50A following a procedure analogous to that described for I-2C. $^{1}$H NMR (400 MHz, $CDCl_3$) δ 4.35-4.10 (m, 2H), 3.59-3.51 (m, 2H), 3.42-3.35 (m, 3H), 1.82-1.09 (m, 12H).

1-((1-methoxy-2-methylpropan-2-yl)sulfonyl)cyclopropyl)methanol (I-50C). I-50B (1 g, 3.7 mmol, 1.0 equiv) was dissolved in THF (10 mL) and cooled to 0° C. LAH (1.0 M in THF) (4.1 mL, 4.1 mmol, 1.1 equiv) was added dropwise and the reaction mixture was stirred at 0° C. for 1 h. The reaction mixture was quenched with aqueous slurry of sodium sulfate, diluted with EtOAc, filtered through a bed of celite, and concentrated to afford the title compound. $^{1}$H NMR (400 MHz, DMSO-d6) δ 3.78 (s, 1H), 3.56 (s, 1H), 3.18 (s, 1H), 1.42-1.03 (m, 4H).

(1-((1-methoxy-2-methylpropan-2-yl)sulfonyl)cyclopropyl)methyl methanesulfonate (I-50) was prepared from I-50C following a procedure analogous to that described for 1-2. $^{1}$H NMR (400 MHz, $CDCl_3$) δ 4.65 (s, 2H), 3.59 (s, 2H), 3.43 (d, J=4.5 Hz, 3H), 3.12 (s, 3H), 1.77-1.66 (m, 2H), 1.51-1.44 (m, 8H).

Intermediate 51

2-(cyclo propyl sulfonyl) propyl methane sulfonate

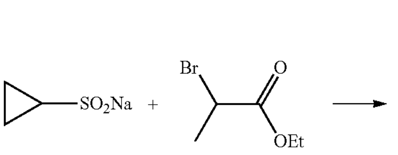

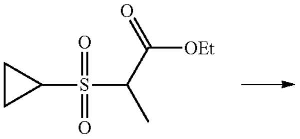

I-51A

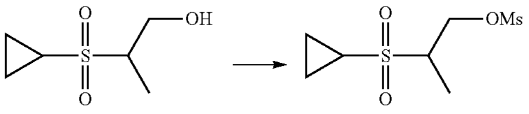

I-51B I-51 ethyl 2-(cyclopropyl sulfonyl) propanoate (I-51A) was prepared from sodium cyclopropane sulfinate and ethyl 2-bromopropanoate following a procedure analogous to that described for I-2B. $^{1}$H NMR (400 MHz, $CDCl_3$) δ 4.33-4.28 (m, 2H), 2.68 (ddd, J=9.7, 6.4, 4.0 Hz, 1H), 1.69 (d, J=7.3 Hz, 3H), 1.44-1.28 (m, 3H), 1.28-1.20 (m, 2H), 1.14-1.06 (m, 2H).

2-(cyclopropyl sulfonyl) propan-1-ol (I-51B). Methanol (15 mL) was added drop wise to a flask containing I-51A (3.2 g, 12.9 mmol, 1.0 equiv) and sodium borohydride (1.96 g, 51.9 mmol, 4.0 equiv) at 0° C. The reaction mixture was quenched with water and extracted with EtOAc. The organic layer was washed with brine, dried over sodium sulfate, and concentrated to afford the title compound. $^{1}$H NMR (400 MHz, DMSO-d6) δ 3.83 (dd, J=11.3, 5.0 Hz, 1H), 3.59 (dd, J=10.5, 3.8 Hz, 1H), 3.20 (d, J=6.0 Hz, 1H), 1.91 (s, 3H), 1.29 (t, J=7.6 Hz, 4H).

2-(cyclopropyl sulfonyl) propyl methane sulfonate (I-51) was prepared from I-51B following a procedure analogous to that described for 1-2. $^{1}$H NMR (400 MHz, DMSO-d6) δ 4.48 (dd, J=13.3, 5.4 Hz, 2H), 3.27 (s, 3H), 2.77-2.73 (m, 1H), 1.37 (d, J=7.1 Hz, 3H), 1.14-0.86 (m, 4H).

Intermediate 52

(1-((1-methoxy cyclopropyl)sulfonyl)cyclopropyl)methyl methane sulfonate

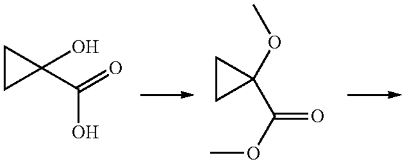

I-52A

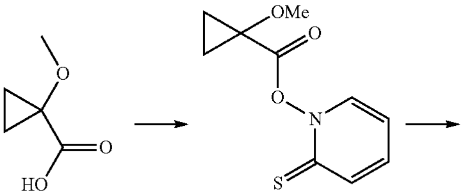

I-52B I-52C

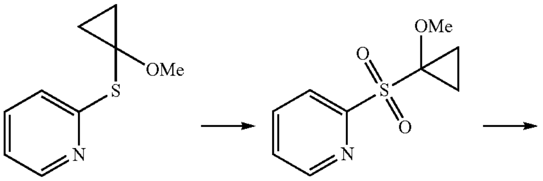

I-52D I-52E

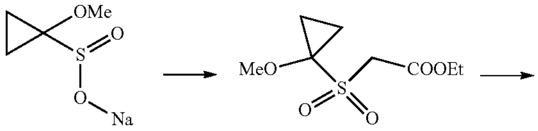

I-52F I-52G

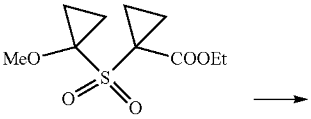

I-52H

-continued

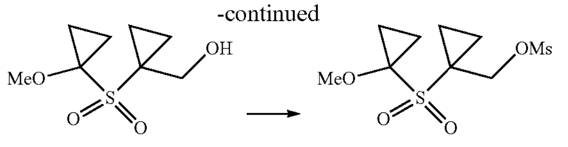

I-52I I-52 methyl 1-methoxycyclopropane-1-carboxylate (I-52A). 1-Hydroxycyclopropane-1-carboxylic acid (5 g, 49.0 mmol, 1.0 equiv) was dissolved in DMF (10 mL) and cooled to 0° C. NaH (60% suspension in mineral oil, 2.94 g, 122.5 mmol, 2.5 equiv) and iodomethane (20.9 g, 147.1 mmol, 3.0 equiv) were added and the reaction mixture was stirred at RT for 24 h. The reaction mixture was quenched with cold water and extracted with diethyl ether. The organic layer was washed with brine, dried over sodium sulfate and concentrated to afford the title compound. $^1$H NMR (400 MHz, DMSO-d6) δ 3.66 (s, 2H), 3.30 (s, 2H), 1.19-1.13 (m, 3H).

1-methoxycyclopropane-1-carboxylic acid (I-52B). To a solution of I-52A (4.3 g, 33.1 mmol, 1.0 equiv) in THF (40 mL), MeOH (10 mL) and water (10 mL) was added LiOH·$H_2O$ (2.8 g, 66.2 mmol, 2.0 equiv). The reaction mixture was stirred at RT for 24 h, after which it was diluted with water and extracted with EtOAc. The aqueous layer was acidified by 1.0 N HCl to pH 2-3 and extracted with EtOAc. The organic layer was washed with brine, dried over sodium sulfate, and concentrated to afford the title compound. $^1$H NMR (400 MHz, DMSO-d6) δ 12.33 (s, 1H), 3.54-2.97 (m, 3H), 2.00-1.82 (m, 2H), 1.64-0.44 (m, 4H).

2-thioxopyridin-1(2H)-yl 1-methoxycyclopropane-1-carboxylate (I-52C) was prepared from I-52B following a procedure analogous to that described for I-7B. $^1$H NMR (400 MHz, DMSO-d6) δ 8.41 (dd, J=7.0, 1.3 Hz, 1H), 7.58-7.54 (m, 1H), 7.44 (ddd, J=7.2, 3.1, 1.4 Hz, 1H), 6.92-6.86 (m, 1H), 3.53-3.46 (m, 3H), 1.63-1.52 (m, 2H), 1.49-1.40 (m, 2H).

2-((1-methoxy cyclopropyl)thio) pyridine (I-52D) was prepared from I-52C following a procedure analogous to that described for I-49B.

2-((1-methoxy cyclopropyl)sulfonyl)pyridine (I-52E) was prepared from I-52D following a procedure analogous to that described for I-49C. 1H NMR (400 MHz, DMSO-d6) δ 8.86-8.82 (m, 1H), 8.21-8.13 (m, 2H), 7.79 (ddd, J=7.3, 4.7, 1.5 Hz, 1H), 3.43 (s, 3H), 1.58 (dd, J=8.5, 5.7 Hz, 2H), 1.39 (dd, J=8.5, 5.8 Hz, 2H).

sodium 1-methoxycyclopropane-1-sulfinate (I-52F) was prepared from I-52E following a procedure analogous to that described for I-49D. $^1$H NMR (400 MHz, DMSO-d6) δ 3.37 (s, 4H), 0.77 (q, J=4.2 Hz, 3H), 0.42 (q, J=4.2 Hz, 3H).

ethyl 2-((1-methoxy cyclopropyl)sulfonyl)acetate (I-52G) was prepared from I-52F following a procedure analogous to that described for I-7E. 1H NMR (400 MHz, DMSO-d6) δ 4.39 (d, J=8.1 Hz, 2H), 4.18 (dd, J=9.3, 4.9 Hz, 2H), 3.52 (s, 3H), 1.39 (d, J=9.5 Hz, 4H), 1.23 (d, J=7.1 Hz, 3H).

ethyl 1-((1-methoxycyclopropyl)sulfonyl)cyclopropane-1-carboxylate (I-52H) was prepared from I-52G following a procedure analogous to that described for I-48C. $^1$H NMR (400 MHz, DMSO-d6) δ 4.21-4.15 (m, 2H), 3.45 (s, 3H), 1.68 (s, 4H), 1.49 (s, 2H), 1.41 (s, 2H), 1.24 (d, J=7.1 Hz, 3H).

(1-((1-methoxycyclopropyl)sulfonyl)cyclopropyl) methanol (I-521) was prepared from I-52H following a procedure analogous to that described for I-50C. $^1$H NMR (400 MHz, DMSO-d6) δ 5.03 (t, J=6.3 Hz, 1H), 3.85 (d, J=6.3 Hz, 2H), 3.48 (s, 3H), 1.38-1.26 (m, 4H), 1.23-1.14 (m, 2H), 1.14-1.03 (m, 2H).

(1-((1-methoxy cyclopropyl)sulfonyl)cyclopropyl)methyl methane sulfonate (I-52) was prepared from 1-521 following a procedure analogous to that described for 1-2. $^1$H NMR (400 MHz, DMSO-d6) δ 4.54 (s, 2H), 3.48 (s, 3H), 3.21 (s, 3H), 1.48 (dd, J=7.5, 5.0 Hz, 2H), 1.42-1.34 (m, 4H), 1.19 (t, J=7.3 Hz, 2H).

Intermediate 53 tert-butyl (1-(amino methyl)cyclopropyl) carbamate

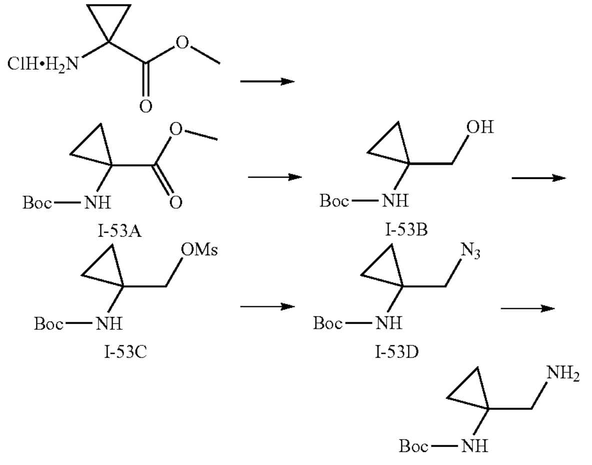

I-53A I-53B I-53C I-53D I-53 methyl 1-((tert-butoxy carbonyl)amino) cyclopropane-1-carboxylate (I-53A). To a mixture of methyl 1-aminocyclopropane-1-carboxylate hydrochloride (5 g, 43.0 mmol, 1.0 equiv) in dichloromethane (50 mL), were added TEA (18.8 mL, 130.0 mmol, 3.0 equiv) and $(Boc)_2O$ (14.2 g, 65.0 mmol, 1.5 equiv). The reaction mixture was stirred at RT for 4 h. The reaction mixture was quenched with water and extracted with dichloromethane. The organic layer was washed with brine, dried over sodium sulfate, and concentrated to afford I-53A. LCMS (m/z): 216.2 [M+H]. $^1$H NMR (400 MHz, DMSO-d6) δ 3.61-3.50 (m, 6H), 1.45 (s, 9H), 1.36 (s, 11H), 1.29 (dd, J=7.7, 4.5 Hz, 4H), 1.00 (dd, J=7.7, 4.4 Hz, 4H).

tert-butyl (1-(hydroxy methyl)cyclopropyl) carbamate (I-53B) was prepared from I-53A following a procedure analogous to that described for I-50C. $^1$H NMR (400 MHz, DMSO-d6) δ 7.05 (s, 1H), 4.57 (t, J=5.8 Hz, 1H), 3.37 (d, J=5.7 Hz, 2H), 0.61 (t, J=3.1 Hz, 2H), 0.52 (d, J=2.1 Hz, 2H).

(1-((tert-butoxy carbonyl)amino) cyclopropyl)methyl methane sulfonate (I-53C) was prepared from I-52B following a procedure analogous to that described for 1-2. tert-butyl (1-(azido methyl)cyclopropyl) carbamate (I-53D). I-53C (1 g, 3.7 mmol, 1.0 equiv) and $NaN_3$ (0.74 g, 11.3 mmol, 3.0 equiv) were added in DMF (10 mL), and the reaction mixture was stirred at 90° C. for 18 h. The reaction mixture was quenched with cold water and extracted with EtOAc. The organic layer was washed with brine, dried over sodium sulfate, and concentrated to afford the title product. $^1$H NMR (400 MHz, DMSO-d6) δ 7.40 (s, 1H), 3.34-3.08 (m, 3H), 1.38 (s, 9H), 0.67 (s, 4H).

tert-butyl (1-(amino methyl)cyclopropyl) carbamate (I-53). I-53D (0.7 g, 3.3 mmol, 1.0 equiv) was dissolved in methanol (10 mL). Pd/C (10% moisture) (0.03 g) was added and the reaction mixture was stirred at RT for 18 h under $H_2$ (gas) atmosphere. The reaction mixture was filtered through a bed of celite, and the filtrate was concentrated to afford the title product.

Intermediate 54

(1-((methyl sulfonyl)methyl)cyclopropyl)

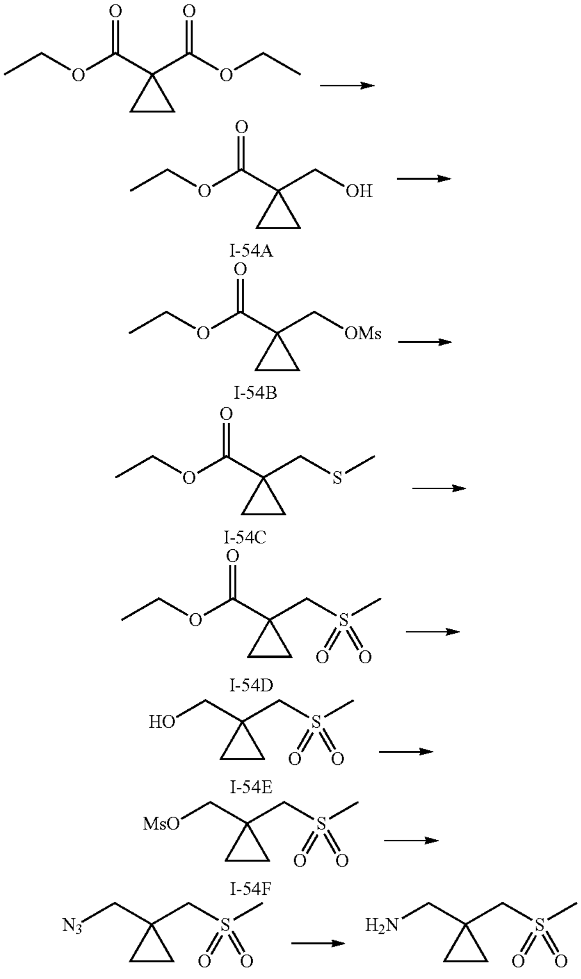

I-54A I-54B I-54C I-54D I-54E I-54F I-54G I-54 ethyl 1-(hydroxy methyl)cyclopropane-1-carboxylate (I-54A). To a solution of diethyl cyclopropane-1,1-dicarboxylate (10 g, 42.9 mmol, 1.0 equiv) in THF (220 mL), was added $LiAlH[OC(CH_3)_3]_3$ (1M in THF) (100 mL) dropwise. The reaction mixture was stirred at 66° C. for 12 h. The reaction mixture was diluted with aqueous 10% sodium bisulfite solution and extracted with EtOAc. The organic layer was washed with brine, dried over sodium sulfate, and concentrated to afford a crude residue. The crude residue was purified by silica gel column chromatography (40% EtOAc/Hexane) to afford the title product. $^1$H NMR (400 MHz, $CDCl_3$) δ 4.17 (q, J=7.1 Hz, 2H), 3.64 (s, 2H), 2.66 (s, 1H), 1.28 (dt, J=9.8, 5.8 Hz, 5H), 0.89 (q, J=4.2 Hz, 2H).

ethyl 1-(((methyl sulfonyl)oxy) methyl)cyclopropane-1-carboxylate (I-54B) was prepared from I-54A following a procedure analogous to that described for 1-2. $^1$H NMR (400

MHz, $CDCl_3$) δ 4.18 (q, J=6.8 Hz, 2H), 3.17-3.13 (m, 2H), 3.10 (s, 3H), 1.46-1.40 (m, 5H), 1.07 (dd, J=7.4, 4.5 Hz, 2H).

ethyl 1-((methyl thio)methyl)cyclopropane-1-carboxylate (I-54C). To a solution of I-54B (7.5 g, 34.0 mmol, 1.0 equiv) in DMF (160 mL) was added $CH_3SNa$ (4.7 g, 68.0 mmol, 2.0 equiv). The reaction mixture was stirred at RT for 24 h, after which it was quenched with water and extracted with diethyl ether. The organic layer was washed with brine, dried over sodium sulfate, and concentrated to afford a crude residue. The crude residue was purified by silica gel column chromatography (5% EtOAc/hexane) to afford I-54C. $^1$H NMR (400 MHz, $CDCl_3$) δ 4.16 (q, J=7.1 Hz, 2H), 2.85 (s, 2H), 2.18 (s, 3H), 1.36-1.30 (m, 2H), 1.27 (t, J=7.1 Hz, 3H), 0.91 (q, J=4.2 Hz, 2H).

ethyl 1-((methyl sulfonyl)methyl)cyclopropane-1-carboxylate (I-54D) was prepared from I-54C following a procedure analogous to that described for I-8C. $^1$H NMR (400 MHz, $CDCl_3$) δ 4.18 (q, J=7.1 Hz, 2H), 3.42 (s, 2H), 2.99 (s, 3H), 1.54 (q, J=4.6 Hz, 2H), 1.31-1.23 (m, 5H).

(1-((methyl sulfonyl)methyl)cyclopropyl) methanol (I-54E). I-54D (3.4 g, 16.5 mmol, 1.0 equiv) was dissolved in THF (34 mL), $LiBH_4$ (2 M in THF) (10 mL, 19.8 mmol, 1.2 equiv) was added drop wise and the reaction mixture was stirred at 66° C. for 4 h. The reaction mixture was quenched with water and extracted with EtOAc. The organic layer was washed with brine, dried over sodium sulfate and concentrated to afford a crude residue. The crude residue was purified by silica gel column chromatography (55% EtOAc/Hexane) to afford I-54E. LCMS (m/z): 165.2 [M+H]. $^1$H NMR (400 MHz, $CDCl_3$) δ 3.63 (s, 2H), 3.19 (s, 2H), 3.03 (s, 3H), 2.68 (s, 1H), 0.80 (t, J=5.7 Hz, 2H), 0.74 (t, J=5.7 Hz, 2H).

(1-((methyl sulfonyl)methyl)cyclopropyl)methyl methane sulfonate (I-54F), was prepared from I-54E following a procedure analogous to that described for 1-2. $^1$H NMR (400 MHz, DMSO-d6) δ 4.22 (s, 2H), 3.27 (s, 2H), 3.19 (s, 3H), 3.01 (s, 3H), 0.84 (t, J=5.6 Hz, 2H), 0.78 (dd, J=11.3, 4.0 Hz, 2H).

1-(azido methyl)-1-((methyl sulfonyl)methyl)cyclopropane (I-54G) was prepared from I-54F following a procedure analogous to that described for I-53D. $^1$H NMR (400 MHz, DMSO-d6) δ 3.45 (s, 2H), 3.24 (s, 2H), 2.99 (s, 3H), 0.78-0.70 (m, 2H), 0.70-0.64 (m, 2H).

(1-((methyl sulfonyl)methyl)cyclopropyl) methanamine (1-54) was prepared from I-54G (1.2 g, 6.3 mmol, 1.0 equiv) following a procedure analogous to that described for 1-53. $^1$H NMR (400 MHz, DMSO-d6) δ 3.24 (d, J=5.2 Hz, 2H), 2.95 (s, 3H), 2.51 (dt, J=3.5, 1.7 Hz, 2H), 1.78 (d, J=30.3 Hz, 2H), 0.60-0.54 (m, 2H), 0.54-0.48 (m, 2H).

Intermediate 55 ethyl 1-(amino methyl)cyclopropane-1-carboxylate

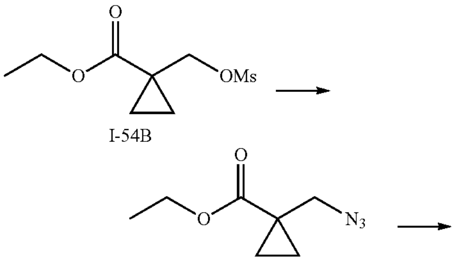

I-54B I-55A

-continued

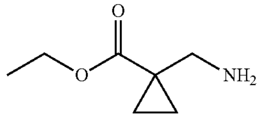

I-55 ethyl 1-(azido methyl)cyclopropane-1-carboxylate (I-55A) was prepared from I-54B following a procedure analogous to that described for I-53D. $^{1}$H NMR (400 MHz, DMSO-d6) δ 4.20-4.02 (m, 1H), 3.68-3.35 (m, 1H), 1.31-1.09 (m, 3H), 1.06-0.89 (m, 1H).

ethyl 1-(amino methyl)cyclopropane-1-carboxylate (I-55). To a solution of I-55A (4.5 g, 26.6 mmol, 1.0 equiv) in methanol (45 mL) in an autoclave, was added Pd/C (0.45 g). The reaction mixture was stirred at RT for 24 h under $H_2$ (gas) pressure (20 bar). The reaction mixture was filtered through a bed of celite, and the filtrate was concentrated to afford the title product. $^{1}$H NMR (400 MHz, DMSO-d6) δ 4.10-3.96 (m, 2H), 2.67 (d, J=19.9 Hz, 2H), 1.19-1.11 (m, 3H), 1.02-0.94 (m, 2H), 0.86-0.78 (m, 2H).

Intermediate 56

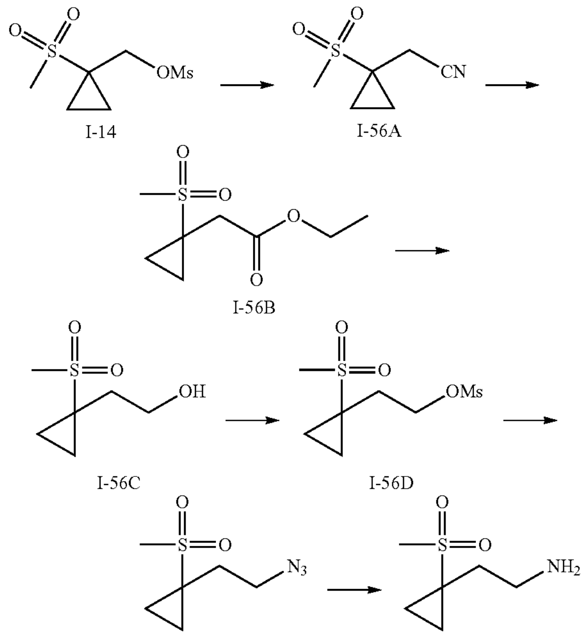

I-14 I-56A I-56B I-56C I-56D I-56E I-56

2-(1-(methyl sulfonyl)cyclopropyl) acetonitrile (I-56A). NaCN (1.9 g, 39.4 mmol, 2.0 equiv) was added to a solution of I-14D (4.5 g, 19.7 mmol, 1.0 equiv) in DMSO (45 mL). The reaction mixture was stirred at 60° C. for 3 h, after which it was quenched with water and extracted with EtOAc. The organic layer was washed with brine, dried over sodium sulfate, and concentrated to afford I-56A. 1H NMR (400 MHz, DMSO-d6) δ 3.11 (s, 2H), 2.51 (m, 3H), 1.40-1.33 (m, 2H), 1.16-1.09 (m, 2H).

ethyl 2-(1-(methyl sulfonyl)cyclopropyl) acetate (I-56B). I-56A (2.5 g, 15.7 mmol, 1.0 equiv) and conc. $H_2SO_4$ (2.5 mL) were added in ethanol (20 mL) in a sealed tube. The reaction mixture was stirred at 120° C. for 12 h. Additional conc. $H_2SO_4$ (2.5 mL) and ethanol (5 mL) were added, and the reaction mixture was stirred at 120° C. for 12 h. The reaction mixture was quenched with water and extracted with EtOAc. The organic layer was washed with brine, dried over sodium sulfate, and concentrated to afford I-56B. 1H NMR (400 MHz, DMSO-d6) δ 4.08 (q, J=7.1 Hz, 2H), 2.99 (s, 3H), 2.91 (s, 2H), 1.34 (q, J=4.6 Hz, 2H), 1.20 (t, J=7.1 Hz, 3H), 1.12-1.07 (m, 2H).

2-(1-(methyl sulfonyl)cyclopropyl) ethan-1-ol (I-56C) was prepared from I-56AB following a procedure analogous to that described for I-51B. $^{1}$H NMR (400 MHz, DMSO-d6) δ 3.59-3.50 (m, 2H), 3.00 (d, J=1.7 Hz, 1H), 2.99 (s, 3H), 2.01-1.98 (m, 2H), 1.18 (t, J=2.9 Hz, 2H), 1.01 (t, J=3.1 Hz, 2H).

2-(1-(methyl sulfonyl)cyclopropyl)ethyl methane sulfonate (I-56D) was prepared from I-56C following a procedure analogous to that described for 1-2. $^{1}$H NMR (400 MHz, DMSO-d6) δ 4.39 (t, J=7.0 Hz, 2H), 3.34 (s, 2H), 3.20 (s, 3H), 3.06 (d, J=3.6 Hz, 3H), 2.28 (t, J=7.0 Hz, 2H), 1.26-1.23 (m, 2H), 1.06 (m, 2H).

1-(2-azidoethyl)-1-(methyl sulfonyl)cyclopropane (I-56E) was prepared from I-56D following a procedure analogous to that described for I-53D. $^{1}$H NMR (400 MHz, DMSO) δ 3.60-3.49 (m, 2H), 3.05 (s, 3H), 2.16-2.04 (m, 2H), 1.26-1.19 (m, 2H), 1.06-0.98 (m, 2H).

2-(1-(methyl sulfonyl)cyclopropyl) ethan-1-amine (I-56) was prepared from I-56E following a procedure analogous to that described for 1-53. LCMS (m/z): 164.1 [M+H]. NMR (400 MHz, DMSO) δ 3.34 (ddd, J=51.0, 25.2, 8.4 Hz, 2H), 3.02-2.94 (m, 3H), 2.73-2.61 (m, 2H), 1.94-1.82 (m, 2H), 1.21-1.13 (m, 2H), 0.95 (td, J=5.5, 1.2 Hz, 2H).

Intermediate 57

2-(1-(amino methyl)cyclopropyl) isothiazolidine 1,1-dioxide

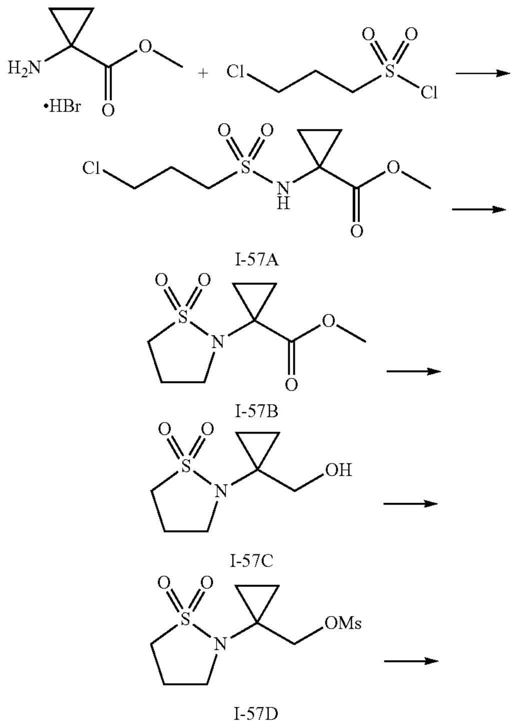

I-57A I-57B I-57C I-57D

-continued

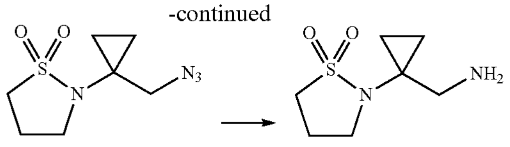

I-57E I-57 methyl 1-((3-chloropropyl) sulfonamido)cyclopropane-1-carboxylate (I-57A) was prepared from methyl 1-aminocyclopropane-1-carboxylate hydrobromide and 3-chloropropane-1-sulfonyl chloride following a procedure analogous to that described for I-18B. LCMS (m/z): 256.3 [M+H]. $^1$H NMR (400 MHz, DMSO-d6) δ 8.30 (s, 1H), 3.75 (dd, J=6.6, 4.2 Hz, 2H), 3.64 (s, 3H), 3.21-3.15 (m, 2H), 2.14 (dt, J=9.7, 6.7 Hz, 2H), 1.38 (p, J=5.5 Hz, 2H), 1.27 (dd, J=7.9, 4.7 Hz, 2H).

methyl 1-(1,1-dioxidoisothiazolidin-2-yl)cyclopropane-1-carboxylate (I-57B) was prepared from I-57A following a procedure analogous to that described for I-18C. LCMS (m/z): 220.2 [M+H]. $^1$H NMR (400 MHz, DMSO-d6) δ 3.65 (d, J=8.4 Hz, 3H), 3.47 (t, J=6.7 Hz, 2H), 3.20 (t, J=7.2 Hz, 2H), 2.31-2.22 (m, 2H), 1.38 (s, 2H), 1.32 (d, J=2.9 Hz, 2H).

2-(1-(hydroxymethyl)cyclopropyl) isothiazolidine 1,1-dioxide (I-57C) was prepared from I-57B following a procedure analogous to that described for I-2D. LCMS (m/z): 192.3 [M+H]. $^1$H NMR (400 MHz, DMSO-d6) δ 4.72 (t, J=5.8 Hz, 1H), 3.58 (d, J=5.8 Hz, 2H), 3.45 (t, J=6.7 Hz, 2H), 3.15 (t, J=7.5 Hz, 2H), 2.16 (dt, J=13.9, 6.9 Hz, 2H), 0.88 (dd, J=6.7, 4.5 Hz, 2H), 0.71 (dd, J=6.8, 4.5 Hz, 2H).

(1-(1,1-dioxidoisothiazolidin-2-yl)cyclopropyl)methyl methane sulfonate (I-57D) was prepared from I-57C following a procedure analogous to that described for 1-2. LCMS (m/z): 287.3 [M+18]. $^1$H NMR (400 MHz, DMSO-d6) δ 3.45 (dt, J=18.6, 6.7 Hz, 4H), 3.20 (s, 3H), 3.18-3.06 (m, 2H), 2.19 (dd, J=14.4, 6.9 Hz, 2H), 1.13 (dd, J=7.2, 5.0 Hz, 2H), 0.93 (dd, J=7.2, 5.0 Hz, 2H).

2-(1-(azidomethyl)cyclopropyl) isothiazolidine 1,1-dioxide (I-57E) was prepared from I-57D following a procedure analogous to that described for I-53D. $^1$H NMR (400 MHz, DMSO-d6) δ 3.52 (s, 1H), 3.42 (t, J=6.7 Hz, 1H), 3.18 (t, J=7.5 Hz, 1H), 2.19 (dd, J=14.0, 6.9 Hz, 1H), 1.06 (q, J=4.9 Hz, 1H), 0.80 (dd, J=7.0, 5.0 Hz, 1H).

2-(1-(amino methyl)cyclopropyl) isothiazolidine 1,1-dioxide (I-57) was prepared from I-57E following a procedure analogous to that described for 1-53. LCMS (m/z): 191.2 [M+H]. $^1$H NMR (400 MHz, DMSO-d6) δ 3.37 (dd, J=13.3, 6.6 Hz, 2H), 3.15 (dd, J=14.1, 6.8 Hz, 2H), 2.83-2.65 (m, 2H), 2.17 (dd, J=13.8, 6.7 Hz, 2H), 1.68 (s, 2H), 0.86 (d, J=4.7 Hz, 2H), 0.70 (d, J=4.4 Hz, 2H).

Intermediate 58

1-(amino methyl)cyclopropyl dimethyl carbamate

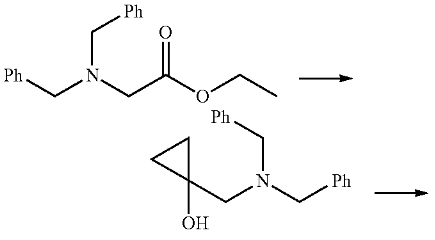

I-58A

-continued

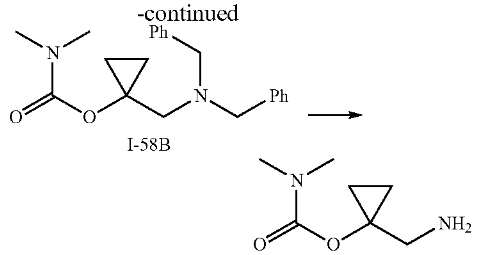

I-58B

I-58

1-((dibenzyl amino)methyl)cyclopropan-1-ol (I-58A). Ethyl dibenzyl glycinate (1 g, 3.5 mmol, 1.0 equiv) was dissolved in diethyl ether (10 mL) and cooled to 0° C. $Ti(OiPr)_4$ (0.25 g, 0.88 mmol, 0.25 equiv) and EtMgBr (3.0 M in diethyl ether) (4.7 mL, 14.1 mmol, 4.0 equiv) were added, and the reaction mixture was stirred at RT for 24 h. The reaction mixture was cooled to 0° C., quenched with saturated aqueous ammonium chloride solution and extracted with EtOAc. The organic layer was washed with brine, dried over sodium sulfate, and concentrated to afford a crude residue. The crude residue was purified by silica gel column chromatography (5% EtOAc/hexane) to afford I-58A. LCMS (m/z): 268.3 [M+H]. $^1$H NMR (400 MHz, DMSO-d6) δ 7.39 (d, J=7.0 Hz, 4H), 7.32 (t, J=7.5 Hz, 4H), 7.23 (t, J=7.2 Hz, 2H), 5.06 (s, 1H), 3.64 (d, J=20.7 Hz, 4H), 2.53 (s, 2H), 0.57-0.54 (m, 2H), 0.33 (dd, J=6.7, 4.6 Hz, 2H).

1-((dibenzyl amino)methyl)cyclopropyl dimethyl carbamate (I-58B). I-58A (5 g, 18.7 mmol, 1.0 equiv) was dissolved in THF (50 mL) and cooled to 0° C. NaH (60% suspension in mineral oil, 0.93 g, 24.3 mmol, 1.3 equiv) and dimethyl carbamic chloride (3 g, 28.1 mmol, 1.5 equiv) were added, and the reaction mixture was stirred at RT for 5 h. The reaction mixture was quenched with saturated aqueous ammonium chloride and was extracted with EtOAc. The organic layer was washed with brine, dried over sodium sulfate, and concentrated to afford a crude residue. The crude residue was purified by silica gel column chromatography (10% EtOAc/Hexane) to afford I-58B. The product was used without further purification. LCMS (m/z): 339.4 [M+H]. $^1$H NMR (400 MHz, DMSO-d6) δ 7.39-7.25 (m, 10H), 3.64 (d, J=15.8 Hz, 4H), 2.83 (d, J=28.9 Hz, 6H), 2.71 (d, J=22.3 Hz, 2H), 0.81-0.74 (m, 2H), 0.63 (dd, J=7.6, 5.7 Hz, 2H).

1-(amino methyl)cyclopropyl dimethyl carbamate (1-58). I-58B (0.9 g, 3.78 mmol, 1.0 equiv) was dissolved in methanol (10 mL), $Pd(OH)_2$ (0.1 g) was added and the reaction mixture was stirred at RT for 24 h under a $H_2$(gas) atmosphere. The reaction mixture was filtered through a bed of celite, and the filtrate was concentrated to afford 1-58. LCMS (m/z): 159.1 [M+H]. $^1$H NMR (400 MHz, DMSO-d6) δ 2.82 (s, 1H), 2.78 (s, 3H), 0.76-0.67 (m, 2H).

Intermediate 59

(1-methoxy cyclopropyl) methanamine

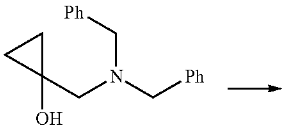

I-58A

-continued

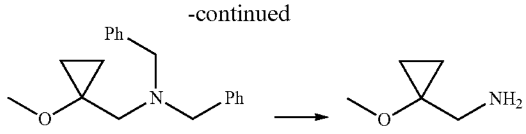

I-59A I-58B

N, N-dibenzyl-1-(1-methoxy cyclopropyl) methanamine (I-59A). I-58A (2 g, 7.5 mmol, 1.0 equiv) was dissolved in THF (20 mL) and cooled to 0° C. NaH (60% suspension in mineral oil, 0.34 g, 8.98 mmol, 1.2 equiv) and iodomethane (1.6 g, 11.2 mmol, 1.5 equiv) were added, and the reaction mixture was stirred at RT for 3 h. The reaction mixture was quenched with saturated aqueous ammonium chloride solution and extracted with EtOAc. The organic layer was washed with brine, dried over sodium sulfate, and concentrated to afford a crude residue. The crude residue was purified by silica gel column chromatography (3% EtOAc /hexane) to afford the title compound. LCMS (m/z): 282.2 [M+H]. $^1$H NMR (400 MHz, DMSO-d6) δ 7.31 (ddd, J=37.8, 14.1, 7.0 Hz, 10H), 3.63 (s, 4H), 3.13 (s, 3H), 2.56 (s, 2H), 0.68 (s, 2H), 0.39 (q, J=5.1 Hz, 2H).

(1-methoxy cyclopropyl) methanamine (1-59) was prepared from I-59A following a procedure analogous to that described for 1-58. LCMS (m/z): 102.0 [M+H]. $^1$H NMR (400 MHz, DMSO) δ 7.56 (s, 2H), 3.21 (s, 3H), 2.97 (s, 2H), 0.79 (dd, J=7.0, 5.2 Hz, 2H), 0.65 (dd, J=7.2, 5.1 Hz, 2H).

Intermediate 60

N-(2-aminoethyl)-N-methylmethanesulfonamide

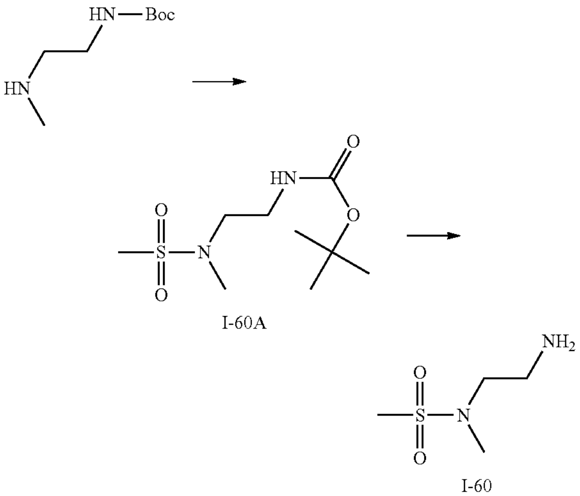

I-60A

I-60 tert-butyl (2-(N-methylmethylsulfonamido)ethyl)carbamate (I-60A). To a solution of tert-butyl (2-(methylamino) ethyl)carbamate (0.9 mL, 4.95 mmol) in DCM (25 mL) chilled to 0° C. were added DIEA (2.59 mL, 14.84 mmol) followed by MsCl (0.424 mL, 5.44 mmol). The resulting mixture was allowed to warm to RT and was stirred overnight. The reaction mixture was diluted with DCM and washed with 2 M HCl (5×). The organic layer was dried over sodium sulfate and concentrated under reduced pressure. The title compound was isolated as a tan solid. LCMS (m/z): 197.1 [M-tBu+H]. $^1$H NMR (400 MHz, DMSO-d6) δ ppm 1.37 (s, 9H) 2.76 (s, 3H) 2.85 (s, 3H) 3.08 (d, J=2.35 Hz, 4H) 6.89 (br. s., 1H).

N-(2-aminoethyl)-N-methylmethanesulfonamide (I-60). To a solution of I-60A (1.17 g, 4.64 mmol) in dioxane (4 mL) was added 4 M HCl in dioxane (6 mL, 24.00 mmol). The resulting solution was stirred at RT. Upon completion of the reaction, the mixture was concentrated under reduced pressure. The title compound was isolated as a tan solid. LCMS (m/z): 153.1. $^1$H NMR (400 MHz, $CD_3OD$) δ ppm 2.91 (s, 6H) 3.14 (t, J=5.67 Hz, 2H) 3.39-3.44 (m, 2H).

Intermediate 61

N-(4-cyanobenzyl)-1,6-dioxo-1,3,4,6-tetrahydro-pyrido[2,1-c][1,4]oxazine-7-carboxamide

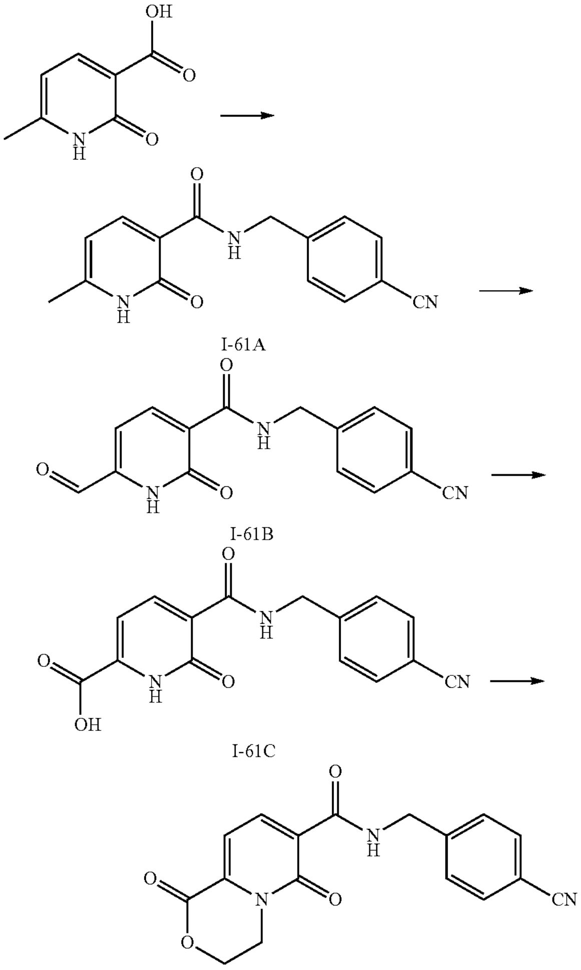

I-61A

I-61B

I-61C

I-61

N-(4-cyanobenzyl)-6-methyl-2-oxo-1,2-dihydropyridine-3-carboxamide (I-61A). To a solution of 6-methyl-2-oxo-1,2-dihydropyridine-3-carboxylic acid (10 g, 65.4 mmol, 1.0 equiv) in THF (250 mL) were added N-methyl morpholine (19.8 g, 196.1 mmol, 3.0 equiv), EDC·HCl (15 g, 78.4 mmol, 1.2 equiv), HOBT (10.6 g, 78.4 mmol, 1.2 equiv), and 4-(aminomethyl)benzonitrile hydrochloride (16.6 g, 98.0 mmol, 1.5 equiv). The reaction mixture was stirred at RT for 24 h. The reaction mixture was quenched with water, and the resulting solid was isolated by filtration. The filter cake was washed with water and hexane and dried to afford the title compound. LCMS (m/z): 268.5 [M+H]. $^1$H NMR (400 MHz, DMSO-d6) δ 12.54 (s, 1H), 10.20 (t, J=6.0 Hz, 1H), 8.24 (d, J=7.4 Hz, 1H), 7.80 (d, J=8.3 Hz, 2H), 7.48 (d, J=8.4 Hz, 2H), 6.32 (d, J=7.4 Hz, 1H), 4.60 (d, J=6.1 Hz, 2H), 2.30 (s, 3H).

N-(4-cyanobenzyl)-6-formyl-2-oxo-1,2-dihydropyridine-3-carboxamide (I-61B) was prepared from I-61A following a procedure analogous to that described for I-47C. LCMS (m/z): 282.1 [M+H]. $^1$H NMR (400 MHz, DMSO-d6) δ 12.78 (s, 1H), 10.23 (s, 1H), 9.71 (s, 1H), 8.51 (d, J=7.1 Hz, 1H), 7.84-7.80 (m, 2H), 7.51 (d, J=8.4 Hz, 2H), 7.17 (d, J=7.1 Hz, 1H), 4.64 (d, J=6.1 Hz, 2H).

5-((4-cyanobenzyl) carbamoyl)-6-oxo-1,6-dihydropyridine-2-carboxylic acid (I-61C) was prepared from I-61B following a procedure analogous to that described for I-47D. LCMS (m/z): 297.9 [M+H]. $^1$H NMR (400 MHz, DMSO-d6) δ 12.42 (s, 1H), 10.25 (s, 1H), 8.41 (d, J=7.3 Hz, 1H), 7.81 (d, J=8.3 Hz, 2H), 7.50 (d, J=8.1 Hz, 2H), 7.08 (d, J=7.2 Hz, 1H), 4.63 (d, J=6.1 Hz, 2H).

N-(4-cyanobenzyl)-1,6-dioxo-1,3,4,6-tetrahydropyrido[2,1-c][1,4]oxazine-7-carboxamide (I-61). I-61C (3.8 g, 12.8 mmol, 1.0 equiv) and 1,2-dibromoethane (4.8 g, 25.6 mmol, 2.0 equiv) were dissolved in DMF (80 mL). TEA (3.9 g, 38.4 mmol, 3.0 equiv) was added, and the reaction mixture was stirred at 80° C. for 4 h. The reaction mixture was quenched with cold water and extracted with EtOAc. The organic layer was washed with water and brine, dried over sodium sulfate, and concentrated to afford 1-61. LCMS (m/z):

324.4 [M+H]. $^1$H NMR (400 MHz, DMSO-d6) δ 10.14 (t, J=6.0 Hz, 1H), 8.46 (d, J=7.5 Hz, 1H), 7.82 (d, J=8.3 Hz, 2H), 7.50 (d, J=8.3 Hz, 2H), 7.32 (d, J=7.5 Hz, 1H), 4.76-4.68 (m, 2H), 4.64 (d, J=6.1 Hz, 2H), 4.36-4.25 (m, 2H).

Intermediate 62

2-(cyclopropyl sulfonyl) ethan-1-amine hydrochloride

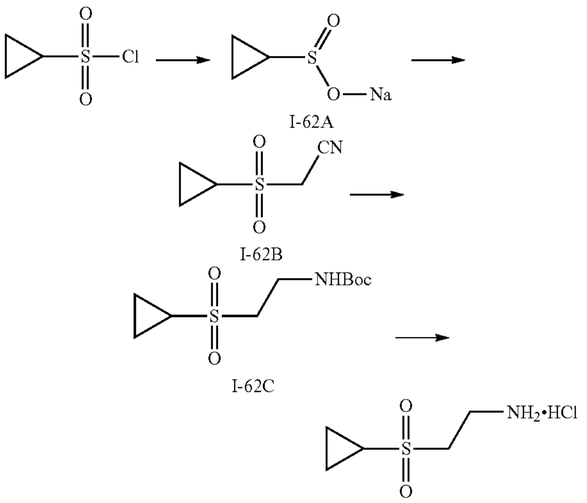

I-62A

I-62B

I-62C

I-62 sodium cyclopropane sulfinate (I-62A). $Na_2SO_3$ (22.6 g, 178.0 mmol, 1.0 equiv) was added in water (250 mL) and stirred at RT for 10 min $Na_2CO_3$ (37.7 g, 356.0 mmol, 2.0 equiv) was added and the reaction mixture was stirred at 60° C. for 10 min Cyclopropane sulfonyl chloride (25 g, 178.0 mmol, 1.0 equiv) was added dropwise and the reaction mixture was stirred at RT for 2 h. The reaction mixture was concentrated to afford a crude residue. The crude residue was dissolved in ethanol (250 mL) and stirred at RT for 20 min. The solid was filtered and washed with ethanol. The filtrate was concentrated to afford the title compound. $^1$H NMR (400 MHz, DMSO-d6) δ 1.64-1.50 (m, 1H), 0.69-0.32 (m, 4H).

2-(cyclopropyl sulfonyl) acetonitrile (I-62B) was prepared from I-62A following a procedure analogous to that described for I-49E. $^1$H NMR (400 MHz, $CDCl_3$) δ 4.11-3.92 (m, 2H), 2.73 (tt, J=7.9, 4.7 Hz, 1H), 1.53-1.36 (m, 2H), 1.35-1.19 (m, 2H).

tert-butyl (2-(cyclopropyl sulfonyl)ethyl) carbamate (I-62C). I-62B (5 g, 34.4 mmol, 1.0 equiv) was added in methanol (50 mL) and cooled to 0° C. $NiCl_2·6H_2O$ (0.82 g, 3.44 mmol, 0.1 equiv) was added and the reaction mixture was stirred at 0° C. for 5 min $NaBH_4$ (5.2 g, 138.0 mmol, 4.0 equiv) was added and the reaction mixture was stirred at RT for 24 h. The reaction mixture was filtered through a bed of celite; the filtrate was concentrated, diluted with water, and extracted with EtOAc. The organic layer was washed with brine, dried over sodium sulfate, and concentrated. The crude residue was purified by silica gel column chromatography (30% EtOAc/Hexane) to afford I-62C. $^1$H NMR (400 MHz, DMSO-d6) δ 7.04 (t, J=5.3 Hz, 1H), 3.36 (d, J=10.1 Hz, 2H), 3.25 (dd, J=7.9, 5.8 Hz, 2H), 2.75 (dd, J=7.8, 2.7 Hz, 1H), 1.38 (d, J=6.2 Hz, 9H), 0.99 (dd, J=6.0, 1.8 Hz, 4H).

2-(cyclopropyl sulfonyl) ethan-1-amine hydrochloride (1-62) was prepared from I-62C following a procedure analogous to that described for 1-49. LCMS (m/z): 150.1 [M+H, free amine] $^1$H NMR (400 MHz, DMSO-d6) δ 8.30 (s, 2H), 3.60-3.41 (m, 2H), 3.31-3.04 (m, 2H), 2.91 (ddd, J=12.6, 7.8, 4.8 Hz, 1H), 1.18-0.90 (m, 4H).

Intermediate 63

N-(1-(amino methyl)cyclopropyl)-N-methyl methane sulfonamide

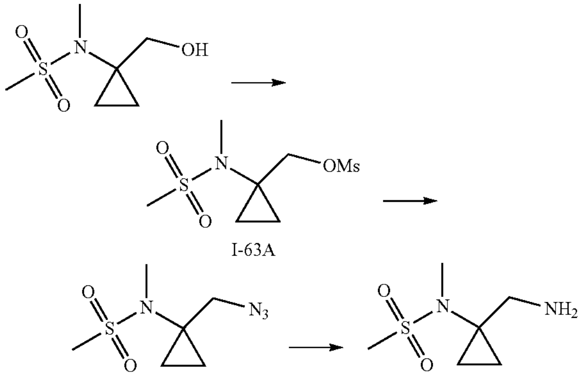

I-63A

I-63B

I-63

(1-(N-methyl methyl sulfonamido)cyclopropyl)methyl methane sulfonate (I-63A) was prepared from N-(1-(hydroxymethyl)cyclopropyl)-N-methylmethanesulfonamide following a procedure analogous to that described for 1-2. $^1$H NMR (400 MHz, DMSO-d6) δ 4.26 (s, 2H), 3.21 (s, 3H), 2.99 (d, J=12.7 Hz, 3H), 2.88 (d, J=8.3 Hz, 3H), 1.13 (t, J=6.2 Hz, 2H), 0.97 (t, J=6.2 Hz, 2H).

N-(1-(azidomethyl)cyclopropyl)-N-methyl methane sulfonamide (I-63B) was prepared from I-63A following a procedure analogous to that described for I-53D. $^1$H NMR (400 MHz, DMSO-d6) δ 3.46 (s, 2H), 2.95 (d, J=7.6 Hz, 3H), 2.90-2.83 (m, 3H), 1.03 (q, J=5.3 Hz, 2H), 0.86 (q, J=5.3 Hz, 2H).

N-(1-(amino methyl)cyclopropyl)-N-methyl methane sulfonamide (I-63) was prepared from I-63B following a procedure analogous to that described for 1-53. LCMS (m/z): 179.2 [M+H]. $^1$H NMR (400 MHz, DMSO-d6) δ 3.00-2.94 (m, 3H), 2.86 (d, J=5.5 Hz, 3H), 2.74-2.65 (m, 2H), 1.68-1.27 (m, 2H), 0.85-0.78 (m, 2H), 0.78-0.71 (m, 2H).

Preparation of Compounds of Formula (I)

Example 1

N-(4-cyanobenzyl)-2-(1-(cyclopropylsulfonyl)cyclopropyl)methyl)-1,6-dioxo-2,3,4,6-tetrahydro-1H-pyrido[1,2-a]pyrazine-7-carboxamide 2-((1-(cyclopropylsulfonyl)cyclopropyl)methyl)-1,6-dioxo-2,3,4,6-tetrahydro-1H-pyrido[1,2-a]pyrazine-7-carboxylic acid (Ex-1A). A solution of I-1 (5 g, 18.92 mmol) in DMF (140 mL) was cooled to 0° C. To the chilled solution was added NaH (60% suspension in mineral oil, 1.135 g, 28.4 mmol). The resulting mixture was stirred at 0° C. until bubbling ceased. To the basic mixture was added 1-2 (6.26 g, 24.60 mmol) in DMF (40 mL). The resulting mixture was allowed to warm to RT. After 72 h, NaH (60% suspension in mineral oil, 0.378 g, 9.46 mmol) was added. After 2 h, the reaction was diluted with $H_2O$. The reaction was stirred at RT for 1 h. The resulting precipitate was isolated via vacuum filtration to afford the sodium salt of Ex-1A as a light tan foam. The filtrate was washed with EtOAc. The aqueous layer was adjusted to pH 1 with 2 M HCl. The acidic aqueous layer was extracted with EtOAc. The combined organic extracts were dried over sodium sulfate and concentrated under reduced pressure to afford a second crop of Ex-1A, a dark tan solid. LCMS m/z: 367 (M+1).

N-(4-cyanobenzyl)-2-((1-(cyclopropylsulfonyl)cyclopropyl)methyl)-1,6-dioxo-2,3,4,6-tetrahydro-1H-pyrido[1,2-a]pyrazine-7-carboxamide (Ex-1). To a slurry of Ex-1A (2.26 g, 6.17 mmol) in DCM (60 mL) was added oxalyl chloride (0.594 mL, 6.79 mmol) followed by a drop of DMF. The reaction immediately released gas and became homogenous. The reaction mixture was stirred at RT for about 1 h, after which it was concentrated under reduced pressure. The residue was taken up in DCM (60 mL) and 4-(aminomethyl) benzonitrile HCl (1.248 g, 7.40 mmol) was added. To the slurry was added DIEA (2.155 mL, 12.34 mmol). The resulting mixture was allowed to stir at RT for about 1 h. The reaction was diluted with DCM and washed with 2 M HCl and saturated aqueous sodium bicarbonate. The organic layer was dried over sodium sulfate and concentrated under reduced pressure. The yellow foam was taken up in DCM and purified on $SiO_2$ (heptane to acetone) to afford the product. The residue was recrystallized by heating in EtOH (890 mL) in a 2 L Erlenmeyer flask at reflux until the solids dissolved, approximately 30-45 min. The solution was allowed to slowly cool to RT over 72 h. The resulting crystalline solid was isolated via vacuum filtration. The filter cake was rinsed with heptane, and the solid was dried under high vacuum overnight. Ex-1 was isolated as slightly yellow needles with melting point=186° C. FIG. 1 shows the XRPD of the product from this reaction (NX-7) compared to the XRPD of a second polymorph (NX-12) that predominates when the two crystal forms are slurried together in ethanol. NX-12 appears to be the more stable polymorph.

Other compounds in the table below were prepared following procedures analogous to those described for Ex-1.

| Example | Structure | Physical Data MS (m/z), $^1$H NMR |
|---|---|---|
| 1 | 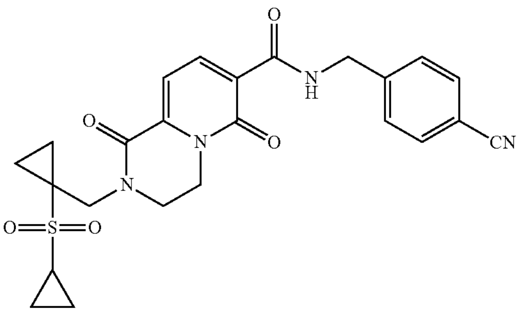 [SMILES: N#Cc1ccc(CNC(=O)c2ccc3n(c2=O)CCN(CC2(S(=O)(=O)C4CC4)CC2)C3=O)cc1] | MS m/z: 481 (M + 1). $^1$H NMR (500 MHz, DMSO-d6) δ ppm 0.97-1.10 (m, 4H) 1.19 (td, J = 5.04, 1.89 Hz, 2H) 1.32 (td, J = 5.04, 1.89 Hz, 2H) 2.91-2.98 (m, 1H) 3.82 (t, J = 5.99 Hz, 2H) 4.10 (s, 2H) 4.27 (t, J = 5.99 Hz, 2H) 4.64 (d, J = 6.31 Hz, 2H) 7.22 (d, J = 7.57 Hz, 1H) 7.51 (d, J = 8.20 Hz, 2H) 7.81 (d, J = 8.20 Hz, 2H) 8.44 (d, J = 7.57 Hz, 1H) 10.19 (t, J = 6.15 Hz, 1H). |
| 2 | 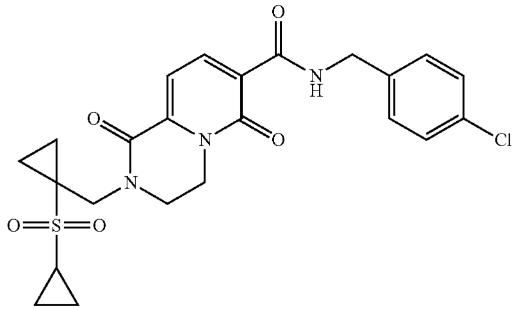 [SMILES: O=C(NCc1ccc(Cl)cc1)c1ccc2n(c1=O)CCN(CC1(S(=O)(=O)C3CC3)CC1)C2=O] | MS m/z: 490 (M + 1). $^1$H NMR (400 MHz, DMSO-d6) δ ppm 0.95-1.08 (m, 4H) 1.13-1.18 (m, 2H) 1.26-1.32 (m, 2H) 2.87-2.96 (m, 1H) 3.79 (t, J = 5.53 Hz, 2H) 4.07 (s, 2H) 4.23 (t, J = 5.53 Hz, 2H) 4.52 (d, J = 5.92 Hz, 2H) 7.20 (d, J = 7.53 Hz, 1H) 7.32 (m, J = 8.31 Hz, 2H) 7.38 (m, J = 8.27 Hz, 2H) 8.42 (d, J = 7.58 Hz, 1H) 10.08 (t, J = 5.82 Hz, 1H) |

-continued

| Example | Structure | Physical Data MS (m/z), $^1$H NMR |
|---|---|---|
| 3-1 | 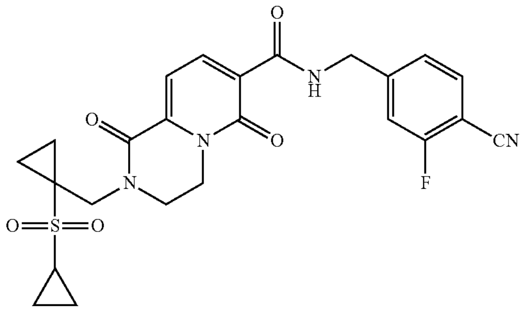 [SMILES: N#Cc1ccc(CNC(=O)c2ccc3n(c2=O)CCN(CC2(S(=O)(=O)C4CC4)CC2)C3=O)cc1F] | MS m/z: 499 (M + 1). $^1$H NMR (400 MHz, DMSO-d6) δ ppm 0.95-1.09 (m, 4H) 1.12-1.20 (m, 2H) 1.25-1.34 (m, 2H) 2.86-2.97 (m, 1H) 3.80 (t, J = 5.70 Hz, 2H) 4.07 (s, 2H) 4.25 (t, J = 5.70 Hz, 2H) 4.62 (d, J = 6.06 Hz, 2H) 7.19 (d, J = 7.53 Hz, 1H) 7.33 (d, J = 8.02 Hz, 1H) 7.41 (d, J = 10.47 Hz, 1H) 7.87 (t, J = 7.43 Hz, 1H) 8.40 (d, J = 7.53 Hz, 1H) 10.16 (t, J = 6.14 Hz, 1H) |
| 3-2 | 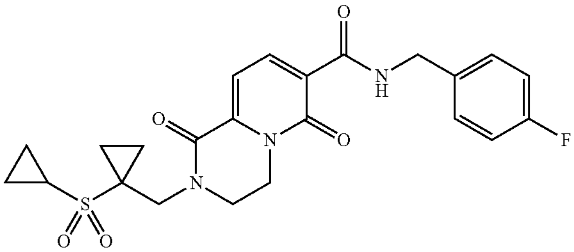 [SMILES: O=C(NCc1ccc(F)cc1)c1ccc2n(c1=O)CCN(CC1(S(=O)(=O)C3CC3)CC1)C2=O] | LCMS (m/z): 474.4 [M + H]. $^1$H NMR (400 MHz, DMSO-d6) δ 10.10 (t, J = 5.8 Hz, 1H), 8.45 (d, J = 7.6 Hz, 1H), 7.37 (dd, J = 8.7, 5.6 Hz, 2H), 7.31-7.11 (m, 3H), 4.53 (d, J = 5.9 Hz, 2H), 4.30-4.17 (m, 2H), 3.86-3.71 (m, 2H), 2.95 (d, J = 4.9 Hz, 1H), 1.31 (t, J = 5.7 Hz, 2H), 1.18 (t, J = 6.2 Hz, 2H), 1.12-0.98 (m, 4H). |
| 3-3 | 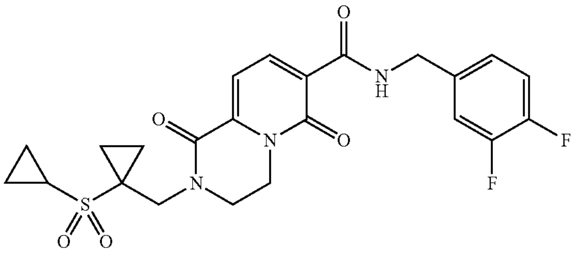 [SMILES: O=C(NCc1ccc(F)c(F)c1)c1ccc2n(c1=O)CCN(CC1(S(=O)(=O)C3CC3)CC1)C2=O] | LCMS (m/z): 492.2 [M + H]. $^1$H NMR (400 MHz, DMSO-d6) δ 10.12 (t, J = 6.1 Hz, 1H), 8.44 (d, J = 7.5 Hz, 1H), 7.40 (dt, J = 17.3, 8.5 Hz, 2H), 7.29-7.11 (m, 2H), 4.53 (d, J = 5.9 Hz, 2H), 4.33-4.17 (m, 2H), 3.90-3.74 (m, 2H), 3.00-2.89 (m, 1H), 1.29 (d, J = 15.5 Hz, 2H), 1.19 (d, J = 6.4 Hz, 2H), 1.11-0.94 (m, 4H). |
| 3-4 | 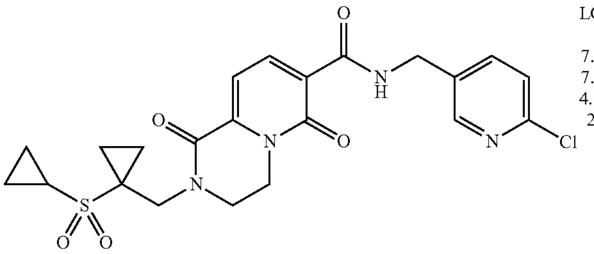 | LCMS (m/z): 491.1 [M + H]. $^1$H NMR (400 MHz, DMSO-d6) δ 10.15 (s, 1H), 8.53-8.24 (m, 3H), 7.81 (d, J = 8.2 Hz, 1H), 7.50 (d, J = 8.3 Hz, 1H), 7.21 (d, J = 7.6 Hz, 1H), 4.56 (d, J = 6.1 Hz, 2H), 4.26 (s, 2H), 4.09 (s, 2H), 3.82 (d, J = 5.8 Hz, 2H), 2.95 (s, 1H), 1.30 (s, 2H), 1.18 (s, 2H), 1.06 (dd, J = 19.4, 11.4 Hz, 4H). |
| 3-5 | 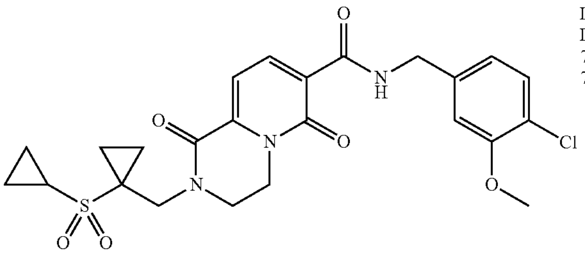 | LCMS (m/z): 520.1 [M + H]. $^1$H NMR (400 MHz, DMSO-d6) δ 10.10 (t, J = 6.0 Hz, 1H), 8.45 (d, J = 7.6 Hz, 1H), 7.38 (d, J = 8.1 Hz, 1H), 7.22 (d, J = 7.6 Hz, 1H), 7.15 (d, J = 1.6 Hz, 1H), 6.90 (d, J = 8.1 Hz, 1H), 4.54 (d, J = 5.9 Hz, 2H), 4.32-4.18 (m, 2H), 4.09 (s, 2H), 3.88-3.75 (m, 5H), 2.94 (td, J = 7.9, 3.9 Hz, 1H), 1.36-1.25 (m, 2H), 1.18 (q, J = 5.2 Hz, 2H), 1.11-0.94 (m, 4H). |

Example 4

N-(4-chlorobenzyl)-2-((4-hydroxybutan-2-yl)sulfonyl)cyclopropyl)methyl)-1,6-dioxo-2,3,4,6-tetrahydro-1H-pyrido pyrazine-7-carboxamide 2-((1-(((4-((tert-butyldimethylsilyl)oxy)butan-2-yl)sulfonyl)cyclopropyl)methyl)-1,6-dioxo-2,3,4,6-tetrahydro-1H-pyrido[1,2-a]pyrazine-7-carboxylic acid (Ex-4A) was prepared from I-1 and 1-3 following a procedure analogous to that described for Ex-1A. Ex-4A was isolated as an orange oil. LCMS m/z: 513 (M+1).

N-(4-chlorobenzyl)-2-((1-((4-hydroxybutan-2-yl)sulfonyl)cyclopropyl)methyl)-1,6-dioxo-2,3,4,6-tetrahydro-1H-pyrido[1,2-a]pyrazine-7-carboxamide (Ex-4). To a solution of Ex-4A (0.2 g, 0.390 mmol) in DCM (3 mL) were added DIEA (0.136 mL, 0.780 mmol) and T3P® (50% in EtOAc, 0.255 mL, 0.429 mmol). The resulting mixture was stirred for about 10 min, after which p-chlorobenzyl amine (0.057 mL, 0.468 mmol) was added. The reaction mixture was stirred at RT for 1 h. The mixture was diluted with DCM, washed with 2 M HCl and saturated sodium bicarbonate, and dried over sodium sulfate. The dried organic layer was concentrated under reduced pressure. The residue was taken up in DCM (3 mL) and treated with HCl 4M in dioxane (1.5 mL, 6.00 mmol). After 30 min, the reaction mixture was diluted with DCM and washed with $H_2O$. The organic layer was dried over sodium sulfate and concentrated under reduced pressure. The crude product was purified using SFC. Ex-4 was isolated as an off-white solid.

Compound 5 in the table below was prepared following procedures analogous to those described for Ex-4.

(R) & (S) N-(4-chlorobenzyl)-2-((1-((4-hydroxybutan-2-yl)sulfonyl)cyclopropyl)methyl)-1,6-dioxo-2,3,4,6-tetrahydro-1H-pyrido[1,2-a]pyrazine-7-carboxamide (Ex-6, Ex-7). Ex-4 was subjected to separation by chiral SFC (AD column, 5 mL/min $CO_2$/EtOH=70/30) to afford enantiomeric title compounds.

(R) & (S) N-(4-cyanobenzyl)-2-((1-((4-hydroxybutan-2-yl)sulfonyl)cyclopropyl)methyl)-1,6-dioxo-2,3,4,6-tetrahydro-1H-pyrido[1,2-a]pyrazine-7-carboxamide (Ex-8, Ex-9). Ex-5 was subjected to separation by chiral HPLC (ADH column, 1 mL/min heptane/IPA=50/50) to afford enantiomeric title compounds.

The stereochemical assignments for Ex-6, Ex-7, Ex-8 and Ex-9 are arbitrary.

| Example | Structure | Physical Data MS (m/z), $^1$H NMR |
|---|---|---|
| 4 | 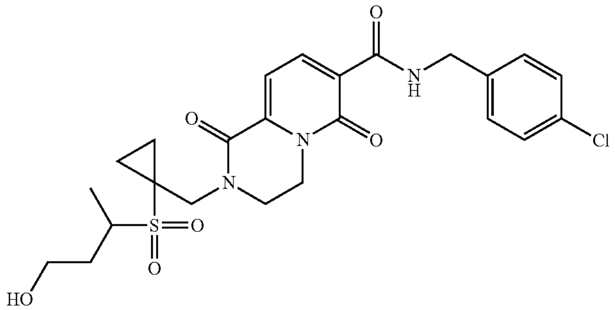 [SMILES: CC(CCO)S(=O)(=O)C1(CN2CCn3c(ccc(C(=O)NCc4ccc(Cl)cc4)c3=O)C2=O)CC1] | LCMS m/z: 522 (M + 1), $^1$H NMR (500 MHz, DMSO-d6) δ ppm 1.18-1.24 (m, 2H) 1.25-1.32 (m, 5H) 1.43-1.52 (m, 1H) 2.07-2.16 (m, 1H) 3.45-3.54 (m, 1H) 3.54-3.63 (m,l H) 3.77-3.86 (m, 3H) 3.97 (d, J = 15.13 Hz, 1H) 4.08 (d, J = 15.13 Hz, 1H) 4.19-4.32 (m, 2H) 4.55 (d, J = 6.03 Hz, 2H) 4.68 (br. s., 1H) 7.22 (d, J = 7.57 Hz, 1H) 7.33-7.37 (m, 2H) 7.39-7.44 (m, 2H) 8.46 (d, J = 7.57 Hz, 1H) 10.11 (t, J = 6.09 Hz, 1H) |
| 5 | 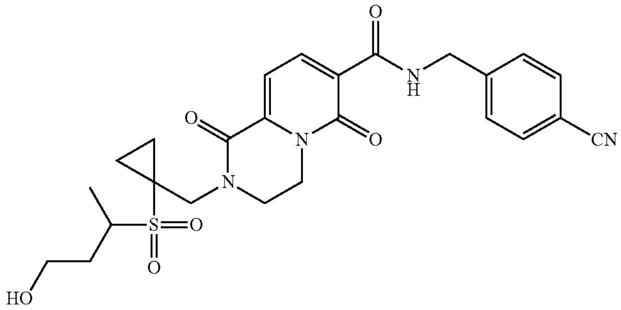 [SMILES: CC(CCO)S(=O)(=O)C1(CN2CCn3c(ccc(C(=O)NCc4ccc(C#N)cc4)c3=O)C2=O)CC1] | MS m/z: 513 (M + 1), $^1$H NMR (500 MHz, DMSO-d6) δ ppm 1.20-1.23 (m, 2H) 1.29 (d, J = 6.74 Hz, 4H) 1.48 (s, 1H) 3.58 (br. s., 2H) 3.79-3.87 (m, 3H) 3.98 (d, J = 15.13 Hz, 1H) 4.08 (d, J = 15.13 Hz, 1H) 4.22-4.33 (m, 2H) 4.65 (d, J = 6.15 Hz, 2H) 4.68 (br. s., 1H) 7.22 (d, J = 7.57 Hz, 1H) 7.51 (m, J = 8.51 Hz, 2H) 7.80-7.84 (m, 2H) 8.45 (d, J = 7.57 Hz, 1H) 10.18 (t, J = 6.15 Hz, 1H) |
| 6 | 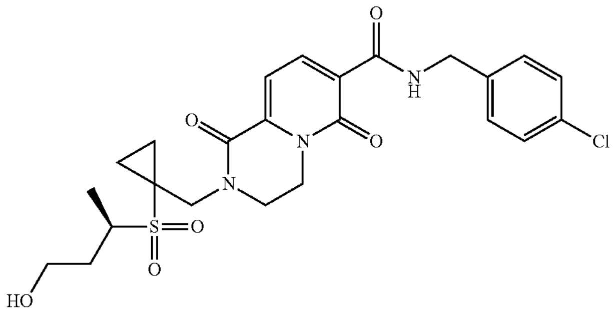 [SMILES: C[C@H](CCO)S(=O)(=O)C1(CN2CCn3c(ccc(C(=O)NCc4ccc(Cl)cc4)c3=O)C2=O)CC1] | MS m/z: 522 (M + 1). $^1$H NMR (500 MHz, $CDCl_3$-d) δ ppm 1.08 (d, J = 1.26 Hz, 2H) 1.45 (d, J = 6.94 Hz, 2H) 1.53-1.62 (m, 5H) 1.67-1.79 (m, 2H) 2.29-2.42 (m, 1H) 3.62 (d, J = 15.45 Hz, 1H) 3.72 (br. s., 1H) 3.75-3.82 (m, 1H) 3.87-3.97 (m, 2H) 3.99-4.07 (m, 1H) 4.24-4.31 (m, 1H) 4.44 (d, J = 15.45 Hz, 1H) 4.52 (ddd, J = 10.80, 7.01, 3.31 Hz, 1H) 4.64 (d, J = 5.99 Hz, 1H) 7.30-7.34 (111, 3H) 7.36 (d, J = 7.57 Hz, 1H) 8.66 (d, J = 7.57 Hz, 1H) 10.06 (t, J = 5.83 Hz, 1H) |

-continued

| Example | Structure | Physical Data MS (m/z), $^1$H NMR |
|---|---|---|
| 7 | 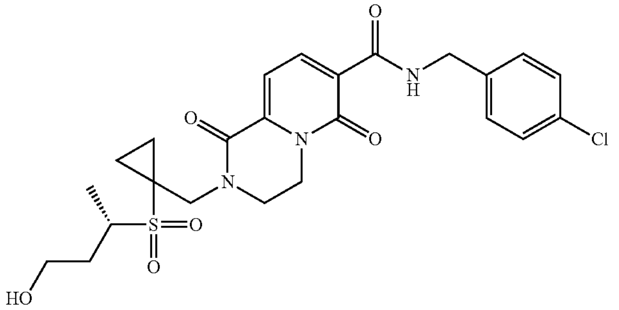 | MS m/z: 522 (M + 1). $^1$H NMR (500 MHz, DMSO-d6) δ ppm 1.17-1.23 (m, 2H) 1.28 (d, J = 6.94 Hz, 5H) 1.41-1.52 (m, 1H) 2.11 (br. s., 1H) 2.65 (d, J = 1.89 Hz, 1H) 3.42-3.54 (m, 1H) 3.54-3.62 (m, 1H) 3.80 (t, J = 5.83 Hz, 3H) 3.96 (d, J = 14.82 Hz, 1H) 4.07 (d, J = 15.13 Hz, 1H) 4.25 (q, J = 6.10 Hz, 2H) 4.54 (d, J = 6.31 Hz, 2H) 4.68 (t, J = 5.20 Hz, 1H) 7.21 (d, J = 7.57 Hz, 1H) 7.35 (d, J = 8.83 Hz, 2H) 7.41 (d, J = 8.51 Hz, 2H) 8.45 (d, J = 7.57 Hz, 1H) 10.11 (t, J = 5.83 Hz, 1H) |
| 8 | 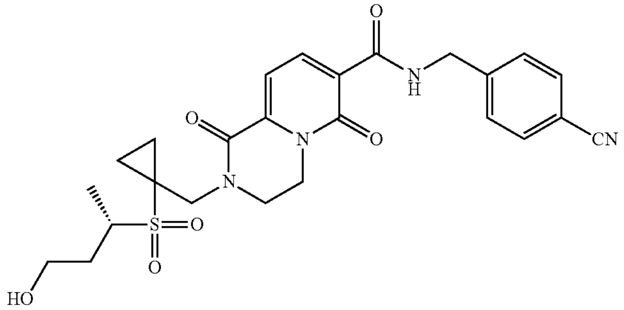 [SMILES: C[C@@H](CCO)S(=O)(=O)C1(CN2CCn3c(ccc(C(=O)NCc4ccc(C#N)cc4)c3=O)C2=O)CC1] | MS m/z: 513 (M + 1), $^1$H NMR (500 MHz, $CDCl_3$-d) δ ppm 1.05-1.12 (m, 2H) 1.45 (d, J = 6.94 Hz, 3H) 1.58-1.61 (m, 2H) 1.69-1.79 (m, 2H) 2.29-2.37 (m, 1H) 3.61 (d, J = 15.45 Hz, 1H) 3.72 (ddd, J = 11.51, 7.72, 4.10 Hz, 1H) 3.80 (ddd, J = 13.16, 6.70, 4.10 Hz, 1H) 3.87-3.98 (m, 2H) 4.00-4.08 (m, 1H) 4.26-4.33 (m, 1H) 4.46 (d, J = 15.45 Hz, 1H) 4.51-4.57 (m, 1H) 4.73 (d, J = 5.99 Hz, 2H) 7.38 (d, J = 7.57 Hz, 1H) 7.45-7.50 (m, 2H) 7.62-7.67 (m, 2H) 8.66 (d, J = 7.57 Hz, 1H) 10.19 (t, J = 6.15 Hz, 1H) |
| 9 | 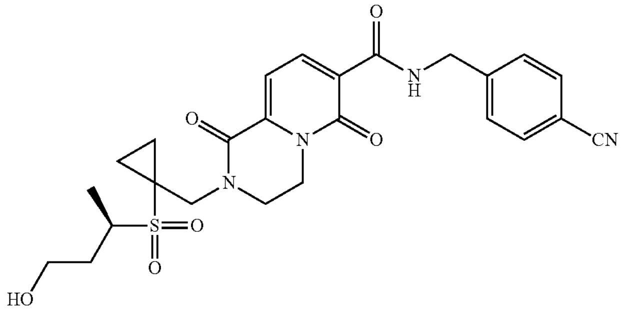 [SMILES: C[C@H](CCO)S(=O)(=O)C1(CN2CCn3c(ccc(C(=O)NCc4ccc(C#N)cc4)c3=O)C2=O)CC1] | MS m/z: 513 (M + 1), $^1$H NMR (500 MHz, $CDCl_3$-d) δ ppm 1.04-1.11 (m, 2H) 1.45 (d, J = 6.94 Hz, 3H) 1.57-1.61 (m, 2H) 1.68-1.80 (m, 2H) 2.29-2.40 (m, 1H) 3.62 (d, J = 15.13 Hz, 1H) 3.72 (ddd, J = 11.51, 7.72, 4.10 Hz, 1H) 3.80 (ddd, J = 13.08, 6.78, 4.10 Hz, 1H) 3.87-3.98 (m, 2H) 4.00-4.10 (m, 1H) 4.25-4.34 (m, 1H) 4.46 (d, J = 15.45 Hz, 1H) 4.54 (ddd, J = 14.19, 6.62, 4.10 Hz, 1H) 4.73 (d, J = 5.99 Hz, 2H) 7.38 (d, J = 7.57 Hz, 1H) 7.45-7.50 (m, 2H) 7.65 (d, J = 8.51 Hz, 2H) 8.66 (d, J = 7.57 Hz, 1H) 10.19 (t, J = 5.83 Hz, 1H) |

Example 10

N-(4-chlorobenzyl)-2-((1-((1-(hydroxymethyl)cyclopropyl)sulfonyl)cyclopropyl)methyl)-1,6-dioxo-2,3,4,6-tetrahydro-1H-pyrido[1,2-a]pyrazine-7-carboxamide 2-((1-((1-((benzyloxy)methyl)cyclopropyl)sulfonyl)cyclopropyl)methyl)-1,6-dioxo-2,3,4,6-tetrahydro-1H-pyrido[1,2-a]pyrazine-7-carboxylic acid (Ex-10A) was prepared from I-1 and 1-4 following a procedure analogous to that described for Ex-1A. Ex-10A was isolated as a yellow solid. LCMS m/z: 487 (M+1).

2-((1-((1-(hydroxymethyl)cyclopropyl)sulfonyl)cyclopropyl)methyl)-1,6-dioxo-2,3,4,6-tetrahydro-1H-pyrido[1,2-a]pyrazine-7-carboxylic acid (Ex-10B). Ex-10A (0.528 g, 1.085 mmol) was taken up in EtOH and treated with 1 drop of $H_2SO_4$. The resulting solution was stirred at reflux. Upon complete conversion of the acid, the reaction was concentrated under reduced pressure. The residue was taken up in AcOH and treated with Pd/C (0.06 g, 0.056 mmol). The atmosphere was exchanged for $H_2$, and the reaction mixture stirred for about 2 h. The reaction was filtered through a pad of Celite, and the pad was rinsed with EtOH. The filtrate was concentrated under reduced pressure. The residue was taken up in EtOH and treated with 2 M NaOH until the pH was basic. When the ester was consumed, the reaction mixture was concentrated under reduced pressure. The residue was taken up in $H_2O$ and washed with EtOAc. The aqueous layer was adjusted to pH 1 with 2 M HCl. The acidic aqueous layer was extracted with DCM. The combined DCM extracts were dried over sodium sulfate and concentrated under reduced pressure. Ex-10B was isolated as a yellow solid. LCMS m/z: 397 (M+1).

N-(4-chlorobenzyl)-2-((1-((1-(hydroxymethyl)cyclopropyl)sulfonyl)cyclopropyl)methyl)-1,6-dioxo-2,3,4,6-tetrahydro-1H-pyrido[1,2-a]pyrazine-7-carboxamide (Ex-10). To a solution of Ex-10B (0.1 g, 0.252 mmol), DIEA (0.088 mL, 0.505 mmol), and p-chlorobenzylamine (0.031 mL, 0.252 mmol) in DCM (1 mL) was added T3P® (50% in EtOAc, 0.083 mL, 0.277 mmol). The resulting mixture was stirred at RT. Upon complete conversion of the starting material, the reaction mixture was diluted with DCM and washed with 2 M HCl and saturated sodium bicarbonate. The organic layer was dried over sodium sulfate and concentrated under reduced pressure. The residue was purified by HPLC (20-60% (0.1% TFA/$H_2O$)/(0.1% TFA/MeCN)). The clean fractions were extracted with EtOAc, and the EtOAc extracts were dried over sodium sulfate and concentrated under reduced pressure. The residue was purified on $SiO_2$ (0-100% acetone/heptane) to afford Ex-10 as a white solid.

Other compounds in the table below were prepared following procedures analogous to those described for Ex-10.

| Example | Structure | Physical Data MS (m/z), $^1$H NMR |
|---|---|---|
| 10 | 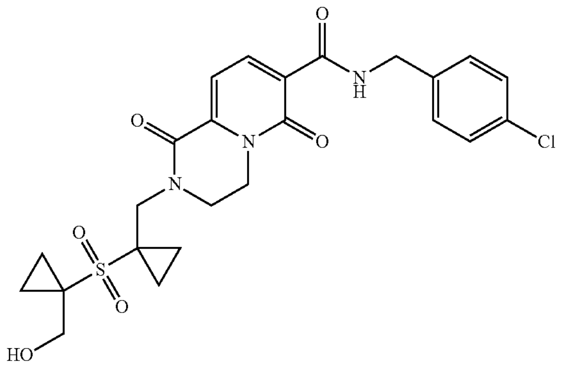 [SMILES: O=C(NCc1ccc(Cl)cc1)c1ccc2n(c1=O)CCN(CC1(S(=O)(=O)C3(CO)CC3)CC1)C2=O] | LCMS m/z: 520, (M + 1). $^1$H NMR (500 MHz, DMSO-d6) δ ppm 1.04-1.10 (m, 2H) 1.10-1.14 (m, 2H) 1.20-1.24 (m, 2H) 1.32-1.37 (m, 2H) 3.74-3.79 (m, 4H) 4.09 (s, 2H) 4.19-4.26 (m, 2H) 4.53 (d, J = 6.31 Hz, 2H) 7.20 (d, J = 7.57 Hz, 1H) 7.33 (d, J = 8.83 Hz, 2H) 7.40 (d, J = 8.51 Hz, 2H) 8.43 (d, J = 7.57 Hz, 1H) 10.11 (t, J = 6.46 Hz, 1H). |
| 11 | 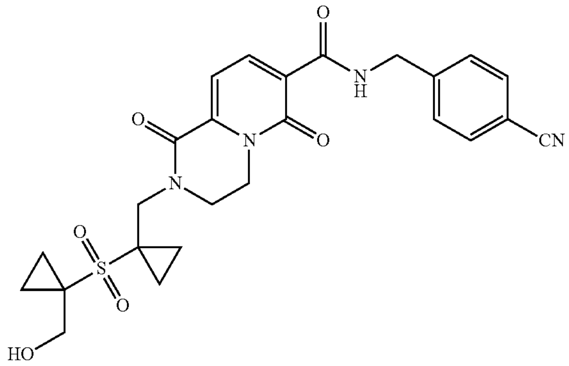 [SMILES: N#Cc1ccc(CNC(=O)c2ccc3n(c2=O)CCN(CC2(S(=O)(=O)C4(CO)CC4)CC2)C3=O)cc1] | MS m/z: 511, (M + 1). $^1$H NMR (500 MHz, DMSO-d6) δ ppm 1.07-1.12 (m, 2H) 1.12-1.17 (m, 2H) 1.22-1.27 (m, 2H) 1.34-1.40 (m, 2H) 3.75-3.84 (m, 4H) 4.09-4.14 (m, 2H) 4.22-4.29 (m, 2H) 4.65 (d, J = 6.15 Hz, 2H) 5.24 (t, J = 5.91 Hz, 1H) 7.21 (d, J = 7.45 Hz, 1H) 7.51 (m, J = 8.39 Hz, 2H) 7.79-7.85 (m, 2H) 8.44 (d, J = 7.57 Hz, 1H) 10.19 (t, J = 6.15 Hz, 1H) |
| 12 | 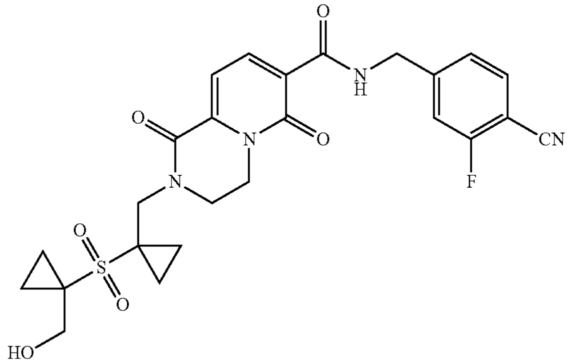 [SMILES: N#Cc1ccc(CNC(=O)c2ccc3n(c2=O)CCN(CC2(S(=O)(=O)C4(CO)CC4)CC2)C3=O)cc1F] | MS m/z: 529, (M + 1). $^1$H NMR (500 MHz, DMSO-d6) δ ppm 1.08-1.12 (m, 2H) 1.13-1.17 (m, 2H) 1.22-1.27 (m, 2H) 1.35-1.40 (m, 2H) 3.75-3.83 (m, 4H) 4.12 (s, 2H) 4.22-4.29 (m, 2H) 4.65 (d, J = 6.15 Hz, 2H) 5.24 (t, J = 5.91 Hz, 1H) 7.21 (d, J = 7.45 Hz, 1H) 7.33-7.38 (m, 1H) 7.45 (dd, J = 10.52, 1.06 Hz, 1H) 7.90 (dd, J = 7.92, 6.98 Hz, 1H) 8.43 (d, J = 7.57 Hz, 1H) 10.20 (s, 1H) |

Compounds in the table below were prepared from I-1 and either 1-5 or 1-6 following procedures analogous to those described for Ex-10.

| Example | Structure | Physical Data MS (m/z), $^1$H NMR |
|---|---|---|
| 13 | 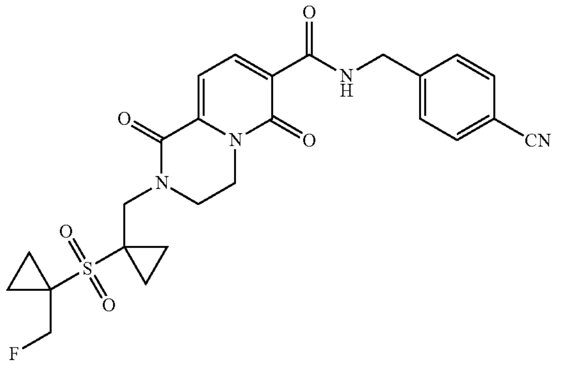 [SMILES: N#Cc1ccc(CNC(=O)c2ccc3n(c2=O)CCN(CC2(S(=O)(=O)C4(CF)CC4)CC2)C3=O)cc1] | MS m/z: 513, (M + 1). $^1$H NMR (500 MHz, DMSO-d6) δ ppm 1.19-1.24 (m, 2H) 1.26-1.31 (m, 2H) 1.41-1.50 (m, 4H) 3.74-3.80 (m, 2H) 4.08 (s, 2H) 4.23-4.28 (m, 2H) 4.65 (d, J = 6.15 Hz, 2H) 4.76 (d, J = 49.80 Hz, 1H) 7.22 (d, J = 7.57 Hz, 1H) 7.51 (m, J = 8.51 Hz, 2H) 7.79-7.85 (m, 2H) 8.44 (d, J = 7.57 Hz, 1H) 10.19 (t, J = 6.15 Hz, 1H) |
| 14 | 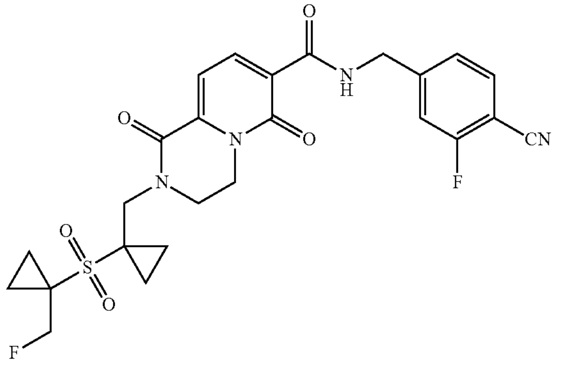 [SMILES: N#Cc1ccc(CNC(=O)c2ccc3n(c2=O)CCN(CC2(S(=O)(=O)C4(CF)CC4)CC2)C3=O)cc1F] | MS m/z: 531, (M + 1). $^1$H NMR (500 MHz, DMSO-d6) δ ppm 1.18-1.25 (m, 2H) 1.25-1.31 (m, 2H) 1.40-1.49 (m, 4H) 3.74-3.82 (m, 2H) 4.08 (s, 2H) 4.23-4.30 (m, 2H) 4.65 (d, J = 6.15 Hz, 2H) 4.76 (d, J = 47.53 Hz, 2H) 7.22 (d, J = 7.57 Hz, 1H) 7.36 (dd, J = 8.04, 1.42 Hz, 1H) 7.45 (d, J = 10.52 Hz, 1H) 7.91 (dd, J = 7.92, 6.98 Hz, 1H) 8.43 (d, J = 7.57 Hz, 1H) 10.20 (t, J = 6.15 Hz, 1H) |
| 15 | 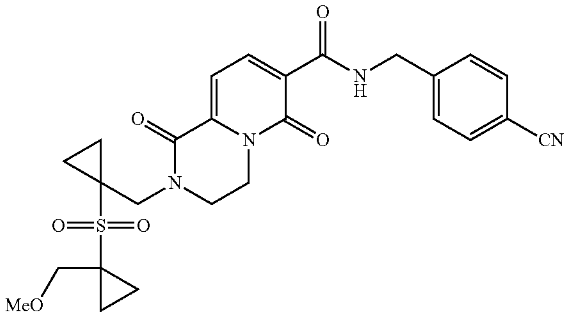 [SMILES: COCC1(S(=O)(=O)C2(CN3CCn4c(ccc(C(=O)NCc5ccc(C#N)cc5)c4=O)C3=O)CC2)CC1] | LCMS m/z: 525 (M + 1). $^1$H NMR (500 MHz, DMSO-d6) δ ppm 1.10-1.17 (m, 4H) 1.33 (td, J = 4.85, 2.25 Hz, 2H) 1.37 (td, J = 4.61, 2.13 Hz, 2H) 3.33 (s, 3H) 3.65 (s, 2H) 3.77 (t, J = 5.79 Hz, 2H) 4.09 (s, 2H) 4.26 (t, J = 5.67 Hz, 2H) 4.65 (d, J = 6.15 Hz, 2H) 7.22 (d, J = 7.57 Hz, 1H) 7.51 (m, J = 8.51 Hz, 2H) 7.80-7.84 (m, 2H) 8.44 (d, J = 7.57 Hz, 1H) 10.19 (t, J = 6.09 Hz, 1H). |

Example 16/17

2-((1-((1-(tert-butoxycarbonyl)azetidin-3-yl)sulfonyl)cyclopropyl)methyl)-1,6-dioxo-2,3,4,6-tetrahydro-1H-pyrido[1,2-a]pyrazine-7-carboxylic acid (Ex-16A) was prepared from I-1 and 1-7 following a procedure analogous to that described for Ex-1A. Ex-16A was isolated as a brown oil. LCMS m/z: 482 (M+1).

tert-butyl 3-((1-((7-((4-cyano-3-fluorobenzyl)carbamoyl)-1,6-dioxo-3,4-dihydro-1H-pyrido[1,2-a]pyrazin-2(6H)-yl)methyl)cyclopropyl)sulfonyl)azetidine-1-carboxylate (Ex-16B) was prepared from Ex-16A following a procedure analogous to that described for Ex-10. Ex-16B was isolated as a yellow oil. MS m/z: 614 (M+1).

2-((1-(azetidin-3-ylsulfonyl)cyclopropyl)methyl)-N-(4-cyano-3-fluorobenzyl)-1,6-dioxo-2,3,4,6-tetrahydro-1H-pyrido[1,2-a]pyrazine-7-carboxamide (Ex-16). To a solution of Ex-16B (0.163 g, 0.266 mmol) in DCM (5.0 mL) was added TFA (1 mL). The resulting mixture was stirred at RT. After 30 min, the reaction mixture was concentrated under reduced pressure. The residue was taken up in DCM and washed with saturated sodium bicarbonate. The aqueous layer was back extracted with DCM. The combined organic layers were dried over sodium sulfate and concentrated under reduced pressure. The crude product was purified by SFC (PPU column, $CO_2$/MeOH 80 mL/min). Ex-16 was isolated as an off-white solid.

N-(4-cyano-3-fluorobenzyl)-2-((1-((1-methylazetidin-3-yl)sulfonyl)cyclopropyl)methyl)-1,6-dioxo-2,3,4,6-tetrahydro-1H-pyrido[1,2-a]pyrazine-7-carboxamide (Ex-17). To a solution of Ex-16 (0.068 g, 0.132 mmol) in DCE (1 mL) were added formaldehyde (0.015 mL, 0.199 mmol) followed by sodium triacetoxyborohydride (0.042 g, 0.199 mmol).

The resulting mixture was stirred at RT overnight. Additional formaldehyde (0.015 mL, 0.199 mmol) and sodium triacetoxyborohydride (0.042 g, 0.199 mmol) were added until complete consumption of starting material. The reaction mixture was diluted with DCM and washed with saturated sodium bicarbonate. The organic layer was dried over sodium sulfate and concentrated under reduced pressure. The crude product was purified by HPLC (SunFire column, $H_2O$/ACN 0.1% TFA). Ex-17 was isolated as a white solid.

Other compounds in the table below were prepared following procedures analogous to those described for Ex-16 and Ex-17.

| Example | Structure | Physical Data MS (m/z), $^1$H NMR |
|---|---|---|
| 16 | 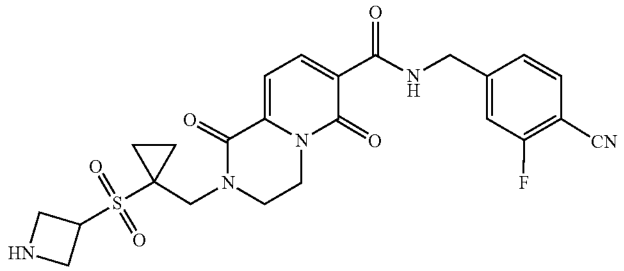 [SMILES: N#Cc1ccc(CNC(=O)c2ccc3n(c2=O)CCN(CC2(S(=O)(=O)C4CNC4)CC2)C3=O)cc1F] | MS m/z: 514 (M + 1), $^1$H NMR (500 MHz, DMSO-d6) δ ppm 1.13-1.18 (m, 2H) 1.26-1.32 (m, 2H) 3.60 (t, J = 8.33 Hz, 2H) 3.75-3.85 (m, 4H) 3.95 (s, 2H) 4.23-4.30 (m, 2H) 4.66 (d, J = 6.15 Hz, 2H) 4.80 (s, 1H) 7.22 (d, J = 7.57 Hz, 1H) 7.36 (dd, J = 8.04, 1.42 Hz, 1H) 7.45 (d, J = 10.40 Hz, 1H) 7.91 (dd, J = 7.92, 6.98 Hz, 1H) 8.44 (d, J = 7.57 Hz, 1H) 10.20 (t, J = 6.21 Hz, 1H) |
| 17 | 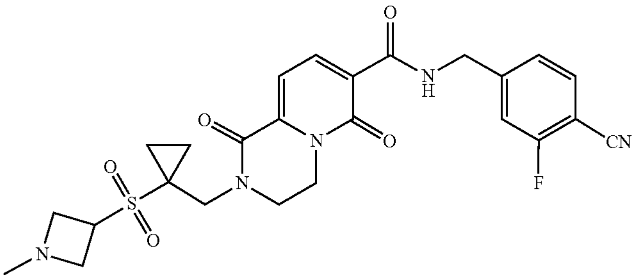 [SMILES: CN1CC(S(=O)(=O)C2(CN3CCn4c(ccc(C(=O)NCc5ccc(C#N)c(F)c5)c4=O)C3=O)CC2)C1] | MS m/z: 528, (M + 1). $^1$H NMR (400 MHz, DMSO-d6) δ ppm 1.23 (br. s., 2H) 1.39 (br. s., 2H) 2.84 (br. s., 3H) 3.74-3.79 (m, 2H) 3.96 (s, 2H) 4.12-4.21 (m, 1H) 4.21-4.29 (m, 2H) 4.29-4.52 (m, 3H) 4.62 (d, J = 6.11 Hz, 2H) 4.89 (br. s., 1H) 7.18 (d, J = 7.58 Hz, 1H) 7.32 (d, J = 7.48 Hz, 1H) 7.41 (d, J = 10.51 Hz, 1H) 7.83-7.90 (m, 1H) 8.42 (d, J = 7.53 Hz, 1H) 10.15 (t, J = 6.26 Hz, 1H) |
| 18 | 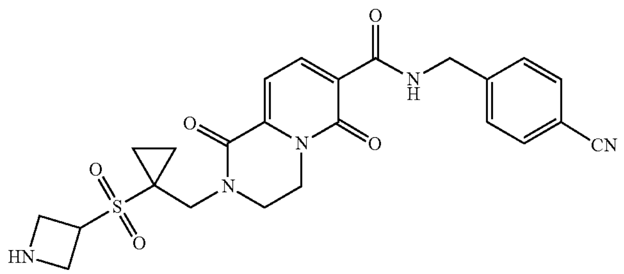 [SMILES: N#Cc1ccc(CNC(=O)c2ccc3n(c2=O)CCN(CC2(S(=O)(=O)C4CNC4)CC2)C3=O)cc1] | MS m/z: 496 (M + 1), $^1$H NMR (500 MHz, DMSO-d6) δ ppm 1.12-1.18 (m, 2H) 1.26-1.33 (m, 2H) 3.60 (t, J = 8.16 Hz, 2H) 3.76-3.85 (m, 4H) 3.94-3.97 (m, 2H) 4.23-4.29 (m, 2H) 4.65 (d, J = 6.03 Hz, 2H) 4.80 (t, J = 7.86 Hz, 1H) 7.22 (d, J = 7.57 Hz, 1H) 7.51 (m, J = 8.51 Hz, 2H) 7.79-7.85 (m, 2H) 8.45 (d, J = 7.57 Hz, 1H) 10.19 (t, J = 6.09 Hz, 1H) |
| 19 | 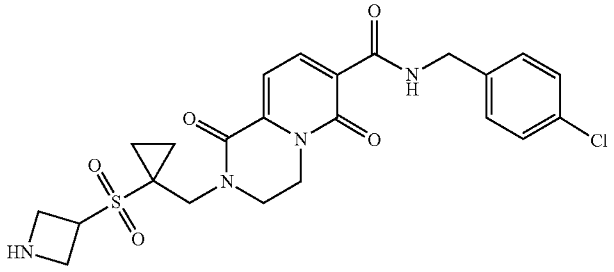 [SMILES: O=C(NCc1ccc(Cl)cc1)c1ccc2n(c1=O)CCN(CC1(S(=O)(=O)C3CNC3)CC1)C2=O] | MS m/z: 505 (M + 1), $^1$H NMR (500 MHz, DMSO-d6) δ ppm 1.12-1.17 (m, 2H) 1.26-1.31 (m, 2H) 3.60 (t, J = 8.45 Hz, 2H) 3.76-3.80 (m, 2H) 3.80-3.84 (m, 2H) 3.95 (s, 2H) 4.22-4.27 (m, 2H) 4.55 (d, J = 6.03 Hz, 2H) 4.75-4.84 (m, 1H) 7.22 (d, J = 7.57 Hz, 1H) 7.33-7.38 (m, 2H) 7.39-7.43 (m, 2H) 8.46 (d, J = 7.57 Hz, 1H) 10.12 (t, J = 6.03 Hz, 1H) |
| 20 | 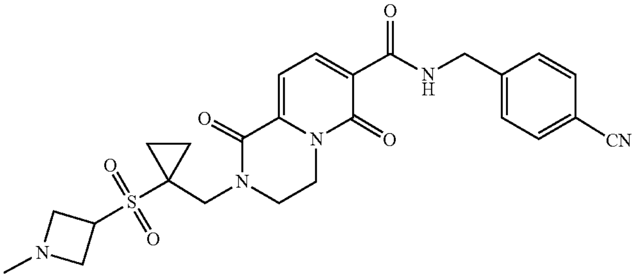 [SMILES: CN1CC(S(=O)(=O)C2(CN3CCn4c(ccc(C(=O)NCc5ccc(C#N)cc5)c4=O)C3=O)CC2)C1] | MS m/z: 510 (M + 1), $^1$H NMR (500 MHz, DMSO-d6) δ ppm 1.27 (br. s., 2H) 1.39-1.46 (m, 2H) 2.88 (s, 3H) 3.76-3.83 (m, 4H) 4.00 (s, 2H) 4.25-4.30 (m, 2H) 4.65 (d, J = 6.03 Hz, 2H) 4.88-4.99 (m, 1H) 7.22 (d, J = 7.57 Hz, 1H) 7.51 (m, J = 8.51 Hz, 2H) 7.80-7.85 (m, 2H) 8.47 (d, J = 7.57 Hz, 1H) 10.18 (t, J = 6.09 Hz, 2H) |

Compounds in the table below were prepared from I-1 and 1-8 following procedures analogous to those described for Ex-1.

| Example | Structure | Physical Data MS (m/z), ¹H NMR |
| --- | --- | --- |
| 21 | 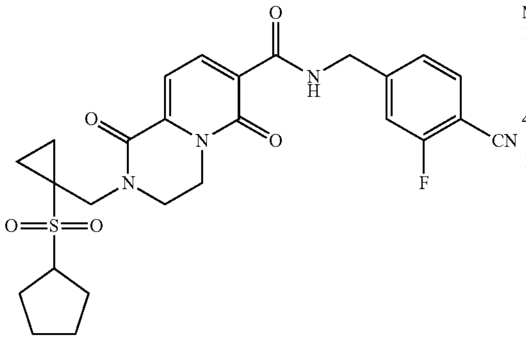 | MS m/z: 527 (M + 1), ¹H NMR (500 MHz, DMSO-d6) δ ppm 1.15-1.21 (m, 2H) 1.27-1.33 (m, 2H) 1.58-1.71 (m, 4H) 1.82-1.91 (m, 2H) 1.97-2.06 (m, 2H) 3.78-3.85 (m, 2H) 4.02-4.07 (m, 2H) 4.07-4.12 (m, 1H) 4.24-4.30 (m, 2H) 4.66 (d, J = 6.15 Hz, 2H) 7.22 (d, J = 7.33 Hz, 1H) 7.34-7.38 (m, 1H) 7.45 (dd, J = 10.64, 1.18 Hz, 1H) 7.91 (dd, J = 7.92, 6.98 Hz, 1H) 8.44 (d, J = 7.57 Hz, 1H) 10.20 (t, J = 6.15 Hz, 1H) |
| 22 | 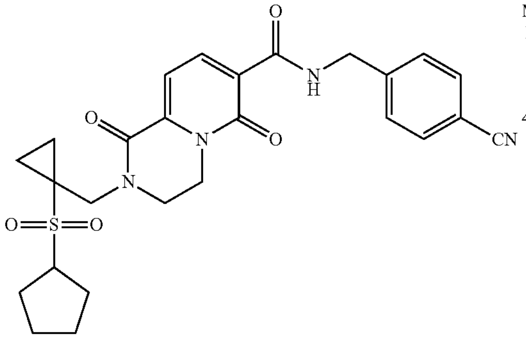 | MS m/z: 509 (M + 1), ¹H NMR (500 MHz, DMSO-d6) δ ppm 1.15-1.20 (m, 2H) 1.27-1.32 (m, 2H) 1.57-1.73 (m, 4H) 1.82-1.91 (m, 2H) 1.97-2.07 (m, 2H) 3.78-3.84 (m, 2H) 4.05 (s, 2H) 4.06-4.14 (m, 1H) 4.24-4.29 (m, 2H) 4.65 (d, J = 6.15 Hz, 2H) 7.22 (d, J = 7.45 Hz, 1H) 7.51 (m, J = 8.51 Hz, 2H) 7.79-7.84 (m, 2H) 8.42-8.47 (m, 1H) 10.18 (t, J = 6.15 Hz, 1H) |

Compounds in the table below were prepared from I-1 and 1-9 following procedures analogous to those described for Ex-4.

| Example | Structure | Physical Data MS (m/z), ¹H NMR |
| --- | --- | --- |
| 23 | 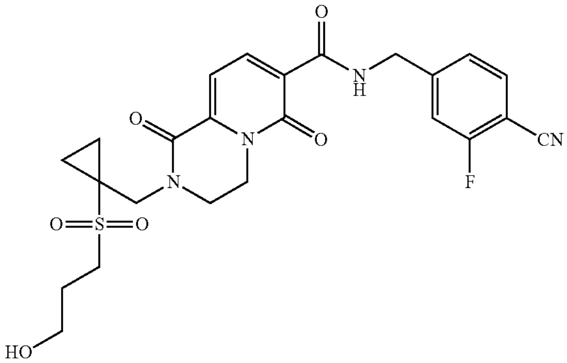 [SMILES: N#Cc1ccc(CNC(=O)c2ccc3n(c2=O)CCN(CC2(S(=O)(=O)CCCO)CC2)C3=O)cc1F] | MS m/z: 516 (M + 1), ¹H NMR (500 MHz, DMSO-d6) δ ppm 1.16-1.21 (m, 2H) 1.27-1.32 (m, 2H) 1.80-1.88 (m, 2H) 3.34-3.38 (m, 2H) 3.50 (q, J = 6.03 Hz, 2H) 3.78-3.84 (m, 2H) 4.02 (s, 2H) 4.24-4.30 (m, 2H) 4.65 (d, J = 6.15 Hz, 2H) 4.70 (t, J = 5.26 Hz, 1H) 7.21 (d, J = 7.57 Hz, 1H) 7.35 (dd, = 8.04, 1.30 Hz, 1H) 7.44 (d, J = 10.52 Hz, 1H) 7.89 (dd, J = 7.86, 7.03 Hz, 1H) 8.43 (d, J = 7.57 Hz, 1H) 10.19 (t, J = 6.15 Hz, 1H) |

-continued

| Example | Structure | Physical Data MS (m/z), $^1$H NMR |
|---|---|---|
| 24 | 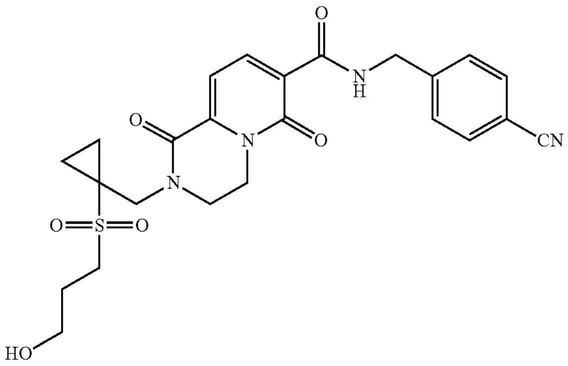 [SMILES: N#Cc1ccc(CNC(=O)c2ccc3n(c2=O)CCN(CC2(S(=O)(=O)CCCO)CC2)C3=O)cc1] | MS m/z: 499, (M + 1), $^1$H NMR (500 MHz, DMSO-d6) δ ppm 1.17-1.21 (m, 2H) 1.27-1.32 (m, 2H) 1.80-1.88 (m, 2H) 3.50 (q, J = 6.03 Hz, 2H) 3.78-3.82 (m, 2H) 4.02 (s, 2H) 4.24-4.29 (m, 2H) 4.64 (d, J = 6.03 Hz, 2H) 4.70 (t, J = 5.26 Hz, 1H) 7.22 (d, J = 7.45 Hz, 1H) 7.50 (m, J = 8.51 Hz, 2H) 7.79-7.83 (m, 2H) 8.44 (d, J = 7.45 Hz, 1H) 10.18 (t, J = 6.15 Hz, 1H) |
| 25 | 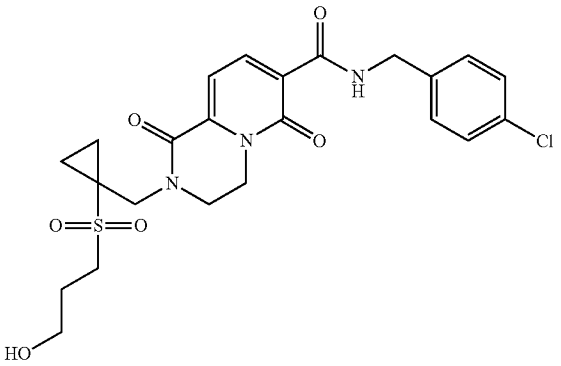 [SMILES: O=C(NCc1ccc(Cl)cc1)c1ccc2n(c1=O)CCN(CC1(S(=O)(=O)CCCO)CC1)C2=O] | MS m/z: 508 (M + 1), $^1$H NMR (500 MHz, DMSO-d6) δ ppm 1.15-1.21 (m, 2H) 1.27-1.32 (m, 2H) 1.79-1.88 (m, 2H) 3.34-3.38 (m, 2H) 3.50 (q, J = 6.15 Hz, 2H) 3.77-3.83 (m, 2H) 4.02 (s, 2H) 4.21-4.28 (m, 2H) 4.54 (d, J = 6.03 Hz, 2H) 4.70 (t, J = 5.26 Hz, 1H) 7.22 (d, J = 7.57 Hz, 1H) 7.32-7.37 (m, 2H) 7.38-7.42 (m, 2H) 8.45 (d, J = 7.45 Hz, 1H) 10.11 (t, J = 6.03 Hz, 1H) |

Compounds in the table below were prepared from I-1 and I-10 following procedures analogous to those described for Ex-1.

| Example | Structure | Physical Data MS (m/z), $^1$H NMR |
|---|---|---|
| 26 | 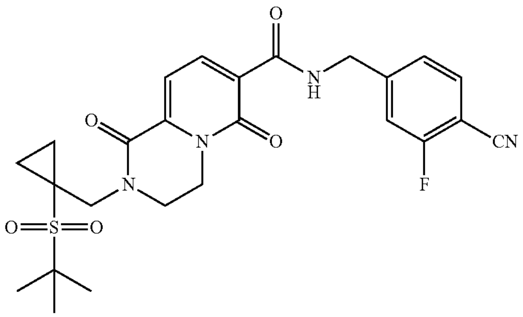 [SMILES: CC(C)(C)S(=O)(=O)C1(CN2CCn3c(ccc(C(=O)NCc4ccc(C#N)c(F)c4)c3=O)C2=O)CC1] | MS m/z: 515 (M + 1). $^1$H NMR (500 MHz, DMSO-d6) δ ppm 1.11-1.15 (m, 2H) 1.33-1.38 (m, 2H) 1.42 (s, 9 H) 3.74-3.82 (m, 2H) 4.12 (s, 2H) 4.23-4.29 (m, 2H) 4.64 (d, J = 6.07 Hz, 2H) 7.20 (d, J = 7.55 Hz, 1H) 7.35 (d, J = 8.13 Hz, 1H) 7.44 (d, J = 10.41 Hz, 1H) 7.90 (t, J = 7.44 Hz, 1H) 8.42 (d, J = 7.55 Hz, 1H) 10.19 (t, J = 6.18 Hz, 1H) |

-continued

| Example | Structure | Physical Data MS (m/z), $^1$H NMR |
|---|---|---|
| 27 | 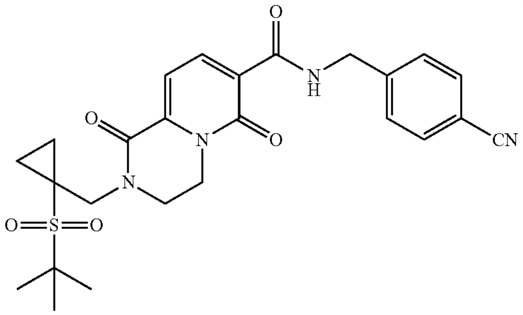 [SMILES: CC(C)(C)S(=O)(=O)C1(CN2CCn3c(ccc(C(=O)NCc4ccc(C#N)cc4)c3=O)C2=O)CC1] | MS m/z: 497 (M + 1), $^1$H NMR (500 MHz, DMSO-d6) δ ppm 1.09-1.17 (m, 2H) 1.32-1.38 (m, 2H) 1.42 (s, 9 H) 3.75-3.81 (m, 2H) 4.12 (s, 2H) 4.23-4.28 (m, 2H) 4.64 (d, J = 6.07 Hz, 2H) 7.20 (d, J = 7.55 Hz, 1H) 7.50 (m, J = 8.13 Hz, 2H) 7.81 (m, J = 8.13 Hz, 2H) 8.43 (d, J = 7.44 Hz, 1H) 10.18 (t, J = 6.12 Hz, 1H) |

Compounds in the table below were prepared from I-1 and I-11 following procedures analogous to those described for Ex-10.

| Example | Structure | Physical Data MS (m/z), $^1$H NMR |
|---|---|---|
| 28 | 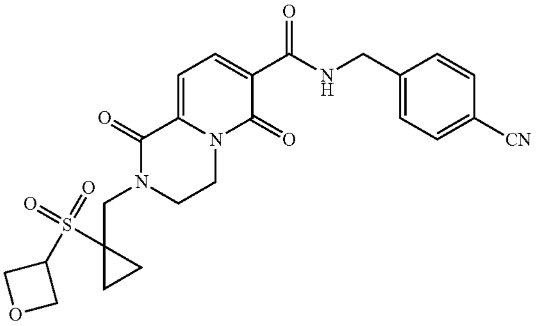 [SMILES: N#Cc1ccc(CNC(=O)c2ccc3n(c2=O)CCN(CC2(S(=O)(=O)C4COC4)CC2)C3=O)cc1] | MS m/z: 497, (M + 1). $^1$H NMR (400 MHz, $CDCl_3$) δ ppm 1.03-1.10 (m, 2H) 1.59-1.65 (m, 2H) 3.83 (t, J = 5.65 Hz, 2H) 3.89 (s, 2H) 4.38 (t, J = 5.65 Hz, 2H) 4.70 (d, J = 5.92 Hz, 2H) 4.87-5.03 (m, 5H) 7.35 (d, J = 7.48 Hz, 1H) 7.45 (m, J = 7.97 Hz, 2H) 7.62 (m, J = 8.02 Hz, 2H) 8.63 (d, J = 7.48 Hz, 1H) 10.15 (t, J = 5.43 Hz, 1H) |
| 29 | 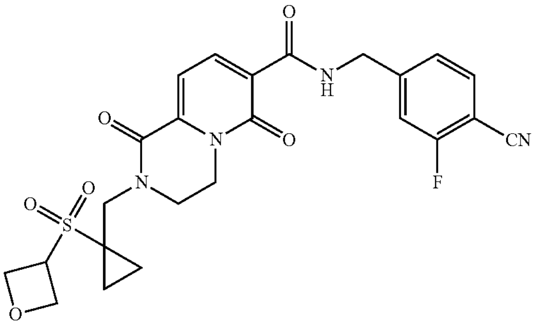 [SMILES: N#Cc1ccc(CNC(=O)c2ccc3n(c2=O)CCN(CC2(S(=O)(=O)C4COC4)CC2)C3=O)cc1F] | MS m/z: 515 (M + 1), $^1$H NMR (400 MHz, $CDCl_3$) δ ppm 1.04-1.11 (m, 2H) 1.63 (s, 2H) 3.84 (t, J = 5.67 Hz, 2H) 3.90 (s, 2H) 4.39 (t, J = 5.26 Hz, 2H) 4.69 (d, J = 5.97 Hz, 2H) 4.88-5.04 (m, 5H) 7.18-7.23 (m, 2H) 7.36 (d, J = 7.43 Hz, 1H) 7.58 (t, J = 7.21 Hz, 1H) 8.63 (d, J = 7.48 Hz, 1H) 10.15-10.26 (m, 1H) |
| 30 | 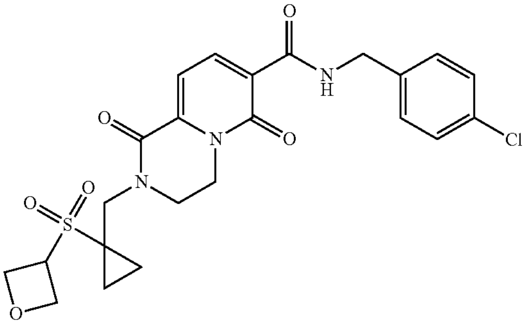 [SMILES: O=C(NCc1ccc(Cl)cc1)c1ccc2n(c1=O)CCN(CC1(S(=O)(=O)C3COC3)CC1)C2=O] | MS m/z: 506 (M + 1), $^1$H NMR (400 MHz, $CDCl_3$) δ ppm 1.03-1.09 (m, 2H) 1.59-1.65 (m, 2H) 3.82 (t, J = 5.43 Hz, 2H) 3.89 (s, 2H) 4.36 (t, J = 5.75 Hz, 2H) 4.61 (d, J = 5.77 Hz, 2H) 4.88-5.03 (m, 5H) 7.29 (s, 4H) 7.34 (d, J = 7.38 Hz, 1H) 8.64 (d, J = 7.63 Hz, 1H) 10.02 (t, J = 7.07 Hz, 1H) |

Compounds in the table below were prepared from I-1 and 1-12 following procedures analogous to those described for Ex-1.

| Example | Structure | Physical Data MS (m/z), $^1$H NMR |
|---|---|---|
| 31 | 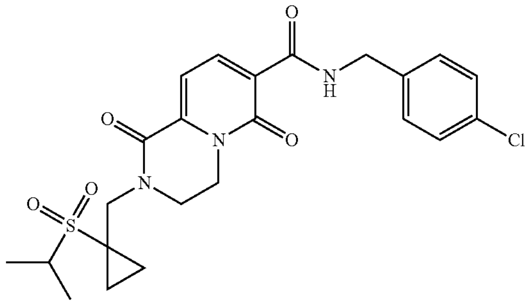 [SMILES: CC(C)S(=O)(=O)C1(CN2CCn3c(ccc(C(=O)NCc4ccc(Cl)cc4)c3=O)C2=O)CC1] | MS m/z: 492, (M + 1). $^1$H NMR (400 MHz, DMSO-d6) δ ppm 1.12-1.19 (m, 2H) 1.24 (d, J = 6.65 Hz, 8 H) 3.73-3.87 (m, 3H) 3.99 (s, 2H) 4.22 (t, J = 5.65 Hz, 2H) 4.52 (d, J = 5.97 Hz, 2H) 7.19 (d, J = 7.63 Hz, 1H) 7.32 (m, J = 8.22 Hz, 2H) 7.38 (m, J = 8.27 Hz, 2H) 8.42 (d, J = 7.43 Hz, 1H) 10.08 (t, J = 5.92 Hz, 1H) |
| 32 | 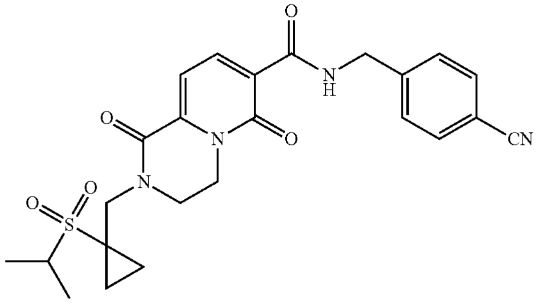 [SMILES: CC(C)S(=O)(=O)C1(CN2CCn3c(ccc(C(=O)NCc4ccc(C#N)cc4)c3=O)C2=O)CC1] | MS m/z: 483 (M + 1). $^1$H NMR (400 MHz, DMSO-d6) δ ppm 1.16 (br. s., 2H) 1.24 (d, J = 6.60 Hz, 7 H) 3.75-3.88 (m, 3H) 4.00 (s, 2H) 4.23 (br. s., 2H) 4.62 (d, J = 5.87 Hz, 2H) 7.19 (d, J = 7.53 Hz, 1H) 7.48 (d, J = 8.27 Hz, 2H) 7.78 (d, J = 7.83 Hz, 2H) 8.41 (d, J = 7.58 Hz, 1H) 10.15 (s, 1H) |
| 33 | 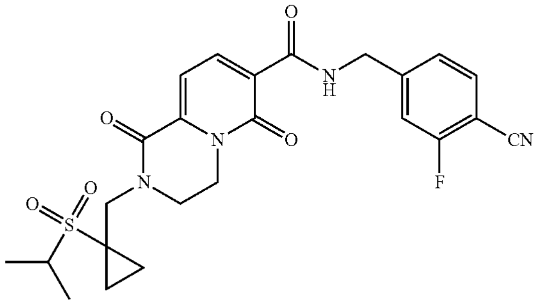 [SMILES: CC(C)S(=O)(=O)C1(CN2CCn3c(ccc(C(=O)NCc4ccc(C#N)c(F)c4)c3=O)C2=O)CC1] | MS m/z: 501 (M + 1), $^1$H NMR (400 MHz, DMSO-d6) δ ppm 1.16 (br. s., 2H) 1.24 (d, J = 6.46 Hz, 8 H) 3.75-3.88 (m, 3H) 4.00 (s, 2H) 4.24 (br. s., 2H) 4.62 (d, J = 6.11 Hz, 2H) 7.18 (d, J = 7.24 Hz, 1H) 7.32 (d, J = 8.22 Hz, 1H) 7.42 (d, J = 10.71 Hz, 1H) 7.87 (t, J = 7.58 Hz, 1H) 8.40 (d, J = 7.29 Hz, 1H) 10.16 (t, J = 5.97 Hz, 1H) |

Compounds in the table below were prepared from I-1 and 1-13 following procedures analogous to those described for Ex-1.

| Example | Structure | Physical Data MS (m/z), $^1$H NMR |
|---|---|---|
| 34 | 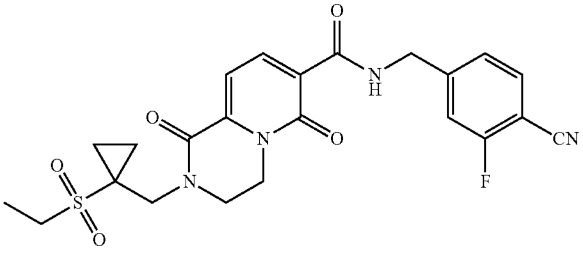 [SMILES: CCS(=O)(=O)C1(CN2CCn3c(ccc(C(=O)NCc4ccc(C#N)c(F)c4)c3=O)C2=O)CC1] | MS m/z: 487, (M + 1). $^1$H NMR (500 MHz, DMSO-d6) δ ppm 1.14-1.21 (m, 2H) 1.24 (t, J = 7.44 Hz, 3H) 1.27-1.32 (m, 2H) 3.77-3.85 (m, 2H) 4.02 (s, 2H) 4.24-4.30 (m, 2H) 4.65 (d, J = 6.18 Hz, 2H) 7.21 (d, J = 7.55 Hz, 1H) 7.35 (d, J = 8.01 Hz, 1H) 7.44 (d, J = 10.53 Hz, 1H) 7.89 (t, J = 7.44 Hz, 1H) 8.43 (d, J = 7.55 Hz, 1H) 10.19 (t, J = 6.12 Hz, 1H) |

-continued

| Example | Structure | Physical Data MS (m/z), ¹H NMR |
|---|---|---|
| 35 | 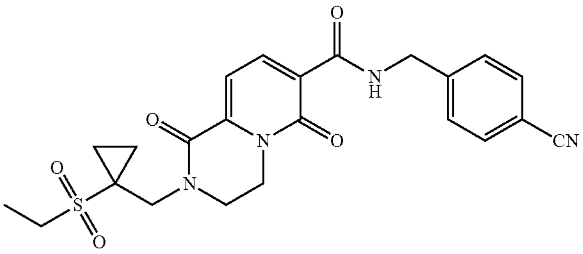 [SMILES: CCS(=O)(=O)C1(CN2CCn3c(ccc(C(=O)NCc4ccc(C#N)cc4)c3=O)C2=O)CC1] | MS m/z: 469, (M + 1). ¹H NMR (500 MHz, DMSO-d6) δ ppm 1.15-1.21 (m, 2H) 1.24 (t, J = 7.44 Hz, 3H) 1.26-1.33 (m, 2H) 3.77-3.84 (m, 2H) 4.02 (s, 2H) 4.22-4.28 (m, 2H) 4.64 (d, J = 6.07 Hz, 2H) 7.22 (d, J = 7.55 Hz, 1H) 7.50 (m, J = 8.13 Hz, 2H) 7.81 (m, J = 8.13 Hz, 2H) 8.44 (d, J = 7.55 Hz, 1H) 10.18 (t, J = 6.07 Hz, 1H) |
| 36 | 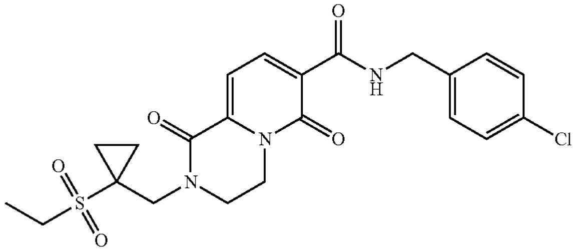 [SMILES: CCS(=O)(=O)C1(CN2CCn3c(ccc(C(=O)NCc4ccc(Cl)cc4)c3=O)C2=O)CC1] | MS m/z: 478, (M + 1). ¹H NMR (500 MHz, DMSO-d6) δ ppm 1.14-1.19 (m, 2H) 1.24 (t, J = 7.44 Hz, 3H) 1.27-1.31 (m, 2H) 3.76-3.83 (m, 2H) 4.02 (s, 2H) 4.21-4.27 (m, 2H) 4.54 (d, J = 5.95 Hz, 2H) 7.22 (d, J = 7.55 Hz, 1H) 7.35 (m, J = 8.47 Hz, 2H) 7.40 (m, J = 8.47 Hz, 2H) 8.44 (d, J = 7.55 Hz, 1H) 10.11 (t, J = 6.01 Hz, 1H) |

Compounds in the table below were prepared from I-1 and 1-14 following procedures analogous to those described for Ex-1.

| Example | Structure | Physical Data MS (m/z), ¹H NMR |
|---|---|---|
| 37 | 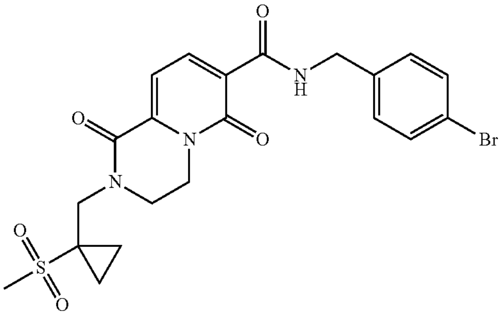 [SMILES: CS(=O)(=O)C1(CN2CCn3c(ccc(C(=O)NCc4ccc(Br)cc4)c3=O)C2=O)CC1] | MS m/z: 509 (M + 1), 510 (M + 3). ¹H NMR (400 MHz, $CDCl_3$) δ ppm 1.07-1.13 (m, 2H) 1.60-1.66 (m, 2H) 3.05-3.09 (m, 3H) 3.81-3.87 (m, 2H) 3.98-4.03 (m, 2H) 4.33-4.40 (m, 2H) 4.59 (d, J = 5.87 Hz, 2H) 7.23 (d, J = 8.36 Hz, 2H) 7.35 (d, J = 7.48 Hz, 1H) 7.45 (d, J = 8.36 Hz, 2H) 8.63 (d, J = 7.48 Hz, 1H) 10.04 (br. s., 1H) |
| 38 | 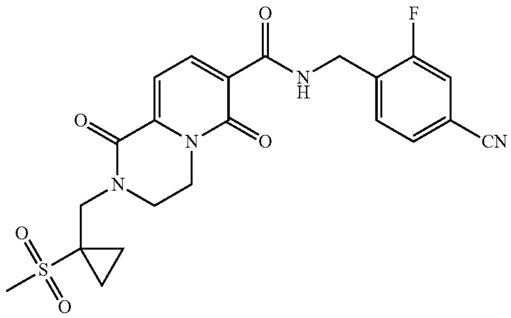 [SMILES: CS(=O)(=O)C1(CN2CCn3c(ccc(C(=O)NCc4ccc(C#N)cc4F)c3=O)C2=O)CC1] | MS m/z: 473 (M + 1). ¹H NMR (400 MHz, $CDCl_3$) δ ppm 1.07-1.14 (m, 2H) 1.60-1.66 (m, 2H) 3.08 (s, 3H) 3.82-3.90 (m, 2H) 4.01 (s, 2H) 4.36-4.42 (m, 2H) 4.73 (d, J = 6.06 Hz, 2H) 7.32-7.38 (m, 2H) 7.42 (d, J = 7.87 Hz, 1H) 7.52 (t, J = 7.56 Hz, 1H) 8.61 (d, J = 7.53 Hz, 1H) 10.16 (1, J = 6.16 Hz, 1H) |

-continued

| Example | Structure | Physical Data MS (m/z), $^1$H NMR |
|---|---|---|
| 39 | 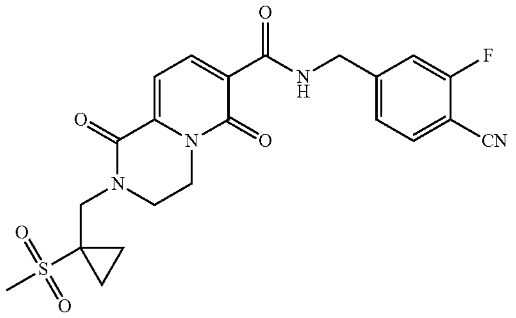 [SMILES: CS(=O)(=O)C1(CN2CCn3c(ccc(C(=O)NCc4ccc(C#N)c(F)c4)c3=O)C2=O)CC1] | MS m/z: 473 (M + 1). $^1$H NMR (400 MHz, $CDCl_3$) δ ppm 1.10 (s, 2H) 1.63 (s, 2H) 3.08 (s, 3H) 3.87 (t, J = 5.82 Hz, 2H) 4.02 (s, 2H) 4.39 (t, J = 5.67 Hz, 2H) 4.69 (d, J = 6.16 Hz, 2H) 7.17-7.23 (m, 2H) 7.37 (d, J = 7.53 Hz, 1H) 7.57 (t, J = 7.29 Hz, 1H) 8.63 (d, J = 7.53 Hz, 1H) 10.22 (t, J = 6.02 Hz, 1H) |
| 40 | 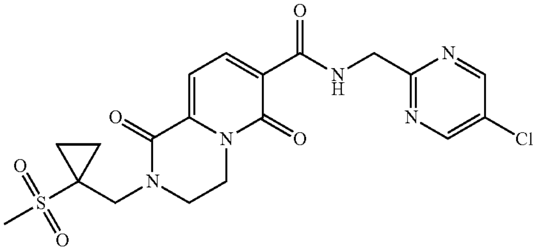 [SMILES: CS(=O)(=O)C1(CN2CCn3c(ccc(C(=O)NCc4ncc(Cl)cn4)c3=O)C2=O)CC1] | MS m/z: 466, (M + 1). $^1$H NMR (400 MHz, $CDCl_3$) δ ppm 1.05-1.16 (m, 2H) 1.60-1.64 (m, 2H) 3.07 (s, 3H) 3.79-3.88 (m, 2H) 4.01 (s, 2H) 4.34-4.48 (m, 2H) 4.92 (d, J = 5.18 Hz, 2H) 7.35 (d, J = 7.48 Hz, 1H) 8.63 (d, J = 7.53 Hz, 1H) 8.70 (s, 2H) 10.51 (br. s., 1H) |
| 41 | 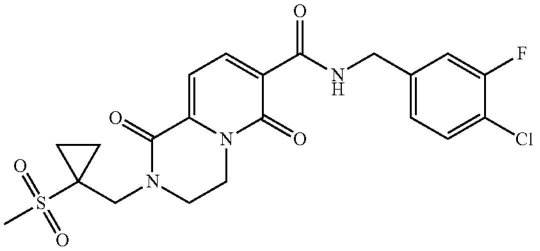 [SMILES: CS(=O)(=O)C1(CN2CCn3c(ccc(C(=O)NCc4ccc(Cl)c(F)c4)c3=O)C2=O)CC1] | MS m/z: 482, (M + 1). $^1$H NMR (400 MHz, $CDCl_3$) δ ppm 1.07-1.15 (m, 2H) 1.60-1.66 (m, 2H) 3.07 (s, 3H) 3.81-3.91 (m, 2H) 4.01 (s, 2H) 4.33-4.42 (m, 2H) 4.61 (d, J = 5.97 Hz, 2H) 7.07 (d, J = 8.22 Hz, 1H) 7.14 (dd, J = 9.78, 1.76 Hz, 1H) 7.29-7.39 (m, 2H) 8.63 (d, J = 7.53 Hz, 1H) 10.10 (br. s., 1H) |
| 42 | 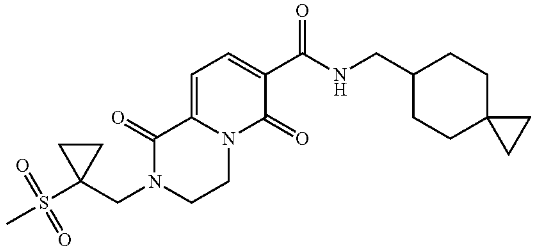 [SMILES: CS(=O)(=O)C1(CN2CCn3c(ccc(C(=O)NCC4CCC5(CC4)CC5)c3=O)C2=O)CC1] | MS m/z: 462 (M + 1). $^1$H NMR (400 MHz, $CDCl_3$) δ ppm 0.18 (br. s., 2H) 0.25 (br. s., 2H) 0.89 (d, J = 11.15 Hz, 2H) 1.10 (br. s., 1H) 1.20 (d, J = 10.81 Hz, 2H) 1.58-1.79 (m, 8 H) 3.07 (br. s., 3H) 3.34 (br. s., 2H) 3.84 (br. s., 2H) 4.00 (br. s., 2H) 4.38 (br. s., 2H) 7.33 (d, J = 6.70 Hz, 1H) 8.61 (d, J = 6.06 Hz, 1H) 9.72 (br. s., 1H) |
| 43 | 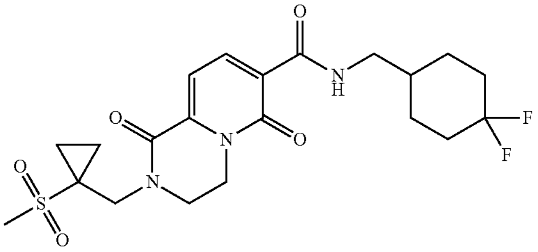 [SMILES: CS(=O)(=O)C1(CN2CCn3c(ccc(C(=O)NCC4CCC(F)(F)CC4)c3=O)C2=O)CC1] | MS m/z: 472 (M + 1). $^1$H NMR (400 MHz, $CDCl_3$) δ ppm 1.10 (br. s., 2H) 1.38 (br. s., 2H) 1.60 (br. s., 5H) 1.85 (br. s., 2H) 2.10 (br. s., 1H) 2.16 (br. s., 1H) 3.07 (br. s., 3H) 3.36 (br. s., 2H) 3.85 (br. s., 2H) 4.01 (br. s., 2H) 4.38 (br. s., 2H) 7.35 (br. s., 1H) 8.61 (br. s., 1H) 9.78 (br. s., 1H) |

-continued

| Example | Structure | Physical Data MS (m/z), ¹H NMR |
|---|---|---|
| 44 | 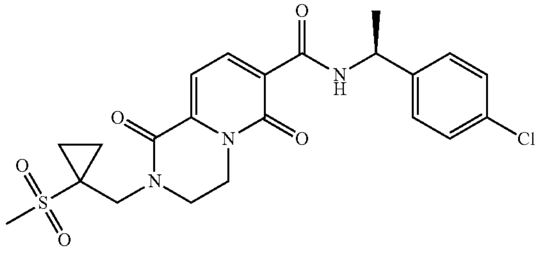 [SMILES: C[C@H](NC(=O)c1ccc2n(c1=O)CCN(CC1(S(C)(=O)=O)CC1)C2=O)c1ccc(Cl)cc1] | MS m/z: 478 (M + 1). ¹H NMR (400 MHz, DMSO-d6) δ ppm 1.12-1.17 (m, 2H) 1.29 (s, 2H) 1.45 (d, J = 6.90 Hz, 3H) 3.11 (s, 3H) 3.75-3.82 (m, 2H) 4.01 (s, 2H) 4.24 (br. s., 2H) 5.07-5.14 (m, 1H) 7.19 (d, J = 7.58 Hz, 1H) 7.34-7.42 (m, 4H) 8.38 (d, J = 7.58 Hz, 1H) 10.14 (d, J = 7.43 Hz, 1H) |
| 45 | 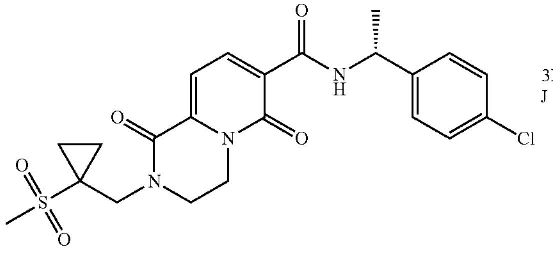 | MS m/z: 478 (M + 1). ¹H NMR (400 MHz, DMSO-d6) δ ppm 1.13-1.18 (m, 2H) 1.26-1.32 (m, 2H) 1.45 (d, J = 6.94 Hz, 3H) 3.11 (s, 3H) 3.78 (t, J = 5.80 Hz, 2H) 4.01 (s, 2H) 4.24 (d, J = 7.73 Hz, 2H) 5.11 (t, J = 7.26 Hz, 1H) 7.19 (d, J = 7.58 Hz, 1H) 7.34-7.41 (m, 4H) 8.38 (d, J = 7.58 Hz, 1H) 10.14 (d, J = 7.68 Hz, 1H) |
| 46 | 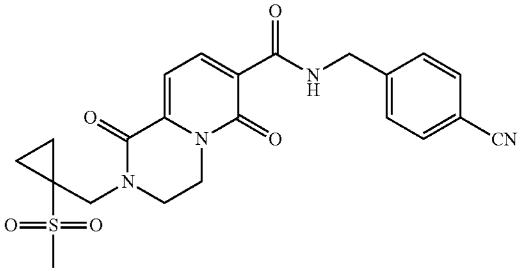 [SMILES: CS(=O)(=O)C1(CN2CCn3c(ccc(C(=O)NCc4ccc(C#N)cc4)c3=O)C2=O)CC1] | MS m/z: 455 (M + 1), ¹H NMR (400 MHz, DMSO-d6) δ ppm 1.12-1.18 (m, 2H) 1.27-1.32 (m, 2H) 3.11 (s, 3H) 3.75-3.82 (m, 2H) 4.02 (s, 2H) 4.21-4.27 (m, 2H) 4.62 (d, J = 6.06 Hz, 2H) 7.20 (d, J = 7.53 Hz, 1H) 7.48 (m, J = 8.31 Hz, 2H) 7.75-7.83 (m, 2H) 8.41 (d, J = 7.53 Hz, 1H) 10.14 (t, J = 6.14 Hz, 1H) |
| 47 | 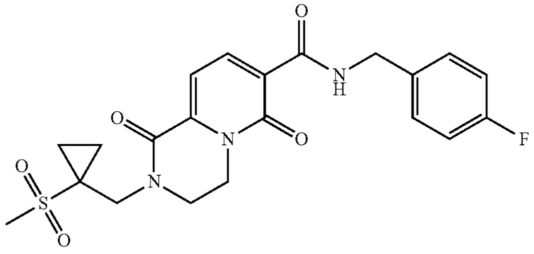 [SMILES: CS(=O)(=O)C1(CN2CCn3c(ccc(C(=O)NCc4ccc(F)cc4)c3=O)C2=O)CC1] | MS m/z: 448 (M + 1), ¹H NMR (400 MHz, DMSO-d6) δ ppm 1.13-1.18 (m, 2H) 1.28-1.32 (m, 2H) 3.12 (s, 3H) 3.76-3.82 (m, 2H) 4.03 (s, 2H) 4.21-4.26 (m, 2H) 4.52 (d, J = 5.92 Hz, 2H) 7.15 (t, J = 8.90 Hz, 2H) 7.21 (d, J = 7.58 Hz, 1H) 7.36 (dd, J = 8.46, 5.67 Hz, 2H) 8.44 (d, J = 7.53 Hz, 1H) 10.07 (t, J = 5.92 Hz, 1H) |
| 48 | 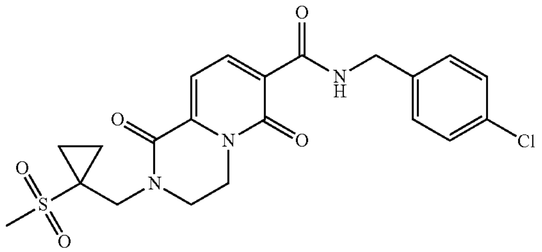 [SMILES: CS(=O)(=O)C1(CN2CCn3c(ccc(C(=O)NCc4ccc(Cl)cc4)c3=O)C2=O)CC1] | MS m/z: 464 (M + 1). 1H NMR (400 MHz, DMSO-d6) δ ppm 1.15 (ddd, J = 5.58, 4.84, 2.20 Hz, 2H) 1.29 (ddd, J = 5.28, 4.01, 2.20 Hz, 2H) 3.11 (s, 3H) 3.78 (t, J = 5.92 Hz, 2H) 4.01 (s, 2H) 4.23 (t, J = 5.72 Hz, 2H) 4.52 (d, J = 6.02 Hz, 2H) 7.20 (d, J = 7.53 Hz, 1H) 7.32 (d, J = 8.41 Hz, 2H) 7.37 (d, J = 8.51 Hz, 2H) 8.42 (d, J = 7.53 Hz, 1H) 10.08 (t, J = 6.02 Hz, 1H) |

Compounds in the table below were prepared from I-1 and 1-15 following procedures analogous to those described for Ex-1.

| Example | Structure | Physical Data MS (m/z), ¹H NMR |
|---|---|---|
| 49 | 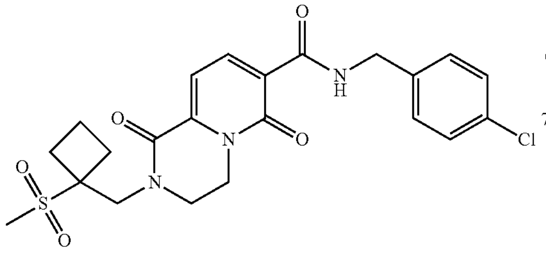 | MS m/z: 478 (M + 1). ¹H NMR (400 MHz, $CDCl_3$) δ ppm 2.13-2.24 (m, 2H) 2.27-2.38 (m, 2H) 2.65-2.76 (m, 2H) 2.98 (s, 3H) 3.82-3.88 (m, 2H) 4.16 (s, 2H) 4.30-4.36 (m, 2H) 4.61 (d, J = 5.92 Hz, 2H) 7.27-7.31 (m, 4H) 7.36 (d, J = 7.48 Hz, 1H) 8.63 (d, J = 7.53 Hz, 1H) 10.04 (br. s., 1H) |

Example 50-1

N-(4-chlorobenzyl)-2-(2-(1,1-dioxidotetrahydrothiophen-2-yl)ethyl)-1,6-dioxo-2,3,4,6-tetrahydro-1H-pyrido[1,2-a]pyrazine-7-carboxamide N-(4-chlorobenzyl)-2-(2-(1,1-dioxidotetrahydrothiophen-2-yl)ethyl)-1,6-dioxo-2,3,4,6-tetrahydro-1H-pyrido[1,2-a]pyrazine-7-carboxamide (Ex-50-1) was prepared from I-1 and 1-16 following procedures analogous to those described for Ex-1 except an EDC amide coupling used in place of acid chloride. To the acid (0.088 g, 0.248 mmol) in DMF (1 mL) were added EDC·HCl (0.057 g, 0.298 mmol) and HOBt (0.046 g, 0.298 mmol). The resulting solution was stirred at RT for about 30 min, after which p-chlorobenzylamine (0.091 mL, 0.745 mmol) was added. After about 2 h, the reaction mixture was diluted with EtOAc, washed with 2 M HCl and brine, and dried over sodium sulfate. The dried organic layer was concentrated under reduced pressure. The crude product was purified by HPLC 0.1% TFA in $H_2O$/ACN to afford the title compound isolated as an off-white solid.

| Example | Structure | Physical Data MS (m/z), ¹H NMR |
|---|---|---|
| 50-1 | 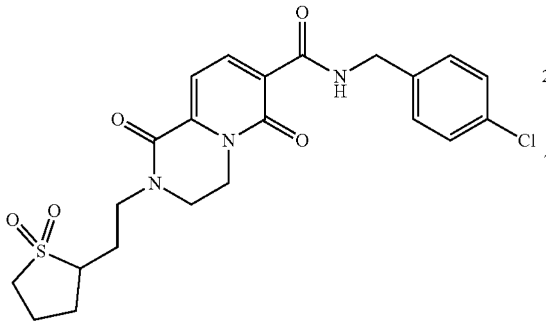 | MS m/z: 478 (M + 1). ¹H NMR (400 MHz, $CDCl_3$) δ ppm 1.75-1.89 (m, 1H) 1.98-2.16 (m, 2H) 2.16-2.28 (m, 2H) 2.43 (br. s., 1H) 2.93-3.06 (m, 2H) 3.18 (td, J = 8.69, 4.03 Hz, 1H) 3.62 (dt, J = 13.77, 6.76 Hz, 1H) 3.68-3.91 (m, 3H) 4.23-4.49 (m, 3H) 4.61 (d, J = 5.92 Hz, 2H) 7.29 (s, 3H) 7.35 (d, J = 7.43 Hz, 1H) 8.63 (d, J = 7.48 Hz, 1H) 10.06 (t, J = 5.01 Hz, 1H) |

Example 50-2

2-((1-((1-(((tert-butyldimethylsilyl)oxy)methyl)cyclopropyl)sulfonyl)cyclopropyl)methyl)-1,6-dioxo-2,3,4,6-tetrahydro-1H-pyrido[1,2-a]pyrazine-7-carboxylic acid (Ex-50-2A) To a solution of I-1 (0.1 g, 0.378 mmol) in DMF (2 mL) was added NaH (60% suspension in mineral oil, 0.023 g, 0.568 mmol). To the basic reaction mixture was added 1-46 (0.196 g, 0.492 mmol) in DMF (2 mL). The resulting reaction mixture was stirred at RT. Upon completion of the reaction, it was diluted with EtOAc and $H_2O$. The phases were separated and the aqueous layer extracted with EtOAc (2×). The aqueous layer was acidified with AcOH and was extracted with EtOAc. The EtOAc extracts were dried over sodium sulfate and concentrated under reduced pressure. The title compound was isolated as an orange solid. MS m/z: 511, (M+1).

2-((1-((1-(((tert-butyldimethylsilyl)oxy)methyl)cyclopropyl)sulfonyl)cyclopropyl)methyl)-N-((6-chloropyridin-3-yl)methyl)-1,6-dioxo-2,3,4,6-tetrahydro-1H-pyrido[1,2-a]pyrazine-7-carboxamide (Ex-50-2B). To a solution of Ex-50-2A (0.135 g, 0.264 mmol) in DCM (1 mL) were added DIEA (0.092 mL, 0.529 mmol) and T3P® (50% in EtOAc, 0.205 mL, 0.344 mmol). The resulting mixture was stirred at RT for 10 min. To the reaction mixture was added (6-chloropyridin-3-yl)methanamine (0.057 g, 0.397 mmol). Upon complete consumption of the starting material, the reaction mixture was diluted with DCM and washed with 2 M HCl, saturated sodium bicarbonate, and dried over sodium sulfate. The dried organic layer was concentrated under reduced pressure. The title compound was isolated as an orange oil. MS m/z: 635, (M+1).

N-((6-chloropyridin-3-yl)methyl)-2-((1-((1-hydroxymethyl)cyclopropyl)sulfonyl)cyclopropyl)methyl)-1,6-dioxo-2,3,4,6-tetrahydro-1H-pyrido[1,2-a]pyrazine-7-carboxamide (Ex-50-2). To a slurry of Ex-50-2B (0.126 g, 0.198 mmol) in DCM was added TFA (1 mL). The reaction mixture was stirred at RT overnight, after which it was concentrated under reduced pressure. The residue was diluted with DCM and washed with saturated sodium bicarbonate. The organic layer was dried over sodium sulfate and concentrated under reduced pressure. The crude product was purified on RP HPLC. Ex-50-2 was isolated as a white solid.

separated and the organic layer was washed with 2 M HCl (3×). The organic layer was dried over sodium sulfate and concentrated under reduced pressure. Ex-51A was isolated as a yellow foam. LCMS m/z: 424 (M+1).

N5-(4-chlorobenzyl)-1-(2-chloroethyl)-N2-(2-(methylthio)ethyl)-6-oxo-1,6-dihydropyridine-2,5-dicarboxamide (Ex-51B). To a solution of Ex-51A (0.25 g, 0.590 mmol) in DCM (6 mL) were added $NEt_3$ (0.247 mL, 1.769 mmol) and MsCl (0.069 mL, 0.885 mmol). Upon complete conversion of the starting material to the alkyl chloride, the reaction mixture was diluted with DCM, washed sequentially with saturated sodium bicarbonate (3×) and 2 M HCl (2×), and dried over sodium sulfate. The dried organic layer was concentrated under reduced pressure. The yellow oil was purified on $SiO_2$ (0-100% EtOAc/heptane) to afford Ex-51B as a yellow residue. LCMS m/z: 442 (M+1), 444 (M+3). $^1H$ NMR (400 MHz, $CDCl_3$) δ ppm 2.14 (s, 3H) 2.73-2.78 (m, 2H) 3.62-3.68 (m, 2H) 3.88 (t, J=6.26 Hz, 2H) 4.55-4.62 (m, 4H) 6.57 (d, J=7.43 Hz, 1H) 7.26-7.32 (m, 4H) 8.53 (d, J=7.43 Hz, 1H) 9.98 (t, J=5.48 Hz, 1H).

N-(4-chlorobenzyl)-2-(2-(methylsulfonyl)ethyl)-1,6-dioxo-2,3,4,6-tetrahydro-1H-pyrido[1,2-a]pyrazine-7-carboxamide (Ex-51). To a solution of Ex-51B (0.153 g, 0.346 mmol) in THF (4 mL) was added NaH (60% suspension in mineral oil, 0.021 g, 0.519 mmol). The resulting mixture was stirred at RT overnight, after which it was diluted with ice water and EtOAc. The phases were separated and the aqueous layer was extracted with EtOAc. The combined organic layers were washed with brine and dried over

| Example | Structure | Physical Data<br>MS (m/z), $^1H$ NMR |
|---|---|---|
| 50-2 | 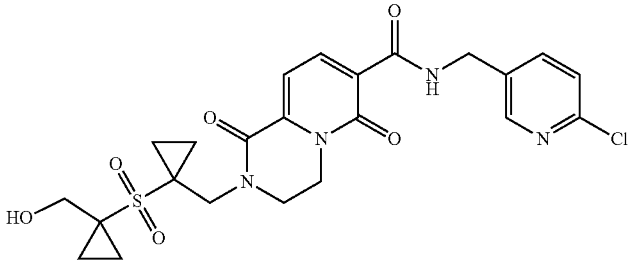 [SMILES: O=C(NCc1ccc(Cl)nc1)c1ccc2n(c1=O)CCN(CC1(S(=O)(=O)C3(CO)CC3)CC1)C2=O] | MS m/z: 521, (M + 1). $^1H$ NMR (500 MHz, DMSO-d6) δ ppm 1.09 (td, J = 5.04, 2.21 Hz, 2H) 1.14 (ddd, J = 5.99, 5.04, 1.89 Hz, 2H) 1.23 (dt, J = 4.10, 2.84 Hz, 2H) 1.36 (td, J = 5.36, 1.58 Hz, 2H) 3.78 (t, J = 5.99 Hz, 3H) 4.10 (s, 2H) 4.23 (t, J = 5.99 Hz, 2H) 4.56 (d, J = 5.99 Hz, 2H) 5.24 (t, J = 5.99 Hz, 1H) 7.20 (d, J = 7.57 Hz, 1H) 7.50 (d, J = 8.83 Hz, 1H) 7.81 (dd, J = 8.35, 2.36 Hz, 1H) 8.39 (d, J = 1.89 Hz, 1H) 8.43 (d, J = 7.57 Hz, 1H) 10.15 (t, J = 5.99 Hz, 1H) |

Example 51

N-(4-chlorobenzyl)-2-(2-(methylsulfonyl)ethyl)-1,6-dioxo-2,3,4,6-tetrahydro-1H-pyrido[1,2-a]pyrazine-7-carboxamide N5-(4-chlorobenzyl)-1-(2-hydroxyethyl)-N2-(2-(methylthio)ethyl)-6-oxo-1,6-dihydropyridine-2,5-dicarboxamide (Ex-51A). To a microwave vial charged with 1-17 (0.225 g, 0.676 mmol) were added ACN (0.5 mL) and 2-(methylthio)ethanamine (0.252 mL, 2.70 mmol). The resulting mixture was microwaved for 30 min at 100° C. The reaction mixture was diluted with DCM and 2 M HCl. The phases were sodium sulfate. The dried organic layer was taken up in DCM (4 mL) and treated with mCPBA (0.155 g, 0.692 mmol). Upon completion of the reaction, the mixture was diluted with DCM and saturated sodium bicarbonate. The phases were separated and the organic layer was washed with saturated sodium bicarbonate (5×). The organic layer was dried over sodium sulfate and concentrated under reduced pressure. The yellow residue was purified on $SiO_2$ (0-100% (5% MeOH/EtOAc)/heptane) to afford Ex-51 as a light yellow solid.

Other compounds in the table below were prepared following procedures analogous to those described for Ex-51.

| Example | Structure | Physical Data MS (m/z), $^1$H NMR |
|---|---|---|
| 51 | 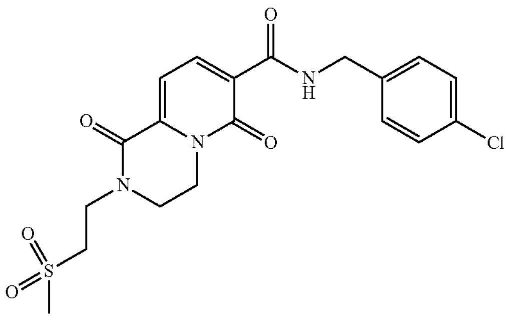 [SMILES: CS(=O)(=O)CCN1CCn2c(ccc(C(=O)NCc3ccc(Cl)cc3)c2=O)C1=O] | LCMS 439 (M + 1). $^1$H NMR (400 MHz, DMSO-d6) δ ppm 3.05 (s, 3H) 3.47 (t, J = 6.85 Hz, 2H) 3.76 (t, J = 1.00 Hz, 2H) 3.88 (t, J = 6.85 Hz, 2H) 4.22 (t, J = 1.00 Hz, 2H) 4.51 (d, J = 6.26 Hz, 2H) 7.19 (d, J = 7.43 Hz, 1H) 7.29-7.35 (m, 2H) 7.35-7.40 (m, 2H) 8.42 (d, J = 7.43 Hz, 1H) 10.07 (t, J = 6.06 Hz, 1H). |
| 52 | 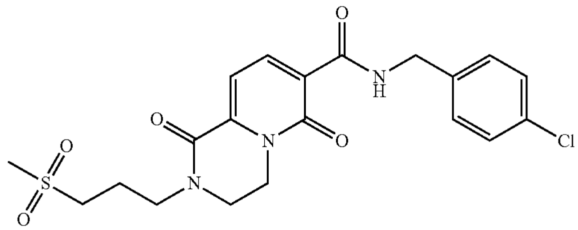 [SMILES: CS(=O)(=O)CCCN1CCn2c(ccc(C(=O)NCc3ccc(Cl)cc3)c2=O)C1=O] | MS m/z: 452 (M + 1). $^1$H NMR (500 MHz, DMSO-d6) δ ppm 1.96-2.05 (m, 2H) 2.98 (s, 3H) 3.14-3.23 (m, 2H) 3.60 (t, J = 6.78 Hz, 2H) 3.74 (t, J = 5.52 Hz, 2H) 4.19-4.33 (m, 2H) 4.54 (d, J = 5.99 Hz, 2H) 7.21 (d, J = 7.57 Hz, 1H) 7.34 (d, J = 8.51 Hz, 2H) 7.40 (d, J = 8.20 Hz, 2H) 8.45 (d, J = 7.57 Hz, 1H) 10.13 (t, J = 5.83 Hz, 1H) |
| 53 | 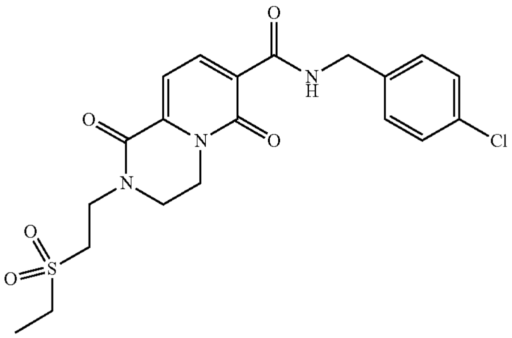 [SMILES: CCS(=O)(=O)CCN1CCn2c(ccc(C(=O)NCc3ccc(Cl)cc3)c2=O)C1=O] | MS m/z: 452 (M + 1). $^1$H NMR (500 MHz, DMSO-d6) δ ppm 1.24 (t, J = 7.41 Hz, 3H) 3.18 (q, J = 7.57 Hz, 2H) 3.47 (t, J = 6.94 Hz, 2H) 3.76-3.82 (m, 2H) 3.89 (t, J = 6.94 Hz, 2H) 4.22-4.27 (m, 2H) 4.54 (d, J = 5.99 Hz, 2H) 7.21 (d, J = 7.57 Hz, 1H) 7.35 (d, J = 8.51 Hz, 2H) 7.40 (d, J = 8.20 Hz, 2H) 8.44 (d, J = 7.57 Hz, 1H) 10.11 (t, J = 5.99 Hz, 1H) |
| 53-1 | 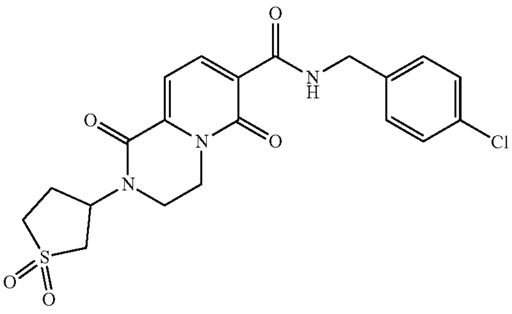 [SMILES: O=C(NCc1ccc(Cl)cc1)c1ccc2n(c1=O)CCN(C1CCS(=O)(=O)C1)C2=O] | LCMS m/z: 450 (M + 1). $^1$H NMR (500 MHz, METHANOL-d4) δ ppm 2.37-2.58 (m, 2H) 3.16-3.28 (m, 1H) 3.35-3.49 (m, 4H) 3.75-3.88 (m, 2H) 4.28-4.45 (m, 2H) 4.62 (s, 2H) 5.25-5.36 (m, 1H) 7.30-7.41 (m, 5H) 8.55 (d, J = 7.57 Hz, 1H) |

Example 54 tert-butyl (2-(7-((4-chlorobenzyl)carbamoyl)-1,6-dioxo-3,4-dihydro-1H-pyrido[1,2-]pyrazin-2 (6H)-yl)ethyl)(methyl)carb amate tert-butyl (2-(5-((4-chlorobenzyl)carbamoyl)-1-(2-hydroxyethyl)-6-oxo-1,6-dihydropyridine-2-carboxamido)ethyl)(methyl)carbamate (Ex-54A) was prepared from I-17 and N-Boc-N-methylethylenediamine following a procedure analogous to that described for Ex-51A. LCMS m/z: 507 (M+1).

tert-butyl (2-(5-((4-chlorobenzyl)carbamoyl)-1-(2-chloroethyl)-6-oxo-1,6-dihydropyridine-2-carboxamido)ethyl)(methyl)carbamate (Ex-54B) was prepared from Ex-54A following a procedure analogous to that described for Ex-51B. LCMS m/z: 525(M+1), 527 (M+3).

tert-butyl (2-(7-((4-chlorobenzyl)carbamoyl)-1,6-dioxo-3,4-dihydro-1H-pyrido[1,2-a]pyrazin-2(6H)-yl)ethyl)(methyl)carbamate (Ex-54): To a solution of Ex-54B (0.106 g, 0.202 mmol) in THF (2.5 mL) was added NaH (60% suspension in mineral oil, 0.012 g, 0.303 mmol). The reaction mixture was stirred overnight at RT, after which it was quenched with $H_2O$. The aqueous mixture was extracted with $CHCl_3$ (3×). The combined organic extracts were dried over sodium sulfate and concentrated under reduced pressure. The residue was purified on $SiO_2$ (0-100% (5% MeOH/EtOAc)/heptane) to afford Ex-54 as a light yellow solid.

Other compounds in the table below were prepared following procedures analogous to those described for Ex-54.

| Example | Structure | Physical Data MS (m/z), $^1$H NMR |
|---|---|---|
| 54 | 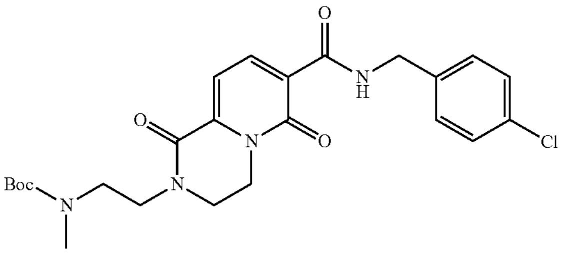 [SMILES: CN(CCN1CCn2c(ccc(C(=O)NCc3ccc(Cl)cc3)c2=O)C1=O)C(=O)OC(C)(C)C] | LCMS 489 (M + 1). $^1$H NMR (500 MHz, METHANOL-d4) δ ppm 1.33-1.42 (m, 9 H) 2.95 (br. s., 3H) 3.56 (t, J = 5.52 Hz, 2H) 3.76 (t, J = 5.67 Hz, 2H) 3.83 (d, J = 5.36 Hz, 2H) 4.36 (d, J = 4.41 Hz, 2H) 4.62 (s, 2H) 7.30 (d, J = 7.57 Hz, 1H) 7.34-7.41 (m, 4H) 8.54 (d, J = 7.25 Hz, 1H). |
| 55 | 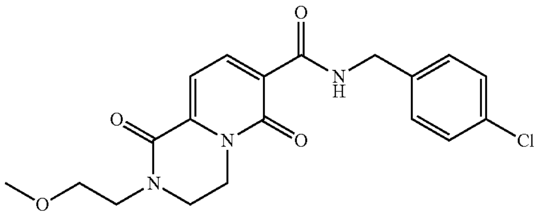 [SMILES: COCCN1CCn2c(ccc(C(=O)NCc3ccc(Cl)cc3)c2=O)C1=O] | LCMS m/z: 390 (M + 1). $^1$H NMR (500 MHz, DMSO-d6) δ ppm 3.24-3.30 (m, 3H) 3.50-3.57 (m, 2H) 3.63-3.69 (m, 2H) 3.71-3.79 (m, 2H) 4.18-4.26 (m, 2H) 4.53 (t, J = 6.31 Hz, 2H) 7.19 (dt, J = 7.65, 3.90 Hz, 1H) 7.31-7.37 (m, 2H) 7.37-7.44 (m, 2H) 8.40-8.46 (m, 1H) 10.12 (d, J = 5.99 Hz, 1H). |
| 56 | 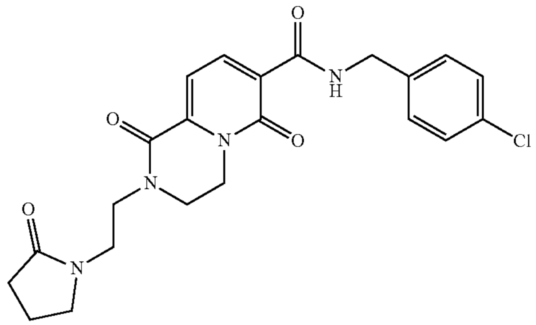 [SMILES: O=C(NCc1ccc(Cl)cc1)c1ccc2n(c1=O)CCN(CCN1CCCC1=O)C2=O] | MS m/z: 443 (M + 1). $^1$H NMR (500 MHz, METHANOL-d4) δ ppm 2.03 (quin, J = 7.57 Hz, 2H) 2.25-2.32 (m, 2H) 3.57-3.63 (m, 4H) 3.79 (dd, J = 6.31, 4.73 Hz, 2H) 3.81-3.87 (m, 2H) 4.30-4.37 (m, 2H) 4.61 (s, 2H) 7.28 (d, J = 7.57 Hz, 1H) 7.35 (s, 4H) 8.52 (d, J = 7.57 Hz, 1H) |
| 57 | 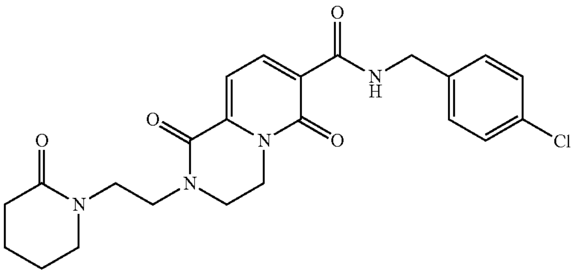 [SMILES: O=C(NCc1ccc(Cl)cc1)c1ccc2n(c1=O)CCN(CCN1CCCCC1=O)C2=O] | LCMS m/z: 457 (M + 1). $^1$H NMR (400 MHz, METHANOL-d4) δ ppm 1.73-1.85 (m, 4H) 2.23 (t, J = 6.65 Hz, 2H) 3.46 (t, J = 5.67 Hz, 2H) 3.69 (d, J = 6.26 Hz, 2H) 3.76-3.84 (m, 4H) 4.29-4.35 (m, 2H) 4.59 (s, 2H) 7.25 (d, J = 7.43 Hz, 1H) 7.33 (s, 4H) 8.51 (d, J = 7.43 Hz, 1H). |

-continued

| Example | Structure | Physical Data MS (m/z), ¹H NMR |
|---|---|---|
| 57-1 | 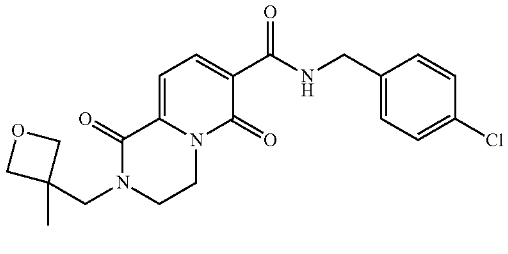 [SMILES: CC1(CN2CCn3c(ccc(C(=O)NCc4ccc(Cl)cc4)c3=O)C2=O)COC1] | LCMS m/z: 416 (M + 1). ¹H NMR (400 MHz, METHANOL-d4) H) δ ppm 8.51 (d, 9-4.35 (m, J = 5.87 Hz, 4H) 4.60 (s, 2H) 4.70 (d, J = 6.26 Hz, 2H) 7.30 (d, J = 7.43 Hz, 1H) 7.34 (s, 4H) 8.53 (d, J = 7.82 Hz, 1H) |

Example 58

N-(4-chlorobenzyl)-2-(2-(N-methylmethylsulfonamido)ethyl)-1,6-dioxo-2,3,4,6-tetrahydro-1H-pyrido[1,2-a]pyrazine-7-carboxamide N-(4-chlorobenzyl)-2-(2-(methylamino)ethyl)-1,6-dioxo-2,3,4,6-tetrahydro-1H-pyrido[1,2-a]pyrazine-7-carboxamide (Ex-58A): To a flask charged with Ex-54 (0.19 g, 0.389 mmol) was added HCl 4M in dioxane (3 mL, 12.00 mmol). The resulting mixture was stirred at RT overnight, after which it was concentrated under reduced pressure. The residue was co-evaporated with EtOAc/heptane, and the resulting solid was dried under vacuum. Ex-58A hydrochloride salt was isolated as a yellow solid. LCMS m/z: 389 (M+1).

N-(4-chlorobenzyl)-2-(2-(N-methylmethylsulfonamido)ethyl)-1,6-dioxo-2,3,4,6-tetrahydro-1H-pyrido[1,2-a]pyrazine-7-carboxamide (Ex-58): To a solution of Ex-58A (0.035 g, 0.082 mmol) and $NEt_3$ (0.029 mL, 0.206 mmol) in DCM (1.5 mL) was added MsCl (7.05 μL, 0.091 mmol). The resulting mixture was stirred at RT overnight, after which it was diluted with DCM and 2 M HCl. The phases were separated and the organic layer washed with 2 M HCl (3×) and brine and dried over sodium sulfate. The dried organic layer was concentrated under reduced pressure, and the residue was purified by flash chromatography. Ex-58 was isolated as a tan solid.

Other compounds in the table below were prepared following procedures analogous to those described for Ex-58.

| Example | Structure | Physical Data MS (m/z), ¹H NMR |
|---|---|---|
| 58 | 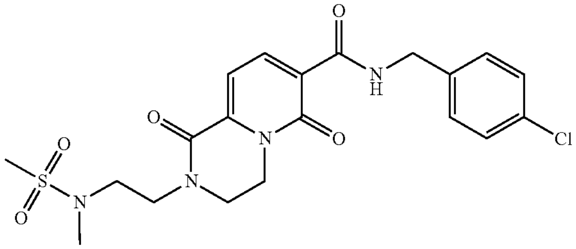 [SMILES: CN(CCN1CCn2c(ccc(C(=O)NCc3ccc(Cl)cc3)c2=O)C1=O)S(C)(=O)=O] | LCMS m/z: 467 (M + 1). ¹H NMR (500 MHz, Methanol-d4) δ ppm 2.86 (s, 3H) 2.94 (s, 3H) 3.43 (t, J = 5.52 Hz, 3H) 3.75-3.80 (m, 2H) 3.80-3.84 (m, 2H) 4.33-4.38 (m, 2H) 4.60 (s, 2H) 7.30 (d, J = 7.57 Hz, 1H) 7.34 (s, 3H) 8.53 (d, J = 7.57 Hz, 1H). |
| 59 | 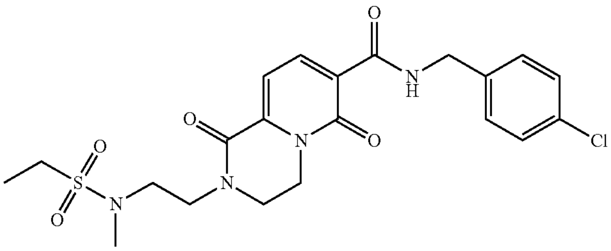 [SMILES: CCS(=O)(=O)N(C)CCN1CCn2c(ccc(C(=O)NCc3ccc(Cl)cc3)c2=O)C1=O] | MS m/z: 481 (M + 1). ¹H NMR (500 MHz, METHANOL-d4) δ ppm 1.30 (t, J = 6.46 Hz, 3H) 2.98 (s, 3H) 3.08 (q, J = 7.46 Hz, 2H) 3.51 (t, J = 5.20 Hz, 2H) 3.78 (t, J = 5.04 Hz, 2H) 3.83 (t, J = 5.52 Hz, 2H) 4.35-4.40 (m, 2H) 4.59-4.63 (m, 2H) 7.31 (d, J = 7.57 Hz, 1H) 7.32-7.38 (m, 4H) 8.51-8.56 (m, 1H) |

-continued

| Example | Structure | Physical Data MS (m/z), $^1$H NMR |
|---|---|---|
| 60 | 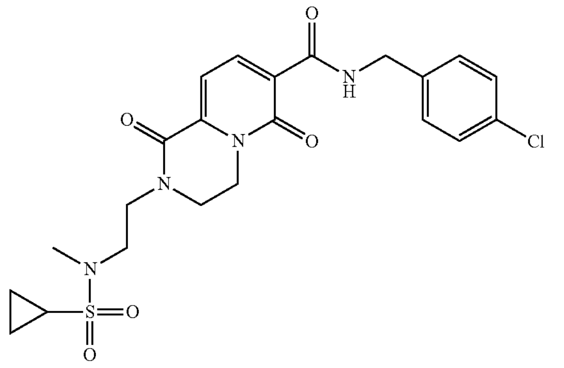 [SMILES: CN(CCN1CCn2c(ccc(C(=O)NCc3ccc(Cl)cc3)c2=O)C1=O)S(=O)(=O)C1CC1] | LCMS 493 (M + 1). $^1$H NMR (500 MHz, METHANOL-d4) δ ppm 0.98-1.11 (m, 4H) 2.49-2.57 (m, 1H) 3.00 (s, 3H) 3.52 (t, J = 5.36 Hz, 2H) 3.81 (dt, J = 17.10, 5.64 Hz, 4H) 4.33-4.41 (m, 2H) 4.62 (d, J = 5.67 Hz, 2H) 7.31 (d, J = 7.25 Hz, 1H) 7.36 (s, 4H) 8.54 (d, J = 7.25 Hz, 1H) 10.45 (br. s., 1H). |
| 61 | 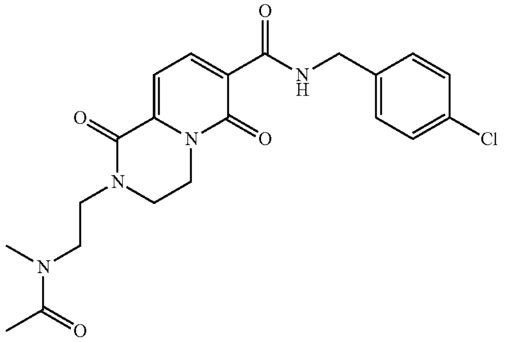 [SMILES: CC(=O)N(C)CCN1CCn2c(ccc(C(=O)NCc3ccc(Cl)cc3)c2=O)C1=O] | LCMS m/z: 431 (M + 1). $^1$H NMR (500 MHz, METHANOL-d4) δ ppm 2.03 (s, 3H) 3.14 (s, 3H) 3.68-3.74 (m, 2H) 3.75-3.81 (m, 2H) 3.81-3.86 (m, 2H) 4.30-4.37 (m, 2H) 4.62 (s, 2H) 7.28 (d, J = 7.57 Hz, 1H) 7.33-7.38 (m, 4H) 8.53 (d, J = 7.57 Hz, 1H). |
| 61-1 | 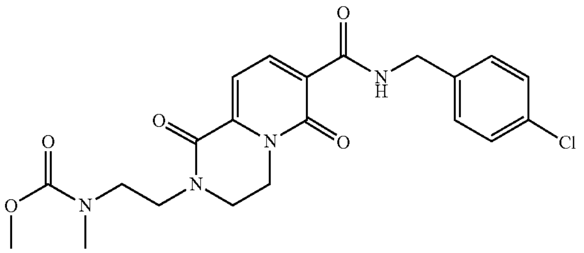 [SMILES: COC(=O)N(C)CCN1CCn2c(ccc(C(=O)NCc3ccc(Cl)cc3)c2=O)C1=O] | LCMS m/z: 447 (M + 1). 1H NMR (400 MHz, $CDCl_3$) δ ppm 2.96 (s, 3H) 3.55-3.62 (m, 5H) 3.72-3.85 (m, 4H) 4.28-4.35 (m, 2H) 4.60 (s, 2H) 7.27 (d, J = 7.43 Hz, 1H) 7.33 (s, 4H) 8.52 (d, J = 7.83 Hz, 1H). |

Example 62

N-(4-chlorobenzyl)-2-(2-(methyl sulfonamido) ethyl)-1,6-dioxo-2,3,4,6-tetrahydro-1H-pyrido[1,2-a] pyrazine-7-carboxamide tert-butyl (2-(5-((4-chlorobenzyl)carbamoyl)-1-(2-hydroxyethyl)-6-oxo-1,6-dihydropyridine-2-carboxamido) ethyl)carbamate (Ex-62A) was prepared from 1-17 and N-Boc-ethylenediamine following a procedure analogous to that described for Ex-51A. LCMS m/z: 493(M+1).

tert-butyl (2-(5-((4-chlorobenzyl)carbamoyl)-1-(2-chloroethyl)-6-oxo-1,6-dihydropyridine-2-carboxamido)ethyl) carbamate (Ex-62B) was prepared from Ex-62A following a procedure analogous to that described for Ex-51B. LCMS m/z: 511(M+1), 513 (M+3).

tert-butyl (2-(7-((4-chlorobenzyl)carbamoyl)-1,6-dioxo-3,4-dihydro-1H-pyrido[1,2-a]pyrazin-2(6H)-yl)ethyl)carbamate (Ex-62C) was prepared from Ex-62B following a procedure analogous to that described for Ex-54. LCMS m/z: 475 (M+1).

2-(2-aminoethyl)-N-(4-chlorobenzyl)-1,6-dioxo-2,3,4,6-tetrahydro-1H-pyrido[1,2-a]pyrazine-7-carboxamide (Ex-62D) was prepared from Ex-62C following a procedure analogous to that described for Ex-58A. LCMS m/z: 375 (M+1).

N-(4-chlorobenzyl)-2-(2-(methylsulfonamido)ethyl)-1,6-dioxo-2,3,4,6-tetrahydro-1H-pyrido[1,2-a]pyrazine-7-carboxamide (Ex-62): To a solution of Ex-62D (0.02 g, 0.053 mmol) and $NEt_3$ (0.019 mL, 0.133 mmol) in DCM (0.5 mL) was added MsCl (4.16 μL, 0.053 mmol). The resulting mixture was stirred at RT. Upon consumption of Ex-62D, the reaction mixture was diluted with DCM and washed with 2 M HCl (2×). The organic layer was purified on $SiO_2$ (0-100% (5% MeOH/EtOAc)/heptane) to afford Ex-62 as an off-white white solid.

Other compounds in the table below were prepared from 1-17 and either N-Boc-N-methylethylenediamine, (S)-2-(aminomethyl)-1-Boc-pyrrolidine, or (R)-2-(aminomethyl)-1-Boc-pyrrolidine following procedures analogous to those described for Ex-62.

| Example | Structure | Physical Data MS (m/z), $^1$H NMR |
|---|---|---|
| 62 | 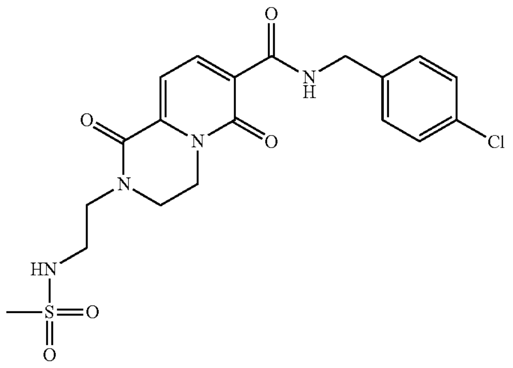 [SMILES: CS(=O)(=O)NCCN1CCn2c(ccc(C(=O)NCc3ccc(Cl)cc3)c2=O)C1=O] | LCMS m/z: 453 (M + 1). $^1$H NMR (500 MHz, METHANOL-d4) δ ppm 2.97 (s, 3H) 3.72 (t, J = 5.67 Hz, 2H) 3.84-3.89 (m, 2H) 4.35-4.42 (m, 2H) 4.62 (d, J = 5.67 Hz, 2H) 7.33 (d, J = 7.57 Hz, 1H) 7.36 (s, 4H) 8.55 (d, J = 7.57 Hz, 1H). |
| 63 | 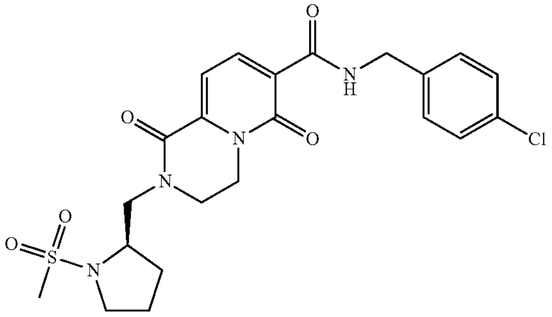 [SMILES: CS(=O)(=O)N1CCC[C@@H]1CN1CCn2c(ccc(C(=O)NCc3ccc(Cl)cc3)c2=O)C1=O] | LCMS m/z: 493 (M + 1). $^1$HNMR (500 MHz, DMSO-d6) δ ppm 1.92-2.12 (m, 4H) 2.87 (s, 3H) 3.40-3.46 (m, 2H) 3.55 (td, J = 14.27, 7.09 Hz, 1H) 3.73 (dd, J = 13.71, 5.20 Hz, 1H) 3.87 (t, J = 5.52 Hz, 2H) 4.14 (br. s., 1H) 4.36 (t, J = 5.67 Hz, 2H) 4.60 (d, J = 5.36 Hz, 2H) 7.29 (d, J = 7.57 Hz, 1H) 7.33 (s, 4H) 8.51 (d, J = 7.57 Hz, 1H) 10.43 (br. s., 1H). |
| 63-1 | 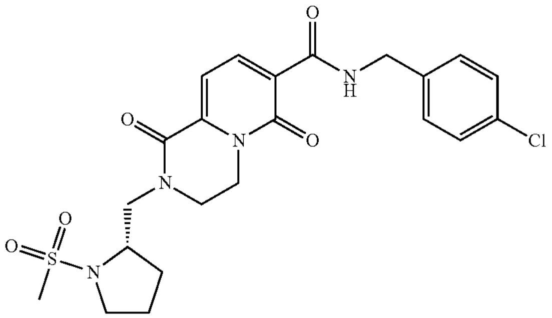 [SMILES: CS(=O)(=O)N1CCC[C@H]1CN1CCn2c(ccc(C(=O)NCc3ccc(Cl)cc3)c2=O)C1=O] | LCMS m/z: 493 (M + 1). 1H NMR (400 MHz, CDCl3) δ ppm 1.88-2.04 (m, 4H) 2.80 (br. s., 3H) 3.29-3.40 (m, 1H) 3.50 (dd, J = 14.08, 6.65 Hz, 2H) 3.76-3.89 (m, 3H) 4.07 (br. s., 1H) 4.29-4.40 (m, 2H) 4.60 (d, J = 5.48 Hz, 2H) 7.28 (br. s., 4H) 7.33 (d, J = 7.43 Hz, 1H) 8.61 (d, J = 7.43 Hz, 1H) 10.07 (br. s., 1H) |

Example 64

N-(4-chlorobenzyl)-2-(2-(1,1-dioxidoisothiazolidin-2-yl)ethyl)-1,6-dioxo-2,3,4,6-tetrahydro-1H-pyrido[1,2-a]pyrazine-7-carboxamide N5-(4-chlorobenzyl)-N2-(2-(1,1-dioxidoisothiazolidin-2-yl)ethyl)-1-(2-hydroxyethyl)-6-oxo-1,6-dihydropyridine-2,5-dicarboxamide (Ex-64E): To a mixture of 1-17 (0.15 g, 0.451 mmol) and I-18D (0.362 g, 1.803 mmol) in ACN (1 mL) was added DIEA (0.394 mL, 2.254 mmol). The resulting mixture was stirred at 90° C. When the starting material was consumed, the reaction mixture was cooled to RT, diluted with $CHCl_3$, and washed with 2 M HCl and saturated sodium bicarbonate. The organic layer was dried over sodium sulfate and concentrated under reduced pressure. Ex-64E was isolated as a dark orange residue. LCMS m/z: 497 (M+1).

N5-(4-chlorobenzyl)-1-(2-chloroethyl)-N2-(2-(1,1-dioxidoisothiazolidin-2-yl)ethyl)-6-oxo-1,6-dihydropyridine-2,5-dicarboxamide (Ex-64F) was prepared from Ex-64E following a procedure analogous to that described for Ex-51B. LCMS m/z: 515(M+1), 517 (M+3).

N-(4-chlorobenzyl)-2-(2-(1,1-dioxidoisothiazolidin-2-yl)ethyl)-1,6-dioxo-2,3,4,6-tetrahydro-1H-pyrido[1,2-a]pyrazine-7-carboxamide (Ex-64): To a solution of Ex-64F (0.081 g, 0.157 mmol) in THF (10 mL) was added NaH (60% suspension in mineral oil, 9.43 mg, 0.236 mmol). The resulting mixture was stirred at RT for 1 h, after which the reaction was quenched with $H_2O$. The aqueous layer was extracted with EtOAc. The organic extracts were washed with 2 M HCl and saturated sodium bicarbonate and dried over sodium sulfate. The dried organic layer was concentrated under reduced pressure. The residue was recrystallized from hot EtOH. Ex-64 was collected via vacuum filtration as yellow needles.

Other compounds in the table below were prepared following procedures analogous to those described for Ex-64.

| Example | Structure | Physical Data MS (m/z), $^1$H NMR |
|---|---|---|
| 64 | 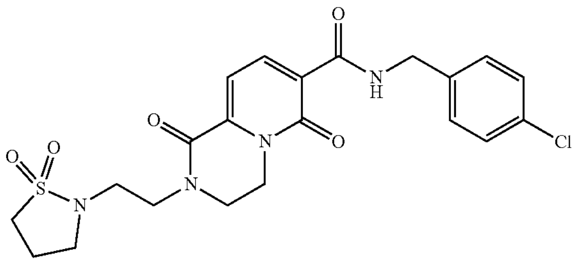 [SMILES: O=C(NCc1ccc(Cl)cc1)c1ccc2n(c1=O)CCN(CCN1CCCS1(=O)=O)C2=O] | LCMS m/z: 479 (M + 1). $^1$H NMR (400 MHz, DMSO-d6) δ ppm 2.14-2.26 (m, 2H) 3.12-3.21 (m, 4H) 3.27-3.31 (m, 2H) 3.66 (t, J = 5.87 Hz, 2H) 3.75 (dd, J = 6.65, 5.09 Hz, 2H) 4.21-4.28 (m, 2H) 4.53 (d, J = 6.26 Hz, 2H) 7.20 (d, J = 7.43 Hz, 1H) 7.34 (d, J = 9.00 Hz, 2H) 7.39 (d, J = 8.61 Hz, 2H) 8.43 (d, J = 7.43 Hz, 1H) 10.10 (t, J = 6.26 Hz, 1H). |
| 65 | 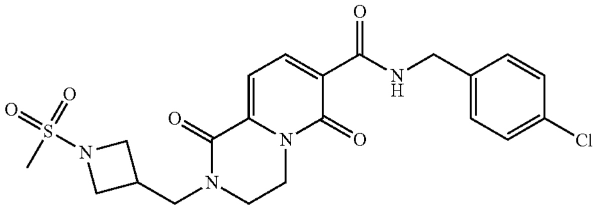 [SMILES: CS(=O)(=O)N1CC(CN2CCn3c(ccc(C(=O)NCc4ccc(Cl)cc4)c3=O)C2=O)C1] | LCMS m/z: 479 (M + 1). $^1$H NMR (400 MHz, METHANOL-d4) δ ppm 2.94 (s, 3H) 3.01-3.05 (m, 1H) 3.77 (dd, J = 8.22, 5.87 Hz, 4H) 3.83 (d, J = 7.43 Hz, 2H) 4.01 (t, J = 8.22 Hz, 2H) 4.30-4.34 (m, 2H) 4.59 (s, 2H) 7.31 (d, J = 7.43 Hz, 1H) 7.33 (s, 4H) 8.52 (d, J = 7.43 Hz, 1H) |
| 66 | 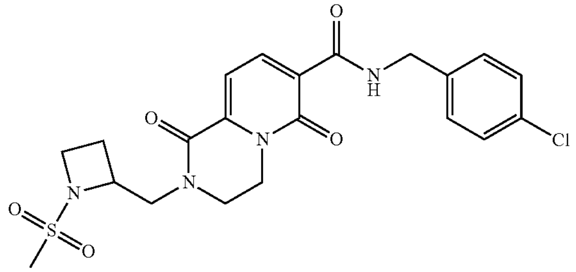 [SMILES: CS(=O)(=O)N1CCC1CN1CCn2c(ccc(C(=O)NCc3ccc(Cl)cc3)c2=O)C1=O] | MS m/z: 479 (M + 1). $^1$H NMR (400 MHz, DMSO-d6) δ ppm 2.01-2.19 (m, 2H) 2.95 (s, 3H) 3.23-3.29 (m, 2H) 3.38-3.44 (m, 1H) 3.47 (dd, J = 10.56, 7.83 Hz, 1H) 3.71 (t, J = 5.87 Hz, 2H) 4.14-4.32 (m, 2H) 4.51 (d, J = 6.26 Hz, 2H) 5.04-5.13 (m, 1H) 7.20 (d, J = 7.83 Hz, 1H) 7.30-7.35 (m, 2H) 7.35-7.41 (m, 2H) 8.42 (d, J = 7.43 Hz, 1H) 10.08 (t, J = 6.06 Hz, 1H) |
| 66-1 | 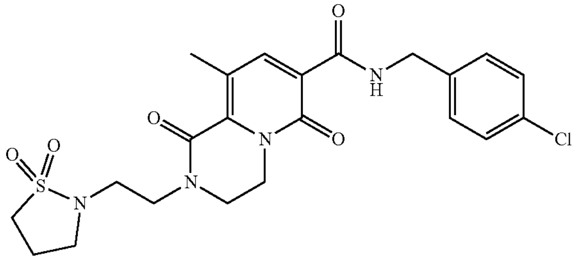 [SMILES: Cc1cc(C(=O)NCc2ccc(Cl)cc2)c(=O)n2c1C(=O)N(CCN1CCCS1(=O)=O)CC2] | MS m/z: 493 (M + 1). $^1$H NMR (400 MHz, $CD_3OD$) δ ppm 2.27-2.36 (m, 2H) 2.51 (s, 3H) 3.11-3.17 (m, 2H) 3.42 (t, J = 6.85 Hz, 2H) 3.70-3.77 (m, 4H) 4.31-4.36 (m, 2H) 4.59 (s, 2H) 7.32 (s, 4H) 8.34 (s, 1H) |

Example 67-1

N-(4-chlorobenzyl)-2-((1-(methylsulfinyl)cyclopropyl)methyl)-1,6-dioxo-2,3,4,6-tetrahydro-1H-pyrazine-7-carboxamide N5-(4-chlorobenzyl)-1-(2-hydroxyethyl)-N2-((1-(methylthio)cyclopropyl)methyl)-6-oxo-1,6-dihydropyridine-2,5-dicarboxamide (Ex-67A) was prepared from 1-17 and (1-(methylthio)cyclopropyl)methanamine following a procedure analogous to that described for Ex-51A. MS m/z 432.3 ($M-H_2O+1$).

N5-(4-chlorobenzyl)-1-(2-chloroethyl)-N2-((1-(methylthio)cyclopropyl)methyl)-6-oxo-1,6-dihydropyridine-2,5-dicarboxamide (Ex-67B). MsCl (0.101 mL, 1.300 mmol) was added to a stirred solution of Ex-67A (531.7 mg, 1.182 mmol) and $NEt_3$ (0.247 mL, 1.773 mmol) in DCM (11.8 mL) at RT. The mixture was stirred overnight at RT. The reaction mixture was partitioned between DI water and DCM, and the aqueous layer was extracted with DCM (2×). The combined organic layer was washed with brine, dried over $Na_2SO_4$, filtered, and concentrated. The crude product was purified on $SiO_2$ (0-100% EtOAc/heptane) to afford Ex-67B. MS m/z 468.3 (M+1).

N-(4-chlorobenzyl)-2-((1-(methylthio)cyclopropyl)methyl)-1,6-dioxo-2,3,4,6-tetrahydro-1H-pyrido[1,2-a]pyrazine-7-carboxamide (Ex-67C) was prepared from Ex-67B following a procedure analogous to that described for Ex-64. The title compound was obtained as an orange solid. MS m/z 432.2 (M+1).

N-(4-chlorobenzyl)-2-((1-(methylsulfinyl)cyclopropyl)methyl)-1,6-dioxo-2,3,4,6-tetrahydro-1H-pyrido[1,2-a]pyrazine-7-carboxamide (Ex-67-1). Oxone (400 mg, 0.650 mmol) was added to a stirred solution of Ex-67C (511 mg, 1.182 mmol) in methanol (44 mL) and DCM (3.6 mL) at RT. Conversion to the sulfoxide was determined to be complete after 1 h, and the reaction mixture was vacuum filtered through a frit. The filtrate was concentrated, and the resulting solid was partitioned between DI water and DCM. The aqueous phase was extracted with DCM (2×), and the combined organic phase was dried over $Na_2SO_4$, filtered, and concentrated to yield a yellow foam. The material was purified by SFC to afford Ex-67-1 as a pale yellow solid.

(R) & (S)—N-(4-chlorobenzyl)-2-((1-(methylsulfinyl)cyclopropyl)methyl)-1,6-dioxo-2,3,4,6-tetrahydro-1H-pyrido[1,2-a]pyrazine-7-carboxamide (Ex-67-2, Ex-67-3). Ex-67-1 was subjected to separation by chiral SFC to afford title enantiomeric sulfoxides. Characterization data are in the table below, and the stereochemical assignments are arbitrary.

| Example | Structure | Physical Data MS (m/z), $^1$H NMR |
|---|---|---|
| 67-1 | 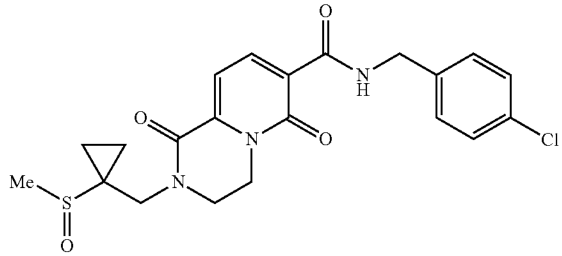 [SMILES: CS(=O)C1(CN2CCn3c(ccc(C(=O)NCc4ccc(Cl)cc4)c3=O)C2=O)CC1] | MS m/z 448.2 (M + 1). $^1$H NMR (400 MHz, $CDCl_3$) δ ppm 0.81-0.92 (m, 1H) 1.03 (s, 2H) 1.09-1.18 (m, 1H) 1.31-1.39 (m, 1H) 2.69 (s, 3H) 3.69-3.75 (m, 1H) 3.76-3.86 (m, 1H) 3.91-4.01 (m, 1H) 4.17-4.24 (m, 1H) 4.24-4.32 (m, 1H) 4.37-4.46 (m, 1H) 4.61 (d, J = 5.92 Hz, 2H) 7.29 (s, 3H) 7.34 (d, J = 7.53 Hz, 1H) 8.63 (d, J = 7.53 Hz, 1H) 9.96-10.11 (m, 1H). |
| 67-2 | 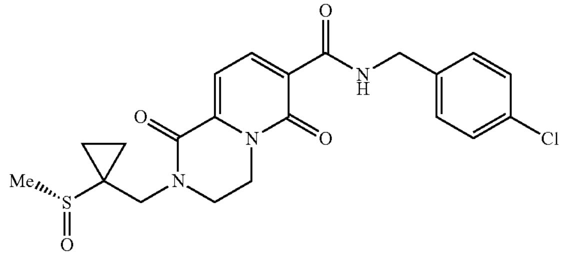 [SMILES: C[S@@](=O)C1(CN2CCn3c(ccc(C(=O)NCc4ccc(Cl)cc4)c3=O)C2=O)CC1] | MS m/z 448.2 (M + 1). $^1$H NMR (400 MHz, $CDCl_3$) δ ppm 0.83-0.94 (m, 1H) 1.03 (br. s., 2H) 1.08-1.18 (m, 1H) 1.30-1.39 (m, 1H) 2.69 (s, 2H) 3.72 (d, J = 14.97 Hz, 1H) 3.76-3.86 (m, 1H) 3.90-4.03 (m, 1H) 4.21 (d, J = 15.01 Hz, 2H) 4.33-4.48 (m, 1H) 4.61 (d, J = 5.82 Hz, 2H) 7.29 (s, 3H) 7.34 (d, J = 7.48 Hz, 1H) 8.63 (d, J = 7.48 Hz, 1H) 9.91-10.11 (m, 1H). |
| 67-3 | 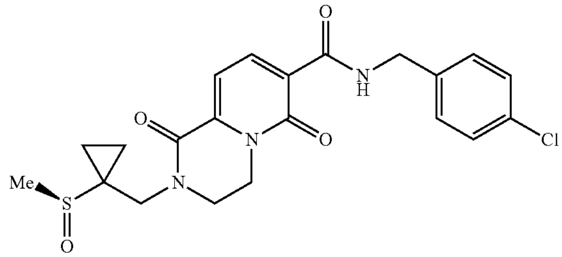 [SMILES: C[S@](=O)C1(CN2CCn3c(ccc(C(=O)NCc4ccc(Cl)cc4)c3=O)C2=O)CC1] | MS m/z 448.2 (M + 1). $^1$H NMR (400 MHz, $CDCl_3$) δ ppm 0.81-0.92 (m, 1H) 1.03 (s, 2H) 1.09-1.18 (m, 1H) 1.31-1.39 (m, 1H) 2.69 (s, 3H) 3.69-3.75 (m, 1H) 3.76-3.86 (m, 1H) 3.91-4.01 (m, 1H) 4.17-4.24 (m, 1H) 4.24-4.32 (m, 1H) 4.37-4.46 (m, 1H) 4.61 (d, J = 5.92 Hz, 2H) 7.29 (s, 3H) 7.34 (d, J = 7.53 Hz, 1H) 8.63 (d, J = 7.53 Hz, 1H) 9.96-10.11 (m, 1H). |

Example 68

N-(4-cyanobenzyl)-2-((1-(methylsulfinyl)cyclopropyl)methyl)-1,6-dioxo-2,3,4,6-tetrahydro-1H-pyrido[1,2-a]pyrazine-7-carboxamide Compounds in the table below were prepared from 1-61 and (1-(methylthio)cyclopropyl)methanamine following procedures analogous to those described for Ex-67.

| Example | Structure | Physical Data MS (m/z), $^1$H NMR |
|---|---|---|
| 68-1 | 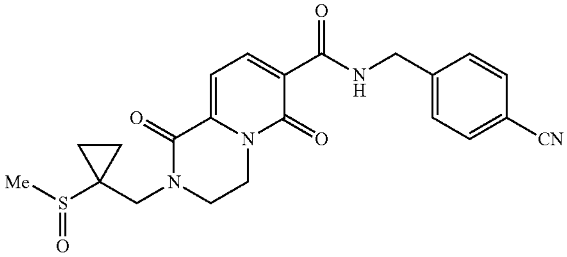 [SMILES: CS(=O)C1(CN2CCn3c(ccc(C(=O)NCc4ccc(C#N)cc4)c3=O)C2=O)CC1] | MS m/z = 439.3 (M + 1). $^1$H NMR (500 MHz, DMSO-d6) δ ppm 0.85-0.99 (m, 2 H) 0.99-1.16 (m, 2 H) 2.62 (s, 3 H) 3.70 (d, J = 14.88 Hz, 1 H) 3.77-3.97 (m, 2 H) 4.09 (d, J = 14.88 Hz, 1 H) 4.26 (t, J = 6.01 Hz, 2 H) 4.64 (d, J = 6.07 Hz, 2 H) 7.21 (d, J = 7.55 Hz, 1 H) 7.50 (d, J = 8.13 Hz, 2 H) 7.81 (d, J = 8.13 Hz, 2 H) 8.43 (d, J = 7.55 Hz, 1 H) 10.18 (t, J = 6.07 Hz, 1 H). |

-continued

| Example | Structure | Physical Data MS (m/z), $^1$H NMR |
|---|---|---|
| 68-2 | 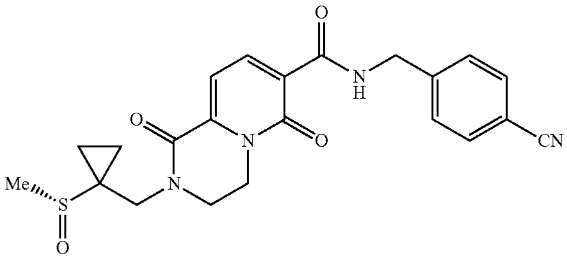 [SMILES: C[S@@](=O)C1(CN2CCn3c(ccc(C(=O)NCc4ccc(C#N)cc4)c3=O)C2=O)CC1] | MS m/z = 439.2 (M + 1). $^1$H NMR (400 MHz, $CDCl_3$) δ ppm 1.09-1.18 (m, 2 H) 1.30-1.42 (m, 3 H) 2.70 (s, 3 H) 3.69-3.89 (m, 3 H) 3.91-4.10 (m, 2 H) 4.14-4.23 (m, 1 H) 4.23-4.36 (m, 1 H) 4.36-4.53 (m, 2 H) 4.70 (d, J = 6.02 Hz, 2 H) 7.35 (d, J = 7.48 Hz, 1 H) 7.45 (d, J = 8.17 Hz, 2 H) 7.62 (d, J = 8.22 Hz, 2 H) 8.62 (s, 1 H) 10.02-10.32 (m, 1 H). |
| 68-3 | 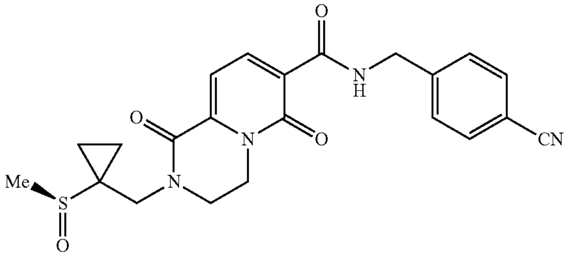 [SMILES: C[S@](=O)C1(CN2CCn3c(ccc(C(=O)NCc4ccc(C#N)cc4)c3=O)C2=O)CC1] | MS m/z = 439.3 (M + 1). $^1$H NMR (400 MHz, $CDCl_3$) δ ppm 1.05-1.20 (m, 3 H) 1.30-1.41 (m, 3 H) 2.70 (s, 3 H) 3.79 (s, 3 H) 3.92-4.04 (m, 1 H) 4.16 (s, 2 H) 4.23-4.35 (m, 1 H) 4.35-4.49 (m, 1 H) 4.70 (d, J = 6.02 Hz, 2 H) 7.35 (d, J = 7.48 Hz, 1 H) 7.45 (d, J = 8.02 Hz, 2 H) 7.62 (d, J = 8.02 Hz, 2 H) 8.63 (d, J = 7.58 Hz, 1 H) 10.07-10.28 (m, 1 H). |

Example 69

N-(4-chlorobenzyl)-2-((1-(methoxymethyl)cyclopropyl)methyl)-1,6-dioxo-2,3,4,6-tetrahydro-1H-pyrido[1,2-a]pyrazine-7-carboxamide N5-(4-chlorobenzyl)-1-(2-hydroxyethyl)-N2-((1-(methoxymethyl)cyclopropyl)methyl)-6-oxo-1,6-dihydropyridine-2,5-dicarboxamide (Ex-69A) was prepared from 1-17 and (1-(methoxymethyl)cyclopropyl)methanaminium chloride following a procedure analogous to that described for Ex-64E. Ex-69A was isolated as a dark brown residue. MS m/z 448.3 (M+1).

N5-(4-chlorobenzyl)-1-(2-chloroethyl)-N2-((1-(methoxymethyl)cyclopropyl)methyl)-6-oxo-1,6-dihydropyridine-2,5-dicarboxamide (Ex-69B) was prepared from Ex-69A following a procedure analogous to that described for Ex-67B. MS m/z 466.2 (M+1).

N-(4-chlorobenzyl)-2-((1-(methoxymethyl)cyclopropyl)methyl)-1,6-dioxo-2,3,4,6-tetrahydro-1H-pyrido[1,2-a]pyrazine-7-carboxamide (Ex-69). Sodium hydride (60% suspension in mineral oil, 7.23 mg, 0.181 mmol) was added to a stirred solution of Ex-69B (56.2 mg, 0.121 mmol) in THF (1.5 mL) at RT, resulting in rapid gas evolution. After 1 h a second portion of sodium hydride (60% suspension in mineral oil, 7.23 mg, 0.181 mmol) was added. After 5 min, the reaction mixture was diluted with water, upon which the product crashed out. The suspension was stirred at RT for 30 min, and the precipitate was collected by vacuum filtration. The solid was dried under vacuum overnight to afford Ex-69 as a pale orange solid.

| Example | Structure | Physical Data MS (m/z), $^1$H NMR |
|---|---|---|
| Ex-69 | 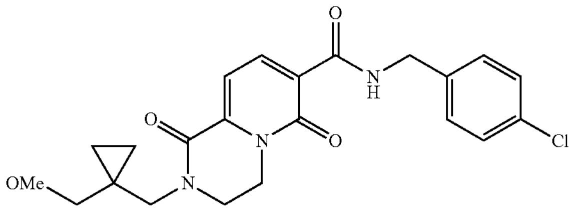 [SMILES: COCC1(CN2CCn3c(ccc(C(=O)NCc4ccc(Cl)cc4)c3=O)C2=O)CC1] | MS m/z 430.3 (M + 1). $^1$H NMR (400 MHz, $CDCl_3$) δ ppm 0.53-0.61 (m, 2 H) 0.63-0.70 (m, 2 H) 1.25 (s, 2 H) 3.25 (s, 5 H) 3.58 (s, 2 H) 3.72-3.87 (m, 2 H) 4.24-4.36 (m, 2 H) 4.61 (d, J = 5.87 Hz, 2 H) 7.29 (s, 4 H) 7.36 (d, J = 7.53 Hz, 1 H) 8.64 (d, J = 7.53 Hz, 1 H) 10.08 (br. s., 1 H). |

Example 70

N-(4-chlorobenzyl)-2-((1-(1,1-dioxidoisothiazolidin-2-yl)cyclopropyl)methyl)-1,6-dioxo-2,3,4,6-tetrahydro-1H-pyrido[1,2-a]pyrazine-7-carboxamide N5-(4-chlorobenzyl)-N2-((1-(1,1-dioxidoisothiazolidin-2-yl)cyclopropyl)methyl)-1)cyclopropyl)methyl)-1-(2-hydroxyethyl)-6-oxo-1,6-dihydropyridine-2,5-dicarboxamide (Ex-70A). Lactam 1-17 (100 mg, 0.301 mmol), 1-57 (229 mg, 1.202 mmol), and MeCN (1.2 mL) were combined in a microwave vial and stirred in the microwave for 30 min sequentially at 100° C., 140° C., and 150° C. in the microwave. $NEt_3$ (50 μL, 0.359 mmol) was added, and the reaction mixture was stirred for another 30 min at 100° C. in the microwave and then at 90° C. with conventional heating overnight. The reaction was cooled to RT and diluted with water and DCM. The mixture was extracted with DCM (3×), and the combined organic layer was washed with 1 N HCl, dried over $Na_2SO_4$, filtered, and concentrated. The crude product was purified on $SiO_2$ (0-100% (10% MeOH/EtOAc)/heptane) to afford Ex-70A. MS m/z 523.3 (M+1).

N5-(4-chlorobenzyl)-1-(2-chloroethyl)-N2-((1-(1,1-dioxidoisothiazolidin-2-yl)cyclopropyl)methyl)-6-oxo-1,6-dihydropyridine-2,5-dicarboxamide (Ex-70B) was prepared from Ex-70A following a procedure analogous to that described for Ex-67B. MS m/z 541.2 (M+1).

N-(4-chlorobenzyl)-2-((1-(1,1-dioxidoisothiazolidin-2-yl)cyclopropyl)methyl)-1,6-dioxo-2,3,4,6-tetrahydro-1H-pyrido[1,2-a]pyrazine-7-carboxamide (Ex-70) was prepared from Ex-70B following a procedure analogous to that described for Ex-69. The title compound was obtained as a white solid.

| Example | Structure | Physical Data MS (m/z), $^1$H NMR |
|---|---|---|
| 70 | 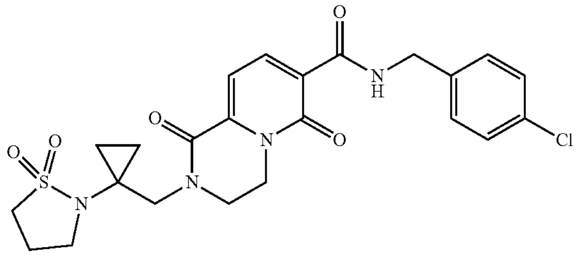 [SMILES: O=C(NCc1ccc(Cl)cc1)c1ccc2n(c1=O)CCN(CC1(N3CCCS3(=O)=O)CC1)C2=O] | MS m/z 505.2 (M + 1). $^1$H NMR (500 MHz, $CDCl_3$) δ ppm 0.84 (m, 2 H) 1.28 (m, 2 H) 2.35 (m, 2 H) 2.99 (t, J = 7.41 Hz, 2 H) 3.58 (m, 4 H) 3.91 (m, 2 H) 4.41 (m, 2 H) 4.64 (d, J = 5.99 Hz, 2 H) 7.31 (s, 4 H) 7.33 (d, J = 7.57 Hz, 1 H) 8.65 (d, J = 7.57 Hz, 1 H) 10.01-10.24 (m, 1 H). |

Example 71

N-(4-chlorobenzyl)-2-(2-(N,N-dimethylsulfamoyl)ethyl)-1,6-dioxo-2,3,4,6-tetrahydro-1H-pyrido[1,2-a]pyrazine-7-carboxamide (Ex-71)

N5-(4-chlorobenzyl)-N2-(2-(N,N-dimethylsulfamoyl)ethyl)-1-(2-hydroxyethyl)-6-oxo-1,6-dihydropyridine-2,5-dicarboxamide (Ex-71A). Lactam 1-17 (200 mg, 0.601 mmol), 1-32 (366 mg, 2.404 mmol), and acetonitrile (1.0 mL) were combined in a microwave vial. The vial was sealed and the mixture was stirred 100° C. for 60 min in the microwave. A second portion of 1-32 (80 mg, 0.526 mmol) was added and the mixture was stirred at 120° C. for 30 min in the microwave. The reaction mixture was partitioned between DI water and DCM. The aqueous layer was extracted with DCM (2×). The combined organic layer was washed with 1 N HCl (2×), dried over $Na_2SO_4$, filtered, and concentrated to yield Ex-71A as a brown oil. MS m/z 485.1 (M+1).

N5-(4-chlorobenzyl)-1-(2-chloroethyl)-N2-(2-(N,N-dimethylsulfamoyl)ethyl)-6-oxo-1,6-dihydropyridine-2,5-dicarboxamide (Ex-71B) was prepared from Ex-71A following a procedure analogous to that described for Ex-67B. MS m/z 503.1 (M+1).

N-(4-chlorobenzyl)-2-(2-(N,N-dimethylsulfamoyl)ethyl)-1,6-dioxo-2,3,4,6-tetrahydro-1H-pyrido[1,2-a]pyrazine-7-carboxamide (Ex-71) was prepared from Ex-71B following a procedure analogous to that described for Ex-64.

| Example | Structure | Physical Data MS (m/z), $^1$H NMR |
|---|---|---|
| 71 | 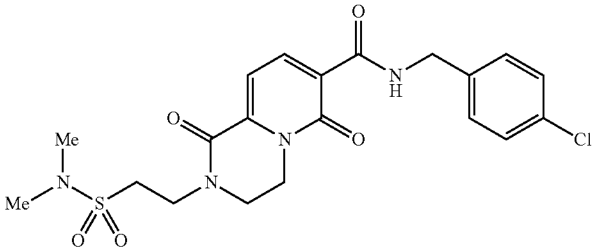 [SMILES: CN(C)S(=O)(=O)CCN1CCn2c(ccc(C(=O)NCc3ccc(Cl)cc3)c2=O)C1=O] | MS m/z 467.2 (M + 1). $^1$H NMR (500 MHz, DMSO-d6) δ ppm 2.80 (s, 6 H) 3.43-3.49 (m, 2 H) 3.80 (d, J = 5.67 Hz, 2 H) 3.85 (d, J = 7.25 Hz, 2 H) 4.24 (d, J = 5.99 Hz, 2 H) 4.54 (d, J = 5.99 Hz, 2 H) 7.22 (d, J = 7.57 Hz, 1 H) 7.31-7.38 (m, 2 H) 7.38-7.45 (m, 2 H) 8.45 (d, J = 7.57 Hz, 1 H) 10.00-10.19 (m, 1 H). |

Example 72

2-((1-(N-acetylsulfamoyl)cyclopropyl)methyl)-N-(4-chlorobenzyl)-1,6-dioxo-2,3,4,6-tetrahydro-1H-pyrido[1,2-a]pyrazine-7-carboxamide N2-((1-(N-(tert-butyl)sulfamoyl)cyclopropyl)methyl)-N5-(4-chlorobenzyl)-1-(2-hydroxyethyl)-6-oxo-1,6-dihydropyridine-2,5-dicarboxamide (Ex-72A). A microwave vial was charged with 1-17 (800 mg, 2.404 mmol), MeCN (4.8 mL), and 1-30 (1.98 g, 9.62 mmol). The vial was sealed and the reaction was stirred under microwave irradiation at 100° C. for 60 min and 140° C. for 30 min. The vial was transferred to an oil bath and stirred at 100° C. overnight. The reaction mixture was partitioned between DCM and 1 N HCl. The organic layer was again washed with 1 N HCl, and then the combined aqueous phase was extracted with DCM (3×). The combined organic layer was dried over $Na_2SO_4$, filtered, and concentrated to afford the Ex-72A, which was used without further purification. MS m/z 539.2 (M+1).

N2-((1-(N-(tert-butyl)sulfamoyl)cyclopropyl)methyl)-N5-(4-chlorobenzyl)-1-(2-chloroethyl)-6-oxo-1,6-dihydropyridine-2,5-dicarboxamide (Ex-72B). To a solution of Ex-72A (1.3 g, 2.4 mmol) in DCM (24 mL) was added $NEt_3$ (669 μL, 4.80 mmol) and MsCl (243 μL, 3.12 mmol). After 4 d, the reaction mixture was partitioned between DCM and DI water. The aqueous layer was extracted with DCM (2×), and the combined organic layer was dried over $Na_2SO_4$, filtered, and concentrated. The crude product was purified on $SiO_2$ (0-100% (10% MeOH/EtOAc)/heptane) to afford a brown solid. The aqueous layer from the extractions, which had an insoluble white precipitate, was partially concentrated to remove any organic solvent. The solid was then collected by vacuum filtration. The solid was transferred to a flask and azeotropically dried with benzene (3×). The two crops of product were combined to afford Ex-72B and were used without further purification. MS m/z 557.3 (M+1).

2-((1-(N-(tert-butyl)sulfamoyl)cyclopropyl)methyl)-N-(4-chlorobenzyl)-1,6-dioxo-2,3,4,6-tetrahydro-1H-pyrido[1,2-a]pyrazine-7-carboxamide (Ex-72-1) was prepared from Ex-72B following a procedure analogous to that described for Ex-64.

N-(4-chlorobenzyl)-1,6-dioxo-2-((1-sulfamoylcyclopropyl)methyl)-2,3,4,6-tetrahydro-1H-pyrido[1,2-a]pyrazine-7-carboxamide (Ex-72-2). TFA (2.3 mL) was added to a stirred solution of Ex-72-1 (480 mg, 0.921 mmol) and anisole (1.0 mL, 9.21 mmol) in DCM (2.3 mL) at RT. After 16 h, the reaction mixture was diluted with DCM and quenched with saturated aqueous $NaHCO_3$. The phases were separated and the aqueous phase was extracted with DCM (2×). The combined organic phase was washed with saturated aqueous $NaHCO_3$ (2×) and brine, dried over $Na_2SO_4$, filtered, and concentrated. The crude product was triturated with MeOH, and the resulting solid was collected by vacuum filtration. The solid was suspended in MeCN, filtered, and dried under high vacuum to afford Ex-72-2 as an off-white powder.

2-((1-(N-acetylsulfamoyl)cyclopropyl)methyl)-N-(4-chlorobenzyl)-1,6-dioxo-2,3,4,6-tetrahydro-1H-pyrido[1,2-a]pyrazine-7-carboxamide (Ex-72-3). To a solution of Ex-72-2 (212.7 mg, 0.457 mmol) in DCM (4.7 mL) and DMF (0.95 mL) were added DMAP (13.97 mg, 0.114 mmol), EDC (96 mg, 0.503 mmol), and AcOH (28.8 μL, 0.503 mmol) in that order. After stirring for 1 h, another portion of each reagent was added: DMAP (4.47 mg, 0.037 mmol), EDC (26.3 mg, 0.137 mmol), AcOH (7.86 μL, 0.137 mmol). After 30 min, the reaction mixture was diluted with DCM and 0.5 N HCl. The layers were separated and the aqueous phase was extracted with DCM (2×). The combined organic layer was dried over $Na_2SO_4$, filtered, and concentrated. The crude product was triturated from MeCN, and the resulting solid was collected by vacuum filtration. The solid was suspended in a minimal amount of MeCN, filtered, and dried under high vacuum to afford Ex-72-3 as an off-white solid.

| Example | Structure | Physical Data MS (m/z), $^1H$ NMR |
|---|---|---|
| 72-1 | 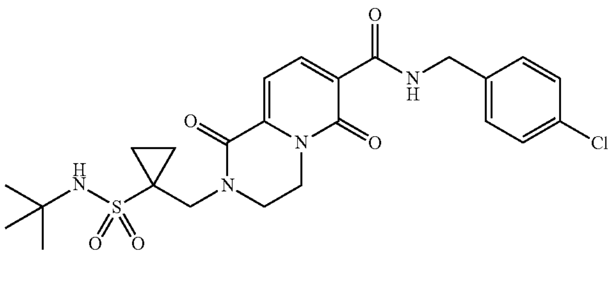 [SMILES: CC(C)(C)NS(=O)(=O)C1(CN2CCn3c(ccc(C(=O)NCc4ccc(Cl)cc4)c3=O)C2=O)CC1] | MS m/z 521.2 (M + 1). $^1H$ NMR (400 MHz, $CDCl_3$) δ ppm 0.93-1.06 (m, 2 H) 1.41 (d, J = 0.64 Hz, 9 H) 1.55-1.63 (m, 3 H) 3.80 (t, J = 5.75 Hz, 2 H) 3.95 (s, 2 H) 4.29-4.45 (m, 2 H) 4.61 (d, J = 5.67 Hz, 2 H) 5.36 (s, 1 H) 7.26 (d, J = 1.03 Hz, 3 H) 7.38 (dd, J =7.51, 0.90 Hz, 1 H) 8.63 (d, J = 6.80 Hz, 1 H) 10.03 (br. s., 1 H). |
| 72-2 | 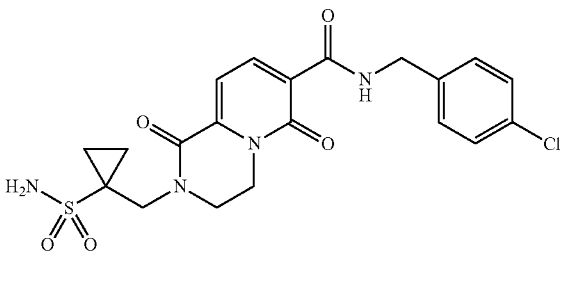 [SMILES: NS(=O)(=O)C1(CN2CCn3c(ccc(C(=O)NCc4ccc(Cl)cc4)c3=O)C2=O)CC1] | MS m/z 465.1 (M + 1) $^1H$ NMR (400 MHz, DMSO-d6) δ ppm 1.00-1.11 (m, 2 H) 1.16-1.27 (m, 2 H) 3.74-3.87 (m, 2 H) 3.95 (s, 2 H) 4.16-4.28 (m, 2 H) 4.51 (d, J = 6.02 Hz, 2 H) 6.91 (s, 2 H) 7.19 (d, J = 7.58 Hz, 1 H) 7.28-7.35 (m, 2 H) 7.35-7.44 (m, 2 H) 8.42 (d, J = 7.58 Hz, 1 H) 10.08 (s, 1 H). |

-continued

| Example | Structure | Physical Data MS (m/z), $^1$H NMR |
|---|---|---|
| 72-1 | 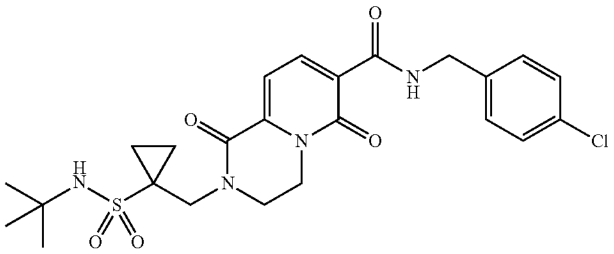 [SMILES: CC(C)(C)NS(=O)(=O)C1(CN2CCn3c(ccc(C(=O)NCc4ccc(Cl)cc4)c3=O)C2=O)CC1] | MS m/z 521.2 (M + 1). $^1$H NMR (400 MHz, $CDCl_3$) δ ppm 0.93-1.06 (m, 2 H) 1.41 (d, J = 0.64 Hz, 9 H) 1.55-1.63 (m, 3 H) 3.80 (t, J = 5.75 Hz, 2 H) 3.95 (s, 2 H) 4.29-4.45 (m, 2 H) 4.61 (d, J = 5.67 Hz, 2 H) 5.36 (s, 1 H) 7.26 (d, J = 1.03 Hz, 3 H) 7.38 (dd, J = 7.51, 0.90 Hz, 1 H) 8.63 (d, J = 6.80 Hz, 1 H) 10.03 (br. s., 1 H). |
| 72-3 | 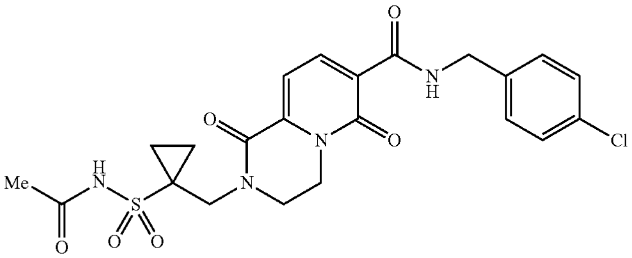 [SMILES: CC(=O)NS(=O)(=O)C1(CN2CCn3c(ccc(C(=O)NCc4ccc(Cl)cc4)c3=O)C2=O)CC1] | MS m/z 507.1 (M + 1). $^1$H NMR (400 MHz, DMSO-d6) δ ppm 1.15-1.30 (m, 3H) 1.39-1.50 (m, 2H) 1.99 (s, 3 H) 3.71-3.85 (m, 2 H) 3.94 (s, 2 H) 4.17-4.29 (m, 2 H) 4.51 (d, J = 5.97 Hz, 2 H) 7.20 (d, J = 7.53 Hz, 1 H) 7.28-7.36 (m, 2 H) 7.36-7.43 (m, 2 H) 8.43 (d, J = 7.58 Hz, 1 H) 10.08 (s, 1 H) 11.53 (s, 1 H). |

Example 73

The following examples were prepared from 1-61 and 1-30 following procedures analogous to those described in Example 72.

| Example | Structure | Physical Data MS (m/z), $^1$H NMR |
|---|---|---|
| 73-1 | 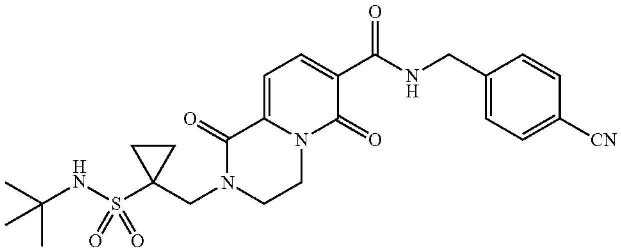 [SMILES: CC(C)(C)NS(=O)(=O)C1(CN2CCn3c(ccc(C(=O)NCc4ccc(C#N)cc4)c3=O)C2=O)CC1] | MS m/z 512.2 (M + 1). $^1$H NMR (400 MHz, $CDCl_3$) δ ppm 0.94-1.02 (m, 2 H) 1.41 (s, 8 H) 1.54-1.68 (m, 3 H) 3.75-3.88 (m, 2 H) 3.96 (s, 2 H) 4.30-4.46 (m, 2 H) 4.70 (d, J = 6.02 Hz, 2 H) 5.35 (s, 1 H) 7.39 (d, J = 7.53 Hz, 1 H) 7.45 (d, J = 8.12 Hz, 2 H) 7.62 (d, J = 8.22 Hz, 2 H) 8.62 (d, J = 7.53 Hz, 1 H) 10.16 (s, 1 H). |
| 73-2 | 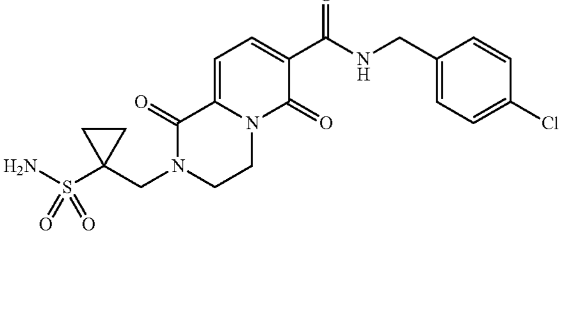 | MS m/z 456.2 (M + 1). $^1$H NMR (400 MHz, $CDCl_3$) δ ppm 1.00 (s, 2 H) 1.58 (s, 3 H) 3.75-3.89 (m, 2 H) 4.01 (s, 2 H) 4.32-4.44 (m, 2 H) 4.70 (d, J = 5.97 Hz, 2 H) 5.22 (s, 2 H) 7.39 (d, J = 7.48 Hz, 1 H) 7.45 (d, J = 8.07 Hz, 2 H) 7.62 (d, J = 8.17 Hz, 2 H) 8.63 (d, J = 7.53 Hz, 1 H) 10.08-10.27 (m, 1 H). |

-continued

| Example | Structure | Physical Data MS (m/z), $^{1}H$ NMR |
| --- | --- | --- |
| 73-3 | 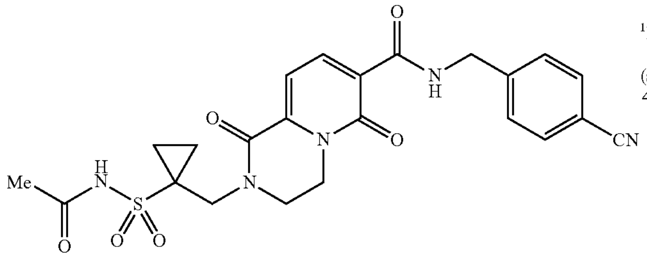 | MS m/z 498.2 (M + 1). $^{1}H$ NMR (400 MHz, $CDCl_3$) δ ppm 1.07-1.17 (m, 2 H) 1.77-1.87 (m, 2 H) 2.25 (s, 3 H) 3.76-3.89 (m, 2 H) 3.97 (s, 2 H) 4.32-4.45 (m, 2 H) 4.70 (d, J = 5.97 Hz, 2 H) 7.38 (d, J = 7.53 Hz, 1 H) 7.45 (d, J = 8.22 Hz, 2 H) 7.62 (d, J = 8.31 Hz, 2 H) 8.48 (s, 1 H) 8.63 (d, J = 7.53 Hz, 1 H) 10.06-10.28 (m, 1 H). |

Example 74

The following examples were prepared from 1-17 and 1-31 following procedures analogous to those described in Example 72.

| Example | Structure | Physical Data MS (m/z), $^{1}H$ NMR |
| --- | --- | --- |
| 74-1 | 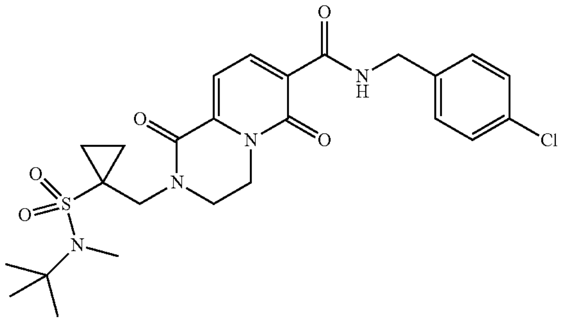 [SMILES: CN(C(C)(C)C)S(=O)(=O)C1(CN2CCn3c(ccc(C(=O)NCc4ccc(Cl)cc4)c3=O)C2=O)CC1] | MS m/z 535.2 (M + 1). $^{1}H$ NMR (500 MHz, DMSO-d6) δ ppm 1.16 (d, J = 1.83 Hz, 2 H) 1.27 (s, 2 H) 1.38 (s, 9 H) 2.76 (s, 3 H) 3.74-3.83 (m, 2 H) 3.96 (s, 2 H) 4.21-4.29 (m, 2 H) 4.54 (d, J = 6.07 Hz, 2 H) 7.21 (d, J = 7.55 Hz, 1 H) 7.31-7.37 (m, 2 H) 7.37-7.45 (m, 2 H) 8.44 (d, J = 7.55 Hz, 1 H) 10.01-10.19 (m, 1 H). |
| 74-2 | 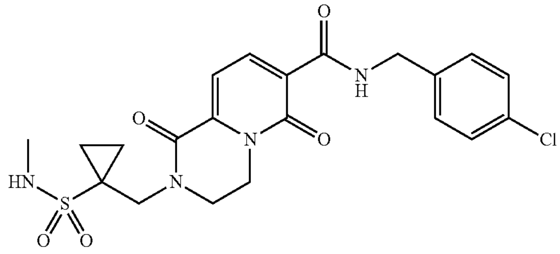 [SMILES: CNS(=O)(=O)C1(CN2CCn3c(ccc(C(=O)NCc4ccc(Cl)cc4)c3=O)C2=O)CC1] | MS m/z 479.1 (M + 1). $^{1}H$ NMR ($CDCl_3$) δ 9.99 (br s, 1H), 8.60 (d, 1H), 7.33 (d, 1H), 7.22-7.24 (m, 5H), 5.34 (br d, 1H), 4.58 (d, 3H), 4.25-4.43 (m, 2H), 3.89 (s, 2H), 3.69-3.84 (m, 3H), 2.84 (d, 3H), 0.90-0.99 (m, 2H) (one set of proton two from the cPr methylene group is buried under the water peak.) |

Example 75

The following examples were prepared from 1-61 and 1-31 following procedures analogous to those described in Example 72.

| Example | Structure | Physical Data MS (m/z), $^1$H NMR |
|---|---|---|
| 75-1 | 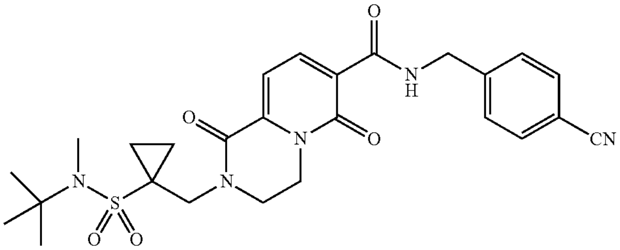 [SMILES: CN(C(C)(C)C)S(=O)(=O)C1(CN2CCn3c(ccc(C(=O)NCc4ccc(C#N)cc4)c3=O)C2=O)CC1] | MS m/z 526.3 (M + 1). $^1$H NMR (400 MHz, $CDCl_3$) δ ppm 1.08 1.19 (m, 2 H) 1.44 (s, 9 H) 2.82 (s, 3 H) 3.84-3.95 (m, 2 H) 3.98 (s, 2 H) 4.30-4.42 (m, 2 H) 4.63-4.76 (m, 3 H) 7.42-7.51 (m, 2 H) 7.56-7.67 (m, 2 H) 8.57-8.69 (m, 1 H) 10.15-10.30 (m, 1 H). |
| 75-2 | 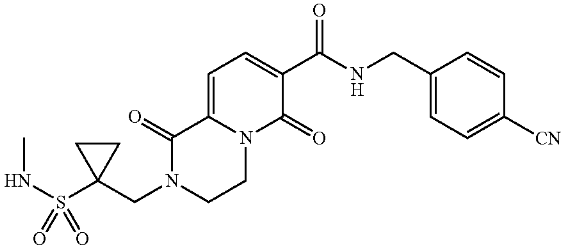 [SMILES: CNS(=O)(=O)C1(CN2CCn3c(ccc(C(=O)NCc4ccc(C#N)cc4)c3=O)C2=O)CC1] | MS m/z 470.2 (M + 1). $^1$H NMR (500 MHz, $CDCl_3$) δ ppm 1.00 (d, J = 1.26 Hz, 2 H) 2.90 (d, J = 5.36 Hz, 2 H) 3.78-3.90 (m, 2 H) 3.95 (s, 2 H) 4.34-4.49 (m, 2 H) 4.73 (d, J = 5.99 Hz, 2 H) 5.34-5.51 (m, 2 H) 7.40 (d, J = 7.57 Hz, 1 H) 7.48 (d, J = 7.88 Hz, 2 H) 7.65 (d, J = 8.51 Hz, 2 H) 8.66 (d, J = 7.57 Hz, 1 H) 10.13-10.27 (m, 2 H). |

Example 76

N-(4-chlorobenzyl)-2-((1-((1-fluorocyclopropyl)sulfonyl)cyclopropyl)methyl)-1,6-dioxo-2,3,4,6-tetrahydro-1H-pyrido[1,2-a]pyrazine-7-carboxamide 2-((1-((1-fluorocyclopropyl)sulfonyl)cyclopropyl)methyl)-1,6-dioxo-2,3,4,6-tetrahydro-1H-pyrido[1,2-a]pyrazine-7-carboxylic acid (Ex-76A). Sodium hydride (60% suspension in mineral oil, 131 mg, 3.26 mmol) was added to a solution of I-1 (575 mg, 2.176 mmol) in DMF (18 mL) at 0° C. and under $N_2$. After 15 min, a solution of 1-21 (711 mg, 2.61 mmol) in DMF (2.5 mL) was added. The mixture was allowed to warm gradually to RT and was stirred overnight. A second portion of sodium hydride (60% suspension in mineral oil, 55 mg, 1.375 mmol) was added, resulting in ester hydrolysis. LiOH (150 mg, 6.26 mmol) was added to the reaction mixture along with $H_2O$ (2 mL). When hydrolysis was determined to be complete, the reaction mixture was partitioned between DCM and water. The aqueous phase was washed twice more with DCM. The combined organic layers were extracted with 1 N NaOH. The combined aqueous layer was then acidified to pH 2 with 2 N HCl and extracted with DCM (3×). The combined organic phase was dried with $Na_2SO_4$, filtered, and concentrated to yield Ex-76A, which was used without further purification. MS m/z 385.2 (M+1).

N-(4-chlorobenzyl)-2-((1-((1-fluorocyclopropyl)sulfonyl)cyclopropyl)methyl)-1,6-dioxo-2,3,4,6-tetrahydro-1H-pyrido[1,2-a]pyrazine-7-carboxamide (Ex-76). T3P® (50% in EtOAc, 395 μL, 0.663 mmol) was added to a solution of Ex-76A (170 mg, 0.442 mmol) in DCM (4.4 mL), followed by $NEt_3$ (185 μL, 1.327 mmol). After 5 min, (4-chlorophenyl)methanamine (64.6 μL, 0.531 mmol) was added, and the mixture was stirred overnight. The reaction was diluted with 0.5 N HCl and DCM. The phases were separated and the aqueous phase was extracted with DCM (2×). The combined organic phase was washed with brine, dried over $Na_2SO_4$, filtered, and concentrated. The crude product was purified by SFC to afford Ex-76 as a white powder.

| Example | Structure | Physical Data MS (m/z), $^1$H NMR |
|---|---|---|
| 76 | 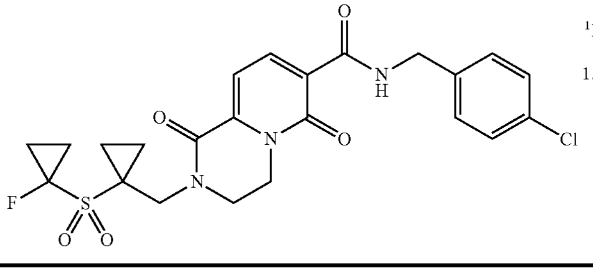 | MS m/z 508.2 (M + 1). $^1$H NMR (500 MHz, DMSO-d6) δ ppm 1.31-1.41 (m, 2 H) 1.42-1.52 (m, 2 H) 1.52-1.73 (m, 4 H) 3.76-3.87 (m, 2 H) 4.12 (s, 2 H) 4.23-4.29 (m, 2 H) 4.55 (d, J = 6.03 Hz, 2 H) 7.22 (d, J = 7.57 Hz, 1 H) 7.31-7.38 (m, 2 H) 7.38-7.46 (m, 2 H) 8.45 (d, J = 7.57 Hz, 1 H) 10.12 (s, 1 H). |

Example 77-1

N-(4-cyanobenzyl)-2-((1-((1-fluorocyclopropyl) sulfonyl)cyclopropyl)methyl)-1,6-dioxo-2,3,4,6-tetrahydro-1H-pyrido[1,2-a]pyrazine-7-carboxamide N-(4-cyanobenzyl)-2-((1-((1-fluorocyclopropyl)sulfonyl) cyclopropyl)methyl)-1,6-dioxo-2,3,4,6-tetrahydro-1H-pyrido[1,2-a]pyrazine-7-carboxamide (Ex-77-1). T3P® (50% in EtOAc, 395 μL, 0.663 mmol) was added to a solution of Ex-76A (170 mg, 0.442 mmol) in DCM (4.4 mL), followed by $NEt_3$ (185 μL, 1.327 mmol). After 5 min, (4-cyanophenyl)methanaminium chloride (89 mg, 0.531 mmol) was added. The reaction was stirred overnight, after which it was diluted with 0.5 N HCl and DCM. The phases were separated and the aqueous phase was extracted with DCM (2×). The combined organic phase was washed with brine, dried over $Na_2SO_4$, filtered, and concentrated. The crude product was purified by SFC to afford Ex-77-1 as a white powder.

Other compounds in the table below were prepared following procedures analogous to that described for Ex-77-1.

| Example | Structure | Physical Data MS (m/z), $^1$H NMR |
|---|---|---|
| 77-1 | 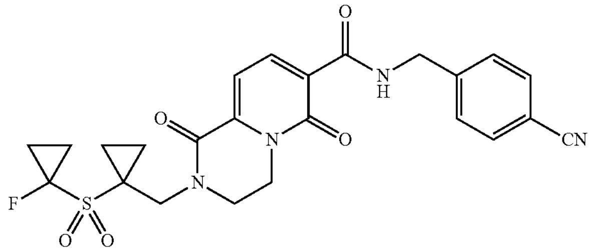 [SMILES: N#Cc1ccc(CNC(=O)c2ccc3n(c2=O)CCN(CC2(S(=O)(=O)C4(F)CC4)CC2)C3=O)cc1] | MS m/z 499.2 (M + 1). $^1$H NMR (500 MHz, DMSO-d6) δ ppm 1.26-1.42 (m, 2 H) 1.42-1.52 (m, 2 H) 1.52-1.78 (m, 4 H) 3.75-3.86 (m, 2 H) 4.13 (s, 2 H) 4.21-4.36 (m, 2 H) 4.65 (d, J = 6.03 Hz, 2 H) 7.22 (d, J = 7.57 Hz, 1 H) 7.51 (d, J = 8.51 Hz, 2 H) 7.74-7.90 (m, 2 H) 8.44 (d, J = 7.57 Hz, 1 H) 10.19 (t, J = 6.15 Hz, 1 H). |
| 77-2 | 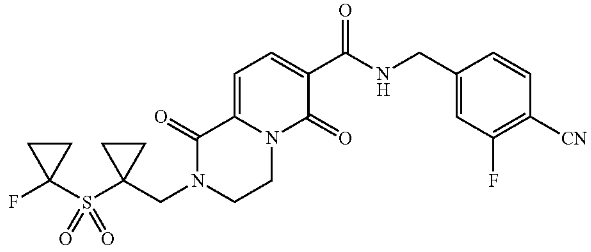 [SMILES: N#Cc1ccc(CNC(=O)c2ccc3n(c2=O)CCN(CC2(S(=O)(=O)C4(F)CC4)CC2)C3=O)cc1F] | MS m/z 517.1 (M + 1). $^1$H NMR (500 MHz, DMSO-d6) δ ppm 1.29-1.39 (m, 2 H) 1.43-1.52 (m, 2 H) 1.55-1.76 (m, 4 H) 3.74-3.89 (m, 2 H) 4.13 (s, 2 H) 4.20-4.33 (m, 2 H) 4.66 (d, J = 6.03 Hz, 2 H) 7.21 (d, J = 7.57 Hz, 1 H) 7.36 (dd, J = 8.04, 1.30 Hz, 1 H) 7.45 (dd, J = 10.52, 0.95 Hz, 1 H) 7.91 (dd, J = 7.86, 7.03 Hz, 1 H) 8.43 (d, J = 7.57 Hz, 1 H) 10.20 (s, 1 H). |

Example 78

N-(4-chlorobenzyl)-2-((1-(cyclobutylsulfonyl)cyclopropyl)methyl)-1,6-dioxo-2,3,4,6-tetrahydro-1H-pyrido[1,2-a]pyrazine-7-carboxamide (Ex-78)

2-((1-(cyclobutylsulfonyl)cyclopropyl)methyl)-1,6-dioxo-2,3,4,6-tetrahydro-1H-pyrido[1,2-a]pyrazine-7-carboxylic acid (Ex-78A) was prepared from I-1 and 1-22 following a procedure analogous to that described for Ex-1A. Ex-78A was isolated as an orange-brown solid. MS m/z 381.3 (M+1).

N-(4-chlorobenzyl)-2-((1-(cyclobutylsulfonyl)cyclopropyl)methyl)-1,6-dioxo-2,3,4,6-tetrahydro-1H-pyrido[1,2-a] pyrazine-7-carboxamide (Ex-78) was prepared from Ex-78A following a procedure analogous to that described for Ex-76. Other compounds in the table below were prepared from Ex-78A following procedures analogous to those described for Ex-76 or Ex-77-1.

| Example | Structure | Physical Data MS (m/z), $^1H$ NMR |
|---|---|---|
| 78 | 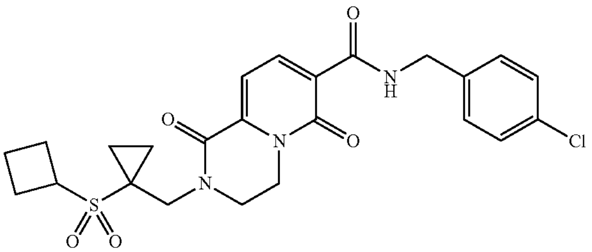 [SMILES: O=C(NCc1ccc(Cl)cc1)c1ccc2n(c1=O)CCN(CC1(S(=O)(=O)C3CCC3)CC1)C2=O] | MS m/z 504.2 (M + 1). $^1H$ NMR (500 MHz, DMSO-d6) δ ppm 1.12 (d, J = 1.95 Hz, 2 H) 1.26 (d, J = 1.72 Hz, 2 H) 1.76-1.92 (m, 1 H) 1.95-2.11 (m, 1 H) 2.25 (br. s., 2 H) 2.35 (d, J = 9.38 Hz, 2 H) 3.73-3.84 (m, 2 H) 3.95 (s, 2 H) 4.18-4.28 (m, 2 H) 4.42 (s, 1 H) 4.54 (d, J = 5 .95 Hz, 2 H) 7.22 (d, J = 7.55 Hz, 1 H) 7.29-7.38 (m, 2 H) 7.38-7.45 (m, 2 H) 8.44 (d, J = 7.55 Hz, 1 H) 10.11 (s, 1 H). |
| 79-1 | 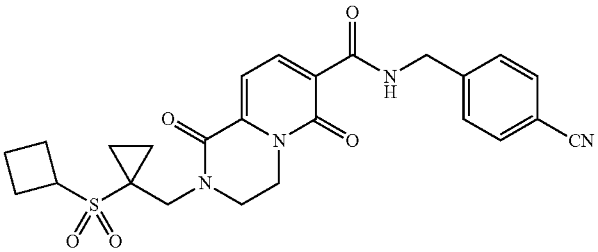 [SMILES: N#Cc1ccc(CNC(=O)c2ccc3n(c2=O)CCN(CC2(S(=O)(=O)C4CCC4)CC2)C3=O)cc1] | MS m/z 495.3 (M + 1). $^1H$ NMR (500 MHz, DMSO-d6) δ ppm 1.12 (d, J = 1.83 Hz, 2 H) 1.26 (d, J = 1.83 Hz, 2 H) 1.76-1.92 (m, 1 H) 1.94-2.11 (m, 1 H) 2.24 (d, J = 9.27 Hz, 2 H) 2.36 (d, J = 9.38 Hz, 2 H) 3.70-3.85 (m, 2 H) 3.95 (s, 2 H) 4.21-4.30 (m, 2 H) 4.42 (s, 1 H) 4.64 (d, J = 6.07 Hz, 2 H) 7.22 (d, J = 7.55 Hz, 1 H) 7.50 (d, J = 8.13 Hz, 2 H) 7.81 (d, J = 8.13 Hz, 2 H) 8.44 (d, J = 7.44 Hz, 1 H) 10.18 (s, 1 H). |
| 79-2 | 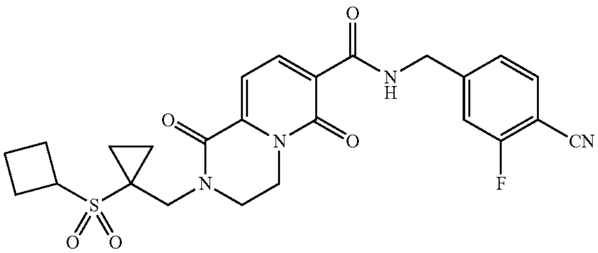 [SMILES: N#Cc1ccc(CNC(=O)c2ccc3n(c2=O)CCN(CC2(S(=O)(=O)C4CCC4)CC2)C3=O)cc1F] | MS m/z 513.2 (M + 1). $^1H$ NMR (500 MHz, DMSO-d6) δ ppm 1.08-1.14 (m, 2 H) 1.21-1.31 (m, 2 H) 1.87 (br. s., 1 H) 2.03 (d, J = 9.73 Hz, 1 H) 2.25 (dd, J = 8.58, 3.78 Hz, 2 H) 2.30-2.45 (m, 2 H) 3.71-3.84 (m, 2 H) 3.95 (s, 2 H) 4.18-4.32 (m, 2 H) 4.43 (t, J = 8.47 Hz, 1 H) 4.65 (d, J = 6.07 Hz, 2 H) 7.21 (d, J = 7.55 Hz, 1 H) 7.35 (d, J = 8.13 Hz, 1 H) 7.44 (d, J = 10.53 Hz, 1 H) 7.90 (t, J = 7.44 Hz, 1 H) 8.43 (d, J = 7.55 Hz, 1 H) 10.19 (t, J = 6.12 Hz, 1 H). |

Example 80-2

N-(4-chlorobenzyl)-2-((1-((1-methylpyrrolidin-3-yl) sulfonyl)cyclopropyl)methyl)-1,6-dioxo-2,3,4,6-tetrahydro-1H-pyrido[1,2-a]pyrazine-7-carboxamide 2-((1-((1-(tert-butoxycarbonyl)pyrrolidin-3-yl)sulfonyl) cyclopropyl)methyl)-1,6-dioxo-2,3,4,6-tetrahydro-1H-pyrido[1,2-a]pyrazine-7-carboxylic acid (Ex-80A) was prepared from I-1 and 1-23 following a procedure analogous to that described for Ex-1A. MS m/z 496.3 (M+1).

Tert-butyl 3-((1-((7-((4-chlorobenzyl)carbamoyl)-1,6-dioxo-3,4-dihydro-1H-pyrido[1,2-a] pyrazin-2 (6H)-yl) methyl)cyclopropyl)sulfonyl)pyrrolidine-1-carboxylate (Ex-80B) was prepared from Ex-80A following a procedure analogous to that described for Ex-76. MS m/z 619.4 (M+1).

N-(4-chlorobenzyl)-1,6-dioxo-2-((1-(pyrrolidin-3-ylsulfonyl)cyclopropyl)methyl)-2,3,4,6-tetrahydro-1H-pyrido[1,2-a]pyrazine-7-carboxamide (Ex-80-1) was prepared from Ex-80B following a procedure analogous to that described for Ex-16. Ex-80-1 as a pale yellow powder.

N-(4-chlorobenzyl)-2-((1-((1-methylpyrrolidin-3-yl) sulfonyl)cyclopropyl)methyl)-1,6-dioxo-2,3,4,6-tetrahydro-1H-pyrido[1,2-a]pyrazine-7-carboxamide (Ex-80-2). To a solution of Ex-80-1 (136.7 mg, 0.263 mmol) in DCM (2.6 mL) at RT was added formaldehyde (19.61 μL, 0.263 mmol) and sodium triacetoxyborohydride (84 mg, 0.395 mmol). After 1 h, the reaction mixture was quenched by addition of saturated aqueous $NaHCO_3$ and extracted with DCM (3×). Upon addition of 1 N HCl to the organic phase, the mixture became an emulsion. The mixture was basified with 6 N NaOH and re-extracted with DCM. The organic phase was dried over $Na_2SO_4$, filtered, and concentrated. The crude product was purified by SFC to afford the Ex-80-2 as a fluffy white powder.

| Example | Structure | Physical Data MS (m/z), $^1H$ NMR |
|---|---|---|
| 80-1 | 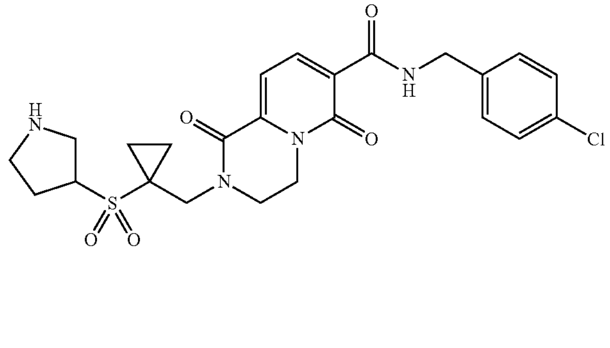 [SMILES: O=C(NCc1ccc(Cl)cc1)c1ccc2n(c1=O)CCN(CC1(S(=O)(=O)C3CCNC3)CC1)C2=O] | MS m/z 519.3 (M + 1). $^1H$ NMR (500 MHz, DMSO-d6) δ ppm 1.19 (s, 2 H) 1.31 (s, 2 H) 1.94-2.03 (m, 1 H) 2.03-.15 (m, 1 H) 2.55 (s, 2 H) 2.80-2.90 (m, 2 H) 3.02-3.10 (m, 1 H) 3.15-3.26 (m, 1 H) 3.74-3.86 (m, 2 H) 4.04 (s, 2 H) 4.14-4.22 (m, 1 H) 4.22-4.30 (m, 2 H) 4.54 (d, J = 5.91 Hz, 2 H) 7.22 (d, J = 7.57 Hz, 1 H) 7.31-7.38 (m, 2 H) 7.38-7.45 (m, 2 H) 8.45 (d, J = 7.57 Hz, 1 H) 10.10 (s, 1H). |

-continued

| Example | Structure | Physical Data MS (m/z), $^1$H NMR |
|---|---|---|
| 80-2 | 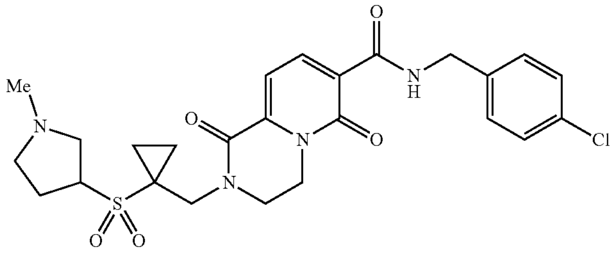 [SMILES: CN1CCC(S(=O)(=O)C2(CN3CCn4c(ccc(C(=O)NCc5ccc(Cl)cc5)c4=O)C3=O)CC2)C1] | MS m/z 533.3 (M + 1). $^1$H NMR (500 MHz, DMSO-d6) δ ppm 1.11-1.24 (m, 2 H) 1.24-1.39 (m, 2 H) 2.03-2.22 (m, 2 H) 2.27 (s, 3 H) 2.34-2.45 (m, 1 H) 2.58-2.69 (m, 2 H) 2.93 (t, J = 9.04 Hz, 1 H) 3.73-3.82 (m, 2 H) 3.95-4.04 (m, 1 H) 4.04-4.11 (m, 1 H) 4.22-4.29 (m, 2 H) 4.36 (dd, J = 9.69, 8.28 Hz, 1 H) 4.55 (d, J = 6.03 Hz, 2 H) 7.23 (d, J = 7.57 Hz, 1 H) 7.31-7.39 (m, 2 H) 7.39-7.45 (m, 2 H) 8.45 (d, J = 7.45 Hz, 1 H) 10.11 (t, J = 6.09 Hz, 1 H). |

Example 81

Compounds in the table below were prepared from Ex-80A following procedures analogous to those described for Ex-77-1 and Ex-80-2.

| Example | Structure | Physical Data MS (m/z), $^1$H NMR |
|---|---|---|
| 81-1 | 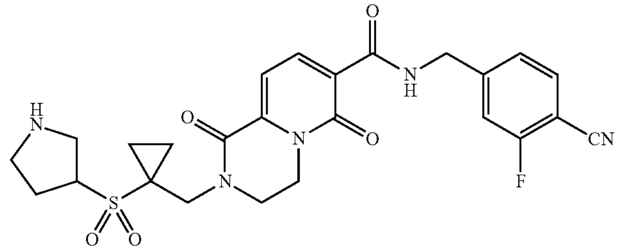 [SMILES: N#Cc1ccc(CNC(=O)c2ccc3n(c2=O)CCN(CC2(S(=O)(=O)C4CCNC4)CC2)C3=O)cc1F] | MS m/z 528.3 (M + 1). $^1$H NMR (500 MHz, DMSO-d6) δ ppm 1.19 (br. s., 2 H) 1.31 (s, 2H) 1.88-2.19 (m, 2 H) 2.81 (br. s., 2 H) 2.94-3.08 (m, 1 H) 3.11-3.24 (m, 1 H) 3.81 (t, J = 5.50 Hz, 2 H) 4.04 (s, 2 H) 4.13-4.22 (m, 1 H) 4.22-4.33 (m, 2 H) 4.65 (d, J = 5.91 Hz, 2 H) 7.21 (d, J = 7.45 Hz, 1 H) 7.35 (d, J = 8.28 Hz, 1 H) 7.44 (d, J = 10.52 Hz, 1 H) 7.89 (s, 1 H) 8.43 (d, J = 7.45 Hz, 1 H) 10.19 (s, 1 H). |
| 81-2 | 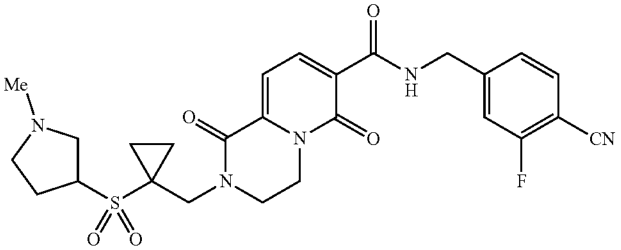 [SMILES: CN1CCC(S(=O)(=O)C2(CN3CCn4c(ccc(C(=O)NCc5ccc(C#N)c(F)c5)c4=O)C3=O)CC2)C1] | MS m/z 542.3 (M + 1). $^1$H NMR (500 MHz, DMSO-d6) δ ppm 1.19 (d, J = 2.25 Hz, 2 H) 1.26-1.40 (m, 2 H) 2.01-2.22 (m, 2 H) 2.30 (s, 3 H) 2.39-2.47 (m, 1 H) 2.60-2.77 (m, 2 H) 2.89-3.04 (m, 1 H) 3.13-3.23 (m, 1 H) 3.74-3.88 (m, 2 H) 4.02 (s, 1 H) 4.07 (s, 1 H) 4.19-4.32 (m, 2 H) 4.32-4.45 (m, 1 H) 4.66 (d, J = 6.15 Hz, 2 H) 7.22 (d, J = 7.57 Hz, 1 H) 7.30-7.40 (m, 1 H) 7.45 (dd, J = 10.52, 1.06 Hz, 1 H) 7.91 (dd, J = 7.92, 6.98 Hz, 1 H) 8.44 (d, J = 7.57 Hz, 1 H) 10.19 (s, 1 H). |
| 81-3 | 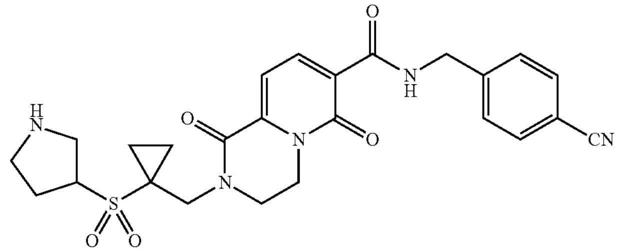 [SMILES: N#Cc1ccc(CNC(=O)c2ccc3n(c2=O)CCN(CC2(S(=O)(=O)C4CCNC4)CC2)C3=O)cc1] | MS m/z 510.4 (M + 1). $^1$H NMR (500 MHz, DMSO-d6) δ ppm 1.20 (s, 2 H) 1.31 (s, 2 H) 1.93-2.16 (m, 2 H) 2.86 (s, 2 H) 3.01-3.14 (m, 1 H) 3.15-3.25 (m, 2 H) 3.75-3.86 (m, 2 H) 4.04 (s, 2 H) 4.15-4.23 (m, 1 H) 4.23-4.32 (m, 3 H) 4.64 (d, J = 6.03 Hz, 2 H) 7.21 (d, J = 7.57 Hz, 1 H) 7.50 (d, J = 8.39 Hz, 2 H) 7.78-7.86 (m, 2 H) 8.44 (d, J = 7.57 Hz, 1 H) 10.17 (s, 1 H). |
| 81-1 | 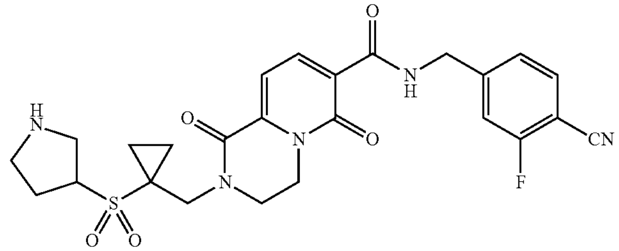 [SMILES: N#Cc1ccc(CNC(=O)c2ccc3n(c2=O)CCN(CC2(S(=O)(=O)C4CCNC4)CC2)C3=O)cc1F] | MS m/z 528.3 (M + 1). $^1$H NMR (500 MHz, DMSO-d6) δ ppm 1.19 (br. s., 2 H) 1.31 (s, 2 H) 1.88-2.19 (m, 2 H) 2.81 (br. s., 2 H) 2.94-3.08 (m, 1 H) 3.11-3.24 (m, 1 H) 3.81 (t, J = 5.50 Hz, 2 H) 4.04 (s, 2 H) 4.13-4.22 (m, 1 H) 4.22-4.33 (m, 2 H) 4.65 (d, J = 5.91 Hz, 2 H) 7.21 (d, J = 7.45 Hz, 1 H) 7.35 (d, J = 8.28 Hz, 1 H) 7.44 (d, J = 10.52 Hz, 1 H) 7.89 (s, 1 H) 8.43 (d, J = 7.45 Hz, 1 H) 10.19 (s, 1 H). |

-continued

| Example | Structure | Physical Data MS (m/z), $^1$H NMR |
|---|---|---|
| 81-4 | 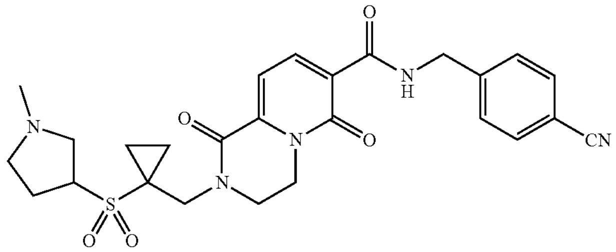 [SMILES: CN1CCC(S(=O)(=O)C2(CN3CCn4c(ccc(C(=O)NCc5ccc(C#N)cc5)c4=O)C3=O)CC2)C1] | MS m/z 524.4 (M + 1). $^1$H NMR (400 MHz, $CDCl_3$) δ ppm 1.40-1.76 (m, 5 H) 2.20-2.47 (m, 4 H) 2.62 (d, J = 8.61 Hz, 1 H) 2.68-2.84 (m, 1 H) 2.89 (br. s., 1 H) 2.96-3.18 (m, 1 H) 3.78-3.91 (m, 2 H) 3.99 (s, 2 H) 4.10-4.25 (m, 1 H) 4.29-4.44 (m, 2 H) 4.70 (d, J = 6.02 Hz, 2 H) 7.35 (d, J = 7.24 Hz, 1 H) 7.45 (d, J = 8.02 Hz, 2 H) 7.62 (d, J = 8.02 Hz, 2 H) 8.63 (d, J = 7.58 Hz, 1 H) 10.16 (br. s., 1 H). |

Example 82

N-(4-cyano-3-fluorobenzyl)-2-((1,1-dioxidotetrahydrothiophen-2-yl)methyl)-1,6-dioxo-2,3,4,6-tetrahydro-1H-pyrido pyrazine-7-carboxamide 2-((1,1-dioxidotetrahydrothiophen-2-yl)methyl)-1,6-dioxo-2,3,4,6-tetrahydro-1H-pyrido[1,2-a]pyrazine-7-carboxylic acid (Ex-82A). Sodium hydride (60% suspension in mineral oil, 74.5 mg, 1.862 mmol) was added to a solution of I-1 (376 mg, 1.424 mmol) in DMF (10 mL) at 0° C. and under $N_2$. After 15 min, a solution of 1-29 (250 mg, 1.095 mmol) in DMF (1 mL) was added. The mixture was allowed to warm gradually to RT and was stirred for 3 d. The crude reaction mixture was partitioned between DCM and water. The aqueous layer was extracted with DCM (2×). The aqueous layer was then acidified with 1 N HCl and extracted with DCM (3×). The combined organic layer was washed with brine, dried over $Na_2SO_4$, filtered, and concentrated. The crude alkylation product was dissolved in THF (8.8 mL) and water (2.2 mL), and lithium hydroxide (131 mg, 5.48 mmol) was added at RT.

Hydrolysis was complete within 30 min, and the reaction mixture was acidified with 1 N HCl and extracted with DCM (3×). The combined organic layer was washed with brine, dried over $Na_2SO_4$, and filtered to yield Ex-82A as a tan solid. MS m/z 341.3 (M+1).

N-(4-cyano-3-fluorobenzyl)-2-((1,1-dioxidotetrahydrothiophen-2-yl)methyl)-1,6-dioxo-2,3,4,6-tetrahydro-1H-pyrido[1,2-a]pyrazine-7-carboxamide (Ex-82) was prepared from Ex-82A following a procedure analogous to that described for Ex-77-1.

| Example | Structure | Physical Data MS (m/z), $^1$H NMR |
|---|---|---|
| 82 | 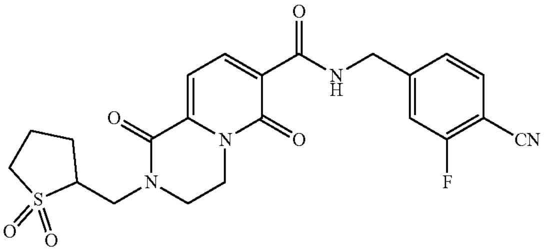 [SMILES: N#Cc1ccc(CNC(=O)c2ccc3n(c2=O)CCN(CC2CCCS2(=O)=O)C3=O)cc1F] | MS m/z 473.3 (M + 1). $^1$H NMR (500 MHz, DMSO-d6) δ ppm 1.72-1.88 (m, 1 H) 1.92-2.06 (m, 1 H) 2.06-2.21 (m, 1 H) 2.24-2.35 (m, 1 H) 3.11 (s, 1 H) 3.15-3.24 (m, 1 H) 3.44-3.55 (m, 1 H) 3.57-3.70 (m, 1 H) 3.82 (d, J = 4.58 Hz, 2 H) 3.86-3.96 (m, 1 H) 4.12-4.25 (m, 1 H) 4.25-4.39 (m, 1 H) 4.64 (d, J = 6.18 Hz, 2 H) 7.21 (d, J = 7.55 Hz, 1 H) 7.35 (d, J = 8.13 Hz, 1 H) 7.44 (d, J = 10.41 Hz, 1 H) 7.89 (s, 1 H) 8.43 (d, J = 7.55 Hz, 1 H) 10.18 (s, 1 H). |

Example 83

N-(4-cyanobenzyl)-2-((3,3-difluorocyclobutyl)sulfonyl)cyclopropyl)methyl)-1,6-dioxo-2,3,4,6-tetrahydro-1H-pyrido[1,2-a]pyrazine-7-carboxamide (Ex-83)

2-((1-((3,3-difluorocyclobutyl)sulfonyl)cyclopropyl)methyl)-1,6-dioxo-2,3,4,6-tetrahydro-1H-pyrido[1,2-a]pyrazine-7-carboxylic acid (Ex-83A) was prepared from I-1 and 1-24 following a procedure analogous to that described for Ex-1A. Ex-83A was obtained as an orange-brown solid. MS m/z 417.2 (M+1).

N-(4-cyanobenzyl)-2-((1-((3,3-difluorocyclobutyl)sulfonyl)cyclopropyl)methyl)-1,6-dioxo-2,3,4,6-tetrahydro-1H-pyrido[1,2-a]pyrazine-7-carboxamide (Ex-83) was prepared from Ex-83A following a procedure analogous to that described for Ex-77-1.

| Example | Structure | Physical Data MS (m/z), $^1$H NMR |
|---|---|---|
| 83 | 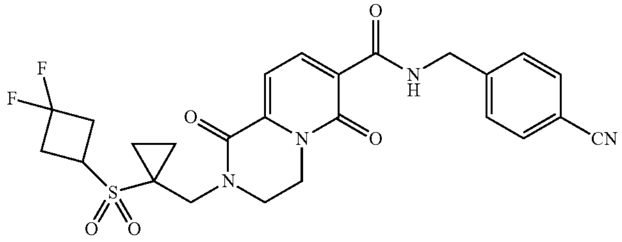 [SMILES: N#Cc1ccc(CNC(=O)c2ccc3n(c2=O)CCN(CC2(S(=O)(=O)C4CC(F)(F)C4)CC2)C3=O)cc1] | MS m/z 531.3 (M + 1). $^1$H NMR (500 MHz, DMSO-d6) δ ppm 1.19 (br. s., 2 H) 1.35 (br. s., 2 H) 2.88-3.13 (m, 4 H) 3.70-3.83 (m, 2 H) 4.02 (br. s., 2 H) 4.25 (d, J = 5.20 Hz, 2 H) 4.33-4.45 (m, 1 H) 4.64 (d, J = 6.15 Hz, 2 H) 7.22 (d, J = 7.33 Hz, 1 H) 7.50 (d, J = 8.04 Hz, 2 H) 7.81 (d, J = 8.28 Hz, 2 H) 8.44 (d, J = 7.57 Hz, 1 H) 10.10-10.24 (m, 2 H). |

Example 84

N-(4-cyanobenzyl)-2-((1-((3,3-difluoroazetidin-1-yl)sulfonyl)cyclopropyl)methyl)-1,6-dioxo-2,3,4,6-tetrahydro-1H-pyrido[1,2-a]pyrazine-7-carboxamide 2-((1-((3,3-difluoroazetidin-1-yl)sulfonyl)cyclopropyl)methyl)-1,6-dioxo-2,3,4,6-tetrahydro-1H-pyrido[1,2-a]pyrazine-7-carboxylic acid (Ex-84A) was prepared from I-1 and 1-25 following a procedure analogous to that described for Ex-82A. MS m/z 418.2 (M+1).

N-(4-cyanobenzyl)-2-((1-((3,3-difluoroazetidin-1-yl)sulfonyl)cyclopropyl)methyl)-1,6-dioxo-2,3,4,6-tetrahydro-1H-pyrido[1,2-a]pyrazine-7-carboxamide (Ex-84-1) was prepared from Ex-84A following a procedure analogous to that described for Ex-77-1.

Other compounds in the table below may be prepared from Ex-84A following the procedures analogous to those described for Ex-76 and Ex-77-1.

| Example | Structure | Physical Data MS (m/z), $^1$H NMR |
|---|---|---|
| 84-1 | 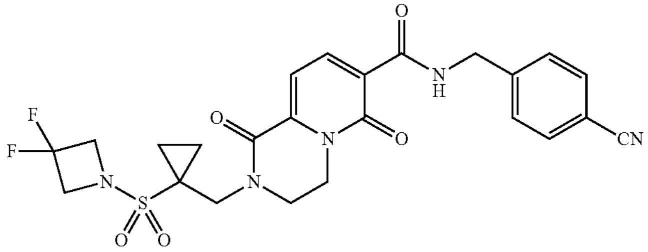 [SMILES: N#Cc1ccc(CNC(=O)c2ccc3n(c2=O)CCN(CC2(S(=O)(=O)N4CC(F)(F)C4)CC2)C3=O)cc1] | MS m/z 532.2 (M + 1). $^1$H NMR (500 MHz, DMSO-d6) δ ppm 1.28 (d, J = 8.58 Hz, 4 H) 3.74-3.87 (m, 2 H) 3.96 (s, 2 H) 4.21-4.31 (m, 2 H) 4.39 (t, J = 12.65 Hz, 4 H) 4.64 (d, J = 6.07 Hz, 2 H) 7.14-7.28 (m, 1 H) 7.51 (d, J = 8.13 Hz, 2 H) 7.81 (d, J = 8.24 Hz, 2 H) 8.37-8.51 (m, 1 H) 10.12-10.27 (m, 1 H). |
| 84-2 | 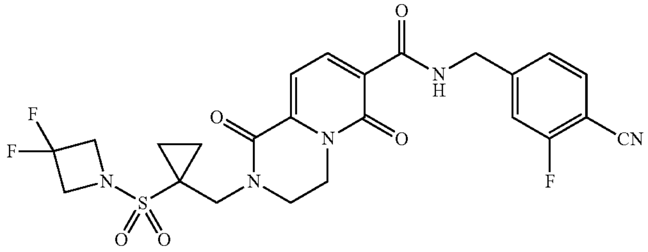 [SMILES: N#Cc1ccc(CNC(=O)c2ccc3n(c2=O)CCN(CC2(S(=O)(=O)N4CC(F)(F)C4)CC2)C3=O)cc1F] | MS m/z 550.3 (M + 1). $^1$H NMR (500 MHz, DMSO-d6) δ ppm 1.28 (d, J = 8.70 Hz, 4 H) 3.74-3.86 (m, 2 H) 3.96 (s, 2 H) 4.21-4.30 (m, 2 H) 4.39 (s, 4 H) 4.59-4.73 (m, 2 H) 7.15-7.28 (m, 1 H) 7.29-7.40 (m, 1 H) 7.40-7.52 (m, 1 H) 7.82-7.99 (m, 1 H) 8.35-8.51 (m, 1 H) 10.06-10.27 (m, 1 H). |
| 84-3 | 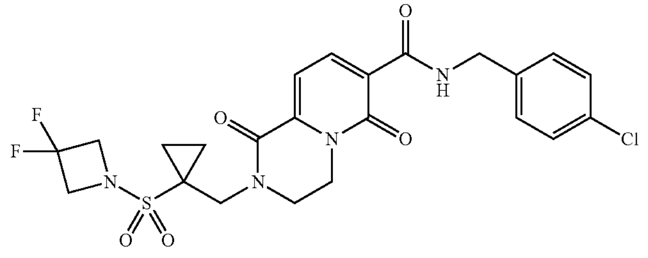 [SMILES: O=C(NCc1ccc(Cl)cc1)c1ccc2n(c1=O)CCN(CC1(S(=O)(=O)N3CC(F)(F)C3)CC1)C2=O] | MS m/z 541.2 (M + 1). $^1$H NMR (500 MHz, DMSO-d6) δ ppm 1.21-1.37 (m, 4 H) 3.75-3.85 (m, 2 H) 3.96 (s, 2 H) 4.19-4.32 (m, 2 H) 4.39 (s, 4 H) 4.51-4.61 (m, 2 H) 7.12-7.26 (m, 1 H) 7.40 (s, 4 H) 8.38-8.52 (m, 1H) 10.00-10.21 (m, 1H). |

Example 85

Methyl 9-methyl-2-(methylsulfonyl)cyclopropyl) methyl)-1,6-dioxo-2,3,4,6-tetrahydro-1H-pyrido[1,2-a]pyrazine-7-carboxylate 9-methyl-1,6-dioxo-2,3,4,6-tetrahydro-1H-pyrido[1,2-a] pyrazine-7-carboxylic acid (Ex-85A) was prepared from 1-35 and 1-14 following a procedure analogous to that described for Ex-82A. MS m/z 411.3 (M+1).

N-(4-cyanobenzyl)-9-methyl-2-((1-(methylsulfonyl)cyclopropyl)methyl)-1,6-dioxo-2,3,4,6-tetrahydro-111-pyrido [1,2-a]pyrazine-7-carboxamide (Ex-85). To a solution of Ex-85A (80 mg, 0.226 mmol) in DCM (2.257 mL) at RT was added oxalyl chloride (0.030 mL, 0.339 mmol) followed by a drop of DMF. After 45 min the mixture was concentrated in vacuo to a yellow solid. This was dissolved in DCM (2 mL) and added dropwise by pipette to a stirred solution of p-CN-benzylamine (41.9 mg, 0.248 mmol) and Huenig's Base (0.138 mL, 0.790 mmol) in DCM (1 mL). After 3 h, T3P® (50% in EtOAc, 43.1 mg, 0.068 mmol) was added. The reaction mixture was diluted with DCM and washed with 1 N HCl (2×) and saturated aq. $NaHCO_3$ (1×). The organic layer was dried over $Na_2SO_4$, filtered, and concentrated to yield a pale yellow solid. The crude product was purified on $SiO_2$ (0-100% (10% MeOH/EtOAc)/heptane) to afford Ex-85 as a white solid.

| Example | Structure | Physical Data MS (m/z), $^1$H NMR |
|---|---|---|
| 85 | 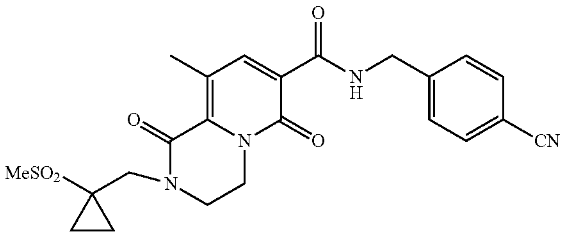 | MS m/z 469.2 (M + 1). $^1$H NMR (400 MHz, $CDCl_3$) δ ppm 0.98-1.14 (m, 2 H) 1.58-1.73 (m, 2 H) 2.53 (s, 3 H) 3.09 (s, 3 H) 3.77 (t, J = 5.33 Hz, 2 H) 4.00 (s, 2 H) 4.37 (t, J = 5.28 Hz, 2 H) 4.69 (d, J = 5.92 Hz, 2 H) 7.44 (d, J = 7.87 Hz, 2 H) 7.61 (d, J = 7.92 Hz, 2 H) 8.45 (s, 1 H) 10.26 (t, J = 5.50 Hz, 1 H). |

Compounds in the table below were prepared from Ex-85A following a procedure analogous to that described for Ex-1.

| Example | Structure | Physical Data MS (m/z), $^1$H NMR |
|---|---|---|
| 86-1 | 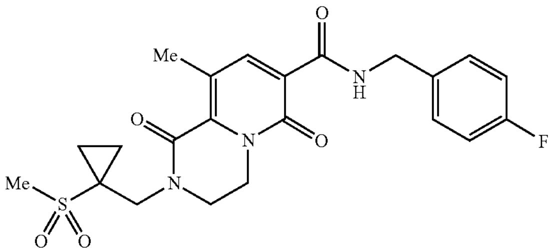 [SMILES: Cc1cc(C(=O)NCc2ccc(F)cc2)c(=O)n2c1C(=O)N(CC1(S(C)(=O)=O)CC1)CC2] | MS m/z 462.2 (M + 1). $^1$H NMR (500 MHz, $CDCl_3$) δ ppm 1.11 (d, J = 1.58 Hz, 2 H) 1.64 (d, J = 1.58 Hz, 2 H) 2.55 (s, 3 H) 3.12 (s, 3 H) 3.73-3.82 (m, 2 H) 4.02 (s, 2 H) 4.33-4.46 (m, 2 H) 4.63 (d, J = 5.99 Hz, 2 H) 7.03 (t, J = 8.67 Hz, 2 H) 7.34 (dd, J = 8.51, 5.36 Hz, 2 H) 8.49 (s, 1 H) 10.05-10.23 (m, 1 H). |
| 86-2 | 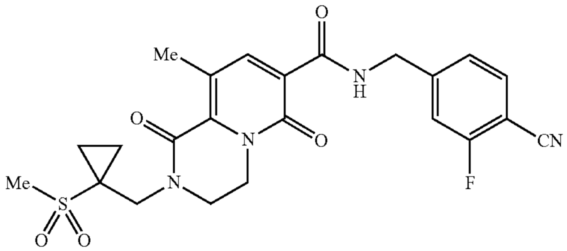 [SMILES: Cc1cc(C(=O)NCc2ccc(C#N)c(F)c2)c(=O)n2c1C(=O)N(CC1(S(C)(=O)=O)CC1)CC2] | MS m/z 487.3 (M + 1). $^1$H NMR (400 MHz, $CDCl_3$) δ ppm 1.09 (d, J = 1.56 Hz, 2 H) 1.62 (d, J = 1.57 Hz, 2 H) 2.53 (s, 3 H) 3.10 (s, 3 H) 3.79 (d, J = 5.67 Hz, 2 H) 4.01 (s, 2 H) 4.38 (d, J = 5.67 Hz, 2 H) 4.68 (d, J = 6.16 Hz, 2 H) 5.27-5.32 (m, 1 H) 7.14-7.24 (m, 2 H) 7.51-7.66 (m, 1 H) 8.45 (s, 1 H) 10.17-10.40 (m, 1 H). |
| 86-3 | 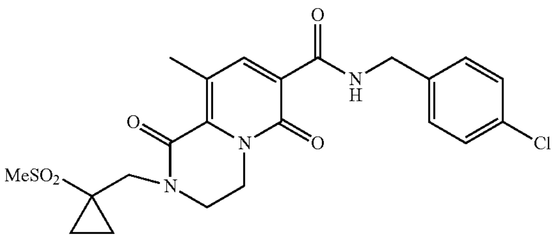 | MS m/z 478.2 (M + 1). 1H NMR (500 MHz, CHLOROFORM-d) δ ppm 1.07-1.14 (m, 2 H) 1.61-1.68 (m, 2 H) 2.55 (s, 3 H) 3.12 (s, 3 H) 3.61-3.92 (m, 2 H) 4.03 (s, 2 H) 4.18-4.43 (m, 2 H) 4.63 (d, J = 5.99 Hz, 2 H) 7.30-7.32 (m, 3 H) 8.49 (s, 1 H) 10.16 (br s, 1 H). |

Example 87

2-((1-(azetidin-1-ylsulfonyl)cyclopropyl)methyl)-N-(4-chlorobenzyl)-1,6-dioxo-2,3,4,6-tetrahydro-1H-pyrido[1,2-a]pyrazine-7-carboxamide 2-((1-(azetidin-1-ylsulfonyl)cyclopropyl)methyl)-1,6-dioxo-2,3,4,6-tetrahydro-1H-pyrido[1,2-a]pyrazine-7-carboxylic acid (Ex-87A) was prepared from I-1 and 1-26 following a procedure analogous to that described for Ex-76A. Ex-87A was obtained as a brown residue. MS m/z 382.3 (M+1).

2-((1-(azetidin-1-ylsulfonyl)cyclopropyl)methyl)-1,6-dioxo-2,3,4,6-tetrahydro-1H-pyrido[1,2-a]pyrazine-7-carbonyl chloride (Ex-87B). To a suspension of Ex-87A (100 mg, 0.262 mmol) in DCM (2.6 mL) under $N_2$ were added oxalyl chloride (34.4 µl, 0.393 mmol) and a drop of DMF. This resulted in rapid gas evolution and a homogeneous solution. After 20 min, the reaction mixture was concentrated in vacuo to yield Ex-87B as a brown residue that was used without further purification. MS m/z in MeOH 396.3 (M+1 of the corresponding methyl ester).

2-((1-(azetidin-1-ylsulfonyl)cyclopropyl)methyl)-N-(4-chlorobenzyl)-1,6-dioxo-2,3,4,6-tetrahydro-1H-pyrido[1,2-a]pyrazine-7-carboxamide (Ex-87). A solution of Ex-87B (34.8 mg, 0.087 mmol) in DCM (1 mL+0.5 mL rinse) was added dropwise to a stirred solution of 4-Cl-benzylamine (15.88 µL, 0.131 mmol) and DIPEA (53.2 µL, 0.305 mmol) in DCM (870 µL) at RT. The mixture was stirred overnight, after which it was partitioned between DI water and DCM. The aqueous phase was extracted with DCM twice more, and the combined organic layer was dried over $Na_2SO_4$, filtered, and concentrated. The crude product was purified by reverse-phase HPLC 20-60% (0.1% TFA MeCN)/(0.1% TFA/water). The product-containing fractions were combined and diluted with 2 M $Na_2CO_3$ and DCM. The phases were separated and the aqueous phase was extracted with DCM (2×). The combined organic phase was washed with 2 M $Na_2CO_3$ (2×) and brine, dried over $Na_2SO_4$, filtered, and concentrated to afford Ex-87 as a white solid.

| Example | Structure | Physical Data MS (m/z), $^1$H NMR |
|---|---|---|
| 87 | 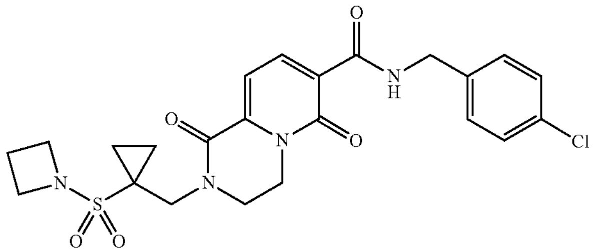 [SMILES: O=C(NCc1ccc(Cl)cc1)c1ccc2n(c1=O)CCN(CC1(S(=O)(=O)N3CCC3)CC1)C2=O] | MS m/z 505.3 (M + 1). $^1$H NMR (400 MHz, $CDCl_3$) δ ppm 1.19 (d, J = 2.01 Hz, 2 H) 1.42 (d, J = 1.96 Hz, 2 H) 2.18-2.34 (m, 2 H) 3.84-4.01 (m, 7 H) 4.30-4.40 (m, 2 H) 4.61 (d, J = 5.87 Hz, 2 H) 7.29 (s, 3 H) 7.33 (d, J = 7.48 Hz, 1 H) 8.63 (d, J = 7.53 Hz, 1 H) 9.98-10.17 (m, 1 H). |

Example 88-1

2-((1-(azetidin-1-ylsulfonyl)cyclopropyl)methyl)-N-(4-cyano-3-fluorobenzyl)-1,6-dioxo-2,3,4,6-tetrahydro-1H-pyrido[1,2-a]pyrazine-7-carboxamide 2-((1-(azetidin-1-ylsulfonyl)cyclopropyl)methyl)-N-(4-cyano-3-fluorobenzyl)-1,6-dioxo-2,3,4,6-tetrahydro-1H-pyrido[1,2-a]pyrazine-7-carboxamide (Ex-88-1). A solution of Ex-87B (34.8 mg, 0.087 mmol) in DCM (1 mL+0.5 mL rinse) was added dropwise to a stirred solution of (4-cyano-3-fluorophenyl)methanaminium chloride (24.35 mg, 0.131 mmol) and DIPEA (53.2 µL, 0.305 mmol) in DCM (870 µL) at RT. The mixture was stirred overnight, after which it was partitioned between DI water and DCM, and the aqueous phase was extracted with DCM twice more. The combined organic layer was dried over $Na_2SO_4$, filtered, and concentrated. The crude product was purified by reverse-phase HPLC 20-60% MeCN/(0.1% TFA/water). The product-containing fractions were combined and diluted with 2 M $Na_2CO_3$ and DCM. The phases were separated and the aqueous phase was extracted twice more with DCM. The combined organic phase was washed with 2 M $Na_2CO_3$ (2×) and brine, dried over $Na_2SO_4$, filtered, and concentrated to afford Ex-88-1 as a white solid.

Other compounds in the table below were prepared from Ex-87B following a procedure analogous to that described for Ex-88-1.

| Example | Structure | Physical Data MS (m/z), $^1$H NMR |
|---|---|---|
| 88-1 | 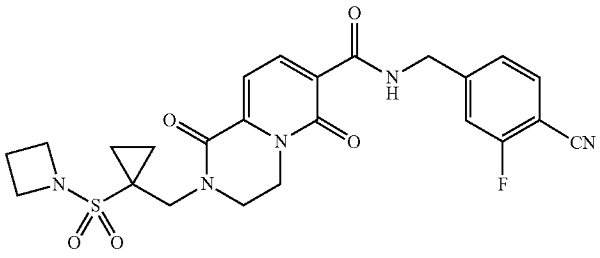 [SMILES: N#Cc1ccc(CNC(=O)c2ccc3n(c2=O)CCN(CC2(S(=O)(=O)N4CCC4)CC2)C3=O)cc1F] | MS m/z 514.2 (M + 1). $^1$H NMR (400 MHz, $CDCl_3$) δ ppm 1.15-1.22 (m, 2 H) 1.39-1.47 (m, 2 H) 2.18-2.41 (m, 2 H) 3.82-4.03 (m, 8 H) 4.33-4.46 (m, 2 H) 4.69 (d, J = 6.11 Hz, 2 H) 7.22 (dd, J = 12.96, 9.54 Hz, 2 H) 7.35 (d, J = 7.53 Hz, 1 H) 7.57 (dd, J = 7.82, 6.60 Hz, 1 H) 8.62 (d, J = 7.53 Hz, 1 H) 10.17-10.35 (m, 1 H). |
| 88-2 | 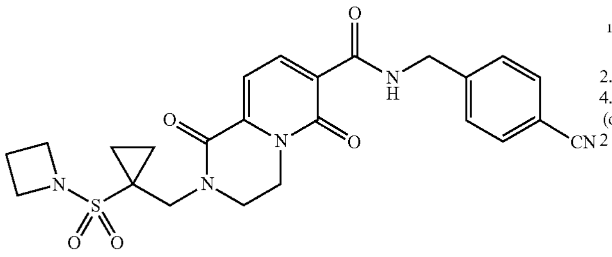 | MS m/z 496.3 (M + 1). $^1$H NMR (400 MHz, $CDCl_3$) δ ppm 1.14-1.23 (m, 2 H) 1.42 (d, J = 1.96 Hz, 2 H) 2.19-2.38 (m, 2 H) 3.82-4.05 (m, 7 H) 4.32-4.43 (m, 2 H) 4.70 (d, J = 6.02 Hz, 2 H) 7.34 (d, J = 7.53 Hz, 1 H) 7.45 (d, J = 8.27 Hz, 2 H) 7.62 (d, J = 8.31 Hz, 2 H) 8.63 (d, J = 7.48 Hz, 1 H) 10.09-10.32 (m, 1 H). |

Example 89-1

N-(4-chlorobenzyl)-1,6-dioxo-2-((1-(2-oxooxazolidin-3-yl)cyclopropyl)methyl)-2,3,4,6-tetrahydro-1H-pyrido[1,2-a]pyrazine-7-carboxamide 1,6-dioxo-2-((1-(2-oxooxazolidin-3-yl)cyclopropyl)methyl)-2,3,4,6-tetrahydro-1H-pyrido[1,2-a]pyrazine-7-carboxylic acid (Ex-89A) was prepared from I-1 and 1-27 following a procedure analogous to that described for Ex-76A. MS m/z 348.3 (M+1).

1,6-dioxo-2-((1-(2-oxooxazolidin-3-yl)cyclopropyl)methyl)-2,3,4,6-tetrahydro-1H-pyrido[1,2-a]pyrazine-7-carbonyl chloride (Ex-89B) was prepared from Ex-89A a procedure analogous to that described for Ex-87B. MS m/z in MeOH 362.3 (M+1 of the corresponding methyl ester).

N-(4-chlorobenzyl)-1,6-dioxo-2-((1-(2-oxooxazolidin-3-yl)cyclopropyl)methyl)-2,3,4,6-tetrahydro-1H-pyrido[1,2-a]pyrazine-7-carboxamide (Ex-89-1) was prepared from Ex-89B following a procedure analogous to that described for Ex-87.

Other compounds in the table below were prepared from Ex-89B following procedures analogous to those described for Ex-88-1.

| Example | Structure | Physical Data MS (m/z), $^1$H NMR |
|---|---|---|
| 89-1 | 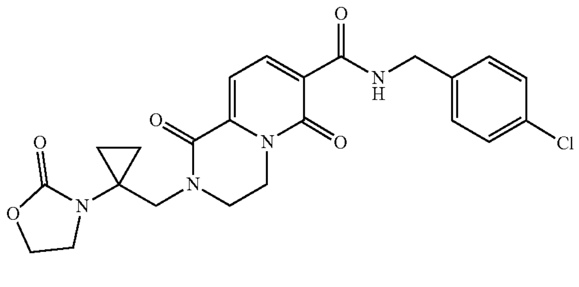 [SMILES: O=C(NCc1ccc(Cl)cc1)c1ccc2n(c1=O)CCN(CC1(N3CCOC3=O)CC1)C2=O] | MS m/z 471.3 (M + 1). $^1$H NMR (500 MHz, DMSO-d6) δ ppm 0.94 (s, 4 H) 3.55-3.70 (m, 4 H) 3.81-3.94 (m, 2 H) 4.08-4.20 (m, 2 H) 4.20-4.32 (m, 2 H) 4.54 (d, J = 6.04 Hz, 2 H) 7.19 (d, J = 7.53 Hz, 1 H) 7.32-7.37 (m, 2 H) 7.37-7.49 (m, 2 H) 8.45 (d, J = 7.53 Hz, 1 H) 10.10 (t, J = 6.04 Hz, 1 H). |
| 89-2 | 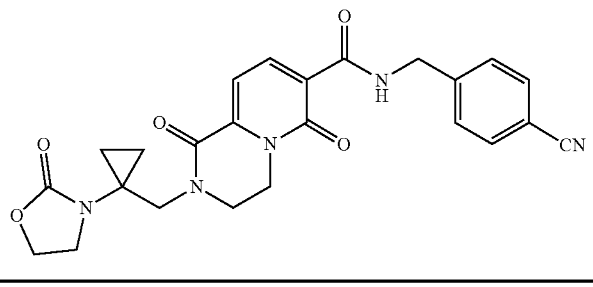 | MS m/z 462.3 (M + 1). $^1$H NMR (500 MHz, DMSO-d6) δ ppm 0.94 (s, 4 H) 3.56-3.72 (m, 4 H) 3.80-3.93 (m, 2 H) 4.07-4.19 (m, 2 H) 4.20-4.34 (m, 2 H) 4.64 (d, J = 6.04 Hz, 2 H) 7.20 (d, J = 7.53 Hz, 1 H) 7.50 (d, J = 8.32 Hz, 2 H) 7.72-7.86 (m, 2 H) 8.44 (d, J = 7.53 Hz, 1 H) 10.17 (t, J = 6.09 Hz, 1 H). |

Example 90-1

N-(4-chlorobenzyl)-2-((1-(N,N-dimethylsulfamoyl) cyclopropyl)methyl)-1,6-dioxo-2,3,4,6-tetrahydro-1H-pyrido[1,2-a]pyrazine-7-carboxamide 2-((1-(N,N-dimethylsulfamoyl)cyclopropyl)methyl)-1,6-dioxo-2,3,4,6-tetrahydro-1H-pyrido[1,2-a]pyrazine-7-carboxylic acid (Ex-90A) was prepared from I-1 and 1-28 following a procedure analogous to that described for Ex-1A. Ex-90A was obtained as a tan solid. MS m/z 370.3 (M+1).

N-(4-chlorobenzyl)-2-((1-(N,N-dimethylsulfamoyl)cyclopropyl)methyl)-1,6-dioxo-2,3,4,6-tetrahydro-1H-pyrido [1,2-a]pyrazine-7-carboxamide (Ex-90-1) was prepared from Ex-90A following a procedure analogous to that described for Ex-1.

Other compounds in the table below were prepared from Ex-90A following a procedure analogous to that described for Ex-1.

with brine, dried over $Na_2SO_4$, filtered, and concentrated to afford an orange solid. The crude product was purified on $SiO_2$ (0-100% (10% MeOH/EtOAc)/heptane) to afford Ex-91A. MS m/z 521.4 (M+1).

Tert-butyl (2-(7-((4-chlorobenzyl)carbamoyl)-4-methyl-1,6-dioxo-3,4-dihydro-1H-pyrido[1,2-a]pyrazin-2(6H)-yl) ethyl)(methyl)carbamate (Ex-91B). Alcohol Ex-91A (166.7 mg, 0.320 mmol) was dissolved in DCM (3.2 mL) under $N_2$ and polymer-bound triphenylphosphine (approx. 3.0 mmol/g, Aldrich) (161 mg, 0.480 mmol) was added. The flask was cooled to 0° C. and neat DIAD (93 μL, 0.480 mmol) was added dropwise to the stirred solution. After 90 min, a second portion of polymer-bound triphenylphosphine was added (40 mg) along with additional DIAD (20 μL). After stirring overnight at RT, the reaction mixture was filtered over celite, rinsing with additional DCM. The filtrate was washed with water and brine, dried over $Na_2SO_4$, filtered, and concentrated to provide Ex-91B as a yellow solid. This was used without further purification. MS m/z 503.2 (M+1).

| Example | Structure | Physical Data MS (m/z), $^1$H NMR |
|---|---|---|
| 90-1 | 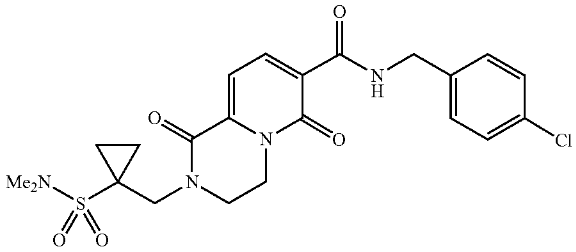 [SMILES: CN(C)S(=O)(=O)C1(CN2CCn3c(ccc(C(=O)NCc4ccc(Cl)cc4)c3=O)C2=O)CC1] | MS m/z 493.3 (M + 1). $^1$H NMR (400 MHz, $CDCl_3$) δ ppm 1.09-1.21 (m, 2 H) 1.45-1.54 (m, 2 H) 2.91 (s, 6 H) 3.83-3.91 (m, 2 H) 3.93 (s, 2 H) 4.24-4.41 (m, 2 H) 4.61 (d, J = 5.92 Hz, 2 H) 7.26 (s, 5 H) 7.33 (d, J = 7.53 Hz, 1 H) 8.63 (d, J = 7.53 Hz, 1 H) 9.96-10.14 (m, 1 H). |
| 90-2 | 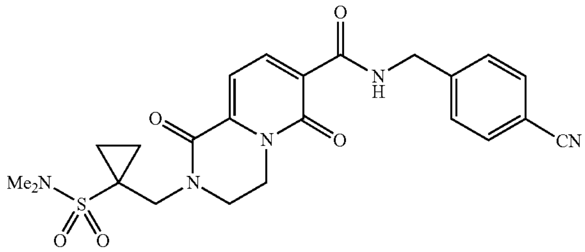 [SMILES: CN(C)S(=O)(=O)C1(CN2CCn3c(ccc(C(=O)NCc4ccc(C#N)cc4)c3=O)C2=O)CC1] | MS m/z 483.2 (M + 1). $^1$H NMR (500 MHz, DMSO-d6) δ ppm 1.06-1.20 (m, 2 H) 1.21-1.33 (m, 2 H) 2.85 (s, 6 H) 3.72-3.82 (m, 2 H) 3.94 (s, 2 H) 4.19-4.32 (m, 2 H) 4.64 (d, J = 5.94 Hz, 2 H) 7.21 (d, J = 7.53 Hz, 1 H) 7.50 (d, J = 8.32 Hz, 2 H) 7.74-7.87 (m, 2 H) 8.44 (d, J = 7.53 Hz, 1 H) 10.18 (t, J = 6.04 Hz, 1 H). |

Example 91

N-(4-chlorobenzyl)-4-methyl-2-(2-(N-methylmethylsulfonamido)ethyl)-1,6-dioxo-2,3,4,6-tetrahydro-1H-pyrido[1,2-]pyrazine-7-carboxamide Tert-butyl (2-(5-((4-chlorobenzyl)carbamoyl)-N-(2-hydroxypropyl)-6-oxo-1,6-dihydropyridine-2-carboxamido) ethyl)(methyl)carbamate (Ex-91A). Acid I-17C (200 mg, 0.652 mmol) was suspended in $CH_2Cl_2$ (4.3 mL) under $N_2$ and treated with $NEt_3$ (0.182 mL, 1.304 mmol) at RT. After 15 min, the resulting solution was treated with TMSCl (0.167 mL, 1.304 mmol) and stirred at RT for 90 min $SOCl_2$ (0.095 mL, 1.304 mmol) was added, and the resulting suspension was stirred at RT for another 90 min. The acid chloride suspension was cooled to 0° C. and 1-33 (606 mg, 2.61 mmol) was added as a solution in $CH_2Cl_2$ (1 mL). The reaction was allowed to warm to RT and was stirred overnight. The reaction mixture was partitioned between DI water and DCM, and the aqueous phase was extracted with DCM twice more. The combined organic layer was washed N-(4-chlorobenzyl)-4-methyl-2-(2-(N-methylmethylsulfonamido)ethyl)-1,6-dioxo-2,3,4,6-tetrahydro-1H-pyrido [1,2-a]pyrazine-7-carboxamide (Ex-91). To a stirred solution of Ex-91B (161 mg, 0.32 mmol) in DCM (2.4 mL) at room temperature was added TFA (0.8 mL). Boc-deprotection was complete within 1 h, and the mixture was concentrated in vacuo to yield a viscous yellow oil.

The TFA salt was dissolved in DCM (2.4 mL). To the stirred solution were sequentially added $NEt_3$ (0.446 mL, 3.20 mmol) and MsCl (0.037 mL, 0.480 mmol). After 30 min, the reaction mixture was partitioned between DCM and water. The aqueous layer was extracted twice more with DCM, and the combined organic layer was dried over $Na_2SO_4$, filtered, and concentrated to provide an orange foam. The crude product was purified on reverse phase HPLC. The isolated solid was dissolved in DCM and washed with 2 M $Na_2CO_3$ (3×). The organic phase was dried over $Na_2SO_4$, filtered, and concentrated to afford Ex-91 as a white powder.

| Example | Structure | Physical Data MS (m/z), $^1H$ NMR |
|---|---|---|
| 91 | 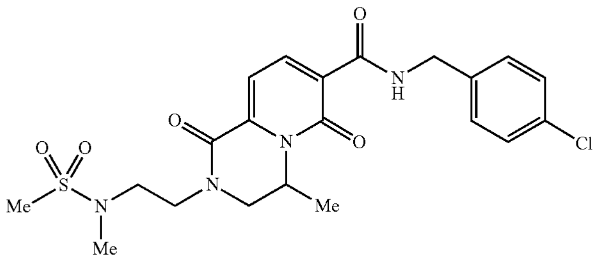 [SMILES: CC1CN(CCN(C)S(C)(=O)=O)C(=O)c2ccc(C(=O)NCc3ccc(Cl)cc3)c(=O)n21] | MS m/z 481.2 (M + 1). $^1H$ NMR (500 MHz, $CDCl_3$) δ ppm 1.45 (d, J = 6.62 Hz, 3 H) 2.82 (s, 4 H) 2.95 (s, 3 H) 3.31-3.50 (m, 3 H) 3.52-3.66 (m, 1 H) 3.93-4.04 (m, 1 H) 4.08 (dd, J = 13.40, 3.94 Hz, 1 H) 4.61 (qd, J = 15.08, 5.83 Hz, 2 H) 4.89-5.10 (m, 1 H) 5.12-5.25 (m, 1 H) 7.30 (s, 4 H) 7.35 (d, J = 7.57 Hz, 1 H) 8.63 (d, J = 7.57 Hz, 1 H) 10.09 (br. s., 1 H). |

Example 92

N-(4-chlorobenzyl)-3-methyl-2-(2-(N-methylmethylsulfonamido)ethyl)-1,6-dioxo-2,3,4,6-tetrahydro-1H-pyrido[1,2-a]pyrazine-7-carboxamide Tert-butyl (2-(5-((4-chlorobenzyl)carbamoyl)-N-(1-hydroxypropan-2-yl)-6-oxo-1,6-dihydropyridine-2-carboxamido)ethyl)(methyl)carbamate (Ex-92A). To a stirred suspension of I-17C (545 mg, 1.778 mmol) and 1-34 (413 mg, 1.778 mmol) in acetonitrile (22.2 mL) was added cesium carbonate (1448 mg, 4.44 mmol) followed by HATU (1555 mg, 4.09 mmol). The resulting suspension was stirred at 50° C. in an oil bath. After 5 h, the reaction was determined to be complete, and the reaction mixture was cooled to RT and partitioned between DI water and DCM. The aqueous phase was extracted with DCM (2×), and the combined organic layer was washed with brine, dried over $Na_2SO_4$, filtered, and concentrated. The crude product was stored at RT overnight during which it isomerized from the ester to the desired amide. The crude product was purified by $SiO_2$ to afford Ex-92A. MS m/z 521.3 (M+1).

Tert-butyl (2-(7-((4-chlorobenzyl)carbamoyl)-3-methyl-1,6-dioxo-3,4-dihydro-1H-pyrido[1,2-a]pyrazin-2(6H)-yl)ethyl)(methyl)carbamate (Ex-92B). To a solution of Ex-92A (80 mg, 0.154 mmol) in THF (1.3 mL) was added triphenylphosphine (60.4 mg, 0.230 mmol). The solution was cooled to 0° C., and diisopropyl azodicarboxylate (0.045 mL, 0.230 mmol) was added. The reaction was allowed to warm to room temperature gradually and was stirred 16 h. The crude reaction mixture was partitioned between DI water and DCM, and the aqueous layer was extracted twice with DCM. The combined organic phase was dried over $Na_2SO_4$, filtered, and concentrated. The crude product was purified by $SiO_2$ (0-100% (10% MeOH/EtOAc)/heptane) to afford Ex-92B. MS m/z 503.3 (M+1).

N-(4-chlorobenzyl)-3-methyl-2-(2-(N-methylmethylsulfonamido)ethyl)-1,6-dioxo-2,3,4,6-tetrahydro-1H-pyrido[1,2-a]pyrazine-7-carboxamide (Ex-92) was prepared from Ex-92B following a procedure analogous to that described for Ex-91.

| Example | Structure | Physical Data MS (m/z), $^1H$ NMR |
|---|---|---|
| 92 | 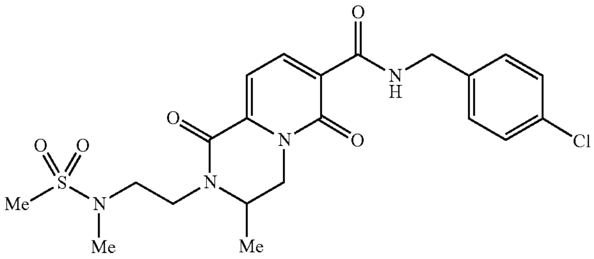 [SMILES: CC1Cn2c(ccc(C(=O)NCc3ccc(Cl)cc3)c2=O)C(=O)N1CCN(C)S(C)(=O)=O] | MS m/z 481.1 (M + 1). $^1H$ NMR (400 MHz, DMSO-d6) δ ppm 1.12 (d, J = 6.65 Hz, 3 H) 2.82 (s, 3 H) 2.87 (s, 3 H) 3.87 (dd, J = 13.89, 3.72 Hz, 1 H) 3.93-4.14 (m, 2 H) 4.51 (d, J = 5.87 Hz, 2 H) 4.61 (d, J = 13.69 Hz, 1 H) 7.18 (d, J = 7.43 Hz, 1 H) 7.36 (q, J = 8.22 Hz, 4 H) 8.43 (d, J = 7.43 Hz, 1 H) 10.03 (t, J = 5.67 Hz, 1 H). |

Example 93-1

N-(4-cyanobenzyl)-2-((1-(cyclopropylsulfonyl)cyclopropyl)methyl)-9-methyl-1,6-dioxo-2,3,4,6-tetrahydro-1H-pyrido[1,2-a]pyrazine-7-carboxamide 2-((1-(cyclopropylsulfonyl)cyclopropyl)methyl)-9-methyl-1,6-dioxo-2,3,4,6-tetrahydro-1H-pyrido[1,2-a]pyrazine-7-carboxylic acid (Ex-93A) was prepared from 1-35 and 1-2 following a procedure analogous to that described for Ex-1. MS m/z 381.3 (M+1).

N-(4-cyanobenzyl)-2-((1-(cyclopropylsulfonyl)cyclopropyl)methyl)-9-methyl-1,6-dioxo-2,3,4,6-tetrahydro-1H-pyrido[1,2-a]pyrazine-7-carboxamide (Ex-93-1) was prepared from Ex-93A following a procedure analogous to that described for Ex-77-1.

Other compounds in the table below were prepared from Ex-93A following procedures analogous to those described in Ex-76 and Ex-77-1.

| Example | Structure | Physical Data MS (m/z), $^1$H NMR |
|---|---|---|
| 93-1 | 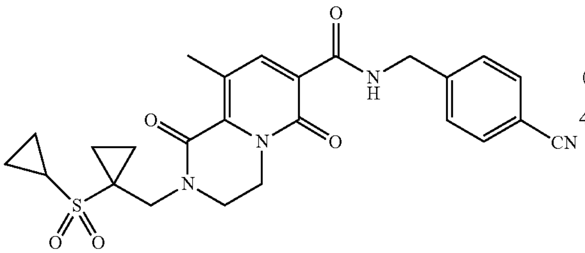 | MS m/z 495.3 (M + 1). $^1$H NMR (500 MHz, DMSO-d6) δ ppm 1.01-1.11 (m, 4 H) 1.17-1.21 (m, 2 H) 1.29-1.34 (m, 2 H) 2.44 (s, 3 H) 2.93-3.00 (m, 1 H) 3.73-3.78 (m, 2 H) 4.10 (s, 2 H) 4.23-4.29 (m, 2 H) 4.65 (d, J = 6.03 Hz, 2 H) 7.51 (m, J = 8.39 Hz, 2 H) 7.79-7.84 (m, 2 H) 8.28 (s, 1 H) 10.25 (t, J = 6.09 Hz, 1 H). |
| 93-2 | 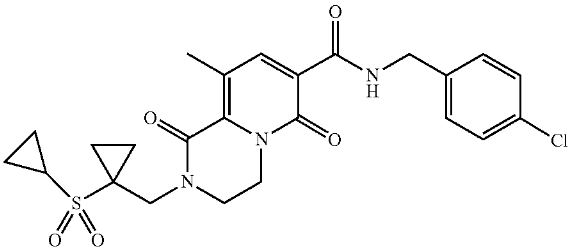 [SMILES: Cc1cc(C(=O)NCc2ccc(Cl)cc2)c(=O)n2c1C(=O)N(CC1(S(=O)(=O)C3CC3)CC1)CC2] | MS m/z 504.2 (M + 1). $^1$H NMR (500 MHz, DMSO-d6) δ ppm 1.01-1.11 (m, 4 H) 1.16-1.20 (m, 2 H) 1.29-1.34 (m, 2 H) 2.44 (s, 3 H) 2.93-2.99 (m, 1 H) 3.71-3.78 (m, 2 H) 4.10 (s, 2 H) 4.25 (dd, J = 6.56, 4.55 Hz, 2 H) 4.55 (d, J = 6.03 Hz, 2 H) 7.33-7.37 (m, 2 H) 7.39-7.43 (m, 2 H) 8.28 (s, 1 H) 10.18 (t, J = 6.03 Hz, 1 H). |
| 93-3 | 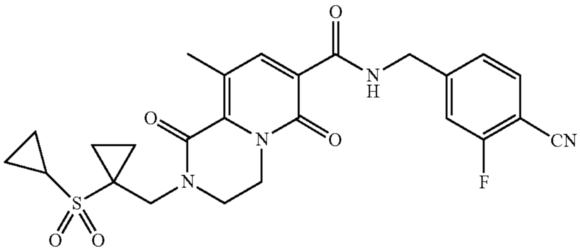 [SMILES: Cc1cc(C(=O)NCc2ccc(C#N)c(F)c2)c(=O)n2c1C(=O)N(CC1(S(=O)(=O)C3CC3)CC1)CC2] | MS m/z 513.3 (M + 1). $^1$H NMR (500 MHz, DMSO-d6) δ ppm 1.01-1.11 (m, 4 H) 1.17-1.21 (m, 2 H) 1.30-1.34 (m, 2 H) 2.44 (s, 3 H) 2.93-3.01 (m, 1 H) 3.72-3.79 (m, 2 H) 4.11 (s, 2 H) 4.27 (dd, J = 6.56, 4.55 Hz, 2 H) 4.66 (d, J = 6.15 Hz, 2 H) 7.33-7.38 (m, 1 H) 7.44 (d, J = 10.52 Hz, 1 H) 7.90 (dd, J = 7.86, 7.03 Hz, 1 H) 8.27 (s, 1 H) 10.26 (t, J = 6.15 Hz, 1 H). |

Example 94

Other compounds in the table below were prepared from I-1 and 1-36 following procedures analogous to those described for Ex-76.

| Example | Structure | Physical Data MS (m/z), $^1$H NMR |
|---|---|---|
| 94-1 | 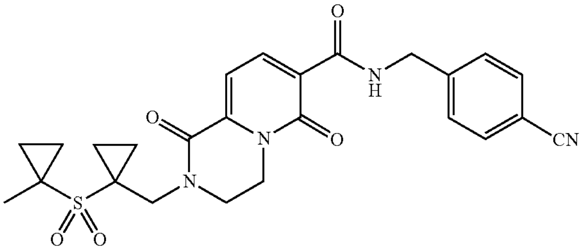 [SMILES: CC1(S(=O)(=O)C2(CN3CCn4c(ccc(C(=O)NCc5ccc(C#N)cc5)c4=O)C3=O)CC2)CC1] | MS m/z 495.3 (M + 1). $^1$H NMR (500 MHz, DMSO-d6) δ ppm 10.21-10.14 (m, 1H), 8.51-8.38 (m, 1H), 7.89-7.74 (m, 2H), 7.55-7.46 (m, 2H), 7.24-7.16 (m, 1H), 4.71-4.59 (m, 2H), 4.30-4.21 (m, 2H), 4.15-4.02 (m, 2H), 3.81-3.72 (m, 2H), 1.53 (s, 3H), 1.33-1.29 (m, 2H), 1.27-1.24 (m, 2H), 1.18-1.15 (m, 2H), 0.95-0.91 (m, 2H) |
| 94-2 | 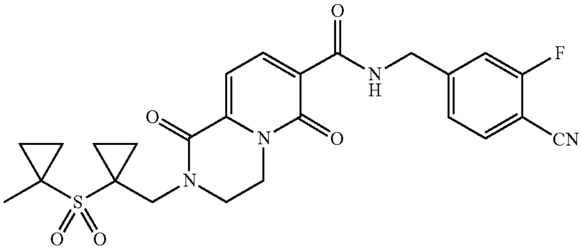 [SMILES: CC1(S(=O)(=O)C2(CN3CCn4c(ccc(C(=O)NCc5ccc(C#N)c(F)c5)c4=O)C3=O)CC2)CC1] | MS m/z 513.3 (M + 1). $^1$H NMR (500 MHz, DMSO-d6) δ ppm 10.19 (t, J = 6.1 Hz, 1H), 8.42 (d, J = 7.6 Hz, 1H), 7.90 (t, J = 7.4 Hz, 1H), 7.47-7.31 (m, 2H), 7.21 (d, J = 7.6 Hz, 1H), 4.64 (d, J = 6.2 Hz, 2H), 4.28-4.20 (m, 2H), 4.08 (s, 2H), 3.83-3.72 (m, 2H), 1.53 (s, 3H), 1.36-1.29 (m, 2H), 1.28-1.20 (m, 2H), 1.19-1.15 (m, 2H), 0.98-0.89 (m, 2H) |

Example 95 N-(4-chlorobenzyl)-2-((1-(S-methyl sulfonimidoyl)cyclopropyl)methyl)-1,6-dioxo-2,3,4,6-tetrahydro-1H-pyrido[1,2-a]pyrazine-7-carboxamide 2-((1-(cyclobutylsulfonyl)cyclopropyl)methyl)-1,6-dioxo-2,3,4,6-tetrahydro-1H-pyrido[1,2-a]pyrazine-7-carboxylic acid (Ex-95A). To Ex-67-1 (300 mg, 0.670 mmol) in acetonitrile (10 mL) was added PhI=NNs (406 mg, 1.005 mmol) and ferric acetylacetonate (47.3 mg, 0.134 mmol). The reaction was stirred at RT overnight. Additional PhI=NNs (406 mg, 1.005 mmol) and ferric acetylacetonate (47.3 mg, 0.134 mmol) were then added, and the reaction was stirred for another 16 h. The reaction mixture was diluted with EtOAc (30 mL) and washed with water (2×10 mL) and brine. The organic layer was concentrated, and the residue was purified on $SiO_2$ (30-100% EtOAc/heptane) to provide the title product. MS m/z 648.0 (M+1).

N-(4-chlorobenzyl)-2-((1-(S-methylsulfonimidoyl)cyclopropyl)methyl)-1,6-dioxo-2,3,4,6-tetrahydro-1H-pyrido[1,2-a]pyrazine-7-carboxamide (Ex-95). To Ex-95A (90 mg, 0.139 mmol) in acetonitrile (3 mL) was added benzenethiol (0.029 mL, 0.278 mmol) and $Cs_2CO_3$ (90 mg, 0.278 mmol). The reaction was stirred at 50° C. overnight. Additional benzenethiol (0.029 mL, 0.278 mmol) and $Cs_2CO_3$ (90 mg, 0.278 mmol) were then added, and the reaction mixture was stirred for another 4 h. The reaction mixture was diluted with EtOAc (20 mL) and washed with water and brine. The organic layer was dried ($Na_2SO_4$) and concentrated. The residue was purified by HPLC to give the title product. MS m/z 463.2 (M+1).

Ex-96-1 and Ex-96-2

(R) & (S)—N-(4-chlorobenzyl)-2-((1-(S-methylsulfonimidoyl)cyclopropyl)methyl)-1,6-dioxo-2,3,4,6-tetrahydro-1H-pyrido[1,2-a]pyrazine-7-carboxamide Ex-95 was subjected to separation by chiral HPLC to afford the title enantiomeric compounds. The stereochemical assignments are arbitrary.

| Example | Structure | Physical Data MS (m/z), $^1$H NMR |
|---|---|---|
| 95 | 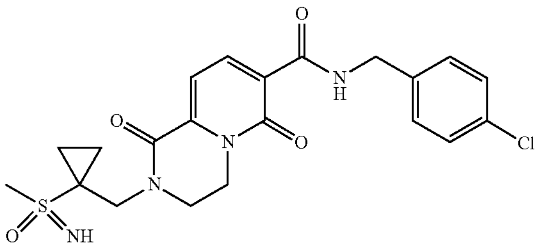 [SMILES: CS(=N)(=O)C1(CN2CCn3c(ccc(C(=O)NCc4ccc(Cl)cc4)c3=O)C2=O)CC1] | MS m/z 463.2 (M + 1). $^1$H NMR (500 MHz, DMSO-d6) δ ppm 10.11 (t, J = 6.0 Hz, 1H), 8.44 (d, J = 7.6 Hz, 1H), 7.42-7.38 (m, 2H), 7.37-7.32 (m, 2H), 7.21 (d, J = 7.6 Hz, 1H), 4.54 (d, J = 6.0 Hz, 2H), 4.25 (t, J = 6.1 Hz, 2H), 4.06-3.95 (m, 2H), 3.89-3.76 (m, 2H), 3.69 (s, 1H), 2.99 (d, J = 0.8 Hz, 3H), 1.41-1.31 (m, 1H), 1.20-1.11 (m, 1H), 1.10-1.00 (m, 2H) |
| 96-1 | 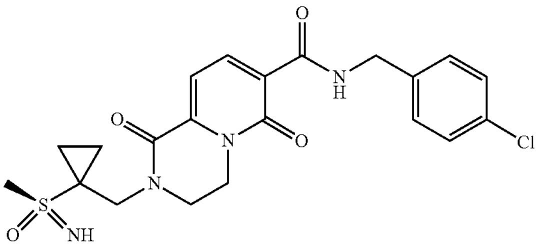 [SMILES: C[S@@](=N)(=O)C1(CN2CCn3c(ccc(C(=O)NCc4ccc(Cl)cc4)c3=O)C2=O)CC1] | MS m/z 463.2 (M + 1). $^1$H NMR (500 MHz, DMSO-d6) δ ppm 10.11 (t, J = 6.0 Hz, 1H), 8.44 (d, J = 7.6 Hz, 1H), 7.42-7.38 (m, 2H), 7.37-7.32 (m, 2H), 7.21 (d, J = 7.6 Hz, 1H), 4.54 (d, J = 6.0 Hz, 2H), 4.25 (t, J = 6.1 Hz, 2H), 4.06-3.95 (m, 2H), 3.89-3.76 (m, 2H), 3.69 (s, 1H), 2.99 (d, J = 0.8 Hz, 3H), 1.41-1.31 (m, 1H), 1.20-1.11 (m, 1H), 1.10-1.00 (m, 2H) |
| 96-2 | 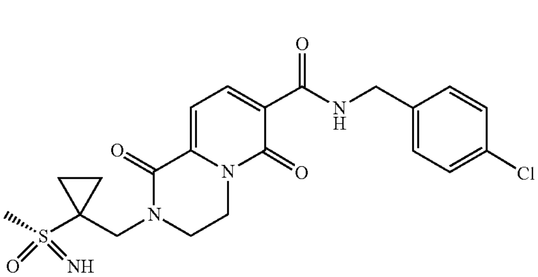 [SMILES: C[S@](=N)(=O)C1(CN2CCn3c(ccc(C(=O)NCc4ccc(Cl)cc4)c3=O)C2=O)CC1] | MS m/z 463.2 (M + 1). $^1$H NMR (500 MHz, DMSO-d6) δ ppm 10.11 (t, J = 6.0 Hz, 1H), 8.44 (d, J = 7.6 Hz, 1H), 7.42-7.38 (m, 2H), 7.37-7.32 (m, 2H), 7.21 (d, J = 7.6 Hz, 1H), 4.54 (d, J = 6.0 Hz, 2H), 4.25 (t, J = 6.1 Hz, 2H), 4.06-3.95 (m, 2H), 3.89-3.76 (m, 2H), 3.69 (s, 1H), 2.99 (d, J = 0.8 Hz, 3H), 1.41-1.31 (m, 1H), 1.20-1.11 (m, 1H), 1.10-1.00 (m, 2H) |

Example 97

Compounds in the table below were prepared from 1-(trifluoromethyl)cyclopropanecarboxylic acid and I-1 following procedures analogous to those described for Ex-76.

| Example | Structure | Physical Data MS (m/z), $^1$H NMR |
|---|---|---|
| 97-1 | 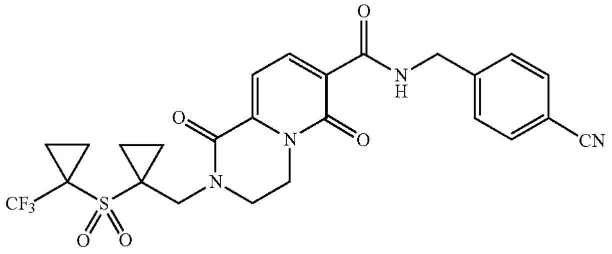 [SMILES: N#Cc1ccc(CNC(=O)c2ccc3n(c2=O)CCN(CC2(S(=O)(=O)C4(C(F)(F)F)CC4)CC2)C3=O)cc1] | MS m/z 549.2 (M + 1). $^1$H NMR (500 MHz, DMSO-d6) δ ppm 10.18 (t, J = 6.1 Hz, 1H), 8.45 (d, J = 7.4 Hz, 1H), 7.87-7.77 (m, 2H), 7.51 (d, J = 8.5 Hz, 2H), 7.22 (d, J = 7.6 Hz, 1H), 4.65 (d, J = 6.0 Hz, 2H), 4.29-4.23 (m, 2H), 4.12 (s, 2H), 3.82-3.71 (m, 2H), 1.71-1.61 (m, 4H), 1.51-1.43 (m, 2H), 1.40-1.32 (m, 2H). |
| 97-2 | 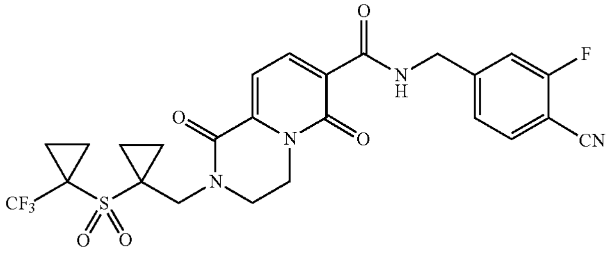 [SMILES: N#Cc1ccc(CNC(=O)c2ccc3n(c2=O)CCN(CC2(S(=O)(=O)C4(C(F)(F)F)CC4)CC2)C3=O)cc1F] | MS m/z 567.2 (M + 1). $^1$H NMR (500 MHz, DMSO-d6) δ ppm 10.20 (t, J = 6.1 Hz, 1H), 8.43 (d, J = 7.6 Hz, 1H), 7.90 (dd, J = 7.1, 7.9 Hz, 1H), 7.45 (dd, J = 1.1, 10.5 Hz, 1H), 7.38-7.32 (m, 1H), 7.22 (d, J = 7.6 Hz, 1H), 4.66 (d, J = 6.1 Hz, 2H), 4.33-4.23 (m, 2H), 4.12 (s, 2H), 3.83-3.73 (m, 2H), 1.73-1.61 (m, 4H), 1.53-1.43 (m, 2H), 1.40-1.31 (m, 2H). |

Example 98

Compounds in the table below were prepared from 2,2-difluorocyclopropanecarboxylic acid and I-1 following procedures analogous to those described for Ex-76.

| Example | Structure | Physical Data MS (m/z), $^1$H NMR |
|---|---|---|
| 98-1 | 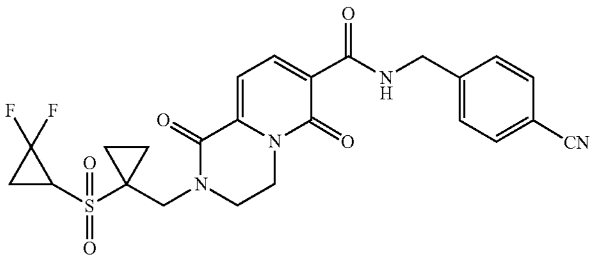 [SMILES: N#Cc1ccc(CNC(=O)c2ccc3n(c2=O)CCN(CC2(S(=O)(=O)C4CC4(F)F)CC2)C3=O)cc1] | MS m/z 517.1 (M + 1). $^1$H NMR (500 MHz, DMSO-d6) δ ppm 10.19 (t, J = 6.1 Hz, 1H), 8.45 (d, J = 7.4 Hz, 1H), 7.89-7.76 (m, 2H), 7.51 (d, J = 8.5 Hz, 2H), 7.24 (d, J = 7.4 Hz, 1H), 4.65 (d, J = 6.0 Hz, 2H), 4.35-4.20 (m, 3H), 4.14 (dt, J = 8.0, 11.5 Hz, 1H), 3.95 (d, J = 15.3 Hz, 1H), 3.83 (t, J = 6.0 Hz, 2H), 2.49-2.41 (m, 1H), 2.36-2.24 (m, 1H), 2.09 (s, 1H), 1.53-1.44 (m, 1H), 1.40-1.21 (m, 3H). |
| 98-2 | 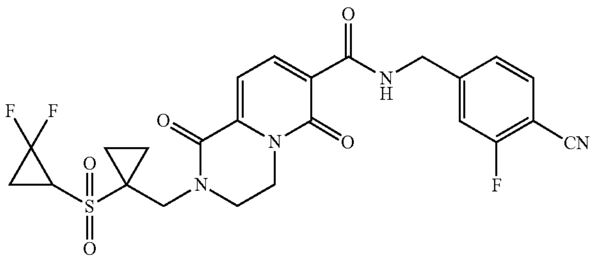 [SMILES: N#Cc1ccc(CNC(=O)c2ccc3n(c2=O)CCN(CC2(S(=O)(=O)C4CC4(F)F)CC2)C3=O)cc1F] | MS m/z 535.2 (M + 1). $^1$H NMR (500 MHz, DMSO-d6) δ ppm 10.20 (t, J = 6.1 Hz, 1H), 8.49-8.40 (m, 1H), 7.91 (dd, J = 7.0, 7.9 Hz, 1H), 7.50-7.32 (m, 2H), 7.24 (d, J = 7.6 Hz, 1H), 4.66 (d, J = 6.1 Hz, 2H), 4.39-4.19 (m, 3H), 4.14 (dt, J = 8.0, 11.5 Hz, 1H), 3.95 (d, J = 15.3 Hz, 1H), 3.88-3.77 (m, 2H), 2.49-2.40 (m, 1H), 2.37-2.23 (m, 1H), 1.55-1.43 (m, 1H), 1.40-1.19 (m, 3H). |

-continued

| Example | Structure | Physical Data<br>MS (m/z), $^{1}$H NMR |
|---|---|---|
| 98-3 | 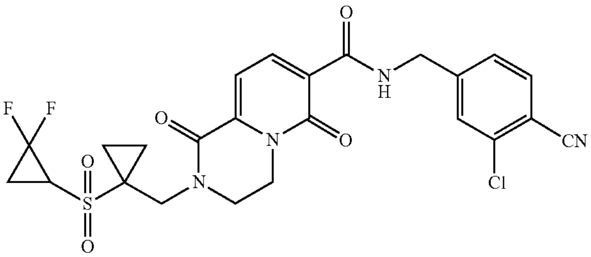 [SMILES: N#Cc1ccc(CNC(=O)c2ccc3n(c2=O)CCN(CC2(S(=O)(=O)C4CC4(F)F)CC2)C3=O)cc1Cl] | MS m/z 551.1 (M + 1).<br>$^{1}$H NMR (500 MHz, DMSO-d6) δ ppm 10.20 (t, J = 6.1 Hz, 1H), 8.44 (d, J = 7.6 Hz, 1H), 7.95 (d, J = 8.0 Hz, 1H), 7.68 (d, J = 1.2 Hz, 1H), 7.52-7.44 (m, 1H), 7.24 (d, J = 7.6 Hz, 1H), 4.64 (d, J = 6.1 Hz, 2H), 4.39-4.19 (m, 3H), 4.18-4.07 (m, 1H), 3.95 (d, J = 15.3 Hz, 1H), 3.84 (t, J = 6.0 Hz, 2H), 2.46 (br. s., 1H), 2.30 (d, J = 8.3 Hz, 1H), 1.55-1.44 (m, 1H), 1.40-1.21 (m, 3H). |

Example 99

Compounds in the table below were prepared from I-1 and 1-37 following procedures analogous to those described for Ex-76.

| Example | Structure | Physical Data<br>MS (m/z), $^{1}$H NMR |
|---|---|---|
| 99-1 | 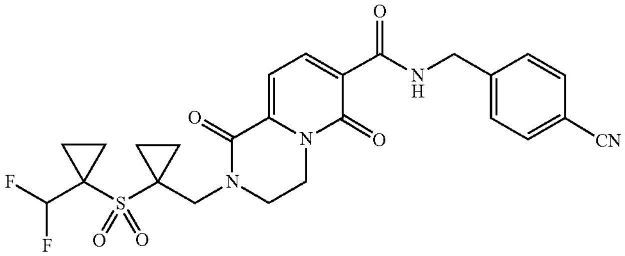 [SMILES: N#Cc1ccc(CNC(=O)c2ccc3n(c2=O)CCN(CC2(S(=O)(=O)C4(C(F)F)CC4)CC2)C3=O)cc1] | MS m/z 531.2 (M + 1).<br>$^{1}$H NMR (500 MHz, DMSO-d6) δ ppm 10.18 (t, J = 6.1 Hz, 1H), 8.44 (d, J = 7.4 Hz, 1H), 7.87-7.78 (m, 2H), 7.51 (d, J = 8.5 Hz, 2H), 7.22 (d, J = 7.6 Hz, 1H), 6.68-6.37 (m, 1H), 4.65 (d, J = 6.0 Hz, 2H), 4.31-4.21 (m, 2H), 4.09 (s, 2H), 3.82-3.73 (m, 2H), 1.55-1.50 (m, 2H), 1.50-1.45 (m, 2H), 1.44-1.39 (m, 2H), 1.30-1.24 (m, 2H). |
| 99-2 | 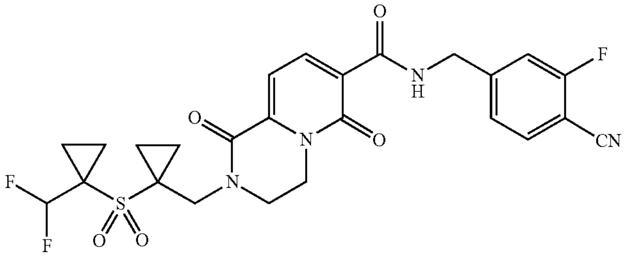 [SMILES: N#Cc1ccc(CNC(=O)c2ccc3n(c2=O)CCN(CC2(S(=O)(=O)C4(C(F)F)CC4)CC2)C3=O)cc1F] | MS m/z 549.1 (M + 1).<br>$^{1}$H NMR (500 MHz, DMSO-d6) δ ppm 10.20 (t, J = 6.1 Hz, 1H), 8.43 (d, J = 7.4 Hz, 1H), 7.90 (dd, J = 7.0, 7.9 Hz, 1H), 7.45 (dd, J = 1.1, 10.5 Hz, 1H), 7.41-7.31 (m, 1H), 7.22 (d, J = 7.6 Hz, 1H), 6.70-6.34 (m, 1H), 4.66 (d, J = 6.1 Hz, 2H), 4.33-4.19 (m, 2H), 4.09 (s, 2H), 3.85-3.66 (m, 2H), 1.52 (br. s., 2H), 1.50-1.45 (m, 2H), 1.44-1.39 (m, 2H), 1.30-1.24 (m, 2H) |
| 99-3 | 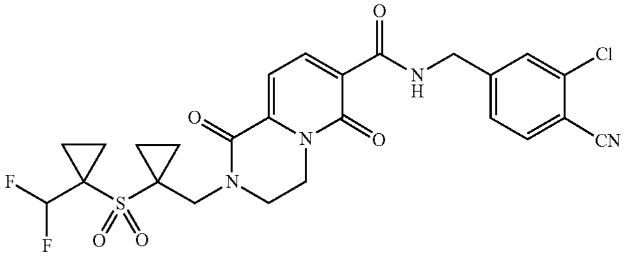 [SMILES: N#Cc1ccc(CNC(=O)c2ccc3n(c2=O)CCN(CC2(S(=O)(=O)C4(C(F)F)CC4)CC2)C3=O)cc1Cl] | MS m/z 565.0 (M + 1).<br>$^{1}$H NMR (500 MHz, DMSO-d6) δ ppm 10.20 (t, J = 6.1 Hz, 1H), 8.43 (d, J = 7.6 Hz, 1H), 7.95 (d, J = 8.0 Hz, 1H), 7.67 (d, J = 1.3 Hz, 1H), 7.48 (dd, J = 1.5, 8.1 Hz, 1H), 7.22 (d, J = 7.6 Hz, 1H), 6.68-6.36 (m, 1H), 4.64 (d, J = 6.1 Hz, 2H), 4.32-4.22 (m, 2H), 4.09 (s, 2H), 3.84-3.74 (m, 2H), 1.55-1.50 (m, 2H), 1.50-1.45 (m, 2H), 1.44-1.39 (m, 2H), 1.30-1.25 (m, 2H). |

Ex-100-1 and Ex-100-2

(R) & (S)—N-(4-cyanobenzyl)-2-((1-((2,2-difluorocyclopropyl)sulfonyl)cyclopropyl)methyl)-1,6-dioxo-2,3,4,6-tetrahydro-1H-pyrido[1,2-a]pyrazine-7-carboxamide Ex-98-1 was subjected to separation by chiral HPLC to afford the enantiomeric title compounds. The stereochemical assignments are arbitrary.

| Example | Structure | Physical Data MS (m/z), $^1$H NMR |
|---|---|---|
| 100-1 | 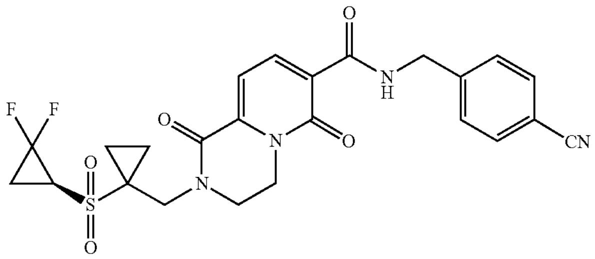 [SMILES: N#Cc1ccc(CNC(=O)c2ccc3n(c2=O)CCN(CC2(S(=O)(=O)[C@H]4CC4(F)F)CC2)C3=O)cc1] | MS m/z 517.1 (M + 1). $^1$H NMR (500 MHz, DMSO-d6) δ ppm 10.19 (t, J = 6.1 Hz, 1H), 8.45 (d, J = 7.4 Hz, 1H), 7.89-7.76 (m, 2H), 7.51 (d, J = 8.5 Hz, 2H), 7.24 (d, J = 7.4 Hz, 1H), 4.65 (d, J = 6.0 Hz, 2H), 4.35-4.20 (m, 3H), 4.14 (dt, J = 8.0, 11.5 Hz, 1H), 3.95 (d, J = 15.3 Hz, 1H), 3.83 (t, J = 6.0 Hz, 2H), 2.49-2.41 (m, 1H), 2.36-2.24 (m, 1H), 2.09 (s, 1H), 1.53-1.44 (m, 1H), 1.40-1.21 (m, 3H). |
| 100-2 | 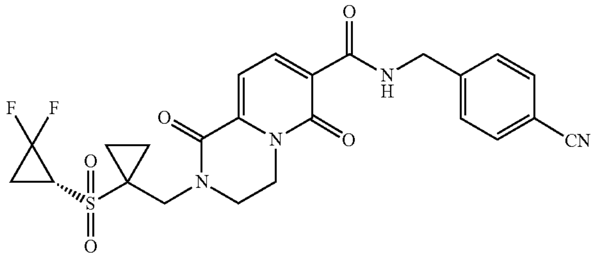 [SMILES: N#Cc1ccc(CNC(=O)c2ccc3n(c2=O)CCN(CC2(S(=O)(=O)[C@@H]4CC4(F)F)CC2)C3=O)cc1] | MS m/z 517.1 (M + 1). $^1$H NMR (500 MHz, DMSO-d6) δ ppm 10.19 (t, J = 6.1 Hz, 1H), 8.45 (d, J = 7.4 Hz, 1H), 7.89-7.76 (m, 2H), 7.51 (d, J = 8.5 Hz, 2H), 7.24 (d, J = 7.4 Hz, 1H), 4.65 (d, J = 6.0 Hz, 2H), 4.35-4.20 (m, 3H), 4.14 (dt, J = 8.0, 11.5 Hz, 1H), 3.95 (d, J = 15.3 Hz, 1H), 3.83 (t, J = 6.0 Hz, 2H), 2.49-2.41 (m, 1H), 2.36-2.24 (m, 1H), 2.09 (s, 1H), 1.53-1.44 (m, 1H), 1.40-1.21 (m, 3H). |

Ex-101-1 and Ex-101-2 (R) & (S)—N-(4-cyano-3-fluorobenzyl)-2-((1-((2,2-difluorocyclopropyl)sulfonyl)cyclopropyl)methyl)-1,6-dioxo-2,3,4,6-tetrahydro-1H-pyrido[1,2-a]pyrazine-7-carboxamide Ex-98-2 was subjected to separation by chiral HPLC to afford the enantiomeric title compounds. The stereochemical assignments are arbitrary.

| Example | Structure | Physical Data MS (m/z), $^1$H NMR |
|---|---|---|
| 101-1 | 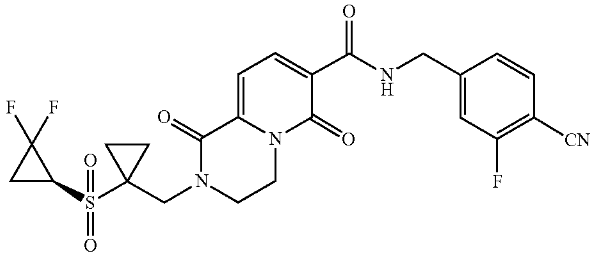 [SMILES: N#Cc1ccc(CNC(=O)c2ccc3n(c2=O)CCN(CC2(S(=O)(=O)[C@H]4CC4(F)F)CC2)C3=O)cc1F] | MS m/z 535.2 (M + 1). $^1$H NMR (500 MHz, DMSO-d6) δ ppm 10.20 (t, J = 6.1 Hz, 1H), 8.49-8.40 (m, 1H), 7.91 (dd, J = 7.0, 7.9 Hz, 1H), 7.50-7.32 (m, 2H), 7.24 (d, J = 7.6 Hz, 1H), 4.66 (d, J = 6.1 Hz, 2H), 4.39-4.19 (m, 3H), 4.14 (dt, J = 8.0, 11.5 Hz, 1H), 3.95 (d, J = 15.3 Hz, 1H), 3.88-3.77 (m, 2H), 2.49-2.40 (m, 1H), 2.37-2.23 (m, 1H), 1.55-1.43 (m, 1H), 1.40-1.19 (m, 3H). |

-continued

| Example | Structure | Physical Data MS (m/z), $^1$H NMR |
|---|---|---|
| 101-2 | 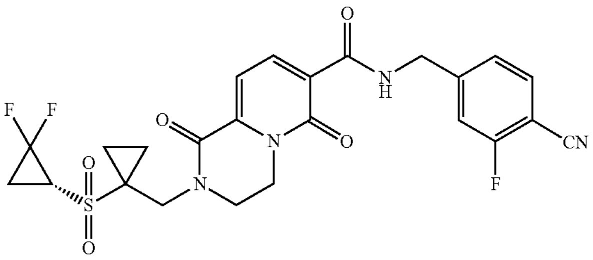 [SMILES: N#Cc1ccc(CNC(=O)c2ccc3n(c2=O)CCN(CC2(S(=O)(=O)[C@@H]4CC4(F)F)CC2)C3=O)cc1F] | MS m/z 535.2 (M + 1). $^1$H NMR (500 MHz, DMSO-d6) δ ppm 10.20 (t, J = 6.1 Hz, 1H), 8.49-8.40 (m, 1H), 7.91 (dd, J = 7.0, 7.9 Hz, 1H), 7.50-7.32 (m, 2H), 7.24 (d, J = 7.6 Hz, 1H), 4.66 (d, J = 6.1 Hz, 2H), 4.39-4.19 (m, 3H), 4.14 (dt, J = 8.0, 11.5 Hz, 1H), 3.95 (d, J = 15.3 Hz, 1H), 3.88-3.77 (m, 2H), 2.49-2.40 (m, 1H), 2.37-2.23 (m, 1H), 1.55-1.43 (m, 1H), 1.40-1.19 (m, 3H). |

Ex-102-1 and Ex-102-2

(R) & (S)—N-(3-chloro-4-cyanobenzyl)-2-((1-((2,2-difluorocyclopropyl)sulfonyl)cyclopropyl)methyl)-1,6-dioxo-2,3,4,6-tetrahydro-1H-pyrido[1,2-a]pyrazine-7-carboxamide Ex-98-3 was subjected to separation by chiral HPLC to afford the title enantiomeric compounds. The stereochemical assignments are arbitrary.

| Example | Structure | Physical Data MS (m/z), $^1$H NMR |
|---|---|---|
| 102-1 | 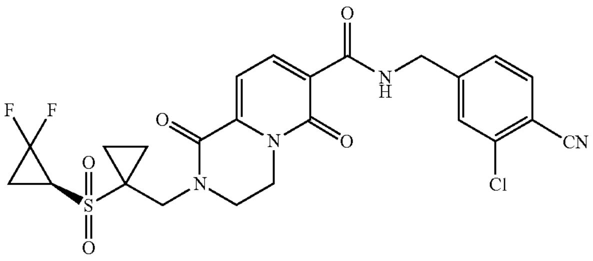 [SMILES: N#Cc1ccc(CNC(=O)c2ccc3n(c2=O)CCN(CC2(S(=O)(=O)[C@H]4CC4(F)F)CC2)C3=O)cc1Cl] | MS m/z 551.1 (M + 1). $^1$H NMR (500 MHz, DMSO-d6) δ ppm 10.20 (t, J = 6.1 Hz, 1H), 8.44 (d, J = 1.6 Hz, 1H), 7.95 (d, J = 8.0 Hz, 1H), 7.68 (d, J = 1.2 Hz, 1H), 7.52-7.44 (m, 1H), 7.24 (d, J = 7.6 Hz, 1H), 4.64 (d, J = 6.1 Hz, 2H), 4.39-4.19 (m, 3H), 4.18-4.07 (m, 1H), 3.95 (d, J = 15.3 Hz, 1H), 3.84 (t, J = 6.0 Hz, 2H), 2.46 (br. s., 1H), 2.30 (d, J = 8.3 Hz, 1H), 1.55-1.44 (m, 1H), 1.40-1.21 (m, 3H). |
| 102-2 | 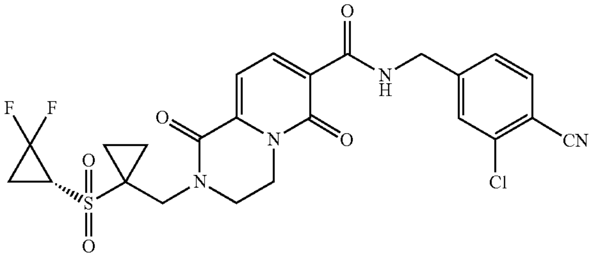 [SMILES: N#Cc1ccc(CNC(=O)c2ccc3n(c2=O)CCN(CC2(S(=O)(=O)[C@@H]4CC4(F)F)CC2)C3=O)cc1Cl] | MS m/z 551.1 (M + 1). $^1$H NMR (500 MHz, DMSO-d6) δ ppm 10.20 (t, J = 6.1 Hz, 1H), 8.44 (d, J = 7.6 Hz, 1H), 7.95 (d, J = 8.0 Hz, 1H), 7.68 (d, J = 1.2 Hz, 1H), 7.52-7.44 (m, 1H), 7.24 (d, J = 7.6 Hz, 1H), 4.64 (d, J = 6.1 Hz, 2H), 4.39-4.19 (m, 3H), 4.18-4.07 (m, 1H), 3.95 (d, J = 15.3 Hz, 1H), 3.84 (t, J = 6.0 Hz, 2H), 2.46 (br. s., 1H), 2.30 (d, J = 8.3 Hz, 1H), 1.55-1.44 (m, 1H), 1.40-1.21 (m, 3H). |

Example 103

Compounds in the table below were prepared from I-1 and 1-38 following procedures analogous to those described for Ex-76.

| Example | Structure | Physical Data MS (m/z), $^1$H NMR |
|---|---|---|
| 103-1 | 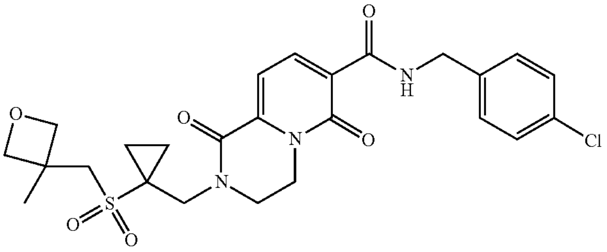 [SMILES: CC1(CS(=O)(=O)C2(CN3CCn4c(ccc(C(=O)NCc5ccc(Cl)cc5)c4=O)C3=O)CC2)COC1] | MS m/z 534.1 (M + 1). $^1$H NMR (500 MHz, DMSO-d6) δ ppm 10.11 (t, J = 6.03 Hz, 1 H) 8.46 (d, J = 7.45 Hz, 1 H) 7.39-7.43 (m, 2 H) 7.34-7.37 (m, 2 H) 7.23 (d, J = 7.57 Hz, 1 H) 4.62 (d, J = 5.91 Hz, 2 H) 4.55 (d, J = 6.03 Hz, 2 H) 4.24-4.30 (m, 2 H) 4.21 (d, J = 5.91 Hz, 2 H) 4.07 (s, 2 H) 3.80-3.84 (m, 2 H) 3.79 (s, 2 H) 1.54 (s, 3 H) 1.30-1.36 (m, 2 H) 1.17-1.23 (m, 2 H) |
| 103-2 | 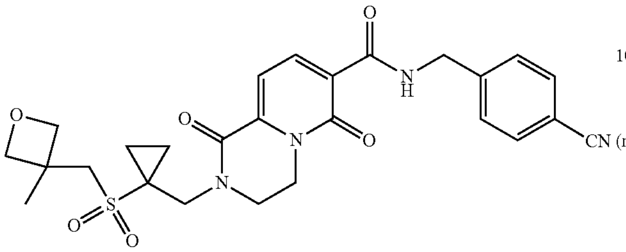 | MS m/z 525.2 (M + 1). $^1$H NMR (500 MHz, DMSO-d6) δ ppm 10.18 (t, J = 6.15 Hz, 1 H) 8.45 (d, J = 7.57 Hz, 1 H) 7.79-7.85 (m, 2 H) 7.51 (d, J = 8.51 Hz, 2 H) 7.23 (d, J = 7.57 Hz, 1 H) 4.64 (dd, J = 12.83, 5.97 Hz, 4 H) 4.25-4.30 (m, 2 H) 4.21 (d, J = 6.03 Hz, 2 H) 4.08 (s, 2 H) 3.80-3.85 (m, 2 H) 3.79 (s, 2 H) 1.54 (s, 3 H) 1.31-1.35 (m, 2 H) 1.18-1.23 (m, 2 H) |
| 103-3 | 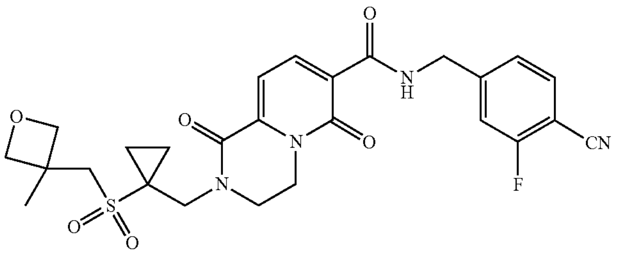 [SMILES: CC1(CS(=O)(=O)C2(CN3CCn4c(ccc(C(=O)NCc5ccc(C#N)c(F)c5)c4=O)C3=O)CC2)COC1] | MS m/z 543.2 (M + 1). $^1$H NMR (500 MHz, DMSO-d6) δ ppm 10.19 (t, J = 6.21 Hz, 1 H) 8.44 (d, J = 7.57 Hz, 1 H) 7.90 (dd, J = 7.92, 6.98 Hz, 1 H) 7.45 (dd, J = 10.52, 0.95 Hz, 1 H) 7.36 (dd, J = 8.04, 1.42 Hz, 1 H) 7.22 (d, J = 7.57 Hz, 1 H) 4.64 (dd, J = 16.02, 5.97 Hz, 4 H) 4.26-4.31 (m, 2 H) 4.21 (d, J = 6.03 Hz, 2 H) 4.08 (s, 2 H) 3.80-3.85 (m, 2 H) 3.79 (s, 2 H) 1.54 (s, 3 H) 1.31-1.36 (m, 2 H) 1.19-1.22 (m, 2 H) |

Example 104

Compounds in the table below were prepared from I-1 and 1-39 following a procedure analogous to those described for Ex-76.

| Example | Structure | Physical Data MS (m/z), $^1$H NMR |
|---|---|---|
| 104-1 | 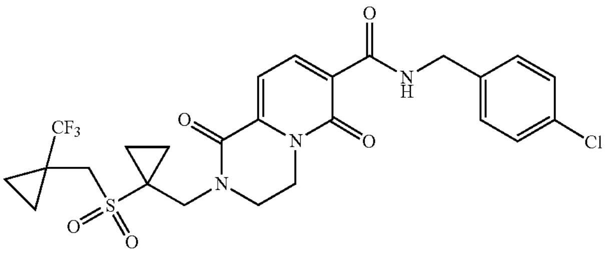 [SMILES: O=C(NCc1ccc(Cl)cc1)c1ccc2n(c1=O)CCN(CC1(S(=O)(=O)CC3(C(F)(F)F)CC3)CC1)C2=O] | MS m/z 572.2 (M + 1). $^1$H NMR (500 MHz, DMSO-d6) δ ppm 10.11 (t, J = 6.03 Hz, 1 H) 8.47 (d, J = 7.57 Hz, 1 H) 7.39-7.43 (m, 2 H) 7.34-7.37 (m, 2 H) 7.22 (d, J = 7.57 Hz, 1 H) 4.55 (d, J = 6.03 Hz, 2 H) 4.22-4.30 (m, 2 H) 4.03 (s, 2 H) 3.75-3.83 (m, 4 H) 1.32-1.38 (m, 2 H) 1.10-1.22 (m, 6 H) |

-continued

| Example | Structure | Physical Data MS (m/z), $^1$H NMR |
|---|---|---|
| 104-2 | 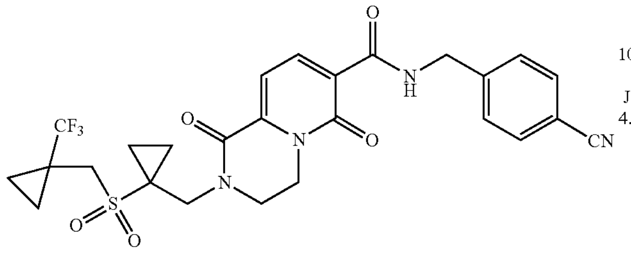 | MS m/z 563.2 (M + 1). $^1$H NMR (500 MHz, DMSO-d6) δ ppm 10.18 (t, J = 6.15 Hz, 1 H) 8.46 (d, J = 7.57 Hz, 1 H) 7.79-7.84 (m, 2 H) 7.51 (d, J = 8.51 Hz, 2 H) 7.22 (d, J = 7.57 Hz, 1 H) 4.65 (d, J = 6.03 Hz, 2 H) 4.24-4.30 (m, 2 H) 4.04 (s, 2 H) 3.76-3.84 (m, 4 H) 1.33-1.40 (m, 2 H) 1.11-1.22 (m, 6 H) |
| 104-3 | 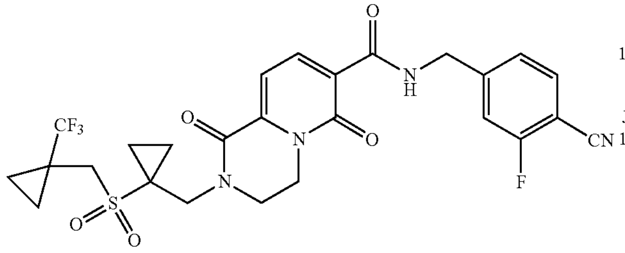 | MS m/z 581.1 (M + 1). $^1$H NMR (500 MHz, DMSO-d6) δ ppm 10.19 (t, J = 6.21 Hz, 1 H) 8.45 (d, J = 7.57 Hz, 1 H) 7.90 (dd, J = 7.86, 7.03 Hz, 1 H) 7.45 (dd, J = 10.40, 0.95 Hz, 1 H) 7.36 (dd, J = 8.04, 1.42 Hz, 1 H) 7.21 (d, J = 7.45 Hz, 1 H) 4.66 (d, J = 6.15 Hz, 2 H) 4.24-4.31 (m, 2 H) 4.04 (s, 2 H) 3.75-3.84 (m, 4 H) 1.33-1.39 (m, 2 H) 1.10-1.24 (m, 6 H) |

Example 105-1

N-(4-chlorobenzyl)-1,6-dioxo-2-((1-((tetrahydro-2H-pyran-4-yl)sulfonyl)cyclopropyl(methyl)-2,3,4,6-tetrahydro-1H-pyrido[1,2-a]pyrazine-7-carboxamide (Ex-105-1)

1,6-Dioxo-2-((1-((tetrahydro-2H-pyran-4-yl)sulfonyl)cyclopropyl)methyl)-2,3,4,6-tetrahydro-1H-pyrido[1,2-a]pyrazine-7-carboxylic acid (Ex-105A) was prepared from I-1 and 1-40 following a procedure analogous to that described for Ex-1A. MS m/z 411 (M+1).

N-(4-chlorobenzyl)-1,6-dioxo-2-((1-((tetrahydro-2H-pyran-4-yl)sulfonyl)cyclopropyl)methyl)-2,3,4,6-tetrahydro-1H-pyrido[1,2-a]pyrazine-7-carboxamide (Ex-105-1). To a solution of Ex-105A (50 mg, 0.12 mmol) and Huenig's Base (0.085 mL, 0.48 mmol) in DCM (5 mL) was added T3P® (50% in EtOAc, 0.14 mL, 0.24 mmol). The mixture was stirred at RT for 5 min, and then (4-chlorophenyl)methanamine (32.8 mg, 0.23 mmol) was added in one portion. The resulting solution was stirred 2 h. The reaction mixture was partitioned between ethyl acetate (80 mL) and water (30 mL). The organic phase was washed with brine, dried over sodium sulfate, filtered and concentrated. The crude compound was purified by HPLC (0.1% TFA/$H_2O$/MeCN). The collected fractions were combined and basified to pH 13 by adding 2 N NaOH. The aqueous solution was extracted with ethyl acetate (2×). The combined organic phase was washed with brine, dried over sodium sulfate, and concentrated to give Ex-105-1.

| Example | Structure | Physical Data MS (m/z), $^1$H NMR |
|---|---|---|
| 105-1 | 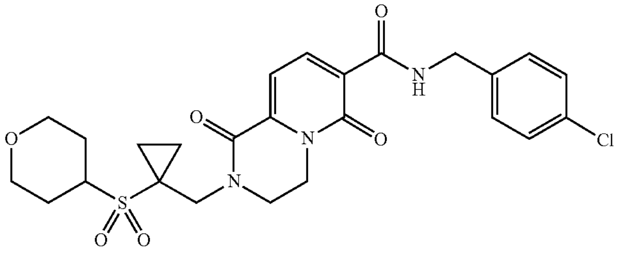 [SMILES: O=C(NCc1ccc(Cl)cc1)c1ccc2n(c1=O)CCN(CC1(S(=O)(=O)C3CCOCC3)CC1)C2=O] | MS m/z 534 (M + 1). 1H NMR (500 MHz, DMSO-d6) δ 8.45 (d, J = 7.57 Hz, 1H), 7.38-7.44 (m, 2H), 7.31-7.37 (m, 2H), 7.22 (d, J = 7.57 Hz, 1H), 4.54 (d, J = 5.99 Hz, 2H), 4.21-4.29 (m, 2H), 4.05 (s, 2H), 3.94-4.01 (m, 3H), 3.77-3.85 (m, 2H), 3.31 (d, J = 0.63 Hz, 2H), 1.94 (d, J = 10.72 Hz, 2H), 1.63 (dd, J = 4.41, 12.61 Hz, 2H), 1.23-1.30 (m, 2H), 1.14-1.21 (m, 2H) |

Example 105-2

N-(4-cyanobenzyl)-2-((1-((1-fluorocyclopropyl)sulfonyl)cyclopropyl)methyl)-1,6-dioxo-2,3,4,6-tetrahydro-1H-pyrido pyrazine-7-carboxamide N-(4-cyanobenzyl)-2-((1-((1-fluorocyclopropyl)sulfonyl)cyclopropyl)methyl)-1,6-dioxo-2,3,4,6-tetrahydro-1H-pyrido[1,2-a]pyrazine-7-carboxamide (Ex-105-2). To a solution of Ex-105A (50 mg, 0.12 mmol) and Huenig's Base (0.085 mL, 0.48 mmol) in DCM (5 mL) was added T3P® (50% in EtOAc, 0.14 mL, 0.24 mmol). The mixture was stirred at RT for 5 min, and then (4-cyanophenyl)methanaminium chloride (39.0 mg, 0.23 mmol) was added in one portion. The resulting solution was stirred for 30 min. The reaction mixture was partitioned between ethyl acetate (80 mL) and water (30 mL). The organic phase was washed with brine, dried over $Na_2SO_4$, filtered, and concentrated. The crude compound was purified by HPLC. The combined fractions were basified to pH 13 by adding 2 N NaOH, and the resulting aqueous solution was extracted with ethyl acetate (2×). The combined organic phase was washed with brine, dried over sodium sulfate, filtered, and concentrated to give Ex-105-2.

Example 107-1

N-(4-chlorobenzyl)-2-((1-((cyclopropylmethyl)sulfonyl)cyclopropyl)methyl)-1,6-dioxo-2,3,4,6-tetrahydro-1H-pyrido[1,2-a]pyrazine-7-carboxamide 2-((1-((Cyclopropylmethyl)sulfonyl)cyclopropyl) methyl)-1,6-dioxo-2,3,4,6-tetrahydro-1H-pyrido[1,2-a] pyrazine-7-carboxylic acid (Ex-107A). To an ice cold solution of I-1 (1152 mg, 4.36 mmol) in DMF (10 mL) was added sodium hydride (60% suspension in mineral oil, 228 mg, 5.70 mmol). After 15 min, a solution of 1-42 (900 mg,

| Example | Structure | Physical Data MS (m/z), $^1H$ NMR |
|---|---|---|
| 105-2 | 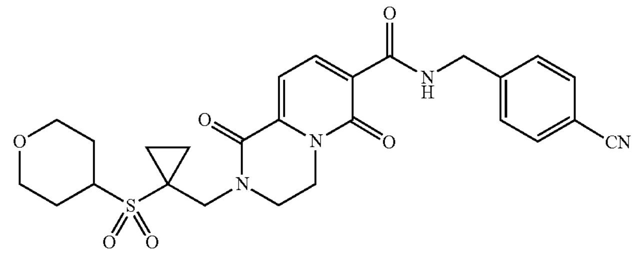 [SMILES: N#Cc1ccc(CNC(=O)c2ccc3n(c2=O)CCN(CC2(S(=O)(=O)C4CCOCC4)CC2)C3=O)cc1] | MS m/z 525.2 (M + 1). $^1H$ NMR (500 MHz, DMSO-d6) δ 10.18 (t, J = 5.99 Hz, 1H), 8.44 (d, J = 7.57 Hz, 1H), 7.81 (d, J = 8.51 Hz, 2H), 7.50 (d, J = 8.20 Hz, 2H), 7.22 (d, J = 7.57 Hz, 1H), 4.64 (d, J = 5.99 Hz, 2H), 4.22-4.31 (m, 2H), 4.05 (s, 2H), 3.94-4.02 (m, 3H), 3.76-3.85 (m, 2H), 3.37-3.42 (m, 2H), 1.94 (d, J = 10.72 Hz, 2H), 1.63 (dq, J = 4.41, 12.40 Hz, 2H), 1.24-1.32 (m, 2H), 1.14-1.21 (m, 2H) |

Example 106

2-((1-(tert-Butylsulfinyl)cyclopropyl)methyl)-N-(4-cyanobenzyl)-1,6-dioxo-2,3,4,6-tetrahydro-1H-pyrido[1,2-a]pyrazine-7-carboxamide 2-((1-(tert-Butylsulfinyl)cyclopropyl)methyl)-1,6-dioxo-2,3,4,6-tetrahydro-1H-pyrido[1,2-a]pyrazine-7-carboxylic acid (Ex-106A) was prepared from I-1 and 1-41 following a procedure analogous to that described for Ex-1. MS m/z 367.2 (M+1).

2-((1-(tert-Butylsulfinyl)cyclopropyl)methyl)-N-(4-cyanobenzyl)-1,6-dioxo-2,3,4,6-tetrahydro-1H-pyrido[1,2-a] pyrazine-7-carboxamide (Ex-106) was prepared from Ex-106A following a procedure analogous to that described for Ex-105-2.

3.35 mmol) in DMF (2 mL) was added. The reaction mixture was stirred at RT for 4 h. The mixture was diluted with DCM (100 mL) and was washed with water and brine. The aqueous phase was acidified to pH 3 by treating with 2 N HCl and was extracted with DCM (3×). The combined organic phase was dried over sodium sulfate, filtered, and concentrated. The resulting residue was dissolved in THF (12 mL) and water (3 mL), and lithium hydroxide (0.32 g, 13.7 mmol) was added. The resulting mixture was stirred at 50° C. in an oil bath for 1 h. The reaction mixture was diluted with DCM (100 mL) and water (80 mL). The aqueous phase was separated and acidified to pH 3 by treating with 2 N HCl. It was then extracted with ethyl acetate (3×). The combined organic phase was dried over

| Example | Structure | Physical Data MS (m/z), $^1H$ NMR |
|---|---|---|
| 106 | 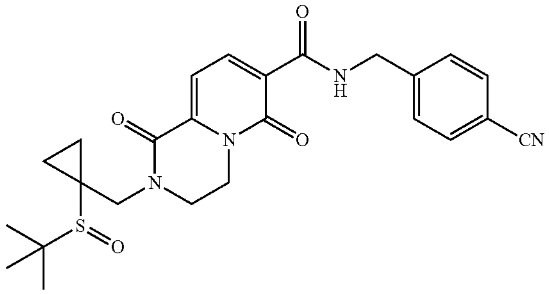 [SMILES: CC(C)(C)S(=O)C1(CN2CCn3c(ccc(C(=O)NCc4ccc(C#N)cc4)c3=O)C2=O)CC1] | MS m/z 481.2 (M + 1). 1H NMR (500 MHz, DMSO-d6) δ 10.20 (t, J = 6.15 Hz, 1H), 8.43 (d, J = 7.57 Hz, 1H), 7.82 (d, J = 8.51 Hz, 2H), 7.50 (d, J = 8.51 Hz, 2H), 7.19 (d, J = 7.57 Hz, 1H), 4.64 (d, J = 6.31 Hz, 2H), 4.29-4.41 (m, 1H), 4.09-4.24 (m, 2H), 3.67-3.83 (m, 3H), 1.28 (s, 9H), 0.98-1.12 (m, 4H) |

sodium sulfate, filtered, and concentrated. The resulting residue dried under high vacuum to give Ex-107A as brown solid. MS m/z 381.2 (M+1).

N-(4-chlorobenzyl)-2-((1-((cyclopropylmethyl)sulfonyl) cyclopropyl)methyl)-1,6-dioxo-2,3,4,6-tetrahydro-1H-pyrido[1,2-a]pyrazine-7-carboxamide (Ex-107-1) was prepared from Ex-107A following a procedure analogous to that described for Ex-105-1.

| Example | Structure | Physical Data MS (m/z), $^1$H NMR |
|---|---|---|
| 107-1 | 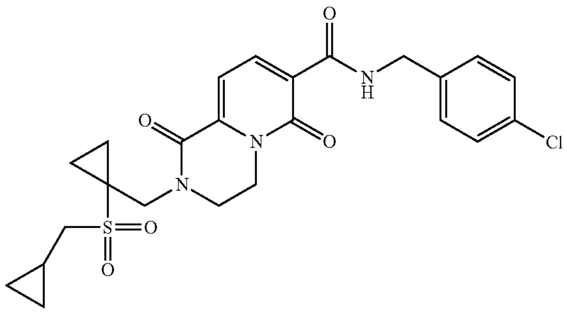 [SMILES: O=C(NCc1ccc(Cl)cc1)c1ccc2n(c1=O)CCN(CC1(S(=O)(=O)CC3CC3)CC1)C2=O] | MS m/z 504.2 (M + 1). $^1$H NMR (500 MHz, DMSO-d6) δ 10.11 (t, J = 6.03 Hz, 1H), 8.45 (d, J = 7.45 Hz, 1H), 7.31-7.51 (m, 4H), 7.22 (d, J = 7.45 Hz, 1H), 4.55 (d, J = 6.03 Hz, 2H), 4.16-4.35 (m, 2H), 4.03 (s, 2H), 3.70-3.88 (m, 2H), 3.32 (d, J = 7.21 Hz, 2H), 1.30-1.38 (m, 2H), 1.14-1.22 (m, 2H), 1.02-1.13 (m, 1H), 0.59-0.69 (m, 2H), 0.35-0.46 (m, 2H) |

Compounds in the table below were prepared from Ex-107A following procedures analogous to that described for Ex-105-2.

| Example | Structure | Physical Data MS (m/z), $^1$H NMR |
|---|---|---|
| 107-2 | 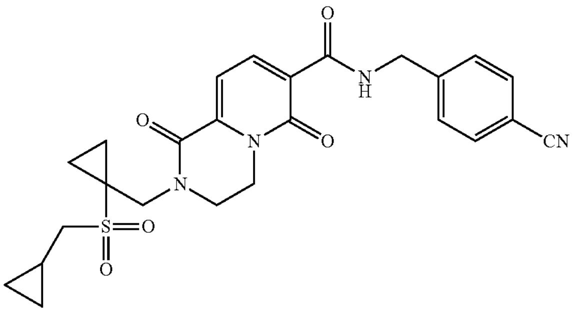 [SMILES: N#Cc1ccc(CNC(=O)c2ccc3n(c2=O)CCN(CC2(S(=O)(=O)CC4CC4)CC2)C3=O)cc1] | MS m/z 495.2 (M + 1). $^1$H NMR (500 MHz, DMSO-d6) δ 8.39-8.48 (m, 1H), 7.81 (d, J = 7.57 Hz, 2H), 7.51 (d, J = 6.94 Hz, 2H), 7.14-7.28 (m, 1H), 4.63 (br. s., 2H), 4.25 (d, J = 3.78 Hz, 2H), 4.02 (d, J = 6.31 Hz, 2H), 3.80 (br. s., 2H), 3.33 (br. s., 2H), 1.32 (d, J = 4.73 Hz, 2H), 1.17 (d, J = 5.04 Hz, 2H), 0.62 (br. s., 2H), 0.39 (br. s., 2H) |
| 107-3 | 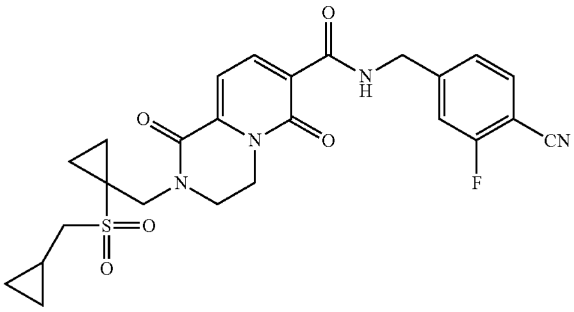 [SMILES: N#Cc1ccc(CNC(=O)c2ccc3n(c2=O)CCN(CC2(S(=O)(=O)CC4CC4)CC2)C3=O)cc1F] | MS m/z 513.2 (M + 1). $^1$H NMR (500 MHz, DMSO-d6) δ 10.20 (t, J = 6.21 Hz, 1H), 8.44 (d, J = 7.57 Hz, 1H), 7.90 (dd, J = 7.09, 7.80 Hz, 1H), 7.45 (d, J = 10.40 Hz, 1H), 7.36 (dd, J = 1.30, 8.04 Hz, 1H), 7.22 (d, J = 7.57 Hz, 1H), 4.66 (d, J = 6.15 Hz, 2H), 4.20-4.39 (m, 2H), 4.04 (s, 2H), 3.74-3.90 (m, 2H), 3.32 (d, J = 7.21 Hz, 2H), 3.18 (d, J = 4.97 Hz, 1H), 1.34 (d, J = 2.25 Hz, 2H), 1.13-1.23 (m, 2H), 1.00-1.12 (m, 1H), 0.55-0.74 (m, 2H), 0.30-0.50 (m, 2H) |

Example 108-1

N-(4-Chlorobenzyl)-2 ((cyanomethyl)sulfonyl)cyclopropyl)methyl)-1,6-dioxo-2,3,4,6-tetrahydro-1H-pyrido[1,2-a]pyrazine-7-carboxamide 2-((1-((Cyanomethyl)sulfonyl)cyclopropyl)methyl)-1,6-dioxo-2,3,4,6-tetrahydro-1H-pyrido[1,2-a]pyrazine-7-carboxylic acid (Ex-108A) was prepared from I-43 following a procedure analogous to that described for Ex-107A. MS m/z 420.2 (M+1).

N-(4-Chlorobenzyl)-2-((1-((cyanomethyl)sulfonyl)cyclopropyl)methyl)-1,6-dioxo-2,3,4,6-tetrahydro-1H-pyrido[1,2-a]pyrazine-7-carboxamide (Ex-108-1) was prepared from Ex-108A following a procedure analogous to that described for Ex-105-1.

| Example | Structure | Physical Data MS (m/z), $^1$H NMR |
|---|---|---|
| 108-1 | 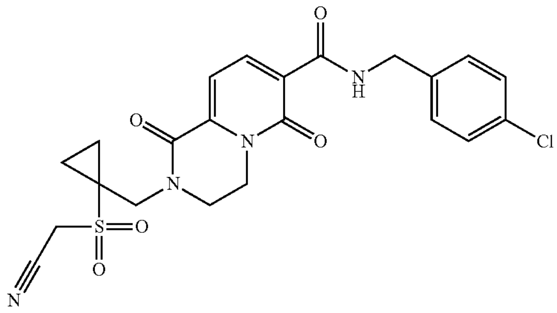 [SMILES: N#CCS(=O)(=O)C1(CN2CCn3c(ccc(C(=O)NCc4ccc(Cl)cc4)c3=O)C2=O)CC1] | MS m/z 544.2 (M + 1). $^1$H NMR (500 MHz, DMSO-d6) δ 8.44 (t, J = 7.72 Hz, 1H), 7.28-7.48 (m, 4H), 7.21 (t, J = 7.88 Hz, 1H), 4.48-4.60 (m, 2H), 4.25 (br. s., 2H), 4.00 (d, J = 7.57 Hz, 2H), 3.79 (br. s., 2H), 3.47 (d, J = 7.88 Hz, 2H), 2.79 (d, J = 7.88 Hz, 2H), 1.16-1.38 (m, 4H), 0.64-0.89 (m, 4H). |

Compounds in the table below were prepared from Ex-108A following a procedure analogous to that described for Ex-105-2.

| Example | Structure | Physical Data MS (m/z), $^1$H NMR |
|---|---|---|
| 108-2 | 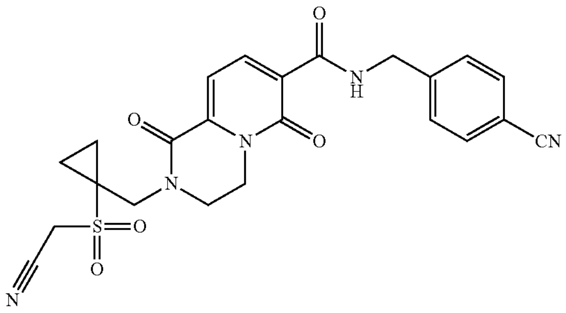 [SMILES: N#CCS(=O)(=O)C1(CN2CCn3c(ccc(C(=O)NCc4ccc(C#N)cc4)c3=O)C2=O)CC1] | MS m/z 534.3 (M + 1). $^1$H NMR (500 MHz, DMSO-d6) δ 8.38-8.52 (m, 1H), 7.72-7.90 (m, 2H), 7.43-7.58 (m, 2H), 7.15-7.28 (m, 1H), 4.63 (br. s., 2H), 4.26 (d, J = 3.78 Hz, 2H), 4.01 (d, J = 6.62 Hz, 2H), 3.80 (br. s., 2H), 3.47 (d, J = 6.94 Hz, 2H), 2.79 (d, J = 7.25 Hz, 2H), 1.11-1.41 (m, 4H), 0.63-0.91 (m, 4H) |
| Ex-108-3 | 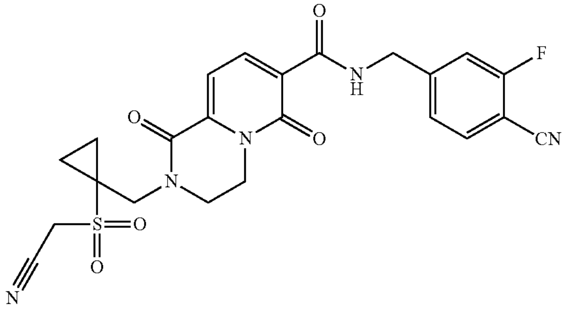 [SMILES: N#CCS(=O)(=O)C1(CN2CCn3c(ccc(C(=O)NCc4ccc(C#N)c(F)c4)c3=O)C2=O)CC1] | MS m/z 552.3 (M + 1). $^1$H NMR (500 MHz, DMSO-d6) δ 7.95 (t, J = 7.88 Hz, 1H), 7.36-7.47 (m, 1H), 6.96 (t, J = 8.83 Hz, 1H), 6.87 (t, J = 7.41 Hz, 1H), 6.73 (t, J = 8.04 Hz, 1H), 4.16 (br. s., 2H), 3.79 (br. s., 2H), 3.53 (d, J = 7.57 Hz, 2H), 3.33 (br. s., 2H), 3.00 (d, J = 7.88 Hz, 2H), 2.32 (d, J = 7.88 Hz, 2H), 0.65-0.95 (m, 4H), 0.14-0.44 (m, 4H) |

Example 109

N-(4-cyano-3-fluorobenzyl)-2-((1-(((1-methylcyclopropyl)methyl)sulfonyl)cyclopropyl)methyl)-1,6-dioxo-1,3,4,6-tetrahydro-2H-pyrido[1,2-a]pyrazine-7-carboxamide 2-((1-(((l-methylcyclopropyl)methyl)sulfonyl)cyclopropyl)methyl)-1,6-dioxo-1,3,4,6-tetrahydro-2H-pyrido[1,2-a]pyrazine-7-carboxylic acid (Ex-109A) was prepared from I-1 and B following a procedure analogous to that described for Ex-1. MS m/z 395.2 (M+1).

N-(4-cyano-3-fluorobenzyl)-2-((1-(((1-methylcyclopropyl)methyl)sulfonyl)cyclopropyl)methyl)-1,6-dioxo-1,3,4,6-tetrahydro-2H-pyrido[1,2-a]pyrazine-7-carboxamide (Ex-109). T3P® (50% in EtOAc, 875 μL, 1.47 mmol) was added to a solution of Ex-109A (290 mg, 0.735 mmol) in DCM (5 mL), followed by DIEA (770 μL, 4.41 mmol). After 5 min, 4-(aminomethyl)-2-fluorobenzonitrile hydrochloride (274 mg, 1.47 mmol) was added and the mixture was stirred overnight. The reaction was diluted with 0.5 N HCl and DCM. The phases were separated and the aqueous phase was extracted with DCM (2×). The combined organic phase was washed with brine, dried over $Na_2SO_4$, filtered, and concentrated. The crude product was purified by SFC to afford Ex-109 as a white powder.

| Example | Structure | Physical Data MS (m/z), $^1$H NMR |
|---|---|---|
| 109 | 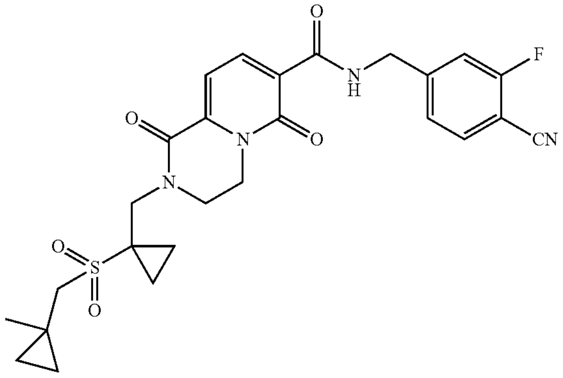 [SMILES: CC1(CS(=O)(=O)C2(CN3CCn4c(ccc(C(=O)NCc5ccc(C#N)c(F)c5)c4=O)C3=O)CC2)CC1] | MS m/z 527.2 (M + 1). |

Example 110

N-(4-chlorobenzyl)-2-((1-(((1-cyanocyclopropyl) methyl)sulfonyl)cyclopropyl)methyl)-1,6-dioxo-1,3,4,6-tetrahydro-2H-pyrido pyrazine-7-carboxamide 2-((1-(((1-cyanocyclopropyl)methyl)sulfonyl)cyclopropyl)methyl)-1,6-dioxo-1,3,4,6-tetrahydro-2H-pyrido[1,2-a] pyrazine-7-carboxylic acid (Ex-110A) was prepared from I-1 and 1-45 following a procedure analogous to that described for Ex-1. Ex-110A was obtained as an orange-brown solid. MS m/z 406.2 (M+1).

N-(4-chlorobenzyl)-2-((1-(41-cyanocyclopropyl)methyl) sulfonyl)cyclopropyl)methyl)-1,6-dioxo-1,3,4,6-tetrahydro-2H-pyrido[1,2-a]pyrazine-7-carboxamide (Ex-110) was prepared from Ex-110A following a procedure analogous to that described for Ex-109.

| Example | Structure | Physical Data MS (m/z), $^1$H NMR |
|---|---|---|
| 110 | 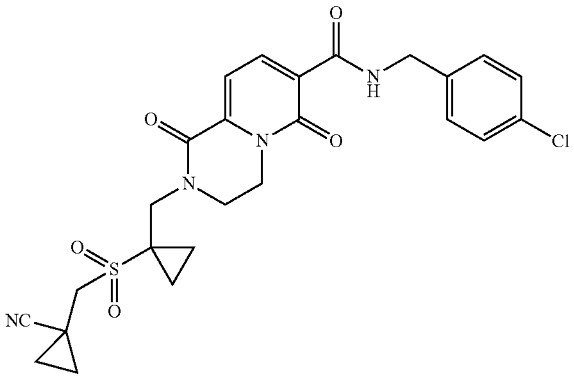 [SMILES: N#CC1(CS(=O)(=O)C2(CN3CCn4c(ccc(C(=O)NCc5ccc(Cl)cc5)c4=O)C3=O)CC2)CC1] | MS m/z 529.1, 531.2 (M + 1). |

Example 111 and 112

Compounds in the table below were prepared from Ex-110A following procedures analogous to that described for Ex-105-2.

| Example | Structure | Physical Data MS (m/z), $^1$H NMR |
|---|---|---|
| 111 | 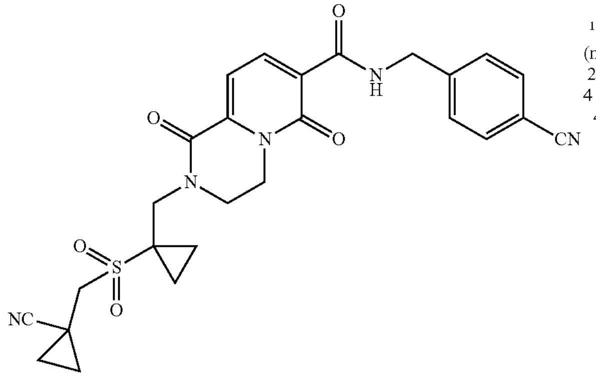 | MS m/z 520.2 (M + 1). $^1$H NMR (400 MHz, DMSO-d6) δ ppm 1.28 (m, 4 H) 1.43 (m, 4 H) 3.74 (s, 2 H) 3.83 (m, 2 H) 4.05 (s, 2 H) 4.28 (m, 2 H) 4.65 (d, J = 4 Hz, 2 H) 7.22 (d, J = 4 Hz, 2 H) 7.51 (d, J = 4 Hz, 2 H) 7.82 (m 2 H) 8.45 (d, J = 8 Hz, 1 H) 10.19 (t, J = 8 Hz 1 H). |
| 112 | 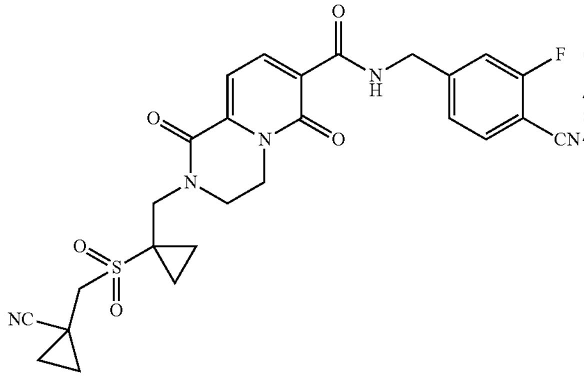 [SMILES: N#Cc1ccc(CNC(=O)c2ccc3n(c2=O)CCN(CC2(S(=O)(=O)CC4(C#N)CC4)CC2)C3=O)cc1F] | MS m/z 538.2 (M + 1). $^1$H NMR (400 MHz, DMSO-d6) δ ppm 1.32 (m, 4 H) 1.45 (m, 4 H) 3.74 (s, 2 H) 3.83 (m, 2 H) 4.05 (s, 2 H) 4.29 (m, 2 H) 4.66 (d, J = 4 Hz, 2 H) 7.22 (d, J = 4 Hz, 1 H) 7.36 (d, J = 8 Hz, 1 H) 7.45 (d, J = 8 Hz, 1 H) 7.90 (t, J = 4 Hz, 1 H) 8.44 (d, J = 8 Hz, 1 H) 10. 2 (t, J = 4 Hz, 1 H). $^{19}$F NMR (400 MHz, DMSO-d6) δ ppm 108.8 |

Example 113

N-(4-chlorobenzyl)-2-ethyl-1,6-dioxo-2,3,4,6-tetrahydro-1H-pyrido[1,2-a]pyrazine-7-carboxamide N-(4-chlorobenzyl)-2-ethyl-1,6-dioxo-2,3,4,6-tetrahydro-1H-pyrido[1,2-a]pyrazine-7-carboxamide (Ex-113). To a solution of I-17C (0.072 g, 0.235 mmol) in ACN (2.5 mL) were added HATU (0.205 g, 0.540 mmol) and $Cs_2CO_3$ (0.268 g, 0.822 mmol). To the resulting mixture was added N-ethylethanolamine (0.027 mL, 0.282 mmol). The reaction mixture was stirred at 60° C. The reaction mixture was diluted with $H_2O$ and EtOAc. The phases were separated and the organic layer was dried over sodium sulfate. The dried organic phase was concentrated to an orange residue, which was purified by RP-HPLC. Clean fractions were combined and lyophilized Ex-113 was isolated as an off-white solid.

| Example | Structure | Physical Data MS (m/z), $^1$H NMR |
|---|---|---|
| 113 | 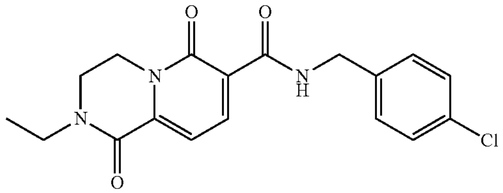 [SMILES: CCN1CCn2c(ccc(C(=O)NCc3ccc(Cl)cc3)c2=O)C1=O] | MS m/z: 360, (M + 1). $^1$H NMR (500 MHz, METHANOL-d4) δ ppm 1.26 (t, J = 7.25 Hz, 3 H) 3.64 (q, J = 7.04 Hz, 2 H) 3.78 (t, J = 5.99 Hz, 2 H) 4.35 (t, J = 5.99 Hz, 2 H) 4.62 (s, 2 H) 7.32 (d, J = 7.57 Hz, 1 H) 7.36 (s, 4 H) 8.55 (d, J = 7.57 Hz, 1 H). |

Example 114

N-(4-chlorobenzyl)-2-methyl-1,6-dioxo-2,3,4,6-tetrahydro-1H-pyrido[1,2-a]pyrazine-7-carboxamide N5-(4-chlorobenzyl)-N2-(2-hydroxyethyl)-N2-methyl-6-oxo-1,6-dihydropyridine-2,5-dicarboxamide, (Ex-114A) was prepared from I-17C and N-methylethanolamine following a procedure analogous to that described for Ex-91A. The title compound was isolated as a yellow solid. MS m/z: 364, (M+1).

N-(4-chlorobenzyl)-2-methyl-1,6-dioxo-2,3,4,6-tetrahydro-1H-pyrido[1,2-a]pyrazine-7-carboxamide Ex-114 was prepared from Ex-114A following a procedure analogous to that described for Ex-92B. The title compound was isolated as a white solid.

| Example | Structure | Physical Data MS (m/z), $^1$H NMR |
|---|---|---|
| 114 | 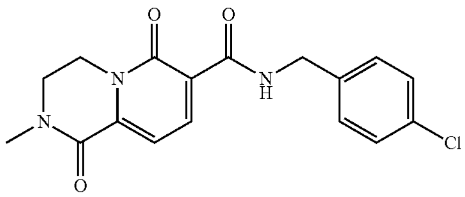 [SMILES: CN1CCn2c(ccc(C(=O)NCc3ccc(Cl)cc3)c2=O)C1=O] | MS m/z: 346, (M + 1). $^1$H NMR (400 MHz, METHANOL-$d_4$) δ ppm 3.15 (s, 3 H) 3.74 (t, J = 5.87 Hz, 2 H) 4.32 (t, J = 5.87 Hz, 2 H) 4.59 (s, 3 H) 7.29 (d, J = 7.43 Hz, 1 H) 7.33 (s, 4 H) 8.51 (d, J = 7.43 Hz, 1 H). |

Example 115

N-(4-chlorobenzyl)-2-(2-(N-cyclopropylmethylsulfonamido)ethyl)-1,6-dioxo-2,3,4,6-tetrahydro-1H-pyrido[1,2-a]pyrazine-7-carboxamide N5-(4-chlorobenzyl)-N2-(2,2-dimethoxyethyl)-1-(2-hydroxyethyl)-6-oxo-1,6-dihydrioyridine-2,5-dicarboxamide, (Ex-115A) was prepared from 1-17 following a procedure analogous to that described for Ex-51A. MS m/z: 438, (M+1).

N5-(4-chlorobenzyl)-1-(2-chloroethyl)-N2-(2,2-dimethoxyethyl)-6-oxo-1,6-dihydripyridine-2,5-dicarboxamide, (Ex-115B) was prepared from Ex-115A following a procedure analogous to that described for Ex-51B. MS m/z: 456(M+1), 458 (M+3).

N-(4-chlorobenzyl)-2-(2,2-dimethoxyethyl)-1,6-dioxo-2,3,4,6-tetrahydro-1H-pyrido[1,2-a]pyrazine-7-carboxamide, (Ex-115C) was prepared from Ex-115B following a procedure analogous to that described for Ex-54. MS m/z: 420 (M+1).

N-(4-chlorobenzyl)-1,6-dioxo-2-(2-oxoethyl)-2,3,4,6-tetrahydro-1H-pyrido[1,2-a]pyrazine-7-carboxamide, (Ex-115D): A solution of Ex-115C (0.15 g, 0.357 mmol) in THF (4 mL) was treated with 2 M HCl (3 mL). Upon completion of the reaction, the mixture was concentrated under reduced pressure. The residue was taken up in DCM and dried over sodium sulfate. The dried organic solution was concentrated under reduced pressure. The title compound isolated as a light yellow residue. MS m/z: 374, (M+1).

N-(4-chlorobenzyl)-2-(2-(cyclopropylamino)ethyl)-1,6-dioxo-2,3,4,6-tetrahydro-1H-pyrido[1,2-a]pyrazine-7-carboxamide (Ex-115E). To a solution of Ex-115D (0.132 g, 0.353 mmol) in DCE (1 mL) was added cyclopropylamine (0.037 mL, 0.530 mmol). The resulting mixture was stirred at RT overnight. Sodium triacetoxyborohydride (0.150 g, 0.706 mmol) and additional amine (0.1 mL) were added. The reaction mixture was diluted with DCM and saturated sodium bicarbonate. The phases were separated, and the organic layer washed with saturated sodium bicarbonate, water, and brine. The organic layer was dried over sodium sulfate and concentrated under reduced pressure. The title compound was isolated as an orange solid. MS m/z: 415, (M+1).

N-(4-chlorobenzyl)-2-(2-(N-cyclopropylmethylsulfonamido)ethyl)-1,6-dioxo-2,3,4,6-tetrahydro-1H-pyrido[1,2-a]pyrazine-7-carboxamide (Ex-115) was prepared from Ex-115E following a procedure analogous to that described in Ex-62.

| Example | Structure | Physical Data MS (m/z), $^1$H NMR |
|---|---|---|
| 115 | 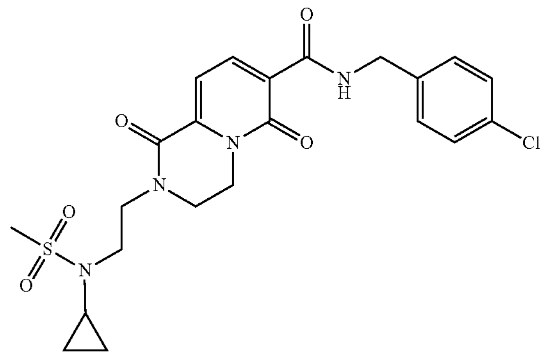 [SMILES: CS(=O)(=O)N(CCN1CCn2c(ccc(C(=O)NCc3ccc(Cl)cc3)c2=O)C1=O)C1CC1] | MS m/z: 493, (M + 1). $^1$H NMR (500 MHz, DMSO-d6) δ ppm 0.81 (m, J = 5.04 Hz, 2 H) 0.90-0.96 (m, 2 H) 2.62 (tt, J = 6.78, 3.63 Hz, 1 H) 2.95 (s, 3 H) 3.53 (t, J = 5.83 Hz, 2 H) 3.75-3.84 (m, 4 H) 4.31-4.38 (m, 2 H) 4.60 (s, 2 H) 7.29 (d, J = 7.57 Hz, 1 H) 7.33 (s, 3 H) 8.52 (d, J = 7.57 Hz, 1 H). |

Example 116

N-(4-chlorobenzyl)-2-(2-hydroxyethyl)-1,6-dioxo-2,3,4,6-tetrahydro-1H-pyrido[1,2-a]pyrazine-7-carboxamide N5-(4-chlorobenzyl)-N2,1-bis(2-hydroxyethyl)-6-oxo-1,6-dihydropyridine-2,5-dicarboxamide (Ex-116A) was prepared from 1-17 and ethanolamine following a procedure analogous to that described for Ex-51A. MS m/z: 394(M+1).

2-(7-((4-chlorobenzyl)carbamoyl)-1,6-dioxo-3,4-dihydro-1H-pyrido[1,2-a]pyrazin-2(6H)-yl)ethyl benzoate (Ex-116B): To a mixture of Ex-116A (0.083 g, 0.211 mmol) in THF (2 mL) were added polymer-bound triphenylphosphine (approx. 3.0 mmol/g, Aldrich) (0.175 g, 0.667 mmol) and DIAD (0.102 mL, 0.527 mmol). The resulting mixture was stirred at RT for 24 h. The reaction mixture was filtered through a small plug of Celite. The filtrate was concentrated under reduced pressure. The resulting residue was taken up in pyridine (2 mL) and treated with benzoic anhydride (0.082 g, 0.362 mmol). Upon completion of the reaction, the mixture was concentrated under reduced pressure. The yellow residue was purified on $SiO_2$ (0-100% EtOAc/heptane) to afford the title compound as an off-white solid. MS m/z 480(M+1).

N-(4-chlorobenzyl)-2-(2-hydroxyethyl)-1,6-dioxo-2,3,4,6-tetrahydro-1H-pyrido[1,2-a]pyrazine-7-carboxamide (Ex-116). To a solution of Ex-116B (9.0 mg, 0.019 mmol) in MeOH (0.5 mL) was added $K_2CO_3$ (2.59 mg, 0.019 mmol). The resulting mixture was stirred at RT overnight, after which it was concentrated under reduced pressure. The orange residue was taken up in $CHCl_3$ and saturated sodium bicarbonate. The aqueous layer was extracted with $CHCl_3$ (2×). The combined organics were dried over sodium sulfate and concentrated under reduced pressure. The residue was purified by RP-HPLC. Clean fractions were combined and lyophilized to afford the title compound.

| Example | Structure | Physical Data MS (m/z), $^1$H NMR |
|---|---|---|
| 116 | 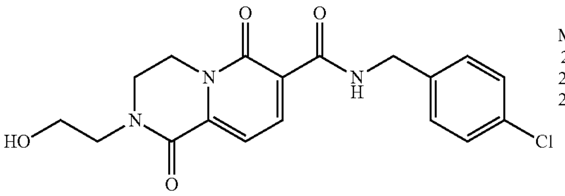 | MS m/z: 376 (M + 1). $^1$H NMR (500 MHz, METHANOL-d4) δ ppm 3.71 (t, J = 5.20 Hz, 2 H) 3.81 (t, J = 5.36 Hz, 2 H) 3.83-3.90 (m, 2 H) 4.33-4.39 (m, 2 H) 4.62 (d, J = 5.99 Hz, 2 H) 7.33 (d, J = 7.57 Hz, 1 H) 7.34-7.40 (m, 4 H) 8.55 (d, J = 7.57 Hz, 1 H). |

Example 117

9-bromo-N-(4-chlorobenzyl)-2-(2-(methylsulfonyl)ethyl)-1,6-dioxo-1,3,4,6-tetrahydro-2H-pyrido[1,2-a]pyrazine-7-carboxamide 3-bromo-$N^5$-(4-chlorobenzyl)-1-(2-hydroxyethyl)-$N^2$-(2-(methylthio)ethyl)-6-oxo-1,6-dihydropyridine-2,5-dicarboxamide (Ex-117A) was prepared from 1-47 and 2-(methylthio)ethan-1-amine following a procedure analogous to that described for I-51A. LCMS (m/z): 502.3 [M+H]. $^1$H NMR (400 MHz, DMSO-d6) δ 9.94 (t, J=6.0 Hz, 1H), 9.23 (t, J=5.7 Hz, 1H), 8.40 (d, J=30.0 Hz, 1H), 7.40 (d, J=8.5 Hz, 2H), 7.34 (d, J=8.4 Hz, 2H), 4.96 (s, 1H), 4.52 (d, J=5.9 Hz, 2H), 3.61 (s, 2H), 3.50 (d, J=6.8 Hz, 2H), 2.68 (d, J=6.1 Hz, 2H), 2.09 (d, J=21.0 Hz, 3H).

3-bromo-$N^5$-(4-chlorobenzyl)-1-(2-chloroethyl)-$N^2$-(2-(methylthio)ethyl)-6-oxo-1,6-dihydropyridine-2,5-dicarboxamide (Ex-117B) was prepared from Ex-117A following a procedure analogous to that described for I-51B. LCMS (m/z): 522.1 [M+H]. $^1$H NMR (400 MHz, DMSO-d6) δ 9.73 (s, 2H), 8.40 (d, J=21.2 Hz, 1H), 7.37 (dd, J=22.5, 8.4 Hz, 4H), 4.52 (d, J=5.9 Hz, 2H), 4.32 (s, 2H), 3.80 (s, 2H), 2.05 (d, J=47.3 Hz, 3H).

9-bromo-N-(4-chlorobenzyl)-2-(2-(methylthio)ethyl)-1,6-dioxo-1,3,4,6-tetrahydro-2H-pyrido[1,2-a]pyrazine-7-carboxamide (Ex-117C). Ex-117B (0.21 g, 0.4 mmol, 1.0 equiv) was dissolved in DMF (2 mL). $Cs_2CO_3$ (0.39 g, 1.2 mmol, 3.0 equiv) was added and the reaction mixture was stirred at RT for 24 h. The reaction mixture was quenched with water and extracted with EtOAc. The organic layer was washed with brine, dried over sodium sulfate, and concentrated to afford Ex-117C. LCMS (m/z): 484.2 [M+H]. $^1$H NMR (400 MHz, DMSO-d6) δ 10.00 (dd, J=18.1, 12.1 Hz, 1H), 8.38 (d, J=13.7 Hz, 1H), 7.36 (dt, J=26.5, 13.2 Hz, 4H), 4.53 (t, J=7.3 Hz, 2H), 4.27 (dd, J=32.1, 26.9 Hz, 2H), 4.08-3.49 (m, 4H), 2.93-2.64 (m, 2H), 2.30-2.05 (m, 3H).

9-bromo-N-(4-chlorobenzyl)-2-(2-(methylsulfonyl)ethyl)-1,6-dioxo-1,3,4,6-tetrahydro-2H-pyrido[1,2-a]pyrazine-7-carboxamide (Ex-117). Ex-117C (0.17 g, 0.4 mmol, 1.0 equiv) was dissolved in dichloromethane (2 mL). m-CPBA (approx. 55%) (0.22 g, 0.7 mmol, 2.0 equiv) was added in portions. The reaction mixture was stirred at RT for 30 min. The reaction mixture was quenched with saturated aqueous sodium bicarbonate solution and extracted with dichloromethane. The organic layer was washed with brine, dried over sodium sulfate and concentrated. The crude residue was purified by preparative HPLC to afford the title compound.

| Example | Structure | Physical Data MS (m/z), $^1$H NMR |
|---|---|---|
| 117 | 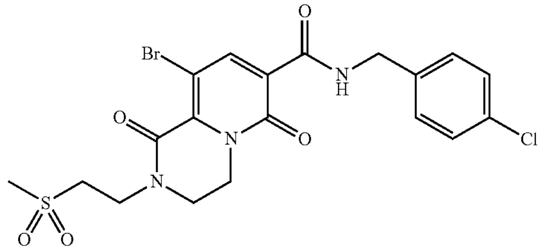 [SMILES: CS(=O)(=O)CCN1CCn2c(c(Br)cc(C(=O)NCc3ccc(Cl)cc3)c2=O)C1=O] | 516.4 [M + H]. $^1$H NMR (400 MHz, DMSO-d6) δ 9.98 (t, J = 5.9 Hz, 1H), 8.39 (s, 1H), 7.40 (d, J = 8.5 Hz, 2H), 7.39-7.25 (m, 2H), 4.54 (d, J = 6.0 Hz, 2H), 4.37-4.15 (m, 2H), 3.89 (t, J = 6.8 Hz, 2H), 3.76 (d, 7= 5.0 Hz, 2H), 3.50 (t, J = 6.7 Hz, 2H), 3.07 (s, 3H). |

Compounds in the table below were prepared from 1-47 and 1-54, 1-56, 1-57, or I-63 following procedures analogous to those described for Ex-117C.

| Example | Structure | Physical Data MS (m/z), $^1$H NMR |
|---|---|---|
| 118 | 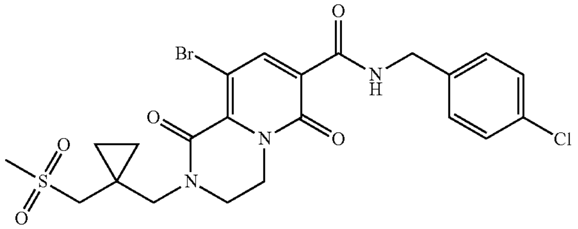 [SMILES: CS(=O)(=O)CC1(CN2CCn3c(c(Br)cc(C(=O)NCc4ccc(Cl)cc4)c3=O)C2=O)CC1] | LCMS (m/z): 556.8 [M + H]. |
| 119 | 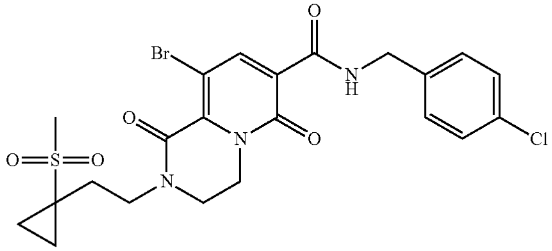 [SMILES: CS(=O)(=O)C1(CCN2CCn3c(c(Br)cc(C(=O)NCc4ccc(Cl)cc4)c3=O)C2=O)CC1] | LCMS (m/z): 556.8 [M + H]. |
| 120 | 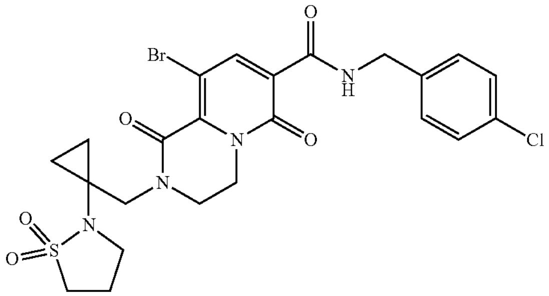 [SMILES: O=C(NCc1ccc(Cl)cc1)c1cc(Br)c2n(c1=O)CCN(CC1(N3CCCS3(=O)=O)CC1)C2=O] | LCMS (m/z): 585.8 [M + H]. $^1$H NMR (400 MHz, DMSO-d6) δ 9.99 (t, J = 6.0 Hz, 1H), 8.40 (d, J = 4.0 Hz, 1H), 7.40 (d, J = 8.5 Hz, 2H), 7.35 (d, J = 8.5 Hz, 2H), 4.54 (d, J = 6.0 Hz, 2H), 4.27 (s, 2H), 3.83-3.77 (m, 2H), 3.50-3.38 (m, 4H), 3.13 (t, J = 7.4 Hz, 2H), 2.23-2.17 (m, 2H), 1.09 (d, J = 5.1 Hz, 2H), 0.86 (d, J = 4.8 Hz, 2H). |

-continued

| Example | Structure | Physical Data MS (m/z), $^1$H NMR |
|---|---|---|
| 121 | 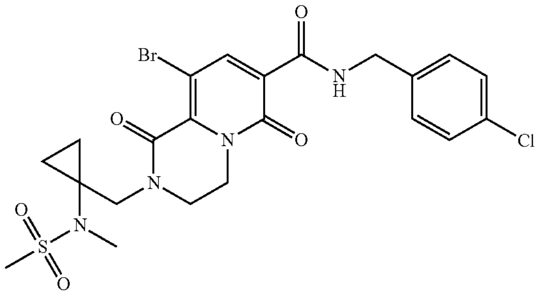 [SMILES: CN(C1(CN2CCn3c(c(Br)cc(C(=O)NCc4ccc(Cl)cc4)c3=O)C2=O)CC1)S(C)(=O)=O] | LCMS (m/z): 571.9 [M + H]. |

Example 122

9-bromo-N-(4-chlorobenzyl)-2-(2-(N-methyl methyl sulfonamido)ethyl)-1,6-dioxo-1,3,4,6-tetrahydro-2H-pyrido[1,2-a]pyrazine-7-carboxamide 3-bromo-N$^5$-(4-chlorobenzyl)-1-(2-hydroxyethyl)-N$^2$-(2-(N-methyl methyl sulfonamido)ethyl)-6-oxo-1,6-dihydro-pyridine-2,5-dicarboxamide (Ex-122A) was prepared from 1-47 and 1-60 following a procedure analogous to that described for Ex-64E. LCMS (m/z): 581.5 [M+18]. $^1$H NMR (400 MHz, DMSO-d6) δ 9.94 (t, J=5.9 Hz, 1H), 9.21 (t, J=5.7 Hz, 1H), 8.36 (s, 1H), 7.40 (d, J=8.5 Hz, 2H), 7.34 (d, J=8.4 Hz, 2H), 4.89 (t, J=5.9 Hz, 1H), 4.52 (d, J=5.9 Hz, 2H), 4.06 (d, J=30.5 Hz, 2H), 3.62 (dd, J=12.5, 6.3 Hz, 2H), 3.50 (d, J=6.2 Hz, 2H), 3.28-3.18 (m, 2H), 2.92 (s, 3H), 2.83 (s, 3H).

3-bromo-N$^5$-(4-chlorobenzyl)-1-(2-chloroethyl)-N$^2$-(2-(N-methyl methyl sulfonamido)ethyl)-6-oxo-1,6-dihydro-pyridine-2,5-dicarboxamide (Ex-122B). Ex-122A (1.8 g, 3.19 mmol, 1.0 equiv) was dissolved in dichloromethane (18 mL). TEA (0.97 g, 9.6 mmol, 3.0 equiv) and $MeSO_2Cl$ (1.64 g, 14.4 mmol, 1.5 equiv) were added and the reaction mixture was stirred at 40° C. for 3 h. The reaction mixture was diluted with water and extracted with dichloromethane. The organic layer was washed with brine, dried over sodium sulfate and concentrated. The crude residue was purified by silica gel column chromatography (50% EtOAc/Hexane) to afford Ex-122B. LCMS (m/z): 581.5 [M+H].

9-bromo-N-(4-chlorobenzyl)-2-(2-(N-methyl methyl sulfonamido)ethyl)-1,6-dioxo-1,3,4,6-tetrahydro-2H-pyrido[1,2-a]pyrazine-7-carboxamide (Ex-122) was prepared from Ex-122B following a procedure analogous to that described for Ex-54.

| Example | Structure | Physical Data MS (m/z), $^1$H NMR |
|---|---|---|
| 122 | 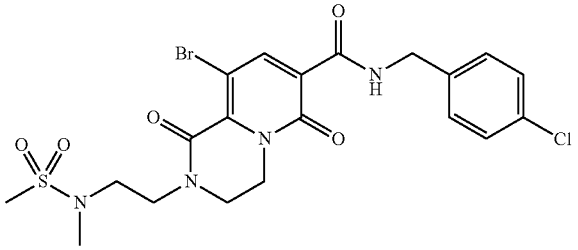 [SMILES: CN(CCN1CCn2c(c(Br)cc(C(=O)NCc3ccc(Cl)cc3)c2=O)C1=O)S(C)(=O)=O] | LCMS (m/z): 545.5 [M + H], $^1$H NMR (400 MHz, DMSO-d6) δ 9.98 (t, J = 5.9 Hz, 1H), 8.39 (s, 1H), 7.40 (d, J = 8.5 Hz, 2H), 7.34 (d, J = 8.5 Hz, 2H), 4.54 (d, J = 5.9 Hz, 2H), 4.25 (s, 2H), 3.69 (dd, J = 12.0,5.8 Hz, 4H), 3.29 (t, J = 5.7 Hz, 2H), 2.90 (s, 3H), 2.83 (s, 3H). |

Example 123

9-bromo-N-(4-chlorobenzyl)-2-(3-(methyl sulfonyl) propyl)-1,6-dioxo-1,3,4,6-tetrahydro-2H-pyrido[1,2-a]pyrazine-7-carboxamide 3-bromo-N$^5$-(4-chlorobenzyl)-1-(2-hydroxyethyl)-N$^2$-(3-(methylthio) propyl)-6-oxo-1,6-dihydropyridine-2,5-dicarboxamide (Ex-123A) was prepared from 1-47 and 3-(methylthio)propan-1-amine following a procedure analogous to that described for Ex-51A. LCMS (m/z): 516.5 [M+H]. $^1$H NMR (400 MHz, DMSO-d6) δ 9.93 (t, J=5.9 Hz, 1H), 9.14 (s, 1H), 8.36 (s, 1H), 7.36 (d, J=6.0 Hz, 2H), 7.34-7.23 (m, 2H), 5.02 (s, 1H), 4.52 (d, J=6.0 Hz, 2H), 4.43 (t, J=20.6 Hz, 2H), 4.02 (d, J=7.1 Hz, 2H), 3.61 (s, 2H), 3.17 (s, 2H), 2.56 (dd, J=14.0, 6.8 Hz, 2H), 2.06 (s, 3H).

3-bromo-N$^5$-(4-chlorobenzyl)-1-(2-chloroethyl)-N$^2$-(3-(methylthio)propyl)-6-oxo-1,6-dihydropyridine-2,5-dicarboxamide (Ex-123B) was prepared from Ex-123A following a procedure analogous to that described for Ex-51B. LCMS (m/z): 536.3 [M+H].

9-bromo-N-(4-chlorobenzyl)-2-(3-(methylthio) propyl)-1,6-dioxo-1,3,4,6-tetrahydro-2H-pyrido[1,2-a]pyrazine-7-carboxamide (Ex-123C) was prepared from Ex-123B following a procedure analogous to that described for Ex-117C. LCMS (m/z): 498.3 [M+H]. $^1$H NMR (400 MHz, DMSO-d6) δ 10.00 (s, 1H), 8.39 (s, 1H), 7.96 (s, 1H), 7.39 (d, J=2.6 Hz, 2H), 7.35 (d, J=4.3 Hz, 2H), 4.54 (d, J=6.0 Hz, 2H), 4.24 (s, 2H), 3.70 (d, J=5.8 Hz, 2H), 3.53 (d, J=7.1 Hz, 2H), 3.01 (dd, J=11.7, 5.5 Hz, 2H), 2.90 (s, 2H), 2.74 (s, 3H).

Step 4. Synthesis of 9-bromo-N-(4-chlorobenzyl)-2-(3-(methyl sulfonyl) propyl)-1,6-dioxo-1,3,4,6-tetrahydro-2H-pyrido[1,2-a]pyrazine-7-carboxamide (Ex-123). Ex-123C (0.23 g, 0.46 mmol, 1.0 equiv) was dissolved in acetonitrile (10 mL) and water (10 mL). Oxone (0.71 g, 1.15 mmol, 2.5 equiv) was added and the reaction mixture was stirred at RT for 6 h. The reaction mixture was quenched with water and extracted with EtOAc. The organic layer was washed with brine, dried over sodium sulfate and concentrated. The crude residue was purified by silica gel column chromatography (0-2% MeOH/DCM) to afford the title product.

| Example | Structure | Physical Data MS (m/z), $^1$H NMR |
|---|---|---|
| 123 | 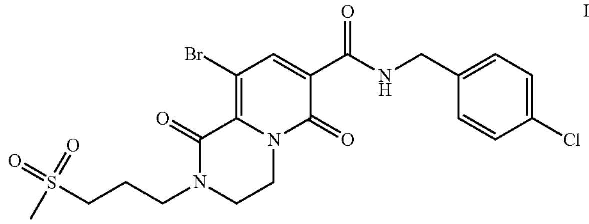 | LCMS (m/z): 530.3 [M + H]. $^1$H NMR (400 MHz, DMSO-d6) δ 10.00 (t, J = 6.1 Hz, 1H), 8.40 (s, 1H), 7.41 (d, J = 8.5 Hz, 2H), 7.34 (d, J = 8.4 Hz, 2H), 4.54 (d, J = 6.0 Hz, 2H), 4.29-4.22 (m, 2H), 3.75-3.68 (m, 2H), 3.58 (t, J = 6.8 Hz, 2H), 3.23-3.15 (m, 2H), 2.05-1.95 (m, 2H). |

Example 124

9-bromo-N-(4-chlorobenzyl)-2-(2-(1,1-dioxidoisothiazolidin-2-yl)ethyl)-1,6-dioxo-1,3,4,6-tetrahydro-2H-pyrido[1,2-a]pyrazine-7-carboxamide 3-bromo-$N^5$-(4-chlorobenzyl)-$N^2$-(2-(1,1-dioxidoisothiazolidin-2-yl)ethyl)-1-(2-hydroxyethyl)-6-oxo-1,6-dihydropyridine-2,5-dicarboxamide (Ex-124A) was prepared from 1-47 and I-18D following a procedure analogous to that described for Ex-64E. LCMS (m/z): 575.2 [M+H]. $^1$H NMR (400 MHz, DMSO-d6) δ 9.94 (t, J=6.0 Hz, 1H), 9.20 (d, J=5.8 Hz, 1H), 8.36 (s, 1H), 7.41 (d, J=8.5 Hz, 2H), 7.34 (d, J=8.5 Hz, 2H), 4.97 (t, J=5.8 Hz, 1H), 4.52 (d, J=5.8 Hz, 2H), 4.03 (d, J=7.1 Hz, 2H), 3.64-3.43 (m, 4H), 3.23 (s, 4H), 3.08 (s, 2H), 2.27-2.21 (m, 2H).

3-bromo-$N^5$-(4-chlorobenzyl)-1-(2-chloroethyl)-$N^2$-(2-(1,1-dioxidoisothiazolidin-2-yl)ethyl)-6-oxo-1,6-dihydropyridine-2,5-dicarboxamide (Ex-124B) was prepared from Ex-124A following a procedure analogous to that described for Ex-122B. LCMS (m/z): 595.6 [M+H]. $^1$H NMR (400 MHz, DMSO-d6) δ 9.84 (t, J=6.1 Hz, 1H), 9.43 (t, J=5.7 Hz, 1H), 8.37 (s, 1H), 7.38 (s, 2H), 7.34 (d, J=8.5 Hz, 2H), 4.51 (d, J=5.8 Hz, 2H), 3.81 (t, J=7.2 Hz, 2H), 3.28-3.19 (m, 6H), 3.03 (s, 4H), 2.26-2.22 (m, 2H).

9-bromo-N-(4-chlorobenzyl)-2-(2-(1,1-dioxidoisothiazolidin-2-yl)ethyl)-1,6-dioxo-1,3,4,6-tetrahydro-2H-pyrido[1,2-a]pyrazine-7-carboxamide (Ex-124) was prepared from Ex-124B following a procedure analogous to that described for Ex-117C. LCMS (m/z): 557.5 [M+H]. $^1$H NMR (400 MHz, DMSO-d6) δ 9.98 (t, J=6.0 Hz, 1H), 8.39 (s, 1H), 7.40 (d, J=8.5 Hz, 2H), 7.34 (d, J=8.6 Hz, 2H), 4.54 (d, J=6.0 Hz, 2H), 4.28-4.22 (m, 2H), 3.73-3.64 (m, 4H), 3.30 (t, J=6.8 Hz, 2H), 3.18 (t, J=7.5 Hz, 4H), 2.26-2.19 (m, 2H).

| Example | Structure | Physical Data MS (m/z), $^1$H NMR |
|---|---|---|
| 124 | 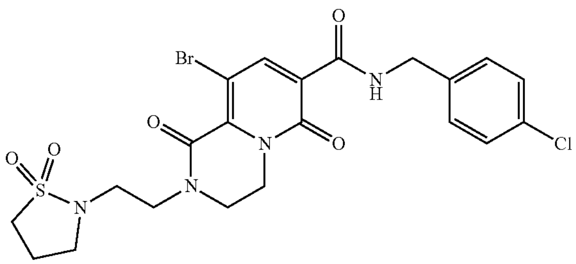 [SMILES: O=C(NCc1ccc(Cl)cc1)c1cc(Br)c2n(c1=O)CCN(CCN1CCCS1(=O)=O)C2=O] | LCMS (m/z): 557.5 [M + H]. $^1$H NMR (400 MHz, DMSO-d6) δ 9.98 (t, J = 6.0 Hz, 1H), 8.39 (s, 1H), 7.40 (d, J = 8.5 Hz, 2H), 7.34 (d, J = 8.6 Hz, 2H), 4.54 (d, J = 6.0 Hz, 2H), 4.28-4.22 (m, 2H), 3.73-3.64 (m, 4H), 3.30 (t, J = 6.8 Hz, 2H), 3.18 (t, J = 7.5 Hz, 4H), 2.26-2.19 (m, 2H). |

Example 125

N-(4-chlorobenzyl)-9-cyano-2-(2-(methylsulfonyl) ethyl)-1,6-dioxo-1,3,4,6-tetrahydro-2H-pyrido[1,2-a] pyrazine-7-carboxamide N-(4-chlorobenzyl)-9-cyano-2-(2-(methylsulfonyl) ethyl)-1,6-dioxo-1,3,4,6-tetrahydro-2H-pyrido[1,2-a]pyrazine-7-carboxamide (Ex-125). Ex-117 (0.2 g, 0.4 mmol, 1.0 equiv) and $Zn(CN)_2$ (0.54 g, 5.0 mmol, 12.0 equiv) were added in DMA (5 mL). The reaction mixture was degassed for 15 min $Pd[P(t\text{-}Bu)_3]_2$ (0.04 g, 0.08 mmol, 0.2 equiv) was added and the reaction mixture was stirred at 70° C. for 24 h. The reaction mixture was quenched with water and extracted with EtOAc. The organic layer was washed with brine, dried over sodium sulfate, and concentrated. The crude residue was purified by preparative HPLC to afford the title compound. LCMS (m/z): 463.3 [M+H]. $^1H$ NMR (400 MHz, DMSO-d6) δ 9.72 (t, J=6.1 Hz, 1H), 8.42 (s, 1H), 7.40 (d, J=8.5 Hz, 2H), 7.35 (d, J=8.5 Hz, 2H), 4.54 (d, J=6.0 Hz, 2H), 4.31-4.24 (m, 2H), 3.92 (t, J=6.9 Hz, 2H), 3.85-3.74 (m, 2H), 3.52 (t, J=6.8 Hz, 2H), 3.09 (s, 3H).

Other compounds in the table below were prepared from the corresponding bromides following procedures analogous to that described for Ex-125.

Example 128

N-(4-chlorobenzyl)-9-cyclopropyl-2-(2-(N-methyl methyl sulfonamido)ethyl)-1,6-dioxo-1, 3, 4, 6-tetrahydro-2H-pyrido[1,2-a]pyrazine-7-carboxamide N-(4-chlorobenzyl)-2-(2-(N-methyl methyl sulfonamido) ethyl)-1,6-dioxo-9-vinyl-1,3,4,6-tetrahydro-2H-pyrido[1,2-a]pyrazine-7-carboxamide (Ex-128A). Ex-122 (0.2 g, 0.4 mmol, 1.0 equiv), potassium vinyltrifluoroborate (0.059 g, 0.4 mmol, 1.2 equiv) were added in n-propanol (2 mL) and the reaction mixture was degassed for 10 min $PdCl_2$(dppf) (0.005 g, 0.01 mmol, 0.02 equiv), TEA (0.037 g, 0.4 mmol, 1.0 equiv) were added and the reaction mixture was stirred at 100° C. for 4 h. The reaction mixture was quenched with water and extracted with EtOAc. The organic layer was washed with brine, dried over sodium sulfate and concentrated to afford Ex-128A. LCMS (m/z): 493.5 [M+H]. $^1H$ NMR (400 MHz, DMSO-d6) δ 10.08 (d, J=5.8 Hz, 1H), 8.58 (s, 1H), 7.39 (s, 2H), 7.36 (s, 2H), 5.79 (d, J=15.8 Hz, 1H), 5.64 (d, J=17.6 Hz, 1H), 5.30 (d, J=11.5 Hz, 1H), 4.55 (d, J=5.8 Hz, 2H), 4.37 (t, J=5.2 Hz, 1H), 4.24 (d, J=5.8 Hz, 2H), 3.70 (d, J=5.1 Hz, 4H), 3.29 (d, J=5.8 Hz, 2H), 2.89 (s, 3H), 2.83 (s, 3H).

| Example | Structure | Physical Data MS (m/z), $^1H$ NMR |
|---|---|---|
| 125 | 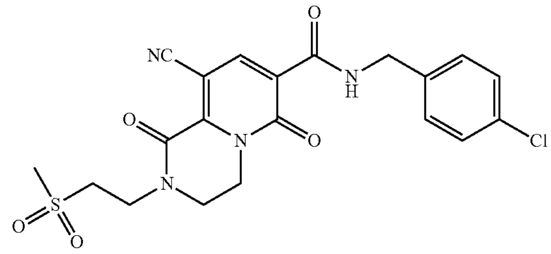 | LCMS (m/z): 463.3 [M + H]. $^1H$ NMR (400 MHz, DMSO-d6) δ 9.72 (t, J = 6.1 Hz, 1H), 8.42 (s, 1H), 7.40 (d, J = 8.5 Hz, 2H), 7.35 (d, J = 8.5 Hz, 2H), 4.54 (d, J = 6.0 Hz, 2H), 4.31-4.24 (m, 2H), 3.92 (t, J = 6.9 Hz, 2H), 3.85-3.74 (m, 2H), 3.52 (t, J = 6.8 Hz, 2H), 3.09 (s, 3H). |
| 126 | 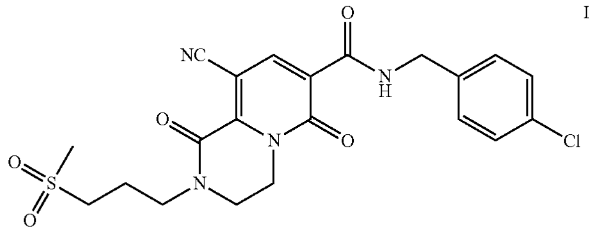 | LCMS (m/z): 476.6 [M + H]. $^1H$ NMR (400 MHz, $CD_3CN$) δ 9.72 (s, 1H), 8.58 (s, 1H), 7.40-7.34 (m, 4H), 4.58 (d, J = 6.1 Hz, 2H), 4.31-4.26 (m, 2H), 3.70 (dd, J = 13.0, 6.5 Hz, 4H), 3.16-3.10 (m, 2H), 2.91 (s, 3H), 2.13 (s, 2H). |
| 127 | 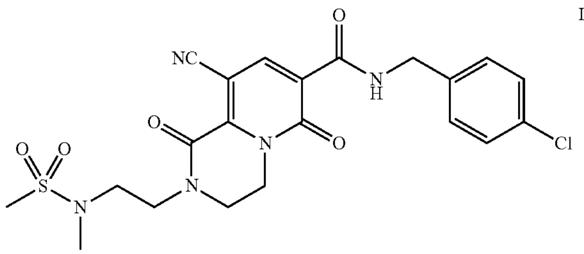 | LCMS (m/z): 492.4 [M + H]. $^1H$ NMR (400 MHz, DMSO-d6) δ 9.72 (t, J = 6.0 Hz, 1H), 8.41 (s, 1H), 7.40 (d, J = 8.6 Hz, 2H), 7.35 (d, J = 8.5 Hz, 2H), 4.54 (d, J = 6.0 Hz, 2H), 4.29-4.23 (m, 2H), 3.80-3.73 (m, 2H), 3.71 (t, J = 5.8 Hz, 2H), 3.31 (d, J = 5.9 Hz, 2H), 2.91 (s, 3H), 2.84 (s, 3H). |

N-(4-chlorobenzyl)-9-cyclopropyl-2-(2-(N-methyl methyl sulfonamido)ethyl)-1,6-dioxo-1,3,4,6-tetrahydro-2H-pyrido[1,2-a]pyrazine-7-carboxamide (Ex-128). Ex-128A (0.14 g, 0.3 mmol, 1.0 equiv) was dissolved in dichloromethane (5 mL) and cooled to 0° C. $Et_2Zn$ (1 M in Hexane) (1.4 mL, 1.4 mmol, 5.0 equiv), diiodomethane (0.76 g, 2.8 mmol, 10.0 equiv) was added drop wise and the reaction mixture was stirred RT for 7 h. The reaction mixture was quenched with saturated aqueous ammonium chloride solution and extracted with EtOAc. The organic layer was washed with brine, dried over sodium sulfate, and concentrated. The crude residue was purified by preparative HPLC to afford the title compound.

Other compounds in table below were prepared from the corresponding bromides following procedures analogous to those described for Ex-128.

| Example | Structure | Physical Data MS (m/z), $^1H$ NMR |
|---|---|---|
| 128 | 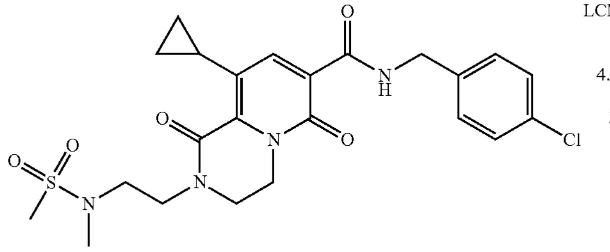 | LCMS (m/z): 507.6 [M + H]. $^1H$ NMR (400 MHz, DMSO-d6) δ 10.17 (s, 1H), 7.96 (s, 1H), 7.43-7.37 (m, 2H), 7.34 (t, J = 5.9 Hz, 2H), 4.53 (t, J = 6.2 Hz, 2H), 4.23 (s, 2H), 3.70 (dd, J = 11.6, 5.5 Hz, 4H), 3.32-3.27 (m, 2H), 2.92-2.81 (m, 7H), 0.92 (d, J = 9.6 Hz, 1H), 0.61 (d, J = 5.3 Hz, 1H). |
| 129 | 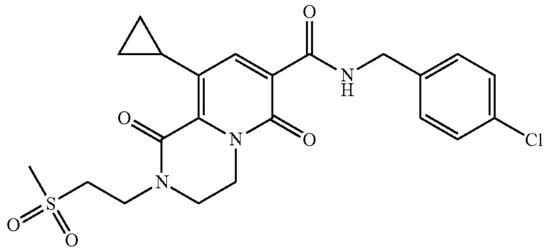 | LCMS (m/z): 464.4 [M + H]. $^1H$ NMR (400 MHz, DMSO-d6) δ 10.08 (s, 1H), 8.59 (s, 1H), 7.44-7.31 (m, 4H), 5.66 (d, J = 18.3 Hz, 1H), 5.32 (d, J = 11.6 Hz, 1H), 4.55 (d, J = 6.0 Hz, 2H), 4.25 (s, 2H), 3.91 (t, J = 6.7 Hz, 2H), 3.74 (s, 2H), 3.50 (t, J = 6.9 Hz, 2H). |
| 130 | 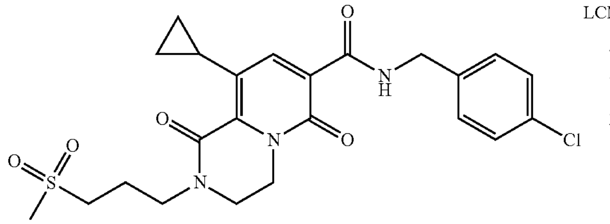 | LCMS (m/z): 492.7 [M + H]. $^1H$ NMR (400 MHz, $CD_3CN$) δ 10.24 (s, 1H), 8.08 (s, 1H), 7.39-7.32 (m, 4H), 4.56 (d, J = 6.0 Hz, 2H), 4.28-4.22 (m, 2H), 3.70-3.62 (m, 4H), 3.14-3.08 (m, 2H), 2.91 (s, 3H), 2.14-2.08 (m, 2H), 1.01-0.94 (m, 2H), 0.67 (q, J = 5.4 Hz, 2H). |
| 131 | 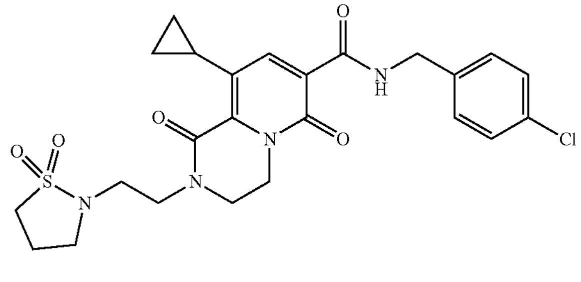 [SMILES: O=C(NCc1ccc(Cl)cc1)c1cc(C2CC2)c2n(c1=O)CCN(CCN1CCCS1(=O)=O)C2=O] | LCMS (m/z): 519.8 [M + H]. $^1H$ NMR (400 MHz, DMSO-d6) δ 10.18 (s, 1H), 7.94 (s, 1H), 7.40 (d, J = 8.4 Hz, 2H), 7.33 (d, J = 8.4 Hz, 2H), 4.52 (d, J = 6.3 Hz, 2H), 4.24 (s, 2H), 3.68 (d, J = 5.3 Hz, 4H), 3.33-3.28 (m, 2H), 3.18 (t, J = 7.5 Hz, 4H), 2.85 (s, 1H), 2.28-2.16 (m, 2H), 0.93 (d, J = 8.5 Hz, 2H), 0.61 (d, J = 5.1 Hz, 2H). |
| 132 | 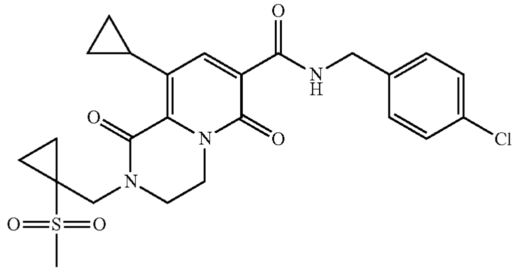 [SMILES: CS(=O)(=O)C1(CN2CCn3c(c(C4CC4)cc(C(=O)NCc4ccc(Cl)cc4)c3=O)C2=O)CC1] | LCMS (m/z): 504.4 [M + H]. $^1H$ NMR (400 MHz, DMSO-d6) δ 10.18 (s, 1H), 8.30 (s, 1H), 7.45-7.30 (m, 4H), 4.53 (t, J = 5.9 Hz, 2H), 4.23 (s, 2H), 4.06 (d, J = 5.3 Hz, 2H), 3.73 (d, J = 4.7 Hz, 2H), 3.13 (t, J = 7.9 Hz, 3H), 2.87 (d, J = 7.4 Hz, 1H), 1.27 (d, J = 25.9 Hz, 4H), 1.17 (q, J = 7.4 Hz, 4H). |

Example 133

N-(4-chlorobenzyl)-9-(cyclopropyl methyl)-2-(2-(1,1-dioxidoisothiazolidin-2-yl)ethyl)-1,6-dioxo-1,3,4,6-tetrahydro-2H-pyrido[1,2-a]pyrazine-7-carboxamide 9-allyl-N-(4-chlorobenzyl)-2-(2-(1,1-dioxidoisothiazolidin-2-yl)ethyl)-1,6-dioxo-1,3,4,6-tetrahydro-2H-pyrido[1,2-a]pyrazine-7-carboxamide (Ex-133A). Ex-124 (0.18 g, 0.3 mmol, 1.0 equiv) was added in n-propanol (5 mL). Allyltrifluoro-$\lambda^4$-borane, potassium salt (0.05 g, 0.3 mmol, 1.2 equiv), TEA (0.03 g, 0.3 mmol, 1.0 equiv) were added and the reaction mixture was degassed for 10 min $PdCl_2$(dppf) (0.004 g, 0.006 mmol, 0.02 equiv) was added and the reaction mixture was stirred at 120° C. for 2 h under microwave irradiation. The reaction mixture was quenched with water and extracted with EtOAc. The organic layer was washed with brine, dried over sodium sulfate and concentrated. The crude residue was purified by silica gel column chromatography (1% MeOH/dichloromethane) to afford the title compound. LCMS (m/z): 519.8 [M+H].

N-(4-chlorobenzyl)-9-(cyclopropyl methyl)-2-(2-(1,1-dioxidoisothiazolidin-2-yl)ethyl)-1,6-dioxo-1,3,4,6-tetrahydro-2H-pyrido[1,2-a]pyrazine-7-carboxamide (Ex-133). Ex-133A (0.12 g, 0.2 mmol, 1.0 equiv) was dissolved in dichloromethane (5 mL) and cooled to −10° C. Diiodomethane (1.2 g, 4.0 mmol, 20.0 equiv) was added and the reaction mixture was stirred at −10° C. for 30 min $Et_2Zn$ (1 M in Hexane) (0.57 g, 4.0 mmol, 20.0 equiv) was added, and the reaction mixture was stirred at −10° C. for 12 h. The reaction mixture was quenched with water and extracted with dichloromethane. The organic layer was washed with brine, dried over sodium sulfate and concentrated. The crude residue was purified by preparative HPLC to afford the title compound.

| Example | Structure | Physical Data MS (m/z), $^1$H NMR |
|---|---|---|
| 133 | 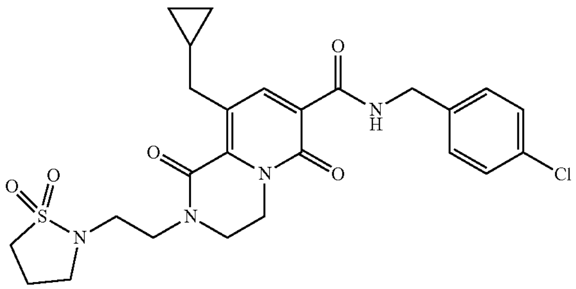 [SMILES: O=C(NCc1ccc(Cl)cc1)c1cc(CC2CC2)c2n(c1=O)CCN(CCN1CCCS1(=O)=O)C2=O] | LCMS (m/z): 504.4 [M + H]. $^1$H NMR (400 MHz, $CD_3OD$) δ 8.39 (s, 1H), 7.35 (d, J = 3.3 Hz, 4H), 4.61 (d, J = 4.6 Hz, 2H), 4.40-4.33 (m, 2H), 3.82-3.73 (m, 4H), 3.44 (t, J = 6.6 Hz, 2H), 3.18 (td, J = 7.5, 3.8 Hz, 2H), 2.95-2.89 (m, 1H), 2.39-2.33 (m, 2H), 1.67 (dd, J = 15.3, 7.6 Hz, 2H), 1.31 (s, 2H), 1.01 (t, J = 7.3 Hz, 2H), 0.92 (t, J = 4.4 Hz, 2H). |

Example 134

N-(4-chlorobenzyl)-9-ethyl-2-(2-(N-methylmethylsulfonamido)ethyl)-1,6-dioxo-1,3,4,6-tetrahydro-2H-pyrido[1,2-a]pyrazine-7-carboxamide N-(4-chlorobenzyl)-9-ethyl-2-(2-(N-methylmethylsulfonamido)ethyl)-1,6-dioxo-1,3,4,6-tetrahydro-2H-pyrido[1,2-a]pyrazine-7-carboxamide (Ex-134). Ex-128A (0.06 g, 0.1 mmol, 1.0 equiv) was dissolved in methanol (2 mL), $PtO_2$ (0.01 g) was added to the solution and the reaction mixture was stirred at room temperature for 15 minutes under $H_2$ (gas) balloon pressure. The reaction mixture was filtered through celite and the filtrate was concentrated to afford a crude product. The crude product was purified by preparative HPLC purification to afford the title compound.

Other compounds in the table below were prepared from the corresponding bromides following procedures analogous to that described for Ex-134.

| Example | Structure | Physical Data MS (m/z), $^1$H NMR |
|---|---|---|
| 134 | 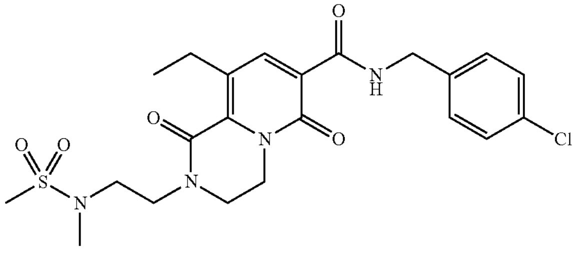 [SMILES: CCc1cc(C(=O)NCc2ccc(Cl)cc2)c(=O)n2c1C(=O)N(CCN(C)S(C)(=O)=O)CC2] | LCMS (m/z): 495.4 [M + H]. $^1$H NMR (400 MHz, DMSO-d6) δ 10.17 (t, J = 5.9 Hz, 1H), 8.29 (s, 1H), 7.40 (d, J = 8.5 Hz, 2H), 7.34 (d, J = 8.5 Hz, 2H), 4.54 (d, J = 6.0 Hz, 2H), 4.22 (d, J = 5.3 Hz, 2H), 3.74-3.64 (m, 4H), 3.28 (t, J = 5.7 Hz, 2H), 2.93-2.80 (m, 8H), 1.14 (t, J = 7.3 Hz, 3H). |

-continued

| Example | Structure | Physical Data MS (m/z), $^1$H NMR |
| --- | --- | --- |
| 135 | 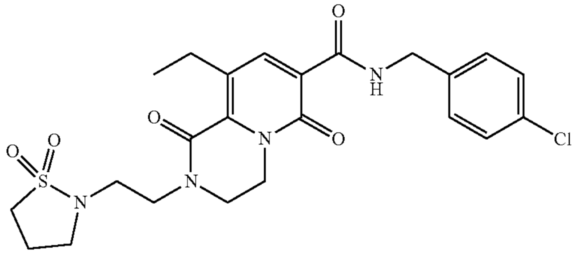 [SMILES: CCc1cc(C(=O)NCc2ccc(Cl)cc2)c(=O)n2c1C(=O)N(CCN1CCCS1(=O)=O)CC2] | LCMS (m/z): 507.8 [M + H]. $^1$H NMR (400 MHz, DMSO-d6) δ 10.18 (s, 1H), 8.29 (s, 1H), 7.40 (d, J = 8.5 Hz, 2H), 7.34 (d, J = 8.5 Hz, 2H), 4.54 (d, J = 5.9 Hz, 2H), 4.23 (s, 2H), 3.68 (d, J = 5.5 Hz, 4H), 3.30 (s, 2H), 3.17 (t, J = 7.4 Hz, 4H), 2.88 (d, J = 7.3 Hz, 2H), 2.23-2.18 (m, 2H), 1.15 (t, J = 7.3 Hz, 3H). |
| 136 | 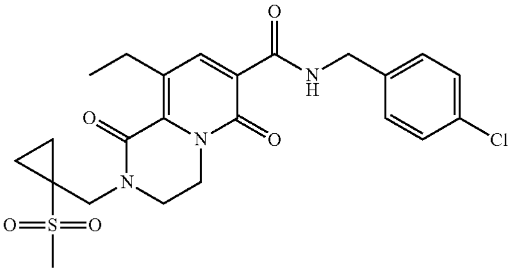 [SMILES: CCc1cc(C(=O)NCc2ccc(Cl)cc2)c(=O)n2c1C(=O)N(CC1(S(C)(=O)=O)CC1)CC2] | LCMS (m/z): 492.5 [M + H]. $^1$H NMR (400 MHz, DMSO-d6) δ 10.18 (t, J = 5.9 Hz, 1H), 8.30 (s, 1H), 7.37 (dd, J = 23.2, 8.5 Hz, 4H), 4.54 (d, J = 5.9 Hz, 2H), 4.23 (d, J = 5.9 Hz, 2H), 4.06 (s, 2H), 3.73 (d, J = 5.3 Hz, 2H), 3.14 (s, 3H), 2.88 (dd, J = 14.6, 7.2 Hz, 2H), 1.30 (s, 2H), 1.16 (t, J = 7.4 Hz, 5H). |

Example 137

N-(4-chlorobenzyl)-9-(hydroxyl methyl)-2-(2-(N-methyl methyl sulfonamido)ethyl)-1,6-dioxo-1,3,4,6-tetrahydro-2H-pyrido[1,2-a]pyrazine-7-carboxamide N-(4-chlorobenzyl)-9-formyl-2-(2-(N-methyl methyl sulfonamido)ethyl)-1,6-dioxo-1,3,4,6-tetrahydro-2H-pyrido[1,2-a]pyrazine-7-carboxamide (Ex-137A). Ex-128A (0.3 g, 0.61 mmol, 1.0 equiv) was dissolved in 1,4-dioxane:water (3:1, 4 mL). 2,6-Lutidine (0.13 g, 1.22 mmol, 2.0 equiv), $OsO_4$ (25% in tert-butanol) (0.012 g, 0.012 mmol, 0.02 equiv), and $NaIO_4$ (0.52 g, 2.43 mmol, 4.0 equiv) were added, and the reaction mixture was stirred at RT for 24 h. The reaction mixture was quenched with water and extracted with EtOAc. The organic layer was washed with brine, dried over sodium sulfate, and concentrated to afford the title compound. LCMS (m/z): 495.5 [M+H].

N-(4-chlorobenzyl)-9-(hydroxyl methyl)-2-(2-(N-methyl methyl sulfonamido)ethyl)-1,6-dioxo-1,3,4,6-tetrahydro-2H-pyrido[1,2-a]pyrazine-7-carboxamide (Ex-137). Ex-137A (0.1 g, 0.21 mmol, 1.0 equiv) was dissolved in THF (4 mL), methanol (1 mL) and cooled to 0° C. Sodium borohydride (0.016 g, 0.42 mmol, 2.0 equiv) was added in portion wise and the reaction mixture was stirred at RT for 45 min. The reaction mixture was quenched with saturated aqueous ammonium chloride solution and extracted with EtOAc. The organic layer was washed with brine, dried over sodium sulfate, and concentrated. The crude residue was purified by preparative HPLC to afford Ex-137.

Other compounds in the table below were prepared from the corresponding bromides following procedures analogous to those described for Ex-137.

| Example | Structure | Physical Data MS (m/z), $^1$H NMR |
| --- | --- | --- |
| 137 | 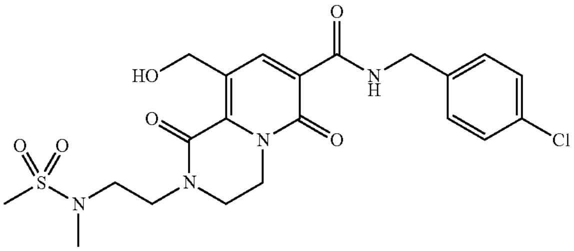 [SMILES: CN(CCN1CCn2c(c(CO)cc(C(=O)NCc3ccc(Cl)cc3)c2=O)C1=O)S(C)(=O)=O] | LCMS (m/z): 497.5 [M + H]. $^1$H NMR (400 MHz, $CDCl_3$) δ 10.04 (s, 1H), 8.65 (s, 1H), 7.31 (s, 4H), 4.64 (d, J = 7.2 Hz, 4H), 4.42-4.37 (m, 2H), 3.84-3.80 (m, 2H), 3.77-3.74 (m, 2H), 3.48-3.45 (m, 2H), 3.05 (d, J = 6.9 Hz, 2H), 2.99 (s, 3H), 2.84 (s, 3H). |

-continued

| Example | Structure | Physical Data MS (m/z), $^1$H NMR |
|---|---|---|
| 138 | 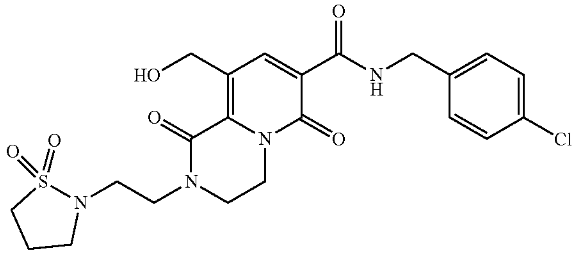 [SMILES: O=C(NCc1ccc(Cl)cc1)c1cc(CO)c2n(c1=O)CCN(CCN1CCCS1(=O)=O)C2=O] | LCMS (m/z): 509.5 [M + H]. $^1$H NMR (400 MHz, DMSO-d6) δ 10.22-10.18 (m, 1H), 8.77 (s, 1H), 7.38 (d, J = 5.3 Hz, 4H), 5.39-5.35 (m, 1H), 4.72 (s, 2H), 4.54 (s, 4H), 4.27-4.24 (m, 2H), 3.67 (s, 4H), 3.17 (s, 4H), 2.21-2.19 (m, 2H). |
| 139 | 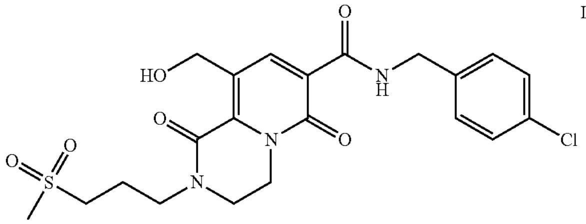 | LCMS (m/z): 482.5 [M + H]. $^1$H NMR (400 MHz, $CD_3CN$) δ 10.18 (s, 1H), 8.63 (s, 1H), 7.37 (s, 4H), 4.67 (s, 2H), 4.59 (d, J = 6.0 Hz, 2H), 4.30-4.25 (m, 2H), 3.97 (s, 1H), 3.67 (dd, J = 13.2, 6.3 Hz, 4H), 3.14-3.09 (m, 2H), 2.91 (s, 3H). |

Example 140

N-(4-chlorobenzyl)-9-(fluoro methyl)-2-(2-(N-methyl methyl sulfonamido)ethyl)-1,6-dioxo-1,3,4,6-tetrahydro-2H-pyrido[1,2-a]pyrazine-7-carboxamide N-(4-chlorobenzyl)-9-(fluoro methyl)-2-(2-(N-methyl methyl sulfonamido)ethyl)-1,6-dioxo-1,3,4,6-tetrahydro-2H-pyrido[1,2-a]pyrazine-7-carboxamide (Ex-140). Ex-137 (0.14 g, 0.3 mmol, 1.0 equiv) was dissolved in dichloromethane (4 mL) and cooled to −40° C. DAST (0.06 g, 0.37 mmol, 1.3 equiv) was added drop wise and the reaction mixture was stirred at RT for 24 h. The reaction mixture was quenched with water and extracted with EtOAc. The organic layer was washed with brine, dried over sodium sulfate and concentrated. The crude residue was purified by preparative HPLC to afford the title compound.

Other compounds in the table below were prepared from the corresponding alcohols following procedures analogous to that described for Ex-140.

| Example | Structure | Physical Data MS (m/z), $^1$H NMR |
|---|---|---|
| 140 | 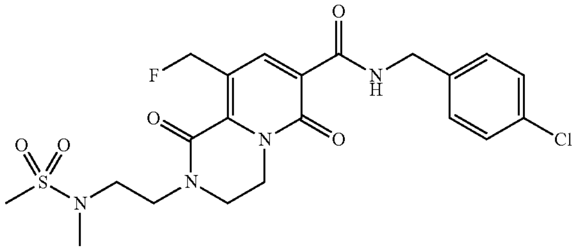 [SMILES: CN(CCN1CCn2c(c(CF)cc(C(=O)NCc3ccc(Cl)cc3)c2=O)C1=O)S(C)(=O)=O] | LCMS (m/z): 499.5 [M + H]. $^1$H NMR (400 MHz, $CDCl_3$) δ 10.07 (s, 1H), 8.89 (s, 1H), 7.31 (s, 4H), 5.79 (s, 1H), 5.67 (s, 1H), 4.64 (d, J = 5.9 Hz, 2H), 4.43-4.38 (m, 2H), 3.77 (dd, J = 11.2, 6.3 Hz, 4H), 3.47-3.42 (m, 2H), 2.98 (s, 3H), 2.84 (s, 3H). |
| 141 | 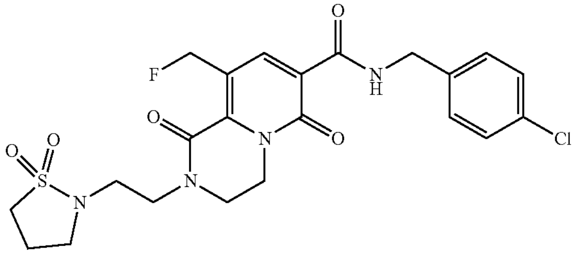 [SMILES: O=C(NCc1ccc(Cl)cc1)c1cc(CF)c2n(c1=O)CCN(CCN1CCCS1(=O)=O)C2=O] | LCMS (m/z): 511.6 [M + H]. $^1$H NMR (400 MHz, DMSO-d6) δ 10.09 (s, 1H), 8.53 (s, 1H), 7.40 (d, J = 8.6 Hz, 2H), 7.35 (d, J = 8.5 Hz, 2H), 5.76 (s, 1H), 5.64 (s, 1H), 4.55 (d, J = 6.1 Hz, 2H), 4.27 (s, 2H), 3.72 (s, 2H), 3.66 (d, J = 5.8 Hz, 2H), 3.30 (t, J = 6.6 Hz, 2H), 3.18 (dd, J = 14.6, 7.3 Hz, 4H), 2.24-2.17 (m, 2H). |

-continued

| Example | Structure | Physical Data MS (m/z), ¹H NMR |
|---|---|---|
| 142 | 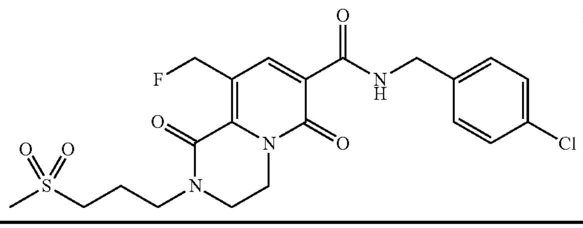 | LCMS (m/z): 484.6 [M + H]. ¹H NMR (400 MHz, DMSO-d6) δ 10.11 (t, J = 6.0 Hz, 1H), 8.54 (s, 1H), 7.41 (d, J = 8.5 Hz, 2H), 7.35 (d, J = 8.6 Hz, 2H), 5.78 (s, 1H), 5.66 (s, 1H), 4.55 (d, J = 6.0 Hz, 2H), 4.28 (d, J = 6.5 Hz, 2H), 3.73-3.68 (m, 2H), 3.59 (t, J = 6.9 Hz, 2H), 3.21-3.16 (m, 2H), 2.98 (s, 3H), 2.02-1.97 (m, 2H). |

Example 143

N-(4-chlorobenzyl)-9-(difluoro methyl)-2-(2-(N-methyl methyl sulfonamido)ethyl)-1,6-dioxo-1,3,4,6-tetrahydro-2H-pyrido[1,2-a]pyrazine-7-carboxamide N-(4-chlorobenzyl)-9-(difluoro methyl)-2-(2-(N-methyl methyl sulfonamido)ethyl)-1,6-dioxo-1,3,4,6-tetrahydro-2H-pyrido[1,2-a]pyrazine-7-carboxamide (Ex-143). Ex-137A (0.18 g, 0.4 mmol, 1.0 equiv) was dissolved in dichloromethane (5 mL) and cooled to −60° C. DAST (0.25 g, 1.5 mmol, 4.0 equiv) was added drop wise and the reaction mixture was stirred at RT for 6 h. The reaction mixture was quenched with water and extracted with EtOAc. The organic layer was washed with brine, dried over sodium sulfate, and concentrated. The crude residue was purified by preparative HPLC to afford the title compound.

Other compounds in the table below were prepared from the corresponding aldehydes following procedures analogous to that described for Ex-143.

| Example | Structure | Physical Data MS (m/z), ¹H NMR |
|---|---|---|
| 143 | 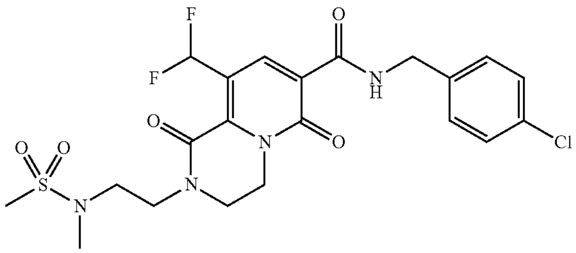 [SMILES: CN(CCN1CCn2c(c(C(F)F)cc(C(=O)NCc3ccc(Cl)cc3)c2=O)C1=O)S(C)(=O)=O] | LCMS (m/z): 517.5 [M + H]. ¹H NMR (400 MHz, DMSO-d6) δ 9.92 (t, J = 6.0 Hz, 1H), 8.56 (s, 1H), 7.58 (d, J = 55.2 Hz, 1H), 7.40 (d, J = 8.5 Hz, 2H), 7.35 (d, J = 8.5 Hz, 2H), 4.55 (d, J = 6.0 Hz, 2H), 4.30-4.24 (m, 2H), 3.76-3.68 (m, 4H), 3.31 (d, J = 5.5 Hz, 2H), 2.90 (s, 3H), 2.83 (s, 3H). |
| 144 | 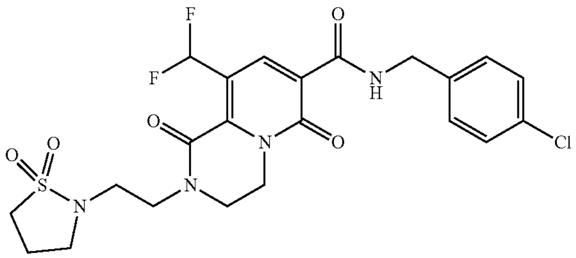 [SMILES: O=C(NCc1ccc(Cl)cc1)c1cc(C(F)F)c2n(c1=O)CCN(CCN1CCCS1(=O)=O)C2=O] | LCMS (m/z): 529.7 [M + H]. ¹H NMR (400 MHz, DMSO-d6) δ 9.93 (t, J = 5.9 Hz, 1H), 8.56 (s, 1H), 7.60 (d, J = 55.3 Hz, 1H), 7.40 (d, J = 8.5 Hz, 2H), 7.35 (d, J = 8.6 Hz, 2H), 4.55 (d, J = 6.1 Hz, 2H), 4.27 (d, J = 6.0 Hz, 2H), 3.81-3.72 (m, 2H), 3.69 (t, J = 5.8 Hz, 2H), 3.30 (t, J = 6.7 Hz, 2H), 3.25-3.11 (m, 4H), 2.27-2.17 (m, 2H). |
| 145 | 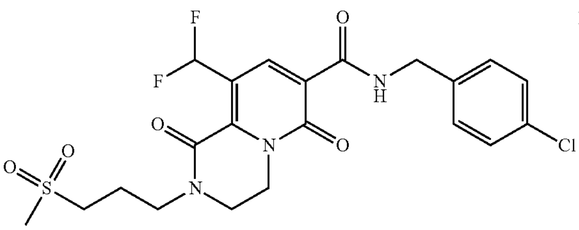 | LCMS (m/z): 502.3 [M + H]. ¹H NMR (400 MHz, DMSO-d6) δ 9.95 (s, 1H), 8.58 (s, 1H), 7.41 (d, J = 8.5 Hz, 2H), 7.35 (d, J = 8.6 Hz, 2H), 4.55 (d, J = 5.9 Hz, 2H), 4.28 (s, 2H), 3.73 (s, 2H), 3.61 (t, J = 6.7 Hz, 2H), 3.23-3.17 (m, 2H), 2.99 (s, 3H), 2.03 (d, J = 8.3 Hz, 2H). |

Example 146

N-(4-chlorobenzyl)-2-(3-(methyl sulfonyl) propyl)-1,6-dioxo-9-(trifluoro methyl)-1,3,4,6-tetrahydro-2H-pyrido[1,2-a]pyrazine-7-carboxamide N-(4-chlorobenzyl)-2-(3-(methyl sulfonyl) propyl)-1,6-dioxo-9-(trifluoro methyl)-1,3,4,6-tetrahydro-2H-pyrido[1,2-a]pyrazine-7-carboxamide (Ex-146). $Me_3SiCF_3$ (0.02 g, 0.14 mmol, 1.0 equiv), AgF (0.017 g, 0.14 mmol, 1.0 equiv) were added in DMF (3 mL) and the reaction mixture was stirred at RT for 20 min Cu-powder (0.017 g, 0.28 mmol, 2.0 equiv) was added and the reaction mixture was stirred at RT for 4 h. Ex-123 (0.075 g, 0.14 mmol, 1.0 equiv) was added and the reaction mixture was stirred at RT for 24 h. The reaction mixture was quenched with water and filtered through a bed of celite. The filtrate was extracted with EtOAc, and the organic layer was washed with brine, dried over sodium sulfate, and concentrated. The crude residue was purified by preparative HPLC to afford the title compound.

Other compounds in the table below were prepared from the corresponding bromides following procedures analogous to that described for Ex-146.

| Example | Structure | Physical Data MS (m/z), $^1$H NMR |
|---|---|---|
| 146 | 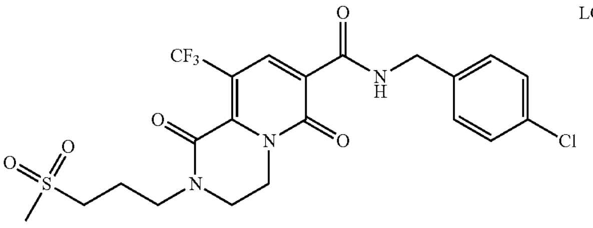 | LCMS (m/z): 520.8 [M + H]. $^1$H NMR (400 MHz, DMSO-d6) δ 9.86 (t, J = 6.1 Hz, 1H), 8.55 (s, 1H), 7.42-7.39 (m, 2H), 7.35 (d, J = 8.5 Hz, 2H), 4.55 (d, J = 6.0 Hz, 2H), 4.32-4.26 (m, 2H), 3.79-3.74 (m, 2H), 3.62 (t, J = 6.8 Hz, 2H), 3.20-3.14 (m, 2H), 2.98 (s, 3H), 2.05-1.97 (m, 2H). |
| 147 | 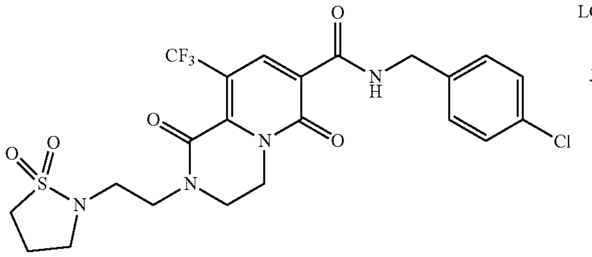 | LCMS (m/z): 547.4 [M + H]. $^1$H NMR (400 MHz, DMSO-d6) δ 10.17 (t, J = 6.1 Hz, 1H), 8.87 (s, 1H), 7.73 (d, J = 8.6 Hz, 2H), 7.68 (d, J = 8.5 Hz, 2H), 4.88 (d, J = 6.1 Hz, 2H), 4.64-4.58 (m, 2H), 4.12-4.06 (m, 2H), 4.03 (t, J = 5.7 Hz, 2H), 3.61 (t, J = 6.7 Hz, 2H), 3.50 (t, J = 7.5 Hz, 4H), 2.56-2.48 (m, 2H). |

Example 148

N-(4-chlorobenzyl)-9-methyl-2-(2-(N-methyl methyl sulfonamido)ethyl)-1,6-dioxo-1,3,4,6-tetrahydro-2H-pyrido[1,2-a]pyrazine-7-carboxamide N-(4-chlorobenzyl)-9-methyl-2-(2-(N-methyl methyl sulfonamido)ethyl)-1,6-dioxo-1,3,4,6-tetrahydro-2H-pyrido[1,2-a]pyrazine-7-carboxamide (Ex-148). Ex-122 (0.15 g, 0.27 mmol, 1.0 equiv) and 2,4,6-trimethyl-1,3,5,2,4,6-trioxatriborinane (0.069 g, 0.55 mmol, 2.0 equiv) were dissolved in DME:$H_2O$ (4:1, 3 mL). $K_2CO_3$ (0.11 g, 0.83 mmol, 3.0 equiv) was added and the reaction mixture was degassed for 10 min $Pd(PPh_3)_4$ (0.063 g, 0.055 mmol, 0.2 equiv) was added and the reaction mixture was stirred at 90° C. for 3 h. The reaction mixture was quenched with water and extracted with EtOAc. The organic layer was washed with brine, dried over sodium sulfate, and concentrated. The crude residue was purified by preparative HPLC to afford the title compound.

Other compounds in the table below were prepared from the corresponding bromides following procedures analogous to that described for Ex-148.

| Example | Structure | Physical Data MS (m/z), $^1$H NMR |
|---|---|---|
| 148 | 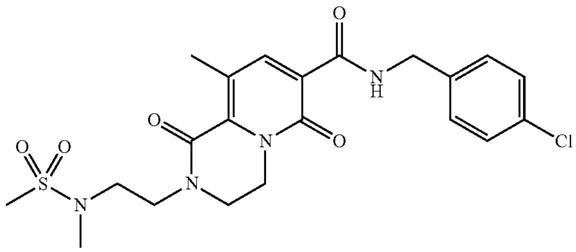 [SMILES: Cc1cc(C(=O)NCc2ccc(Cl)cc2)c(=O)n2c1C(=O)N(CCN(C)S(C)(=O)=O)CC2] | LCMS (m/z): 481.4 [M + H]. $^1$H NMR (400 MHz, DMSO-d6) δ 10.18 (s, 1H), 8.27 (s, 1H), 7.40 (d, J = 8.5 Hz, 2H), 7.34 (d, J = 8.5 Hz, 2H), 4.54 (d, J = 6.0 Hz, 2H), 4.24 (s, 2H), 3.68 (s, 4H), 3.29 (d, J = 5.5 Hz, 2H), 2.89 (s, 3H), 2.83 (s, 3H), 2.43 (s, 3H). |
| 149 | 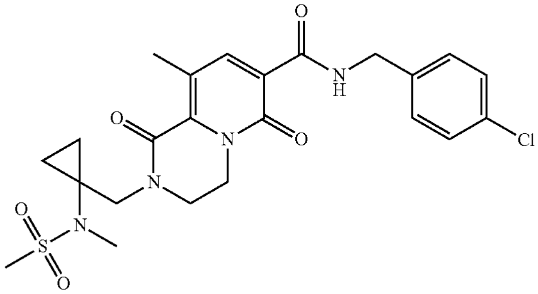 [SMILES: Cc1cc(C(=O)NCc2ccc(Cl)cc2)c(=O)n2c1C(=O)N(CC1(N(C)S(C)(=O)=O)CC1)CC2] | LCMS (m/z): 507.5 [M + H]. $^1$H NMR (400 MHz, DMSO-d6) δ 10.19 (t, J = 5.9 Hz, 1H), 8.26 (s, 1H), 7.40 (d, J = 8.5 Hz, 2H), 7.34 (d, J = 8.5 Hz, 2H), 4.54 (d, J = 6.0 Hz, 2H), 4.25 (s, 2H), 3.75 (s, 2H), 3.61 (s, 2H), 2.85 (s, 6H), 2.43 (s, 3H), 0.90 (d, J = 35.3 Hz, 4H). |
| 150 | 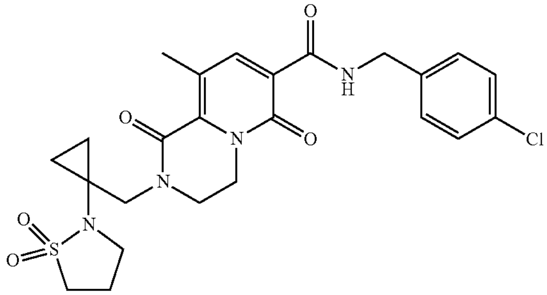 [SMILES: Cc1cc(C(=O)NCc2ccc(Cl)cc2)c(=O)n2c1C(=O)N(CC1(N3CCCS3(=O)=O)CC1)CC2] | LCMS (m/z): 519.8 [M + H]. $^1$H NMR (400 MHz, DMSO-d6) δ 10.20 (t, J = 6.1 Hz, 1H), 8.27 (s, 1H), 7.40 (d, J = 8.5 Hz, 2H), 7.34 (d, J = 8.5 Hz, 2H), 4.54 (d, J = 6.0 Hz, 2H), 4.29-4.23 (m, 2H), 3.77 (d, J = 5.4 Hz, 2H), 3.62 (s, 2H), 3.41 (t, J = 6.7 Hz, 2H), 3.07 (t, J = 7.4 Hz, 2H), 2.46 (s, 3H), 2.19 (p, J = 7.1 Hz, 2H), 1.10 (s, 2H), 0.87 (s, 2H). |
| 151 | 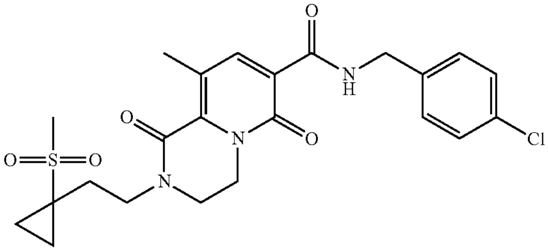 [SMILES: Cc1cc(C(=O)NCc2ccc(Cl)cc2)c(=O)n2c1C(=O)N(CCC1(S(C)(=O)=O)CC1)CC2] | LCMS (m/z): 492.8 [M + H]. $^1$H NMR (400 MHz, DMSO-d6) δ 10.19 (s, 1H), 8.27 (s, 1H), 7.37 (dd, J = 25.2, 8.5 Hz, 4H), 4.54 (d, J = 6.1 Hz, 2H), 4.22 (s, 2H), 3.66 (d, J = 16.3 Hz, 4H), 3.08 (s, 3H), 2.44 (s, 3H), 2.12 (d, J = 7.8 Hz, 2H), 1.25 (d, J = 5.5 Hz, 2H), 1.02 (s, 2H). |
| 152 | 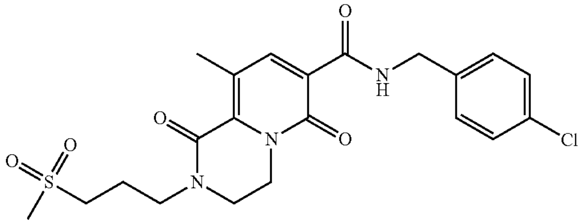 | LCMS (m/z): 466.5 [M + H]. $^1$H NMR (400 MHz, DMSO-d6) δ 10.20 (t, J = 6.0 Hz, 1H), 8.27 (s, 1H), 7.43-7.38 (m, 2H), 7.34 (d, J = 8.5 Hz, 2H), 4.54 (d, J = 6.0 Hz, 2H), 4.29-4.22 (m, 2H), 3.70-3.64 (m, 2H), 3.58 (t, J = 6.8 Hz, 2H), 3.22-3.14 (m, 2H), 2.99 (s, 3H), 2.45 (s, 3H), 1.99 (dd, J = 15.3, 7.4 Hz, 2H). |
| 153 | 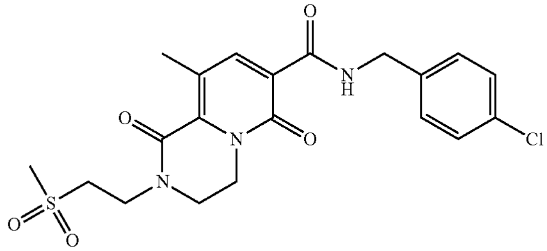 [SMILES: Cc1cc(C(=O)NCc2ccc(Cl)cc2)c(=O)n2c1C(=O)N(CCS(C)(=O)=O)CC2] | LCMS (m/z): 452.4 [M + H]. $^1$H NMR (400 MHz, DMSO-d6) δ 10.18 (s, 1H), 8.27 (s, 1H), 7.37 (dd, J = 23.8, 8.5 Hz, 4H), 4.54 (d, J = 6.0 Hz, 2H), 4.24 (s, 2H), 3.90 (t, J = 6.8 Hz, 2H), 3.72 (s, 2H), 3.49 (t, J = 6.7 Hz, 2H), 3.07 (s, 3H), 2.45 (s, 3H). |

-continued

| Example | Structure | Physical Data MS (m/z), $^1$H NMR |
|---|---|---|
| 154 | 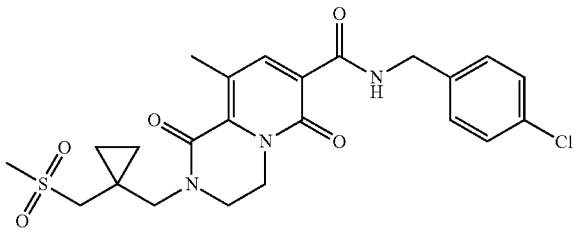 [SMILES: Cc1cc(C(=O)NCc2ccc(Cl)cc2)c(=O)n2c1C(=O)N(CC1(CS(C)(=O)=O)CC1)CC2] | LCMS (m/z): 492.8 [M + H]. $^1$H NMR (400 MHz, DMSO-d6) δ 10.20 (t, J = 6.0 Hz, 1H), 8.28 (s, 1H), 7.40 (d, J = 8.5 Hz, 2H), 7.34 (d, J = 8.4 Hz, 2H), 4.54 (d, J = 5.9 Hz, 2H), 4.25 (d, J = 5.9 Hz, 2H), 3.76 (d, J = 5.2 Hz, 2H), 3.63 (s, 2H), 3.26 (s, 2H), 3.01 (s, 3H), 2.44 (s, 3H), 0.77 (s, 4H). |

Example 155

N-(4-chlorobenzyl)-9-(3-hydroxyprop-1-yn-1-yl)-2-(2-(N-methyl methyl sulfonamido)ethyl)-1,6-dioxo-1,3,4,6-tetrahydro-2H-pyrido[1,2-a]pyrazine-7-carboxamide N-(4-chlorobenzyl)-9-(3-hydroxyprop-1-yn-1-yl)-2-(2-(N-methyl methyl sulfonamido)ethyl)-1,6-dioxo-1,3,4,6-tetrahydro-2H-pyrido[1,2-a]pyrazine-7-carboxamide (Ex-155). Ex-122 (0.3 g, 0.5 mmol, 1.0 equiv), CuI (0.01 g, 0.05 mmol, 0.1 equiv) were added in DIPEA:DMF (3:2, 4 mL) and the reaction mixture was degassed for 15 min. $Pd(OAc)_2$ (0.012 g, 0.05 mmol, 0.1 equiv), $Cy_3P$ (0.03 g, 0.1 mmol, 0.2 equiv), and prop-2-yn-1-ol (0.06 g, 1.1 mmol, 2.0 equiv) were added, and the reaction mixture was stirred at RT for 2 h. The reaction mixture was quenched with water and extracted with EtOAc. The organic layer was washed with brine, dried over sodium sulfate, and concentrated. The crude residue was purified by preparative HPLC to afford the title compound.

Other compounds in the table below were prepared from the corresponding bromides following procedures analogous to that described in Ex-155.

| Example | Structure | Physical Data MS (m/z), $^1$H NMR |
|---|---|---|
| 155 | 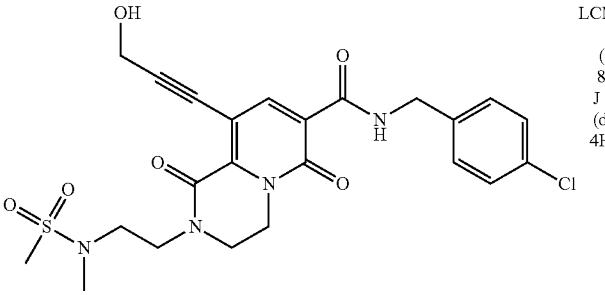 | LCMS (m/z): 521.4 [M + H]. $^1$H NMR (400 MHz, DMSO-d6) δ 9.94 (t, J = 6.0 Hz, 1H), 8.28 (s, 1H), 7.40 (d, J = 8.5 Hz, 2H), 7.35 (d, J = 8.5 Hz, 2H), 5.33 (t, J = 5.9 Hz, 1H), 4.54 (d, J = 5.9 Hz, 2H), 4.30 (d, J = 5.9 Hz, 2H), 4.23 (d, J = 5.7 Hz, 2H), 3.68 (dd, J = 13.4, 7.4 Hz, 4H), 3.29 (t, J = 5.8 Hz, 2H), 2.90 (s, 3H), 2.83 (s, 3H). |
| 156 | 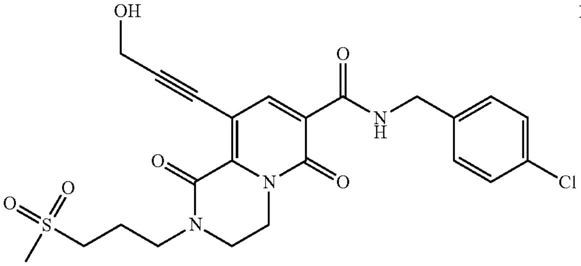 | LCMS (m/z): 506.6 [M + H]. $^1$H NMR (400 MHz, $CD_3CN$) δ 10.00 (s, 1H), 8.43 (s, 1H), 7.40-7.32 (m, 4H), 4.58 (d, J = 6.0 Hz, 2H), 4.38 (s, 2H), 4.29-4.24 (m, 2H), 3.65 (t, J = 7.0 Hz, 4H), 3.14-3.09 (m, 2H), 2.91 (s, 3H), 2.11 (m, 3H). |

Example 157

N-(4-chlorobenzyl)-9-(3-hydroxypropyl)-2-(2-(N-methyl methyl sulfonamido)ethyl)-1,6-dioxo-1,3,4,6-tetrahydro-2H-pyrido[1,2-a]pyrazine-7-carboxamide N-(4-chlorobenzyl)-9-(3-hydroxypropyl)-2-(2-(N-methyl methyl sulfonamido)ethyl)-1,6-dioxo-1,3,4,6-tetrahydro-2H-pyrido[1,2-a]pyrazine-7-carboxamide (Ex-157). Ex-155 (0.14 g, 0.27 mmol, 1.0 equiv) was dissolved in methanol (5 mL), $PtO_2$ (0.05 g) was added to the solution and the reaction mixture was stirred at room temperature for 30 min under $H_2$ (balloon pressure). The reaction mixture was filtered through a Millipore filter, and the filtrate was concentrated. The crude product was purified by preparative HPLC to afford the title compound.

| Example | Structure | Physical Data MS (m/z), $^1$H NMR |
|---|---|---|
| 157 | 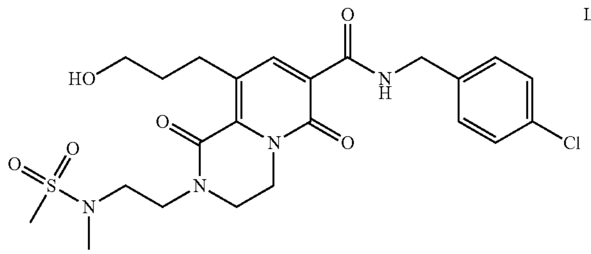 | LCMS (m/z): 525.6 [M + H]. $^1$H NMR (400 MHz, DMSO-d6) δ 10.18 (t, J = 5.8 Hz, 1H), 8.28 (s, 1H), 7.40 (d, J = 8.5 Hz, 2H), 7.34 (d, J = 8.4 Hz, 2H), 4.54 (d, J = 6.0 Hz, 2H), 4.46 (t, J = 5.1 Hz, 1H), 4.24 (s, 2H), 3.73-3.62 (m, 4H), 3.41 (dd, J = 11.5, 6.1 Hz, 2H), 3.28 (t, J = 5.5 Hz, 2H), 2.93-2.80 (m, 8H), 1.74-1.66 (m, 2H). |

Example 158

N-(4-chlorobenzyl)-2-(3-(methyl sulfonyl) propyl)-1,6-dioxo-9-(pyrrolidin-1-yl)-1,3,4,6-tetrahydro-2H-pyrido[1,2-a]pyrazine-7-carboxamide N-(4-chlorobenzyl)-2-(3-(methyl sulfonyl) propyl)-1,6-dioxo-9-(pyrrolidin-1-yl)-1)-1,3,4,6-tetrahydro-2H-pyrido [1,2-a]pyrazine-7-carboxamide (Ex-158). Ex-123 (0.1 g, 0.19 mmol, 1.0 equiv) was mixed with pyrrolidine (4 mL) and the reaction mixture was stirred at 125° C. for 20 min under microwave irradiation. The reaction mixture was quenched with water and extracted with EtOAc. The organic layer was washed with brine, dried over sodium sulfate, and concentrated. The crude residue was purified by preparative HPLC to afford the title compound.

| Example | Structure | Physical Data MS (m/z), $^1$H NMR |
|---|---|---|
| 158 | 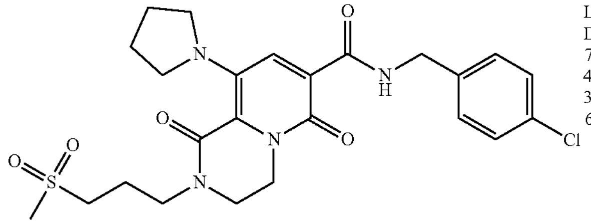 | LCMS (m/z): 521.5 [M + H]. $^1$H NMR (400 MHz, DMSO-d6) δ 10.57 (t, J = 5.9 Hz, 1H), 8.35 (s, 1H), 7.40 (d, J = 8.5 Hz, 2H), 7.34 (d, J = 8.5 Hz, 2H), 4.54 (d, J = 5.9 Hz, 2H), 4.12 (s, 2H), 3.70 (s, 2H), 3.58 (t, J = 6.8 Hz, 2H), 3.15 (dd, J = 15.6, 7.2 Hz, 6H), 2.98 (s, 3H), 2.01-1.93 (m, 2H), 1.86 (s, 4H). |

Example 159

N-(4-chlorobenzyl)-9-(5-methyl-1,2,4-oxadiazol-3-yl)-2-(2-(methyl sulfonyl)ethyl)-1,6-dioxo-1,3,4,6-tetrahydro-2H-pyrido[1,2-a]pyrazine-7-carboxamide (Z)—N-(4-chlorobenzyl)-9-(N'-hydroxycarbamimidoyl)-2-(2-(methyl sulfonyl)ethyl)-1,6-dioxo-1,3,4,6-tetrahydro-2H-pyrido[1,2-a]pyrazine-7-carboxamide (Ex-159A). Ex-125 (0.21 g, 0.4 mmol, 1.0 equiv) and potassium acetate (0.14 g, 1.4 mmol, 3.0 equiv) were added in ethanol:water (1:2, 2 mL). $NH_2OH$ (50% in water) (0.3 mL, 4.5 mmol, 10.0 equiv) was added and the reaction mixture was stirred at RT for 24 h. The reaction mixture was quenched with water and extracted with EtOAc. The organic layer was washed with brine, dried over sodium sulfate, and concentrated to afford the title compound. LCMS (m/z): 496.6 [M+H]. $^1$H NMR (400 MHz, DMSO-d6) δ 8.37-8.10 (m, 1H), 7.35 (dd, J=21.3, 8.5 Hz, 4H), 4.51 (d, J=5.7 Hz, 2H), 4.21 (s, 2H), 3.86 (dd, J=16.2, 9.4 Hz, 4H), 3.46 (dd, J=13.1, 6.6 Hz, 2H).

N-(4-chlorobenzyl)-9-(5-methyl-1,2,4-oxadiazol-3-yl)-2-(2-(methyl sulfonyl)ethyl)-1,6-dioxo-1,3,4,6-tetrahydro-2H-pyrido[1,2-a]pyrazine-7-carboxamide (Ex-159). Ex-159A (0.2 g, 0.4 mmol, 1.0 equiv) and acetic anhydride (0.045 g, 0.4 mmol, 1.1 equiv) were added in acetic acid (2 mL). The reaction mixture was stirred at 80° C. for 24 h. The reaction mixture was quenched with water, neutralized by solid sodium bicarbonate, and extracted with EtOAc. The organic layer was washed with brine, dried over sodium sulfate, and concentrated. The crude residue was purified by preparative HPLC to afford the title compound.

| Example | Structure | Physical Data MS (m/z), $^1$H NMR |
|---|---|---|
| 159 | 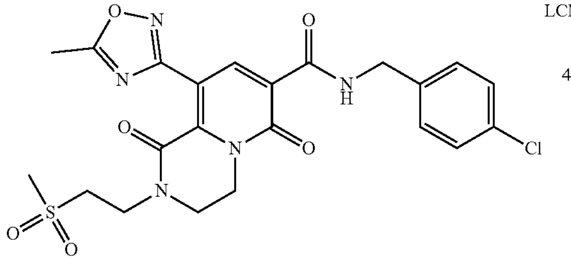 | LCMS (m/z): 520.2 [M + H]. $^1$H NMR (400 MHz, DMSO-d6) δ 8.28 (s, 1H), 7.38 (dd, J = 20.8, 8.4 Hz, 4H), 4.55 (d, J = 5.8 Hz, 2H), 4.29 (s, 2H), 3.85 (d, J = 6.4 Hz, 4H), 3.45 (t, J = 6.8 Hz, 2H), 3.04 (s, 3H), 2.66 (d, J = 15.8 Hz, 3H). |

Example 160

N-(4-chlorobenzyl)-9-fluoro-2-(2-(N-methyl methyl sulfonamido)ethyl)-1,6-dioxo-1,3,4,6-tetrahydro-2H-pyrido[1,2-a]pyrazine-7-carboxamide N-(4-chlorobenzyl)-9-fluoro-2-(2-(N-methyl methyl sulfonamido)ethyl)-1,6-dioxo-1,3,4,6-tetrahydro-2H-pyrido[1,2-a]pyrazine-7-carboxamide (Ex-160). Ex-58 (0.19 g, 0.4 mmol, 1.0 equiv) was added in acetonitrile (15 mL), Selectfluor® (0.21 g, 0.6 mmol, 1.5 equiv) was added and the reaction mixture was stirred at 80° C. for 8 h. The reaction mixture was diluted with water and extracted with EtOAc. The organic layer was washed with brine, dried over sodium sulfate, and concentrated. The crude residue was purified by preparative HPLC to afford the title compound.

Other compounds in the table below were prepared following procedures analogous to that described for Ex-160.

| Example | Structure | Physical Data MS (m/z), $^1$H NMR |
|---|---|---|
| 160 | 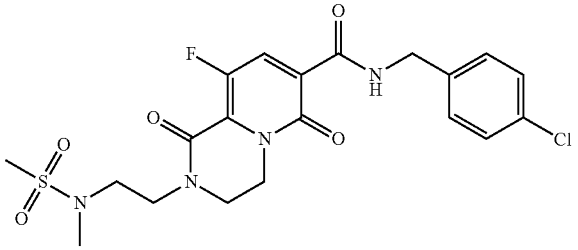 [SMILES: CN(CCN1CCn2c(c(F)cc(C(=O)NCc3ccc(Cl)cc3)c2=O)C1=O)S(C)(=O)=O] | LCMS (m/z): 485.7 [M + H]. $^1$H NMR (400 MHz, $CD_3CN$) δ 10.17 (s, 1H), 8.36 (d, J = 11.1 Hz, 1H), 7.43-7.31 (m, 4H), 4.58 (d, J = 6.1 Hz, 2H), 4.28-4.23 (m, 2H), 3.71 (dd, J = 11.6, 6.2 Hz, 4H), 3.36 (t, J = 5.8 Hz, 2H), 2.90 (s, 3H), 2.81 (s, 3H). |

-continued

| Example | Structure | Physical Data MS (m/z), $^1$H NMR |
|---|---|---|
| 161 | 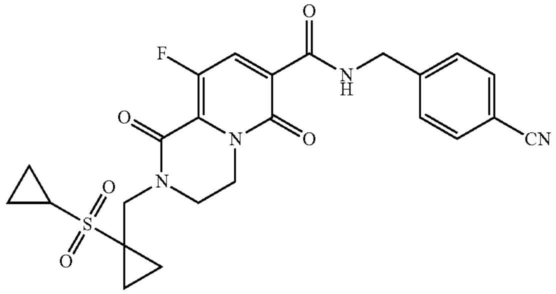 [SMILES: N#Cc1ccc(CNC(=O)c2cc(F)c3n(c2=O)CCN(CC2(S(=O)(=O)C4CC4)CC2)C3=O)cc1] | LCMS (m/z): 498.9 [M + H]. $^1$H NMR (400 MHz, DMSO-d6) δ 10.19 (t, J = 6.2 Hz, 1H), 8.31 (d, J = 11.0 Hz, 1H), 7.82 (d, J = 8.2 Hz, 2H), 7.51 (d, J = 8.1 Hz, 2H), 4.64 (d, J = 6.0 Hz, 2H), 4.24 (s, 2H), 4.08 (s, 2H), 3.79 (s, 2H), 2.93 (s, 1H), 1.31 (s, 2H), 1.19 (s, 2H), 1.09-1.00 (m, 4H). |
| 162 | 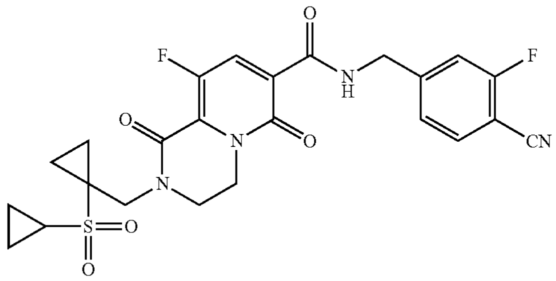 [SMILES: N#Cc1ccc(CNC(=O)c2cc(F)c3n(c2=O)CCN(CC2(S(=O)(=O)C4CC4)CC2)C3=O)cc1F] | LCMS (m/z): 517.0 [M + H]. $^1$H NMR (400 MHz, DMSO-d6) δ 10.20 (t, J = 6.2 Hz, 1H), 8.30 (d, J = 10.9 Hz, 1H), 7.96-7.86 (m, 1H), 7.45 (d, J = 10.3 Hz, 1H), 7.35 (d, J = 8.1 Hz, 1H), 4.63 (t, J = 12.5 Hz, 2H), 4.24 (s, 2H), 4.08 (s, 2H), 3.79 (d, J = 5.5 Hz, 2H), 2.93 (d, J = 4.8 Hz, 1H), 1.31 (s, 2H), 1.19 (s, 2H), 1.10-1.00 (m, 4H). |
| 163 | 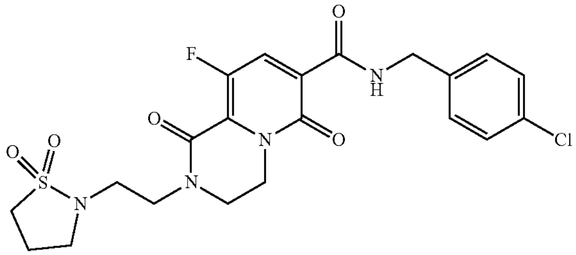 [SMILES: O=C(NCc1ccc(Cl)cc1)c1cc(F)c2n(c1=O)CCN(CCN1CCCS1(=O)=O)C2=O] | LCMS (m/z): 497.6 [M + H]. $^1$H NMR (400 MHz, DMSO-d6) δ 10.11 (s, 1H), 8.30 (d, J = 11.0 Hz, 1H), 7.40 (d, J = 8.5 Hz, 2H), 7.35 (d, J = 8.6 Hz, 2H), 4.54 (d, J = 6.1 Hz, 2H), 4.23 (s, 2H), 3.73 (d, J = 5.6 Hz, 2H), 3.65 (t, J = 5.8 Hz, 2H), 3.30 (t, J = 6.7 Hz, 2H), 3.17 (t, J = 7.5 Hz, 4H), 2.25-2.17 (m, 2H). |
| 164 | 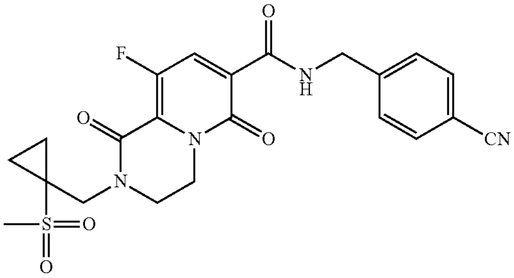 [SMILES: CS(=O)(=O)C1(CN2CCn3c(c(F)cc(C(=O)NCc4ccc(C#N)cc4)c3=O)C2=O)CC1] | LCMS (m/z): 473.5 [M + H]. $^1$H NMR (400 MHz, DMSO-d6) δ 10.19 (t, J = 5.9 Hz, 1H), 8.30 (d, J = 10.9 Hz, 1H), 7.82 (d, J = 8.1 Hz, 2H), 7.51 (d, J = 8.0 Hz, 2H), 4.64 (d, J = 5.9 Hz, 2H), 4.24 (s, 2H), 4.03 (s, 2H), 3.78 (s, 2H), 3.13 (s, 3H), 1.31 (s, 2H), 1.18 (s, 2H). |
| 165 | 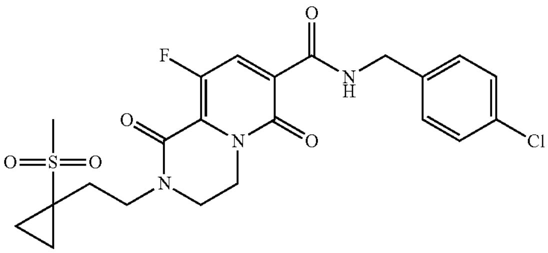 [SMILES: CS(=O)(=O)C1(CCN2CCn3c(c(F)cc(C(=O)NCc4ccc(Cl)cc4)c3=O)C2=O)CC1] | LCMS (m/z): 496.8 [M + H]. $^1$H NMR (400 MHz, DMSO-d6) δ 10.13 (s, 1H), 8.30 (d, J = 11.0 Hz, 1H), 7.38 (dd, J = 23.7, 8.4 Hz, 4H), 4.54 (d, J = 6.1 Hz, 2H), 4.21 (s, 2H), 3.75-3.61 (m, 4H), 3.08 (s, 3H), 2.12-2.07 (m, 2H), 1.25 (d, J = 3.4 Hz, 2H), 1.03 (s, 2H). |

-continued

| Example | Structure | Physical Data MS (m/z), $^1$H NMR |
|---|---|---|
| 166 | 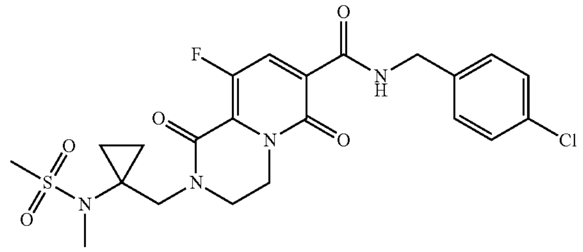 [SMILES: CN(C1(CN2CCn3c(c(F)cc(C(=O)NCc4ccc(Cl)cc4)c3=O)C2=O)CC1)S(C)(=O)=O] | LCMS (m/z): 511.1 [M + H]. $^1$H NMR (400 MHz, $CD_3CN$) δ 10.18 (s, 1H), 8.36 (d, J = 11.1 Hz, 1H), 7.44-7.31 (m, 4H), 4.58 (d, J = 6.1 Hz, 2H), 4.32-4.26 (m, 2H), 3.79 (s, 2H), 3.70-3.54 (m, 2H), 2.91 (s, 3H), 2.79 (s, 3H), 1.04 (d, J = 32.4 Hz, 4H). |
| 167 | 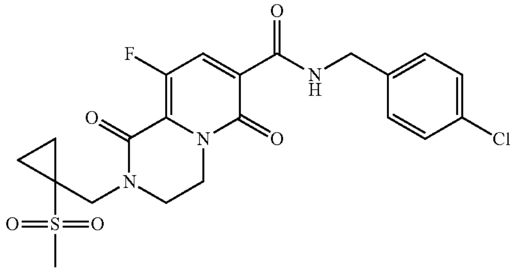 [SMILES: CS(=O)(=O)C1(CN2CCn3c(c(F)cc(C(=O)NCc4ccc(Cl)cc4)c3=O)C2=O)CC1] | LCMS (m/z): 482.8 [M + H]. $^1$H NMR (400 MHz, DMSO-d6) δ 10.12 (t, J = 6.0 Hz, 1H), 8.31 (d, J = 11.0 Hz, 1H), 7.38 (dd, J = 22.8, 8.5 Hz, 4H), 4.54 (d, J = 6.0 Hz, 2H), 4.29-4.17 (m, 2H), 4.02 (s, 2H), 3.85-3.72 (m, 2H), 3.13 (s, 3H), 1.31 (t, J = 5.8 Hz, 2H), 1.18 (q, J = 5.2 Hz, 2H). |
| 168 | 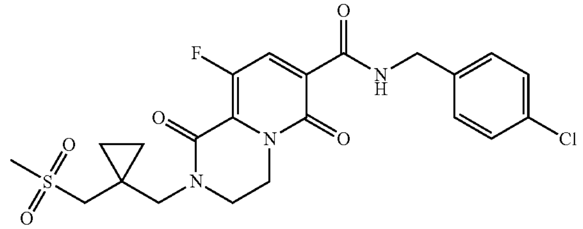 [SMILES: CS(=O)(=O)CC1(CN2CCn3c(c(F)cc(C(=O)NCc4ccc(Cl)cc4)c3=O)C2=O)CC1] | LCMS (m/z): 496.8 [M + H]. $^1$H NMR (400 MHz, $CD_3CN$) δ 10.22-10.15 (m, 1H), 8.38 (d, J = 11.2 Hz, 1H), 7.37 (d, J = 2.1 Hz, 4H), 4.58 (d, J = 6.0 Hz, 2H), 4.30-4.23 (m, 2H), 3.81-3.76 (m, 2H), 3.68 (s, 2H), 3.16 (s, 2H), 2.95 (s, 3H), 0.85 (d, J = 6.4 Hz, 4H). |
| 169 | 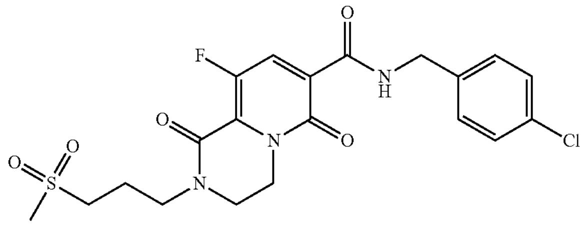 | LCMS (m/z): 497.5 [M + H]. $^1$H NMR (400 MHz, $CDCl_3$) δ 10.04 (s, 1H), 8.65 (s, 1H), 7.31 (s, 4H), 4.64 (d, J = 1.2 Hz, 4H), 4.42-4.37 (m, 2H), 3.84-3.80 (m, 2H), 3.77-3.74 (m, 2H), 3.48-3.45 (m, 2H), 3.05 (d, J = 6.9 Hz, 2H), 2.99 (s, 3H), 2.84 (s, 3H). |

Example 170

N-(4-chlorobenzyl)-2-(2-(1-(methyl sulfonyl)cyclopropyl)ethyl)-1,6-dioxo-1,3,4,6-tetrahydro-2H-pyrido[1,2-a]pyrazine-7-carboxamide $N^5$-(4-chlorobenzyl)-1-(2-hydroxyethyl)-$N^2$-(2-(1-(methyl sulfonyl)cyclopropyl)ethyl)-6-oxo-1,6-dihydropyridine-2,5-dicarboxamide (Ex-170A). 1-17 (0.5 g, 1.5 mmol, 1.0 equiv) was dissolved in acetonitrile (1 mL), DIPEA (0.97 g, 7.5 mmol, 5.0 equiv), 1-56 (0.78 g, 3.3 mmol, 2.2 equiv) were added and the reaction mixture was stirred at 130° C. for 1 h under microwave irradiation. The reaction mixture was quenched with water and extracted with EtOAc. The organic layer was washed with brine, dried over sodium sulfate, and concentrated to afford the title compound. LCMS (m/z): 496.7 [M+H]. $^1$H NMR (400 MHz, DMSO-d6) δ 10.08 (t, J=6.1 Hz, 1H), 9.02 (s, 1H), 8.37 (d, J=7.4 Hz, 1H), 7.38 (dd, J=22.9, 8.5 Hz, 4H), 6.59 (d, J=7.4 Hz, 1H), 4.94 (t, J=5.5 Hz, 1H), 4.52 (d, J=5.9 Hz, 2H), 4.24 (d, J=6.1 Hz, 2H), 3.60 (d, J=5.8 Hz, 2H), 3.48-3.39 (m, 2H), 3.09-2.99 (m, 3H), 2.14-1.98 (m, 2H), 1.25 (d, J=5.2 Hz, 2H), 1.02 (s, 2H).

$N^5$-(4-chlorobenzyl)-1-(2-chloroethyl)-$N^2$-(2-(1-(methyl sulfonyl)cyclopropyl)ethyl)-6-oxo-1,6-dihydropyridine-2,5-dicarboxamide (Ex-170B) was prepared from Ex-170A following a procedure analogous to that described for Ex-122B. LCMS (m/z): 514.7 [M+H]. $^1$H NMR (400 MHz, DMSO-d6) δ 9.96 (t, J=6.0 Hz, 1H), 9.18 (d, J=5.7 Hz, 1H), 8.41 (d, J=7.4 Hz, 1H), 7.38 (dd, J=19.9, 8.5 Hz, 4H), 6.67 (d, J=7.4 Hz, 1H), 4.52 (d, J=5.9 Hz, 2H), 4.42 (t, J=6.7 Hz, 2H), 3.88 (t, J=6.6 Hz, 2H), 3.44 (dd, J=13.8, 6.7 Hz, 2H), 3.18-2.99 (m, 5H), 2.14-2.03 (m, 2H), 1.26 (t, J=5.7 Hz, 2H), 1.02 (d, J=4.7 Hz, 2H).

N-(4-chlorobenzyl)-2-(2-(1-(methyl sulfonyl)cyclopropyl)ethyl)-1,6-dioxo-1, 3, 4, 6-tetrahydro-2H-pyrido[1,2-a]pyrazine-7-carboxamide (Ex-170) was prepared from Ex-170B following a procedure analogous to that described for Ex-117C.

| Example | Structure | Physical Data MS (m/z), $^1$H NMR |
| --- | --- | --- |
| 170 | 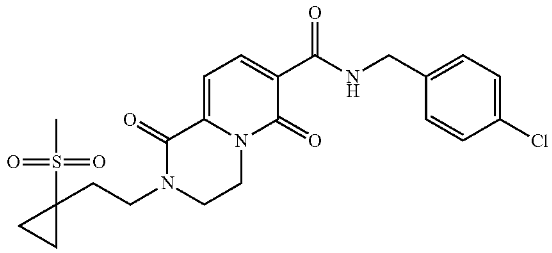 [SMILES: CS(=O)(=O)C1(CCN2CCn3c(ccc(C(=O)NCc4ccc(Cl)cc4)c3=O)C2=O)CC1] | LCMS (m/z): 478.8 [M + H]. $^1$H NMR (400 MHz, DMSO-d6) δ 10.12 (s, 1H), 8.44 (d, J = 7.5 Hz, 1H), 7.37 (dd, J = 24.2, 8.3 Hz, 4H), 7.19 (d, J = 7.6 Hz, 1H), 4.54 (d, J = 6.0 Hz, 2H), 4.25 (s, 2H), 3.69 (dd, J = 26.0, 17.9 Hz, 4H), 3.08 (s, 3H), 2.16-2.05 (m, 2H), 1.25 (d, J = 5.0 Hz, 2H), 1.02 (s, 2H). |

Example 171

N-(4-chlorobenzyl)-2-((1-methoxy cyclopropyl) methyl)-1,6-dioxo-1,3,4,6-tetrahydro-2H-pyrido[1,2-a]pyrazine-7-carboxamide $N^5$-(4-chlorobenzyl)-1-(2-hydroxyethyl)-$N^2$-((1-methoxy cyclopropyl)methyl)-6-oxo-1,6-dihydropyridine-2,5-dicarboxamide (Ex-171A) was prepared from 1-17 following a procedure analogous to that described for Ex-170A. LCMS (m/z): 434.3 [M+H]. $^1$H NMR (400 MHz, DMSO-d6) δ 10.10 (t, J=6.0 Hz, 1H), 9.17 (t, J=6.0 Hz, 1H), 8.38 (dd, J=7.5, 3.2 Hz, 1H), 7.41 (dd, J=8.7, 2.2 Hz, 2H), 7.35 (d, J=8.6 Hz, 2H), 6.56 (t, J=7.0 Hz, 1H), 4.91 (t, J=5.4 Hz, 1H), 4.53 (d, J=6.0 Hz, 2H), 4.22 (t, J=6.4 Hz, 2H), 3.67-3.60 (m, 2H), 3.48 (d, J=5.9 Hz, 2H), 3.24 (d, J=6.3 Hz, 3H), 0.72 (t, J=5.9 Hz, 2H), 0.62 (dd, J=6.9, 5.3 Hz, 2H).

$N^5$-(4-chlorobenzyl)-1-(2-chloroethyl)-$N^2$-((1-methoxy cyclopropyl)methyl)-6-oxo-1,6-dihydropyridine-2,5-dicarboxamide (Ex-171B) was prepared from Ex-171A following a procedure analogous to that described for Ex-51B. LCMS (m/z): 452.4 [M+H]. $^1$H NMR (400 MHz, DMSO-d6) δ 9.97 (s, 1H), 9.31 (s, 1H), 8.41 (d, J=7.4 Hz, 1H), 7.41 (d, J=8.4 Hz, 2H), 7.35 (d, J=8.3 Hz, 2H), 6.62 (d, J=7.4 Hz, 1H), 4.52 (d, J=5.7 Hz, 2H), 4.38 (d, J=6.9 Hz, 2H), 3.85 (t, J=7.0 Hz, 2H), 3.50 (t, J=12.6 Hz, 2H), 3.25 (s, 3H), 0.82-0.59 (m, 4H).

N-(4-chlorobenzyl)-2-((1-methoxy cyclopropyl)methyl)-1,6-dioxo-1,3,4,6-tetrahydro-2H-pyrido[1,2-a]pyrazine-7-carboxamide (Ex-171) was prepared from Ex-171B following a procedure analogous to that described for Ex-117C, with a reaction temperature of 90° C.

Example 172

1-((7-((4-chlorobenzyl) carbamoyl)-1,6-dioxo-1,3,4,6-tetrahydro-2H-pyrido[1,2-a]pyrazin-2-yl)methyl) cyclopropyl dimethyl carbamate 1-((5-((4-chlorobenzyl) carbamoyl)-1-(2-hydroxyethyl)-6-oxo-1,6-dihydropyridine-2-carboxamido)methyl)cyclopropyl dimethyl carbamate (Ex-172A) was prepared from 1-17 and 1-58 following a procedure analogous to that described for Ex-170A, with a reaction temperature of 150° C. LCMS (m/z): 491.3 [M+H]. $^1$H NMR (400 MHz, DMSO-d6) δ 10.09 (s, 1H), 9.11 (d, J=67.6 Hz, 1H), 8.37 (dd, J=11.6, 7.4 Hz, 1H), 7.38 (dd, J=22.7, 8.4 Hz, 4H), 6.65-6.53 (m, 1H), 4.95 (dd, J=10.8, 5.4 Hz, 1H), 4.53 (d, J=5.9 Hz, 2H), 4.22 (t, J=6.2 Hz, 2H), 3.62 (t, J=5.7 Hz, 2H), 3.40-3.35 (m, 2H), 2.76 (d, J=18.6 Hz, 6H), 0.89-0.81 (m, 3H), 0.58 (d, J=5.6 Hz, 1H).

1-((5-((4-chlorobenzyl) carbamoyl)-1-(2-chloroethyl)-6-oxo-1,6-dihydropyridine-2-carboxamido)methyl)cyclopropyl dimethyl carbamate (Ex-172B) was prepared from Ex-172A following a procedure analogous to that described for Ex-51B. LCMS (m/z): 509.2 [M+H]. $^1$H NMR (400 MHz, DMSO-d6) δ 9.96 (d, J=5.9 Hz, 1H), 9.43 (d, J=52.2 Hz, 1H), 8.47-8.36 (m, 1H), 7.38 (dd, J=20.5, 8.4 Hz, 4H), 6.71-6.60 (m, 1H), 4.52 (d, J=6.2 Hz, 2H), 4.40 (t, J=7.0 Hz, 2H), 3.87 (dd, J=8.0, 5.7 Hz, 2H), 3.62 (d, J=6.1 Hz, 2H), 2.75 (d, J=15.2 Hz, 6H), 1.02-0.80 (m, 4H).

1-((7-((4-chlorobenzyl) carbamoyl)-1,6-dioxo-1,3,4,6-tetrahydro-2H-pyrido[1,2-a] pyrazin-2-yl)methyl)cyclopropyl dimethyl carbamate (Ex-172) was prepared from Ex-172B following a procedure analogous to that described for Ex-117C, with a reaction temperature of 90° C.

| Example | Structure | Physical Data MS (m/z), $^1$H NMR |
| --- | --- | --- |
| 171 | 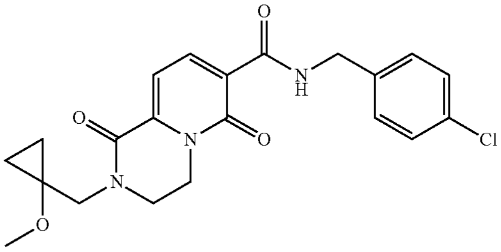 [SMILES: COC1(CN2CCn3c(ccc(C(=O)NCc4ccc(Cl)cc4)c3=O)C2=O)CC1] | LCMS (m/z): 416.4 [M + H]. $^1$H NMR (400 MHz, DMSO-d6) δ 10.13 (t, J = 6.0 Hz, 1H), 8.44 (d, J = 7.5 Hz, 1H), 7.38 (dd, J = 23.1, 8.5 Hz, 4H), 7.22 (d, J = 7.5 Hz, 1H), 4.54 (d, J = 6.0 Hz, 2H), 4.29-4.21 (m, 2H), 3.86-3.78 (in, 2H), 3.74 (s, 2H), 3.23 (s, 3H), 0.78-0.65 (m, 4H). |

| Example | Structure | Physical Data MS (m/z), $^1$H NMR |
|---|---|---|
| 172 | 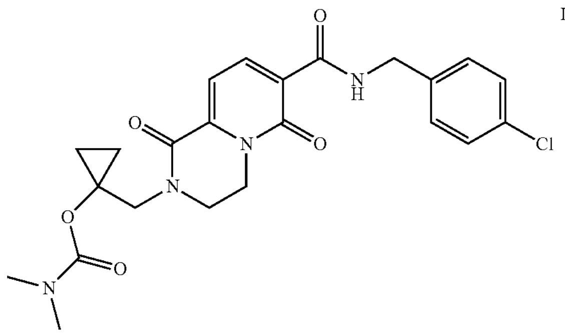 | LCMS (m/z): 473.4 [M + H]. $^1$H NMR (400 MHz, DMSO-d6) δ 10.13 (t, J = 5.8 Hz, 1H), 8.44 (d, J = 7.6 Hz, 1H), 7.37 (dd, J = 24.0, 8.5 Hz, 4H), 7.20 (d, J = 7.5 Hz, 1H), 4.54 (d, J = 6.0 Hz, 2H), 4.30-4.21 (m, 2H), 3.81 (d, J = 5.1 Hz, 4H), 2.72 (t, J = 17.8 Hz, 6H), 0.95-0.83 (m, 4H). |

Example 173

N-(4-chlorobenzyl)-2-((1-((methyl sulfonyl)methyl) cyclopropyl)methyl)-1,6-dioxo-1,3,4,6-tetrahydro-2H-pyrido[1,2-a]pyrazine-7-carboxamide $N^5$-(4-chlorobenzyl)-1-(2-hydroxyethyl)-$N^2$-((1-((methyl sulfonyl)methyl)cyclopropyl)methyl)-6-oxo-1,6-dihydro-pyridine-2,5-dicarboxamide (Ex-173A) was prepared from 1-17 and 1-54 following a procedure analogous to that described for Ex-170A, with microwave irradiation at 120° C. for 12 h. LCMS (m/z): 496.8 [M+H]. $^1$H NMR (400 MHz, DMSO-d6) δ 10.10 (d, J=6.1 Hz, 1H), 9.04 (s, 1H), 8.38 (d, J=7.4 Hz, 1H), 7.41 (d, J=8.5 Hz, 2H), 7.35 (d, J=8.6 Hz, 2H), 6.62 (d, J=7.4 Hz, 1H), 4.96 (t, J=5.3 Hz, 1H), 4.52 (d, J=6.0 Hz, 2H), 4.21 (d, J=6.1 Hz, 2H), 3.62 (d, J=5.8 Hz, 2H), 3.44 (d, J=5.6 Hz, 2H), 3.30-3.25 (m, 2H), 3.00 (s, 3H), 0.71 (d, J=8.6 Hz, 4H).

$N^5$-(4-chlorobenzyl)-1-(2-chloroethyl)-$N^2$-((1-((methyl sulfonyl)methyl)cyclopropyl)methyl)-6-oxo-1,6-dihydro-pyridine-2,5-dicarboxamide (Ex-173B) was prepared from Ex-173A following a procedure analogous to that described for Ex-51B. LCMS (m/z): 514.7 [M+H]. $^1$H NMR (400 MHz, DMSO-d6) δ 9.97 (t, J=6.0 Hz, 1H), 9.22 (t, J=5.9 Hz, 1H), 8.41 (d, J=7.4 Hz, 1H), 7.41 (d, J=8.6 Hz, 2H), 7.36 (d, J=8.6 Hz, 2H), 6.71 (d, J=7.4 Hz, 1H), 4.53 (d, J=5.9 Hz, 2H), 4.39 (t, J=6.8 Hz, 2H), 3.87 (t, J=6.8 Hz, 2H), 3.46 (d, J=5.9 Hz, 2H), 3.10 (dt, J=12.1, 7.2 Hz, 2H), 3.03-2.99 (m, 3H), 0.72 (d, J=9.0 Hz, 4H).

N-(4-chlorobenzyl)-2-((1-((methyl sulfonyl)methyl)cyclopropyl)methyl)-1,6-dioxo-1,3,4,6-tetrahydro-2H-pyrido [1,2-a]pyrazine-7-carboxamide (Ex-173) was prepared from Ex-173B following a procedure analogous to that described for Ex-54.

Compounds in the table below were prepared following from 1-17 following procedures analogous to those described for Ex-173.

| Example | Structure | Physical Data MS (m/z), $^1$H NMR |
|---|---|---|
| 173 | 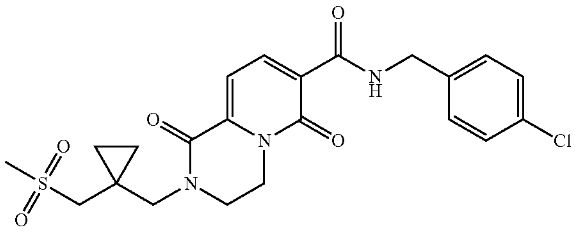 [SMILES: CS(=O)(=O)CC1(CN2CCn3c(ccc(C(=O)NCc4ccc(Cl)cc4)c3=O)C2=O)CC1] | LCMS (m/z): 478.2 [M + H]. $^1$H NMR (400 MHz, $CD_3CN$) δ 10.22-10.16 (m, 1H), 8.51 (d, J = 7.6 Hz, 1H), 7.37 (s, 4H), 7.25 (d, J = 7.5 Hz, 1H), 4.58 (d, J = 6.1 Hz, 2H), 4.32-4.26 (m, 2H), 3.84-3.80 (m, 2H), 3.68 (s, 2H), 3.15 (s, 2H), 2.95 (s, 3H), 0.85 (d, J = 4.3 Hz, 4H). |
| 174 | 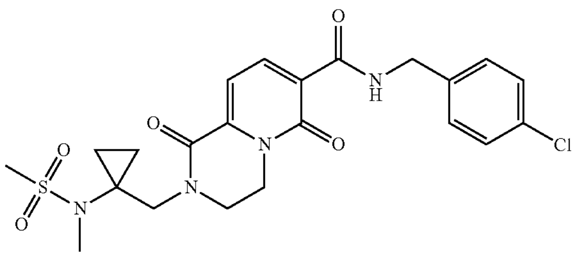 [SMILES: CN(C1(CN2CCn3c(ccc(C(=O)NCc4ccc(Cl)cc4)c3=O)C2=O)CC1)S(C)(=O)=O] | LCMS (m/z): 493.2 [M + H]. $^1$H NMR (400 MHz, $CD_3CN$) δ 10.22-10.15 (m, 1H), 8.49 (d, J = 7.5 Hz, 1H), 7.37 (s, 3H), 7.22 (d, J = 7.5 Hz, 1H), 4.58 (d, J = 6.0 Hz, 2H), 4.36-4.26 (m, 2H), 3.82 (s, 2H), 2.91 (s, 3H), 2.78 (s, 3H), 1.00 (s, 4H). |

Example 175

2-((1-((7-((4-chlorobenzyl) carbamoyl)-1,6-dioxo-1,3,4,6-tetrahydro-2H-pyrido[1,2-a]pyrazin-2-yl) methyl)cyclopropyl)sulfonyl)-2-methylpropanoic acid butyl 2-((1-((1-(tert-butoxy)-2-methyl-1-oxopropan-2-yl) sulfonyl)cyclopropyl)methyl)-1,6-dioxo-1,3,4,6-tetrahydro-2H-pyrido[1,2-a]pyrazine-7-carboxylate (Ex-175A). 1-48 (0.26 g, 0.75 mmol, 1.0 equiv) was added in DMF (4 mL), and I-1 (0.2 g, 0.75 mmol, 1.0 equiv) and $Cs_2CO_3$ (0.49 g, 1.5 mmol, 2.0 equiv) were added. The reaction mixture was stirred at 80° C. for 18 h. The reaction mixture was quenched with cold water and extracted with EtOAc. The organic layer was washed with saturated aqueous ammonium chloride solution, dried over sodium sulfate, and concentrated to afford the title compound.

(50% in EtOAc, 0.082 g, 0.26 mmol, 1.2 equiv) was added and the reaction mixture was stirred at RT for 2 h. The reaction mixture was quenched with cold water and extracted with dichloromethane. The organic layer was washed with brine, dried over sodium sulfate and concentrated to afford the title compound.

2-((1-((7-((4-chlorobenzyl) carbamoyl)-1,6-dioxo-1,3,4,6-tetrahydro-2H-pyrido[1,2-a] pyrazin-2-yl)methyl)cyclopropyl)sulfonyl)-2-methylpropanoic acid (Ex-175). Ex-175C (0.1 g, 0.17 mmol, 1.0 equiv) was dissolved in dichloromethane (2 mL) and cooled to 0° C. TFA (1 mL) was added and the reaction mixture was stirred at RT for 1 hour. The reaction mixture was concentrated to afford a crude residue. The crude residue was purified by preparative HPLC to afford the title compound.

| Example | Structure | Physical Data MS (m/z), $^1$H NMR |
|---|---|---|
| 175 | 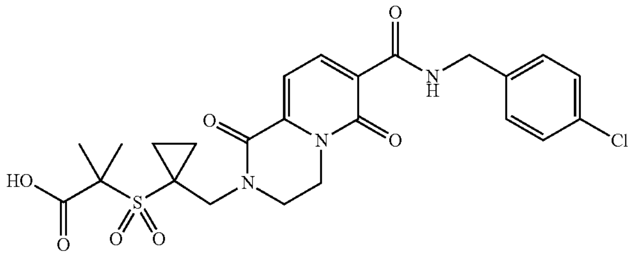 [SMILES: CC(C)(C(=O)O)S(=O)(=O)C1(CN2CCn3c(ccc(C(=O)NCc4ccc(Cl)cc4)c3=O)C2=O)CC1] | $^1$H NMR (400 MHz, DMSO-d6) δ 13.77 (s, 1H), 10.12 (t, J = 5.9 Hz, 1H), 8.44 (d, J = 7.6 Hz, 1H), 7.37 (dd, J = 24.6, 8.5 Hz, 4H), 7.20 (d, J = 7.6 Hz, 1H), 4.54 (d, J = 5.9 Hz, 2H), 4.27-4.20 (m, 2H), 4.11 (s, 2H), 3.80-3.70 (m, 2H), 1.60 (s, 6H), 1.39 (s, 2H), 1.19 (d, J = 2.0 Hz, 2H). |

2-((1-((1-(tert-butoxy)-2-methyl-1-oxopropan-2-yl)sulfonyl)cyclopropyl)methyl)-1,6-dioxo-1,3,4,6-tetrahydro-2H-pyrido[1,2-a]pyrazine-7-carboxylic acid (Ex-175B). Ex-175A (0.17 g, 0.32 mmol, 1.0 equiv) was dissolved in THF (3 mL), MeOH (1 mL), and water (1 mL). $LiOH·H_2O$ (0.02 g, 0.48 mmol, 1.5 equiv) was added and the reaction mixture was stirred at RT for 1 h. The reaction mixture was concentrated, diluted with water, and extracted with EtOAc. The aqueous layer was acidified by 1.0 N HCl aqueous solution to pH 2-3 and extracted with EtOAc. The organic layer was washed with brine, dried over sodium sulfate and concentrated to afford the title compound.

tert-butyl 2-((1-((7-((4-chlorobenzyl) carbamoyl)-1,6-dioxo-1,3,4,6-tetrahydro-2H-pyrido[1,2-a] pyrazin-2-yl) methyl)cyclopropyl)sulfonyl)-2-methyl propanoate (Ex-175C). Ex-175B (0.1 g, 0.21 mmol, 1.0 equiv), DIPEA (0.083 g, 0.64 mmol, 3.0 equiv), and (4-chlorophenyl) methanamine (0.036 g, 0.25 mmol, 1.2 equiv) were dissolved in dichloromethane (2 mL) and cooled to 0° C. T3P®

Example 176

N-(4-chlorobenzyl)-2-((1-((2-methyl-1-(methyl sulfonamido)-1-oxopropan-2-yl)sulfonyl)cyclopropyl)methyl)-1,6-dioxo-1,3,4,6-tetrahydro-2H-pyrido [1,2-a]pyrazine-7-carboxamide N-(4-chlorobenzyl)-2-((1-((2-methyl-1-(methyl sulfonamido)-1-oxopropan-2-yl) sulfonyl)cyclopropyl)methyl)-1,6-dioxo-1,3,4,6-tetrahydro-2H-pyrido[1,2-a] pyrazine-7-carboxamide (Ex-176). Ex-175 (0.2 g, 0.37 mmol, 1.0 equiv) was dissolved in DMF (5 mL), and DIPEA (0.14 g, 1.1 mmol, 3.0 equiv) and TBTU (0.13 g, 0.41 mmol, 1.5 equiv) were added. The reaction mixture was stirred at RT for 5 min, and methanesulfonamide (0.039 g, 0.41 mmol, 1.5 equiv) was added. The reaction mixture was stirred at RT for 4 h, after which it was quenched with cold water and extracted with EtOAc. The organic layer was washed with brine, dried over sodium sulfate, and concentrated. The crude residue was purified by preparative HPLC to afford the title compound.

| Example | Structure | Physical Data MS (m/z), ¹H NMR |
|---|---|---|
| 176 | 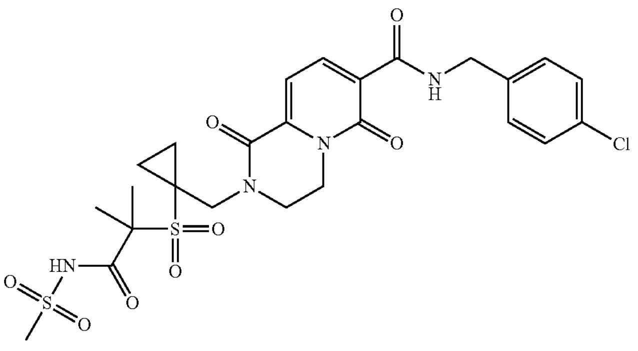 [SMILES: CC(C)(C(=O)NS(C)(=O)=O)S(=O)(=O)C1(CN2CCn3c(ccc(C(=O)NCc4ccc(Cl)cc4)c3=O)C2=O)CC1] | LCMS (m/z): 613.4 [M + H]. ¹H NMR (400 MHz, DMSO-d6) δ 10.12 (t, J = 5.9 Hz, 1H), 8.43 (d, J = 7.5 Hz, 1H), 7.37 (dd, J = 24.9, 8.5 Hz, 4H), 7.20 (d, J = 7.6 Hz, 1H), 4.53 (d, J = 5.9 Hz, 2H), 4.28-4.18 (m, 2H), 4.07 (s, 2H), 3.77-3.73 (m, 2H), 3.30 (s, 3H), 1.70 (d, J = 14.3 Hz, 6H), 1.39 (s, 2H), 1.20 (s, 2H). |

Example 178

2-((1-((2-(1,2,4-oxadiazol-5-yl) propan-2-yl)sulfonyl)cyclopropyl)methyl)-N-(4-chlorobenzyl)-1,6-dioxo-1,3,4,6-tetrahydro-2H-pyrido[1,2-a]pyrazine-7-carboxamide 2-((1-((1-amino-2-methyl-1-oxopropan-2-yl)sulfonyl)cyclopropyl)methyl)-N-(4-chlorobenzyl)-1,6-dioxo-1,3,4,6-tetrahydro-2H-pyrido[1,2-a]pyrazine-7-carboxamide (Ex-177). Ex-175 (0.2 g, 0.37 mmol, 1.0 equiv) was added in dichloromethane (1.5 mL) and cooled to 0° C. Oxalyl chloride (0.071 g, 0.56 mmol, 1.0 equiv) was added drop wise and the reaction mixture was stirred at 0° C. for 30 minutes. The reaction mixture was added in cooled solution of liquid ammonia (5 mL). The precipitated solid was filtered, washed with water, n-pentane and dried to afford the title compound.

(Z)—N-(4-chlorobenzyl)-2-((1-((1-(((dimethyl amino) methylene)amino)-2-methyl-1-oxopropan-2-yl)sulfonyl)cyclopropyl)methyl)-1,6-dioxo-1,3,4,6-tetrahydro-2H-pyrido[1,2-a]pyrazine-7-carboxamide (Ex-178A). Ex-177 (0.12 g, 0.22 mmol, 1.0 equiv) was added in DMF:DMA (2 mL) and the reaction mixture was stirred at 80° C. for 2 h. The reaction mixture was concentrated to afford the title compound. LCMS (m/z): 591.4 [M+H]. ¹H NMR (400 MHz, DMSO-d6) δ 10.12 (s, 1H), 8.47 (s, 1H), 8.42 (s, 1H), 7.37 (dd, J=24.9, 8.4 Hz, 4H), 7.19 (d, J=7.6 Hz, 1H), 4.53 (d, J=5.6 Hz, 2H), 4.24 (s, 2H), 4.14 (s, 2H), 3.74 (s, 2H), 3.16 (t, J=7.2 Hz, 6H), 1.59 (s, 6H), 1.32 (s, 2H), 1.09 (s, 2H).

2-((1-((2-(1,2,4-oxadiazol-5-yl) propan-2-yl)sulfonyl)cyclopropyl)methyl)-N-(4-chlorobenzyl)-1,6-dioxo-1,3,4,6-tetrahydro-2H-pyrido[1,2-a]pyrazine-7-carboxamide (Ex-178) Ex-178A (0.12 g, 0.2 mmol, 1.0 equiv) was dissolved in 1,4-dioxane (2 mL), and $NH_2OH{\cdot}HCl$ (0.018 g, 0.26 mmol, 1.3 equiv) and AcOH (0.033 g, 0.55 mmol, 2.8 equiv) were added. The reaction mixture was stirred at 80° C. for 3 h, after which it was quenched with water and extracted with EtOAc. The organic layer was washed with brine, dried over sodium sulfate, and concentrated. The crude residue was purified by preparative HPLC to afford the title compound.

| Example | Structure | Physical Data MS (m/z), ¹H NMR |
|---|---|---|
| 177 | 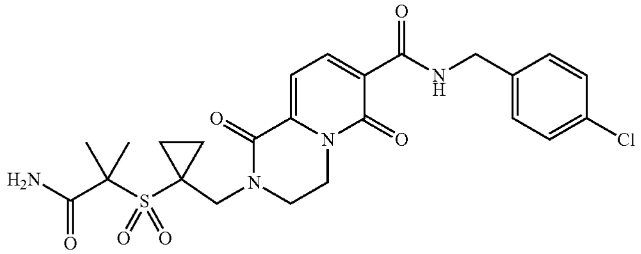 [SMILES: CC(C)(C(N)=O)S(=O)(=O)C1(CN2CCn3c(ccc(C(=O)NCc4ccc(Cl)cc4)c3=O)C2=O)CC1] | LCMS (m/z): 535.4 [M + H]. ¹H NMR (400 MHz, DMSO-d6) δ 10.12 (t, J = 6.1 Hz, 1H), 8.43 (d, J = 7.6 Hz, 1H), 7.70 (s, 2H), 7.41-7.33 (m, 4H), 7.19 (d, J = 7.6 Hz, 1H), 4.53 (d, J = 6.0 Hz, 2H), 4.23 (d, J = 5.7 Hz, 2H), 4.08 (s, 2H), 3.77 (d, J = 5.6 Hz, 2H), 1.57 (s, 6H), 1.37 (t, J = 5.8 Hz, 2H), 1.17 (s, 2H). |
| 178 | 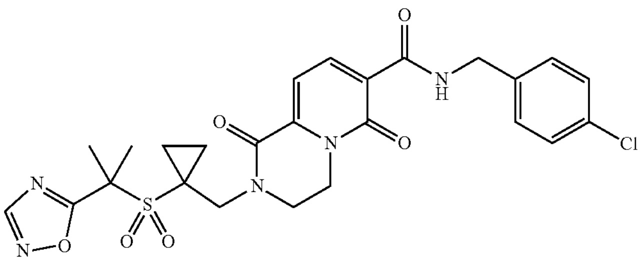 [SMILES: CC(C)(c1ncno1)S(=O)(=O)C1(CN2CCn3c(ccc(C(=O)NCc4ccc(Cl)cc4)c3=O)C2=O)CC1] | LCMS (m/z): 560.4 [M + H]. ¹H NMR (400 MHz, DMSO-d6) δ 10.11 (t, J = 6.1 Hz, 1H), 9.20 (s, 1H), 8.43 (d, J = 7.6 Hz, 1H), 7.37 (dd, J = 24.8, 8.4 Hz, 4H), 7.19 (d, J = 7.5 Hz, 1H), 4.53 (d, J = 6.0 Hz, 2H), 4.26-4.18 (m, 2H), 3.94 (s, 2H), 3.73-3.64 (m, 2H), 1.94 (s, 6H), 1.11 (d, J = 6.7 Hz, 4H). |

The compound in the table below was prepared from Ex-175B following procedures analogous to those described for Ex-178.

| Example | Structure | Physical Data MS (m/z), $^1$H NMR |
|---|---|---|
| 179 | 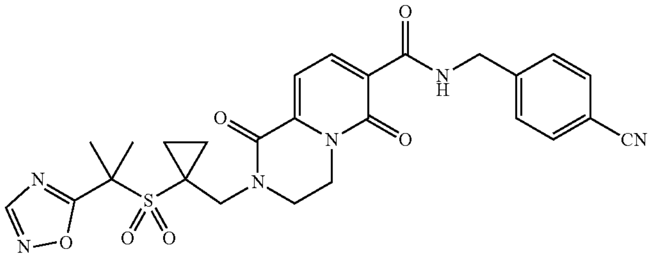 [SMILES: CC(C)(c1ncno1)S(=O)(=O)C1(CN2CCn3c(ccc(C(=O)NCc4ccc(C#N)cc4)c3=O)C2=O)CC1] | LCMS (m/z): 551.5 [M + H]. $^1$H NMR (400 MHz, DMSO-d6) δ 10.18 (t, J = 6.0 Hz, 1H), 9.20 (s, 1H), 8.43 (d, J = 7.6 Hz, 1H), 7.81 (d, J = 8.2 Hz, 2H), 7.50 (d, J = 8.1 Hz, 2H), 7.19 (d, J = 7.6 Hz, 1H), 4.63 (d, J = 5.9 Hz, 2H), 4.25 (d, J = 5.1 Hz, 2H), 3.94 (s, 2H), 3.71 (d, J = 5.1 Hz, 2H), 1.94 (s, 6H), 1.11 (d, J = 7.3 Hz, 4H). |

Example 181

2-((1-((1-amino-2-methylpropan-2-yl)sulfonyl)cyclopropyl)methyl)-N-(4-chlorobenzyl)-1,6-dioxo-1,3,4,6-tetrahydro-2H-pyrido[1,2-a]pyrazine-7-carboxamide N-(4-chlorobenzyl)-2-((1-((1-hydroxy-2-methylpropan-2-yl)sulfonyl)cyclopropyl)methyl)-1,6-dioxo-1,3,4,6-tetrahydro-2H-pyrido[1,2-a]pyrazine-7-carboxamide (Ex-180) Ex-175 (0.9 g, 0.17 mmol, 1.0 equiv) was dissolved in THF (5 mL) and cooled to 0° C. TEA (0.025 g, 0.25 mmol, 1.5 equiv) and isobutyl chloroformate (0.029 g, 0.22 mmol, 1.3 equiv) were added and the reaction mixture was stirred at 0° C. for 3 h. The reaction mixture was filtered, and a solution of $NaBH_4$ (0.005 g, 0.14 mmol, 1.0 equiv) in water (5 mL) was added. The reaction mixture was stirred at 0° C. for 20 min, after which it was diluted with water and extracted with EtOAc. The organic layer was washed with brine, dried over sodium sulfate and concentrated to afford the title compound.

2-((1-((7-((4-chlorobenzyl) carbamoyl)-1,6-dioxo-1,3,4,6-tetrahydro-2H-pyrido[1,2-a]pyrazin-2-yl)methyl)cyclopropyl)sulfonyl)-2-methylpropyl trifluoro methanesulfonate (Ex-181A). Ex-180 (0.08 g, 0.15 mmol, 1.0 equiv) was dissolved in dichloromethane (2 mL) and cooled to 0° C. Pyridine (0.072 g, 0.92 mmol, 6.0 equiv) and triflic anhydride (0.11 g, 0.38 mmol, 2.5 equiv) were added and the reaction mixture was stirred at room RT for 3 h. Another portion of pyridine (0.072 g, 0.92 mmol, 6.0 equiv) and triflic anhydride (0.11 g, 0.38 mmol, 2.5 equiv) were added, and the reaction mixture was stirred at RT for 3 h. The reaction mixture was quenched with water and extracted with dichloromethane. The organic layer was washed with dilute HCl and brine, dried over sodium sulfate, and concentrated to afford the title compound. LCMS (m/z): 654.4 [M+H]. $^1$H NMR (400 MHz, DMSO-d6) δ 10.12 (t, J=5.8 Hz, 1H), 8.44 (dd, J=7.6, 1.6 Hz, 1H), 7.42-7.31 (m, 4H), 7.20 (dd, J=7.6, 3.0 Hz, 1H), 4.54 (d, J=6.0 Hz, 2H), 4.24 (s, 2H), 4.13 (d, J=8.4 Hz, 2H), 3.87 (d, J=6.6 Hz, 2H), 3.80-3.70 (m, 2H), 1.23-1.11 (m, 4H), 0.91-0.81 (m, 6H).

2-((1-((1-amino-2-methylpropan-2-yl)sulfonyl)cyclopropyl)methyl)-N-(4-chlorobenzyl)-1,6-dioxo-1,3,4,6-tetrahydro-2H-pyrido[1,2-a]pyrazine-7-carboxamide (Ex-181). Ex-181A (0.06 g, 0.092 mmol, 1.0 equiv) was dissolved in THF (5 mL) in an autoclave. The reaction mixture was stirred at 80° C. for 24 h under ammonia gas (10 kg pressure). The reaction mixture was concentrated and purified by preparative TLC (5% MeOH/dichloromethane) to afford the title compound.

| Example | Structure | Physical Data MS (m/z), $^1$H NMR |
|---|---|---|
| 180 | 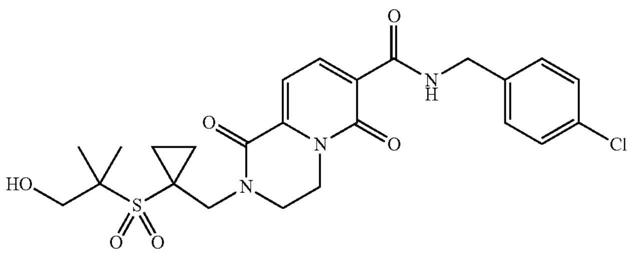 [SMILES: CC(C)(CO)S(=O)(=O)C1(CN2CCn3c(ccc(C(=O)NCc4ccc(Cl)cc4)c3=O)C2=O)CC1] | LCMS (m/z): 522.4 [M + H]. $^1$H NMR (400 MHz, DMSO-d6) δ 10.12 (s, 1H), 8.43 (d, J = 7.6 Hz, 1H), 7.37 (dd, J = 24.9, 8.5 Hz, 4H), 7.19 (d, J = 7.5 Hz, 1H), 5.39 (t, J = 5.7 Hz, 1H), 4.54 (d, J = 5.7 Hz, 2H), 4.24 (s, 2H), 4.14 (s, 2H), 3.77 (s, 2H), 3.65 (d, J = 5.6 Hz, 2H), 1.11 (s, 2H), 0.91 (d, J = 6.7 Hz, 8H). |

-continued

| Example | Structure | Physical Data MS (m/z), ¹H NMR |
|---|---|---|
| 181 | 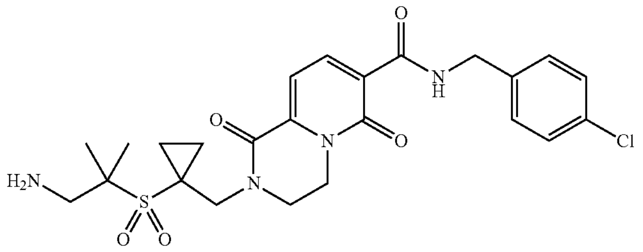 [SMILES: CC(C)(CN)S(=O)(=O)C1(CN2CCn3c(ccc(C(=O)NCc4ccc(Cl)cc4)c3=O)C2=O)CC1] | LCMS (m/z): 521.4 [M + H]. ¹H NMR (400 MHz, DMSO-d6) δ 10.12 (s, 1H), 8.43 (d, J = 7.8 Hz, 1H), 7.37 (dd, J = 24.8, 8.3 Hz, 4H), 7.20 (d, J = 7.5 Hz, 1H), 4.53 (s, 2H), 4.23 (s, 2H), 4.12 (s, 2H), 3.76 (s, 2H), 1.35 (s, 8H), 1.10 (s, 2H). |

Compounds in the table below were prepared from Ex-175B following procedures analogous to those described for Ex-180 and Ex-181.

| Example | Structure | Physical Data MS (m/z), ¹H NMR |
|---|---|---|
| 182 | 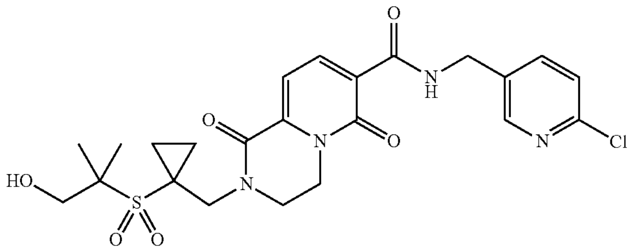 | LCMS (m/z): 523.5 [M + H]. ¹H NMR (400 MHz, DMSO-d6) δ 10.16 (t, J = 6.0 Hz, 1H), 8.40 (dd, J = 13.1, 5.0 Hz, 2H), 7.80 (dd, J = 8.3, 2.5 Hz, 1H), 7.49 (d, J = 8.2 Hz, 1H), 7.19 (d, J = 7.6 Hz, 1H), 5.39 (t, J = 5.5 Hz, 1H), 4.56 (d, J = 6.0 Hz, 2H), 4.31-4.19 (m, 2H), 4.14 (s, 2H), 3.82-3.73 (m, 2H), 3.65 (d, J = 5.5 Hz, 2H), 1.48-1.24 (m, 8H), 1.17-1.06 (m, 2H). |
| 183 | 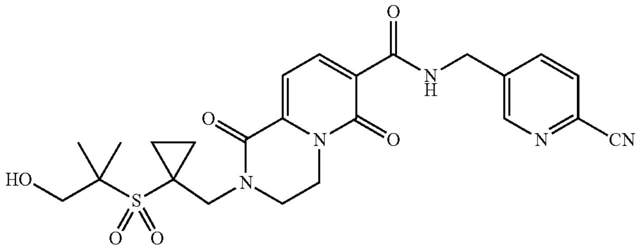 [SMILES: CC(C)(CO)S(=O)(=O)C1(CN2CCn3c(ccc(C(=O)NCc4ccc(C#N)nc4)c3=O)C2=O)CC1] | LCMS (m/z): 514.5 [M + H]. ¹H NMR (400 MHz, DMSO-d6) δ 8.72 (s, 1H), 8.41 (d, J = 7.6 Hz, 1H), 8.01 (d, J = 8.2 Hz, 1H), 7.95 (d, J = 8.1 Hz, 1H), 7.19 (d, J = 7.6 Hz, 1H), 5.38 (t, J = 5.6 Hz, 1H), 4.66 (d, J = 6.2 Hz, 2H), 4.25 (d, J = 5.9 Hz, 2H), 4.14 (s, 2H), 3.78 (s, 2H), 3.66 (d, 7 = 5.6 Hz, 2H), 1.36 (d, J = 10.6 Hz, 8H), 1.11 (s, 2H). |
| 184 | 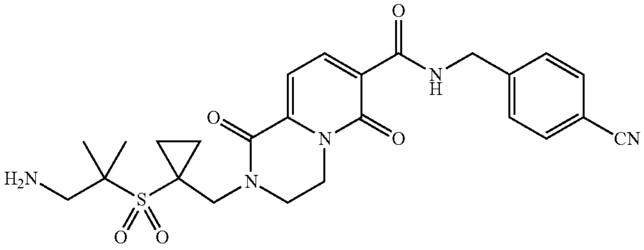 [SMILES: CC(C)(CN)S(=O)(=O)C1(CN2CCn3c(ccc(C(=O)NCc4ccc(C#N)cc4)c3=O)C2=O)CC1] | LCMS (m/z): 512.2 [M + H]. ¹H NMR (400 MHz, DMSO-d6) δ 10.19 (t, J = 6.3 Hz, 1H), 8.43 (d, J = 7.6 Hz, 1H), 7.81 (d, J = 8.3 Hz, 2H), 7.50 (d, J = 8.2 Hz, 2H), 7.20 (d, J = 7.6 Hz, 1H), 4.64 (d, J = 6.0 Hz, 2H), 4.30-4.20 (m, 2H), 4.13 (s, 2H), 3.82-3.73 (m, 2H) 1.39-1.23 (m, 8H), 1.11 (d, J = 2.0 Hz, 2H). |
| 184-1 | 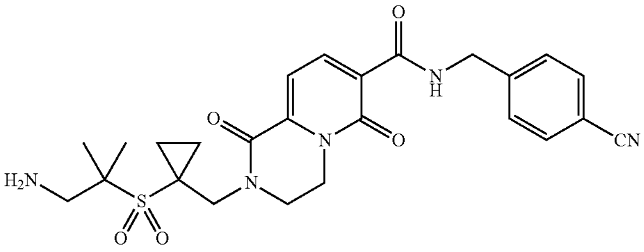 [SMILES: CC(C)(CN)S(=O)(=O)C1(CN2CCn3c(ccc(C(=O)NCc4ccc(C#N)cc4)c3=O)C2=O)CC1] | LCMS (m/z): 513.2 [M + H]. 1H NMR (500 MHz, DMSO-d6) δ ppm 1.12 (m, 2H) 1.35 (s, 6H) 1.38 (m, 2H) 3.66 (br. s., 2H) 3.78 (t, J = 5.67 Hz, 2H) 4.15 (s, 2H) 4.26 (t, J = 5.67 Hz, 2H) 4.64 (d, J = 5.99 Hz, 2H) 7.20 (d, J = 7.57 Hz, 1 H) 7.50 (d, J = 8.20 Hz, 2H) 7.82 (d, J = 8.20 Hz, 2H) 8.43 (d, J = 7.25 Hz, 1H) 10.19 (t, J = 6.15 Hz, 1H). |

Example 186

2-((1-((2-(1H-tetrazol-5-yl)propan-2-yl)sulfonyl)cyclopropyl)methyl)-N-(4-chlorobenzyl)-1,6-dioxo-1,3,4,6-tetrahydro-2H-pyrido[1,2-a]pyrazine-7-carboxamide N-(4-chlorobenzyl)-2-((1-((2-cyanopropan-2-yl)sulfonyl)cyclopropyl)methyl)-1,6-dioxo-1,3,4,6-tetrahydro-2H-pyrido[1,2-a]pyrazine-7-carboxamide (Ex-185). Ex-177 (0.15 g, 0.28 mmol, 1.0 equiv) was added in DMF (1.5 mL) and cooled to 0° C. Thionyl chloride (0.033 g, 0.028 mmol, 0.1 equiv) was added and the reaction mixture was stirred at 0° C. for 4 h. The reaction mixture was quenched with cold water and extracted with EtOAc. The organic layer was washed with saturated aqueous ammonium chloride, dried over sodium sulfate, and concentrated to afford a crude residue. The crude residue was purified by flash chromatography (67% EtOAc/Hexane) to afford the title compound.

2-((1-((2-(1H-tetrazol-5-yl)propan-2-yl)sulfonyl)cyclopropyl)methyl)-N-(4-chlorobenzyl)-1,6-dioxo-1,3,4,6-tetrahydro-2H-pyrido[1,2-a]pyrazine-7-carboxamide (Ex-186). Ex-185 (0.3 g, 0.58 mmol, 1.0 equiv) was added in DMSO (6 mL), $NaN_3$ (0.056 g, 0.087 mmol, 1.5 equiv) and $CuSO_4 \cdot 5H_2O$ (0.21 g, 0.087 mmol, 1.5 equiv) were added, and the reaction mixture was stirred at 90° C. for 12 h under microwave irradiation. The reaction mixture was quenched with cold water, filtered through a bed of celite and extracted with EtOAc. The organic layer was washed with brine, dried over sodium sulfate, and concentrated to afford a crude residue. The crude residue was purified by preparative HPLC to afford the title compound.

| Example | Structure | Physical Data MS (m/z), $^1$H NMR |
|---|---|---|
| 185 | 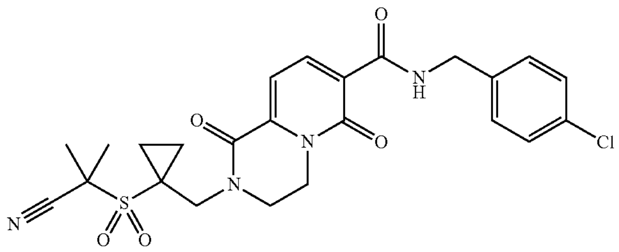 [SMILES: CC(C)(C#N)S(=O)(=O)C1(CN2CCn3c(ccc(C(=O)NCc4ccc(Cl)cc4)c3=O)C2=O)CC1] | LCMS (m/z): 517.4 [M + H]. $^1$H NMR (400 MHz, DMSO-d6) δ 10.12 (t, J = 6.1 Hz, 1H), 8.44 (d, J = 7.6 Hz, 1H), 7.37 (dd, J = 25.5, 8.5 Hz, 4H), 7.22 (d, J = 7.6 Hz, 1H), 4.54 (d, J = 6.0 Hz, 2H), 4.25 (d, J = 9.5 Hz, 4H), 3.85-3.74 (m, 2H), 1.82 (s, 6H), 1.52 (t, J = 6.2 Hz, 2H), 1.38-1.29 (m, 2H). |
| 186 | 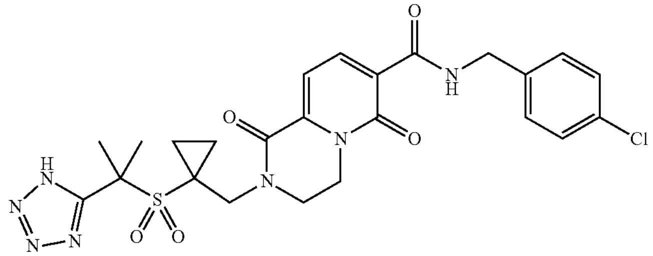 [SMILES: CC(C)(c1nnn[nH]1)S(=O)(=O)C1(CN2CCn3c(ccc(C(=O)NCc4ccc(Cl)cc4)c3=O)C2=O)CC1] | LCMS (m/z): 560.5 [M + H]. $^1$H NMR (400 MHz, DMSO-d6) δ 17.32-16.71 (m, 1H), 10.11 (t, J = 5.9 Hz, 1H), 8.43 (d, J = 7.6 Hz, 1H), 7.37 (dd, J = 25.9, 8.4 Hz, 4H), 7.18 (d, J = 7.6 Hz, 1H), 4.53 (d, J = 5.9 Hz, 2H), 4.21 (s, 2H), 3.74 (s, 2H), 3.63 (s, 2H), 2.01 (d, J = 56.3 Hz, 6H), 0.97 (t, J = 38.9 Hz, 4H). |

The compound in the table below was prepared from I-1 and 1-50 following procedures analogous to those described for Ex-175C.

| Example | Structure | Physical Data MS (m/z), $^1$H NMR |
|---|---|---|
| 187 | 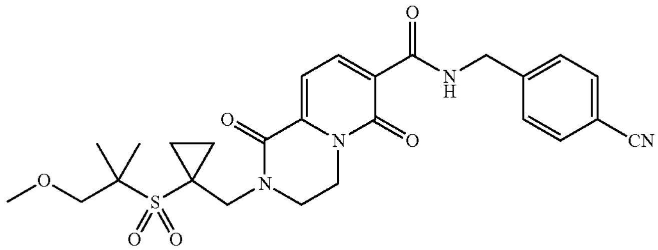 [SMILES: COCC(C)(C)S(=O)(=O)C1(CN2CCn3c(ccc(C(=O)NCc4ccc(C#N)cc4)c3=O)C2=O)CC1] | LCMS (m/z): 527.2 [M + H]. $^1$H NMR (400 MHz, DMSO-d6) δ 10.19 (t, J = 6.1 Hz, 1H), 8.43 (d, J = 7.5 Hz, 1H), 7.81 (d, J = 8.3 Hz, 2H), 7.50 (d, J = 8.2 Hz, 2H), 7.20 (d, J = 7.6 Hz, 1H), 4.64 (d, J = 6.1 Hz, 2H), 4.31-4.20 (m, 2H), 4.10 (s, 2H), 3.80-3.75 (m, 2H), 3.56 (s, 2H), 3.37 (d, J = 19.9 Hz, 3H), 1.37 (s, 8H), 1.12 (d, J = 2.1 Hz, 2H). |

Compounds in the table below were prepared from I-1 and 1-52 following procedures analogous to those described for Ex-175C.

| Example | Structure | Physical Data MS (m/z), $^1$H NMR |
|---|---|---|
| 188 | 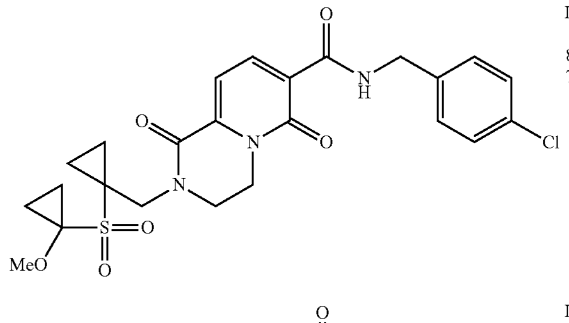 | LCMS (m/z): 520.4 [M + H]. 1H NMR (400 MHz, DMSO-d6) δ 10.12 (t, J = 6.2 Hz, 1H), 8.44 (d, J = 7.5 Hz, 1H), 7.40 (d, J = 8.5 Hz, 2H), 7.34 (d, J = 8.6 Hz, 2H), 7.20 (d, J = 7.5 Hz, 1H), 4.54 (d, J = 6.0 Hz, 2H), 4.30-4.21 (m, 2H), 4.12 (s, 2H), 3.84-3.73 (m, 3H), 1.45-1.28 (m, 6H), 1.23 (s, 2H). |
| 189 | 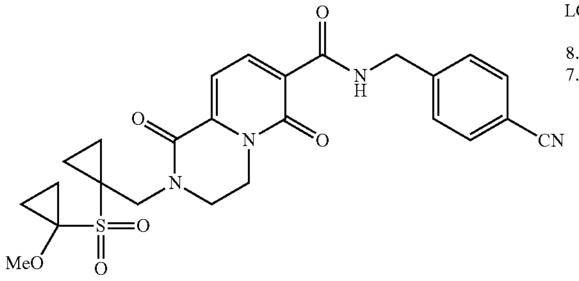 | LCMS (m/z): 511.4 [M + H]. $^1$H NMR (400 MHz, DMSO-d6) δ 10.18 (t, J = 6.1 Hz, 1H), 8.43 (d, J = 7.6 Hz, 1H), 7.81 (d, J = 8.3 Hz, 2H), 7.50 (d, J = 8.2 Hz, 2H), 7.20 (d, J = 7.6 Hz, 1H), 4.64 (d, J = 6.0 Hz, 2H), 4.29-4.21 (m, 2H), 4.13 (s, 2H), 3.83-3.76 (m, 2H), 3.50 (s, 3H), 1.42-1.33 (m, 6H), 1.24-1.18 (m, 2H). |
| 190 | 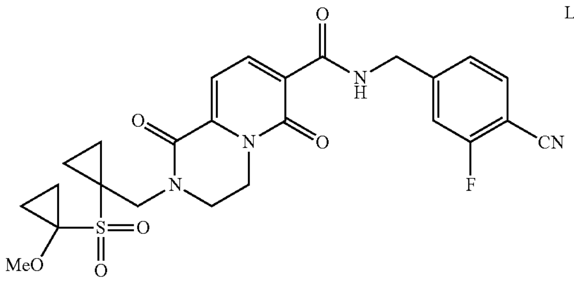 | LCMS (m/z): 529.3 [M + H]. $^1$H NMR (400 MHz, DMSO-d6) δ 10.19 (s, 1H), 8.42 (d, J = 7.5 Hz, 1H), 7.94-7.85 (m, 1H), 7.44 (d, J = 10.3 Hz, 1H), 7.35 (d, J = 7.1 Hz, 1H), 7.20 (d, J = 7.6 Hz, 1H), 4.64 (d, J = 6.0 Hz, 2H), 4.26 (s, 2H), 4.13 (s, 2H), 3.81 (s, 2H), 3.50 (s, 3H), 1.37 (d, J = 11.5 Hz, 4H), 1.25 (d, J = 14.8 Hz, 4H). |

Compounds in the table below were prepared from I-1 and 1-51 following procedures analogous to those described for Ex-175C.

| Example | Structure | Physical Data MS (m/z), $^1$H NMR |
|---|---|---|
| 191 | 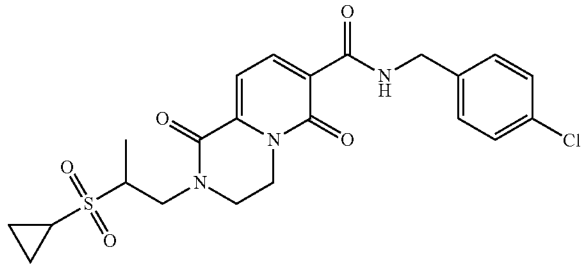 [SMILES: CC(CN1CCn2c(ccc(C(=O)NCc3ccc(Cl)cc3)c2=O)C1=O)S(=O)(=O)C1CC1] | $^1$H NMR (400 MHz, DMSO-d6) δ 10.13 (d, J = 5.9 Hz, 1H), 8.45 (d, J = 7.5 Hz, 1H), 7.37 (dd, J = 25.2, 8.5 Hz, 4H), 7.22 (d, J = 7.6 Hz, 1H), 4.54 (d, J = 6.1 Hz, 2H), 4.37-4.17 (m, 2H), 3.92-3.70 (m, 4H), 2.80 (d, J = 7.7 Hz, 1H), 1.30 (t, J = 19.0 Hz, 3H), 1.12-0.86 (m, 4H). |

-continued

| Example | Structure | Physical Data MS (m/z), $^1$H NMR |
|---|---|---|
| 192 | 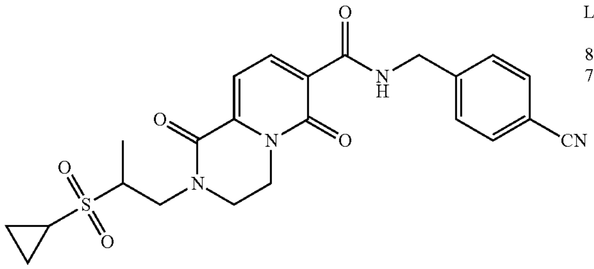 | LCMS (m/z): 469.1 [M + H]. $^1$H NMR (400 MHz, DMSO-d6) δ 10.18 (d, J = 6.2 Hz, 1H), 8.44 (d, J = 7.5 Hz, 1H), 7.82 (d, J = 8.3 Hz, 2H), 7.50 (d, J = 8.2 Hz, 2H), 7.22 (d, J = 7.6 Hz, 1H), 4.64 (d, J = 5.9 Hz, 2H), 4.40-4.22 (m, 2H), 3.84 (dd, J = 16.8, 10.9 Hz, 4H), 3.69 (d, J = 6.8 Hz, 1H), 2.81 (s, 1H), 1.30 (t, J = 19.1 Hz, 3H), 1.14-0.94 (m, 4H). |

Compounds in the table below were prepared from 1-62 and either 1-17 or 1-61 following procedures analogous to those described for Ex-64.

| Example | Structure | Physical Data MS (m/z), $^1$H NMR |
|---|---|---|
| 193 | 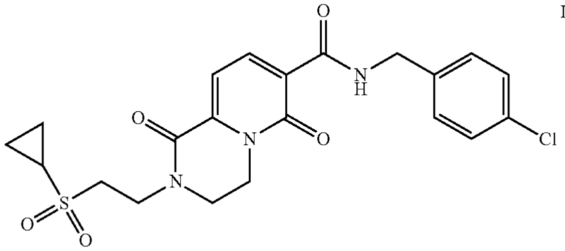 [SMILES: N#Cc1ccc(CNC(=O)c2ccc3n(c2=O)CCN(CCS(=O)(=O)C2CC2)C3=O)cc1] | LCMS (m/z): 464.0 [M + H]. $^1$H NMR (400 MHz, DMSO-d6) δ 10.11 (t, J = 6.0 Hz, 1H), 8.44 (d, J = 7.5 Hz, 1H), 7.37 (dd, J = 24.0, 8.5 Hz, 4H), 7.21 (d, J = 7.5 Hz, 1H), 4.54 (d, J = 6.0 Hz, 2H), 4.30-4.18 (m, 2H), 3.93 (t, J = 6.9 Hz, 2H), 3.86-3.75 (m, 2H), 3.54 (t, J = 6.9 Hz, 2H), 2.81 (ddd, J = 12.5, 7.7, 5.1 Hz, 1H), 1.03 (dd, J = 10.4, 5.9 Hz, 4H). |
| 194 | 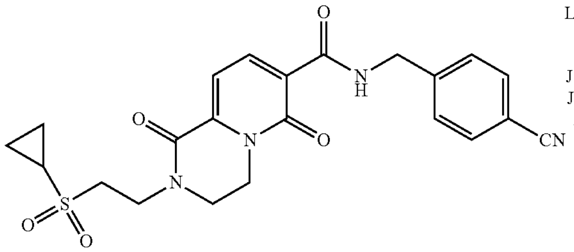 | LCMS (m/z): 455.3 [M + H]. $^1$H NMR (400 MHz, DMSO-d6) δ 10.18 (s, 1H), 8.44 (d, J = 7.6 Hz, 1H), 7.81 (d, J = 8.3 Hz, 2H), 7.50 (d, J = 8.1 Hz, 2H), 7.21 (d, J = 7.5 Hz, 1H), 4.64 (d, J = 5.5 Hz, 2H), 4.26 (s, 2H), 3.92 (d, J = 7.3 Hz, 2H), 3.80 (s, 2H), 3.55 (d, J = 7.4 Hz, 2H), 2.82 (s, 1H), 1.04 (d, J = 10.3 Hz, 4H). |
| 195 | 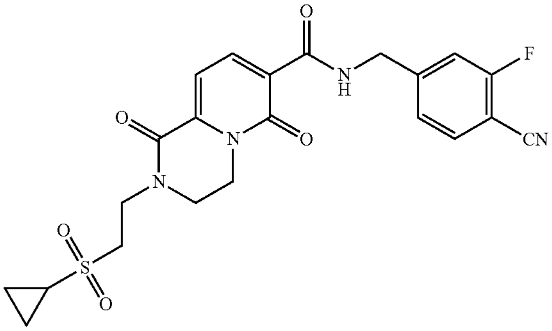 [SMILES: N#Cc1ccc(CNC(=O)c2ccc3n(c2=O)CCN(CCS(=O)(=O)C2CC2)C3=O)cc1F] | LCMS (m/z): 473.3 [M + H]. $^1$H NMR (400 MHz, DMSO-d6) δ 10.19 (t, J = 6.1 Hz, 1H), 8.42 (d, J = 7.6 Hz, 1H), 7.87 (t, J = 7.5 Hz, 1H), 7.42 (d, J = 10.4 Hz, 1H), 7.34 (d, J = 8.2 Hz, 1H), 7.21 (d, J = 7.6 Hz, 1H), 4.63 (d, J = 6.1 Hz, 2H), 4.29-4.15 (m, 2H), 3.93 (t, J = 6.9 Hz, 2H), 3.82-3.70 (m, 2H), 3.52 (d, J = 6.7 Hz, 2H), 2.79 (s, 1H), 1.03 (dd, J = 11.1, 6.8 Hz, 4H). |

Example 196

N-(4-cyanobenzyl)-2-((1-((1-hydroxy cyclopropyl) sulfonyl)cyclopropyl)methyl)-1,6-dioxo-1,3,4,6-tetrahydro-2H-pyrido[1,2-a]pyrazine-7-carboxamide N-(4-cyanobenzyl)-2-((1-((1-hydroxy cyclopropyl)sulfonyl)cyclopropyl)methyl)-1,6-dioxo-1,3,4,6-tetrahydro-2H-pyrido[1,2-a]pyrazine-7-carboxamide (Ex-196). Ex-189 (0.15 g, 0.3 mmol, 1.0 equiv) was added in toluene (2 mL). $AlCl_3$ (0.078 g, 0.59 mmol, 2.0 equiv) was added, and the reaction mixture was stirred at reflux for 5 h. The reaction mixture was quenched with cold water and extracted with EtOAc. The organic layer was washed with brine, dried over sodium sulfate, and concentrated. The crude residue was purified by preparative HPLC to afford the title compound.

| Example | Structure | Physical Data MS (m/z), $^1$H NMR |
|---|---|---|
| 196 | 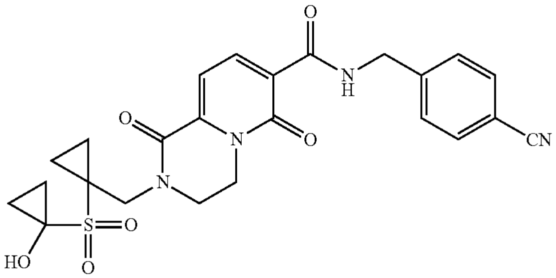 [SMILES: N#Cc1ccc(CNC(=O)c2ccc3n(c2=O)CCN(CC2(S(=O)(=O)C4(O)CC4)CC2)C3=O)cc1] | LCMS (m/z): 497.3 [M + H]. $^1$H NMR (400 MHz, $CDCl_3$) δ 10.10 (s, 1H), 8.57 (d, J = 7.5 Hz, 1H), 7.56 (d, J = 8.3 Hz, 2H), 7.41 (t, J = 16.0 Hz, 2H), 7.30 (d, J = 7.5 Hz, 1H), 4.64 (d, J = 6.0 Hz, 2H), 4.36-4.26 (m, 2H), 3.99 (s, 2H), 3.83-3.67 (m, 2H), 1.20 (d, J = 7.8 Hz, 6H), 1.05 (t, J = 6.6 Hz, 2H). |

Compounds in the table below were prepared following procedures analogous to those described for Ex-58.

| Example | Structure | Physical Data MS (m/z), $^1$H NMR |
|---|---|---|
| 197 | 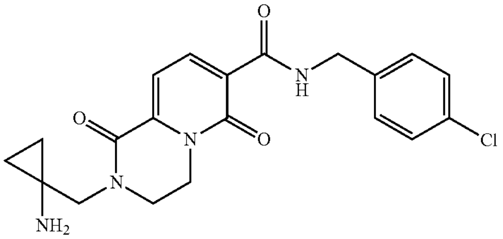 [SMILES: NC1(CN2CCn3c(ccc(C(=O)NCc4ccc(Cl)cc4)c3=O)C2=O)CC1] | LCMS (m/z): 401.8 [M + H]. $^1$H NMR (400 MHz, $CD_3CN$) δ 10.19 (s, 1H), 8.51 (d, J = 7.5 Hz, 1H), 8.09 (s, 1H), 7.37 (s, 4H), 7.25 (d, J = 7.5 Hz, 1H), 4.59 (d, J = 6.0 Hz, 2H), 4.41-4.25 (m, 2H), 3.86-3.73 (m, 2H), 3.60 (d, J = 20.5 Hz, 2H), 0.65 (d, J = 7.8 Hz, 4H). |
| 198 | 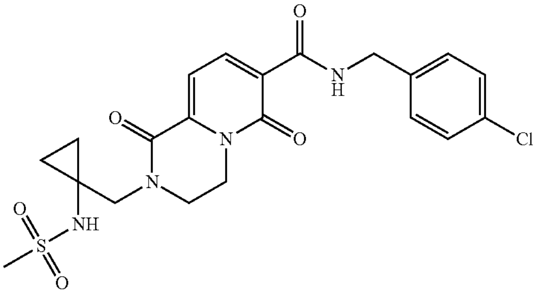 [SMILES: CS(=O)(=O)NC1(CN2CCn3c(ccc(C(=O)NCc4ccc(Cl)cc4)c3=O)C2=O)CC1] | LCMS (m/z): 478.9 [M + H]. $^1$H NMR (400 MHz, $CDCl_3$) δ 10.16 (s, 1H), 8.53 (d, J = 7.3 Hz, 1H), 7.31 (s, 4H), 5.84 (s, 1H), 4.63 (d, J = 5.7 Hz, 2H), 4.34 (s, 2H), 3.95 (s, 2H), 3.73 (s, 2H), 2.99 (s, 3H), 2.03 (s, 2H), 1.86 (s, 2H), 1.07 (d, J = 15.3 Hz, 4H). |
| 199 | 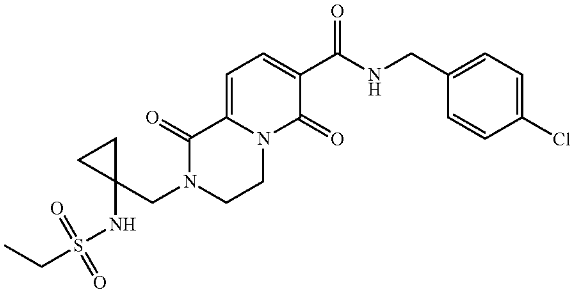 [SMILES: CCS(=O)(=O)NC1(CN2CCn3c(ccc(C(=O)NCc4ccc(Cl)cc4)c3=O)C2=O)CC1] | LCMS (m/z): 492.9 [M + H]. $^1$H NMR (400 MHz, $CDCl_3$) δ 10.16 (d, J = 5.5 Hz, 1H), 8.56 (d, J = 6.7 Hz, 1H), 7.32 (d, J = 10.8 Hz, 4H), 5.50 (s, 1H), 4.63 (d, J = 5.9 Hz, 2H), 4.44-4.25 (m, 2H), 4.03-3.87 (m, 2H), 3.73 (s, 2H), 3.03 (q, J = 7.3 Hz, 2H), 1.32-1.25 (m, 3H), 1.11-1.02 (m, 2H), 1.00 (t, J = 6.1 Hz, 2H). |

-continued

| Example | Structure | Physical Data MS (m/z), $^1$H NMR |
|---|---|---|
| 200 | 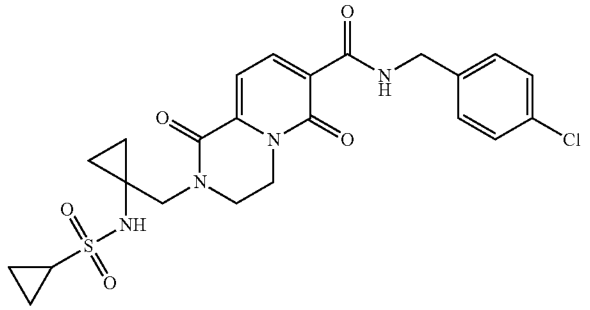 [SMILES: O=C(NCc1ccc(Cl)cc1)c1ccc2n(c1=O)CCN(CC1(NS(=O)(=O)C3CC3)CC1)C2=O] | LCMS (m/z): 504.9 [M + H]. |

Example 201

N-(4-chlorobenzyl)-1,6-dioxo-2-((1-(2-oxopyrrolidin-1-yl)cyclopropyl)methyl)-1,3,4,6-tetrahydro-2H-pyrido[1,2-a]pyrazine-7-carboxamide ethyl 4-((1-((7-((4-chlorobenzyl) carbamoyl)-1,6-dioxo-1,3,4,6-tetrahydro-2H-pyrido[1,2-a] pyrazin-2-yl)methyl) cyclopropyl) amino) butanoate (Ex-201A). Ex-197 (0.1 g, 0.25 mmol, 1.0 equiv) was dissolved in DMF (2 mL) in a sealed tube. $K_2CO_3$ (0.041 g, 0.3 mmol, 1.2 equiv) and ethyl 4-bromobutanoate (0.058 g, 0.3 mmol, 1.2 equiv) were added, the tube was sealed, and the reaction mixture was stirred at 90° C. for 18 h. The reaction mixture was quenched with water and extracted with EtOAc. The organic layer was washed with brine, dried over sodium sulfate and concentrated to afford the desired product. LCMS (m/z): 515.2 [M+H].

4-((1-((7-((4-chlorobenzyl) carbamoyl)-1,6-dioxo-1,3,4,6-tetrahydro-2H-pyrido[1,2-a] pyrazin-2-yl)methyl)cyclopropyl) amino) butanoic acid (Ex-201B). Ex-2011A (0.08 g, 0.15 mmol, 1.0 equiv) was dissolved in THF (4 mL) and water (1 mL). LiOH·$H_2O$ (0.019 g, 0.46 mmol, 3.0 equiv) was added and the reaction mixture was stirred at RT for 6 h. The reaction mixture was concentrated, diluted with water, acidified by 1.0 N HCl aqueous solution to pH 2-3, and extracted with 5% MeOH/dichloromethane. The organic layer was washed with brine, dried over sodium sulfate, and concentrated to afford the title compound. LCMS (m/z): 487.9 [M+H].

N-(4-chlorobenzyl)-1,6-dioxo-2-((1-(2-oxopyrrolidin-1-yl)cyclopropyl)methyl)-1,3,4,6-tetrahydro-2H-pyrido[1,2-a]pyrazine-7-carboxamide (Ex-201). Ex-201B (0.12 g, 0.25 mmol, 1.0 equiv) was dissolved in THF (7 mL), and DIPEA (0.047 g, 0.37 mmol, 1.5 equiv), EDC·HCl (0.071 g, 0.37 mmol, 1.5 equiv), and HOBt (0.033 g, 0.25 mmol, 1.0 equiv) were added. The reaction mixture was stirred at RT for 18 h. The reaction mixture was quenched with water and extracted with EtOAc. The organic layer was washed with brine, dried over sodium sulfate, and concentrated. The crude residue was purified by preparative HPLC to afford the title compound.

| Example | Structure | Physical Data MS (m/z), $^1$H NMR |
|---|---|---|
| 201 | 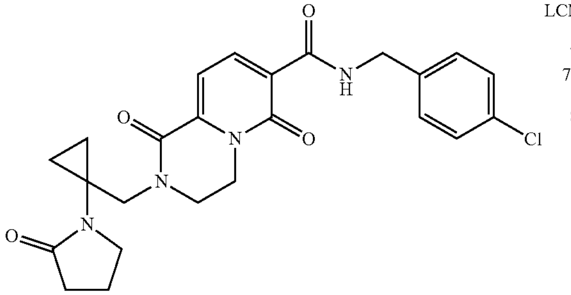 | LCMS (m/z): 468.9 [M + H]. $^1$H NMR (400 MHz, DMSO-d6) δ 10.11 (s, IH), 8.43 (d, J = 7.5 Hz, 1H), 7.41-7.33 (m, 4H), 7.18 (d, J = 7.7 Hz, 1H), 4.54 (d, J = 5.7 Hz, 2H), 4.24 (s, 2H), 3.88 (s, 2H), 3.61 (s, 2H), 2.02 (d, J = 8.1 Hz, 2H), 1.82 (s, 2H), 1.28 (s, 2H), 0.88 (d, J = 6.7 Hz, 4H). |

-continued

| Example | Structure | Physical Data MS (m/z), $^1$H NMR |
|---|---|---|
| 202 | 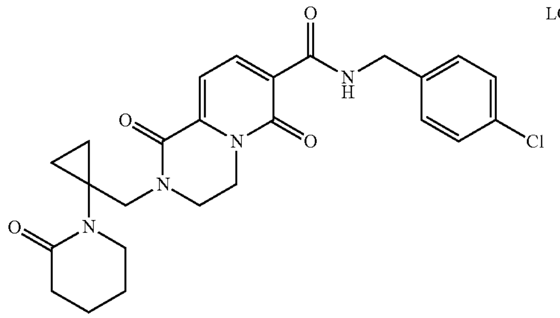 | LCMS (m/z): 483.4 [M + H]. $^1$H NMR (400 MHz, DMSO-d6) δ 10.12 (t, J = 6.1 Hz, 1H), 8.44 (d, J = 7.5 Hz, 1H), 7.34 (dt, J = 51.4, 25.7 Hz, 4H), 7.17 (d, J = 7.5 Hz, 1H), 4.54 (d, J = 6.0 Hz, 2H), 4.25 (s, 4H), 4.03-3.57 (m, 4H), 3.30 (s, 4H), 2.03 (s, 2H), 1.66 (s, 2H), 1.57 (d, J = 5.9 Hz, 2H). |
| 203 | 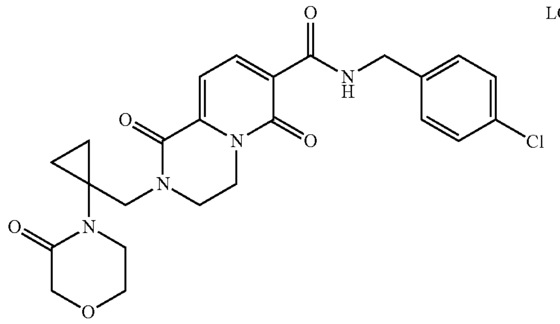 | LCMS (m/z): 485.2 [M + H]. $^1$H NMR (400 MHz, $CD_3OD$) δ 10.46 (s, 6H), 8.54 (d, J = 7.6 Hz, 8H), 7.36 (s, 27H), 7.31 (d, J = 7.6 Hz, 7H), 4.66-4.60 (m, 14H), 3.94 (s, 12H), 3.87 (t, J = 4.9 Hz, 14H), 3.71-3.68 (m, 6H), 3.57 (dd, J = 12.1, 7.7 Hz, 19H), 3.37 (s, 23H), 0.97 (dd, J = 43.4, 11.9 Hz, 25H). |

Example 204

N-(4-chlorobenzyl)-2-((1-(methyl amino)cyclopropyl)methyl)-1,6-dioxo-1,3,4,6-tetrahydro-2H-pyrido [1,2-a] pyrazine-7-carboxamide N-(4-chlorobenzyl)-2-((1-(methyl amino)cyclopropyl) methyl)-1,6-dioxo-1,3,4,6-tetrahydro-2H-pyrido[1,2-a] pyrazine-7-carboxamide (Ex-204). Ex-197 (0.1 g, 0.25 mmol, 1.0 equiv) was dissolved in HFIP (0.1 mL). TEA (0.037 g, 0.4 mmol, 1.5 equiv) and MeOTf (0.061 g, 0.4 mmol, 1.5 equiv) were added, and the reaction mixture was stirred at RT for 24 h. The reaction mixture was concentrated, and the crude residue was purified by preparative HPLC to afford the title compound.

| Example | Structure | Physical Data MS (m/z), $^1$H NMR |
|---|---|---|
| 204 | 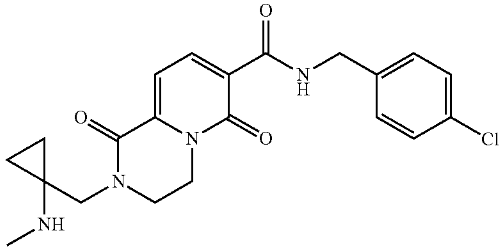 | LCMS (m/z): 415.4 [M + H]. $^1$H NMR (400 MHz, DMSO-d6) δ 10.14 (s, 1H), 8.45 (d, J = 7.6 Hz, 1H), 7.38 (dd, J = 24.5, 8.5 Hz, 4H), 7.22 (d, J = 7.6 Hz, 1H), 4.54 (d, J = 6.1 Hz, 2H), 4.33-4.24 (m, 2H), 3.83-3.75 (m, 2H), 3.55 (s, 2H), 2.28 (d, J = 7.9 Hz, 3H), 0.54 (d, J = 15.6 Hz, 4H). |

Compounds in the table below were prepared from Ex-204 following procedures analogous to those described for Ex-62.

| Example | Structure | Physical Data MS (m/z), ¹H NMR |
|---|---|---|
| 205 | 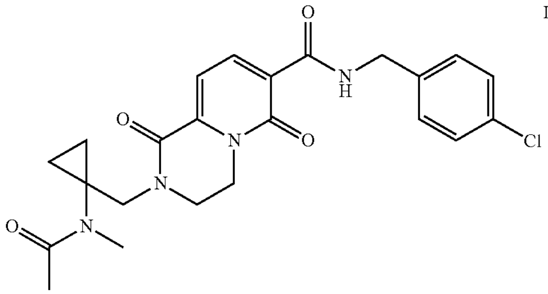 | LCMS (m/z): 457.7 [M + H]. ¹H NMR (400 MHz, DMSO-d6) δ 10.12 (d, J = 5.9 Hz, 1H), 8.44 (dd, J = 7.5, 2.5 Hz, 1H), 7.37 (dd, J = 24.2, 8.5 Hz, 4H), 7.19 (dd, J = 7.5, 4.7 Hz, 1H), 4.54 (d, J = 6.0 Hz, 2H), 4.32-4.16 (m, 2H), 3.78 (s, 2H), 3.35 (d, J = 14.1 Hz, 2H), 2.85 (d, J = 69.2 Hz, 3H), 2.08 (s, 2H), 1.81 (s, 1H), 1.22-0.80 (m, 4H). |
| 206 | 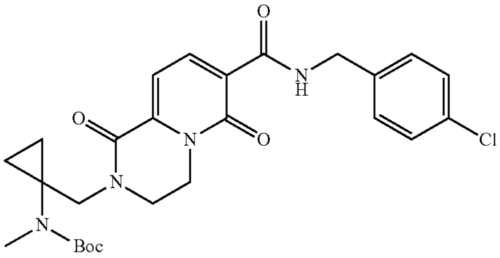 [SMILES: CN(C(=O)OC(C)(C)C)C1(CN2CCn3c(ccc(C(=O)NCc4ccc(Cl)cc4)c3=O)C2=O)CC1] | LCMS (m/z): 515.5 [M + H]. ¹H NMR (400 MHz, DMSO-d6) δ 10.11 (t, J = 6.1 Hz, 1H), 8.43 (t, J = 8.2 Hz, 1H), 7.38 (dd, J = 23.1, 8.5 Hz, 4H), 7.20 (dd, J = 7.5, 4.9 Hz, 1H), 4.53 (d, J = 6.0 Hz, 2H), 4.28 (s, 2H), 3.81 (s, 2H), 3.77-3.40 (m, 2H), 2.77 (d, J = 20.2 Hz, 3H), 1.31-1.22 (m, 9H), 0.86 (m, 4H). |

Example 207 ethyl 1-((7-((4-chlorobenzyl) carbamoyl)-1,6-dioxo-1,3,4,6-tetrahydro-2H-pyrido[1,2-a] pyrazin-2-yl) methyl)cyclopropane-1-carboxylate ethyl 1-((5-((4-chlorobenzyl) carbamoyl)-1-(2-hydroxy-ethyl)-6-oxo-1,6-dihydropyridine-2-carboxamido)methyl) cyclopropane-1-carboxylate (Ex-207A). 1-17 (1.23 g, 3.7 mmol, 1.0 equiv), 1-55 (1.13 g, 7.9 mmol, 2.1 equiv) were added in acetonitrile (2.3 mL) and the reaction mixture was stirred at 140° C. for 75 minutes under microwave irradiation. The reaction mixture was quenched with water and extracted with EtOAc. The organic layer was washed with brine, dried over sodium sulfate and concentrated to afford the desired product. LCMS (m/z): 476.9 [M+H]. ¹H NMR (400 MHz, DMSO-d6) δ 10.09 (t, J=6.0 Hz, 1H), 9.02 (s, 1H), 8.37 (d, J=7.4 Hz, 1H), 7.45-7.32 (m, 4H), 6.53 (d, J=7.4 Hz, 1H), 4.52 (d, J=6.0 Hz, 2H), 4.22-4.13 (m, 2H), 3.65-3.59 (m, 2H), 3.51 (d, J=5.0 Hz, 2H), 1.19-1.12 (m, 7H).

ethyl 1-((5-((4-chlorobenzyl) carbamoyl)-1-(2-chloro-ethyl)-6-oxo-1,6-dihydropyridine-2-carboxamido)methyl) cyclopropane-1-carboxylate (Ex-207B) was prepared from Ex-207A following a procedure analogous to that described for Ex-122B. LCMS (m/z): 495.2 [M+H]. ¹H NMR (400 MHz, DMSO-d6) δ 9.97 (t, J=6.0 Hz, 1H), 9.18 (t, J=5.5 Hz, 1H), 8.41 (d, J=7.4 Hz, 1H), 7.39 (t, J=10.8 Hz, 4H), 6.61 (d, J=7.4 Hz, 1H), 4.52 (d, J=6.0 Hz, 2H), 4.37 (t, J=6.9 Hz, 2H), 3.51 (d, J=5.5 Hz, 2H), 3.18 (d, J=5.5 Hz, 2H), 1.21-1.18 (m, 7H).

ethyl 1-((7-((4-chlorobenzyl) carbamoyl)-1,6-dioxo-1,3,4,6-tetrahydro-2H-pyrido[1,2-a] pyrazin-2-yl)methyl)cyclopropane-1-carboxylate (Ex-207) was prepared from Ex-207B following a procedure analogous to that described for Ex-117C.

| Example | Structure | Physical Data MS (m/z), ¹H NMR |
|---|---|---|
| 207 | 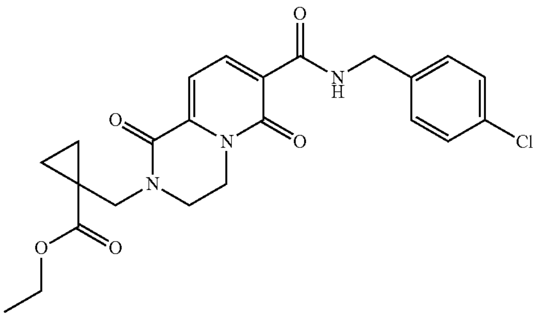 [SMILES: CCOC(=O)C1(CN2CCn3c(ccc(C(=O)NCc4ccc(Cl)cc4)c3=O)C2=O)CC1] | LCMS (m/z): 458.9 [M + H]. ¹H NMR (400 MHz, DMSO-d6) δ 10.12 (t, J = 6.0 Hz, 1H), 8.44 (d, J = 1.6 Hz, 1H), 7.37 (dd, J = 23.8, 8.5 Hz, 4H), 7.20 (d, J = 7.6 Hz, 1H), 4.54 (d, J = 6.0 Hz, 2H), 4.31-4.12 (m, 2H), 4.06 (q, J = 7.1 Hz, 2H), 3.91-3.78 (m, 2H), 3.75 (s, 2H), 1.40-1.11 (m, 7H). |

Example 208

2-((1-(azetidine-1-carbonyl)cyclopropyl)methyl)-N-(4-chlorobenzyl)-1,6-dioxo-1,3,4,6-tetrahydro-2H-pyrido[1,2-a]pyrazine-7-carboxamide 1-((7-((4-chlorobenzyl) carbamoyl)-1,6-dioxo-1,3,4,6-tetrahydro-2H-pyrido[1,2-a] pyrazin-2-yl)methyl)cyclopropane-1-carboxylic acid (Ex-208A) was prepared from Ex-207 following a procedure analogous to that described for Ex-201B. LCMS (m/z): 430.7 [M+H]. $^1$H NMR (400 MHz, DMSO-d6) δ 12.49-12.23 (m, 2H), 10.13 (t, J=6.0 Hz, 1H), 8.43 (d, J=7.6 Hz, 1H), 7.37 (dd, J=24.2, 8.5 Hz, 4H), 7.19 (d, J=7.6 Hz, 1H), 4.54 (d, J=5.9 Hz, 2H), 4.26-4.18 (m, 2H), 3.88-3.80 (m, 2H), 3.73 (s, 2H), 1.16 (d, J=3.0 Hz, 2H), 1.08-1.04 (m, 2H).

2-((1-(azetidine-1-carbonyl)cyclopropyl)methyl)-N-(4-chlorobenzyl)-1,6-dioxo-1,3,4,6-tetrahydro-2H-pyrido[1,2-a]pyrazine-7-carboxamide (Ex-208). Ex-208A (0.2 g, 0.47 mmol, 1.0 equiv) was dissolved in DMF (6 mL). TEA (0.19 g, 1.86 mmol, 4.0 equiv), EDC·HCl (0.11 g, 0.56 mmol, 1.2 equiv), HOBT (0.075 g, 0.56 mmol, 1.2 equiv), and azetidine hydrochloride (0.052 g, 0.56 mmol, 1.2 equiv) were added, and the reaction mixture was stirred at RT for 24 h. The reaction mixture was quenched with water and extracted with EtOAc. The organic layer was washed with brine, dried over sodium sulfate, and concentrated. The crude residue was purified by preparative HPLC to afford the title compound.

Other compounds in the table below were prepared from Ex-208A following procedures analogous to those described for Ex-208.

| Example | Structure | Physical Data MS (m/z), $^1$H NMR |
|---|---|---|
| 208 | 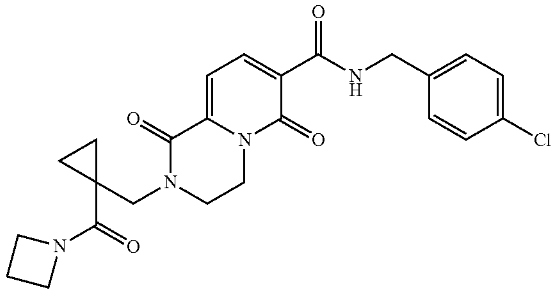 [SMILES: O=C(NCc1ccc(Cl)cc1)c1ccc2n(c1=O)CCN(CC1(C(=O)N3CCC3)CC1)C2=O] | LCMS (m/z): 469.9 [M + H]. $^1$H NMR (400 MHz, DMSO-d6) δ 8.44 (d, J = 7.5 Hz, 1H), 7.37 (dd, J = 23.3, 8.5 Hz, 4H), 7.21 (d, J = 7.5 Hz, 1H), 4.54 (d, J = 6.0 Hz, 2H), 4.30 (s, 2H), 4.24-4.14 (m, 2H), 3.83-3.71 (m, 3H), 3.74 (s, 4H), 3.66 (s, 2H), 2.26-2.11 (m, 2H), 0.87 (d, J = 4.0 Hz, 2H), 0.78 (d, J = 4.0 Hz, 2H). |
| 209 | 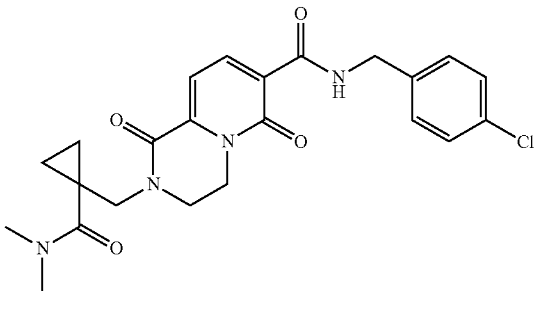 [SMILES: CN(C)C(=O)C1(CN2CCn3c(ccc(C(=O)NCc4ccc(Cl)cc4)c3=O)C2=O)CC1] | LCMS (m/z): 458.0 [M + H]. $^1$H NMR (400 MHz, DMSO-d6) δ 8.43 (d, J = 7.5 Hz, 1H), 7.51-7.28 (m, 4H), 7.19 (t, J = 10.9 Hz, 1H), 4.54 (d, J = 6.0 Hz, 2H), 4.27-4.15 (m, 2H), 3.82-3.72 (m, 2H), 3.69 (s, 2H), 3.17 (s, 3H), 2.89-2.64 (m, 3H), 0.86 (s, 4H). |
| 210 | 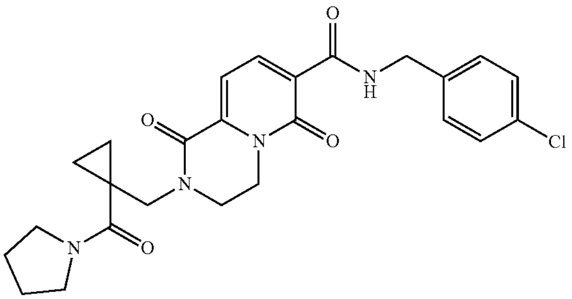 [SMILES: O=C(NCc1ccc(Cl)cc1)c1ccc2n(c1=O)CCN(CC1(C(=O)N3CCCC3)CC1)C2=O] | LCMS (m/z): 483.5 [M + H]. $^1$H NMR (400 MHz, DMSO-d6) δ 10.11 (t, J = 6.0 Hz, 1H), 8.43 (d, J = 7.5 Hz, 1H), 7.37 (dd, J = 23.3, 8.4 Hz, 4H), 7.17 (d, J = 7.6 Hz, 1H), 4.54 (d, J = 6.0 Hz, 2H), 4.21 (s, 2H), 3.76 (s, 2H), 3.68 (d, J = 17.4 Hz, 4H), 3.16 (s, 2H), 1.81 (d, J = 43.6 Hz, 4H), 0.90-0.78 (m, 4H). |

-continued

| Example | Structure | Physical Data MS (m/z), $^1$H NMR |
|---|---|---|
| 211 | 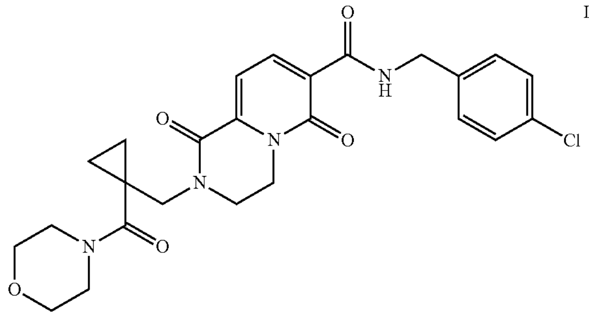 | LCMS (m/z): 500.0 [M + H]. $^1$H NMR (400 MHz, $CD_3CN$) δ 8.49 (d, J = 7.5 Hz, 1H), 7.41-7.32 (m, 4H), 7.20 (t, J = 6.9 Hz, 1H), 4.58 (d, J = 6.0 Hz, 2H), 4.26-4.22 (m, 2H), 3.79 (dd, J = 6.7, 5.1 Hz, 2H), 3.73-3.34 (m, 10H), 0.99-0.93 (m, 2H), 0.89-0.83 (m, 2H). |

Example 212

N-(4-cyano-3-(methyl amino)benzyl)-2-((1-(cyclopropyl sulfonyl)cyclopropyl)methyl)-1,6-dioxo-1,3,4,6-tetrahydro-2H-pyrido[1,2-a]pyrazine-7-carboxamide N-(4-cyano-3-(methyl amino)benzyl)-2-((1-(cyclopropyl sulfonyl)cyclopropyl)methyl)-1,6-dioxo-1,3,4,6-tetrahydro-2H-pyrido[1,2-a]pyrazine-7-carboxamide (Ex-212). Methyl amine (2.0 M in THF) (0.8 mL) was added to a solution of Ex-3-1 (0.2 g, 0.4 mmol, 1.0 equiv) in DMSO (1 mL). The reaction mixture was stirred at 100° C. for 2 h, after which it was diluted with water. The precipitated solid was collected by filtration and was washed with cold water and hexane. The solid product was triturated with diethyl ether, filtered, and dried to afford Ex-212.

| Example No. | Structure | Physical Data MS (m/z), $^1$H NMR |
|---|---|---|
| 212 | 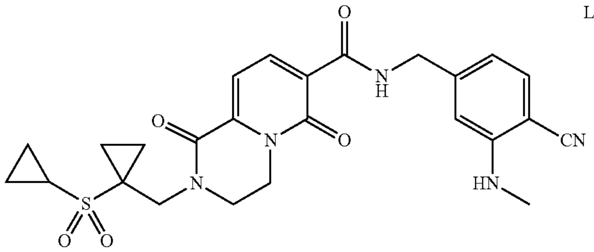 | LCMS (m/z): 510.4 [M + H]. $^1$H NMR (400 MHz, DMSO) δ 10.09 (s, 1H), 8.45 (d, J = 7.5 Hz, 1H), 7.42 (d, J = 8.0 Hz, 1H), 7.22 (d, J = 7.6 Hz, 1H), 6.66 (s, 1H), 6.58 (d, J = 7.5 Hz, 1H), 6.23 (d, J = 4.9 Hz, 1H), 4.52 (d, J = 5.8 Hz, 2H), 4.25 (d, J = 5.6 Hz, 2H), 4.09 (s, 2H), 3.81 (s, 2H), 2.95 (s, 1H), 2.76 (d, J = 4.8 Hz, 3H), 1.31 (s, 2H), 1.19 (d, J = 6.6 Hz, 2H), 1.08-1.00 (m, 4H). |

Bioactivity of the compounds of the invention was determined using the following methods.

CMV and HSV Polymerase Protein Production

Both human CMV DNA polymerase UL54 and human HSV DNA polymerase UL30 were produced as N-terminal MBP fusion of the full length, wild type recombinant proteins in order to enhance soluble expression in insect cell expression system. The proteins were expressed in sf9 insect cells via baculovirus transduction and cells were harvested after 48 hours. The soluble proteins were purified using the standard Ni-IMAC purification strategy via the N-terminal hexa-Histidine tag, followed by heparin affinity chromatography. Both of the final MBP fusion proteins were more than 90% pure and the yield of UL54 was up to 1.8 mg per liter culture while UL30 was up to 15 mg per liter culture. All purification steps were performed on ice, with buffers chilled on ice and FPLC fraction collectors set at 6° C. The final UL54 protein was concentrated and stored in buffer containing 35 mM Tris pH7.5, 375 mM NaCl, 42.5% Glycerol, and 1 mM TCEP at −20° C. UL30 protein was stored in buffer containing 20 mM HEPES, pH7.0, 420 mM NaCl, 20% glycerol, 6 mM Imidazole, and 0.8 mM DTT at−80° C.

CMV and HSV Polymerase Biochemical Assay

DNA polymerase activity was measured using a molecular beacon-based assay, as described in Ma et. al.

100 pM CMV polymerase or 625 pM HSV polymerase was added to a buffer containing 20 mM Tris, pH=7.5, 100 mM NaCl, 10 mM $MgCl_2$, 0.01% Tween-20, 0.5 mM EDTA, 10% Sucrose and 1 mM DTT. The inhibitor was pre-incubated with the polymerase for 30 minutes at room temperature. Reactions were initiated by the addition of a mixture containing 1.25 uM dATP, 1.25 uM dCTP, 1.25 uM dTTP, 1.25 uM dGTP, 200 nM Primer B (5'-GAC GGG AAG-3'5'-GAC GGG AAG-3') and 100 nM molecular beacon (5'-5,6-FAM-CCT CTC CGT GTC TTG TAC TTC CCG TCA GAG AGG-BHQ1-3'). For human CMV polymerase the reactions were incubated for 60 minutes at room temperature. For HSV polymerase the reactions were incubated for 20 minutes at room temperature. The reactions were then read on a Perkin-Elmer EnVision 2101 reader (fluorescence) using an excitation of 480 nm and emission of 535 nm. 1050s were determined using an internal Novartis software (Helios).

REFERENCES

Ma et. al. (2006). Real-time monitoring of DNA polymerase activity using molecular beacon. *Analytical Biochemistry,* 353 (1): 141-143

CMV Polymerase and HSV Polymerase Assay Protocols 100 pM CMV polymerase or 625 pM HSV polymerase was added to a buffer containing 20 mM Tris, pH=7.5, 100 mM NaCl, 10 mM $MgCl_2$, 0.01% Tween-20, 0.5 mM EDTA, 10% Sucrose and 1 mM DTT. The inhibitor was pre-incubated with the polymerase for 30 minutes at room temperature. Reactions were initiated by the addition of a mixture containing 1.25 uM dATP, 1.25 uM dCTP, 1.25 uM dTTP, 1.25 uM dGTP, 200 nM Primer B (5'-GAC GGG AAG-3'5'-GAC GGG AAG-3') and 100 nM molecular beacon (5'-5,6-FAM-CCT CTC CGT GTC TTG TAC TTC CCG TCA GAG AGG-BHQ1-3'). For human CMV polymerase the reactions were incubated for 60 minutes at room temperature. For HSV polymerase the reactions were incubated for 20 minutes at room temperature. The reactions were then read on a Perkin-Elmer EnVision 2101 reader (fluorescence) using an excitation of 480 nm and emission of 535 nm.

Cellular Herpesvirus Replication Assays

Compound Dilutions:

For all viral assays, 10 mM DMSO stock compound solutions were serially diluted in DMSO at 3.16 fold dilutions in 96-well clear round bottom plates. Compounds were then diluted in assay media at 1:20 and subsequently 10 μL of these dilutions were added to cells for final compound concentrations ranging either from 0.0159 μM to 50 μM in 0.5% DMSO/assay media, or from 0.00318 to 10 μM in 0.5% DMSO/assay media.

CMV Luciferase assay:

The assay uses a Luciferase-encoding HCMV. Luciferase is expressed under the control of a late viral gene (pp28) promoter in the AD169 strain, so that expression of the reporter is dependent on viral DNA replication. Compounds that affect any stage from viral entry to DNA replication result in a change in luciferase levels.

Viral replication in the presence or absence of compounds was measured by luciferase activity according to the following procedure: Neo-natal normal human dermal fibroblast cells (NN-NHDF, from ATCC cat #201-010) were seeded at 9,000 cells/well in 96-well white solid bottom plate at 80 uL/well in assay media: 2% FBS, 4 mM GlutaMax® (Invitrogen cat #35050) in DMEM/high glucose/no glutamine/no phenol red media (Invitrogen cat #31053). After 2 hrs at 37° C., 10 uL of compound diluted in assay media or 5% DMSO (final 0.5% DMSO/well) was added and the plates returned to 37° C. One hour later, 10 uL of virus diluted in assay media was added at a final Multiplicity of infection (MOI) of 1. Plates were incubated at 37° C. for 72 hrs. At 72 hours post-infection (hpi), plates were equilibrated to room temperature. After 25 min, 100 uL Renilla-Glo® Luciferase Assay Reagent (Promega cat # E2750) was added to each well and incubated for 10 min. Plates were covered to protect from light. Luminescence was measured on the PHERAstar FS®.

The following controls were included in the data analysis: No virus, no compound (0.5% DMSO)=IC (maximal inhibitory control); Virus, no compound (0.5% DMSO)=NC (neutral control). Data were analyzed using an internal Novartis software (Helios). The means of the controls (NC, IC) were used to normalize the results to a % scale using the formula:

$$\% \text{ Control}=100-(100*(\text{Sample value}-\text{NC})/(\text{IC}-\text{NC})).$$

For each compound, the software derived an EC50 using a 4-parameter logistical model.

HSV-1 qPCR assay: The assay uses KOS strain of HSV-1 virus (ATCC cat #VR-1493). Viral replication in the presence or absence of compounds was measured by qPCR according to the following procedure: NN-NHDF cells were plated at 9,000 cells/well in 96-well white-wall clear bottom plates in 80 μL/well of assay media (same as CMV) and left at room temperature in laminar flow hood for 20 mins followed by incubation at 37° C. One hr later, 10 μL of diluted compound, or 10 μL of 5% DMSO as a control were added to each well (0.5% DMSO final). One hr later, virus was added at a final MOI of 0.01, in 10 uL/well assay media. Cells were then incubated at 37° C. After 24 hrs, medium was removed, cells were washed once with 100 μL DPBS (Invitrogen, cat #21-031-CV), and lysed using the prepGEM® tissue kit (ZyGEM, cat # PTI0500K), by addition of 100 μL of prepGEM® master mix (89 μL $H_2O$, 10 μL 10× prepGEM® Buffer, 1 μL prepGEM® enzyme per well) to each well. Plates were sealed with aluminum foil sealers, and lysed on a heat block at 75° C. for 15 min. Plates were then allowed to cool to room temperature with light shaking before proceeding to the qPCR setup.

VZV qPCR assay: The assay uses co-infection with VZV Ellen strain-infected MRC-5 cells (ATCC cat #VR-1367). Viral replication in the presence or absence of compounds was measured by qPCR according to the following procedure: 12,000 uninfected MRC-5 cells were mixed with VZV-infected MRC-5 cells at a ratio of 1 to 10 infected to uninfected cells, in 96-well white-wall clear bottom plates in 90 μL/well of assay media: 4% FBS in EMEM (ATCC cat #30-2003). After 1 hr at 37° C., 10 μL of diluted compound, or 10 μL of 5% DMSO as a control were added to each well (0.5% DMSO final). Cells were then incubated at 37° C. The chosen ratio of infected to uninfected cells gave approximately 3% VZV-positive cells at 6 hours post co-culturing, as detected by immunofluorescent staining of VZV Immediate Early 62 gene. After two days, medium was removed, cells were washed once with 100 μL DPBS and lysed using the prepGEM tissue kit as described above.

EBV qPCR assay: The assay uses the SNU-719 gastric carcinoma cell line which is latently infected with EBV. Upon reactivation with chemical reagents, EBV DNA copy number was measured by qPCR. Viral replication in the presence or absence of compounds was measured according to the following procedure: SNU-719 cells were plated at 2×104 cells/well in 96-well clear bottom plates, black in 80 μL/well of assay media: 2% FBS in RPMI 1640 (ATCC cat # 30-2001). After 1 hr at 37° C., 10 μL of diluted compound, or 10 μL of 5% DMSO as a control, were added to each well (0.5% DMSO final). Lytic replication of the virus was then activated by addition of 10 μL of a mixture of 20 ng/ml tetradecanoyl phorbol acetate (TPA) and 3 mM sodium butyrate (NaB). At 18 hpi, media was removed, fresh assay media with compound or DMSO was added, and cells were returned to 37° C. After 72 hrs of lytic replication, media was removed, cells were washed with 100 μL DPBS and lysed using the prepGEM tissue kit as before.

qPCR Procedure and Data Analysis for HSV, VZV and EBV:

qPCR reactions were carried out in a total reaction volume of 20 μL, using the QuantiFast® Multiplex PCR kit (Qiagen cat #204656). Eighteen μL of qPCR master mix (10 μL of 2× QuantiFast® Multiplex PCR Master Mix, 1 μL of 20× Primer/Probe Mix specific to housekeeping gene, 1 μL of 20× Primer/Probe Mix specific to viral gene, 6 μL of $H_2O$) was distributed into each well of a 384 well plate. Two μL of cell lysate was added to each well. Each cell lysate was run in duplicate. Plates were sealed with a clear sealer, spun down, and qPCR reactions were performed in an ABI 7900HT instrument using the following conditions: 95° C. for 5 min, then 40 cycles: 95° C. for 30 sec, 60° C. for 30 sec.

Relative quantification was calculated with the ΔΔCT Method, and then converted into percent inhibitions. Virus+DMSO samples (without drug) were used to determine the calibrator. EC50 values were calculated using XLFit Dose Response One Site Model 205.

qPCR Primers and Probes

| Primer/probe specificity | Sequence (5'-3') |
|---|---|
| HSV-1 qPCR: | |
| HSV-1 gpJ gene, forward primer | TAGTCGGTGGGCTGTGT |
| HSV-1 gpJ gene, reverse primer | AACTGGGTCCATGTAGGAT |
| HSV-1 gpJ gene, probe | TGCTTGAGCTCCTGCGTCGTAC |
| VZV qPCR: | |
| VZV IE62 gene, forward primer | CCTCCGTATCGGGACTTCAA |
| VZV IE62 gene, reverse primer | TGACCGTCCTCGCATACGTA |
| VZV IE62 gene, probe | TTGGCGAAGAGCTAAC |
| Housekeeping gene for HSV and VZV assays: | |
| Forward MT-ATP6 primer | ACACCCCTTATCCCCATACTAG |
| Reverse MT-ATP6 primer | ATGGTTGATATTGCTAGGGTGG |
| MT-ATP6 probe | ACCGCTAACATTACTGCAGGCCA |
| EBV qPCR: | |
| EBV BNRF1 forward primer | CGGCCGTGATGGAGGCTATG |
| EBV BNRF1 reverse primer | AGACAGAGGCCACCACGG |
| EBV BNRF1 probe | TGACCTTTGGCTCGGCCTCCTGC |
| Housekeeping gene for EBV assay: | |
| HuALB forward primer | GCTGTCATCTCTTGTGGGCTGT |
| HuALB reverse primer | AAACTCATGGGAGCTGCTGGTT |
| HuALB probe | CCTGTCATGCCCACACAAATCTCTCC |

Table of Bioactivity Data

| Example # | CMV-polymerase Biochemical IC50 (uM) | CMV-Luc Cellular EC50 (uM) | HSV-polymerase Biochemical IC50 (uM) |
|---|---|---|---|
| 1 | 0.0008 | 0.0232 | 0.0273 |
| 2 | 0.0002 | 0.0081 | 0.0155 |
| 3-1 | 0.0008 | 0.0177 | 0.0381 |
| 3-2 | 0.0030 | 0.0848 | 0.0787 |
| 3-3 | 0.0079 | 0.0640 | 0.1494 |
| 3-4 | 0.0051 | 0.2226 | 0.1599 |
| 3-5 | 0.0020 | 0.2111 | 0.1167 |
| 4 | 0.0004 | 0.0404 | |
| 5 | 0.0022 | 0.4695 | 0.1053 |
| 6 | 0.0024 | 0.0928 | 0.0548 |
| 7 | 0.0010 | 0.0328 | 0.0356 |
| 8 | 0.0046 | 0.7838 | 0.1111 |
| 9 | 0.0017 | 0.1672 | 0.0738 |
| 10 | 0.0003 | 0.0049 | 0.0188 |
| 11 | 0.0004 | 0.0267 | 0.0243 |
| 12 | 0.0004 | 0.0197 | 0.0235 |
| 13 | 0.0004 | 0.0193 | 0.0283 |
| 14 | 0.0003 | 0.0100 | 0.0279 |
| 15 | 0.0007 | 0.0302 | 0.0260 |
| 16 | 0.0061 | 3.4201 | 0.2848 |
| 17 | 0.0147 | 0.9053 | 0.3798 |
| 18 | 0.0042 | 2.9997 | 0.1614 |
| 19 | 0.0039 | 0.5381 | 0.1489 |
| 20 | 0.0132 | 1.5026 | 0.3188 |

-continued

Table of Bioactivity Data

| Example # | CMV-polymerase Biochemical IC50 (uM) | CMV-Luc Cellular EC50 (uM) | HSV-polymerase Biochemical IC50 (uM) |
|---|---|---|---|
| 21 | 0.0008 | 0.0580 | 0.0354 |
| 22 | 0.0019 | 0.0888 | 0.0563 |
| 23 | 0.0032 | 0.4522 | 0.1244 |
| 24 | 0.0047 | 0.8321 | 0.1684 |
| 25 | 0.0028 | 0.0889 | 0.0808 |
| 26 | 0.0006 | 0.0089 | 0.0455 |
| 27 | 0.0003 | 0.0068 | 0.0252 |
| 28 | 0.0027 | 0.1159 | 0.0687 |
| 29 | 0.0018 | 0.0864 | 0.0635 |
| 30 | 0.0015 | 0.0363 | 0.0380 |
| 31 | 0.0009 | 0.0124 | 0.0306 |
| 32 | 0.0016 | 0.0520 | 0.0495 |
| 33 | 0.0010 | 0.0331 | 0.0482 |
| 34 | 0.0016 | 0.0412 | 0.0695 |
| 35 | 0.0026 | 0.0544 | 0.0689 |
| 36 | 0.0007 | 0.0249 | 0.0423 |
| 37 | 0.0013 | 0.0623 | 0.1112 |
| 38 | 0.0120 | 0.8677 | 0.6301 |
| 39 | 0.0035 | 0.1022 | 0.1048 |
| 40 | 0.4799 | 10.0000 | 28.2719 |
| 41 | 0.0028 | 0.0429 | 0.1234 |
| 42 | 0.0432 | 7.4918 | 12.7839 |
| 43 | 0.0625 | 6.4208 | 7.8552 |
| 44 | 0.7634 | 10.0000 | 62.9240 |
| 45 | 0.4580 | 10.0000 | 129.6303 |
| 46 | 0.0060 | 0.2288 | 0.1270 |
| 47 | 0.0200 | 0.7832 | 0.3931 |
| 48 | 0.0030 | 0.0333 | 0.0513 |
| 49 | 0.0418 | 2.7950 | 2.5232 |
| 50-1 | 0.0356 | 0.3065 | 0.1883 |
| 50-2 | 0.0064 | 0.1215 | 0.0728 |
| 51 | 0.2251 | 1.8719 | 0.7892 |
| 52 | 0.1628 | 2.9472 | 0.7912 |
| 53 | 0.1494 | 1.4617 | 0.3654 |
| 53-1 | 0.7289 | 11.2356 | 4.4368 |
| 54 | 0.2925 | 4.3443 | 1.9346 |
| 55 | 0.7079 | 6.7144 | 11.4664 |
| 56 | 0.3124 | 3.8335 | 4.7611 |
| 57 | 0.3738 | 7.2648 | 6.1298 |
| 57-1 | 2.6569 | 29.2285 | 31.2666 |
| 58 | 0.0756 | 0.8832 | 0.8461 |
| 59 | 0.1375 | 1.6360 | 1.4822 |
| 60 | 0.1242 | 1.2484 | 0.8882 |
| 61 | 0.3637 | 6.3408 | 5.5647 |
| 61-1 | 0.7402 | 5.0013 | 10.7716 |
| 62 | 0.6567 | 19.8972 | 4.3032 |
| 63 | 0.4200 | 12.3052 | 19.7830 |
| 63-1 | 1.3984 | 42.7028 | 23.3618 |
| 64 | 0.0336 | 0.0961 | 0.1812 |
| 65 | 0.6142 | 15.0755 | 11.5441 |
| 66 | 0.1119 | 1.5165 | 1.1815 |
| 66-1 | 0.0375 | 0.4171 | 0.1254 |
| 67-1 | 0.0573 | 0.8681 | 1.7765 |
| 67-2 | 0.0358 | 0.4777 | 1.1198 |
| 67-3 | 0.2917 | 7.2536 | 13.0802 |
| 68-1 | 0.1457 | 3.1690 | 3.8001 |
| 68-2 | 0.0622 | 2.8576 | 2.7293 |
| 68-3 | 0.1975 | 7.5583 | 9.1889 |
| 69 | 0.6564 | 10.0000 | 5.2459 |
| 70 | 0.0014 | 0.0401 | 0.0281 |
| 71 | 0.3472 | 3.0539 | 2.7764 |
| 72-1 | 0.0006 | 0.0292 | 0.0235 |
| 72-2 | 0.0012 | 0.0502 | 0.0264 |
| 72-3 | 0.0008 | 0.8052 | 0.0311 |
| 73-1 | 0.0015 | 0.0937 | 0.0469 |
| 73-2 | 0.0033 | 0.5751 | 0.1112 |
| 73-3 | 0.0016 | 9.3079 | 0.0459 |
| 74-1 | 0.0004 | 0.0137 | 0.0227 |
| 74-2 | 0.0016 | 0.0145 | 0.0521 |
| 75-1 | 0.0011 | 0.0356 | 0.0459 |
| 75-2 | 0.0027 | 0.0622 | 0.0773 |
| 76 | 0.0019 | 0.0469 | 0.0595 |
| 77-1 | 0.0032 | 0.1260 | 0.0954 |

-continued

Table of Bioactivity Data

| Example # | CMV-polymerase Biochemical IC50 (uM) | CMV-Luc Cellular EC50 (uM) | HSV-polymerase Biochemical IC50 (uM) |
|---|---|---|---|
| 77-2 | 0.0019 | 0.0577 | 0.0772 |
| 78 | 0.0010 | 0.0157 | 0.0300 |
| 79-1 | 0.0013 | 0.0337 | 0.0334 |
| 79-2 | 0.0020 | 0.0343 | 0.0654 |
| 80-1 | 0.0034 | 0.2155 | 0.0976 |
| 80-2 | 0.0097 | 0.2473 | 0.1773 |
| 81-1 | 0.0038 | 1.0656 | 0.1524 |
| 81-2 | 0.0113 | 0.4865 | 0.2044 |
| 81-3 | 0.0070 | 1.1866 | 0.2158 |
| 81-4 | 0.0233 | 1.0758 | 0.4736 |
| 82 | 1.0866 | 10.0000 | 20.8591 |
| 83 | 0.0044 | 0.1460 | 0.1013 |
| 84-1 | 0.0039 | 0.0696 | 0.1018 |
| 84-2 | 0.0028 | 0.0548 | 0.0806 |
| 84-3 | 0.0014 | 0.0310 | 0.0526 |
| 85 | 0.0047 | 0.1768 | 0.1025 |
| 86-1 | 0.0112 | 1.5226 | 0.2871 |
| 86-2 | 0.0046 | 0.2256 | 0.2758 |
| 86-3 | 0.0018 | 0.0346 | 0.0453 |
| 87 | 0.0012 | 0.0257 | 0.0351 |
| 88-1 | 0.0020 | 0.0242 | 0.0651 |
| 88-2 | 0.0032 | 0.0395 | 0.0735 |
| 89-1 | 0.0793 | 4.9015 | 1.2628 |
| 89-2 | 0.1735 | 3.3294 | 2.5192 |
| 90-1 | 0.0004 | 0.0134 | 0.0123 |
| 90-2 | 0.0005 | 0.0340 | 0.0198 |
| 91 | 0.1858 | 2.4793 | 2.2545 |
| 92 | 0.3115 | 2.9775 | 1.3412 |
| 93-1 | 0.0011 | 0.0386 | 0.0467 |
| 93-2 | 0.0008 | 0.0153 | 0.0286 |
| 93-3 | 0.0059 | 0.0210 | 0.0283 |
| 94-1 | 0.0006 | 0.0133 | 0.0332 |
| 94-2 | 0.0003 | 0.0079 | 0.0253 |
| 95 | 0.0166 | 0.2629 | 0.7215 |
| 96-1 | 0.0126 | 0.2444 | 0.3716 |
| 96-2 | 0.0665 | 0.8474 | 1.9194 |
| 97-1 | 0.0050 | 0.2215 | 0.1220 |
| 97-2 | 0.0032 | 0.1891 | 0.0908 |
| 98-1 | 0.0015 | 0.0652 | 0.0575 |
| 98-2 | 0.0012 | 0.0410 | 0.0576 |
| 98-3 | 0.0017 | 0.1017 | 0.1996 |
| 99-1 | 0.0010 | 0.0439 | 0.0494 |
| 99-2 | 0.0007 | 0.0301 | 0.0524 |
| 99-3 | 0.0008 | 0.1715 | 0.2012 |
| 100-1 | 0.0014 | 0.0936 | 0.0482 |
| 100-2 | 0.0010 | 0.0431 | 0.0395 |
| 101-1 | 0.0010 | 0.0555 | 0.0487 |
| 101-2 | 0.0006 | 0.0296 | 0.0329 |
| 102-1 | 0.0020 | 0.2286 | 0.1991 |
| 102-2 | 0.0015 | 0.0852 | 0.1619 |
| 103-1 | 0.0094 | 0.2366 | 0.1092 |
| 103-2 | 0.0011 | 1.2684 | 0.1076 |
| 103-3 | 0.0108 | 0.7914 | 0.1702 |
| 104-1 | 0.0186 | 0.6386 | 0.1849 |
| 104-2 | 0.0243 | 1.8224 | 0.3006 |
| 104-3 | 0.0101 | 1.0801 | 0.2731 |
| 105-1 | 0.0015 | 0.0501 | 0.0397 |
| 105-2 | 0.0025 | 0.1776 | 0.0643 |
| 106 | 0.0334 | 1.1156 | 0.9718 |
| 107-1 | 0.0019 | 0.1114 | 0.0616 |
| 107-2 | 0.0025 | 0.1996 | 0.1504 |
| 107-3 | 0.0022 | 0.1739 | 0.0726 |
| 108-1 | 0.0081 | 0.2279 | 0.1159 |
| 108-2 | 0.0169 | 0.7496 | 0.1822 |
| 108-3 | 0.0096 | 0.3850 | 0.1385 |
| 109 | 0.0032 | 0.1115 | 0.1209 |
| 110 | 0.0019 | 0.0817 | 0.0335 |
| 112 | 0.0022 | 0.1870 | 0.0441 |
| 111 | 0.0036 | 0.4328 | 0.0595 |
| 113 | 3.1283 | NT | 23.6485 |
| 114 | 3.9937 | NT | 25.0003 |
| 115 | 0.7467 | 15.0020 | 13.5554 |
| 116 | 2.1385 | 24.7201 | 14.0539 |

-continued

Table of Bioactivity Data

| Example # | CMV-polymerase Biochemical IC50 (uM) | CMV-Luc Cellular EC50 (uM) | HSV-polymerase Biochemical IC50 (uM) |
|---|---|---|---|
| 117 | 0.2850 | 1.4363 | 0.5773 |
| 118 | | | |
| 119 | | | |
| 120 | | | |
| 121 | | | |
| 122 | 0.3499 | NT | 5.0507 |
| 123 | 0.3730 | NT | 1.8854 |
| 124 | 0.0831 | 0.8738 | 0.3099 |
| 125 | 0.5663 | 20.2487 | 1.0118 |
| 126 | 1.2033 | 50.0000 | 1.9688 |
| 127 | 0.5452 | 19.8911 | 4.7860 |
| 128 | 0.1532 | 2.3848 | 2.5552 |
| 129 | 0.2644 | 1.0776 | 0.6927 |
| 130 | 0.3841 | 13.2841 | 2.4159 |
| 131 | 0.0618 | 0.9491 | 0.3108 |
| 132 | 0.0031 | 0.0707 | 0.1381 |
| 133 | 0.0228 | 1.0164 | 0.3238 |
| 134 | 0.2675 | 2.8741 | 2.1220 |
| 135 | 0.0652 | 0.7491 | 0.3417 |
| 136 | 0.0025 | 0.0867 | 0.1365 |
| 137 | 0.3483 | 19.6810 | 3.8990 |
| 138 | | | |
| 139 | 0.9888 | 50.0000 | 3.5802 |
| 140 | 0.2423 | 2.2208 | 4.2642 |
| 141 | 0.0728 | 1.6474 | 0.3284 |
| 142 | 0.3512 | NT | 2.1632 |
| 143 | 0.6492 | 30.6231 | 6.3061 |
| 144 | 0.2370 | 10.3908 | 1.1121 |
| 145 | 1.4095 | 30.1674 | 6.8212 |
| 146 | 0.9048 | 47.1717 | 14.8046 |
| 147 | 0.5584 | 21.3509 | 5.0540 |
| 148 | 0.1808 | 1.6588 | 1.5120 |
| 149 | 0.1119 | 7.9093 | 2.2031 |
| 150 | 0.0025 | 0.0677 | 0.0653 |
| 151 | 0.2629 | 10.0000 | 9.2524 |
| 152 | 0.6530 | 9.1857 | 1.6707 |
| 153 | 0.1178 | 0.6262 | 0.3885 |
| 154 | 0.0229 | 0.6618 | 0.2829 |
| 155 | 0.2011 | 37.2069 | 1.9519 |
| 156 | 0.9129 | 50.0000 | 2.1054 |
| 157 | 0.2233 | 7.7204 | 1.8021 |
| 158 | 0.3699 | 13.3447 | 4.0922 |
| 159 | 1.7778 | 26.5509 | 5.6639 |
| 160 | 0.1221 | 3.6039 | 2.0190 |
| 161 | 0.0015 | 0.0599 | 0.0571 |
| 162 | 0.0019 | 0.0413 | 0.0796 |
| 163 | 0.0232 | 0.3697 | 0.1410 |
| 164 | 0.0130 | 0.2487 | 0.3049 |
| 165 | 2.8438 | 10.0000 | 137.0169 |
| 166 | 0.1727 | 10.0000 | 7.6966 |
| 167 | 0.0055 | 0.0573 | 0.0718 |
| 168 | 0.0215 | 1.0955 | 0.2919 |
| 169 | 0.5458 | 10.0000 | 1.8681 |
| 170 | 0.1132 | 9.0271 | 9.3496 |
| 171 | 0.0729 | 0.6373 | 2.8015 |
| 172 | 2.4009 | 10.0000 | 71.0123 |
| 173 | 0.0206 | 0.3639 | 0.2323 |
| 174 | 0.0643 | 4.1987 | 2.6814 |
| 175 | 0.0008 | 6.0472 | 0.0244 |
| 176 | 0.0046 | 7.2266 | 0.0619 |
| 177 | 0.0015 | 0.0124 | 0.0181 |
| 178 | 0.0003 | 0.0434 | 0.0100 |
| 179 | 0.0004 | 0.1249 | 0.0169 |
| 180 | 0.0002 | 0.0062 | 0.0227 |
| 181 | 0.0011 | 0.0051 | 0.0374 |
| 182 | 0.0027 | 0.0483 | 0.0386 |
| 183 | 0.0029 | 0.1451 | 0.0367 |
| 184 | 0.0039 | 0.0316 | 0.0603 |
| 184-1 | 0.0004 | 0.0097 | 0.0196 |
| 185 | 0.0012 | 0.0189 | 0.0295 |
| 186 | 0.0012 | 6.6552 | 0.0205 |
| 187 | 0.0004 | 0.0149 | 0.0529 |
| 188 | 0.0008 | 0.0116 | |

-continued

| Table of Bioactivity Data | | | |
|---|---|---|---|
| Example # | CMV-polymerase Biochemical IC50 (uM) | CMV-Luc Cellular EC50 (uM) | HSV-polymerase Biochemical IC50 (uM) |
| 189 | 0.0011 | 0.0557 | 0.0598 |
| 190 | 0.0014 | 0.0478 | 0.0665 |
| 191 | 0.0765 | 3.4610 | 5.4564 |
| 192 | 0.1941 | 8.0511 | 3.0147 |
| 193 | 0.0341 | 1.2371 | 0.4202 |
| 194 | 0.1032 | 4.2236 | 0.8546 |
| 195 | 0.0671 | 2.6118 | 0.6492 |
| 196 | 0.0077 | 0.5094 | 0.2048 |
| 197 | 0.1275 | 4.7871 | 3.6049 |
| 198 | 0.0372 | 1.6757 | 1.5034 |
| 199 | 0.0537 | 1.7201 | 1.1126 |
| 200 | 0.2325 | 6.7685 | 2.5593 |
| 201 | 0.1816 | 4.8126 | 4.0609 |
| 202 | 0.3054 | 7.6470 | 6.4737 |
| 203 | 0.4103 | 10.0000 | 12.1638 |
| 204 | 0.1559 | 4.0429 | 5.4675 |
| 205 | 0.2489 | 3.7596 | 8.5852 |
| 206 | 1.7423 | 10.0000 | 250.0000 |
| 207 | 0.0497 | 3.7925 | 2.8998 |
| 208 | 0.1462 | 5.1813 | 4.5349 |
| 209 | 0.0510 | 2.4893 | 1.6386 |
| 210 | 0.0257 | 0.4940 | 0.4284 |
| 211 | 0.2193 | 7.8104 | 4.7745 |
| 212 | 0.0006 | 0.3153 | 0.0514 |

Activity against various human herpesviruses for the compound of Example 1 (n>3)

| | Human herpesvirus | | | |
|---|---|---|---|---|
| | CMV | HSV-1 | VZV | EBV |
| EC50 (nM) | 24 (+/−7) | 32 (+/−12) | 20 (+/−8) | 12 (+/−3) |

The invention claimed is:

1. A compound of Formula (IV):

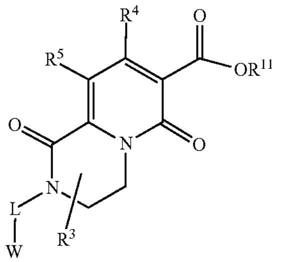

(IV)

wherein:

$R^{11}$ is H or $C_1$-$C_6$ alkyl optionally substituted up to three times with Z;

$R^3$ represents up to two (0-2) optional substituents on the ring to which -L-W is directly attached, each of which is independently selected from halo, CN, $C_{1-3}$ alkoxy, $C_{1-3}$ alkyl, COOR', and C(O)NR'R';

$R^4$ is H, halo, or $C_{1-3}$ alkyl;

$R^5$ is selected from H, halo, CN, $C_{1-3}$ alkoxy, —NR'R', $C_{1-3}$ alkyl substituted up to three times with $Z^5$, $C_{2-4}$ alkenyl substituted up to three times with $Z^5$, $C_{2-4}$ alkynyl substituted up to three times with $Z^5$, and a ring selected from a 3-6 membered cycloalkyl ring, a 4-6 membered heterocyclic ring containing one or two heteroatoms selected from N, O and S as ring members, and a 5-6 membered heteroaryl ring containing up to four heteroatoms selected from N, O and S as ring members, where the 3-6 membered cycloalkyl ring, 4-6 membered heterocyclic ring, or 5-6 membered heteroaryl ring is optionally substituted with 1-2 $Z^5$;

L is a $C_1$-$C_4$ straight chain or branched alkylene linker;

W is H, —OH, —OR, —C(O)NR'R', —COOR', —NR'R', —NR'COOR, —NR'C(O)R, —$SO_2$R, —$SO_2$NR'R', —NR'$SO_2$R, —P(O)(OR')$_2$, or an optionally substituted ring selected from 3-6 membered cycloalkyl, phenyl, 5-6-membered heterocyclyl containing one or two N, O or S heteroatoms as ring members, and 5-membered heteroaryl containing up to 4 heteroatoms selected from N, O and S as ring members that is optionally fused to phenyl, wherein the optional substituents for said optionally substituted ring are 1-3 groups selected independently from $C_{1-3}$ alkyl, oxo, halo, $C_{1-3}$ haloalkyl, -$L^2$-OH, -$L^2$-OR, -$L^2$-OC(O)—NR'R', -$L^2$-$SO_2$R, -$L^2$-$SO_2$NR'R', -$L^2$-$SO_2$NR'—C(O)R, -$L^2$-C(O)—NR'—$SO_2$R, -$L^2$-SOR, -$L^2$-S(═O)(═NR')R, -$L^2$-NR'$SO_2$NR'R', -$L^2$-NR'$SO_2$R, -$L^2$-NR'R', -$L^2$-NR'C(O)R', -$L^2$-NR'COOR, -$L^2$-C(O)NR'R', and -$L^2$-COOR';

R at each occurrence is selected independently from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups independently selected from $C_{1-4}$ alkyl, $C_{1-2}$ haloalkyl, oxo, -$L^3$-CN, -$L^3$-halo, -$L^3$-$C_{1-3}$ alkoxy, -$L^3$-OH, -$L^3$-OC(O)—NR'R', -$L^3$-$SO_2$R', -$L^3$-$SO_2$NR'R', -$L^3$-$SO_2$NR'—C(O)R', -$L^3$-C(O)—NR'—$SO_2$R', -$L^3$-SOR', -$L^3$-S(═O)(═NR')R', -$L^3$-NR'$SO_2$NR'R', -$L^3$-NR'$SO_2$R', -$L^3$-NR'R', -$L^3$-NR'C(O)R', -$L^3$-NR'COOR', -$L^3$-C(O)NR'R', and -$L^3$-COOR', -$L^3$-(5-6-membered heterocyclyl containing one or two N, O or S heteroatoms as ring members), -$L^3$-$C_{3-5}$ cycloalkyl, and -$L^3$-(5-6 membered heteroaryl ring having up to four heteroatoms comprising 1-4 nitrogen atoms, 0-1 oxygen atoms, and 0-1 sulfur atoms as ring members), where the $C_{1-4}$ alkyl, 5-6-membered heterocyclyl, $C_{3-5}$ cycloalkyl and 5-6 membered heteroaryl ring are each optionally further substituted with up to three groups independently selected from halo, $C_{1-3}$ alkyl, $C_{1-3}$ haloalkyl, -$L^4$-OR', -$L^4$-CN, and -$L^4$-N(R')$_2$;

R' at each occurrence is independently selected from H, $C_{1-4}$ alkyl optionally substituted with halo, —OH, amino, or $C_{1-2}$ alkoxy, and $C_{3-6}$ alkyl optionally substituted with halo, —OH, amino, or $C_{1-2}$ alkoxy;

or two R' taken together with a nitrogen atom to which both are directly attached can form a 4-6 membered ring optionally containing an additional N, O or S as a ring member and optionally substituted with one to three groups selected from $C_{1-2}$ alkyl, $C_{1-2}$ alkoxy, oxo, and hydroxy;

each $L^2$ and $L^3$ and $L^4$ is independently a bond or a straight chain or branched $C_{1-3}$ alkylene;

Z and $Z^5$ are independently selected at each occurrence from halo, hydroxy, CN, $C_{1-3}$ alkoxy, $C_{1-3}$ alkyl, and $C_{3-5}$ cycloalkyl, and two Z groups, or two $Z^5$ groups, taken together with a carbon atom to which both are directly attached can form a 3-5 membered cycloalkyl ring or a 4-6 membered heterocyclic ring containing O, N or S as a ring member and optionally substituted by up to two groups selected from oxo and $C_{1-3}$ alkyl;

or a salt thereof.

2. The compound of claim 1, wherein $R^{11}$ is H or $C_1$-$C_6$ alkyl.

3. The compound of claim 1, wherein $R^3$ is absent.

4. The compound of claim 1, wherein $R^4$ and $R^5$ are each H.

5. The compound according to claim 1, wherein:

W is —$SO_2$R, —$SO_2$NR'R', —NR'$SO_2$R, or an optionally substituted $C_1$-$C_3$ alkyl, or an optionally substituted 3-6 membered cycloalkyl;

wherein the optional substituents for said optionally substituted $C_1$-$C_3$ alkyl and optionally substituted cycloalkyl are 1-3 groups independently selected from $C_{1-3}$ alkyl, oxo, halo, $C_{1-3}$ alkoxy, OH, —$SO_2$R, —$SO_2$NR'R', —NR'$SO_2$NR'R', —NR'$SO_2$R, —NR'R', —OR, —NR'COOR, —C(O)NR'R', and COOR', R at each occurrence is independently selected from $C_{1-4}$ alkyl, 3-6 membered cycloalkyl, phenyl, 5-6 membered heteroaryl containing up to 4 heteroatoms selected from N, O and S as ring members, and 4-6 membered heterocyclyl containing one or two heteroatoms selected from N, O and S as ring members, wherein each R is optionally substituted with one or two groups selected from $C_{1-3}$ alkyl, oxo, CN, halo, $C_{1-3}$ alkoxy, OH, and $C_{3-5}$ cycloalkyl;

R' at each occurrence is independently selected from H and $C_{1-4}$ alkyl optionally substituted with halo, —OH or $C_{1-2}$ alkoxy;

or two R' taken together with a nitrogen atom to which both are directly attached can form a 4-6 membered ring optionally containing an additional N, O or S as a ring member and optionally substituted with one or two groups selected from $C_{1-2}$ alkyl, $C_{1-2}$ alkoxy, oxo, and hydroxy.

6. The compound according to claim 1, wherein the group W-L- is selected from the group consisting of:

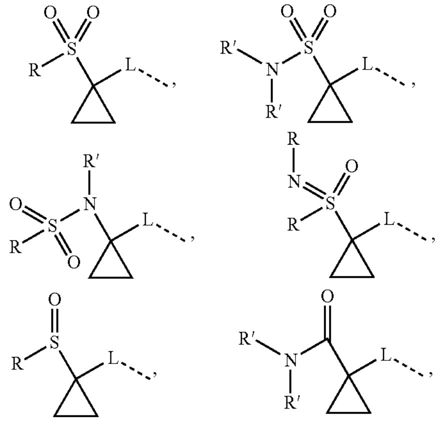

-continued

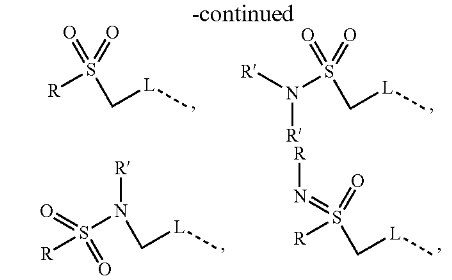

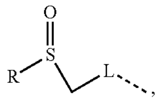

and

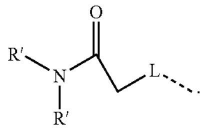

7. The compound according to claim 1, wherein L is $CH_2$.

8. The compound according to claim 1, wherein R at each occurrence is selected independently from methyl, ethyl, isopropyl and cyclopropyl.

9. The compound according to claim 1, wherein R' at each occurrence is selected independently from H and methyl.

10. The compound of claim 1, selected from the group consisting of:

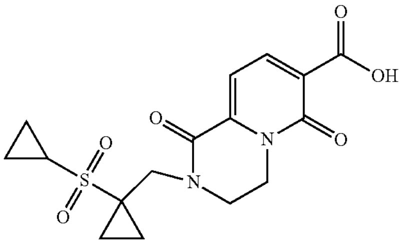 [SMILES: O=C(O)c1ccc2n(c1=O)CCN(CC1(S(=O)(=O)C3CC3)CC1)C2=O]

6-(dimethoxymethyl)-2-oxo-1,2-dihydropyridine-3-carboxylic acid;

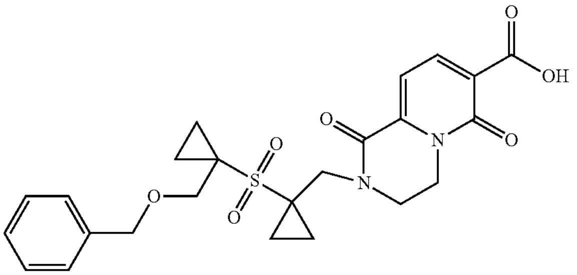 [SMILES: O=C(O)c1ccc2n(c1=O)CCN(CC1(S(=O)(=O)C3(COCc4ccccc4)CC3)CC1)C2=O]

2-((1-((1-((benzyloxy)methyl)cyclopropyl)sulfonyl)cyclopropyl)methyl)-1,6-dioxo-2,3,4,6-tetrahydro-1H-pyrido[1,2-alpyrazine-7-carboxylic acid;

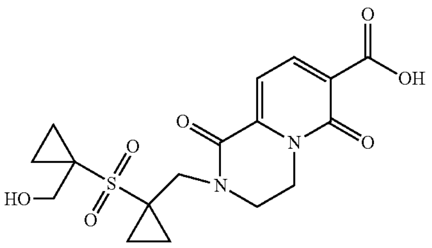 [SMILES: O=C(O)c1ccc2n(c1=O)CCN(CC1(S(=O)(=O)C3(CO)CC3)CC1)C2=O]

2-((1-((1-(hydroxymethyl)cyclopropyl)sulfonyl)cyclopropyl)methyl)-1,6-dioxo-2,3,4,6-tetrahydro-1H-pyrido[1,2-a]pyrazine-7-carboxylic acid;

-continued

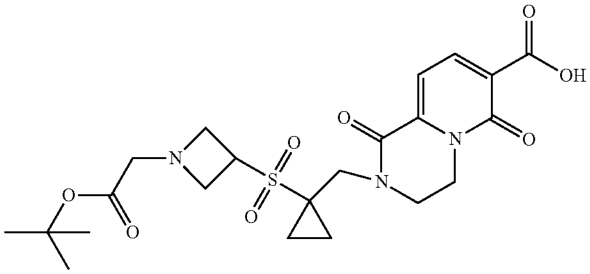 [SMILES: CC(C)(C)OC(=O)CN1CC(S(=O)(=O)C2(CN3CCn4c(ccc(C(=O)O)c4=O)C3=O)CC2)C1]

2-((1-((1-(tert-butoxycarbonyl)azetidin-3-yl)sulfonyl)cyclopropyl)methyl)-1,6-dioxo-2,3,4,6-tetrahydro-1H-pyrido[1,2-a]pyrazine-7-carboxylic acid;

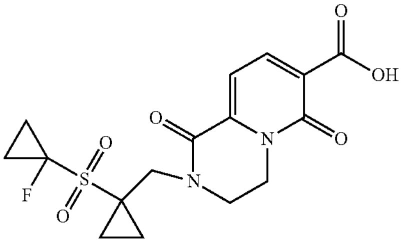 [SMILES: O=C(O)c1ccc2n(c1=O)CCN(CC1(S(=O)(=O)C3(F)CC3)CC1)C2=O]

2-((1-((1-fluorocyclopropyl)sulfonyl) cyclopropyl)methyl)-1,6-dioxo-2,3,4,6-tetrahydro-1H-pyrido[1,2-a]pyrazine-7-carboxylic acid;

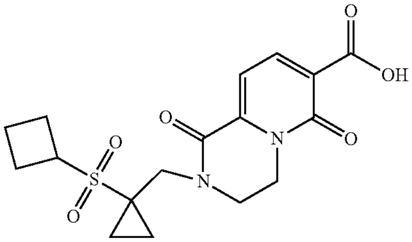 [SMILES: O=C(O)c1ccc2n(c1=O)CCN(CC1(S(=O)(=O)C3CCC3)CC1)C2=O]

2-((1-(cyclobutylsulfonyl)cyclopropyl)methyl)-1,6-dioxo-2,3,4,6-tetrahydro-1H-pyrido[1,2-a]pyrazine-7-carboxylic acid;

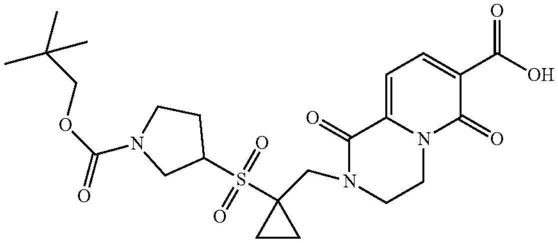 [SMILES: CC(C)(C)COC(=O)N1CCC(S(=O)(=O)C2(CN3CCn4c(ccc(C(=O)O)c4=O)C3=O)CC2)C1]

2-((1-((1-(tert-butoxycarbonyl)pyrrolidin-3-yl)sulfonyl)cyclopropyl)methyl)-1,6-dioxo-2,3,4,6-tetrahydro-1H-pyrido[1,2-a]pyrazine-7-carboxylic acid;

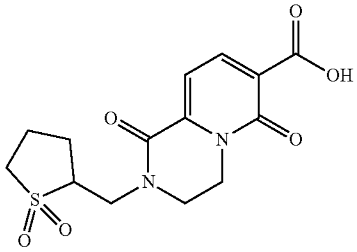 [SMILES: O=C(O)c1ccc2n(c1=O)CCN(CC1CCCS1(=O)=O)C2=O]

2-((1,1-dioxidotetrahydrothiophen-2-yl)methyl)-1,6-dioxo-2,3,4,6-tetrahydro-1H-pyrido[1,2-a]pyrazine-7-carboxylic acid;

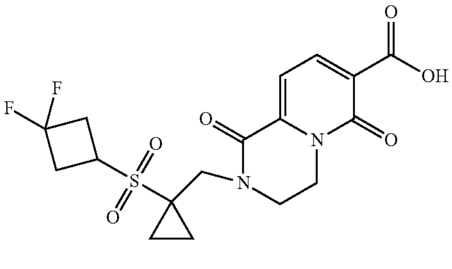

2-((1-((3,3-difluorocyclobutyl) sulfonyl)cyclopropyl)methyl)-1,6-dioxo-2,3,4,6-tetrahydro-1 H-pyrido[1,2-a]pyrazine-7-carboxylic acid;

-continued

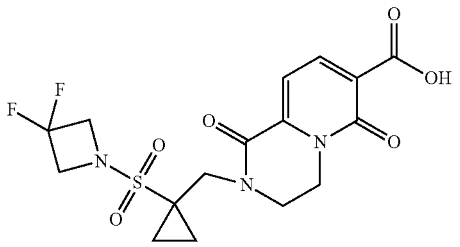 [SMILES: O=C(O)c1ccc2n(c1=O)CCN(CC1(S(=O)(=O)N3CC(F)(F)C3)CC1)C2=O]

2-((1-((3,3-difluoroazetidin-1-yl)sulfonyl)cyclopropyl)methyl)-1,6-dioxo-2,3,4,6-tetrahydro-1H-pyrido[1,2-a]pyrazine-7-carboxylic acid;

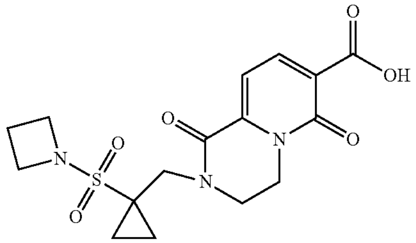

2-((1-(azetidin-1-ylsulfonyl)cyclopropyl)methyl)-1,6-dioxo-2,3,4,6-tetrahydro-1H-pyrido[1,2-a]pyrazine-7-carboxylic acid;

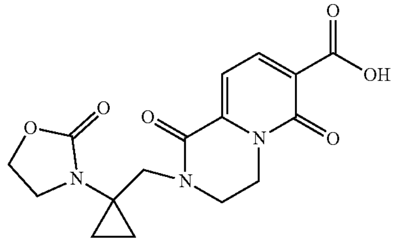 [SMILES: O=C(O)c1ccc2n(c1=O)CCN(CC1(N3CCOC3=O)CC1)C2=O]

1,6-dioxo-2-((1-(2-oxooxazolidin-3-yl)cyclopropyl)methyl)-2,3,4,6-tetrahydro-1H-pyrido[1,2-alpyrazine-7-carboxylic acid;

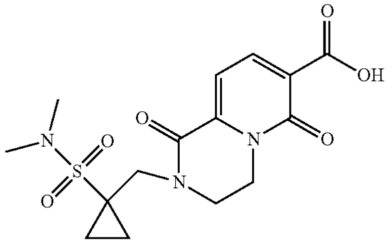 [SMILES: CN(C)S(=O)(=O)C1(CN2CCn3c(ccc(C(=O)O)c3=O)C2=O)CC1]

2-((1-(N,N-dimethylsulfamoyl)cyclopropyl)methyl)-1,6-dioxo-2,3,4,6-tetrahydro-1H-pyrido[1,2-a]pyrazine-7-carboxylic acid;

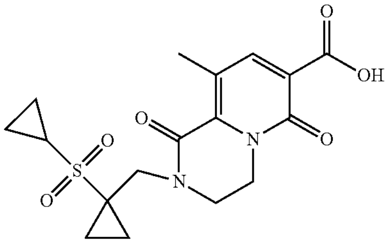 [SMILES: Cc1cc(C(=O)O)c(=O)n2c1C(=O)N(CC1(S(=O)(=O)C3CC3)CC1)CC2]

2-((1-(cyclopropylsulfonyl)cyclopropyl)methyl)-9-methyl-1,6-dioxo-2,3,4,6-tetrahydro-1H-pyrido[1,2-a]pyrazine-7-carboxylic acid;

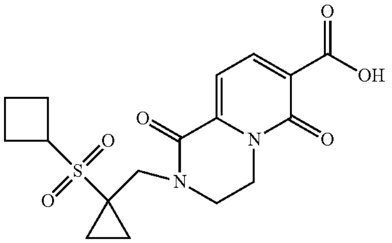 [SMILES: O=C(O)c1ccc2n(c1=O)CCN(CC1(S(=O)(=O)C3CCC3)CC1)C2=O]

2-((1-(cyclobutylsulfonyl)cyclopropyl)methyl)-1,6-dioxo-2,3,4,6-tetrahydro-1H-pyrido[1,2-a]pyrazine-7-carboxylic acid;

-continued

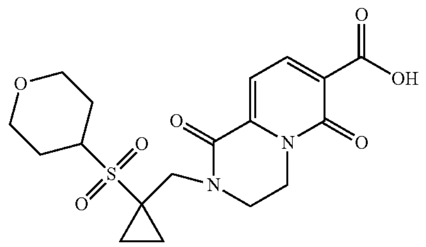 [SMILES: O=C(O)c1ccc2n(c1=O)CCN(CC1(S(=O)(=O)C3CCOCC3)CC1)C2=O]

1,6-Dioxo-2-((1-((tetrahydro-2H-pyran-4-yl)sulfonyl)cyclopropyl)methyl)-2,3,4,6-tetrahydro-1H-pyrido[1,2-a]pyrazine-7-carboxylic acid;

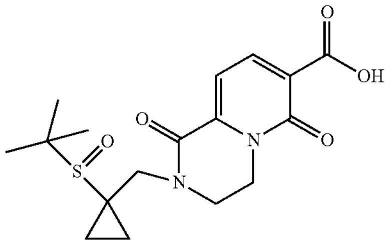 [SMILES: CC(C)(C)S(=O)C1(CN2CCn3c(ccc(C(=O)O)c3=O)C2=O)CC1]

2-((1-(tert-Butylsulfinyl)cyclopropyl)methyl)-1,6-dioxo-2,3,4,6-tetrahydro-1H-pyrido[1,2-a]pyrazine-7-carboxylic acid;

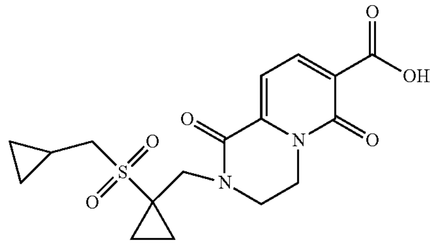 [SMILES: O=C(O)c1ccc2n(c1=O)CCN(CC1(S(=O)(=O)CC3CC3)CC1)C2=O]

2-((1-((Cyclopropylmethyl)sulfonyl)cyclopropyl)methyl)-1,6-dioxo-2,3,4,6-tetrahydro-1H-pyrido[1,2-a]pyrazine-7-carboxylic acid;

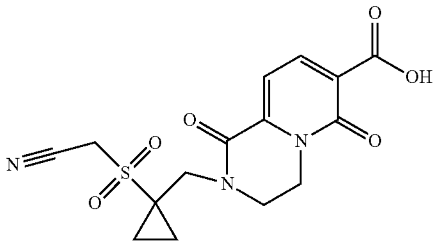 [SMILES: N#CCS(=O)(=O)C1(CN2CCn3c(ccc(C(=O)O)c3=O)C2=O)CC1]

2-((1-((Cyanomethyl)sulfonyl)cyclopropyl)methyl)-1,6-dioxo-2,3,4,6-tetrahydro-1H-pyrido[1,2-a]pyrazine-7-carboxylic acid;

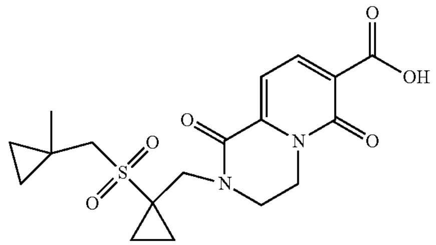 [SMILES: CC1(CS(=O)(=O)C2(CN3CCn4c(ccc(C(=O)O)c4=O)C3=O)CC2)CC1]

2-((1-(((1-methylcyclopropyl)methyl)sulfonyl)cyclopropyl)methyl)-1,6-dioxo-1,3,4,6-tetrahydro-2H-pyrido[1,2-a]pyrazine-7-carboxylic acid;

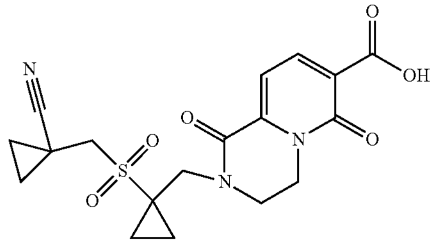 [SMILES: N#CC1(CS(=O)(=O)C2(CN3CCn4c(ccc(C(=O)O)c4=O)C3=O)CC2)CC1]

2-((1-(((1-cyanocyclopropyl)methyl)sulfonyl)cyclopropyl)methyl)-1,6-dioxo-1,3,4,6-tetrahydro-2H-pyrido[1,2-a]pyrazine-7-carboxylic acid;

-continued
| | |
|---|---|
| 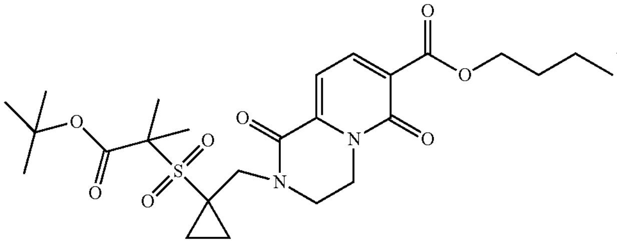 [SMILES: CCCCOC(=O)c1ccc2n(c1=O)CCN(CC1(S(=O)(=O)C(C)(C)C(=O)OC(C)(C)C)CC1)C2=O] | butyl 2-((1-((1-(tert-butoxy)-2-methyl-1-oxopropan-2-yl) sulfonyl)cyclopropyl)methyl)-1,6-dioxo-1,3,4,6-tetrahydro-2H-pyrido[1,2-a]pyrazine-7-carboxylate; and |
| 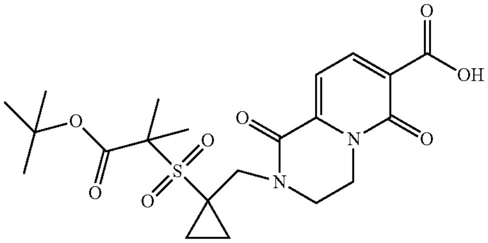 [SMILES: CC(C)(C)OC(=O)C(C)(C)S(=O)(=O)C1(CN2CCn3c(ccc(C(=O)O)c3=O)C2=O)CC1] | 2-((1-((1-(tert-butoxy)-2-methyl-1-oxopropan-2-yl) sulfonyl)cyclopropyl)methyl)-1,6-dioxo-1,3,4,6-tetrahydro-2H-pyrido[1,2-a]pyrazine-7-carboxylic acid; |
or a salt thereof.
* * * * *